US006183957B1

(12) United States Patent
Cole et al.

(10) Patent No.: US 6,183,957 B1
(45) Date of Patent: Feb. 6, 2001

(54) METHOD FOR ISOLATING A POLYNUCLEOTIDE OF INTEREST FROM THE GENOME OF A MYCOBACTERIUM USING A BAC-BASED DNA LIBRARY APPLICATION TO THE DETECTION OF MYCOBACTERIA

(75) Inventors: Stewart Cole, Clamart; Roland Buchrieser-Brosch; Stephen Gordon, both of Paris; Alain Billault, Roissy-en-Brie, all of (FR)

(73) Assignee: Institut Pasteur, Paris (FR)

( * ) Notice: Under 35 U.S.C. 154(b), the term of this patent shall be extended for 0 days.

(21) Appl. No.: 09/060,756

(22) Filed: Apr. 16, 1998

(51) Int. Cl.$^7$ .............................. C12Q 1/68; C12P 19/34; C07H 21/04

(52) U.S. Cl. ............................ 435/6; 435/91.1; 435/91.2; 536/23.1; 536/24.3; 536/24.31; 536/24.32

(58) Field of Search ................................ 435/6; 536/23.1, 536/24.3, 24.31, 24.32

(56) References Cited

FOREIGN PATENT DOCUMENTS

WO99/54487 * 10/1999 (WO) .

OTHER PUBLICATIONS

Cole et al Novartis Foundation Symposium 1998 pp. 160–177.*

Philipp et al., "Physical mapping of *Mycobacterium bovis* BCG Pasteur reveals differences from the genome map of *Mycobacterium tuberculosis* H37Rv and from *M. bovis*"; Microbiology, vol. 142:3135–3145; (1996).

Philipp et al., "An integrated map of the genome of the tubercle bacillus, *Mycobacterium tuberculosis* H37Rv, and comparison with *Mycobacterium leprae*"; Microbiology, vol. 93:3132–3137; (1996).

Zimmer et al., "Construction and Characterization of a Large–Fragment Chicken Bacterial Artificial Chromosome Library", Genomics, vol. 42:217–226; (1997).

Brosch et al., "Use of a *Mycobacterium Tuberculosis* H37Rv Bacterial Artifical Chromosome Library for Genome Mapping, Sequencing, and Comparative Genomics," *Infection and Immunitgy,* vol. 66, No. 5, pp. 2221–2229 (May 1998).

Cole et al., "Deciphering the Biology of *Mycobacterium Tuberculosis* From the Complete Genome Sequence," *Nature,* vol. 393, pp. 537–545 (Jun. 11, 1998).

* cited by examiner

*Primary Examiner*—Kenneth R. Horlick
*Assistant Examiner*—Jeffrey Siew
(74) *Attorney, Agent, or Firm*—Finnegan, Henderson, Farabow, Garrett & Dunner, L.L.P.

(57) ABSTRACT

The present invention relates to a method for isolating a polynucleotide of interest that is present in the genome of a first mycobacterium strain and/or is expressed by the first mycobacterium strain, where the polynucleotide of interest is also absent or altered in the genome of a second mycobacterium strain and/or is not expressed in the second mycobacterium. The method comprises: (a) contacting the genomic DNA of the first mycobacterium strain under hybridizing conditions with the DNA of a least one clone that belongs to a bacterial artificial chromosome (BAC) genomic DNA library of the second mycobacterium strain, and (b) isolating the polynucleotide of interest that does not form a hybrid with the DNA of the second mycobacterium strain. This invention further pertains to a *Mycobacterium tuberculosis* strain H37Rv genomic DNA library, as well as a *Mycobacterium bovis* BCG strain Pasteur genomic DNA library, and the recombinant BAC vectors that belong to those genomic DNA libraries. This invention also relates to a method, as well as a kit, for detecting a nucleic acid of a mycobacterium in a biological sample.

43 Claims, 12 Drawing Sheets

Figure 1A:
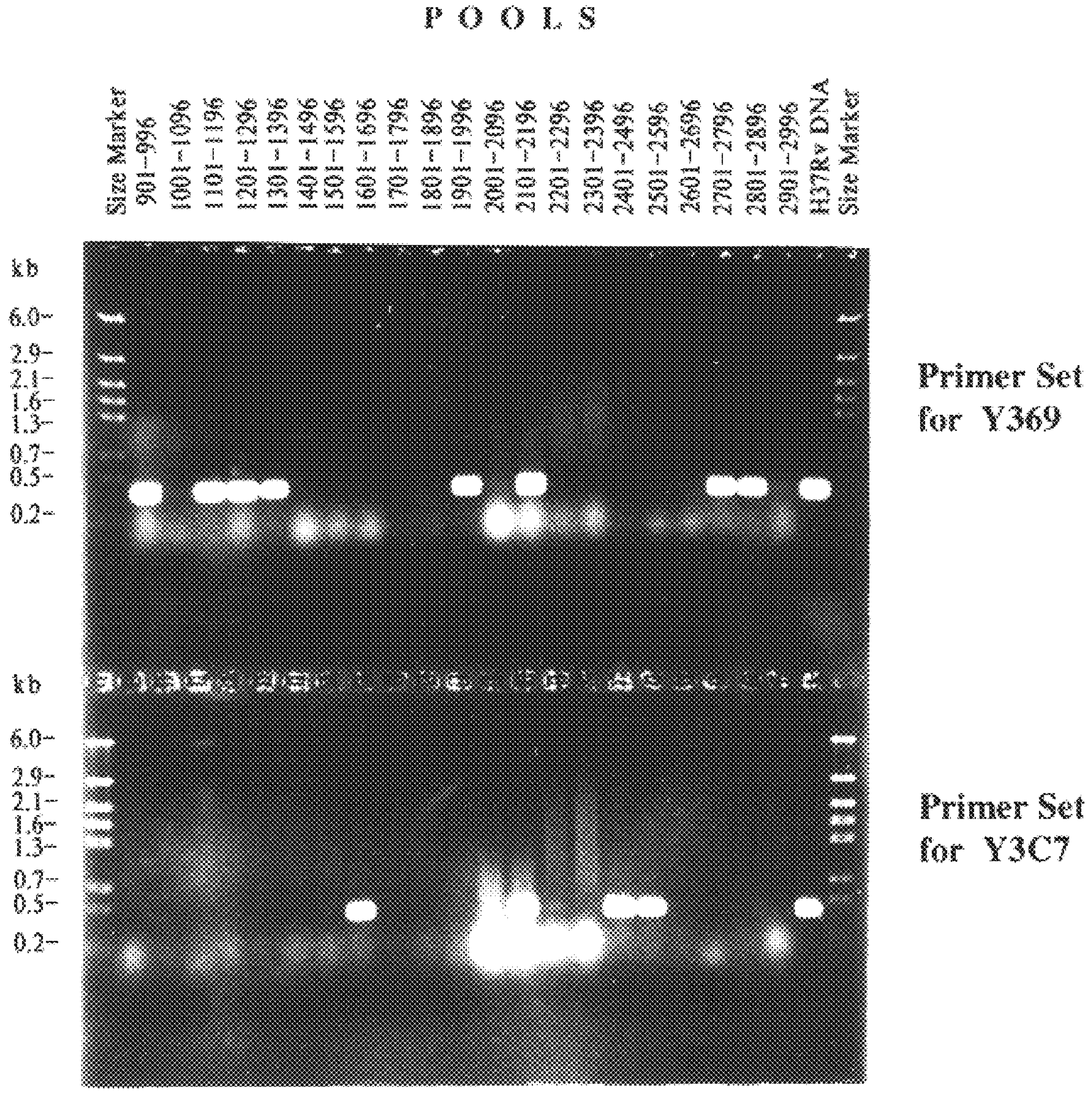

```
(SEQ ID NO. 727) H37Rv ·····PTQTLTGRPLIGNGTPGAVGSGATGAPGGWLLGDGGAGGSGAAGSGAPGGAGGAAGLWGT   837273
                 ···········::::::::::::::::::::::::::::::::::::::::::::::::::::::::::
(SEQ ID NO. 728) BCG ·······PTQTLTGRPLIGNGTPGAVGSGATGAPGGWLLGDGGAGGSGAAGSGAPGGAGGAAGLWGT

                 H37Rv ···GGAGGAGGSSAGGGGAGGAGGAGGWLLGDGGAGGIGGASTVLGGTGGGGGVGGLWGAGGA   837453
                 ······································::::::::::::::::::::::::::::
                 BCG ····------------------------------GGAGGIGGASTVLGGTGGGGGVGGLWGAGGA

                 H37Rv ···GGAGGTGLVGGDGGAGGAGGTGGLLAGLIGAGGGHGGTGGLSTNGDGGVGGAGGNAGMLA   837633
                 ········::::::::::::::::::::::::::::::::::::::::::::::::::::::::
                 BCG ·····GGAGGTGLVGGDGGAGGAGGTGGLLAGLIGAGGGHGGTGGLSTNGDGGVGGAGGNAGMLA

                 H37Rv ···GPGGAGGAGGDGENLDTGGDGGAGGSAGLLFGSGGAGGAGGFGFLGGDGGAGGNAGLLLS   837813
                 ········::::::::::::::::::::::::::::::::::::::::::::::::::::::::
                 BCG ·····GPGGAGGAGGDGENLDTGGDGGAGGSAGLLFGSGGAGGAGGFGFLGGDGGAGGNAGLLLS

                                                   837897
                 H37Rv ···SGGAGGFGGFGTAGGVGGAGGNAGWLGF-------------------------------
                 ········:::::::::::::::::::::::::::::·······························
                 BCG ·····SGGAGGFGGFGTAGGVGGAGGNAGWLGFGAGGIGGIGGNANGGAGGNGGTGGQLWGSGGA

                 H37Rv ···--------------GGAGGVGGSAGLIGTGGNGGNGGTGANAGSPGTGGAGGLLLGQNGLNGLP   838047
                 ······················::::::::::::::::::::::::::::::::::::::::::::::
                 BCG ·····GVEGGAALSVGDTGGAGGVGGSAGLIGTGGNGGNGGTGANAGSPGTGGAGGLLLGQNGLNGLP
```

FIG. 6 pBeloBAC11

(SEQ ID NO. 728) GCGGCCGCAA GGGGTTCGCG TCAGCGGGTG TTGGCGGGTG TCGGGGCTGG
*Not*I restriction site

CTTAACTATG CGGCATCAGA GCAGATTGTA CTGAGAGTGC ACCATATGCG

GTGTGAAATA CCGCACAGAT GCGTAAGGAG AAAATACCGC ATCAGGCGCC

ATTCGCCATT CAGGCTGCGC AACTGTTGGG AAGGGCGATC GGTGCGGGCC

TCTTCGCTAT TACGCCAGCT GGCGAAAGGG GGATGTGCTG CAAGGCGATT
primer T7-BAC1

AAGTTGGGTA ACGCCAGGGT TTTCCCAGTC ACGACGTTGT AAAACGACGG

CCAGTGAATT GTAATACGAC TCACTATAGG GCGAATTCGA GCTCGGTACC
T7-promoter sequence

CGGGGATCCT CTAGAGTCGA CCTGCAGGCA TGCAAGCTTG AGTATTCTAT
primer T7-Belo2 · *Hind*III cloning site · SP6-promoter AGTGTCACCT AAATAGCTTG GCGTAATCAT GGTCATAGCT GTTTCCTGTG
sequence (complementary strand) · primer SP6-Mid (complementary strand)

TGAAATTGTT ATCCGCTCAC AATTCCACAC AACATACGAG CCGGAAGCAT

AAAGTGTAAA GCCTGGGGTG CCTAATGAGT GAGCTAACTC ACATTAATTG
primer SP6-BAC1 (complementary strand)

CGTTGCGCTC ACTGCCCGCT TTCCAGTCGG GAAACCTGTC GTGCCAGCTG

CATTAATGAA TCGGCCAACG CGAACCCCTT GCGGCCGCCC GGGCCGTCGA
*Not*I restriction site

FIG. 7

SEQUENCE LISTING

```
<160> NUMBER OF SEQ ID NOS: 743

<210> SEQ ID NO 1
<211> LENGTH: 12732
<212> TYPE: DNA
<213> ORGANISM: Mycobacterium tuberculosis

<400> SEQUENCE: 1

acctgcgctt gcagagatca aatagggcgc atgggtcagc atagtacagg tcgtcgcgca     60

tctttgatgc atcggaataa gatgtcaggc aattaaaaga gaagccacgg cgactcgcgg    120

cattcagcat gtcgagcgtc gcttcgatgt gagcgcacca ttccgtgtcc aacgatttca    180

gacgaacatt gaatattcca ctcgcgacgc tatagtccgc ctcccgatct atgcgcgccg    240

cgcagatgaa gtctgcgttc gcccgacctt cgaaacgtag tgcggccgcg cgcaccattt    300

cgggggagac gtcgatgccg gtgtaatcag ttttgaagcc acgcgcatct aggtagtcca    360

gtagagcccc atagccacag cctagatcgt tgatcgaaaa tgggtccgcc gcattgacaa    420

tgcgcaccag ctggtcaaag cgcaacgcct gcccggcttc gccgttccaa tcgacgccgc    480

gcgggtgccg tgtgcttcga gtttcgatgc gtagtaacgg gccacgtcag cgagcatggt    540

cgttgcgtct tccgccatga agctgcctca cgatttgtgt gtgtgggcgt cggtgcgtgg    600

gtccgagact ataccttcaa cagttgcatg ccgaggctgc ggcgggcaat gacccaaaaa    660

cccgccggca cggttcgccg agcaaggaag cgtggagacg atagataatt tcactggcga    720

cagtacctca aatagtccgg agcctcggct ccgacgttaa agagcagatc cagaatcgac    780
```

-continued

```
acggcgggct cgaaccctcc ccacaattgc ttataatcgc ggtagccgtc ataatcgaac    840
caagttaccc ggatgctaag ttcgtcgaac acgcgctcat cgacatacga acgggctgag    900
gggccagaga catattcggt cgctgcggcc tgttggcaga ggttggccag tctctcggtc    960
ttgccgtcgg ctaattcgta gtcccacgaa tttgccagtc gcgtgctgat accgagataa   1020
ctgcaaatcg cattcaatag acgcctgttg agtaaggaaa gattcgtgtg ctgttcttcg   1080
aggtaaatcg gcgcgagcca gtcagcgatc tccgcaaaat gagcggccgc gctgtagttg   1140
aattctagtg cccgccagtg cgctttcgcc caatcggtgc cgtcgatcag cgtctcacgt   1200
atcttttgat ggaaacgtcc cttcacctgg acgggaacag ttatccactg taacccctgg   1260
ctcgttttga tccgatttct gtttcgccaa tcacgcttgg tatattgcat gtcatcatag   1320
atgatgaatt catcgacgaa tgcaatcagg tcaaaatatc ctcgccaagg tatgtaattt   1380
gattgaacaa tcgcgacttt cttcaacgcg gtgtctccaa tttagaataa caaatacgtc   1440
gcgcccgcga cagctccgct ggagcgagtt caagcgattc tgcgacatat tcaatatggt   1500
gctcgggaag gccaggatgg gccgcgaccc ggggcgtccg gtgcgcgatg aacgtcgcat   1560
cgtctcctgt gagataattg catccgatca tatagggctg gctgcggcta ggttgctggc   1620
aaaaagatat cgcggccgat ccgtttctgg ttttgtcttg atgatcaaat ccgcttccgt   1680
tcacgagatc gattcctggt cttcccccag cgtcgcgatg tcgataggtg tcgcgctttg   1740
ttcgtacccg cactacgcgg cggcgagaac ctcgccaccg aatcgggatt ggggggagga   1800
taccactcgg tcgaggcccg tcaccggcct tctagcgggt tgaccatcag tgtttgcagg   1860
gccctatccc ggtatggcgc accacgggat cggcagcgtt ccggttgctg gcgtggtacc   1920
tcgttgtggc gccgtggtcc atgtcgattg agtgcgtgga tcagtgtaaa ccgttgcgcg   1980
ccatgttctg taggcactgg ttcgggttgt ggttaggctg cacggttggc aggttaccaa   2040
ccactgagcc cctgggcgga tgtgagctcg gactccgcct atggggtgta attttggcag   2100
attgggccgg gtccccgtgg tgaggactcc tcaaccggat tgggtaagca tgaggtggtg   2160
ctggcagcgg tgtcctggtc gctctcccga gtaggcccgt tgtgactgtc atgtgggcga   2220
gcgggtttgc gcgcgtagga gacgatgatt actacgcacg tgaccaacca caagaacggt   2280
gcccatgtca ccgtggtgaa aacgagtggc gtggtaccga ctaccccttt ggctcccagc   2340
tgtccataga gcggcacgta gaacggctgg cccgggaccg cgacgttgac gatgctcagc   2400
gccacggcca aactcacgca gacgccgacc gcgcggcggc ggtctccatg ggctgcgagt   2460
tggtcgaata tcccagcacc aggaggcccg ttggggtctc gggctaccag tgcagcgatt   2520
ggcaagacga aaacgagata gtagaaggcg acgtccgcgg gggagaaggt ggcggtggcg   2580
agcaacacaa tccccaccat gacaggcggg atacggcgtc cgagcgccag cacggcgacc   2640
acgactatga ctaggacagc aaacccgatc tgcgttcgcg gaccagtgag gaaaccctct   2700
gggatcttgc ccgattgata gttcttgatg ctatcgggga tcagcaggag tgccttgcca   2760
aaggacacgt tccgcgggtc tcgaagccct ccgaacgaac tattgaactt gatgatgccg   2820
tggatcgact gtgcgatcgt ccccgggaag cctcgtggcc acaacagaaa ggctgcgata   2880
ttggacacca ccacgccggt gatcccgata ccagcccacc gccattgtcg agccgccaac   2940
aacaccacgc cgagaacgac gaactgcggc tttaccagga cggccaagat caccgtgatg   3000
gtggcgaggc cccaccgctg tcgggacaac gccacgaagt aagccagcgc gatcggtacc   3060
acgaaccctg tcgagttgcc tcgatcgatg acccccacg ccgggatggc cgcggcgccc   3120
agtgtcacga agatgaccac tcgctccaga ccacgtgccc cccgggccgc ccagatggcg   3180
```

-continued

```
ggagatatga ccgccatcgt tagggcgacc aggtaacaga tcagccccaa gcgcggcgca   3240
cccagccaat ggctgggtag tccgaaaatc gcatacggta tgcgggcggg ggcccatgca   3300
gcaaccgcgg tcggctggta atcggcgggt agcgagatca ggtagtccgc gggattgggt   3360
tgaatcccgg cggcggcgac catggcgtag tcgctgaagc agtgccgacc gatattcatg   3420
ccccaatcaa gccaacagtc cccagggact accaaaagag tggaaaagac gtcgaccgcg   3480
taccactgac tgagggcgta cgccgtcgcc gccgaaatca ccgacgccag caggatggtg   3540
ccgagcatga gggtgcgctc ggattgggag ccgatcgccc agagccgctc ccggctcgcg   3600
gtcacggcac cgcgcaacac ctccggggtt cgcttcatct ggattctcct cggttctgcg   3660
cgaaacggta gcagagcgcc atggttgcca acgcggtcgc cgggcagtct agaccggatc   3720
ttcctcgtgg caaccgacaa caggacgtcg ttgccgaaag ggcgctgggc accgacatct   3780
aggatgaacc cacagccacg ccccgacgtt atgccatggc gaagagcgac cggcaggagc   3840
gggaacccag tgaagcgagc gctcatcacc ggaatcacag gaccggacgg ctcgtatctc   3900
gctaagctcc cgctgaaggg atatgtggcc gctggtagcc cggccgaggt ctatttctgc   3960
tgggcgacac ggaattatcg cgaattgtat gggttgctcg cggtcaacag catctggttc   4020
aatcacgaat caccgcgtca cggcgagaca ttcatgactc gtaatcctgc accatatcgc   4080
ggtcggcaac gaggcgctga tcgatgcgca gacgctgatg cgccggccca cccggatagg   4140
tatcagtatt ggggcgttcc ggccagcgta cgaggcgtga tcgaccgcgc aatgggtgtt   4200
tgcgttgagt aataatctga accgtgtgaa cgcatgcatg gatggattcc ttgcccgtat   4260
ccgctcacat gttgatgcgc acgcgccaga attgcgttca ctgttcgata cgatggcggc   4320
cgaggcccga tttgcacgcg actggctgtc cgaggacctc gcgcggttgc ctgtcggtgc   4380
agcattgctg gaagtgggcg ggggggtact tctgctcagc tgtcaactgg cggcggaggg   4440
atttgacatc accgccatcg agccgacggg tgaaggtttt ggcaagttca gacagcttgg   4500
cgacatcgtg ctggaattgg ctgcagcacg acccaccatc gcgccatgca aggcggaaga   4560
ctttatttcc gagaagcggt tcgacttcgc cttctcgctg aatgtgatgg agcacatcga   4620
ccttccggat gaggcagtca ggcgggtatc ggaagtgctg aaaccggggg ccagttacca   4680
cttcctgtgc ccgaattacg tattcccgta cgaaccgcat ttcaatatcc caacattctt   4740
caccaaagag ctgacatgcc gggtgatgcg acatcgcatc gagggcaata cgggcatgga   4800
tgacccgaag ggagtctggc gttcgctcaa ctggattacg gttcccaagg tgaaacgctt   4860
tgcggcgaag gatgcgacgc tgaccttgcg cttccaccgt gcaatgttgg tatggatgct   4920
ggaacgcgcg ctgacggata aggaattcgc tggtcgccgg gcacaatgga tggtcgctgc   4980
tattcgctcg gcggtgaaat tgcgtgtgca tcatctggca ggctatgttc ccgctacgct   5040
gcagcccatc atggatgtgc ggctaacgaa gaggtaatga catggcgcaa gcgacatcgg   5100
gcattcgcgc ggcactttcg caacctgctg tgtatgaggc gtatcagcgg attgcgggcg   5160
ctaaaagcgg gcttgcgtgg atcacaaccg accccatcca gtcgttgcca ggcatgcgta   5220
ctctcgacct cggttgctgg ccagcggtga tacacagctc cccgccagtg gacgtgacat   5280
gtacgagaga cggcatgagc gcggaatgtg cgaccgtgcc gtcgagatga ccgacgtcgg   5340
cgctacggca gcccccaccg gacctatcgc gcggggcagc gtcgctcggg tcggcgcggc   5400
gaccgcgttg gccgttgcct gcgtctacac ggtcatctat ctggcggccc gcgacctacc   5460
cccggcttgt ttttcgatat tcgcggtgtt ttggggggcg ctcggcattg ccaccggcgc   5520
```

-continued

```
cacccacggc ctcctgcaag aaacgacccg cgaggtccgc tgggtgcgct ccacccaaat   5580
agttgcgggc catcgtaccc atccgctgcg ggtggccggg atgattggca ccgtcgcggc   5640
cgtcgtaatt gcgggtagct caccgctgtg gagccgacag ctattcgtcg aggggcgctg   5700
gctgtccgtg gggctactca gcgttggggt ggccgggttc tgcgcgcagg cgaccctgct   5760
gggcgcgctg gccggcgtcg accggtggac acagtacggg tcactgatgg tgaccgacgc   5820
ggtcatccgg ttggcggtcg ccgcggcagc ggttgtgatc ggatggggtc tggccgggta   5880
cttgtgggcc gccaccgcgg gagcggtggc gtggctgctc atgctgatgg cctcgcccac   5940
cgcgcgcagc gcggccagcc tgctgacgcc cgggggaatc gccacgttcg tgcgcggtgc   6000
cgctcattcg ataaccgccg cgggtgccag cgcgattctg gtaatgggtt tcccagtgtt   6060
gctcaaagtg acctccgacc agttaggggc aaagggcgga gcggtcatcc tggctgtgac   6120
cttgacgcgt gcgccgcttc tggtcccact gagcgcgatg caaggcaacc tgatcgcgca   6180
tttcgtcgac cggcgcaccc aacggcttcg ggcgctgatc gcaccggcgc tggtcgtcgg   6240
cggcatcggt gcggtcggga tgttggccgc agggcttacc ggtccctggt tgctgcgtgt   6300
tggattcggc cccgactacc aaactggcgg ggcgttgctg gcctggttga cggcagcggc   6360
ggtagctatc gccatgctga cgctgaccgg cgccgccgcg gtcgcggccg cactgcaccg   6420
ggcgtatttg ctgggctggg tcagcgcgac ggtggcgtcg acgctgttgc tgctgctgcc   6480
gatgccgctg gagacgcgca ccgtgatcgc gctgttgttc ggtccaacgg tgggaatcgc   6540
catccatgtg gccgcgttgg cgcggcgacc cgactgattt gtgccccagg tcgacaaatc   6600
acgccgtctc gtcagtgagc actccgtcct cgggtccgat ccttccagga gacgttgcaa   6660
cctgatttgg ctcaaattgg tgcgcaccga gggtcgggca catcgtaggg tcgcaacagt   6720
cacatgtgtc actgcaccgg gcgacacccg atgtcccggc tctcagcgac agctgtctga   6780
cctgtggttt tgttcccaag ttggtcgtgg ctgtgcggga ttggaggtgg cgtgggggtc   6840
gcgtcgtatg gattctcctc ctcggttccg cgcgaaacgg ccgcaggcgc aatggtcacc   6900
aacttggccg cggtggagtc tagcctcaca ttttcctggt cgcccccgac aaccaggagg   6960
tcgctgcaga acgggcgttc cctacccaca tctactatga agcgacagcg gcgccccgct   7020
gtgatggctg agcatgaccg acagaggcgg gaagacagtg aagcgagcgc tcatcaccgg   7080
aatcaccggc caggacggct cgtatctcgc cgaactgctg ctggccaagg ggtatgaggt   7140
tcacgggctc atccggcgcg cttcgacgtt caacacctcg cggatcgatc acctctacgt   7200
cgacccgcac caaccgggcg cgcggctgtt tctgcactat ggtgacctga tcgacggaac   7260
ccggttggtg accctgctga gcaccatcga acccgacgag gtgtacaacc tggcggcgca   7320
gtcacacgtg cgggtgagct tcgacgaacc cgtgcacacc ggtgacacca ccggcatggg   7380
atccatgcga ctgctggaag ccgttcggct ctctcgggtg cactgccgct tctatcaggc   7440
gtcctcgtcg gagatgttcg gcgcctcgcc gccaccgcag aacgagctga cgccgttcta   7500
cccgcggtca ccgtatggcg ccgccaaggt ctattcgtac tgggcgaccc gcaattatcg   7560
cgaagcgtac ggattgttcg ccgttaacgg catcttgttc aatcacgaat caccgcggcg   7620
cggtgagacg ttcgtgaccc gaaagatcac cagggccgtg gcacgcatca aggccggtat   7680
ccagtccgag gtctatatgg gcaatctgga tgcggtccgc gactgggggt acgcgcccga   7740
atacgtcgaa ggcatgtggc ggatgctgca gaccgacgag cccgacgact tcgttttggc   7800
gaccgggcgc ggtttcaccg tgcgtgagtt cgcgcgggcc gcgttcgagc atgccggttt   7860
ggactggcag cagtacgtga aattcgacca acgctatctg cggcccaccg aggtggattc   7920
```

-continued

```
gctgatcggc gacgcgacca aggctgccga attgctgggc tggagggctt cggtgcacac   7980
tgacgagttg gctcggatca tggtcgacgc ggacatggcg gcgctggagt gcgaaggcaa   8040
gccgtggatc gacaagccga tgatcgccgg ccggacatga acgcgcacac ctcggtcggc   8100
ccgcttgacc gcgcggcccg ggtctacatc gccgggcatc gcggcctggt cgggtccgcg   8160
ctgctacgca cgtttgcggg cgcggggttc accaacctgc tggtgcggtc acgcgccgag   8220
cttgatctga cggatcgggc cgcgacgttc gacttcgttc tcgagtcgag gccgcaggtc   8280
gtcatcgacg cggcggcccg ggtcggcggc atcctggcca acgacaccta cccggccgat   8340
ttcctgtcgg aaaacctcca gatccaggtc aacctgctgg atgccgccgt ggcggcgcgg   8400
gtgccgcggc tgctgttcct gggctcgtcg tgcatctacc cgaaactcgc cccgcagccg   8460
atcccggaga gcgcgctgct caccggtccg ttggagccga ccaacgacgc gtacgcgatc   8520
gccaaaatcg ccggcatcct tgcggtccag gcggtgcgcc gccaacatgg cctgccgtgg   8580
atctcggcga tgcccaccaa cctgtacggg ccaggcgaca acttttcgcc gtccggctcg   8640
catctgctgc cggcactcat ccgccgctat gacgaggcca aagccagtgg cgcgcccaac   8700
gtgaccaact ggggcaccgg cacgccccga cgggagttgc tgcacgtcga cgacctggcg   8760
agcgcatgcc tgtatctgct ggaacatttc gacgggccga cccatgtcaa cgtgggaacc   8820
ggcatcgacc acaccatcgg cgagatcgcc gagatggtcg cctcggcggt aggctatagc   8880
ggcgaaaccc gctgggatcc aagcaaaccg gacggaacac cacgcaaact gctggatgtt   8940
tcggtgctac gggaggcggg atggcggcct tcgatcgcgc tgcgcgacgg catcgaggcg   9000
acggtggcgt ggtatcgcga gcacgcggga acggttcggc aatgaggctg gcccgtcgcg   9060
ctcggaacat cttgcgtcgc aacggcatcg aggtgtcgcg ctactttgcc gaactggact   9120
gggaacgcaa tttcttgcgc caactgcaat cgcatcgggt cagtgccgtg ctcgatgtcg   9180
gggccaattc ggggcagtac gccaggggtc tgcgcggcgc gggcttcgcg ggccgcatcg   9240
tctcgttcga gccgctgccc gggccctttg ccgtcttgca gcgcagcgcc tccacggacc   9300
cgttgtggga atgccggcgc tgtgcgctgg gcgatgtcga tggaaccatc tcgatcaacg   9360
tcgccggcaa cgagggcgcc agcagttccg tcttgccgat gttgaaacga catcaggacg   9420
cctttccacc agccaactac gtgggcgccc aacgggtgcc gatacatcga ctcgattccg   9480
tggctgcaga cgttctgcgg cccaacgata ttgcgttctt gaagatcgac gttcaaggat   9540
tcgagaagca ggtgatcgcg ggtggcgatt caacggtgca cgaccgatgc gtcggcatgc   9600
agctcgagct gtctttccag ccgttgtacg agggtggcat gctcatccgc gaggcgctcg   9660
atctcgtgga ttcgttgggc tttacgctct cgggattgca acccggtttc accgaccccc   9720
gcaacggtcg aatgctgcag gccgatggca tcttcttccg gggcagcgat tgacgcgccg   9780
gcgcgtcaat ctatttcgac attcgcgtga agacgttttc ccagaatcga ctgttgtagg   9840
cgtagaactc ccggccgcgt aggtaggcat gtgatattcg ccttcccccg aacgggtagc   9900
ggcgatgaag gtcgcccatg cggcgcagat caccgaagac cgcgcttggt tcccggtgcg   9960
agccgacgcc cgtggtgtcg aactcgcaca gcacacaccg aatcgtgacc ggctcgcata  10020
ccagcgcggc ccgcaatatg aattcctggt cggcggcgat cccgaaatca aggtcgtagc  10080
caccgatctt ggccaccagc gatgatccga agaacgatgc ttgatgcgga acaacctgct  10140
tgccggccag gaatttgcgc aggctgaaag gtatcgggcc gcgcacccga tcgagcccga  10200
cgagacgatc catcccgaag ccccacaatt cggacaccgg tcccttgccg gatagcgcct  10260
```

-continued

```
ccacggcctg ggctaccacg tcgggcccgg aaaaacgatc ggcggagtgc aagaaccaca  10320
acagatcacc cgatgcgtgc gcgatgccct ggttcatcgc gtcgtaccgc ccgccgtcgg  10380
gctcggactg ccaatacgcg aagcctggtt cacacccgga caggtatgcc accacgtcgt  10440
cgccgctgcc accgtcgatt acgatgtgct cgatgcgtcc ccggtagcgt tgcgcccgca  10500
cacttttcac cgtgcgctgc aacccgtcga ggtcgttgaa cgagatcgtt atcaccgaga  10560
cggtcggagc agacgtcacc gagttcccct aggttgctgg cggcgattgt ggatcaccgg  10620
gtcttgatac cgatgaaggt gcctcgaaga ttcgccgcat aggaacctcc gagcaacgac  10680
tcggcgatgc ttggttccaa gttgtcgtac tcctccatca ccaggtcgac gccgacgtct  10740
ttgatggcct gaagtaggtg ctcgcgttga atccagaatg accggcgatt gtcccaggac  10800
gcccattttg cggtgtcgcg ctggccaaac gagcggtcgt cggaaaactc ggtaaaccac  10860
ctaccgggaa gtccctcatg ttcggtgggc gccgagagca tgaacttcac cggcgccggc  10920
cgccgcagca accgatcggt caattgtcgt gccgtcgtgg gcaaccggag ccatttatcg  10980
ctccggttga tgatcgagaa gtgcgtctgg agaatcagca gcttgttcgt taccgacgag  11040
agggtttcca ggtattgctt cggattctcc aggtggtaga agaggccgca gcagaagacg  11100
gtatcgaaga gcccgtggtt ggcgatgttg agggcgttgt cgtggacgaa ccggagattc  11160
ggcaggttgg tcttcgattt gatgtagttg caggccgcca tgttcagctc gcgaacctcg  11220
atcccgagga cctgaaatcc catgcgcgcg aacccgaccg cgtacccgcc ttccaagcag  11280
ccgacatcgg ccaggcgtag gtggctcttg tccccgggaa agacggtttc cagaatcccg  11340
cgcgccgaga tgaaccagga cgattcgtct aacgtgcgcg aggactccgg tatcgtcaag  11400
gttccgtcgt cgaggcgaac gttgtgggcg gtgaattgta ccgcgccggc cgaatgttcc  11460
tgtgccatca cttggttagc cccttcggct ggtcctgggt ttgtcgacat ggtcaggctc  11520
gacagccgcg tcggagccgg gagggccaca catccacgag ccccctgcgg ctcggcgtcg  11580
cggcggcgag cttgcgccac tggtcttga gccgccgcgc gggtgtcgcc ccgcggtgct  11640
gcagcgccag catggcgatc cggggatggc gcgcgatggt ttcctgcagc gcggcgcgcc  11700
cctccgggcc tggaacgttg gcgatctggc gaaggatcca gtcggccatg acggcgatga  11760
gctcctcgcg cgcggggtct cccgggaaca ggtcgagcat cgcgtcaaac gtcgccgcat  11820
gccccggacc ctgcgtcaac cagaactttg gcgggtccac cacctggttg tgccacatgc  11880
cttgggcgtg gcggcgatac acggccatgg tgtcgggcaa catggcgatg tcgccatgca  11940
ccgcgtgccg gacgtgcaga taccagtcca ggggcatgac gtcggcagga atgtcgtcgt  12000
agcgctcgag gcgacggtac acggccgagt tggtctggat gaagttcatc aagatcaacg  12060
catccaggct caagttgccc cgcacccgaa ccgggggggaa cttcgagtcc ttggcatggc  12120
cgtcctccca tatcactcgg acgggatgga agcacaccgt cgtcttgggg tgccggtcga  12180
ggaatgcgac ctgtttgctt agcttcagcg gatcgatcca gtagtcgtcc gcctcgcaca  12240
acgcgacgta ctcgccgcga gcggccgaca gggcgccggt caggttccca ttgaggccga  12300
ggttttcggt cctgaagatc ggccggaaca cgtgcgggta ccgctcggcg tactcacgga  12360
tgatcgccgg ggtggcatcg gtcgacgcgt cgtcggcgac gatgatctcc accgggaagt  12420
cggtttgctg gtcgagaaag ctgtcgaagg cctgacgggc gtagcccgcc tggttgtgag  12480
tggtcgagac gatgctcacc ttggggcaaa gctggggact caccgtcggc ccttttcctg  12540
cgcggccgca agggtattgc gatggcgaac gtgaatcgcc tgtgcccgcc ggccgtcggc  12600
cgtcgtggcc tggtggtcgg cggacgtacg gcacacgctg gcgaagtata gcgagggtgc  12660
```

-continued actgacgttg ggctcgaacc gcgtggcgcg cggtgtgggc gcaccgtctc gagtcggtgc 12720
tggttggctc gc 12732

<210> SEQ ID NO 2
<211> LENGTH: 289
<212> TYPE: DNA
<213> ORGANISM: Mycobacterium tuberculosis

<400> SEQUENCE: 2
atactcaagc ttgccgcaat cgaaaccaac ctgtttgtgc cgcaagaaat tacgccgtgg 60
cccggcgccg atcaagaaac gccccggcgc gcggcggtgt cgtcgtatgg catgacgggc 120
accaatgtgc acgccattgt cgagcaggca ccggtgccag cccccgaatc cggtgcacca 180
ggcgacaccc cggccacacc cggtatcgac ggcgcgctgc tgttcgcgct gtcggccagc 240
tcgcaggacg cgctgcggca aaccgccgcg cggctggccg attgggtct 289

<210> SEQ ID NO 3
<211> LENGTH: 278
<212> TYPE: DNA
<213> ORGANISM: Mycobacterium tuberculosis

<400> SEQUENCE: 3
ttggcgggtt ggccacacac ccgccggtga cggcgacgat gctgggctgg ttgcggccct 60
gcgccaccgc ggcttgcatg ctggttggct gtcttgggac gatcccgaaa tagtccacgc 120
ggatctggtg attttgcggg ctacccgcga ttaccccgcg cggctcgacg agtttttggc 180
ctggactacc cgcgtggcca atctgctgaa ctcgcggccg gtggtggcct ggaatgtcca 240
cgccgttcac ctacgtgacc ttgatgggat ccgggggt 278

<210> SEQ ID NO 4
<211> LENGTH: 1280
<212> TYPE: DNA
<213> ORGANISM: Mycobacterium tuberculosis

<400> SEQUENCE: 4
ccgacccaga cactgaccgg gcgaccgctg atcggcaacg gcacccccgg ggcggtcggc 60
agcggggcca ccggggcccc cggtgggtgg ctgctcggcg acggcggggc cggcgggtcc 120
ggcgcggcgg gctcgggcgc gcccggcggg gcgggcgggg ctgccgggct gtggggtacc 180
ggcggggccg gcgggatcgg cggagccagc accgtactcg gcggcaccgg cgggggaggc 240
ggggtcggtg ggctgtgggg cgccggtggg gccggcgggg ccggtggaac cggccttgtt 300
ggtggcgacg gcggggccgg tggggccggc gggaccggcg gactgctggc cgggctgatc 360
ggtgccggcg gaggtcacgg cgggaccggc gggctcagca ctaatggcga cggcggggtt 420
ggcggggccg gcgggaatgc cggaatgctc gccgggccgg gcggcgccgg cggagccggc 480
ggtgacggcg aaaacctgga caccggtggg gacggcgggg ccggcggtag cgcagggctg 540
ctgttcggca gcggcggcgc cggcggcgcc ggcggatttg gtttcctcgg tggggacggc 600
ggggccggtg gcaacgccgg gctgctgttg tccagcggcg gggccggcgg gttcggcggg 660
ttcggcaccg ccggtggggt cggtggggcc ggcggcaatg ccggctggct gggcttcggc 720
ggggccgggg gcatcggcgg aatcggcggt aacgctaacg gggcgccggg tgggaacggc 780
ggcaccggcg gtcagttatg ggtagcggc ggcgccggcg tcgaaggcgg cgcagcctta 840
agcgtcggcg acaccggcgg ggccggtggc gtcggcggca gcgccgggct gatcggcacc 900

-continued ggcggcaacg gcggcaacgg cggcaccggc gccaacgccg gcagccccgg aaccggcggc 960
gccggcgggt tgctgctggg ccaaaacggg ctcaacgggt tgccgtagcc gggcggcacg 1020
gcatggcttc cgggcgtcaa ccactcgccg gtgatgcaga tcggctgcgg agcgggccgc 1080
caaaatgggg gccgccgcgc caggtatctc ggcgaagatc cccggcgctc gagcgctttg 1140
tcagaggccc gtcgcgggtc gtcgtgacga cggctatccg ggcggtgcgg gtttcgcggc 1200
gcgccctgtg cccggcaccg ccgcccgttt gtcggcaacg ccgccgcgac ccgtgagccg 1260
tccagcagct ggcgcctgcg 1280

<210> SEQ ID NO 5
<211> LENGTH: 127
<212> TYPE: DNA
<213> ORGANISM: Mycobacterium tuberculosis

<400> SEQUENCE: 5
gggcatcggc ggaatcggcg gtaacgctaa cgggggcgcc ggtgggaacg gcggcaccgg 60
cggtcagtta tggggtagcg gcggcgccgg cgtcgaaggc ggcgcagcct taagcgtcgg 120
cgacacc 127

<210> SEQ ID NO 6
<211> LENGTH: 434
<212> TYPE: DNA
<213> ORGANISM: Mycobacterium tuberculosis

<400> SEQUENCE: 6
aatactcaag cttgcccagc cgtcgatgac aagaaatatg tccgcaaaag actcagcggc 60
cgactttgct cgcagctggc ggtaccgcgc caccgattct atgccgtggt cgcggaaaaa 120
tgcctcccga aatcgcacgg ccgactccag ttcggcgagc atccgcgatg ccagctgcgg 180
ctgcgccctg ccggccacgg cacccacatg cggcagttcg tccacctggg ccagcgcccc 240
gccgccgaat tccaaacaat agaactgcac ccggcccgca tcgtgggtaa cagccaacgc 300
catgatcagc gtccgcagcg cggttgactt gcccgtttgc ggtgcaccta cgaacgcgac 360
attgcctgcg gccccggaca agtcgatcgt gcgcggcacc cgtgactgct ctaacgggcg 420
attgaaattc cgat 434

<210> SEQ ID NO 7
<211> LENGTH: 332
<212> TYPE: DNA
<213> ORGANISM: Mycobacterium tuberculosis

<400> SEQUENCE: 7
ccacccgtgt aatttgggat gggcaaaaag gcgaagcacc gcgtggccac gaacgccggg 60
agggacaatc tcgggcggtt agggcttctc gcgggaaggc ccgaacgtac ggcgtttcaa 120
cacctcgcgt cgccctccga ccgcgaacat tcggggatgg cagcaacctg ctggcaccct 180
ggccgggcga tgatctgcag cgtcgccgcg ggtagtcgcc gcccgggcgg ctacactctg 240
aaacgcgatg accatcgatg tgtggatgca gcatcccgac gcaacggttc ctacaccgcg 300
atatgttcgc ctcgctgccc cggtggaccg gt 332

<210> SEQ ID NO 8
<211> LENGTH: 354
<212> TYPE: DNA
<213> ORGANISM: Mycobacterium tuberculosis

<400> SEQUENCE: 8

-continued aatactcaag ctttccgccg atacccgcca tgtcgcgcac atccaggact tctgggggga 60
tccgctgaca gcggcgggat cccaaagtgc ggatgatcgg gccgcctacg tcgtggtgta 120
cctcgtcggt aacaacgaaa ccgaagcgta tgactcggtc cacgcggtgc ggcacatggt 180
ggacaccaca ccgccaccgc acggggtgaa ggcctatgtc accggtccgg cagcactcaa 240
tgccgaccag gccgagggcg gagacaaaag tatcgctaag gtcaccgcga tcaccaacat 300
ggtgatcgca gcaatgttgc tagtgatcta tcgctccgta attaccgcgg ttct 354

<210> SEQ ID NO 9
<211> LENGTH: 353
<212> TYPE: DNA
<213> ORGANISM: Mycobacterium tuberculosis

<400> SEQUENCE: 9
gtgccgttcc aacccgaatt ggctttcggc gccatcggtg aggacggcgt gcgggtgctc 60
aacgacgacg tcgtccgcgg gacacacctc gatgctgccg ccatggacgc ggtcgaacgc 120
aagcagctga tcgagctaca acgccgcgcg gaacgcttcc gccgcgggcg tgaccgcatc 180
ccgttgaccg ggcggatcgc ggtgatcgtc gatgacggca tcgccaccgg agcgacggcc 240
aaggcggcgt gccaggtcgc ccgggcgcac ggtgcggaca aggtggtgct ggcggtcccg 300
atcggcccag acgacatcgt ggcgagattc gccgggtacg ccgatgaggt ggt 353

<210> SEQ ID NO 10
<211> LENGTH: 279
<212> TYPE: DNA
<213> ORGANISM: Mycobacterium tuberculosis

<400> SEQUENCE: 10
aatactcaag ctttcggcgg aaacggacac attgcgaata ttgatgacaa aataaaaatc 60
attgatggtt tgagtcacca ggccgatcaa gccttcgccg agccaaattc caatcaagag 120
gcccaagccc gtaccaatca gcccggcaac gagggattcc gtcattatca gccaaaataa 180
ctgctctcgg gttacaccca aacagcgcaa tatggcgaaa aacggtcgcc gttgcacgac 240
attaaatgtc acggtattgt agattaaaaa gatacccac 279

<210> SEQ ID NO 11
<211> LENGTH: 376
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 11
tgctcccgaa acctgggggt gtgcctgctc tgtatgcacg gcatacggac atccttcccc 60
tgagacccgc ggtcgaacca gccacgtgtc catcatagng ggtcaacccc ggccaagggc 120
gacggcacgc caagttcgcc gaccgttaac ctagtgctgt tagcttcatt tgctgcgatc 180
aaaacagctg gtcggccgtt aggaactgaa ttgaaactca accgatttgg tgccgccgta 240
ggtgtcctgg ctgcgggtgc gctggtgttg tccgcgtgtg gtaacgacga caatgtgacc 300
gggggaggtg caaccactgg ccaggcgtcg gcaaaggtcg attgcggggg gaagaagaca 360
ctcaaagcca gtgggt 376

-continued

<210> SEQ ID NO 12
<211> LENGTH: 393
<212> TYPE: DNA
<213> ORGANISM: Mycobacterium tuberculosis

<400> SEQUENCE: 12
atactcaagc tttgccgacg agcgggcgat gttgatgacg ggaaacccca gcgcacaacc 60
gacgattttg gcgtagccgg cggacgtctg ctcgattccg atcacgtcgg cgctcgcatc 120
gagcatggcg ccggcgacgg ctagcagcga tccgccgtcg tcgaggagca cgacacgagc 180
cgtacgcccg gccgtaagcc gcgcccagga ttcggcgaaa aaccgttcta cgtggcgggt 240
gtactgggtg tcgaatgatt cgtggggtgc gtaggcgtcg ctgcaatcgt cgacatagat 300
gccgtcgggc cgcatcgcgt cgacaactcc gggtgagtgg aatagcactt gccgatcacc 360
gcgacgttgc gcggatgagg ccgaacccga ata 393

<210> SEQ ID NO 13
<211> LENGTH: 272
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 13
tcctatgtcc ctgccgagca ngtgatcgaa cgcggtgaca gatttgtcta tcctggacct 60
gacggtgagg tcgaagtttt ccaggaattc ggcaaaatcg gtaagagcct gaagaattcg 120
gtatcgccgg acgaaatctg cgacgcatac gggggcatat acgcttcggg tttacgagat 180
gtcgatgggg ccgctggagg cttcacgtcc atgggccaca aaggatgttg tcggcgcgta 240
ccgttttctg cagcgggtgt ggcgcttggt cg 272

<210> SEQ ID NO 14
<211> LENGTH: 286
<212> TYPE: DNA
<213> ORGANISM: Mycobacterium tuberculosis

<400> SEQUENCE: 14
atactcaagc ttgattccgc cgaaaccgac cgtgagcacc ccgccagcca ccacgctcgg 60
gtcgggcgcc gggcccgggc cgccaggctg ctccgctcgg tgatggcacg ccaccgcgac 120
accacccggc tgcgctacgt ctaaccattc caggcggagc tacatcagct cggccgccca 180
gtgttcgggc cctctttcca ggtcgaagtc tataccgata tgcgcatccg cagccgccac 240
cctggagaac agaacgatgc cctactaatg cttgtctggc ggggcc 286

<210> SEQ ID NO 15
<211> LENGTH: 357
<212> TYPE: DNA
<213> ORGANISM: Mycobacterium tuberculosis

<400> SEQUENCE: 15
ggtacgcttc ggtcgcagtc tgcgagtgat gcatgacgac cgggacctcg tcggcatctt 60
ccatagcccg ccacaccttc agttgctcac cggaatccaa ccggtagaag gtcggcgagc 120
gctcggcatt ggtcatcggg atatgccgct cgggacggtc agagccctcg ggtccggcca 180
gcactccgca ggcttcgtcg gggtggtcgc gacgcgcatg ggccaccatc gcattcacca 240
ggtctgcgcg aatcaccagc acgtagacgg ttcctttcct aagcaacacc gaagtttcag 300

-continued gacccgaatg ctccgggaaa catgtcacgg taggtcggta ttccggctac cggctga 357

<210> SEQ ID NO 16
<211> LENGTH: 83
<212> TYPE: DNA
<213> ORGANISM: Mycobacterium tuberculosis

<400> SEQUENCE: 16
ggcgtcaacg gtgtcggaac ccgcgtcaag caattggtag gcctgcagtc tgtgaatcag 60
gccgacgctg tggccgccgc ggc 83

<210> SEQ ID NO 17
<211> LENGTH: 383
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 17
ggctngcgta cccggtaccg gccgcgggcc taccacgtgc cggaactgga agcgcagtaa 60
gccctcaacg cgccaccgct ttggcccgcg cgcccggcgt aggcgcatcg gcggtggccg 120
tggggcggcg cactgcgacc tcaccagcgg ctttcgagct ttgttcgatc aaccggccag 180
catggtcgan gatgcattcg agaccatatt cgaaattggt ttcatcgggg gccccgatcc 240 gatgcccccct cccagttgcg tgagcaanca gcggagtcnt cgcgggatcg atggccacgg 300
ggtgttcaat ggcggatggt ccgctgcccg ccgactggct cttgcgggag aaccgatcta 360
gcaccaccga tccgcgcacg tng 383

<210> SEQ ID NO 18
<211> LENGTH: 603
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 18
cgtaatntcg cgcacancca ngacttctgg ggggatcngc tgacagtggt nggatcccaa 60
attgcggatg atcgggccgc cnacgtcgtt gtgtacctcn tcngtcacaa cnaanccgaa 120
ncgtatgact cggtccacgc ggtgcggcac atggtggaca ccacaccgcc accgcncggg 180
gtgaaggcct atgtcaccgg tccggcaaca ctcaatgccg accaggccga ngccggacac 240
nanagtatcn ctaacgtcac cgcgatcacg agcatggtga tcgnncaatg ttnctantga 300
tctatcgctc cgtaattacc gcggttctcg tcttgatcat ggtcgcancg aactccggcg 360
caatccgcgg attcatcgnc ttgctcgccg atcacatatt ttcagccttt cacattgcaa 420
cnaacctgct cgtctcatgg ngatgcggcg acacggacta ccgatatcat gctcgccgtt 480
acacaatcnc gccacgccgc gaagacngga aacgcttcta cacaatnttc ncgggacgcc 540
actnaacttg gttcnggttt gacattgccg cgcatgtntg cccagctttg ccggctcccc 600
tta 603

<210> SEQ ID NO 19
<211> LENGTH: 190

-continued

<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 19
tgaatttccc gatcccacaa tctcggttca gatacaggtc gccatacccc ttacttcggc 60
aacgctgggc ggattggccc tgcngctgca gcanaccatc gacgccatcg aattgccggc 120
aatctcgttc agccaatcca tacccatcga cattccgccg atcgacatcc cggccttcnc 180
cctttaacgg 190

<210> SEQ ID NO 20
<211> LENGTH: 506
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 20
aacagctatg accatgntta cgccaagcta tttaggtaac actatanaat actcaagctt 60
ttacggtgat cgcgcatcac ctggttcatg aactggaagc agcgcancgc ttccttttcg 120
gccgcaacat gagccagcct ctcgtccgcg gtcnggtgca ggtgctcggg cagctcggcc 180
gcgacagccg cctgaccctg aaaccagctt ccatatcccg cgacnaacna cnccagtccg 240
ctacgtaacc cctccgcgac tgtccatgga caacagcgcg ttctccaccg accgggcccg 300
ggtgtggggt gtttcggcga ccggcagcca ggtggtccac actgccgacg ggcgccgcga 360
gccgttcacc gaccaagccg ccgaacaagt ccgcccgatc gcatactcca accggttgcg 420
gtactgcagg tcagctggcg tacctcctcn tcncgctcgg cgaagtcttg ctccancacg 480
tcgcagaacg gcaaggaaca cgttca 506

<210> SEQ ID NO 21
<211> LENGTH: 388
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 21
gaccgnncca tgtttccaca atgtggtgcc agtncggngg ctacgtgcca tcnanacact 60
ggcgcaggct atcgcacccg ttatcngcta cgaacaaatc ncggtatgcg ttctttanca 120
tgagtcggcg accgncgatc atggtcgaca cccacgacng aaatacgcag atcgccntcn 180
agcntgtgtg ccgcggatta tcangactga cctcctggct gaccggnntg tntggtcgcg 240
atgcctggcg cccggccggc gtgntcgtgg tcggctcgga tagcgaagtc agctaattct 300
cgtggcagct cgaaagggtc ctgccggtgc cggtctttgc gcaaaccatg cncatgttac 360
ggtccctcgg gtgcggcctg gcggcggc 388

<210> SEQ ID NO 22
<211> LENGTH: 138

-continued

<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 22
gggatgggcg ggcccgctaa actcttcgtg ttccactaac tccgggaggg ncaatctcgg 60
gccgttatgg ctcacgtcgc gtcgccctcc gaccgcgaac attcggagtt ggcagcaacc 120
tggtagcacc ctggccgg 138

<210> SEQ ID NO 23
<211> LENGTH: 142
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 23
nccgtcgttg acaagtaaat atgtccgcaa aagtctcagc ggccgacttt gctcgcaggt 60
ggcggtaccg cgccaccgag tcgatgccgt ggtcgcggaa gaatgcctcc cgaaatcgca 120
cggccttccc nntttaaacg ga 142

<210> SEQ ID NO 24
<211> LENGTH: 441
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 24
tttaggtgac actatagaat actcaagctt ttggtctagc cggccgagca cgatacgggt 60
gtcattggcc accggcggcg gctgtccggg aaatggcggg tccccggtgg ttttgctgat 120
gagtgctgaa ccgtantcga agtgggcggc gtcagactcc acccanccag caggcagcgc 180
gaagctgaat cctccaaccg ggttgtcnat ccggacaagt tggggtgcgt ttggggcaat 240
gacaggtggc ngcggtgcgt tcgggtccgc cggcggaagt gctgcgttgg gatcncccgc 300
tgggcattcg gcntttttgc ggcggccggt ggtngggggg caacaggtnt cccngtgcgg 360
gtggcgctca acggtcnacg gcgcaagccg ccgttgttgg taccnggggc gctggctccg 420
gatcgcgttg gcggtcnccg g 441

<210> SEQ ID NO 25
<211> LENGTH: 453
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 25
ctacaccatc gaatacgacg gcgtcgccna ctttccgcgg tacccgctca actttgtgtc 60

-continued

```
gaccctcaac gccattgccg gcacctacta cgtgcactcc aactacttca tcctgacgcc    120

ggaacaaatt gacgcagcgg ttccgctgac caatacggtc ggtcccacga tgacccagta    180

ctacatcatt cgcacggana acctgccgct gctagagcca ctgcgatcgg tgccgatcgt    240

ggggaaccca ctggcgaacc tggttcaacc aaacttgaan gtgattgtta acctgggcta    300

cngcgacccg gcctatggtt attcnacctc nccgcccaat gttgcgactc cgttcgggtt    360

gttcccanaa gtcnnccccgg tcgtcatcgc cgaanctctc ntcccgggac ccacagggaa    420

tcngcnattt cncctacaaa tcanccacct cca                                 453


<210> SEQ ID NO 26
<211> LENGTH: 228
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as “n”

<400> SEQUENCE: 26

gcatgatcgg ccacctttcg ggccgcccgg catacggcgg cgtaccgatc tccgcgtcat     60

acacccgcgg gtaatcgccg acggtgccgg ttcgcgagcc gaaggtgacg actctgattg    120

aatcgagttc caggtccagc gggtggcgca ccaacggcgc gagctcaacg acgtcaatcn    180

cgttgtcgct ttctacggtc accgaccctg gtgaccgtag ttcncccg                 228


<210> SEQ ID NO 27
<211> LENGTH: 357
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as “n”

<400> SEQUENCE: 27

gacactatag aatactcaag cttgccaacc gccagcctgc atccggcggc gancactgct     60

ccgccgacca gtacgaacca acctgcggtg cccaggccat tgacgatgtg ctggtcggcg    120

cccgcgagtc cgcgcaccat caacgccgcg ggcaccacca nggcggcccc accctgcacg    180

gcgacgatca ttccggcgcc gctcacggcg ggcggggctc gaacangcac agcatcaacg    240

tngtcacccg gccgtgaccg gcccgcatcg tcacaccacc caagcccatt gccgtcctcc    300

tcaacngggc gacccggccc gcatcgtcac acggnctaag gccattgccg tcctcct       357


<210> SEQ ID NO 28
<211> LENGTH: 384
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as “n”

<400> SEQUENCE: 28

tcggcgccat cggcaccttc gaggacctgt atttcgacgc cgtggccnac ctgaggttgg     60

cggtggacna agtgtgcacc cggttgattc gctcggcctt gccggatgcc acccngcgcc    120

tggtggtcga tccgcnaana gacaanttgt ggtggangct tctgctgcct gcgacaccca    180
```

-continued cnacgtggtg gcaccgggca gctttagctg gcatgtcctg accgcgctgg ccgacnactc 240
cagacnttcc acnaanggtc gccnncccaa tgtnccgnan tgtctccggn tccctttacc 300
ncccaatggg cngnttccac nggttacggg ccccntnccg gcgggtctnc ctcccaanct 360
accaaatacg cccgacnttc cgga 384

<210> SEQ ID NO 29
<211> LENGTH: 266
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 29
atactcaagc ttttatggtg atcgcgcatc acctggttca tgaactggaa gcagcgcagc 60
gcttcctttt cggccgcaac atgagccagc ctctcgtcgg cggtcgggtg caggtgctcg 120
ggcagctcgg ccgcgaacag cccggcttga accctgaaaa ccngctttcc atatcccgcg 180
acgaaagaac gccagttccg ctacttaacc cctccgcgaa ccgtccatgg acaacagcgc 240
gttctccacc aaccgggccc gggtgt 266

<210> SEQ ID NO 30
<211> LENGTH: 423
<212> TYPE: DNA
<213> ORGANISM: Mycobacterium tuberculosis

<400> SEQUENCE: 30
tcggctcagg ccgcgctgct ggtagagtcg ctgaccggtg caggtttcga caatgtggtg 60
ccggttcggc ggctacgtgc catcgagaca ctggcgcagg ctatcgcacc cgttatcggc 120
tacgaagcaa atcgcggtat gcgttcttga gcatgagtcg gcgaccgtcg tcatggtcga 180
cacccacgac ggaaagacgc agatcgccgt caagcatgtg tgccgcggat tatcaggact 240
gacctcctgg ctgaccggca tgtttggtcg cgatgcctgg cgcccggccg gcgtggtcgt 300
ggtcggctcg gatagcgagg tcagcgaatt ctcgtggcag ctcgaaaggg tcctgccggt 360
gccggtcttt gcgcaaacaa tagcgcaggt tacggtcgcg cggggtgcgg cctggcggcg 420
gcc 423

<210> SEQ ID NO 31
<211> LENGTH: 455
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 31
caagctattt aggtgacact atagaatact caagcttcgc gtctacgccg gcccggagca 60
tccgcacagc gctcagcagc cggttccgta cganctcaag caggtggcgc aatgaccgaa 120
accaccccag ccccgcaaac cccggcggcc ccggccgggc ccgcacaatc gttcgtgttg 180
gagcggccca tccanaccgt tgggcgccgt aaggangccg tggtacgaat gcggctggtg 240
cccggcaccg gcaagttcga cctcaacggc cgcagcttgg angactactt cccaaacaag 300
gtgcaccagc agttgatcaa ggcaccccctg gtcaccgtgg atcgggtgga aagtttcgac 360

-continued atctttgccc acctgggcgg cggcggccgt ccggtcaggc cgggcctgcc ctgggtatcg 420
cccgggcatt gattctggta tccccngaag aaccg 455

<210> SEQ ID NO 32
<211> LENGTH: 371
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 32
cggttggcca ccgcttctgc ggtgccgccg ccgtcgacaa tgaccgtgtc gtccttgctg 60
accaccacgc gtcgggccga gcccagcacc tccaagccca cctcgcgcag caccatgccg 120
gcgtcggggt tgaccacctg gccacccgtc accaccgcca ggtcctcaag gaaacgcctt 180
acggcggtca ccgaagtacg gccccttgac cgcgaccgct ttcaacgtct tgcgaatcgc 240
gttgacgacc agcgtcgcca acgcttcgcc ctccacgtct tcagccacga tcagtagtgg 300
cttacccgtt cctgcaacct tttccagcaa tggcaacaga tcgggaagcg anctgatctt 360
gtcttggtgc n 371

<210> SEQ ID NO 33
<211> LENGTH: 320
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 33
ccaagctatt taggtgacac tatagaatac tcaagctttt ggctgggtcg ccttcgaatt 60
cngcgtgcac cgctatgggt tgcancagcg gctggcgccg cacaccccac tggcccgggt 120
gttttcgccc cgaacccgga tcatggtgag cgaaaaggan attcncctgt tcgatgctgg 180
gattcgccac gccaaggcat ctancgatta ctctccncgg ggtgggaaaa gtgcccaatc 240
cccctccctc caactttccn aacaatcatt ccggttccnc cntccggttg gnggtaaccn 300
nccaataaaa cccctgcccg 320

<210> SEQ ID NO 34
<211> LENGTH: 383
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 34
gcccgcncat ggccaatccc cgaagacatc attggccagt ggccgggcgc taacaggttc 60
cagcccccca ccantgccgc tcgaacatgc ggtgcaaccc attcgcaggc cggcagggaa 120
agcaccgcgg aagccgcaaa gggctgcagt tccgcgccca ataatgtcgt ccgcaaccag 180
atgcgctcna aaaccncncc ggcagtcagc gcacccgacg cgangtcgaa agacgtcntc 240
agcgcgccca catggggtgc caatcggcac ggcaggtatg ccgcgcgcaa cccgagcgcg 300

-continued tggtgcatgc ccacggtccg cangangcgc ancacccgcc aatgccgaan cccacgaaac 360
atcgggcgca tccaccttca acc 383

<210> SEQ ID NO 35
<211> LENGTH: 275
<212> TYPE: DNA
<213> ORGANISM: Mycobacterium tuberculosis

<400> SEQUENCE: 35
atactcaagc ttgcccagcc gtcgatgaca agaaatatgt ccgcaaaaga ctcagcggcc 60
gactttgctc gcagctggcg gtaccgcgcc accgagtcga tgccgtggtc gcggaagaat 120
gcctcccgaa ttcgcacggc caattccatt ccgggaagca tccgcaatgc cagctgcggt 180
tgccccctgc cggccacggc acccacttgc ggcattgcgt ccacctgggc cagcgccccg 240
ccgccaaatt ccaaacaata aaaattgcac ccggc 275

<210> SEQ ID NO 36
<211> LENGTH: 322
<212> TYPE: DNA
<213> ORGANISM: Mycobacterium tuberculosis

<400> SEQUENCE: 36
ccacccgtgt attttgggat gggcaaaaag gcgaagcacc gcgtggccac gaacgccggg 60
agggacaatc tcgggcggct agggcttctc gcgggaaggc ccgaacgtac ggcgtttcaa 120
cacgtcgcgt cgccctccga ccgcgaacat tcggggatgg cagcaacctg gtagcaccct 180
ggccgggcga tgatctgcag cgtcgccgcg ggtagtcgcc gcccgggcgg ctacagtctg 240
aaacgcgatg accatcgatg tgtggatgca gcatccgacg caacggttcc tacacggcga 300
tatgttcgcc tccctgcccc gt 322

<210> SEQ ID NO 37
<211> LENGTH: 167
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 37
ctgcccatgt ttggggacgc ccgaccagcc gatgctggag gcctacacgg cccttggtgc 60
gctggccacg gcgaccgagc ggctgcaact gggcgcgttg gtgaccggca atacctaccg 120
cagccngacc cctntcncaa naggatnttg ttcgccggac cccnctc 167

<210> SEQ ID NO 38
<211> LENGTH: 287
<212> TYPE: DNA
<213> ORGANISM: Mycobacterium tuberculosis

<400> SEQUENCE: 38
ccgactttcc gcggtacccg ctcaactttg tgtcgaccct caacgccatt gccggcacct 60
actacgtgca ctccaactac ttcatcctga cgccggaaca aattgacgca gcggttccgc 120
tgaccaatac ggtcggtccc acgatgaccc agtactacat cattcgcacg gagaacctgc 180
cgctgctaga gccactgcga tcggtgccga tcgtggggaa cccactggcg aacctggttc 240
aaccaaactt gaaggtgatt gttaacctgg gctacgcgac cgccttt 287

-continued

<210> SEQ ID NO 39
<211> LENGTH: 322
<212> TYPE: DNA
<213> ORGANISM: Mycobacterium tuberculosis

<400> SEQUENCE: 39
atactcaagc tttgtcacac caagtgtttc gaccaggcgc tccatccggc gagtggatac 60
tcccagcagg tagcaggtcg ccaccacgct ggtcagtgcg cgttcagctc gcttgcggcg 120
ctgcagcagc cattcgggga aatacctgcc ctggcgcagc tgggggatcc caacttcaat 180
ggttgcggca cgggtgtcaa attcacggtg gcggtagccg ttgccctaat tggaccgctc 240
atcgctgctt tcgcggtacc ccgccccgca cagggcttcg gcttcagccc ccatcagggc 300
ggcaataaac ttcaagagca cc 322

<210> SEQ ID NO 40
<211> LENGTH: 471
<212> TYPE: DNA
<213> ORGANISM: Mycobacterium tuberculosis

<400> SEQUENCE: 40
gaggcagctt cgccggcaat tctactagcg agaagtctgg cccgatacgg atctgaccga 60
agtcgctgcg gtgcagccca ccctcattgg cgatggcgcc gacgatggcg cctggaccga 120
tcttgtgccg cttgccgacg gcgacgcggt aggtggtcaa gtccggtcta cgcttgggcc 180
tttgcggacg gtcccgacgc tggtcgcggt tgcgccgcga aagcggcggg tcgggtgcca 240
tcaggaatgc ctcaccgccg cggcactgca cggccagtgc cgcggcgatg tcagccatcg 300
ggacatcatg ctcgcgttca tactcctcga ccagtcggcg gaacagctcg attcccggac 360
cgcccagcgc attggtgatg gaatcggcga acttggccac ccgctgggtg ttgacatcct 420
cgacggtggg caattgcgcc tcggtaagct ttgccgcgta gccttttcat c 471

<210> SEQ ID NO 41
<211> LENGTH: 247
<212> TYPE: DNA
<213> ORGANISM: Mycobacterium tuberculosis

<400> SEQUENCE: 41
atactcaagc ttcactgaca agggacgaat tcgtcggccg cctgttcgac tgggtggtgg 60
ccgagctggt cgccaccact caggccgcgg tcacggcggt accggcgcgg gagcaaactc 120
gcgcgggcat ggccaacttc ttgcggacca tcaccgcaga cgcccgcttc ggacccctgc 180
tgtccaccac acagttggcc aacgcattaa tcacccgcaa gcttgcggaa tccaccgccc 240
tgttcgc 247

<210> SEQ ID NO 42
<211> LENGTH: 325
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 42
tccatcaccc gatgtggcng gagcactgcc atgtcgatct caactaccac ctccggccgt 60
ggcggttgcg cgccccgggg ggtccgcgcg aactcgacga ggcggtcgga gaaatcgcca 120

-continued

```
ncaccccgct gaaccgcgac cacccgctgt gggagatgta cttcgttgag gggcttgcca    180

accaccggat cgcggtggtt gccaaaattc accatgcgtt ggctgacggt gttgcctcgg    240

caaacatgat ggcacggggg atggatctgc cgccgggacc ggaggtcggc cgctatgtgc    300

ctgaccccgc tcctaccaag cggca                                          325
```

<210> SEQ ID NO 43
<211> LENGTH: 221
<212> TYPE: DNA
<213> ORGANISM: Mycobacterium tuberculosis

<400> SEQUENCE: 43

```
agctttgcag ttgctgagta atgtcggcca acgtcaccac aaccgcgatg aattcaatca     60

tgccgcccag ggcggccaac ccaatggtgg ccgcgagcgg cagctcgatc gcagcgcgga    120

ggttgccggc cgccagttga ttcacgaaca gggtgaggtc ataggcgggc aggatagtga    180

cgaaggcaag acctccatct gccgtcggaa gaagtatcga g                        221
```

<210> SEQ ID NO 44
<211> LENGTH: 285
<212> TYPE: DNA
<213> ORGANISM: Mycobacterium tuberculosis

<400> SEQUENCE: 44

```
agcttcagaa caggcctgtt gtgggcgcac ccggctcgcc gagttctgca cgcaccgcct     60

caagtgcggc ccgcaccgcc ggcatctccc ggtcacgcag ggccgcggcc cgcgccgcag    120

cgacggcgtg ttcgcgcagt tcgccgtcaa tgatgctgac ctgatcggcc acccgggcgt    180

tctcggcgtc gtcgcgttca ctaatcgcgg tgctcagcag cgtctcgaca gccaccaccc    240

gagtggcgac cagctgctcc accacggacc gcagcgatgc ccgtc                    285
```

<210> SEQ ID NO 45
<211> LENGTH: 179
<212> TYPE: DNA
<213> ORGANISM: Mycobacterium tuberculosis

<400> SEQUENCE: 45

```
atactcaagc ttcagttcct ccacgacgcg ttcccaaatg aatttcccga tcccacaatc     60

tcggttcaga tacaggtcgc catacccctt acttcggcaa cgctgggcgg attggccctg    120

ccgctgcacc aaaccatcaa cgccttcaaa ttgccggcaa tctcgttcag ccaatccat     179
```

<210> SEQ ID NO 46
<211> LENGTH: 315
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 46

```
gctctacgcc gcctacgggt cgaacatgca tcccgagcag atgctcgagc gcgcacccca     60

ctcgccgatg gccggaaccg gctggttacc cgggtggcgg ctgacgttcg gcggcgagga    120

catcngctgg gaaggggcgc ttgccaccgt cgtcnaagac ccaaattcga aggtgttcgt    180

cgtgctctac gacatgaccc cggcggacga gaagaacctt gaccggtggg aaggctccga    240

gttcggtatc caccagaaga tccgatgccg cgtggagcgc atttcctcgg acaccacaac    300
```

-continued

```
gggatcccgt cctcg                                                   315


<210> SEQ ID NO 47
<211> LENGTH: 285
<212> TYPE: DNA
<213> ORGANISM: Mycobacterium tuberculosis

<400> SEQUENCE: 47

atactcaagc ttgccaaaga gacctcgtcc accaagcagg acgcgaccgt cgaggtggcg     60

atccggcttg gcgtcgaccc gcgtaaggca aaccagatgg ttcgcggcac ggtcaacctg    120

cccacaccgg cactggttaa gaactgcccg cgtcgcggtt ttcgcggttg gtgaaaaggc    180

caatgcctgc gtttgccgtg ggggcggatg ttgtcgggag tgacaatctg atcaaaagga    240

ttcagggcgg ttggctggaa ttcaatgccg caatcgcgac accgg                    285


<210> SEQ ID NO 48
<211> LENGTH: 369
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 48

ccacggcgtg gatcaaggta ccggccggga tgttgcgcaa tggcaggttg ttgcccggct     60

tgatgtcggc gttagcgccg gattccacca catccccttg cgaaagtccg ttgggtgcaa    120

tgatgtagcg cttctcccca tcgagatagt ggagcaacgc aatccgtgcg gtacggttcg    180

ggtcgtactc gatgtgcgcg accttggcgt tgacaccatc tttgtcattg cggcgaaagt    240

cgatcatccg gtaagcgcgc ttatgaccgc cgcctttgtg ccgggtggta atccggccat    300

gcgcgttgcg tccaccgcga cgtgcagcgg gcgcaccagc gacttctccg gggttgaccg    360

ggtnatctc                                                            369


<210> SEQ ID NO 49
<211> LENGTH: 461
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 49

gcagcatgac ggcggtagcg aacaccgccg gatgcagcgc aagtagcgtc gatgtgctca     60

cggaatcgcc ccggcaccgc gatctcgang atcaccagtg ccaccccctg cagcgcnaca    120

ccgacgattc cgtacaccgc cacgccgatc aggccctggg ccatctgatt ggagctggcg    180

tanatggcgg cgatggtgac gatggccagc gccacataca ttgtggcggc cagaaccacg    240

gcgttggggc ggcggtcgat gaacactagg cgacgcagat cgcccggggt caacaggttg    300

accatcagaa agcctgcgac tagcacggcg gcgccactag gaagtacaag aangtggcca    360

ccaccccatg caggatcggg gtaaggctga tggtcccgaa atcgactccg gcctaataca    420

tgactctctc ctttgcgtca tcgccttact tgtgcgcgga a                        461


<210> SEQ ID NO 50
```

```
<211> LENGTH: 127
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 50

gggacacacc tcgatgctgc cgcnatggac gcggtcgaac gcaagcagct gatcgagcta    60

caacgccgcg cggaacgctt ccgccgcggg cgtgacgcat cccgttgacc ggccggancn   120

ctctcta                                                             127

<210> SEQ ID NO 51
<211> LENGTH: 305
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 51

tgggcgcctc tttcggcctt cccnntttaa acgnagcang acattctggg tatcgagttg    60

tactggatgg tgttggcgat gtcggtgatc ctgctcctgg cggtgggatc cgactacaat   120

ctgctgctga tttcccggtt gaaagaggaa attggggccg gattgaacac cggaattatc   180

cgtgccatgg ctggtaccgg gggagtggtg acggctgccg gcatggtgtt cgccgttacc   240

atgtcgttgt ttgtgttcag cgatttgcga attattggtc agatcggtac caccatcgcc   300

ttccc                                                               305

<210> SEQ ID NO 52
<211> LENGTH: 449
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 52

ccgatcggcg ccgcanctgg ttggtgttnc ggatgaatcc gcagcgaaaa tgtagctgcg    60

gtggcgtgtc gtgactcgtn ggcgtcgacg ctcgtggcag ccaccgancg gttggtccag   120

gatctggatg ggcaaagttg tgcggcccgg ccggtgacgg ccgatgagct gaccgaggtc   180

gacagcgccg tgttggctga cttggaaccg acatggagtc gccccggttg gcgtcacctc   240

aagcatttca atggttatgc gaccagtttt tgggttacgc cgtcagacat cacgtcggag   300

acttggatga gctgtgtctg ccagatagcc ccgaatcggg acgaccgtgg tcacggtgcg   360

tctgaccact cgggtcgggt cgcccgcgct atcggcatgg gtgcgtnatc acagcgacac   420

gcgcctgccc aaggangtnc ggncggacc                                    449

<210> SEQ ID NO 53
<211> LENGTH: 160
<212> TYPE: DNA
<213> ORGANISM: Mycobacterium tuberculosis
<220> FEATURE:
<221> NAME/KEY: unsure
<222> LOCATION: (various positions within the sequence)
```

-continued

<223> OTHER INFORMATION: applicants are uncertain of bases designated as "n"

<400> SEQUENCE: 53
cgggttgcgg atccacgcgt gcgggttgtc agcagctacg gcactgaacc gcgcccacag 60
ctcgccgatc cgctttcggt ggttctcgat cgactcgccg taggcgatgc gcagcgcctg 120
ctcgaatatc gggtacacgt aggccggcct tcccncttta 160

<210> SEQ ID NO 54
<211> LENGTH: 308
<212> TYPE: DNA
<213> ORGANISM: Mycobacterium tuberculosis

<400> SEQUENCE: 54
cttgattttg atcatcatga cgatcatcac cctaattttg ctacccgcac tggttatcgt 60
gggtaccgtc gtgctttcca tgggcgcctc tttcgggctt tccgtattgg tctggcagga 120
cattctgggt atcgatttgt actggatggt gttggcgatg tcggtgatcc tgctcctggc 180
ggtgggatcc gactacaatc tgctgctgat ttcccggttg aaaaaggaaa ttggggccgg 240
attgaacacc ggaattatcc gtgccatggc tggtaccggg ggagtggtga cggctgccgg 300
catggtgt 308

<210> SEQ ID NO 55
<211> LENGTH: 460
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 55
ggggatccct agatcgacct gcaggcatgc aagcttggcg tgtcgttcca acccgaattg 60
gctttcggcg ccatcggtga ggcgggacac acctcgatgc tgccgccatg gacgcggtcg 120
aacgcaagca gctgatcgag ctacaacgcc gcgcggaacg cttccgccgc gggcgtgacc 180
gcatcccgtt gaccgggcgg atcgcggtga tcgtcgatga cggcatcgcc accggagcna 240
ctgtcaaggc ggcgtgccag gtcgcccggg cgcacggtgc ggacaaggtg gtgctggcgg 300
tcccgatcgg cccagacgac atcgtggcga gattcgncgg gtacgccgat gaggtggtgt 360
gtttggcgac gccggcgtng ttcttcgccg ncgggcangg ttaccgcaac ttcacccaga 420
cctccgacga cgaggtggtg gcgtctcctg gatcgtgctc 460

<210> SEQ ID NO 56
<211> LENGTH: 299
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 56
aaggctgcag gtcgaagcgg ntggttacga ctccctgtgt gtgatggacc agttctacta 60
tctgcgtcta cacggccctt ggtgcgctgg ccacggcgac cgagcggctg caactgggcg 120
cgttggtgac cggcaatacc taccgcagcc ccgaccctgc tggcaaagat natcaccacg 180
ctcgacgtgg ttagcgccgg tcgagcgatc ctcggcattg gagccggcgg gtttgaactg 240

-continued

```
gaacaccgcc agctcggctt cgagtccggc acttccagtg accggttcaa ccggctcga     299


<210> SEQ ID NO 57
<211> LENGTH: 373
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 57

ctttccgcgg tacccgctca actttgtgtc gaccctcaac gccattgccg gcacctacta      60

cgtgcactcc aactacttca tcctgacgcc ggaacaaatt gacgcngcgg ttccgctgac     120

caatacggtc ggtcccacga tgacccagta ctacatcatt cgcacggaga acctgccgct     180

gctacagcca ctgcgatcgg tgccgatcgt ggggaaccca ctggcgaacc tggttcaacc     240

aaacttgaag gtgattgtta acctgggcta cggcgacccg gcctatggtt attcgacctc     300

gccgnccaat gttgcgactc cgttcgggtt gttccagang tcagcccggt cgtcatcgcc     360

gacgctctcg tcn                                                        373


<210> SEQ ID NO 58
<211> LENGTH: 338
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 58

cggtcatagc cctcgggtcc ggccagcact ccgcaggctt cgtcggggtg gtcgcgacgc      60

gcatgggcca ccatcgcatt caccaggtct gcgcgaatca ccagcacgta gacggttcct     120

ttcctaagca acaccgaagt ttcacgaccc gaatgctccg ggaaacatgt cacggtaggt     180

cggtattccg gctaccggct gagcattgag cacgccggcc agcaccgcac gagccaggca     240

atcagccgcc gccgcaccga tcgcggtgac cagctgagtc tccggagaca atgcggccgg     300

cacgccggnc tccggcggca ccgctacngc gcccgtgg                             338


<210> SEQ ID NO 59
<211> LENGTH: 374
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 59

gtgatggcac gccaccgcga caccacccgg ctgcgctacn tcgagccata ccgggcggag      60

ctacatcggc tcggccgccc agtgttcggg ccctctttcg aggtcgaggt cgataccgat     120

ttgcgcatcc gcanccgcnc cctggacgac agaaccgtgc cctacgagtg cttgtcgggc     180

ggggccaaag aacagcttgg catcctggcg cgattggccg gcgcggcgct ggtcgccaag     240

gacgacgccg ttccggtgct gatcgacgac gcgctggggt tcaccgatcc ggagcgacta     300

tcaagatggg ggaggtctct gacaccatcg gccccnacgg acatgtgatc gtgccgacgt     360
```

-continued gcagtcccac cccg 374

<210> SEQ ID NO 60
<211> LENGTH: 448
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 60
gcgaaagtcc gttgggtgca atgatgtagc gcttctcccc atcgagatag tggagcaacg 60
caatccgtgc ggtacggttc gggtcgtact cgatgtgcgc gaccttggcg ttgacaccat 120
ctttgtcatt gcggcgaaag tcgatcatcc ggtnngcgcg cttatgaccg ccgcctttgt 180
gccgggtggt aatccggcca tgcgcgttgc gtccaccgcg accgtgcagc gggcgcacca 240
gcgacttctc cggggttgac cgggtgatct cggcgaaatc agatacgctg gcgccgcgac 300
gaccaggcgt cgtgggcttg tncttgcgaa ttgncatgtc taatcangtc tttctctcac 360
gctctcgtcg ccgggctagg ccgcattgcc ctgctcctcc tcatcgcttc gctctgcatc 420
gtccccgggc taagcccgtg ccccgaaa 448

<210> SEQ ID NO 61
<211> LENGTH: 356
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 61
gatggttcgc ggcacggtca acctgccaca cggcactggt aagactgccc gcgtcgcggt 60
attcgcggtt ggtgaaaagg ccgatgctgc cgttgccgcg ggggcggatg ttgtcgggag 120
tgacgatctg atcgagagga ttcagggcgg ctggctggaa ttcgatgccg cgatcgcgaa 180
caccggatca gaatggccaa agtcggtcgc atcgctcggg tgctgggtcc gcgcggcctg 240
atgcccaacc cgaaaaccgg caccgtcacc gccgactccc catggcgtcc cggatatcaa 300
gggccggcaa atcaacttcc cggttgatca gcaaggcaac ctgcctccnc ctccgg 356

<210> SEQ ID NO 62
<211> LENGTH: 336
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 62
atactcaagc ttcgtcataa gaccatggtg cgctttcttt cacccgtcca gagtcggggg 60
catccgcacc ggctcgcatc gcatcatcct cccacgacgg gccgctcatc agcttgggcc 120
atttcaatgt acttgatacc ccgcgctgcg ggtaggccac tgcgacaatt caaacacggt 180
gtcacacggt gaatagtgtc gagatgggct ctgatcaacc gtcgcaaacc cggtttcgca 240
tcaatagcgg aatcccaccg ggttgcatgg aggctgctga ccttggaaaa caaaattttt 300

-continued

```
tcattacaac aaaacaaccg ccncggaaac tttgca                               336


<210> SEQ ID NO 63
<211> LENGTH: 489
<212> TYPE: DNA
<213> ORGANISM: Mycobacterium tuberculosis

<400> SEQUENCE: 63

cgaattcggc gtgcaccgct atgggttgca gcagcggctg gcgccgcaca ccccactggc     60

ccgggtgttt tcgccccgaa cccggatcat ggtgagcgaa aaggagattc gcctgttcga    120

tgctgggatt cgccaccgcg aggccatcga ccgattactc gccaccgggg tgcgagaggt    180

gccgcagtcc cgctccgtcg acgtctccga cgatccatcc ggcttccgcc gtcgggtggc    240

ggtagccgtc gatgaaatcg ctgccggccg ctacctgcaa ggtgattctg tcccgttgtg    300

tcgaagtgcc tttcgcgatc gactttccgt tgacctaccg gctggggcgt cggcacaaca    360

ccccggtgag gtcgtttttg ttgcagttgg gcggaatccg tgctctgggt tacagccccg    420

aactcgtcac ggcggtgcgc gccgacggag ttgttatcac cgatccgttg gccgtaccgc    480

gccttgggc                                                            489


<210> SEQ ID NO 64
<211> LENGTH: 448
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 64

tcagactcca cccagccagc aggcagcgcg aagctgaatc ctccaaccgg gttgtcgatc     60

cggacaggtt ggggtgcgtt tggggcaatg acaggtggcg gcggtgcgtt cgggtcggcc    120

ggcggaggtg ctgcgttggg atcgcccggc tgggcattcn gcgtgttggc ggcggccggt    180

ggtggggggg caacaggtgt cgccggtgcg ggtggcgctg cagcggtcga cggcggcgaa    240

gcggccgttg tgggtaccgg gggcgctggc tccggatcgg cgttggcggt cgcgggcacc    300

gcaacggtca ccaagctggc gctggccatc gccgcgatag ccagtgccgc caatcgtccc    360

ttgcgacgtg tcaagtnggg gtccacctga tgcatggcca aagaacctac cgtgttaacg    420

gcncaacnca aggaccgcgc cggtcgcn                                       448


<210> SEQ ID NO 65
<211> LENGTH: 346
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 65

tttccgcggt acccgctcaa ctttgtgtcn accctcaacg ccattgccgg cacctactac     60

gtncactcca actacttcat cctgacgccg gaacaaattg acgcagcggg tccgctgaac    120

aattcggtcc gtcccacgaa agaaccagtt ttncntcttt cncacggaga acctgccgct    180

gctagagcca ctgcgatcgg tgccgatcgt ggggaaccca ctggcgaacc tgtgtttcaa    240
```

-continued ccaacactta gagtgtaatt gtaaacctgg gctaggggaa accggctcta gtttttccac 300
cntctccgcc ccntgtttcg aatactccgt tcgggttgtc cccaaa 346

<210> SEQ ID NO 66
<211> LENGTH: 277
<212> TYPE: DNA
<213> ORGANISM: Mycobacterium tuberculosis

<400> SEQUENCE: 66
gcttccggct cgtatgttgt gtggaattgt gaccggatac caatttcaca caggaaacag 60
ctatgaccat gattacgcca agctagttag gtgacactat acaatactca agcttgccgg 120
ctggtgggcc gaccacttcg atggcacgac ccgtgaactg ctgcccggcc aattcttctt 180
ggtcgcccgg accgatggac cgcggctggg attccagaag gtgcccgatc ccgcccctgg 240
gaaaaaccgc gtgcacctct acttcacgac caacgac 277

<210> SEQ ID NO 67
<211> LENGTH: 434
<212> TYPE: DNA
<213> ORGANISM: Mycobacterium tuberculosis

<400> SEQUENCE: 67
ccgatcgact gatgcgccga caaccacgcc ccaacaactg gaatgaaccg tcgtgaccat 60
catcagcacg cggttgtagg cgacttgcga catgttcaac ccgccgtact cggacggaat 120
cttcaaaccg aaacagccca gctcggccag gcctttcacg tactcgtcgg ggatctgggc 180
accacgctcg aggacgctgc cgtccacggt gtctaggaat tcccgcagtt tgaccagaaa 240
cgcctcggtt cgggcctcct cggcgtccga cggcttggga aatgggtgta tgagccctac 300
gggaaaccgg cccacaaaga gttctttggc gaaggacggt ttatcccaac cactttcgcg 360
agattcctcg gcaagggccc gcgcttgctc ctcggtgacc tgagtttgct gtgccatcgc 420
cgcctcctcc ctga 434

<210> SEQ ID NO 68
<211> LENGTH: 465
<212> TYPE: DNA
<213> ORGANISM: Mycobacterium tuberculosis

<400> SEQUENCE: 68
tgcatccggc tcgtatgttg tgtggaattg tgagcggata acaatttcac acaggaaaca 60
gctatgacca tgattacgcc aagctattta ggtgacacta tagaatactc aagcttttac 120
ggtgatcgcg catcacctgg ttcatgaact ggaagcagcg cagcgcttcc ttttcggccg 180
caacatgagc cagcctctcg tcggcggtcg ggtgcaggtg ctcgggcagc tcggccgcga 240
cagccgcctg accctgaaac cagcttccat atcccgcgac gaacgacgcc agtccgctac 300
gtaacccctc cgcgactgtc catggacaac agcgcgttct ccaccgaccg ggcccgggtg 360
tggggtgttt cggcgaccgg cagccaggtg gtccacactg ccgacgggcg ccgcgagccg 420
ttcaccgacc aggccgccga gcaagtccgc ccgatcgcat actcc 465

<210> SEQ ID NO 69
<211> LENGTH: 463
<212> TYPE: DNA
<213> ORGANISM: Mycobacterium tuberculosis

<400> SEQUENCE: 69
gggggcgctg ctggtatagt cgctgaccgg tgcaggtttc gacaatgtgg tgccggttcg 60

-continued

```
gcggctacgt gccatcgaga cactggcgca ggctatcgca cccgttatcg gctacgagca    120

aatcgcggta tgcgttcttg agcatgagtc ggcgaccgtc gtcatggtcg acacccacga    180

cggaaagacg cagatcgccg tcaagcatgt gtgccgcgga ttatcaggac tgacctcctg    240

gctgaccggc atgtttggtc gcgatgcctg gcgcccggcc ggcgtggtcg tggtcggctc    300

ggatagcgag gtcagcgaat tctcgtggca gctcgaaagg gtcctgccgg tgccggtctt    360

tgcgcaaacg atggcgcagg ttacggtcgc gcggggtgcg gcctggcggc ggccagagca    420

cgagttcacc gatgcgcagc tagtggcgac agcgtcagcc aac                      463


<210> SEQ ID NO 70
<211> LENGTH: 447
<212> TYPE: DNA
<213> ORGANISM: Mycobacterium tuberculosis

<400> SEQUENCE: 70

tgcttccggc tcgtatgttg tgtggaattg tgagcggata acaatttcac acaggaaaca     60

gctatgacca tgattacgcc aagctattta ggtgacacta tagaatactc aagcttccgt    120

acaggtcgcc tccaacacgg cggggaagcg acaccagcct accgagcttg gagtccagga    180

cgccagcggc ggcgtcggtc tgcgtcgtgg tgccgccggg gtggcgttgg ctggcaacga    240

tctccaccca gccggtcggg ttacccacga tctcggcata gacgcgggcc gaggccggtg    300

cgataccgta ttgcgtcaat tgggacgcgg ttgtgcattc ggctagctcg gttgccacac    360

ccgtcagggg ttcgacgttg gcgggttcgg cgggccccag caccgctgtc accatgcccg    420

ccaagccgac ctgcggcgcc accaact                                        447


<210> SEQ ID NO 71
<211> LENGTH: 460
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 71

cggcatgacc accgacaggc ccgactggtc gtaccactcg aacgccgggg tgttgatgtc     60

ccagccgctg aagtcgtcct gcgcgcgcag gccgtcgagc aggtacaggg cgggcgagtt    120

ggcaccacca ctttggaatt ggaccttgat gtcacggccc atcgacggcg acggcacctg    180

caggtactcc accggcaagc ccggccggga aaatgccccc gcggtcgccg tgccaccgac    240

ggcgccgacc agacccgaca ctagggccgc gccgacggcc ccgaccacga gtcgacgcga    300

catacccgtg acggcgccac gaaccctgtc aacaagctgc attcttgctt ccctcatcct    360

catctcaacg catccatgca tgtttgggcg catcctgaat tangtcagac tgcaggcgct    420

gggccggcag tgctcgtgta tcaaccacaa cttcgggcgt                          460


<210> SEQ ID NO 72
<211> LENGTH: 404
<212> TYPE: DNA
<213> ORGANISM: Mycobacterium tuberculosis

<400> SEQUENCE: 72

ttccaaccct aattggcttt cggccccatc cgtgaggacg gggtgcgggt gctcaacaac     60

aacgtcgtcc gcgggacaca cctctatgct gccgccatgg acgcggtcca acgcaagcag    120
```

-continued ctgatcgagc tacaaccccg cgcggaacgc ttccgccgcg ggcgtgaccg catcccgttg 180
accgggcgga tcgcggtgat cgtcgatgac ggcatcgcca ccggagcgac ggccaaggcg 240
gcgtgccacg tcgcccgggc gcacggtgcg gacaaggtgg tgctggcggt cccgatcggc 300
ccaaacgaca tcgtggcgag attcgccggg tacgccgatg aggtggtgtg tctggcgacg 360
ccggcgttgt tcttcgccct cgggcagggt taccgcaact tcac 404

<210> SEQ ID NO 73
<211> LENGTH: 465
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 73
caggcatgca agctttccgc cgatacccgc catgtcgcgc acatccagga cttctggggg 60
gatccgctga cagcggcggg atcccaaagt gcggatgatc gggccgccta cgtcgtggtg 120
tacctcgtcg gtaacaacga aaccgaagcg tatgactcgg tccacgcggt gcggcacatg 180
gtggacacca caccgccacc gcacggggtg aaggcctatg tcaccggtcc ggcagcactc 240
aatgccgacc aggccgaggc cggagacaaa agtatcgcta aggtcaccgc cgatcacnag 300
catggtgatc gcagcaatgt tgctagtgat ctatcgctcc gtaattaccg cggttctcgt 360
cttgatcatg gtcggcatcg actcggccaa tccgcggatt catcgccttg ctcgccgaac 420
acaacatttt cacctttcac atttgcacca acctgctctt ctcat 465

<210> SEQ ID NO 74
<211> LENGTH: 387
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 74
cactactcaa gctctctcnt cattaccacc cctgtaattt gggatgggca aaaaggcgaa 60
gcaccgcttg gccacnaacg ccgggaggga caatctcggg cggctatggc ttctcccggg 120
aaggccccaa cgtacggcgt ttcaacacgt cgcgtcgccc tccgaccgcg aacattcggg 180
gattggcacc aacctgntac caccctggcc gggcgatgat ctgcagcgtc gccgcgggta 240
gtccccgccc gggcggctac agtctgaaac cccgatgacc atcgatgtgt ggatgcagca 300
tccgacgcaa cggttcctac acggcggata tgttctcctc gctgcgccgg tggaccggtg 360
ggtctatccc ctgaaaccga catcccn 387

<210> SEQ ID NO 75
<211> LENGTH: 445
<212> TYPE: DNA
<213> ORGANISM: Mycobacterium tuberculosis

<400> SEQUENCE: 75
caggcatgca agctttcgtc agttcattgc gccagcagac caacaagagc atcgggacat 60
acggagtcaa ctacccggcc aacggtgatt tcttggccgc cgctgacggc gcgaacgacg 120
ccagcgacca cattcagcag atggccagcg cgtgccgggc cacgaggttg gtgctcggcg 180

-continued

```
gctactccca gggtgcggcc gtgatcgaca tcgtcaccgc cgcaccactg cccggcctcg    240

ggttcacgca gccgttgccg cccgcagcgg acgatcacat cgccgcgatc gccctgttcg    300

ggaatccctc gggccgcgct ggcgggctga tgagcgccct gacccctcaa ttcgggtcca    360

agaacatcaa cctctgcaac aacggcgacc catttgttcg gacggcaacc ggtggcaacg    420

cacctaagct acttgcccgg gatga                                          445
```

<210> SEQ ID NO 76
<211> LENGTH: 345
<212> TYPE: DNA
<213> ORGANISM: Mycobacterium tuberculosis

<400> SEQUENCE: 76

```
gtttatgcac tggttaggtg tttccatgag tttcattctg aacatccttt aatcattgct     60

ttgcgttttt ttattaaatc ttgcaattta ctgcaaagca acaacaaaat cgcaaagtca    120

tcaaaaaacc gcaaagttgt ttaaaataag agcaacacgt acacaaggag ataagaagag    180

cacatacctc agtcacttat tatcactagc gcccgccgca gccgtgtaac cgagcatagc    240

gagcgaactg gcgaggaagc aaagaagaac tgttctgtca gatagctctt acgctcagcg    300

caagaagaaa tatccaccgt ggggaaaaac tccaggtaga ggtac                    345
```

<210> SEQ ID NO 77
<211> LENGTH: 139
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 77

```
atactcaagc ttgggtgtag ccgatcaccg gaagtcncat gatcagccac gttccgcgcc     60

gcccggcata cggtggtgta ccgatctccg cgtcatacac ccgcgggtaa tcgccgacgg    120

tgccggttcg cgagccgaa                                                 139
```

<210> SEQ ID NO 78
<211> LENGTH: 298
<212> TYPE: DNA
<213> ORGANISM: Mycobacterium tuberculosis

<400> SEQUENCE: 78

```
agctttatcg aaagcgcgaa cagctcgcgg cggcccacga cgtgctgcgt cggattgccg     60

gcggcgagat caattccagg cagctcccgg acaatgcggc tctgctggcc cgcaacgaag    120

gactcgaggt caccccggtg cccggggtcg tggtgcacct gccgatcgca caggttggcc    180

cacaaccggc cgcttgatgc ccggtcggca agcccggcag ttgccaaacc catcgtgatc    240

aggctcggct cgcgagttcg gcgaagaaat ggttcgcctg atcacctacc atcggcca      298
```

<210> SEQ ID NO 79
<211> LENGTH: 300
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as "n"

-continued

<400> SEQUENCE: 79
tcaacacgcc gccagccacc acgcgcgggt cgggcgccgg gcccgggcct ccaggctnct 60
ccgctcggtg atggcacgcc accgcgacac cacccggctg cgctacgtcg agccataccg 120
ggcggagcta catcggcccg gccgcccagt gttcgggccc tctcgcccag gtcgaggtcg 180
acaccgattt gcgcatccgc agccgcaccc tgcgacgaca gaaccgcggc cctacccact 240
gcttgtcggg cgggggccaa agaaccagct tgncatcctg ccacaattgg ccggcgcccg 300

<210> SEQ ID NO 80
<211> LENGTH: 321
<212> TYPE: DNA
<213> ORGANISM: Mycobacterium tuberculosis

<400> SEQUENCE: 80
caggcatgca agcttcacgt ccgtacggct cgggtacgct tcggtcgcag tgtgcgagtg 60
atagatgacg accgggacct cgtcggcatc ttccatagcc cgccacacct tcagttgctc 120
accggaatcc aaccggtaga aggtcggcca gcgctcggca ttggtcatcg ggatatgccg 180
ctcgggacgg tcagagccct cgggtccggc cagcactccg caggcttcgt cggggtggtc 240
gcgacgcgca tgggccacca tcgcattcac caggtctgcg cgaatcacca gcacgtagac 300
ggttcctttc ctaagcaaca c 321

<210> SEQ ID NO 81
<211> LENGTH: 340
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 81
aatattcaag ctttcggcgg aaacggacnc cttgcgaaca ttgataacaa aatagaaatc 60
attgatggtt tgagtcacca ggccgatcaa gccttcgccg agccaaattc caatcaagag 120
gcccaagccc gtaccaatca gcccggcaac gagggattcc gtcnttatca gccnaaataa 180
ctgctctcgg gtaccaccca aacagcgcaa tatggcgaaa aacggtcgcc gttgcacaac 240
attaaatgtc tcggtattgt tgattaaaaa gatacccacc accagggcaa tccaactgag 300
agcggttaaa ttgaccgtaa aaacctcccg tcatctgttt 340

<210> SEQ ID NO 82
<211> LENGTH: 394
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 82
caggcatgca agcttgctgc atcttcctgt gactgctccc gaaacctggg ggtgtgcctg 60
ctgtgtatgc acggcatacg gacatccttc ccctgatacc cgcggtcgaa ccagccacgt 120
gtccatcatc aggggtcaac cccggccaag ggcgacggca cgccaagttc gccgaccgtt 180
aacctagtgc tgttagcttc atttgctgcg agcaaaacag ctggtcggcc gttaggaact 240
gaattgaaac tcaaccgatt tggtgccgcc gtaagtgtcc tgtctgcggg tgcgctggtg 300

-continued ttgtccgcgt gtggtaacga cgacaatgtg accgggggag gtgcaaccac tggccaggcg 360
tccgcgaaag tccattgcng ggggaagaag acac 394

<210> SEQ ID NO 83
<211> LENGTH: 487
<212> TYPE: DNA
<213> ORGANISM: Mycobacterium tuberculosis

<400> SEQUENCE: 83
gaaagtgccc caaggtgttg gtgaaactcg ctggacggtc cccaggatgt tggcagcaca 60
ttcaccggac atgaccggag caagaccgga catcctccca taccgtcgtc gccgtgtaca 120
tccgtagccc gtcctggcag gtgctgggtt gaacaaaatc agcccaacac ctgccacgac 180
gaagaagcgg gttgcgctgg catgtcttgt cggctcggcg atcgaattct acgaattcct 240
tatctacggg accgctgcgg cgctggtgtt tcccaccgtg ttcttcccac acctggatcc 300
cacggtggcc gccgtggcct ccaaggggac atttgctgtg gcgttcctat cccggccgtt 360
cggcgcggcc gtctttggat actttggaga ccgcctcggc cgccagaaga ccctggtcgc 420
cacactgttg atcatgggcc tggcaaccgt gactgttggg ctggttccac gacagtggcc 480
atcgcgc 487

<210> SEQ ID NO 84
<211> LENGTH: 418
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as “n”

<400> SEQUENCE: 84
atattcaagc tttgtcacac caagtgttcc gaccaancgc tccatccggc gagtggatac 60
tcccagcagg tagcaggtcg ccaccacgct ggtcagtgcg cgttcatctc gcttgcggcg 120
ctgcagcagc cagtccggga aatagctgcc ctggcgcagc ttggggatcg cgacgtcgat 180
ggttgcggca cgggtgtcga aatcacggtg gcggtagccg ttgcgctgat tggaccgctc 240
atcgctgcgt tcgcggtagc ccnccccgca cagggcgtcg gcttcagccc ccatccaagg 300
cggcgatgaa cgtcgagagc agcccgcgca gcaaatccgg gctcgcctgt gcgagttggt 360
cagccagaag ctgctcggtg tcataagatg agaagaggtc agtgcgtcct ttccttcg 418

<210> SEQ ID NO 85
<211> LENGTH: 399
<212> TYPE: DNA
<213> ORGANISM: Mycobacterium tuberculosis

<400> SEQUENCE: 85
caggcatgca agctttttga gcgtctcgcg gggcagcttc gccggcaatt ctactagcga 60
gaagtctggc ccgatacgga tctgaccgaa gtcgctgcgg tgcagcccac cctcattggc 120
gatggcgccg acgatggcgc ctggaccgat cttgtgccgc ttgccgacgg cgacgcggta 180
ggtggtcaag tccggtctac gcttgggcct ttgcggacgg tcccgacgct ggtcgcggtt 240
gcgccgccaa agcggcgggt cgggtgccat catgaatgcc tcaccgccgc cgcactgcac 300
ggccagtgcc ccggcgatgt cagccatcgg gacatcatgc tcgcgttcat actcctcgac 360
cagtccgcgg aacagctcca ttcccggacc gcccaacgc 399

-continued

<210> SEQ ID NO 86
<211> LENGTH: 474
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 86
atactcaagc ttttggctgg gtcgccttcc aattcagcgt gcaccgctat gggttgcagc 60
agcggctggc nccgcacacc ccactggccc gggtgttttc gccccgaacc cggatcatgg 120
tgagcgaaaa ggagattcnc ctgttcgatg ctgggattcg ccaccgcgag gccatcgacc 180
gattactcgc caccggggtg cgagaggtgc cgcagtcccg ctccgtcgac gtctccgacg 240
atccatccgg cttccgccgt cgggtggcgg tagccgtcga tgaaatcgct gccggccgct 300
accacaaggt gattctgtcc cgttgtgtcc aagtgccttt cgcgatcgac tttccgttga 360
cctaccggct ggggcgtcgg cacaacaccc cggtgaggtc gtttttgttg cagttgggcg 420
gaatccgtgc tctgggttac agccccgaac tcgtcacggc ggtgcgccgc cgac 474

<210> SEQ ID NO 87
<211> LENGTH: 383
<212> TYPE: DNA
<213> ORGANISM: Mycobacterium tuberculosis

<400> SEQUENCE: 87
caggcatgca agcttcaacc tattgacgca ttgtgcgaac tgacggcgcc cgcgcatggc 60
caatccggaa gaccatcatt ggccagtggc cgggcgctaa caggttccag ccccccacca 120
gtgccgctcg aacatgcggt gcaacccatt cgcaggccgg cagggaaagc accgcggaag 180
ccgcaaaggg ctgcagttcc gcgcccaata gtgtcgtccg caaccagatg cgctcgaaaa 240
ccgccgccgg cagtcagcgc acccgacgcg aggtcgagag acgtcgtcag cgcgcccaca 300
tggggtgcca atcggcacgg caggtaggcc gcgcgcaacc ccaacgcgtg gtgcatgcca 360
cggtccgcag gaggccacca ccc 383

<210> SEQ ID NO 88
<211> LENGTH: 455
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 88
atactcaagc ttcccggccg caggtgacgg cgcggcctag cgccacttga tgccgcaccc 60
gatcgacggn cgttggtcgg ggttgactgg ccgcccggcg agcagggcgt caaccgcggc 120
ccggacgtcg gcggccgtca ccggtcggcc attgcccggg cgggagtcgt cgagctgacc 180
acggtagaca agtcggcgct ggccgtcgaa gacaaacgtg tcgggtgtgc aggccgcgga 240
gaaggcgcng gcgacgtctc gggtttcgtc gtagagatac gggaacgtcc agccgtggcg 300
gcgggcctcg gcgaccatct gatcgggccc gtcctgcggg taggtgacca cgtccttact 360
ggagataccg accatcggga ccctttgatc ggcgaggtcc cggccgaccg tggccaatcc 420

-continued

```
ggcggcgacg tgtcgcccgt accggccagt ggttc                          455


<210> SEQ ID NO 89
<211> LENGTH: 429
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 89

caggcatgca agctttanca ncatcaaccc cgccccgcac cagcaccgac acgatgtcga     60

tgccatcgag gtgaatgtcg aactggcnca aaccatctgg cgaccgcgac caccggcaac    120

atgggtaccg gcgatttccg gtgccaatgc cgacccgacg ggccgctctc accgcaggtg    180

acctcgatca ccgagaccag ccggccgtta tactcacgca cccctaccgt gtcacgccca    240

aaacggcgct ggtggtcgat tgccggagtg caccccgcac ccagtgtcgt gcccggatcc    300

gccgaccaat cccgcaccca cgtcgccaaa cccgaaatca ccgtgatgcc gtggtaactg    360

accaccgaca gtaacgtcac tacggccgcc acgccgacgc cgaaccacca cgcacatgat    420

gatcggctg                                                        429


<210> SEQ ID NO 90
<211> LENGTH: 321
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 90

atattcaacc ttgcacacat tgacgatacc ttggtcacga gaccccaaaa gctggcctcc     60

accgcgcgcc ggggaccacg gtcatacctt gannengctt tcgatcgttg atgctgcgtc    120

ttggtccgcg gaaaccgcag gctggcatat gcacgtgggc gcactggcga tctgcgatcc    180

ccaccgattc gcccgaatac agctttcagc ggctccccaa gttgatcatc gaccggctgc    240

cggatatccc gcacttgcgg tggcgggtca ccggcgcccc gctcggactg gaccggccgt    300

ggttcgtcga ggaccacgaa c                                          321


<210> SEQ ID NO 91
<211> LENGTH: 134
<212> TYPE: DNA
<213> ORGANISM: Mycobacterium tuberculosis

<400> SEQUENCE: 91

caggcatgca agcttcatgc ccgcggcatg atagccacat gcacgcaatc gaactcagcg     60

aaaccggcgg gccaggcgtc ttacgccacc tcaccagcgc gcaacctcaa cccggccacg    120

gagacctcct gatc                                                   134


<210> SEQ ID NO 92
<211> LENGTH: 513
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
```

-continued as "n"

<400> SEQUENCE: 92
atactcaagc ttgattttga tcatcatgat gatcatcacc cgaattgtgg tagccgcagt 60
ggttatcgtg ggtaccgtcg tgctttccat gggcgcctct ttcgggcttt ccgtattggt 120
ctggcaggac attctgggta tcgagttgta ctggatggtg ttggcgatgt cggtgatcct 180
gctcntggcg gtgggatccg actacaatct gctgctgatt tcccggttga aagaggaaat 240
tggggccgga ttgaacaccg gaattatccg tgccatggct ggtaccgggg gagtggtgac 300
ggctgccggc atggtgttcg ccgttaccat gtcgttgttt gtgttcagcg atttgcgaat 360
tattggtcag atcggtacca ccatcggcct gggcttgctg ttcgacaccc tcgtcgtgcc 420
tcgttcatga aaccgtccat tgctgccctg ctgggacctg gttctggtgg ccgctacggg 480
tgcgcccgcg cccggcagtc aaatcttccg ccg 513

<210> SEQ ID NO 93
<211> LENGTH: 345
<212> TYPE: DNA
<213> ORGANISM: Mycobacterium tuberculosis

<400> SEQUENCE: 93
caggcatgca agcttggcgt gccgttccaa cccgaattgg ctttcggcgc catcggtgag 60
gacggcgtgc gggtgctcaa cgacgacgtc gtccgcggga cacacctcga tgctgccgcc 120
atggacgcgg tcgaacgcaa gcagctgatc gagctacaac gccgcgcgga acgcttccgc 180
cgcgggcgtg accgcatccc gttgaccggg cggatcgcgg tgatcgtcga tgacggcatc 240
gccaccggag cgacggccaa ggcggcgtgc caggtcgccc gggcgcacgg tgcggacaac 300
gtggtgctgg cggtccccat cggcccagac gacatcgtgg cgaga 345

<210> SEQ ID NO 94
<211> LENGTH: 302
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 94
atactcaagc ttttacggtg atcgcgcatc acctggttca tgaactggaa gcagcgcagc 60
gcttcctttt cggccgcaac atgagccagc ctctcgtcgg cggtcgggtg caggtgctcg 120
ggcagctcgg ccgcgacagc cgcctgaccc tgaaaccagc ttccatatcc cgcgacgaac 180
gacgccagtc cgctacgtaa cccctccgcg actgtccatg gacaacagcg cgttctccac 240
cgaccgggcc cgggtgtggg gtgtttcggc gaccggcagc cangtggtcc acactgccga 300
ag 302

<210> SEQ ID NO 95
<211> LENGTH: 286
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 95

-continued tagtcgctga ccggtgcagg tttcgacnat gtggtgccgg ttcggcggct acgtgccatc 60
gagacactgg cgcaggctat cgcacccgtt atcggctacg agcaaatcgc ggtatgcgtt 120
cttgagcatg agtcggcgac cgtcgtcatg gtcgacaccc acgacggaaa gacgcagatc 180
gccgtctanc ntgtgtgccg cggattatca ggactgacct cctggctgac cggcatgttt 240
ggtcgcgatg cctggcgccc ggccggcgtg gtcgtggtcg gctcgg 286

<210> SEQ ID NO 96
<211> LENGTH: 482
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 96
atactcaagc tttccgccga tacccgccat gtcgcgcaca tccagaactt ctggggggat 60
ccgctgacag cggcgggatc ccaaagtgcg gatgatcggg ccgcctacgt cgtggtgtac 120
ctcgtcggta acaacgaaac cgaagcgtat gactcggtcc acgcggtgcg gcacatggtg 180
gacaccacac cgccaccgca cggggtgaag gcctatgtca ccggtccggc agcactcaat 240
gccgaccagg ccgaggccgg agacaaaagt atcgctaagg tcaccgcgat cacgagcatg 300
gtgatcgcag caatgttgct agtgatctat cgccccgtaa ttaccgcggt tctcgtcttg 360
atcatggtcg gcatcgacct cggcgcaatc cgcggattcn tcgccttgct cgccgaccac 420
aacattttca gcctttcaac atttgcgaca acctgctcgt tctcatggcg attgcngcga 480
ac 482

<210> SEQ ID NO 97
<211> LENGTH: 395
<212> TYPE: DNA
<213> ORGANISM: Mycobacterium tuberculosis

<400> SEQUENCE: 97
caggcatgca agcttggcgt gccgttccaa cccgaattgg ctttcggcgc catcggtgag 60
gacggcgtgc gggtgctcaa cgacgacgtc gtccgctgga cacacctcga tgctgccgcc 120
atggacgcgg tcgaacgcaa gcagctgatc gagctacaac gccgcgcgga acgcttccgc 180
cgcgggcgtg accgcatccc gttgaccggg cggatcgcgg tgatcgtcga tgacggcatc 240
gccaccggag cgacggccaa ggcggcgtgc caggtcgccc gggcgcacgg tgcggacaag 300
gtggtgctgg cggtcccgat cggcccagac gacatcgtgg cgagattcgc cgggtacgcc 360
gatgaagtgg tgttgtttgg cgacccggcg ttgtt 395

<210> SEQ ID NO 98
<211> LENGTH: 439
<212> TYPE: DNA
<213> ORGANISM: Mycobacterium tuberculosis

<400> SEQUENCE: 98
atactcaagc tttggcattg tgcacatttt ccacccgtgc tctattaatg ctgagccgct 60
aattgtgacc ccagtcggga aacacgcgga gcaccaaatt caccgcagcg gccggggcgg 120
ttcaactcac catggatcgc tctcgtcgtc tggtgctgga caatcgtcgc tgtagcgcgt 180
cgcgaacacc tcagcttctg ctgccgcggc ttcttccggc gatggtaacc cccaggtttc 240

-continued

```
gcccacggtc ttacgtagca gtgcgacgcg gtgttcatct gcatcgacct gttgactcat    300

cctgtcaagg atgaaggcgt actgggccga ctgcgccttc tgccgcgcca ggtcggcaat    360

caccaggatc tcagaaacga gctgcgactc actcttccag gccaccctgg ccgaaagctc    420

gacatggtca atccggccg                                                 439


<210> SEQ ID NO 99
<211> LENGTH: 348
<212> TYPE: DNA
<213> ORGANISM: Mycobacterium tuberculosis

<400> SEQUENCE: 99

caggcatgca agcttgcggg ccggagtggt ttcgacggcc gctcgcttct cggcatcggt     60

ttgggctgtc accagcagtt ggtagttctt cacgtactgt tgttcgagcg tcgagccgcc    120

gcgcgtgtcg aggtcgccgg acgcgtatcc cgccaggccg gtcagggtgc ccttccagtc    180

cacgccgctg tggtcggcga accgcttatc ttcaatcgag acgatcgcca gcttcatcgt    240

gttggcgatc ttgtccgagg gcacctcgaa ccggcgctgc gagtacagcc acgcgatcgt    300

gttgcccttc gcgtcgacca tcgtcgatac cgcaggcact tgcccctc                 348


<210> SEQ ID NO 100
<211> LENGTH: 436
<212> TYPE: DNA
<213> ORGANISM: Mycobacterium tuberculosis

<400> SEQUENCE: 100

atactcaagc ttcccggcgg ccagtaccga aagcgcgaac agctcgcggc agcccacgac     60

gtgctgcgtc ggattgccgg cggcgaaatc aattccaggc agctcccgga caatgcggct    120

ctgctggccc gcaacgaagg actcgaggtc accccggtgc ccggggtcgt ggtgcacctg    180

ccgatcgcac aggttggccc acaaccggcc gcttgatgcc cggtcggcaa gcccggcagt    240

tgccaaaccc agcgtgatca ggctcggctc gcgagttcgg cgaagaagtg gctcgcctga    300

tcacctacca tcggccagga tctgcgtgtc atcacaacgc tcgccaagga ggttgttgtg    360

gtgctatcga cggcctttag ccagatgttc ggaatcgact atccgatagt gtccgcgcca    420

atggacttga tcgccg                                                    436


<210> SEQ ID NO 101
<211> LENGTH: 445
<212> TYPE: DNA
<213> ORGANISM: Mycobacterium tuberculosis

<400> SEQUENCE: 101

agcttcggtg tagccgatca ccggaagccg catgatcagc cacgtttcgc gccgcccggc     60

atacggcggc gtaccgatct ccgcgtcata cacccgcggg taatcgccga cggtgccggt    120

tcgcgagccg aaggtgacga cgctgattga atcgagttcc aggtccagcg ggtggcgcag    180

caacggcgcg agctcaacga cgtcaatcac gttgtcgctt tctacggtca ccgacccggt    240

gaccgtagtc gcccggtgcg ctcggccgag aagttgcacc gccaccaccg cgacaccgtc    300

ttgcacgcgg acgccacccc cggatcggtt gttggccaag gtaattgggt cattccattt    360

gacgggacgc cgaccccgca gccccagtac cgcccacgac cacgccggct gacccaccac    420

tgtacgaaca ccaaggcgac gccga                                          445


<210> SEQ ID NO 102
```

-continued

<211> LENGTH: 261
<212> TYPE: DNA
<213> ORGANISM: Mycobacterium tuberculosis

<400> SEQUENCE: 102
atactcaagc ttcggtggct tcgcccgccc tgccgggtgg acttcatgac aacgcggggg 60
cgattacccc cgctaccgcc agcagcatga cggcggtacc taacaccgcc cggatgcctc 120
gcacgtgcct cgatgtgctc acggaatcgc cccggcaccg cgatctcgag gatcaccagc 180
gttacccccg gcagcgcgac accgacaatt ccgtacaccg ccacgccgat ccggccctgg 240
gccagctgat tggagctggc g 261

<210> SEQ ID NO 103
<211> LENGTH: 244
<212> TYPE: DNA
<213> ORGANISM: Mycobacterium tuberculosis

<400> SEQUENCE: 103
caggcatgca agcttccaca tgtacggatc cacgaacatc ccgttgaact gacaggtgcg 60
gcccggctcg atcaggccgg ccacttgttc tacgcggtta ccgaagatct cttcggtgac 120
ctgcccgccg ccggccagct cggcccagtg cccggcgttg gccgccgcgg cgacgatctt 180
ggcgtccacg gtggtccggg tcttgcccgc tagcacgatc cgcgagtcgg ccggtcaccc 240
gggt 244

<210> SEQ ID NO 104
<211> LENGTH: 376
<212> TYPE: DNA
<213> ORGANISM: Mycobacterium tuberculosis

<400> SEQUENCE: 104
atactcaagc tttccaagtc ccaagtgtcg atcatggcca aagagctcga caaagccgta 60
gaggcgtttc ggacccgccc gctcgatgcc ggcccgtata ccttcctcgc cgccgacgcc 120
ctggtgctca aggtgcgcga ggcaggccgc gtcgtcgggg tgcacacctt gatcgccacc 180
ggcgtcaacg ccgagggcta ccgaaagatc ctgggcatcc aggtcacctc cgccgaagac 240
ggggccggct ggctggcgtt cttccgcgac ctggtcgccc gcggcctgtc cggggtcgcg 300
ctggtcacca gcgacgccca cgccggcctg gtggccgcga tcggggccac cctgcccgca 360
gcggcctggc agcgct 376

<210> SEQ ID NO 105
<211> LENGTH: 284
<212> TYPE: DNA
<213> ORGANISM: Mycobacterium tuberculosis

<400> SEQUENCE: 105
caggcatgca agcttcacac gtaggcgccg tcgataaatg actccgccgc gcttcgcaca 60
tcctcgtagc gatccttggc gagcaggtca accgggcgct gcccgtcgag gagccggttt 120
ttggcgtgca gccactggcc gacacctcgg ggggtaagcg aatccgagag caggaggacg 180
aggtcacgaa gctgcgccag ccggtcgtac cgctcagggc ggatgtcgcc ggtccgccac 240
ccgcgtaccg cccgatcgga cacctgtatg accgcggcga cgtc 284

<210> SEQ ID NO 106
<211> LENGTH: 140
<212> TYPE: DNA
<213> ORGANISM: Mycobacterium tuberculosis -continued

<400> SEQUENCE: 106
cgcggcggcg cattaccccc gctaccgtca gcagcttgac ggcggtagcg aacaccgccg 60
gatgcagcgc aggtgcgtct atgtgcacac ggaatcgccc cggcaccgcg atctcgagga 120
tcaccagtgc ccgccccctg 140

<210> SEQ ID NO 107
<211> LENGTH: 491
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 107
gggatcgagg aacagcgcgt tgaactgata ggtgcggccc ggctcgagca ggccggccat 60
ttgttcgatg cggttaccga agatctcttc ggtgacctgc ccgccgccgg ccagctcggc 120
ccagtgcccg gcgttggccg ccgcggcgac gatcttggcg tccacggtgg tcggggtcat 180
gcccgcgagc aggatcggcg agcggccggt cagccgggtg aacttcgtcg agagcttgac 240
cctgccgtcg gggaggcgaa ccacggtcgg tgcgtatctc gaccaggccc gggcaacctc 300
gggggtggcg ccgacggtga acaggttgcg ctggccaccg cgggtagccg ccggcactat 360
gccgatgccc aggccgcgga tcaccggtgc ggtcagtcgg gtcaggatgt cgcccggccc 420
caggtcgaag atccagcggg cgccggccgc gtggacacng gtgatctcgt ccaccatcga 480
ctttctgatc a 491

<210> SEQ ID NO 108
<211> LENGTH: 364
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 108
taactcaagg cttgcgttga ggccccaggc ccatcgacgg tttggcggcc ttaaatgcac 60
tgaggtcgtc aattgacccc acagcggaaa tgccgactat tcgcaggcct ccttcgcctt 120
ggctgccgga gaggggctcc gcgggaaccg catgcaggta tatgacctcg gtttctcggg 180
tgctaccgcg tgccttgtcg aggatgaact cggcgttgga attgtccagc cggcccaatt 240
catcgagcgc agattcgtac acatggccgg cggcgacata cgcttcaccg tggatctgct 300
ccacacggac cgccctgtcg ggatcctgct cacgggtaaa ggaacttacn tggcnctcgg 360
tgcc 364

<210> SEQ ID NO 109
<211> LENGTH: 453
<212> TYPE: DNA
<213> ORGANISM: Mycobacterium tuberculosis

<400> SEQUENCE: 109
ccttctgcgc cacccacacc gtcaacgccc gcgaagtcga cgtcgtccag gccatcggcg 60
gcctcacgga tggattcggc gcggacgtgg tgatcgacgc cgtcggccga ccggaaacct 120

-continued

```
accagcaggc cttctacgcc cgcgatctcg ccggaaccgt tgtgctggtg ggtgtgccga    180

cgcccgacat gcgcctggac atgccgctgg tcgacttctt ctctcacggc ggtgcgctga    240

agtcgtcgtg gtacggcgat tgcctgcccg aaagcgactt ccccacgctg atcgaccttg    300

acctgcatgg ccggctgccg ctgcagcggt tcgtttccga acgcatcggg ctcgaagacg    360

tcgaggaggc gttccacaag atgcatggcg gcaaggtatt gcgttcggtg gtgatgttgt    420

gatggccgcc atcgagcgcg tcatcaccca cgg                                 453
```

<210> SEQ ID NO 110
<211> LENGTH: 329
<212> TYPE: DNA
<213> ORGANISM: Mycobacterium tuberculosis

<400> SEQUENCE: 110

```
atactcaagc ttgattttga tcatcatgat gatcatcacc cgaagtgtgg tagccgcagt     60

ggttatcgtg ggtaccgtcg tgctttccat gggcgcctct ttcgggcttt ccgtattggt    120

ctggcaggac attctgggta tcgagttgta ctggatggtg ttggcgatgt cggtgatcct    180

gctcctggcg gtgggatccg actacaatct gctgctgatt tcccggttga aaaaagaaat    240

tggggccgga ttgaacaccg gaattatccg tgccatggct ggtaccgggg gagtggttac    300

cgctgccggc atggtgttcg ccgttacca                                      329
```

<210> SEQ ID NO 111
<211> LENGTH: 438
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 111

```
attgnctttc ggcgccatcg gtgaggacgg cgtgcgggtg ctcaacgacg acgtcgtccg     60

cgggacacac ctcgatgctg ccgccatgga cgcggtcgaa cgcaagcagc tgatcgagct    120

acaacgccgc gcggaacgct tccgccgcgg gcgtgaccgc atcccgttga ccgggcggat    180

cgcggtgatc gtcgatgacg gcatcgccac cggagcgacg gccaaggcgg cgtgccaggt    240

cgcccgggcg cacggtgcgg acaaggtggt gctggcggtc ccgatcggcc cagacgacat    300

cgtggcgaga ttcgccgggt acgccgatga ggtggtgtgt ttggcgacgc cggcgttgtt    360

cttcgccgtc gggcagggtt accgcaactt cacccagacc tccgacgaag aagtggtggc    420

gttttctgga tcgtgctc                                                  438
```

<210> SEQ ID NO 112
<211> LENGTH: 438
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 112

```
atactcaagc ttttcccgtc cgtcatcgcc caagcgcgtg aggccgaagc ggctggttac     60

gactccctgt ttgtgatgga ccacttctac caactgccca tgttggggac gcccgaccag    120

ccgatgctgg aggcctacac ggcccttggt gcgctggcca cggcgaccga gcggctgcaa    180
```

-continued

```
ctgggcgcgt tggtgaccgg caatacctac cgcagcccga ccctgctggc aaagatcatc    240

accacgctcg acgtggttag cgccggtcga gcgatcctcg gcattggagc cggttggttt    300

gagctggaac accgccagct cggcttcgag ttcggcactt tcagtgaccg gttcaaccgg    360

ctcgaanagg cgctacagat cctcgagcca atggtcaagg gtgagcgcca acgtttttcg    420

gcgattggta cccaccga                                                  438
```

<210> SEQ ID NO 113
<211> LENGTH: 482
<212> TYPE: DNA
<213> ORGANISM: Mycobacterium tuberculosis

<400> SEQUENCE: 113

```
cggccaccgg ggccactccg cacaatctgt acccgaccaa gatctacacc atcgaatacg     60

acggcgtcgc cgactttccg cggtacccgc tcaactttgt gtcgaccctc aacgccattg    120

ccggcaccta ctacgtgcac tccaactact tcatcctgac gccggaacaa attgacgcag    180

cggttccgct gaccaatacg gtcggtccca cgatgaccca gtactacatc attcgcacgg    240

agaacctgcc gctgctagag ccactgcgat cggtgccgat cgtggggaac ccactggcga    300

acctggttca accaaacttg aaggtgattg ttaacctggg ctacggcgac ccggcctatg    360

gttattcgac ctcgccgccc aatgttgcga ctccgttcgg gttgttccca gaggtcagcc    420

cggtcgtcat cgccgacgct ctcgtcgccg ggaccagcag ggaatcggcg atttcgccta    480

ca                                                                   482
```

<210> SEQ ID NO 114
<211> LENGTH: 388
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 114

```
atactcaagc ttggggtggc gctgtcggtc ggtgtgcttg gcggcgtcgg tatcaacacc     60

gcccacgaaa tggggcacaa gaaggattcg ctggagcggt ggctgtccaa aatcaccctc    120

gcccagacct gctacgggca cttctacatc gagcacaacc gtggccatca cntccgggtg    180

tccacaccgg aggacccggc gtcggcgcgg ttcggcgaaa cgttgtggga gttcctgccc    240

cgcagtgtta tcggcggctt gcgctcggcc gttcatttgg aggcccaacg gctgcgtcgg    300

ctcggcgtca gcccctggaa tcccatgacg tatctgcgca acgacgtgcn caacncgtgg    360

ctgatgtcng tggtgttgtg gggtgggc                                       388
```

<210> SEQ ID NO 115
<211> LENGTH: 455
<212> TYPE: DNA
<213> ORGANISM: Mycobacterium tuberculosis

<400> SEQUENCE: 115

```
tcgccaccgc accgcggcga acgctcaaag gcacctactg gcaccaaggc cccacacgtc     60

accctgtgac ctcctgcgcc gaccccgccc gaggtcctgg ccgttaccac cgaacgggcg    120

agccgggagt ctggtacgca tcgaacaaag agcaaggtgc atgggcggag ttgttccgcc    180

acttcgtcga tgacggggtc gatccattcg aggtccgtcg ccgcgtcggt cgagtggcgg    240
```

-continued tcacactcca ggtactcgac ctcacagacg agaggactcg atcccatcta ggtgtggacg 300
aaacagatct tctgtccgac gactacacca ccacccaggc catcgccgcc gcccgcgatg 360
ccaacttcga cgccgtactg gccccggcgg cggcgctccc cggttgtcaa acactttgcc 420
gtgttcgttc acgcactgcc caacatcgag cccga 455

<210> SEQ ID NO 116
<211> LENGTH: 328
<212> TYPE: DNA
<213> ORGANISM: Mycobacterium tuberculosis

<400> SEQUENCE: 116
atgaaataag aagagcacat ccctcagtcg gttatcatca ctagcgctcg ccgcacccgt 60
gtaaccgatc atagcgagcg aactggcgag gaagcaaaga atatctgttc tgtcagatag 120
ctcttacgct cagcgcaaga agaaatatcc cccgcgggaa caactccagg tagaggtaca 180
cacgcggata gccaattcag agtaataaac tgtgacactc acaccctcat caatgatgac 240
gaactacacc ccgatatccg gtcacatgac gaagggaaag agaaggatat catctgtgac 300
aaactgccct caaatttggc ttccttaa 328

<210> SEQ ID NO 117
<211> LENGTH: 318
<212> TYPE: DNA
<213> ORGANISM: Mycobacterium tuberculosis

<400> SEQUENCE: 117
atactcaagc ttgtcgaact ccttcttgaa taccggccgg ccatccacag atgcccggaa 60
gaacttccag gtacccatgg cggctggatc agggggcggc acagttggtc ttgtcctgcc 120
tcgagtggcg tcgttgtccg gcttggacgg ggctccgacg gtaccggagg gcagcgacaa 180
aacacttatg cacttgggcg acccgccgag acggtgcgac acccatcccg acggcacaag 240
ctcagccgcg gccgctcttg ttcttcgtcg gatcgacatt cacccacttc tgaccgggct 300
tgggcgaagg aagcagaa 318

<210> SEQ ID NO 118
<211> LENGTH: 405
<212> TYPE: DNA
<213> ORGANISM: Mycobacterium tuberculosis

<400> SEQUENCE: 118
ggtatagtcg ctgaccggtg caggtttcga caatgtggtg ccggttcggc ggctacgtgc 60
catcgagaca ctggcgcagg ctatcgcacc cgttatcggc tacgagcaaa tcgcggtatg 120
cgttcttgag catgagtcgg cgaccgtcgt catggtcgac acccacgacg gaaagacgca 180
gatcgccgtc aagcatgtgt gccgcggatt atcaggactg acctcctggc tgaccggcat 240
gtttggtcgc gatgcctggc gcccggccgg cgtggtcgtg gtcggctcgg atagcgaggt 300
cagcgaattc tcgtggcagc tcgaaagggt cctgccggtg ccggtctttg cgcaaacgat 360
ggcgcaggtt acggtcgcgc ggggtgcggc cctggcggcg gccca 405

<210> SEQ ID NO 119
<211> LENGTH: 89
<212> TYPE: DNA
<213> ORGANISM: Mycobacterium tuberculosis
<220> FEATURE:
<221> NAME/KEY: unsure
<222> LOCATION: (various positions within the sequence)

-continued

<223> OTHER INFORMATION: applicants are uncertain of bases designated as "n"

<400> SEQUENCE: 119
gacactatat natactcaag cttcaggtca atgtgcgcca agccctgacg ctggccgacc 60
aggccaccgc cgccggancc ctntctaga 89

<210> SEQ ID NO 120
<211> LENGTH: 354
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 120
ctgtagccac ctgttgccat ccccgtcatg cccgactctg gtcatctcgg atccgctgac 60
accccgctaa ggctgctcct ctcggtgcat tacctcaccg acggcgaacn cccccagctt 120
tacgactatc cggatgacgg cacctggttg ccggctaact tcaccgtcag cttggacggc 180
ggcgctaccg tcgatggcgc cagcggggcg atggccgggc ccggcgaccg attcgtcntc 240
ancctgtcgc gtgaacttgc cgacgtcatc gtggtcggtg tgggcaccgt gcgcattgag 300
ggctactccg gcgtccggat gggtgtcgtc aagcgcccgc accggcaggc ccga 354

<210> SEQ ID NO 121
<211> LENGTH: 379
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 121
atactcaagc ttcgcacgct cggcgcgcgc ggtaccgccc aggtcgccca acagatcgtc 60
gatgttcgcg tcgtccgcct cgcgcacgtg gtctgtcacc agtcaacgtt aacgccgccg 120
cacatgtcct gcggccgggc aaaaacgtga aaaacgagcg ggcgactgcn atgtcatgac 180
accgacggcc gccgatgggc ccagggtctg gcaaattcga tctgtgcggc cagtgccagc 240
agcgtcgcct cgtcatacgg ccggccgacg agttgaaccg acatgggcag gccgtcgccg 300
tcgaagtccc acggcaccac gggcgcgggc tggccggtca gattccaaaa ttgaaagtac 360
ggaaccgctg caccaccaa 379

<210> SEQ ID NO 122
<211> LENGTH: 393
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 122
atcgtttcga ccaggcgctc catccggcga gtggatactc ccagcaggta gcaggtcgcc 60
accacgctgg tcagtgcgcg ttcagctcgc ttgcggcgct gcagcagcca gtccgggaaa 120
tagctgccct ggcgcagctt ggggatcgcg acgtcgatgg ttgcggcacg ggtgtcgaaa 180

-continued

```
tcacggtggc ggtagccgtt gcgctgattg gaccgctcat cgctgcgttc gcggtagccc    240

gccccgcaca gggcgtcggc ttcagccccc atcaaggcgg cgatgaacgt cgagagcagc    300

ccgcgcagca gatccgggct cgcctgtgcg agttggtcag ccagaagctg ctcggtgtcg    360

ataagatgan aagaagtcat tgcgttattt cct                                 393
```

<210> SEQ ID NO 123
<211> LENGTH: 333
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 123

```
atactcaagc ttgggtgttg ccgatcaccg gaagccgcat gatcagccac gtttcgcgcc     60

gcccggcata cggcggcgta ccgatctccg cgtcatacac ccgcgggtaa tcgccgacgg    120

tgccggttcg cgagccgaag gtgacgacgc tgattgaatc gagttccagg tccagcgggt    180

ggcgcagcaa cggcgcgagc tcaacnacgt caatcacgtt gtcgctttct acggtcaccg    240

acccggtgac cgtagtcgcc cggtgcgctc ggccgagaag ttgcaccgcc accaccgcga    300

caacgtcttg cacgcggacg ccaccccccg gat                                 333
```

<210> SEQ ID NO 124
<211> LENGTH: 426
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 124

```
gcgcnaacag ctcgcggcag cccacgacgt gctgcgtcgg attgccggcg gcgagatcaa     60

ttccaggcag ctcccggaca atgcggctct gctggcccgc aacgaaggac tcgaggtcac    120

cccggtgccc ggggtcgtgg tgcacctgcc gatcgcacag gttggcccac aaccggccgc    180

ttgatgcccg gtcggcaagc ccggcagttg ccaaacccag cgtgatcagg ctcggctcgc    240

gagttcggcg aaaaagtggc tcgcctgatc acctaccatc ggccaggatc tgcgtgtcat    300

cacgacgctc gccaaggagg ttgttgtggt gctatcgacg gcctttagcc agatgttcgg    360

aatcgactat ccgatagtgt ccgcgccaat ggacttgatc gccggcggtg agctggctgc    420

cgcngt                                                               426
```

<210> SEQ ID NO 125
<211> LENGTH: 336
<212> TYPE: DNA
<213> ORGANISM: Mycobacterium tuberculosis

<400> SEQUENCE: 125

```
atactcaagc tttctccgat acccgccatg tcgcgcacat ccaggacttc tgggggggatc     60

cgctgacagc ggcgggatcc caaagtgcgg atgatcgggc cgcctacgtc gtggtgtacc    120

tcgtcggtaa caacgaaacc gaagcgtatg actcggtcca cgcggtgcgg cacatggtgg    180

acaccacacc gccaccgcac ggggtgaagg cctatgtcac cggtccggca gcactcaatg    240
```

-continued

```
ccgaccaggc cgaggccgga aacaaaagta tcgctaaggt caccgcgatc acgaacatgg    300

tgatcgcagc aatgttgcta gtgatctatc gctccg                              336


<210> SEQ ID NO 126
<211> LENGTH: 347
<212> TYPE: DNA
<213> ORGANISM: Mycobacterium tuberculosis

<400> SEQUENCE: 126

ccatgagcac cgccagccga gcacgaggcc aaactccgcc gacgcaggcc ggttggactt     60

gtcgtgctgg acaaggggtt tagccgccga agcagtgacg tacatcggcg aagagcagtt    120

cgcctgtcga ccgacggcgc aaaccgtgag gctagggaag cgaggagcac atggccgccg    180

acccgcaatg tacacgctgc aagcaaacca tcgaacccgg atggctatac atcaccgccc    240

atcgccgcgg tcaagccggg atcgtcgatg acggcgcagt actgattcac gtgcccggtg    300

aatgccgcac cccggggagc actttccgcc aaaactaacc cggttgg                  347


<210> SEQ ID NO 127
<211> LENGTH: 315
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 127

cgggtgtcat tggccaccgg cggcggctgt ccgggaaatg gcgggtcccc ggtggttttg     60

ctgaggagtg ctgaaccgta gtcgaagtgg gcggcgtcag actccaccca gccagcaggc    120

agcgcgaanc tgaatcctcc aaccgggttg tcnatccgga caggttgggg tgcgtttggg    180

gcaatnacag gtggcggcgg tgcgttcggg tcggccggcg gaggtgctgc nttgggatcc    240

ccggctgggc attcggcntg ttggcggcgg ccggtggtgg ggggggcaac acgtgtcncc    300

ggtgcgggtg gccct                                                     315


<210> SEQ ID NO 128
<211> LENGTH: 354
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 128

ccaagatcta caccatcgaa tacgacggcg tcgccgactt tccgcggtac ccgctcaact     60

ttgtgtcgac cctcaacgcc attgccggca cctactacgt gcactccaac tacttcatcc    120

tgacgccgga acaanttgac gcagcggttc cgctgaccaa tacggtcggt cccacgatga    180

cccagtacta catcattcgc acggagaacc tgccgctgct agagccactg cgatcggtgc    240

cgatcgtggg ganacccact ggcgaacctg ggttcaacca aacttgaagg tgattgttaa    300

cctgggctac ggcgacccgg cctatggtta ttcgacctcg ccgcccaaat gttg          354


<210> SEQ ID NO 129
<211> LENGTH: 360
<212> TYPE: DNA
<213> ORGANISM: Mycobacterium tuberculosis
```

-continued

<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 129
agcttcccga gttcggcttt ggatcaagac cccagtccgc gggcgcgatc cggcngctcg 60
gtgactacat caagccacaa atcgacggct ttcggggtgc cgataccgat gacgtggcgg 120
atgtcgagtg ttgagttctc ggcggggcgg atgctcacct ggcgatcacc tgcctctcgt 180
tgacgatcga tcgtctatgc cgccgtctct gcgggaacag gccnccagta catcgccaca 240
gacgggatcc acccgcattt cggctacggt tgctcgtttc ggtgttcgga ctagtcggtc 300
ctggtgacgt gccggtgatg cggaccggtc ctagcactga ccaatggcca aaatgcgggc 360

<210> SEQ ID NO 130
<211> LENGTH: 483
<212> TYPE: DNA
<213> ORGANISM: Mycobacterium tuberculosis

<400> SEQUENCE: 130
cggggggcct cttaatagtg taggaaagaa gctctacata ttcaggagga ttcaccatgg 60
ctcgtgcggt cgggatcgac ctcgggacca ccaactccgt cgtctcggtt ctggaaggtg 120
gcgacccggt cgtcgtcgcc aactccgagg gctccaggac caccccgtca attgtcgcgt 180
tcgcccgcaa cggtgaggtg ctggtctgcc agcccgccaa gaaccaggca gtgaccaacg 240
tcgatcgcac cgtgcgctcg gtcaagcgac acatgggcag cgactggtcc atagagattg 300
acggcaagaa atacaccgcg ccggagatca gcgcccgcat tctgatgaag ctgaagcgcg 360
acgccgaggc ctacctcggt gaggacatta ccgacgcggt tatcacgacg cccgcctact 420
tcaatgacgc ccagcgtcag gccaccaagg acccggccag atcgccggtc tcacgtgctg 480
cgg 483

<210> SEQ ID NO 131
<211> LENGTH: 423
<212> TYPE: DNA
<213> ORGANISM: Mycobacterium tuberculosis

<400> SEQUENCE: 131
atactcaagc ttcataacag gcctgttgtg ggcgcacccg gctcgccgag ttctgcacgc 60
accgcctcaa gtgcggcccg caccgccggc atctcccggt cacgcagggc cgcggcccgc 120
gccgcagcga cggcgtgttc gcgcagttcg ccgtcaatga tgctgacctg atcggccacc 180
cgggcgttct cggcgtcttc gcgttcacta atcgcggtgc tcagcagcgt ctcgacagcc 240
accacccgag tggcgaccag ctgctccacc acggaccgca gcgatgccgt cacctcaccc 300
gtccagcggt ccaccacgac acggtcgtgc accagcgcgc gggcattcac cacccaggcg 360
gtcaccgcca ggccgatcgc cacacccgcc accatccccg atgcagccag gccgggagta 420
aga 423

<210> SEQ ID NO 132
<211> LENGTH: 338
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated -continued as “n”

<400> SEQUENCE: 132
ctggtgctgg acggagccta gtacaacttc ctctccaatg ctcttgcccc gatcgcggcg 60
accaggatga cccaggacat cctgccgccc gaagtactgg aaaagctcac acccgagttc 120
gtcgcaccgg tggtggccta cctgtgcacc gaggagtgtg ccgacaaccc atcggtgtac 180
gtcgtcagtg gtggttaggt gcagcgagtt gcgctgtttg gcaacgacgg cgccaacttc 240
gacaaaccgc cgtcngtaca agatgttgcg gcgcggtggg ccgagatcnc cgatctgtcc 300
ggtgcgaaaa ttgctggatt caagttgtag aactaaat 338

<210> SEQ ID NO 133
<211> LENGTH: 173
<212> TYPE: DNA
<213> ORGANISM: Mycobacterium tuberculosis

<400> SEQUENCE: 133
atactcaagc ttttccggcg tcgtccacct gacccaaaaa gcgcaggtgc gccgccaaac 60
ggcccgcctg gccgcgcaac tggtcggcgt cgccgtggcc gacaatcagt agctggacat 120
ccggaaaccg ctgcaccacc ttcggcagcg cgtcaagcaa aaacggccat tcc 173

<210> SEQ ID NO 134
<211> LENGTH: 255
<212> TYPE: DNA
<213> ORGANISM: Mycobacterium tuberculosis

<400> SEQUENCE: 134
tttcagatct catttttatg acatgactgg agatctgtct agattgcagc tcctgtgagc 60
gtgggtaccg gattcaagcc ggtcggtcac gccgcggtgg taccggcttt gcggcagtgc 120
tcggcctcga gttcggcgat cgcgcgcgaa gtgcgtttcg cgcaccaaga tcgcggccta 180
atggccggcg atgaccgcga tgaccagcgc gatccaggaa aaaccgttcc aaccagtgct 240
gggcggccat ccccg 255

<210> SEQ ID NO 135
<211> LENGTH: 285
<212> TYPE: DNA
<213> ORGANISM: Mycobacterium tuberculosis

<400> SEQUENCE: 135
atactcaagc ttcccgacca caagttgaac agcaccgatt tcggcgagca cttcgtcaac 60
ttccagggtg cccgcaccaa gtatttcgac aagtatttcc gtcgggccgc cgccgccggc 120
gcgcggcagg tggtcatcct ggcggcgggg ctggactccc gcgcgtaccg gctgccttgg 180
cccgacggga ccacggtttt tgagctggac cgcccgcagg tccttgattt caagcgcgag 240
gtgctcgcca gccacggtgc ccaaccgcgc gccctgcgcc cgcga 285

<210> SEQ ID NO 136
<211> LENGTH: 494
<212> TYPE: DNA
<213> ORGANISM: Mycobacterium tuberculosis

<400> SEQUENCE: 136
gtgtgctgtc aattcagagc tgagcctgat gcactcaact tactgagcat gctaacgctg 60
gtcgtgcggg tcttgttccc gcgtgtcggc agggcacacg ctcggggcgt agctgggaga 120
ggccccggtc aagcccggag agcagtgctc agtccgccag cttgaccgac tttcgatgag 180

-continued

```
aacgcgcttc tcgccgtatt gaactggcgt gctgacggtc gctgagcagc gctcgccgag    240

tgcggccgct gattctttca tcgagccagg aggcgcattc gtgttcggcc gcctgcgggt    300

cggccccatc gtcgacgcga tccgtcaccc actcctcgat caggtctgcc tcatcgaacg    360

ggccaacggt gctgtcggag tatgtgtgcg tgggcacggc gagccgggtg ctgtggtaca    420

cccaccgttg catgaccaag ttgacgcctg actggctgag caccgcgatc cgctcacagg    480

tcggaacgtt ggtg                                                      494
```

<210> SEQ ID NO 137
<211> LENGTH: 357
<212> TYPE: DNA
<213> ORGANISM: Mycobacterium tuberculosis

<400> SEQUENCE: 137

```
atactcaagc ttttggtcta gccggccgag cccgatacag gtgtcattgg ccaccggcgg     60

cggctgtccg ggaaatggcg ggtccccggt ggttttgctg aggagtgctg aaccgtatgc    120

gaagtgggcg gcgtcagact ccacccagcc agcaggcagc gcgaaactga atcctccaac    180

cgggttgtcg atccggacag gttggggtgc gtttggggca atgacaggtg gcggcggtgc    240

gtccgggtcg gccggcggaa gtgctgcgtt gggatcgccc ggctgggcat tctgcgtgtt    300

ggcggcggcc ggtggtgggg gggcaacagg tgtctccggt gcgggtggcg ctgcacc       357
```

<210> SEQ ID NO 138
<211> LENGTH: 458
<212> TYPE: DNA
<213> ORGANISM: Mycobacterium tuberculosis

<400> SEQUENCE: 138

```
ggggccactc cgcacaatct gtacccgacc aagatctaca ccatcgaata cgacggcgtc     60

gccgactttc cgcggtaccc gctcaacttt gtgtcgaccc tcaacgccat tgccggcacc    120

tactacgtgc actccaacta cttcatcctg acgccggaac aaattgacgc agcggttccg    180

ctgaccaata cggtcggtcc cacgatgacc cagtactaca tcattcgcac ggagaacctg    240

ccgctgctag agccactgcg atcggtgccg atcgtgggga acccactggc gaacctggtt    300

caaccaaact tgaaggtgat tgttaacctg ggctacggcg acccggccta tggttattcg    360

acctcgccgc ccaatgttgc gactccgttc gggttgttcc cagaggtcag cccggtcgtc    420

atcgccgacg ctctcgtcgc cgggacccag cacggaat                            458
```

<210> SEQ ID NO 139
<211> LENGTH: 595
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 139

```
ttctntcttc ccnnattcgt nnntctcnta ctaccngggc cncaaaacac cttggcnaac     60

gctcaaaggc gntacnggca ccaaggcccc acacgtcacc ctgtgacctc ctgcgccgac    120

cccgcccgag gtcctggccg ttaccactga acgggcgagc cgggagtctg gtacgcatcg    180

aacaaagagc aaggtgcatg ggcggagttg ttccgccnct ttttttatga cggggtcgat    240

ccattcgagg tccgtcgccg cgtcggtcga gtggcggtca cactccaggt actcgacctc    300
```

-continued ncagacgaga ggactcgatc ccatctangt gtggacnaaa cagatcttct gtccgacgac 360
tacacaccac ccaggccatc gccgccgccc gcgatgccaa cttcnacncc gtnctggccc 420
cggcggcggc gctccccggt tgtcaaacac ctgccgtgtt cgttcacnca ctgcccaaca 480
tcnagcccga ncnatccnag gtccgtccaa cgcctccgcg gctcnccaac ctnctcccnc 540
tgatcntccg caccaaacac atgcccgact ccntgcnccn attgcttgna tccct 595

<210> SEQ ID NO 140
<211> LENGTH: 434
<212> TYPE: DNA
<213> ORGANISM: Mycobacterium tuberculosis

<400> SEQUENCE: 140
ccgctatcgg tcggtgtgct tggcggcgtc ggtatcaaca ccgcccacga aatggggcac 60
aagaaggatt cgctggagcg gtggctgtcc aagatcaccc tcgcccagac ctgctacggg 120
cacttctaca tcgagcacaa ccgtggccat cacgtccggg tgtccacacc ggaggacccg 180
gcgtcggcgc ggttcggcga gacgttgtgg gagttcctgc cccgcagtgt tatcggcggc 240
ttgcgctcgg ccgttcattt ggaggcccaa cggctgcgtc ggctcggcgt cagcccctgg 300
aatcccatga cgtatctgcg caacgacgtg ctcaacgcgt ggctgatgtc ggtggtgttg 360
tggggtgggc tgatcgcggt cttcggcccg gcgctgatcc cgttcgtcat catccaggca 420
gtcttcggct tcag 434

<210> SEQ ID NO 141
<211> LENGTH: 321
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 141
atactcatgc ttgccgaagt tccgatgggt cgcgccggcg ancccagcga agtcgctagc 60
gtggccgtgt tcttggcttc ggatctatcc tcgtacatga ccggcaccgt gttggacgtg 120
actggcggcc ggttcatatg acaccgagat cattgccacg gtacggcaat tcgtcaagaa 180
ggaaatcttt cccaatgcac cggccctcga acgtggcaac agctacccgc aagaaatcgt 240
cgatcggctg ggtgttattg gcttgctcgg tcgccggctg caagggtatc gacaccaccg 300
agttcattct ccgggcgtgc c 321

<210> SEQ ID NO 142
<211> LENGTH: 348
<212> TYPE: DNA
<213> ORGANISM: Mycobacterium tuberculosis

<400> SEQUENCE: 142
ggcgtcaacg gtgtcggcac cggcgtcctg cagttggtag gcctgcagtt tgtgcatcag 60
gccgatgccg cggccctcgt ggccacgcat gtacagcacc acgccgcgcc cctcacgggc 120
gaccatcgcc agcgcggcgt ccagctgagg cccgcaatcg cagcggcgtg acccaaacac 180
atcgccggtc aagcactccg aatgcacccg gaccagcacg tcgtcaccgt cggcgttggg 240
cccggcgatc tcgccgcgga ccagcgcgac atgttccacg tcctcgtaga tgctggtgta 300
gccgatggcg cgaatctccc atgacgagtc ggaatccgcg cctcggcg 348

-continued

<210> SEQ ID NO 143
<211> LENGTH: 339
<212> TYPE: DNA
<213> ORGANISM: Mycobacterium tuberculosis

<400> SEQUENCE: 143
atactcaagc ttcggcctcg ctgcaggagt gggagccgca gggctggaaa tccgaaaaac 60
gagccggtga tcgcactgtc gccgatcggg gccgcacctg gttggtgtta ccgatgaatc 120
cgcacccaaa atgtggctgc ggtggcgttt cttgactcct tggcgtcgac tcttgtggca 180
gccaccgagc ggttggtcca ggatctggat gggcaaagtt gtgcggcccg gccggtgacg 240
gccgatgagc tgaccgaggt cgacagcgcc gtgttggctg acttggaacc gacatggatt 300
cgccccggtt ggcgtcacct caagcatttc aatggttat 339

<210> SEQ ID NO 144
<211> LENGTH: 269
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as “n”

<400> SEQUENCE: 144
atgcgtcacc ccgatgcgcc cagatcgggg cttcgcaaat aaagcacgaa caggcgggca 60
aaacgtctat ctcggagccg gaagggcaat cagccgaccg tcgacgaacg acaccggcga 120
taaccactta ggcgttgaac ggccggccca aacattacgc ctccgttgat aaggctttcg 180
gtctcttccc cggtcatccc aagcaccttg cggcaaattt gaacgctttc ctgtccgggc 240
accggccccg ggctttgggg tccntccga 269

<210> SEQ ID NO 145
<211> LENGTH: 285
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as “n”

<400> SEQUENCE: 145
atactcaagc ttcaatcgcg ccgccacaat ccaaatatgc gtctagcgtc tcgatgagcg 60
tcggtccggc atcggctagg ggccgcatca cgtcggtatg cagggccacg atcgcccaag 120
gcgtcgccca tcaagggcgc gttcgggcaa aaattcccct atccagcacg ggccgcggcg 180
ctccgcncca gccggcgacg gcgttcatcc cggagatcgc ctcgctagcg ctgcggtgcg 240
ccgcggtcag catgggcgcc gtggggccga tgaccaccgg ggcgt 285

<210> SEQ ID NO 146
<211> LENGTH: 75
<212> TYPE: DNA
<213> ORGANISM: Mycobacterium tuberculosis

<400> SEQUENCE: 146
ttcggcgggt ctgtagattg cggtcggcca ccccacaggc actcatgaac cgcagcccac 60
gatcgatctc ggtgg 75

-continued

<210> SEQ ID NO 147
<211> LENGTH: 164
<212> TYPE: DNA
<213> ORGANISM: Mycobacterium tuberculosis

<400> SEQUENCE: 147
gcgcaccatc gccagtaggt gcccgtggtc gggcgcgtcg agccacccga gcggaaacgc 60
gagtccgaac agcaacagca ggacgggcgc aaccagggcg gtgaccatgc ccccggcgct 120
gaacatcaac cacaggaagg gctccgccga gcgtccgcgc gacc 164

<210> SEQ ID NO 148
<211> LENGTH: 228
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 148
catcgtcgaa cttcggtccg ggttgntagn accgcagcac caaacgcacc caccgacccc 60
cacgcttcac gccaaccctt tagttcattg gcgtgaacag cagcgtagcc ggttgccccg 120
atatatgtgg aaaaatcgtt cggacgtaca aaaaaagttc ctgacgctgg cgtcaactcg 180
aaactgcctc ggaagtcaat gatgatccat cagtcaatat taaagtcg 228

<210> SEQ ID NO 149
<211> LENGTH: 238
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 149
atactcaagc ttgtctgctg cctcagcgta tgcatccaac agcgcatcgc gatcaacgat 60
caggcgcgcc gatttcgggc cgcgggcagt ggcactggcc agatggccgt ttttttcgag 120
aaacttcaac gcctgagcgc tgcttcccat cgagagaccg gtggcctcta caaccgatgc 180
gacagttgga ccggcgatgt tcgccagcag cgcttcacat acggcaagtn tggcgcgg 238

<210> SEQ ID NO 150
<211> LENGTH: 162
<212> TYPE: DNA
<213> ORGANISM: Mycobacterium tuberculosis

<400> SEQUENCE: 150
ttgtccaggc ggggaatcgg gcagggagac gacaccttcg ttcggttcga tcgtcgcgaa 60
cgggtagttg gccgcgacca cgttgtttcg ggtcagcgcg ttgaaaagtg tcgacttgcc 120
gacgttgggc aggcccacga tccccaggct caagctcaca ga 162

<210> SEQ ID NO 151
<211> LENGTH: 377
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated -continued as “n”

<400> SEQUENCE: 151
atactcatgc ttggcgcctg ggtggcagcc cacctgccca ccacacggac cgcggtgcgg 60
acgcggctga cgcgcctggt ggtcagcatc gtggccggtc tgctgttgta tgccaacttc 120
ccgccgcgca actgctggtg ggcggcggtg gttgcgctcg cattgctggc ctgggtgctg 180
acccnccgcn cnacaacacc ggtgggtggg ctgggctacg gcctgctatt cggcctggtg 240
ttctacgtct cgttgttgcc gtggatcggc gagctggtgg gccccgggcc ctggttggca 300
ctggcgacga cgtncgcgct gttccccggc atcttcggtc tgttcgccgt cgtggtaccc 360
tgttgccggg ttggccc 377

<210> SEQ ID NO 152
<211> LENGTH: 308
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 152
cgccaattca cgatatcgtt aaccgatatc ccgagccgat agctggcggg ctcgggtggt 60
ggccagcggc gctgcgacga aaggtgtgac cgtcatgaaa cagacaccac cggcggccgt 120
cggccgtcgt cacctgctcg agatctcagc atccgcagcc ggtgtgatcg cgctttcggc 180
gtgtagtggg tcgccgcccg accccggcaa aggccggccc gacacaaccc cggaacagga 240
agtcccggtc accgcgcccg aagnacttga tgcgcgaacn cggagtgctc caaacgcatc 300
ctgctgat 308

<210> SEQ ID NO 153
<211> LENGTH: 377
<212> TYPE: DNA
<213> ORGANISM: Mycobacterium tuberculosis

<400> SEQUENCE: 153
atactcaagc ttgggcactg acttcggtac cccctccgcc tttggccagc agcagccaca 60
gcgcggttcg cggaccgaac gtggacatca atagcccgga atcggtgtgt gcaagttggt 120
aaacggtgtt gatcccaagc tttgccagcc ttttcgtagt cttgggcccc acaccccaca 180
gtgcttcgac ggtacggtca cccatgatgg ccatccagtt ggcatcggtg agctgataaa 240
tgccagctgg tttcgccaac ccggtagcga tcttggcgcg ctgcttgttg tcactgatac 300
ctatcgagca agacagcccg gtttgcgaca aaatgacttt tcggatctct tcggcgactt 360
cgatggggtc gtcggga 377

<210> SEQ ID NO 154
<211> LENGTH: 259
<212> TYPE: DNA
<213> ORGANISM: Mycobacterium tuberculosis

<400> SEQUENCE: 154
aaagtcctgt gccggttcgc taaacacccg gcggacactc agacggtgct ggtggtgcgg 60
catggcaccg cgggcagcaa agcgcacttc tccgggggac gacagcaagc gaccgctaga 120
caagaggggt cgtgcgcagg cagaaacgtt ggtacacagc tgctggcgtt cggcgccacc 180

-continued

```
gatgtttatg ccgccgaccg ggtgcgctgc caccagacga tggagccact cgccgcggaa    240

ctgaacgtga ccatacaca                                                 259


<210> SEQ ID NO 155
<211> LENGTH: 372
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 155

atactcaagc ttgggttcca cgcccgcgca gccacgccgt cacctttcca cgagacctca     60

cctgccgatc cgaaatggaa tcggccgtga cggaattggc gcaccgaaca cccaacgagg    120

tggtggcttc gtcgcgaacc gtcacccgag tcgcggccac cgtgcgcacg gcgacgttct    180

acacccgcac caagatccga aagctgcaag ctcccagcac cgatcccgac gtcatcaccg    240

ctgccgcccg gcacgtcctt gacctattcg agctggatcg gcccgtccgg ttgctgggag    300

tgcggttaga actggcctag aaccggcggg cacaccgcnc ctgggcgggg cgaattcttg    360

accgcnccgg cc                                                        372


<210> SEQ ID NO 156
<211> LENGTH: 290
<212> TYPE: DNA
<213> ORGANISM: Mycobacterium tuberculosis

<400> SEQUENCE: 156

cgcggttggc gtagttggac gggtcgccct ccgaggccaa tgatgacgat gaccacgccg     60

atcacgatgg ccaccgagag ggacaacaac agaaagctga cgaatccctc cttggcggcc    120

ggggctttgt ggtcgccggt cgcgatgggc gcgaatttac ggcccgctcc cccaggccgc    180

cgcgaagcag ggtccccagc cagttggcgt aggcggaatt aacgatcagc gccaccgcga    240

taacctgcca tgcctcgggc atatcgatgt gcggccagaa caggccgaac              290


<210> SEQ ID NO 157
<211> LENGTH: 470
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 157

ccaacaagag catcgggaca tacggagtca actacccggc caacggtgat ttcttggccg     60

ccgctgacgg cgcgaacgac gccagcgacc acattcagca gatggccagc gcgtgccggg    120

ccacgaggtt ggtgctcggc ggctactccc agggtgcggc cgtgatcgac atcgtcaccg    180

ccgcaccact gcccggcctc gggttcacgc agccgttgcc gcccgcagcg gacgatcaca    240

tcgccgcgat cgccctgttc gggaatccct cgggccgcgc tggcgggctg atgagcgccc    300

tgacccctca attcgggtcc aagaccatca ncctctgcaa caacggcgac ccgatttgtt    360

cngacggcaa ccggtggcga gcgcacctag gctacgtgcc cgggatgacc aaccaggcgg    420

cgcgtttcgt cgcgagcagg atctaaccgc gagccgccca tagattcccg              470
```

-continued

<210> SEQ ID NO 158
<211> LENGTH: 434
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 158
taanacccgt gtaatttggg atgggcaaaa aggccaagca ccgcgtggcc acgaacgccg 60
ggagggacaa tctcgggcgg ctagggcttc tcgcgggaag gcccgaacgt acggcgtttc 120
aacacgtcgc gtcnccctcc gaccgcgaac attcggggat ggcagcaacc tggtagcncc 180
ctggccgggc gatgatctgc agcgtcgccg cgggtagtcg ccgcccgggc ggctacagtc 240
tgaaacgcga tgaccatcga tgtgtggatg cagcatccga cgcaacggtt cctacacggc 300
gatatgttcg cctcgctgcg ccggtggacc ggtgggtcta tcccggagac cgacntcccg 360
atcgaagcga ccgtctcctc gatggacgcc ggcggcgtca ccctgggttt gctcaccgcc 420
tggcgtggcc ccaa 434

<210> SEQ ID NO 159
<211> LENGTH: 363
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 159
gtccgcaaaa gactcagcgg ccgactttgc tcgcagctgg cggtaccgcg ccaccgattc 60
gatgccgtgg tcgcggaaga atgcctcccg aaatcgcacg gccgactcca gttcggcgag 120
catccgcgat gccagctgcg gctgcgccct gccggccacg gcacccacat gcggcagttc 180
gtccacctgg gccagcgccc cgccgccgaa gtccaaacaa tagaactgca cccggcccgc 240
atcgtgggta gcagccaacg ccatgatcag cgtccgcagc gcggttgact tgcccgtttg 300
cggtgcacct acgaccgcga cattgcctgc ggccccggac aagtcgatcg tcagcggcac 360 ccn 363

<210> SEQ ID NO 160
<211> LENGTH: 301
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 160
cgtggccacg aacgccggga gggacantct cgggcggcta gggcttctcg cgggaaggcc 60
cgaacgtacg gcgtttcaac acgtcgcgtc gccctccgac cgcgaacatt cggggatggc 120
agcaacctgg cagctacctg gccgggcgat gatctgcagc gtcgccgcgg gtagtcgccg 180
cccgggcggc tacagtctga aacgcgatga ccatcgatgt gtggatgcat catccgacgc 240
aacggttcct acacggcgat atgttcncct cgctgcgccg gtggaccggt gggtctatcc 300
c 301

<210> SEQ ID NO 161
<211> LENGTH: 436
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 161
atactcaagc tttgcggcgg gcgccgaaat gtgaacgcac caaacccgcc cgctgcgggt 60
cggcgggcca ctcgacctcg aatttcgccg ccgtgaccat ccagcccgac ggcagttggg 120
cacccggccc cccggtcgcg gcataactgt tggcgtcgcc gtcataaagc tcgaacagca 180
ccgaaaccga ctccaccacc ggccggtgcg cctcaaaatc cacgccgatc tccacatacc 240
gggaaaacgt cggtgtccca tcgggtttcg gcttgcccgc cagctgcaca ccaccggtgg 300
cctcggccac cttcgcggcc tgagcgcagc tacncatcct gacgatcatc accccgcccc 360
cggctcacgc ttggcctccg tgaccgcacg catcgcccgg ttgcgcgcac cgcgacgccc 420
gtacagccgc gcgcac 436

<210> SEQ ID NO 162
<211> LENGTH: 390
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 162
agcttgccgg gactgcggaa cagaagcggc ggttcctacc gcggtgtgcg gccggcgcga 60
tatcggcctt tttactaacc gaacccgatg tgggctccga tccggcgcgc atggcatcga 120
cggcgacgcc gatcgatgac ggccaggctt acgagcttga gggtgtgaag ttgtggacca 180
ccaacggtgt ggtagcggac ctgctagtgg ttatggcgcg ggtaccgcgc agtgaagggc 240
accgaggggg aatcagcgcc tttgtcgtcg aggctgattc gcccgggatc accgtggagc 300
ggcgcaacaa gttcatggga ctgcgtggca tcnaaaacgg cgtgacccgg cttcatcgcg 360
tcngggtgcc caaagacaac ttgatcggca 390

<210> SEQ ID NO 163
<211> LENGTH: 75
<212> TYPE: DNA
<213> ORGANISM: Mycobacterium tuberculosis

<400> SEQUENCE: 163
ctcaagcttg gcgatgcggg ctggccaaaa ctggccgggc gggggttggc ttgttcaatc 60
aagggtgggt tgccg 75

<210> SEQ ID NO 164
<211> LENGTH: 110
<212> TYPE: DNA
<213> ORGANISM: Mycobacterium tuberculosis

<400> SEQUENCE: 164
ccgaaggccc gttcccgggc gttcagcaag cgatcgtcgg ttggcccact gcgggtcgaa 60

-continued tcttgcggcc gcgccggtcg tggaacgccc aggtcacccg gcggcgtacc 110

<210> SEQ ID NO 165
<211> LENGTH: 455
<212> TYPE: DNA
<213> ORGANISM: Mycobacterium tuberculosis

<400> SEQUENCE: 165
atactcaagc ttttttctgc tcatgaaggt tagatgcctg ctgcttaagt aattcctctt 60
tatctgtaaa ggctttttga agtgcatcac ctgaccgggc aaatagttca ccggggtgag 120
aaaaaagagc aacaactgat ttaggcaatt tggcggtgtt gatacagcgg gtaataatct 180
tacgtgaaat attttccgca tcagccagcg cagaaatatt tccagcaaat tcattctgca 240
atcggcttgc ataacgctga ccacgttcat aagcacttgt tgggcgataa tcgttaccca 300
atctggataa tgcagccatc tgctcatcat ccagctcgcc aaccagaaca cgataatcac 360
tttcggtaag tgcagcagct ttacgacggc gactcccatc ggcaatttct atgacaccag 420
atactcttcg accgaacgcc ggtgtctgtt gacca 455

<210> SEQ ID NO 166
<211> LENGTH: 309
<212> TYPE: DNA
<213> ORGANISM: Mycobacterium tuberculosis

<400> SEQUENCE: 166
ctcaagcttg gtgccgacat ggccgggctg gagcccgcgt atggcaaggt tccgctcaat 60
gtggttgtga tgcagcagga ctacgttcgc ctcaatcagc tcaaacgtca cccccgtggc 120
gtgctgcgca gcatgaaggt cggcgcccgc acgatgtggg cgaaggcaac aggtaaaaac 180
ctggtcggca tgggtcgagc cctcattggg ccgttgcgga tcgggttgca ccgcgccgga 240
gtgccggtcg aactcaacac cgccttcacc gatcttttcg tcaaaaatgg cgtcgtgtcc 300
ggggtatac 309

<210> SEQ ID NO 167
<211> LENGTH: 232
<212> TYPE: DNA
<213> ORGANISM: Mycobacterium tuberculosis

<400> SEQUENCE: 167
ccgaagcgtg ggaaatcctg accgaatacc gcgacgtgct ggacactttg gccggcgagc 60
tgctggaaaa ggagaccctg caccgacccg agctggaaag catcttcgct gacgtctaaa 120
agcggccgcg gctcaccatg ttcgacgact tcggtggccg gatcccgtcg gacaaaccgc 180
ccatcaagac acccggggga gatcgcgatc gaaacgcggc gaaacttggg cc 232

<210> SEQ ID NO 168
<211> LENGTH: 455
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as “n”

<400> SEQUENCE: 168
cgactcgaca agcattcttg acagttgttt tggctcggca tggttagcca aggttctgcg 60
gtcccaccag atcatcttgg tccggtagcg ctcgtccggg tatgctgccg ccgggattct 120

-continued

```
cgctgctatt actccccccg aaaaacgcca ccggtccagc gcgtgggccg ccgcggtccc    180

catcacaaac tgaaccccca acaggggaca tgcttagcgg tagggcgcgc gccaaggcgg    240

cagcaatcgc atcactgcgc tgcgcgtcac tattaaccca cccggacttc acttccacga    300

ccccgaatgg cgcccggtca ttgatcatct tgcgcaccgc ggataatccg ggattgccag    360

cccattcgac taccgcatgc gagtcatcgg ctgaccgcag cggtccgatt acccgagcgc    420

cccgantaca tctcctccaa tatcaatggg cgcaa                               455


<210> SEQ ID NO 169
<211> LENGTH: 428
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 169

gcggtntagc ttcccgtcgt accggcgacc gccagccgag aagctcgttt tcccagtgtt     60

gctggggatt ctcacgctgc tgctgagtgc gtgccagacc gcttccgctt cgggttacaa    120

cgagccgcgg ggctacgatc gtgcgacgct gaagttggtg ttctccatgg acttggggat    180

gtgcctgaac cggttcacct acgactccaa gctggcgccg tctcgtccgc aggtcgttgc    240

ttgcgatagc cgggaggccc ggatccgcaa tgacggattc catgccaacg ctccgagttg    300

catgcggatc gactacgaat tgatcaccca gaaccatcgg gcgtattact gcctgaagta    360

cctggtgcgg gtcggatact gctatccggc ggtgacgacc cccggcaagc cgccatccgt    420

gctgctgt                                                              428


<210> SEQ ID NO 170
<211> LENGTH: 385
<212> TYPE: DNA
<213> ORGANISM: Mycobacterium tuberculosis

<400> SEQUENCE: 170

ctcaagcttg ggcgtgacgg ccaccggggc cactccgcac aatctgtacc cgaccaagat     60

ctacaccatc gaatacgacg gcgtcgccga ctttccgcgg tacccgctca actttgtgtc    120

gaccctcaac gccattgccg gcacctacta cgtgcactcc aactacttca tcctgacgcc    180

ggaacaaatt gacgcagcgg ttccgctgac caatacggtc ggtcccacga tgacccagta    240

ctacatcatt cgcacggaga acctgccgct gctaaagcca ctgcgatcgg tgccgatcgt    300

ggggaaccca ctggcgaacc tggttcaacc aaacttgaag gtgattgtta acctgggcta    360

cggcgacccg gcctatggtt attcc                                          385


<210> SEQ ID NO 171
<211> LENGTH: 318
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 171

cgggtgtcat tggccaccgg cggcggctgt ccgggaaatg gcgggtcccc ggtggttttg     60

ctgaggagtg ctgaaccgta gtcgaagtgg gcggcgtcag actccaccca gccagcaggc    120
```

-continued

```
agcgcgaagc tgaatcctcc aaccgggttg tcgatccgga caggttgggg tgcgtttggg    180

gcaatgacag gtggcggcgg tgcgttcggg tcggccggcg gaggtgctgc gttgggatcg    240

cccggctggg cattcggcgt gttggcggcg gccggtggtg ggggggcaac angtgtcgcc    300

ggtgcgggtg gcgctgca                                                  318
```

<210> SEQ ID NO 172
<211> LENGTH: 443
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 172

```
ncttgatatt ggcgtcaacg gtgtcggcac cggcgtcctg cagttggtag gcctgcagtt     60

tgtgcatcag gccgatgccg cggccctcgt ggccacgcat gtacagcacc acgccgcgcc    120

cctcacgggc gaccatcgcc agcgcggcgt ccagctgagg cccgcaatcg cagcggcgtg    180

acccaaacac atcgccggtc aagcactccg aatgcacccg gaccagcacg tcgtcaccgt    240

cggcgttggg cccggcgatc tcgccgcgga ccagcgcgac atgttccacg tcctcgtaga    300

tgctggtgta gccgatggcg cgaaactccc catgacgagt cggaatccgc gcctcggcga    360

cccgctcaat gtgcttctcg tgcttgcgcc gccattcgat caagtcagca atggtgatca    420

gcgccagacc gtgctcntcg gcg                                            443
```

<210> SEQ ID NO 173
<211> LENGTH: 420
<212> TYPE: DNA
<213> ORGANISM: Mycobacterium tuberculosis

<400> SEQUENCE: 173

```
cataagggcc ggcgtacccg gtaccggccg cgggcctacc acgtgccgga actggaagcg     60

cagtaagccc tcaacgcgcc accgctttgg cccgcgcgcc cggcgtaggc gcatcggcgg    120

tggccgtggg gcggcgcact gcgacctcac cagcggcttt cgagctttgt tcgatcaacc    180

ggccagcatg gtcgaggatg cattcgagac catattcgaa attggtttca tcgggggccc    240

cgatccgatg ccccctccca gttgcgtgag caagcagcgg agtcgtcgcg ggatcgatgg    300

ccacggggtg ttcaatggcg gatggtccgc tgcccgccga ctggctcttg cgggagagcc    360

gatctagcac caccgatccg cgcacgtgga ccgaaaccgc cgagtagatg tcgaaagcgt    420
```

<210> SEQ ID NO 174
<211> LENGTH: 336
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 174

```
cgtccttttc cccaagatag aaaggcagga gagtgtcttc tgcatgaata tgaagatctg     60

gtacccatcc gtgatacatt gaggctgttc cctgggggtc gttaccttcc acnagcaaaa    120

cacgtagccc cttcagagcc nnatcctgag caanatgaac agaaactgag gttttgtaaa    180
```

-continued cgccaccttt atgggcagca accccgatca ccggtggaaa tacgtcttca gcacgtcgca 240
atcgcgtacc aaacacatca cgcatatgat taatttgttc aattgtataa ccaacacgtt 300
gctcaacccg tcctcgaatt tccatatccg ggtgcg 336

<210> SEQ ID NO 175
<211> LENGTH: 264
<212> TYPE: DNA
<213> ORGANISM: Mycobacterium tuberculosis

<400> SEQUENCE: 175
ctcaagcttc atgtccgtac ggctcgggta cgcttccgtc gcagtgtgcg agtgataaat 60
gacgaccggg acctcgtcgg catcttccat agcccgccac accttcagtt gctcaccgga 120
atccaaccgg tagaaggtcg gcgagcgctc ggcattggtc atcgggatat gccgctcggg 180
acggtcagag ccctcgggtc cggccagcac tccgcaggct tcgtcggggt ggtcgcgaca 240
cgcatgggcc accatcgcat tcac 264

<210> SEQ ID NO 176
<211> LENGTH: 325
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 176
ncgccgccag ccaccacgcg cgggtcgggc gccgggcccg ggccgccagg ctgctccgct 60
cggtgatggc acgccaccgc gacaccaccc ggctgcgcta cgtcgagcca taccgggcgg 120
agctacatcg gctcggccgc ccagtgttcg ggccctcttt cgaggtcgag gtcgataccg 180
atttgcgcat ccgcagccgc accctggacg acagaaccgt gccctacgan tgcttgtcgg 240
gcggggccaa agaacagctt ggcatcctgg cgcgattggc cggcgcggcg ctggtctcca 300
aagaagacgc ccttccggtg ctgat 325

<210> SEQ ID NO 177
<211> LENGTH: 243
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 177
cgccacgttc atgggcaaca accccgatca ccggtggaaa tacgtcttca gcacgtcgca 60
atcgcgtacc aaacacatca cgcatatgat taattcgtcc aattgtataa ccaacacgtt 120
gctcaacccg tcctcgaatt tccatatccg ggtgcggtag tcgccctgct ttctcggcat 180
ctctgatagc ctgagaagaa accccaacta aatccgctgc ttcncctatt ctccagcgcc 240
ggg 243

<210> SEQ ID NO 178
<211> LENGTH: 430
<212> TYPE: DNA
<213> ORGANISM: Mycobacterium tuberculosis

<400> SEQUENCE: 178

-continued atactcaagc ttcaaccgat tgacgcattg tgcgaactga cggcgcccgc gcatggccaa 60
tccggaagac catcattggc cagtggccgg gcgctaacag gttccagccc cccaccagtg 120
ccgctcgaac atgcggtgca acccattcgc aggccggcag ggaaagcacc gcggaagccg 180
caaagggctg cagttccgcg cccaatagtg tcgtccgcaa ccagatgcgc tcgaaaaccg 240
cgccggcagt cagcgcaccc gacgcgaggt cgagagacgt cgtcagcgcg cccacatggg 300
gtgccaatcg gcacggcagg taggccgcgc gcaacccgaa cgcgtggtgc atgcccacgg 360
tccgcaggag gcgcagcacc cgccaatgcc gaagcccacg aaacatcggg cgcatccacg 420
cttcaacctc 430

<210> SEQ ID NO 179
<211> LENGTH: 448
<212> TYPE: DNA
<213> ORGANISM: Mycobacterium tuberculosis

<400> SEQUENCE: 179
agcttttggc agggtctcct tcgaattcgg cgtgcaccgc tatgggttgc agcagcggct 60
ggcgccgcac accccactgg cccgggtgtt ttcgccccga acccggatca tggtgagcga 120
aaaggagatt cgcctgttcg atgctgggat tcgccaccgc gaggccatcg accgattact 180
cgccaccggg gtgcgagagg tgccgcagtc ccgctccgtc gacgtctccg acgatccatc 240
cggcttccgc cgtcgggtgg cggtagccgt cgatgaaatc gctgccggcc gctaccacaa 300
ggtgattctg tcccgttgtg tcgaagtgcc tttcgcgatc gactttccgt tgacctaccg 360
gctggggcgt cggcacaaca ccccggtgag gtcgtttttg ttgcagttgg gcggaatccg 420
tgctctgggt tacagcccga atcgtcac 448

<210> SEQ ID NO 180
<211> LENGTH: 380
<212> TYPE: DNA
<213> ORGANISM: Mycobacterium tuberculosis

<400> SEQUENCE: 180
atactcaagc tttgtcacac caactgtttc caccaggcgc tccatccggc gagtggatac 60
tcccagcagg tagcaggtcg ccaccacgct ggtcagtgcg cgttcagctc gcttgcggcg 120
ctgcagcagc cagtccggga aatagctgcc ctggcgcagc ttggggatcg cgacttctat 180
ggttgcggca cgggtgtcga aatcacggtg gcggtagccg ttgcgctgat tggaccgctc 240
atcgctgcgt tcgcggtagc ccgccccgca cagggcgtcg gcttcagccc ccatcaaggc 300
ggcgatgaac gtcgagagca gcccgcgcag cagatccggg ctcgcctgtg cgagttggtc 360
agccagaacc tgctcggtgt 380

<210> SEQ ID NO 181
<211> LENGTH: 532
<212> TYPE: DNA
<213> ORGANISM: Mycobacterium tuberculosis

<400> SEQUENCE: 181
ccttaagccc cgcagggccc ggcacgcgcg gtaccgccca ggtcgcccaa cagatcgtcg 60
atgttcgcgt cgtccgcctc gcgcacgtgg tctgtcacca gtcaacgtta acgccgccgc 120
acatgtcctg cggccgggca aaaacgtgaa aaacgagcgg gcgactgcaa tgtcatgaca 180
ccgacggccg ccgatgggcc cagggtctgg cagattcgat ctgtgcggcc agtgccagca 240

-continued gcgtcgcctc gtcatacggc cggccgacga gttgaaccga catgggcagg ccgtcgccgt 300
cgaagtccca cggcaccacg gccgcgggct ggccggtcag attccagact tgaaagtacg 360
gaacccgctg caccaccagc agcaacgtcg aaactgcacc ccggcgttgg taggcgccga 420
tgcgggacgg gccggtcgcg gcgcctggcg tcacaactac gtcgacatcg tcgaagatcg 480
actggatcgg ctgctcacac cactcggcgg ccgcaggccg ccatccgccg tc 532

<210> SEQ ID NO 182
<211> LENGTH: 477
<212> TYPE: DNA
<213> ORGANISM: Mycobacterium tuberculosis

<400> SEQUENCE: 182
agctttttga gcgtcgcgcg gggcagcttc gccggcaatt ctactagcga gaagtctggc 60
ccgatacgga tctgaccgaa gtcgctgcgg tgcagcccac cctcattggc gatggcgccg 120
acgatggcgc ctggaccgat cttgtgccgc ttgccgacgg cgacgcggtg ggtggtcaag 180
tccggtctac gcttgggcct ttgcggacgg tcccgacgct ggtcgcggtt gcgccgcgaa 240
agcggcgggt cgggtgccat caggaatgcc tcaccgccgc ggcactgcac ggccagtgcc 300
gcggcgatgt cagccatcgg gacatcatgc tcgcgttcat actcctcgac cagtcggcgg 360
aacagctcga ttcccggacc gcccagcgca ttggtgatgg aatcggcgaa cttggccacc 420
cgctgggtgt tgacatcctc gacggtgggc aattgccccc ggtaacgttt gccgcct 477

<210> SEQ ID NO 183
<211> LENGTH: 461
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as “n”

<400> SEQUENCE: 183
cggtccgacc ctgttcgacg gctacctgaa tcaacccgat gccaccgccg cggcgttcga 60
cgccgacagc tggtaccgca ccggcgacgt cgcggtggtc gacggcagtg ggatgcaccg 120
catcgtggga cgcgagtcgg tcgacttgat caagtcgggt ggataccggg tcggcgccgg 180
tgaaattgaa acggtgctgc tcgggcatcc ggacgtggcg gaggcggcag tcgtcggggt 240
gcccgacgat gatctaggcc agcggatcgt tgcctacgta gtcggctcag cgaatgtcga 300
tgcggacggg cttatcaact ttgttgccca acaactttcg gtgcacaagc gcccgcgcga 360
ggtgcgtatc gtanatgcgc tgccgcgcaa cgccttgggg aaagtgctcc agaacattgc 420
tgtcagaagc tganctacgc gaattatcgt gttacgctgg a 461

<210> SEQ ID NO 184
<211> LENGTH: 440
<212> TYPE: DNA
<213> ORGANISM: Mycobacterium tuberculosis

<400> SEQUENCE: 184
atactcaagc ttgccgaagt tccgatgggt cgcgccggcg agcccagcga agtcgctacc 60
gtggccgtgt tcttggcttc ggatctatcc tcgttcatga ccggcaccgt gttggacgtg 120
actggcggcc ggtccatatg acaccgagat cattgccacg gtacggcaat tcgtcaagaa 180
ggaaatcttt cccaatgcac cggccctcga acgtggcaac agctacccgc aagaaatcgt 240

-continued

```
cgatcggctg ggtgttattg gcttgctcgg tcgccggctg caagggtatc gacaccaccg    300

agttcattct cgggcgtgcc ggcgcattcg agctggcggt gcgcgctgcc cagcaccgtc    360

ataggtactt gacgatggtc cacgtcggac gagcgcctcc acgtcgctgc cgaacggtat    420

gcatggcggc tacgattctc                                                440


<210> SEQ ID NO 185
<211> LENGTH: 515
<212> TYPE: DNA
<213> ORGANISM: Mycobacterium tuberculosis

<400> SEQUENCE: 185

cggtgtcggc accggcgtcc tgcagttggt aggcctgcag tttgtgcatc aggccgatgc     60

cgcggccctc gtggccacgc atgtacagca ccacgccgcg cccctcacgg gcgaccatcg    120

ccagcgcggc gtccagctga ggcccgcaat cgcagcggcg tgacccaaac acatcgccgg    180

tcaagcactc cgaatgcacc cggaccagca cgtcgtcacc gtcggcgttg ggcccggcga    240

tctcgccgcg gaccagcgcg acatgttcca cgtcctcgta gatgctggtg tagccgatgg    300

cgcgaaactc cccatgacga gtcggaatcc gcgcctcggc gacccgctca atgtgcttct    360

cgtgcttgcg ccgccattcg atcaagtcag caatggtgat cagcgccaga ccgtgctcat    420

cggcgaacac cgcaattcat cggtgttgcg ccatcgagcc ctcatctttt tggctgacga    480

tctcgcaaat cgcccccgcg ggttgcagcc ggcat                               515


<210> SEQ ID NO 186
<211> LENGTH: 345
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 186

atactcaagc tttgggtgaa agccgatcac cggaagccgc atgatcagcc acgtttcgcg     60

ccgcccggca tacggcggcg taccgatctc cgcgtcatac acccgcgggt aatcgccgac    120

ggtgccggtt cgcgagccga aggtgacgac gctgattgaa tcgagttcca ggtccagcgg    180

gtggcgcagc aacggcgcga gctcaacgac gtcaatcacg ttgtcgcttt ctacggtcac    240

cgacccggtg accgtnctcg cccggtgcgc tcggccgata agttgcaccg ccaccaccgc    300

gacaccgtct tgcacgcgga cccacccccg gatccgttgt tggcc                    345


<210> SEQ ID NO 187
<211> LENGTH: 366
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 187

agcttgctgg catccgctcc agtagcgccc cgcgcgtggc ttccagcgcc cgcagatgct     60

ccatgagccg gccggtcgag tcggcgccgg cgttcaccgc cacccgccag gagctggcgg    120

ccagcatctc cgccttcacg cattgcgcga tcacagagag aatatacgtc tcatattcgt    180

tggaggtcgt cgcaggcaat cggtcgatga cggatttgat ggcatcgagc tgtgcttcgg    240
```

-continued

```
cgtagccctc cagcacgtcg gtatcgctgt ggcggtccac gacgaccgca ccggcgcggc    300

ggacagccgt cgggttggac gntgtgcggc gatcagtccg gccagctccg cctcgggatc    360

agcggc                                                               366


<210> SEQ ID NO 188
<211> LENGTH: 423
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as “n”

<400> SEQUENCE: 188

atactcaagc ttgctgcagc ttcctatgac tgctcccgaa acctgggggt gtgcctgctg     60

tgtatgcacg gcatacggac atccttcccc tgagacccgc ggtcgaacca gccacgtgtc    120

catcatcagg ggtcaacccc ggccaagggc gacggcacgc caagttcgcc gaccgttaac    180

ctagtgctgt tagcttcatt tgctgcgagc aaaacagctg gtcggccgtt aggaactgaa    240

ttgaaactca accgatttgg tgccgccgta ggtgtcctgg ctgcgggtgc gctggtgttg    300

tccgcgtgtg gtaacnacna caatgtgacc gggggaggtg caaccactgg ccaggcgtcg    360

gcgaaggtcg attgcggggg gaagaagaac tcaaagccag tgggtcgacg cgcaggccaa    420

cgc                                                                  423


<210> SEQ ID NO 189
<211> LENGTH: 453
<212> TYPE: DNA
<213> ORGANISM: Mycobacterium tuberculosis

<400> SEQUENCE: 189

agcttgacgc ggagacggac acattgcgaa cattgatgac aaaatagaaa tcattgatgg     60

tttgagtcac caggccgatc aagccttcgc cgagccaaat tccaatcaag aggcccaagc    120

ccgtaccaat cagcccggca acgagggatt ccgtcattat cagccaaaat aactgctctc    180

gggttacacc caaacagcgc aatatggcga aaaacggtcg ccgttgcacg acattaaatg    240

tcacggtatt gtagattaaa aagataccca ccaacaaggc aatcaaactg agagcggtta    300

aattgaccgt aaaagcgtcc gtcatctgtt tgacggtgtc ccgttgggta tccgacgttt    360

ccatacgcac accggccggc agtctttgtt ggatgcgtgt tgcagtggcc tcatctttga    420

tgatcaaatc gatgtggctc agtcttccgg gca                                453


<210> SEQ ID NO 190
<211> LENGTH: 402
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as “n”

<400> SEQUENCE: 190

atactcaagc ttcggctcag gcggcgctgc tggtaaagtc gctgaccggt gcaggtttcg     60

acaatgtggt gccggttcgg cggctacgtg ccatcgagac actggcgcag gctatcgcac    120

ccgttatcgg ctacgagcaa atcgcggtat gcgttcttga gcatgagtcg gcgaccgtcg    180
```

```
tcatggtcga cacccacgac ggaaagacgc agatcgccgt caagcatgtg tgccgcggat    240

tatcaggact gacctcctgg ctgaccggca tgtttggtcg cgatgcctgg cgcccggccg    300

gcgtggtcgt ggtccgctcg gatagcgagg tcagcgaatt cncntggcag ctccaaaggg    360

tcctgccggt gccggtcttt gcgcaaacna aggcncaggt ta                       402
```

<210> SEQ ID NO 191
<211> LENGTH: 427
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 191

```
tgatcgcgca tcacctgctt cataaactgg aagcagcgca gcgcttcctt ttcggccgca     60

acatgagcca gcctctcgtc ggcggtcggg tgcaggtgct cgggcagctc ggccgcgaca    120

gccgcctgac cctgaaacca gcttccatat cccgcgacga acgacgccag tccgctacgt    180

aacccctccg cgactgtcca tggacaacag cgcgttctcc accgaccggg cccgggtgtg    240

gggtgtttcg gcgaccggca gccaggtggt ccacactgcc gacgggcgcc gcgagccgtt    300

caccgaccag gccgccgagc aagtccgccc gatcgcatac tccaaccggt tgcggtactg    360

caggttcagc tggcgtactc ctcgtcgcgc tcggcgaggt cttgctccag cacgtcgcan    420

acggcag                                                              427
```

<210> SEQ ID NO 192
<211> LENGTH: 347
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 192

```
caaagcgcga actgctcgcg gcagcccacg acgtgctgcg tcggattgcc ggcggcgaaa     60

tcaattccag gcagctcccg gacaatgcgg ctctgctggc ccgcaacgaa ggactcgagg    120

tcaccccggt gcccggggtc gtggtgcacc tgccgatcgc acaggttggc ccacaaccgg    180

ccgcttgatg cccggtcggc aagcccggca gttgccaaac ccagcgtgat caggctcggc    240

tcgcgagttc cgggaagaag tggctccgcc tgatcaccta ccatccgcca ggatctgcgt    300

gtcttcacca cgcccgccaa ggaggttgtt gtggtgctat cgaccgn                  347
```

<210> SEQ ID NO 193
<211> LENGTH: 330
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 193

```
ccggaagccg catgatcagc caagtttcgc gccgcccggc atacggcggc gtaccgatct     60

ccgcgtcata cacccgcggg taatcgccga cggtgccggt tcgcgagccg aaggtgacga    120
```

-continued

```
cgctgattga atcgagttcc aggtccagcg ggtggcgcag caacggcgcg agctcaacga    180

cgtcaatcac gttgtcgctt tctacggtca ccgacccggt gaccgtngtc gcccggtgcg    240

ctcggccgaa aanttgcacc gccaccaccg cgaaaccgtc ttgcacnccg gaagccaccc    300

ccgatccgtt gttgggccag gttattgggt                                      330
```

<210> SEQ ID NO 194
<211> LENGTH: 215
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 194

```
ccggaaccgc cgacggcacg gtataacgcc tccgcatatg ggtcgacaac cagcgggtcg     60

gacttctggg cttctagcgt tcgcgcngtc gcgacaaaca gcgcggtcga accgacactc    120

gttgtgatgt cctagctatc acgttcggta cgcacccaat cgagtctagc gcgggtagnt    180

cagccccgat ctccangctc cgccgagcca ggcgc                                215
```

<210> SEQ ID NO 195
<211> LENGTH: 225
<212> TYPE: DNA
<213> ORGANISM: Mycobacterium tuberculosis

<400> SEQUENCE: 195

```
ctggtttatg tcccgttgaa gttccatcac ccgatgtggc gggagcactg ccaggtcgat     60

ctcaactacc acatccggcc gtggcggttg cgcgccccgg ggggtcggcg cgaactcgac    120

gaggcggtcg gagaaatcgc cagcaccccg ctgaaccgcg accacccgct gtgggagatg    180

tacttcgttg aggggcttgc caaccaccgg atcgcggtgg ttgcc                     225
```

<210> SEQ ID NO 196
<211> LENGTH: 161
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 196

```
ccgagcagtt gggaatcgct ctgcancaaa ccaatattct gcgcgacgtc gcgcgacgag     60

ctggaccgat taggcgtacg cctccgnctg gacgacaccg gggcactcga tgaccccgac    120

gcctacgctc gcaggatatt gttcgccgga cccctctcta g                         161
```

<210> SEQ ID NO 197
<211> LENGTH: 240
<212> TYPE: DNA
<213> ORGANISM: Mycobacterium tuberculosis

<400> SEQUENCE: 197

```
tatataatac tcaagcttgc cgacgccaac gctcgcgcga tgttgttagc ccgacccggc     60

tcttacatgg caccggtgcc ccacacgtca gcctgtgacg tcctgcaccg cgactcttta    120

catagaatgt ggattgccgg attggggatg tccggcatcg ctcaatctgt agtccgcgtt    180

gtcccgcgag ggccatgtgg atggggggaa ggatccgtgg cgtccgggat caccatgggg    240
```

-continued

<210> SEQ ID NO 198
<211> LENGTH: 348
<212> TYPE: DNA
<213> ORGANISM: Mycobacterium tuberculosis

<400> SEQUENCE: 198
atactcaagc ttgccgaagt tccgatgggt cgcgccggcg agcccaacga aatcgctagc 60
gtggccgtgt tcttggcttc ggatctatcc tcgtacatga ccggcaccgt gttggacgtg 120
actggcggcc ggttcatatg acaccgagat cattgccacg gtacggaaat tcgtccagaa 180
ggaaatcttt cccaatgcac cggccctcga acgtggcaac agctacccgc aagaaatcgt 240
caatcggctg ggtgttattg gcttgctcgg tcgccggctg cgagggtttc tacaccaccg 300
agttcattct cgggcgtgcc ggcgcattcg aactggcggt gcgcgctg 348

<210> SEQ ID NO 199
<211> LENGTH: 371
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 199
gcaccggcgt cctgcagttg gtaggcctgc agtttgtgca tcaggccgat gccgcggccc 60
tcgtggccac gcatgtacag caccacgccg cgcccctcac gggcgaccat cgccagcgcg 120
gcgtccagct gaggcccgca atcgcagcgg cgtgacccaa acacatcgcc ggtcaagcac 180
tccgaatgca cccggaccag cacgtcttca ccgtcggcgt tgggcccggc gatctcgccg 240
cggaccaacg cgacatgttc cacgtcctcg tagatgctgg tgtagccgat ggcgcgaaac 300
tccccangac aagtcggaat ccgcgcctcg gcgaaccgct caatgtgcct ctcgtgcttg 360
cgccgccatt c 371

<210> SEQ ID NO 200
<211> LENGTH: 165
<212> TYPE: DNA
<213> ORGANISM: Mycobacterium tuberculosis

<400> SEQUENCE: 200
tggtccgtgt gcgcatacca atacaacgcg ccgggcacct gacgcggcgg ccgcaaccaa 60
tcggtggcca tcgccatctt ctgctacccg gtcaacggac gcaccttctc ctggccgacg 120
tagtgcgccc acccgccgcc gttgcgtccc atcgatccgg tcaac 165

<210> SEQ ID NO 201
<211> LENGTH: 390
<212> TYPE: DNA
<213> ORGANISM: Mycobacterium tuberculosis

<400> SEQUENCE: 201
ggcgtgttgg ccaccggggc cactccgcac aatctgtacc cgaccaagat ctacaccatc 60
gaatacgacg gcgtcgccga ctttccgcgg tacccgctca actttgtgtc gaccctcaac 120
gccattgccg gcacctacta cgtgcactcc aactacttca tcctgacgcc ggaacaaatt 180
gacgcagcgg ttccgctgac caatacggtc ggtcccacga tgacccagta ctacatcatt 240
cgcacggaga acctgccgct gctaaagcca ctggcgatcg gtgccgatcg tggggaaccc 300

-continued actggcgaac ctggttcaac caaacttgaa ggtgattgtt tacctgggct acggcgaccc 360
ggcctatggt tattcgacct ccccgcccaa 390

<210> SEQ ID NO 202
<211> LENGTH: 427
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 202
cgtccgtgnc ccctcaancg cgtgnngccg aagcggctgg ttacgactcc ctgtttgtga 60
tggacacttc taccaactgc ccatgttggg gacgcccgac cagccgatgc tggaggccta 120
cacggccctt ggtgcgctgg ccacggcgac cgancggctg caactgggcg cgttggtgac 180
cggcaatacc taccgcagcc cgaccctgct ggcaaagatc atcaccacgc tcgacgtggt 240
tagcgccggt cgagcgatcc tcggcattgg agccggttgg tttgagctgg aaacaccgcc 300
agctcggctt cgagttcggc actttcagtg accggttcaa ccggctcgaa gaggcgctac 360
agatcctcca gccaatggtc aagggtgagc gcccaacgtt tttcggcgat tggtacacca 420
ccgaatc 427

<210> SEQ ID NO 203
<211> LENGTH: 498
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 203
ccgcttccgt gtaaccgagc anngcgagcg anctggcgag gaagcaaaga agaactgttc 60
tgtcagatag ctcttacgct cagcgcaaga agaaatatcc accgtgggaa aaactccagg 120
tagaggtaca cacgcggata gccaattcag agtaataaac tgtgataatc aaccctcatc 180
aatgatgacg aactatcccc cgatatcagg tcacatgacg aagggaaaga gaaggaaatc 240
aactgtgaca aactgccctc aaatttggct tccttaaaaa ttacagttca aaaagtatga 300
gaaaatccat gcaggctgaa ggaaacagca aaactgtgac aaattaccct cagtaggtca 360
gaacaaatgt gacgaaccnc cctcaaatct gtgacagata accctcagac tatcctgtcg 420
tcatggaagt gatatcgcgg aaggaaaata cgatntgagt cgtctggcgg cctttctttt 480
tctcaatgta tgagagcg 498

<210> SEQ ID NO 204
<211> LENGTH: 265
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 204
tgacacccaa cagagggcac ttaagatggc aatgcggccg cctacctgca cgttttcgcg 60

-continued atgtcagagg atgccgaggg agaacaatgc gagcacggcc gctgacnttg ctcaccgctt 120
tggcggcggt gacattggtg gtggttgcgg gctgcnaggc ccgantcnag gccgaagcat 180
atagcgcggc cgaccgcatt tcgtctcgac cgcaagcgcg acctcagccg cagccggtgg 240
agctactgct gcgcgccatc acgcc 265

<210> SEQ ID NO 205
<211> LENGTH: 369
<212> TYPE: DNA
<213> ORGANISM: Mycobacterium tuberculosis

<400> SEQUENCE: 205
acgggcgacg ctgaggtggg cccgcggcta ttcatgctgt cgtccacgtc cagcgacgca 60
ctgcgccaga cggcccgcca actagccacc tgggtggaag aacaccagga ctgcgtggcg 120
gcctcggatc tggcctacac gctggcgcgt ggccgcgcgc accggccggt gcgcaccgcg 180
gtggttgccg ccaacctgcc ggagctcgtc gagggtttgc gcgaggtggc cgacggtgac 240
ccctctatga cgcggcggtg ggacactgtg atctaagacc ggtctgggtc ttctccgggc 300
aagggtctca gtgggcggcg atgggcaccc aattgctcgc cagcgaacca gtgttcgcgg 360
ccaccatcg 369

<210> SEQ ID NO 206
<211> LENGTH: 428
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as “n”

<400> SEQUENCE: 206
atactcaagc ttcgcgagat ccggatggca ctcacgctgg acaagacctt cacaaaatct 60
gaaatcctga cccgatactt gaacctggtc tcgttcggca ataactcgtt cggcgtgcag 120
gacgcggcgc aaacgtactt cggcatcaac gcgtccgacc tgaattggca gcaagcggcg 180
ctgctggccg gcatggtgca atcgaccagc acgctcaacc cgtacaccaa ccccgacggc 240
gcgctggccc ggcggaacgt ggtcctcgac accatgatcn aaaacttccc ggggaggcgg 300
aggcgttgcg tgccgcccag ggcgaaccgc tgggggttct gccgcagccc aatgattgcc 360
gcgcggctgc atcgcgggcg gcgaccgcca ttcttctgcg aatacgtcca ggagtactgt 420
ctcggggc 428

<210> SEQ ID NO 207
<211> LENGTH: 378
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as “n”

<400> SEQUENCE: 207
agcttatgtg gccgcccacc taccttatct agcctagcta actaaatcca gtgccgacag 60
tgcgcggctg gccacccagc atgaggttat gaccacggca tatgccagcg cgctggcggc 120
gatgccgacg ctgaccgagt tggccgctaa tcacaccagc catgcggtgt tgctgggaac 180

-continued gaatttcttt ggaatcaata cgatcccgat cgcgctcaat gaggccgact atgcgcggat 240
gtggattcag gcggccacca cgatgagtat ctatgagggc acctccgatg cggcgctggc 300
gtcngcaccg caaaccacac cggctccggt actgttcaac ggcggtgctg gcgtttgcca 360
gcgcctgccg gcgatctc 378

<210> SEQ ID NO 208
<211> LENGTH: 284
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 208
atactcaagc ttgccaccca tgccgagcaa ggtcgactca gcgatgacga attgttcttc 60
ttcgcggtgt tgctgctggt tgcgggctat gagagcactg ctcatatgat tagcacnttg 120
tttctgacgc tggccgacta tccagatcag ctgacactcc ttgcgcagca accagacctg 180
atcccgtcgg cgatcgagga gcacctccgc tttatatcgc aatccaaaac atctgccgca 240
caacgcgcgt cgactattcg gtcggtcaag cggtcatccc ggga 284

<210> SEQ ID NO 209
<211> LENGTH: 236
<212> TYPE: DNA
<213> ORGANISM: Mycobacterium tuberculosis

<400> SEQUENCE: 209
ccggggtaga acgatgcgat ctgggccatg tcgacatcgg tggtacaggt aaaccgcgcc 60
gtgtgcgcgg tctcggagat cagaacgtgg tcgcagttga caccgcgggc tttcagccag 120
tcgcgataat cggcgaagtc ggcgcctgcc gccccaacta gcgcgacctc gccacctagc 180
acaccgatgg cgaaggccat gtttccggcc acgccgccgc ggtgcatcat caactc 236

<210> SEQ ID NO 210
<211> LENGTH: 278
<212> TYPE: DNA
<213> ORGANISM: Mycobacterium tuberculosis

<400> SEQUENCE: 210
atactcaagc ttggcggcaa cgccactacc gggctcacca ggtcctgtgc cgccaccgcc 60
ggcgccgaaa gcaccatcag gtcgtagttg tctggacgtt cgacaccgta agcgaacaca 120
atgccgccgc ccatgctgtg cccgagcacg atgcgcttgc acccgggata ttcccgggtg 180
gcgatcccaa cgagggtgtc gaagtcagcg gtgtatctga gatgtctctc actatcatcc 240
gtttggcacc cgagcgggca tgcccgcggg gggtcaac 278

<210> SEQ ID NO 211
<211> LENGTH: 360
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 211
gtcgacggca tcaaggtccg cagtgatggt gttcatctca cccaggaagg cgtgaagtgg 60
ctgataccgt ggcttgagga ttcggtgcgg gtcgccagtt aatccgccgt gtgctccgga 120
tgagcgcgac ggtaaccctg gaattgtgct gtgtgctggc tgtgtcgttg tgatgagcct 180
gtctaagtgg tgcgtaaccg tttgacgagc cgcggcctcg ctgcaaacat tgaagcccgc 240
acgtctgggt ttgtatttac acaacgaggg cgctccccga tctggcgcgc gcaacgaggt 300
gcncactatc cattcgaggt gaactggact ccttgatgct catgccggtg cggttttgtc 360

<210> SEQ ID NO 212
<211> LENGTH: 256
<212> TYPE: DNA
<213> ORGANISM: Mycobacterium tuberculosis

<400> SEQUENCE: 212
atactcaagc ttgcgttcga tgaagtagtc gtcggtcagc gccgcctctt cgagctcctt 60
ggcgatgccc agcaaggagt catcgccgcc gagcttggcc aggatcttgt cggcctgttc 120
cttgacgatg cgggcccgcg gatcgtagtt cttgtagaca cgatgaccga aacccatcaa 180
tttgaccccg gcctcgcggt tcttgacctt gcgttacaaa ctcgctgacg tcgtcgccgc 240
tgtcgcgaat gccctc 256

<210> SEQ ID NO 213
<211> LENGTH: 262
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 213
ngtcaagccg agcatgcgcg aggnaacgac gaacccaaca agccatggtg gttggcgccg 60
tcgagaggtc ggcggtcgcc acaacgggaa gatcgccttg agcgtcgctc gaccgccgcc 120
tcgagttggg tcataacgaa gtagctgatg ccgatcatgt cgacgtttcc gtcgcatcag 180
cgtgcagcgg cgacccactc gacgaggtct cggtgccgcc gcggccaggg caccagcagt 240
gacgattcca ggcgccgtcg gg 262

<210> SEQ ID NO 214
<211> LENGTH: 336
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 214
cgataatcgc ttccggtaag tgcagcagct ttacgacggc gactcccatc ggcaatttct 60
atgacaccag atactcttcg accgaacgcc ggtgtctgtt gaccagtcag tagaaaagaa 120
gggatgagat ctccccgtgc gtcctcagta agcagctcct ggtcgcgttc attacctgac 180
catacccgag aggtcttctc aacactatca ccccggagca cttctagagt aaacttccca 240
tcccgaccac atataggcta aggtaatggg cattaccgcg agccattact cctacgcgcg 300
caattaacga atccaccatc ggggccgctg gtgtcn 336

<210> SEQ ID NO 215

-continued

<211> LENGTH: 259
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 215
naatactcaa gctttctcgt gattaccacc cgtgtaattt gggatgggca aaaaggcgaa 60
tcaccgcgtg gccacaaacg ccgggaggga caatctcggg cggctagggc ttctcgcggg 120
aaggcccgaa cgtacggcgt ttcaacacgt cgcgtcgccc tccgaccgcg aacattcggg 180
gatggcagca acctggtatc accctggccg ggcaatgatc tgcagcgtcg ccgcgggtag 240
tgnccgcccg ggcggctac 259

<210> SEQ ID NO 216
<211> LENGTH: 325
<212> TYPE: DNA
<213> ORGANISM: Mycobacterium tuberculosis

<400> SEQUENCE: 216
ccaactagag catcgggaca tacggagtca actacccggc caacggtgat ttcttggccg 60
ccgctgacgg cgcgaacgac gccagcgacc acattcagca gatggccagc gcgtgccggg 120
ccacgatgtt ggtgctcggc ggctactccc agggtgcggc cgtgatcgac atcgtcaccg 180
ccgcaccact gcccggtctc gggttcacgc agccgttgcc gcccgcagcg gacgatcaca 240
tcgccgcgat cgccctgttc gggaatccct cggggccgcg ctggcgggct gatgatcgcc 300
ctgacccctc aattcgggtc caaga 325

<210> SEQ ID NO 217
<211> LENGTH: 300
<212> TYPE: DNA
<213> ORGANISM: Mycobacterium tuberculosis

<400> SEQUENCE: 217
atactcaagc ttgctgcagc ttcctgtgac tgctcccgaa acctgggggt gtgcctgctg 60
tgtatgcacg gcatacggac atccttcccc tgagacccgc ggtcgaacca gccacgtgtc 120
catcatcagg ggtcaacccc ggccaagggc gacggcacgc caagttcgcc gaccgttaac 180
ctagtgctgt tagcttcatt tgctgcgagc aaaacagctg gtcggccgtt aggaactgaa 240
ttgaaactca accgatttgg tgccgcccgt aagtgtcctg gctgccggtg cgctggtgtt 300

<210> SEQ ID NO 218
<211> LENGTH: 265
<212> TYPE: DNA
<213> ORGANISM: Mycobacterium tuberculosis

<400> SEQUENCE: 218
agcttgcgcg gcgtggcgat cgcggttcaa ggcgcgctct tcgagcacaa cgagcgaaga 60
cagctcggcg acggagcctt tatcgacatc cgttcgggct ggctgaccgg cggcgaagaa 120
ctgctggacg cgttgttgtc gacggtgccg tggcgagccg agcgccgtca gatgtacgac 180
cgggtggtcg atgtgccgcg gctggtgagt tttcacgacc tgaccatcga agatccgccg 240
catccgcagc tggcgcggat gcgcc 265

<210> SEQ ID NO 219

-continued

<211> LENGTH: 362
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 219
aatactcaag cttgcgcacg accaggacgt cgagtggcgc ttgcagtgac ttggcgacct 60
caaaggccac cggtaccccg ccgcgcggca agccaaggac nacnacggcc ttgccggata 120
gctgcgccag gcgttgcgcc aactggcgtc cagcgtcgcc acgatcgtca aagagcttca 180
tctgccgagt gtgtcgccat ctcatggctc caaatatgga attaggtccc tgggccgact 240
gacgacagtc cctcagcgac cggattgcgc atcccgcctt gtacgctgct ccgcaaatcc 300
cgggcttgcg tccgcggaag cgaactcggc ggcgctacgg tggtggctca cttcggccgt 360
gc 362

<210> SEQ ID NO 220
<211> LENGTH: 486
<212> TYPE: DNA
<213> ORGANISM: Mycobacterium tuberculosis

<400> SEQUENCE: 220
ggttggtgcg gtccaccttc gcggcggcgg cgcgatatgc cttgctggtc ttgctcattt 60
gatatccaat ctatgggtcg tggttactca gcgggccgaa gctggccctc ccacgggtag 120
ggccctattc gacggtgatg cccatcgacc gagcggtacc ggcgatgatc ttggccgcag 180
cgtcgacgtc gttggcgttg aggtccgtct tcttggtctc ggcgatttcg cggacttgat 240
cccaggtgac tttggcgacc ttggtcttgt gcggctccgc cgaacccttc gccacaccag 300
cggccttaag cagcagcttg gcggcgggcg gcgtcttcag cgtgaaagtg aagctacggt 360
cttcataaac ggtgatctcc accgggatga cgttgccgcg ctggttctcc gtcgcggcgt 420
tgtacgcctt gcagaactcc atgatgttga cccgtgctga ccgaacgcgg ggcccactgg 480
cggggc 486

<210> SEQ ID NO 221
<211> LENGTH: 373
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 221
atactcaagc ttttcgaccc gcaagccggc ggtgcccctc ctcgttccgc tgcccggtct 60
gctcgatcgg ttcggggtcg ccgcgctagg cccaattgcc cggctcctcc tcgggccgtt 120
ccacaacccg catcgtcgcc gggctaggtt caagccatgc cggtaaaccc caggacgcca 180
gtgctgatcg gctatggaca ggtcaaccac cgaggcgaca tcgacgccna aaatcagtcc 240
atcgaacccg tcgacctgat ggccnccgcg gcccggaaag ccgccgagtc caccgtgctc 300
gaagcggtgg attccatccg tgtggtgcac atgctgtcgg cgcattaccg gaattcccgg 360
gcgtctcctc ggc 373

-continued

<210> SEQ ID NO 222
<211> LENGTH: 331
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 222
ncctggttca tgaactggaa gcagcgcagc gcttcctttt cggccgcaac atgagccagc 60
ctctcgtcgg cggtcgggtg caggtgctcg ggcagctcgg ccgcgacagc cgcctgaccc 120
tgaaaccagc ttccatatcc cgcgacgaac gacgccagtc cgctacgtaa cccctccgcg 180
actgtccatg gacaacagcg cgttctccac cgaccggggc cgggtgttgg ggtgttcggc 240
aacggcaacc aagttggtcc acactgccga cgggcgccgc aaatccgttc accgaaccag 300
gccgccnaaa caattccgcc cgatcccata t 331

<210> SEQ ID NO 223
<211> LENGTH: 377
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 223
atactcaagc ttgtcgggat caatctcgag ggcatccacg cacgaaaagt aaactctatc 60 aagcttttg acgacaccca cggacgcccc atatatgttc gggtgggcaa gaacggtccc 120
tacctggaac gtttggtggc cggcgacacc ggtgagccca cgccgcagcg ggccaacctc 180
agcgactcga ttaccccgga cgaactgact ctacaggtgg ccgaagagct ctttgccaca 240
ccgcaacagg gacggacttt gggcttggac ccagaaaccg gccacgaaat ctttgccagg 300
ggaaggccgg tttgggcctt atgttaccta tatcctgccg gaacctgcgg ctgatgcggc 360
cgcggccgct cagggan 377

<210> SEQ ID NO 224
<211> LENGTH: 436
<212> TYPE: DNA
<213> ORGANISM: Mycobacterium tuberculosis

<400> SEQUENCE: 224
agcagctagc cgcgctcgcc gcgctggtcg gtgcgtgcat gctcgcagcc ggatgcacca 60
acgtggtcga cgggaccgcc gtggctgccg acaaatccgg accactgcat caggatccga 120
taccggtttc agcgcttgaa gggctgcttc tcgacttgag ccagatcaat gccgcgctgg 180
gtgcgacatc gatgaaggtg tggttcaacg ccaaggcaat gtgggactgg agcaagagcg 240
tggccgacaa gaattgcctg ggctatcgac ggtccagcac aggaaaaggt ctatgccggc 300
accgggtgga ccgctatgcg cggccaacgg ctggatgaca gcatcgatga ctccaagaaa 360
cgcgaccact acgccattca agcggtcgtc ggcttcccga ccgcacatga tgccgaagaa 420
ttctacagct cctccg 436

<210> SEQ ID NO 225
<211> LENGTH: 539
<212> TYPE: DNA

-continued

<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as “n”

<400> SEQUENCE: 225
cgcgactggc tccccggncg gctgctcggg tccgccgata gagaccggga tgtcgcccga 60
cgacgggcag ccgggttgcg tgggacgggg cgggggtcgg gcagcccaag caacgggcta 120
gtccccgaat cctacggagc cgtcacctac gcctacgtaa tagtagctat caataacagt 180
tgacatacgc aacgatctgt gagatcaata ttgcctgacg catgtcaaga caggcgtcaa 240
gacaggtgtc aataattcgc tccgctggtg acggtaaccg gtcgtgcggg tgtgtgacgc 300
ctaaggaagg agtgtgggtg gtgacgctga gagtggttcc tgagggtttg gcggccgcca 360
gtgcggcggt ggaggcgttg accgcacggc tggccgccgc acacgctggc gcggcgccgg 420
cgattacggc ggtggtggcg cccgcggcgg atccggtgtc gttgcagaat gcggtggggt 480
ttagcgcctt aagtagccag catgccgcga tcgccggcga aagggtccaa gaactgggt 539

<210> SEQ ID NO 226
<211> LENGTH: 517
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as “n”

<400> SEQUENCE: 226
atactcaagc ttattgaacc gcgggtcgca ggcaaagtgg acctcataac gactcgggtc 60
cagcgaccgc gccaacacga acggccggac gacgtgggcc agggtcgcgg cctcccctac 120
aaacaggatc cgttgcctgc gaacgacagg ctccggtgcg gcgttgggcg ccgtgctcgt 180
cccagcgtcc ggtcccgggt cgccggcgac gcttgtttcc tccatactcg ccccctaatc 240
tcgaggcagc ccgtacccgc aggcaacctc ccaaaaatgc aatcccgcaa aatgcaatgc 300
gtcnagctat ttctcacacc gaccgctagt tgcggatcag aaatccgttg ggcgcggaag 360
tccagccgaa tttgttctcc cgctccgcat catgcttgta atcgtttgga aattcatcct 420
catatgcctc gatcgcttca tagggtccag gcccaaaccc gggcaggact gggtggccgt 480
tgatgttgga atcctccact actaggtatt caccggc 517

<210> SEQ ID NO 227
<211> LENGTH: 488
<212> TYPE: DNA
<213> ORGANISM: Mycobacterium tuberculosis

<400> SEQUENCE: 227
gtctcgatca tggccaaaga gctcgacgaa gccgtagagg cgtttcggac ccgcccgctc 60
gatgccggcc cgtatacctt cctcgccgcc gacgccctgg tgctcaaggt gcgcgaggca 120
ggccgcgtcg tcggggtgca caccttgatc gccaccggcg tcaacgccga gggctaccga 180
gagatcctgg gcatccaggt cacctccgcc gaggacgggg ccggctggct ggcgttcttc 240
cgcgacctgg tcgcccgcgg cctgtccggg gtcgcgctgg tcaccggcga cgcccacgcc 300
ggcctggtgg ccgcgatcgg cgccaccctg cccgcagcgg cctggcagcg ctgcagaacc 360
cactacgcag ccaatctgat ggcagccacc ccgaagccct cctggccgtg ggtgcgcacc 420

-continued ctgctgcact ccatctacga ccagcccgac gccgaatcag ttgttgccaa tatgatcggg 480
ttctcgac 488

<210> SEQ ID NO 228
<211> LENGTH: 264
<212> TYPE: DNA
<213> ORGANISM: Mycobacterium tuberculosis

<400> SEQUENCE: 228
atactcaagc tttcgtcagt tcatggcgcc agcagaccaa caagagcatc gggacatacg 60
gagtcaacta cccggccaac ggtgatttct tggccgccgc tgacggcgcg aacgacgcca 120
gcgaccacat tcagcaaatg gccagcgcgt gccgggccac gaggttggtg ctcggcggct 180
actcccaggg tgcggccgtg atcaagatct tcaccgccgc accactgccc ggcctcgggt 240
tcacgcatcc gtttggccgc cgcc 264

<210> SEQ ID NO 229
<211> LENGTH: 229
<212> TYPE: DNA
<213> ORGANISM: Mycobacterium tuberculosis

<400> SEQUENCE: 229
gccccgtgta atttgggatg ggcaaaaagc gaagcaccgc gtggccacga acgccgggag 60
ggacaatctc gggcggctag ggcttctcgc gggaaggccc gaacgtacgg cgtttcaaca 120
cgtcgcgtcg ccctccgacc gcgaacattc ggggatggca gcaacctggt agcaccctgg 180
ccgggcgatg atctgcagcg tcgccgcggg tagtctccgc ccgggccgc 229

<210> SEQ ID NO 230
<211> LENGTH: 266
<212> TYPE: DNA
<213> ORGANISM: Mycobacterium tuberculosis

<400> SEQUENCE: 230
atactcaagc ttcctttgac cgaacgcgtc caccgcaccg tgagattggt ggcgccattc 60
gtcgtggtgt agctgctgtt ggcggcgtcg ccgtattgtg cgggccagcc ttgtgcgggg 120
gccgcttcta cccacaagtc ggcacttccg caaccgccca gctcgaccgc gaattacggc 180
ggccgcaacg gccgccggaa ggcgtcacgc aatcgcttat cctttccagg ttcccaaatc 240
ctccgcttac ttgggtcctt catcgg 266

<210> SEQ ID NO 231
<211> LENGTH: 258
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 231
ggcagcggcg acaaccggaa cgtccgcacg gtgctcaatc acgggtgcac ggtgtgcatc 60
agaatggcgg gggttcgttg tcgcggtgag gcgttcggcg aggaggtagt gtctacccct 120
tgcccgcggg ttcgtgcgga ctgaaaggga tttcattggg aacccacggc tgcgtatcgc 180
agggcctcgg tgacgtctgc ttcctcnagc tcaggaagtt cggcgagaat ctcggtggat 240
gttatttggt ccgcctac 258

-continued

<210> SEQ ID NO 232
<211> LENGTH: 224
<212> TYPE: DNA
<213> ORGANISM: Mycobacterium tuberculosis

<400> SEQUENCE: 232
atactcaagc tttctcggct tctctgatag cctgagaaga aaccccaagt taatccgctg 60
cttcacctat tctccagcgc cgggttattt tcctcgcttc cgggctgtca tcattaaact 120
gtgcaatggc gatagccttc gtcatttcat gaccagcgtt tatgcactgg ttaagtgttt 180
ccatgagttt cattctgaac atcctttatt cattgttttg cgtt 224

<210> SEQ ID NO 233
<211> LENGTH: 333
<212> TYPE: DNA
<213> ORGANISM: Mycobacterium tuberculosis

<400> SEQUENCE: 233
atactcaagc ttggtgaccg gcaccgcgat acgttgcggc aggcatctgg gctggcggtg 60
gttcgccgct ccgaagccgt cgaacaccat cgccagcgcg gcttccacat caacgaccat 120
ttcggccagc ttgcggcgca tcagcggctt gtcgatgagc gccccaccga atgcccgccg 180
ctgcccggcg tatcacatcg attcgaccat cgcgcggcgc gcgttgccga gggcgaacga 240
ggcggtgccc aaccgcaatc tgtttggtca gctccctcat gcgggttgat tccttgccgt 300
ccggacgggc ccgcgtcatg cgctcggttc gcc 333

<210> SEQ ID NO 234
<211> LENGTH: 407
<212> TYPE: DNA
<213> ORGANISM: Mycobacterium tuberculosis

<400> SEQUENCE: 234
ccgttgcgca gcgtgagccg atagttgaca tccggctcgg tgaaggtgaa atcgatggcc 60
aggtcgaggt cccatgcgcg tgggccattg atgctgatcg ccaggacgtc aaagatttgg 120
tccggcgtca gctgggcgaa aaacgtgggc gccgggactt gcccggagct gcccgggttc 180
ccgtcgcgca gctcggcggc cccggtcaga aagaaattgc gccaggtcgc acactccgcg 240
ccgtaggcca gctgctccag ggtgtcggca tagagcccgc gggccgcagc gtgctcgctg 300
tcggcgaaca ccgcatggtc gagaagcgtt gccgcccaac gggaaatcac ctgcgtcgaa 360
agcttcgcgg gccagctcca gcactcggtc gatgccaccc aacgcgt 407

<210> SEQ ID NO 235
<211> LENGTH: 389
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 235
atactcaagc ttgcggatgt taccccctgac agcgtgaact atgtcnaaac acacggcacc 60
ggaacggtgt tgggggaccc catcgagttc gagtcgctgg cggccactta tggcctgggt 120
aaaggccagg gcgagagccc gtgcgcattg ggtcggtca aaaccaacat cggccacctg 180
gaggcggccg ccggtgtggc tggattcatc aaggcggtgc tggcggtgca acgtgggcac 240

-continued

```
attccccgca acttgcactt cacccggtgg aacccggcca tcaacacgtc ggcgacgcgg    300

ctgttcgtgc cgaccgaaag cgccccgtgg ccggcggctg ccggtccacg cagggctgcg    360

gtgtcatcgt tcggcctcag cgggaccaa                                      389


<210> SEQ ID NO 236
<211> LENGTH: 432
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 236

ccggtaacca gatcagctcg tcgacctcac tgccgggggt gaattcccca ccggtgctgc     60

gcgctgccca gtagtgcacc ttcttgacgc ctcgaaaagg ggagtcggtc gggtaggtca    120

ccgtcaggag ccgcctaccc aggttggcgc ggtgaccggt ctcctcgagt atctcccgca    180

ccgcccccac cggtgcggtc tcgcccggat ccactttgcc cttgggcagc gaccagtcgt    240

cgtaacgggg gcggtgaatg acagcgatct cgaccggccc ttccgaatcg gcactgccgg    300

gtcgccagaa caccgcaccg gcggcgtaca caatccggcc cgccgagcgc cggcgggcgg    360

acganttctg gatcgacacc tcaactcctg caggtcaatt cggccaagct gctcgcggtc    420

gtggatgtgg tc                                                        432


<210> SEQ ID NO 237
<211> LENGTH: 287
<212> TYPE: DNA
<213> ORGANISM: Mycobacterium tuberculosis

<400> SEQUENCE: 237

atactcaagc ttgatgccgc cgaaaccgag cgtgagcacg ccgccaccca ccacgcgcgg     60

gtcgggcgcc gggcccgggc cgccaggctg ctccgctcgg tgatggcacg ccaccgcgac    120

accacccggc tgcgctacgt cgagccatac cgggcggagc tacatcggct cggccgccca    180

gtgttcgggc cctctttcga ggtcgaggtc tataccgatt tgcgcatccg cagccgcacc    240

ctggtcgtct cgtaccgtgc cctacctctg cttgtcgggc ggggcca                  287


<210> SEQ ID NO 238
<211> LENGTH: 272
<212> TYPE: DNA
<213> ORGANISM: Mycobacterium tuberculosis

<400> SEQUENCE: 238

tccgtacggc ccgggtacgc ttcggtcgca gtgtgcgagt gatagatgac gaccgggacc     60

tcgtcggcat cttccatagc ccgccacacc ttcagttgct caccggaatc caaccggtag    120

aaggtcggcg agcgctcggc attggtcatc gggatatgcc gctcgggacg gtcagagccc    180

tcgggtccgg ccagcactcc gcaggcttcg tcggggtggt cgcgacgcgc atgggccacc    240

atccatccac caggtctgcg cgaatcaccc gc                                  272


<210> SEQ ID NO 239
<211> LENGTH: 410
<212> TYPE: DNA
<213> ORGANISM: Mycobacterium tuberculosis
<220> FEATURE:
<221> NAME/KEY: unsure
```

-continued

<222> LOCATION: (various positions within the sequence)
<223> OTHER INFORMATION: applicants are uncertain of bases designated
as "n"

<400> SEQUENCE: 239
ggacacattg cgaacattga tgacaaaata gaaatcattg atggtttgag tcaccaggcc 60
gatcaagcct tcgccgagcc aaattccaat caagaggccc aagcccgtac caatcagccc 120
ggcaacgagg gattccgtca ttatcagcca aaataactgc tctcgggtta cacccaaaca 180
gcgcaatatg gcgaaaaacg gtcgccgttg cacgacatta aatgtcacgg tattgtaaat 240
taaaaagata cccaccaaca aggcaatcaa actgagagcg gttaaattga ccgtaaaagc 300
gtccgtcatc tgtttgacgg tgtcccgttg ggtntccgac gtttccatac gcacaccggc 360
cggcagtctt tgttggatgc gtgttgcagt ggcctcatct ttgatgatca 410

<210> SEQ ID NO 240
<211> LENGTH: 439
<212> TYPE: DNA
<213> ORGANISM: Mycobacterium tuberculosis

<400> SEQUENCE: 240
gcctggccca ggtgaaggcc gacctcgacg ccaaagccgc tgatccggca catgagtcgg 60
tggactggga cttgaagtcg ctgcgatggg cgtggaaccg agccaaagat gacgtggcgc 120
cgtggtgggc cgagaattcc aaggagtgct actcgtcggg gttggccgat ctggcccagg 180
gcctggctaa ttggaaagct ggcaagaacg ggacccgcaa aggccggcgg gtgggcttcc 240
cgcgattcaa atccgggcgg cgtgatcctg gcagggtgcg gttcaccacc ggcaccatgc 300
gcatagagga tgaccggcgc acgatcacgg tcccggtgat cgggccgctg cgggccaagg 360
agaacacccg ccgggtgcaa cgccacctcg tgagcgggcg cgcgcagatc ctgaacatga 420
ccttgtcgca gcggtgggg 439

<210> SEQ ID NO 241
<211> LENGTH: 356
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 241
taactcaagc ttcaagtccg cngtccgacc ctgttcgacg gctacctgaa tcaacccgat 60
gccccgccgc ggcgttcgac ccgacagctg gtaccgcacc ggcgacgtcg cggtggtcga 120
cggcagtggg atgcaccgca tcgtgggacg cgagtcggtc gacttgatca agtcgggtgg 180
ataccgggtc ggcgccggtg aaattgaaac ggtgctgctc gggcatccgg acgtggcgga 240
ngcggcagtc gtcggggtgc tcgactatta tctaggccag cggatcgttg cctacgtagt 300
cggctcagcg aatgtcgatg cggacgggct tatcaacttt gttgcccaac aacttt 356

<210> SEQ ID NO 242
<211> LENGTH: 341
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 242
ccatgtcgcc caacatatcg tcgatgttcg cgtcgtccgc ctcgcgcacg tggtctgtca 60
ccagtcaacg ttaacgccgc cgcacatgtc ctgcggccgg gcaaaaacgt gaaaaacgag 120
cgggcgactg caatgtcatg acaccgacgc cgccgatggg cccagggtct ggcagattcg 180
atctgtgcgg ccagtgccag cagcgtcgcc tcgtcatacg gccggccgac gagttgaacc 240
gacatgggca tgccgtcgcc gtcgaagtcc cacggcacca cggccgcggg ctggccggtc 300
agattccana cttgaaagta ctgaagccgc tgcaccacca g 341

<210> SEQ ID NO 243
<211> LENGTH: 336
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 243
cgaaagcgtg aaacagctcg cggcagcccc cgacgtgctg cgtcggatag ccggcgggcg 60
aagatcaatt ccaggcagct cccggacaat gcggctctgc tggcccgcaa cgaaggactc 120
gaggtcaccc cggtgcccgg ggtcgtggtg cacctgccga tcgcacaggt tggcccacaa 180
ccggccgctt gatgcccggt cggcaagccc ggcagttgcc aaacccagcg tgatcntgct 240
cngctctnta nttcggcgaa gaagtggctc gcctgatcac ctaccatcgg ccaggatctg 300
cgtgtcatca caacgctcgc caaggaggtt gttgtg 336

<210> SEQ ID NO 244
<211> LENGTH: 337
<212> TYPE: DNA
<213> ORGANISM: Mycobacterium tuberculosis

<400> SEQUENCE: 244
tccgccacgc ttcgcgccgc ccggcatacg gcgcgtaccg atctccgcgt catacaccgc 60
gggtaatcgc cgacggtgcc ggttcgcgag ccgaaggtga cgacgctgat tgaatcgagt 120
tccaggtcca gcgggtggcg cagcaacggc gcgagctcaa cgacgtcaat cacgttgtcg 180
ctttctacgg tcaccgaccc ggtgaccgta gtcgcccggt gcgctcggcc gagaagctgc 240
accgccacca ccgcgacacc gtcttgcacg cggacccacc ccggatcggt tgttggccaa 300
ggtaattggg tcattccatt tgacgggacg ccgaccc 337

<210> SEQ ID NO 245
<211> LENGTH: 337
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 245
cattctttaa cagttgtttt gggctcggca tggttagcca acgttctgcg gtccaccata 60
tcatcttggt ccggtagcgc tcgtccgggg tatgctgccg ccgggattct cgctgctatt 120
actccccccg aagaaccgcc accggtccag cgcgtgggcc gncgcggtcc catcacaaac 180

-continued

```
tgaaccccca acagggacat gcttatcggt agggcgcgcg ccaaggcggc agcaatcgca      240

tcactgcgct ctgcgcgtca ctattaaccc acccggactt cacttccacc accccgaatg      300

gcgcccggtc attgatcatc tggcgcaccg cggataa                               337
```

<210> SEQ ID NO 246
<211> LENGTH: 343
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 246

```
cggtgtcctg cagttggtag gcctgcagtt tgtgcatcat gccgatgccg cggcctcgtg       60

gccacgcatg tacagcacca cgccgcgccc ctcacgggcg aacatcgcca gcgcggcgtc      120

cagctgaagc ccgcaatcgc agcggcgtga ccaaacacat cgccggtcaa gcactccgaa      180

tgcaccggac cagcacgtcg tcaccgtcgg cgttgggccc ggcgatctcg ccgcggacca      240

tgcgcgacat gttccacgtc ctcgtanatg ctggtgtagc cgatggcgcg aaactcccca      300

tgacgagtcg gaatccgcgc ctcggcgacc cgctcaatgt gct                        343
```

<210> SEQ ID NO 247
<211> LENGTH: 340
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 247

```
cggcatctgg cggctgaacc tgttcttggg caacatgccg aggatcgcct cttccaccac       60

gcggtcgggg tggcgttgca ttacctcacc gatggtgcgc ttgtgcaggc cgccgggata      120

ccccgagtgc cggtaaacca tcttgtgctg cagtttgtcg ccgctgatgg cgaccttgtc      180

ggcgttgatc acgatnacna atcaccgcca ncgacattgg gggcgaacgt cggctcgtgc      240

ttgccgcgca gcaggctggc cgccgcgacg caaggcgcca accaccacgt ccgtggcgtc      300

gatgacgtac caccatcgcg tggtgtcacc cgccttgggc                            340
```

<210> SEQ ID NO 248
<211> LENGTH: 322
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 248

```
gcggcaaaaa ttgaagcact cntggccact nccgccggga gggacaatct cgggcggcta       60

gggcttctcg cgggaaggcc cgaacgtact gcgtttcaac acgtcgcgtc gccctccgac      120

cgcgaacatt ctgggatggc agcaacctgt tagcaccctg gccgggcgat gatctgcagc      180

gtcgccgcgg gtagtcgccc ccgggcggct acagtctgaa acgcgatgac catcgatgtg      240

tggacgccgc atccgacnca acggttccta cactgtgata tgttcgcctc gctgcgccgg      300

tggacggtgg gtctatcccg ga                                               322
```

<210> SEQ ID NO 249
<211> LENGTH: 278
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 249
cgcgttgaac tgaaggggtg ccgcccggct cgagcaggca agccatttgt tcgatgcggt 60
taccgaagat ctcttcggtg actgcccgcc gccggccagc tcggctcagt gtccggcgtt 120
ggtcgccgcg gcgacaatct tggcgtccac ggtggtcggg gtcatgcccg cgagcaggat 180
tggcgagcgg ncggtcagcc gggtgaactt cgtcaagagc tgacgctgcg gttggggagg 240
cgaatcatgg tcggtgcgta gcctcgacta ggcccggg 278

<210> SEQ ID NO 250
<211> LENGTH: 336
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 250
tgacaacgcg gcggcgatta ccccgctacc gcagcagcat gacgcggtag cgaacaccgc 60
cggatgcagc gcaggtgcgt cgatgtgctc acggaatcgc cccggcaccg cgatctcgag 120
gatcaccagt gccacccct gcagcgcgac accgacgatt ccgtacaccg ccacgccgat 180
caggccctgg gccagctgat tggagctggc gtatatggcg gcgatggtga cgatggtcat 240
cgcctcttac attgtggcgg ccagaaccac ggcgttgggg cggcggtcga tgaacactag 300
gcgaccanat ccccggggtc aacaggttga ccatcc 336

<210> SEQ ID NO 251
<211> LENGTH: 95
<212> TYPE: DNA
<213> ORGANISM: Mycobacterium tuberculosis

<400> SEQUENCE: 251
cgcggacatc ccgaacgagg acacgcgacc gcttcggtgt gtgatctatc agggctcgca 60
ccacgcgcaa ccgcttccgg ctacctagac gcggt 95

<210> SEQ ID NO 252
<211> LENGTH: 94
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 252
gcatgcgggt gatgccgttc tcagtgcgca acagcgttcg acgcggcata cccagccgca 60
catgccgtgc acgccggngc cggggcggga atct 94

-continued

<210> SEQ ID NO 253
<211> LENGTH: 302
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 253
ctcaagcttc agnccntcta agcggtctgc gcggcgatcg caaagatcgc cctttgccgg 60
cgttgggggc ttctgctcgg gggtgttgta caccttctcg aacacctcgg caccgacacc 120
accaccgtcg gcttgaacac cgccaacatc ggcagcanat cttgatgtcc tggtgaatcc 180
acggtgactt tggagtggaa ggcggccata ctgatcgcgc gcgccaccac atgagctagc 240
ggcaggaaaa ccagcagccg ctcacccttg cgcagcagcg tcgggtgata tgcctggcgc 300
cc 302

<210> SEQ ID NO 254
<211> LENGTH: 291
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 254
agtcgaangt cagtccggtc tcctctccga ctacggccaa gaactggggc gacggtgtca 60
gtgcagaaca gcggaaactg gtggcgccct aggcgagcga acgctcacaa acggcggtga 120
ccgcttctgg tcgtgcacca tcgagccgtg cccagcccgg ccgcgtgccg tcagccgcat 180
ccactggatg cccttctcgg cggtttcaat cangtacagg cgacgttcgc caccatcgtg 240
ccggggcacg gttagcgaga aacgccgact tcaccgattg cctcggtgat g 291

<210> SEQ ID NO 255
<211> LENGTH: 454
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 255
agcttcgcgg cgtggcgatc gcggttcaag gcgcgctctt cgagcacaac gagcgaagac 60
agctcggcga cggagccttt atcgacatcc gttcgggctg gctgaccggc ggcgaagaac 120
tgctggacgc gttgttgtcg acggtgccgt ggcgagccga gcgccgtcag atgtncgacc 180
gggtggtcga tgtgccgcgg ctggtgagtt ttcacgacct gaccatcgaa gatccgccgc 240
atccgcagct ggcgcggatg cgccggcggc tcaacgacat ctacggcggc gaactgggtg 300
agcccttcac caccgccggg ctgtgctact accgcgacgg ctctgacagc gtcgcctggc 360
atggcgacac cattggtcgc ggcagcactg aggacactat ggtggcgatc gtcagcctcg 420
gcgccacccg cgtcttcgcg ctgcggccgc gtgg 454

<210> SEQ ID NO 256
<211> LENGTH: 346

-continued

<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 256
agcttcagct gatactcgac cagccccact cgggccaata cgtgaatgtc tagcatcttc 60
acccgttcac gggctantcg agtagtagac attgattagc ctgaacgtac ctccgacgcc 120
agctgacgaa cgggtatgac ggatggattt cgtggtgtcg cgcccgaggt caattcgtta 180
cggatgtatc tcggggccgg atcggggccg atgttggcgg ccgcggcggc ctgggacgga 240
ctatccgacg aactggcggt ggcggcgtcg tggtttgggt cggtgacctc gggcctggcg 300
gatgcggcgt ggcgcggccc gcggcggttg cgatggcncg cgcggt 346

<210> SEQ ID NO 257
<211> LENGTH: 339
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 257
ctggtcatgg acgttgctcc ggtagtggct cactgccgat cctcctcgtt gagagtgcca 60
cctcagggtt gggtagggtt gggtactcga aaccaagtta cccaccagta acaccgtcaa 120
aatatatccg ttgcataggt caatgcaagt tgatgtgagc tacattgcac caactaacta 180
accaaccggt tgggttagcg gtgatcctgg ccgtgtcggt cctctcacct gcggtgatag 240
cgatcaaatg aagaatatgc ggagtctagg gcggcagcgc ctggcancgt agatcatcgg 300
ctcacgcgga tgcggcctct tggtacggac atgcgcgcg 339

<210> SEQ ID NO 258
<211> LENGTH: 182
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 258
ctcgtgagta gcacccctgt aatttgggat cggcaaaaag gcgaatcacc gcgtggccac 60
gacacgccgg gagggacnat ctcgggcggc tagggcttct cgcgggaagg cccgaacgta 120
cggcgtttca acacgtcgcg tcgccctccg accgcgaaca ttcggggatg gcagcaacct 180
gg 182

<210> SEQ ID NO 259
<211> LENGTH: 213
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

-continued

<400> SEQUENCE: 259
ggatcaacta ccggccaacg gtgattcttg ggcgccgctg acgcgcgaac gacccagcga 60
cacattcagc agatggccag cgcgtgccgg gccacgatgt tggtgctcgg cggctactcc 120
catggtgcgg cncgtgatcg acatcgtcac cgccgcacca ctgccggcct cgggttcacg 180
cagccgttgc cgcccgcagc ggacgatcac atc 213

<210> SEQ ID NO 260
<211> LENGTH: 321
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 260
aggaccgtca gcacggcgac gtgctactcg ccgagcagtg ggaatcgctc tgcagcaaac 60
cattactctg cgcgacgttc gagatgacct tctgaatgga cggatctacc tgccgcgcga 120
cgacctggac cgcgtatgcg tccgcctccg cctggacgac accggggcac tctatgaccc 180
cgacggacgg ctcgcggtac tgctgcggtt caccgccgac gcccgcacgg tacgcgtcgg 240
gactgcgctg agtccancct cgacgccgta gcgctgctgc tgtgcggcca tgtctggcat 300
ctaccgccgt cgctcccttg a 321

<210> SEQ ID NO 261
<211> LENGTH: 334
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 261
cgactctgtt ggccactgcg ggtcgatctt gcggccgccc cggtcgtgga acgcccaggt 60
cacccggcgg cgcaccgcgg tcagcgcgtc gttggccagc gtggtcacat ggaagtggtc 120
gacgacgagc ttggcgttgg gcagcagccc gggcgtgcgg atcgccgagg cgtatgcagc 180
ggcggggtcg atggccaccg tactggatgc tctcccggaa ctgcggtgtg cgcgcttgca 240
gccatgccag caccgccgcg ccgccgcggc cttcatgctg cccataaacc ctgataccgg 300
ccaggtcgac naaccngtat cccacggtca accc 334

<210> SEQ ID NO 262
<211> LENGTH: 208
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 262
cacacggacg gcggtgcgga cgcagctgac gcgcatggtg gtcagcatcg cggccggtct 60
gctgttgtat gcctacttcg cgccgcgcaa atgctggtgg gcggcggtgg tggcgctcgc 120
atggctgggc tgggtgctga cccaactctc gaaccacacc ggtgggtggg ctgggctatg 180

-continued gcctgccata tcggcctggt gttctacn 208

<210> SEQ ID NO 263
<211> LENGTH: 233
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 263
ccgatatccg agccgatagc tggcgggctc gggtggtngc cagcggcgct gcgacgaaag 60
tgtgaccgtc atgaaacaga caccaccggc ggccgtcggc cgtcgtcacc tgctcgagat 120
ctcagcatcc gcagccggtg tgatcgcgct ttcggcgtgt agtgggtcgc cgcccgagcc 180
cggcaaacgc cggcccgaca caaccccgga acaggaagtc cggtcaccgc gcc 233

<210> SEQ ID NO 264
<211> LENGTH: 320
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 264
gcttcaggac aaattgnatc cctatgcacc cgttgtcacg ccgatgagtg aagactgcac 60
gcaatcgccg gaatccggca aaaccctgca caagcgaaat caaccggagg ctgacaaggc 120
aacgtcggtg atccgtaccg cctggttgga caaacggcag aaggcgcctc gtccggtcca 180
tctacgccga gcacactggt gatagcgcca tcggcatcgg tgcggccacg gtggagacga 240
acgtccgcng gcgtctgggt cagtaacccg ccgaccagtt ctcgggcaag ctggtcaaca 300
tcgggcgcca cgtctccaac 320

<210> SEQ ID NO 265
<211> LENGTH: 304
<212> TYPE: DNA
<213> ORGANISM: Mycobacterium tuberculosis

<400> SEQUENCE: 265
gtttggcggc cttattgcac tgaggtcgtc aattgaccca cagcggaaat gccgactatt 60
cgcaggcctc cttcgccttg gctgccggag atgggctccg cgggaaccgc atgcaggtat 120
atgacctcgg tttctcgggt gctaccgcgt gccttgtcga ggatgaactc ggcgttggaa 180
ttgtccagcc ggcccaattc atcgagcgca gattcgtaca catggccggc ggcgacatac 240
cttcaccgtg gatctgctcc acacggaccg ccctgtcggg atctgctcac gggtaaagga 300
atta 304

<210> SEQ ID NO 266
<211> LENGTH: 217
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

-continued

<400> SEQUENCE: 266
gcgcactcct ccttatcgct ccgctctgca tcgtcgcggc gcggtcaggt gcaaacgcct 60
tcgggggtgg gggtcctgcg gagcacaccg gatacggagc gcaacgcgtc gcgttgtgcg 120
ggcaaacaag tgtgcaggnn ccaatgccat gtccagcagc ttatcagtgt cgaacgtgcg 180
aacgtcgcgc cttcgccggt gcctgaatct ctacaag 217

<210> SEQ ID NO 267
<211> LENGTH: 174
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 267
cgctgaaagc caccattcgc gggtcgggcg ccgggctcgg gccgccaggc tgctccgctc 60
ggtgatggca cgccaccgcg acaccacccg gctgcgctac gtcgagccat accgggcgga 120
gctacatcgg ctcggccgcc tagtgttcgg gncctctttc gaggtcgagg tcga 174

<210> SEQ ID NO 268
<211> LENGTH: 144
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 268
tgtaatttgg gatgggcaaa aagcaaanca ccgcgtggcc acaaacgcgg ggagggacaa 60
tctcgggcgg ctagggcttc tcgcgggaag cccgaaacgt acggcgtttc aacacgtcgc 120
gtcgcctccg acgcgaaatt cggg 144

<210> SEQ ID NO 269
<211> LENGTH: 216
<212> TYPE: DNA
<213> ORGANISM: Mycobacterium tuberculosis

<400> SEQUENCE: 269
cttgggcaac atgctgagga tcgccttttc accacgcggt cggggtggcg ttgcattagc 60
tcaccgatgg tgcgcttgtt gcaggccgcc gggatacccg agtgccggta aaccatcttg 120
tgctgcagtt tgtcccgctg atggcgacct tgtcgcgttg atcacgatga cgaagtcacc 180
gccatcgaca ttgggggcga actcggcttg tgcttg 216

<210> SEQ ID NO 270
<211> LENGTH: 199
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 270
gcatgcttca ttatctaatc tccagccgtg gtttaatcag acgatcgaaa attcatgcag 60

-continued

```
acggtcccaa atagaaagac attctccagg caccagttga agaggttgat caatggtctg    120

ttcaaaaaca agttctcatc cggattgaac tttaccaact tcatccgttt catgtacaac    180

atttttagaa ncatgcttc                                                 199
```

<210> SEQ ID NO 271
<211> LENGTH: 230
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 271

```
atactcaagc ttgatgccgc cgaaaccgag cgtgagcacg ccgccagcca ccacgcgcgg     60

gtcgggcgcc gggcccgggc cgccaggctg ctccgctcgg tgatggcacg ccaccgcgac    120

accacccggc tgcgctacgt ctatccatac cgggcggagc tacatcggct cggccgccca    180

ttgttcnggc cctctttcga ggtcgaggtc tataccgatt tgcgcatccg               230
```

<210> SEQ ID NO 272
<211> LENGTH: 188
<212> TYPE: DNA
<213> ORGANISM: Mycobacterium tuberculosis

<400> SEQUENCE: 272

```
tccgtactgg tcgggtacgc ttcggtcgca gtgtgcgagt gatagatgac gaccgggacc     60

tcgtcggcat cttccatagc ccgccacacc ttcagttgct caccggaatc caaccggtag    120

aaggtcggcg agcgctcggc attggtcatc gggatatgcc gctcgggacg gtcagaacct    180

cgggtccg                                                             188
```

<210> SEQ ID NO 273
<211> LENGTH: 158
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 273

```
gttctcgcac gatttcggat tagcgggatg gtctcaattg ggtatgcggg gaaggcgctg     60

acattcgccg cgattagctg tttgatggac cgggggtgat ttttgatcac ggaaatgggt    120

gtttatncag gtcgcacgct ttcatccggg gcggaacg                           158
```

<210> SEQ ID NO 274
<211> LENGTH: 237
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 274

```
gggtgtgcct gctgtgtatg cacggcatac ggacatcctt cccctgaaga cccgcggtcg     60

aacagccacg tgtccatcat canggggtca accccggcca agggcgacgg cacgccaagt    120
```

-continued

```
tcgccgaccg ttaacctagt gctgttagct tcatttgctg cgagcaaaac agctggtcgg    180

ncgttaggaa tgaattgaaa ctcaaccgat ttggtgccgc cgtaggtgtc ctggctg       237


<210> SEQ ID NO 275
<211> LENGTH: 262
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 275

actacccggc caacggtgat ntcttggccg ccgctgacng cgcgaacgac gccagcgacc     60

acattcagca gatggccagc gcgtgccggg ccacgangtt ggtgctcggc ggctactccc    120

anggtgcggn cgtgatcgac atcntcaccg ccgcaccact gcccggcctc gggttcacca    180

gccgttgccg cccgcagcgg acgatcacat cgcttttatt tnntnttcng gaatccctcg    240

ggccgcgctg gcgggctgat ga                                             262


<210> SEQ ID NO 276
<211> LENGTH: 222
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 276

acgtcgggan actgttcgcg ttcatcctcg tctcggcgga ttggtctgct gcgccggacc     60

gaccgatctt cagcgggggg tcacgctccg tggggtgccg ttacttccga tcgcccagtg    120

tgcgcgtgct gtggctgatg ctgaacctca ccgcgttgan ttggatcggt tcgggatctg    180

gctggtggcc ggaacgcnat ttatgtcgct acgggcgccg gc                       222


<210> SEQ ID NO 277
<211> LENGTH: 166
<212> TYPE: DNA
<213> ORGANISM: Mycobacterium tuberculosis

<400> SEQUENCE: 277

gctcaaaggc actactggca ccaaggccca cacgtcacct gtgactcctg cgccgacccg     60

cccgaggtct ggccgttaca ccgaacgggc gagccgggag ttggtaccat cgaacaagac    120

aaggtgcatg ggcggagttg ttccgccact tcgtcgatga cgggtc                   166


<210> SEQ ID NO 278
<211> LENGTH: 330
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 278

cgataccggc tgcttaccga gacatccacc atgccacccg aatcaccgca cgcgccgaaa     60

tcgcacaaca gcttgacgcc ttgcaggttc cgcgattgga attgccgacg gtctctgacg    120
```

-continued

```
gcgtcgacct tggcagcctc tacgagctct cggaatcact tgcccagcag ggggttcgat    180

gagtgtcaca ccgaagacct cgatatgggc gcaatcctgg ccgacacatc caaccgggtg    240

gttgtgtgct gcggcgccgg tggggtcngc aanacactac cgcggccgcg ctggcgttgc    300

gcgcggccga atatggccgc actgtggtcg                                     330
```

```
<210> SEQ ID NO 279
<211> LENGTH: 332
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 279

cgtcgtcgtc gtggtatgcg atagccatcc cgtcgggcta ctcgccatca ccgatcagct     60

tcgccccgaa gccgccgcgg cgatttccgc tgcgaccaaa ctgaccgggg ccaaaccggt    120

attgcttacc ggcgacaacc gggccaccgc cgatcggctc ggtgtacang ttggcatcga    180

cgacgtacgg gccgggctac tgccgacgac aangtcgcag ccgtgcngcn gctgcaagct    240

ggaggtgcca gattgaccgt ggtcggtgac ggtatcaacg acctccggcc ttagcggccg    300

cgcatgtcgc atcgccatgg gcagcgcccg ac                                  332
```

```
<210> SEQ ID NO 280
<211> LENGTH: 222
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 280

gcacgcaatc gaagtcaccc aaaccgggcg ggccaggcgt ctnacgccac gtcnaccagc     60

cgcaacctca acccggccac ggcgagctcc tgatcaaggc cgaggccatc ggtgtctact    120

tcatcgacac ctacttccgc tccgggcaat atccgcgcga actcccgttc gtcatctgct    180

ccgaagtatg cggcacggtg gangccgtcg gccaggggtt ac                       222
```

```
<210> SEQ ID NO 281
<211> LENGTH: 184
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 281

tcgactgtgt ggccacagat cacgccccgc atgccgagca cgagaaatgc gtcgaattcg     60

ccgcgggccg gccggcatgc tcgggttgca gacggcattg tcggtggtgg tgcatacaat    120

ggtggcgccg gcttgttgan ttnggcgcga tatcgcgcgg gtgatgagtg anaaccggcg    180

tgca                                                                 184
```

```
<210> SEQ ID NO 282
<211> LENGTH: 409
<212> TYPE: DNA
```

-continued

<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 282
gaacctgaca ccctggtcac gggtgagcac ggacttgatt tcttcnctat tggtcggcgc 60
tgttgagcac accacgccgc tgacggccgt cgcgtcctcg ctgtgctcgg tctggtggag 120
cgcgctgccc gcggccnaac atcntaaatc aagcgtattc gtcaacagat atcatcaatg 180
tcggcgctgg actattcaaa tcatcgatat actggtgacc tggtccttcg ccatcgatca 240
atggcgatag tcacgcaaat cgtcacggac atcgtcggcg tcccagctgg cccgtgccaa 300
cagatgctgc aacccatcgg ggtggtatca ccgcggtgct cggcgatggt ccacaattct 360
tgcggtccaa gcccnaaaca tcccgggcat gaattcaccg gcatgcgcn 409

<210> SEQ ID NO 283
<211> LENGTH: 413
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 283
ctatcgtacc cgcgccggtc accttctgga tatcgccggc ctggtcaagg gggcgtccga 60
gggagccggg ctgggtnaca agttcctggc tcatatccgc gaatgcgacg ccatttgtca 120
ggtggtgcgg gtgttcgtcg acgacgacgt gactcatgtc accggacggg tcgatcccca 180
gtccgacatt gaggtcgtcg agaccgagct gatcctggca gatctgcaaa ccctggagcg 240
ggccacgggc cggctggaga atgaagcgcg caccaacaag gcgcgcaagc cggtctacga 300
agcggcactg cgtgcccagc angtgctcga cgccgggcaa gacgctgttc gccgcggggg 360
tggatgccgc cgcgttgcgc gactgaaact gctgaccacc aagcccttcc tgt 413

<210> SEQ ID NO 284
<211> LENGTH: 283
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 284
tactcaagct tcaggccgcc acgtccgccg tccgtcggcg acgtgacctc gagcgccgag 60
ttcgactcga catcgccgcc ggcgcatgcc gacatgaacg cggcactcac cgcaagcccg 120
tcggacgtca ggtcgatcga ctccgcttca agcaccggat cgtccgggca actcgcggcc 180
tcggcctgtg cgaacggcac acccgtcgtg gcggcncccc gcgcggaact gggctcatca 240
cggtcgttgc gagccggtcg cgtcaccgcg taccgacgcc gtc 283

<210> SEQ ID NO 285
<211> LENGTH: 397
<212> TYPE: DNA
<213> ORGANISM: Mycobacterium tuberculosis -continued

<400> SEQUENCE: 285
ccgacatcga gtgggctcgc agtgacttgg cgacctccaa gccaccggta cccgccgcgc 60
ggcaagccaa ggacgacgac ggccttgccg gatagctgcg ccaggcgttg cgccaactgg 120
cgtccagcgt cgccacgatc gtcaaagagc ttcatctgcc gagtgtgtcg ccatctcatg 180
gctccaaata tggaattagg tccctgggcc gactgacgac agtccctcag cgaccggatt 240
gcgcatcccg ccttgtacgc tactccgcaa atcccgggct tgcgtccgcg gaagcgaact 300
cggcggcgct acgtggtggt tcacttcggc cgtgcgcact cggatcgacg ggccgatggt 360
ggccgggccc gcgcgcttct tggtcatccg attgagt 397

<210> SEQ ID NO 286
<211> LENGTH: 342
<212> TYPE: DNA
<213> ORGANISM: Mycobacterium tuberculosis

<400> SEQUENCE: 286
atactcaagc ttgtcgcggt aaaccgcacg cagggcggtg ggtgcggtgt caaagacacc 60
cacacttctt tgcggttcgg tgatctcgac accggccgcg agccgaccac catgcgcgcg 120
tagatcggcg atcagcgcgt cggctatcgc ctgggtgccg cccaccggaa tcggccagcc 180
gaccgaatgg gccagcgttg ccagcatcag tccggcgccg gccgacacca gtgacggcaa 240
cggtgaaatc gcgtgggcgg caacgccggt gaacaacgcg cgggcatcct cgcccgccaa 300
cgaccgccag gcagggtgcc tgggccatca tccgcagccc ga 342

<210> SEQ ID NO 287
<211> LENGTH: 430
<212> TYPE: DNA
<213> ORGANISM: Mycobacterium tuberculosis

<400> SEQUENCE: 287
tggactcata acgatcgggt cagcgacgcg ccaacacgaa cggccggacg agtgggccag 60
ggtcgcgcct cccctacaaa caggatccgt tgcctgcgag cgacaggctc cggtgcggcg 120
ttgggcgccg tgctcgtccc agcgtccggt cccgggtcgc cggcgacgct tgtttcctcc 180
atactcgccc cctaatctcg aggcagcccg tacccgcagg caacctccca aaaatgcaat 240
cccccaaaat gcaatgcgtc gagctatttc tcacaccgac cgctagttgc ggatcagaaa 300
tccgttgggc gcggaagtcc agccgaattt gttctcccgc tccgcatcat gcttgtaatc 360
gtttggaaat catcctcata tgcctcgatc gcttcatagg tcaagcccaa acccggcagg 420
atgggtggcc 430

<210> SEQ ID NO 288
<211> LENGTH: 473
<212> TYPE: DNA
<213> ORGANISM: Mycobacterium tuberculosis

<400> SEQUENCE: 288
ctttacactt tatgcttccg gctcgtatgt tgtgtggaat tgtgagcgga taacaatttc 60
acacaggaaa cagctatgac catgattacg ccaagctatt taggtgacac tatagaatac 120
tcaagcttag tggttgcgca cgtaaattcg tcaggtgacc gatcccctgc tgtctcactc 180
gcctcacagc gaccaccacg gctggcgctc aaggcgggca cgtgcggagc agatgaggaa 240
tgtgcgacgt cttgatgcag cctgtcagaa caccgagacc ctcgacgaac ttacgatcga 300
aaccgcttag gccaaccggt gacgggggtg tctttccgcg gctagggcgc cttatcgtcc 360

-continued

```
gaaggccgtg ggtggtgatc gccttctggg tcgcgcttgc gggtctgctt gcgccgacgg    420

tgccgtccct ggaccgatct cccagcggca tccagtggcg attctgccat cgg           473


<210> SEQ ID NO 289
<211> LENGTH: 418
<212> TYPE: DNA
<213> ORGANISM: Mycobacterium tuberculosis

<400> SEQUENCE: 289

caggcatgca agcttgcgat gtatcaacac gccgttgcgc agcgtgagcc gatagttgac     60

atccggctcg gtgaaggtga aatcgatggc caggtcgagg tcccatgcgc gtgggccatt    120

gatgctgatc gccaggacgt caaagatttg gtccggcgtc agctgggcga aaaacgtggg    180

cgccgggact tgcccggagc tgcccgggtt cccgtcgcgc agctcggcgg ccccggtcag    240

aaagaaattg cgccaggtcg cacactccgc gccgtaggcc agctgctcca cggtgtcggc    300

atatagcccg cgggccgcag cgtgctcgct gtcggcgaac accgcatggt cgagaagcgt    360

tgccgcccaa cggaaatcac tgcgtcaaag cttcgccggg ccactccagc actccgtc      418


<210> SEQ ID NO 290
<211> LENGTH: 194
<212> TYPE: DNA
<213> ORGANISM: Mycobacterium tuberculosis

<400> SEQUENCE: 290

atactcaagc ttgaccgacg ctgatcgcac cgcacgcggg aacctcaagg gcactactgg     60

cacaagggcc cacacgtcaa cctgttaact cctgcgccga ccccggccga agtccttggc    120

gttaacaccg aacgggccaa cccgggaatt tgggttccat caaaacaaat agcaggtgcc    180

tgggcggagt gttc                                                      194


<210> SEQ ID NO 291
<211> LENGTH: 166
<212> TYPE: DNA
<213> ORGANISM: Mycobacterium tuberculosis

<400> SEQUENCE: 291

gtcgtcgtgt gctggggcgt ccgtatcagc acgcccacga aatggggcac aagaaggatt     60

cctggaacgg tggctgtcca agatcaccct cgcccaaaac tgctacgggc acttctacat    120

cgagcacaac cgtggccatc acgtccgcgg tgtccacacc gggagg                   166


<210> SEQ ID NO 292
<211> LENGTH: 291
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 292

atatgccttg ctgagctttt cggatcgcag cgagtcgtac ccgcgccggt caccttcgtg     60

gatatcgccg gcctggtcaa gggggcgtcc gagggagccg ggctgggtaa caagttcctg    120

gctcatatcc gcgaatgcga cgccatttgt caggtggtgc gggtgttcgt cgacaacgac    180

gtgactcatg tcaccggacg ggtcgatccc cagtccgaca ttgaggtcgt cgagaccgag    240

ctgatcctgg cagatctgca agccctggag cgggccacgg ggcggctnga a             291
```

-continued

<210> SEQ ID NO 293
<211> LENGTH: 442
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 293
gacaccctgg tcacgggtga gcaggactcg atttcttcgc tattggtcgg cgctgttgag 60
gcacagcacg ccgctgaggc cgtcgcgtcc tcgctgtgct cggtctggtg gagcgcgctg 120
cccgcggccg aacatcgtaa atcaagcgta ttcgtcaaca gatatcatca atgtcggcgc 180
tggactattc aaatcatcga tatactggtg acctggtcct tcgccatcga tcaatggcga 240
tagtcacgca gatcgtcacg gacatcgtct gcgtcccagc tggcccgtgc caacagatgc 300
tgcaacccat cggggtggta tcnccgcggt gctcggcgat ggtccaacaa ttcttgcggt 360
ccaagcccga aaccatccgg ccatgagttc accggcatgg cgcaacggct ggtgccgggc 420
aaaacgcggc gcgatcgaat tc 442

<210> SEQ ID NO 294
<211> LENGTH: 150
<212> TYPE: DNA
<213> ORGANISM: Mycobacterium tuberculosis

<400> SEQUENCE: 294
tgtagaaggt gggtcccgtc caacttcgcg gcggcggcgc gatatgcctt gctggtcttg 60
ctcatttgat atccaatcta tgggtcgtgg ttactcaacg ggccgaagct ggccctccca 120
cgggtagggt cctattcgac ggtgatgtcc 150

<210> SEQ ID NO 295
<211> LENGTH: 321
<212> TYPE: DNA
<213> ORGANISM: Mycobacterium tuberculosis

<400> SEQUENCE: 295
cccgaatccg gtggccggca gggggcctgg cgacgtggac accttctaac ttgtctttac 60
cggtcactgt tgcaccccaa cacctttaac gacgtggacg gacgttacat cggattcgac 120
ggtgtcatcc acagcgttgc cattgggcac acccactacg ccaatttctc cgactgggac 180
acctaccgca gcctcgcccc actgcaggga ctgttgttcc cgcaacgggc catcgacatg 240
atccagtcgt tggtgaccga cgcggagcag actggtgcgt atccgcgttg ggcgctggcg 300
aaattccgcc accggcatga t 321

<210> SEQ ID NO 296
<211> LENGTH: 184
<212> TYPE: DNA
<213> ORGANISM: Mycobacterium tuberculosis

<400> SEQUENCE: 296
ttgagatgct ggtcgggatg ccgatggttg gaacatggtc ccctggcgtc gaatacgcgc 60
gagcgcatga gctcaccggt tcggaacaac gtatcgaaga actcgcactg ctggcagatg 120
gtatctccga tgtggttgta atttgtatcc caactctaac tgtgctatcg gatctgcgtg 180
aata 184

<210> SEQ ID NO 297
<211> LENGTH: 259
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 297
cgtaatcacg atcccgctga gacacttgac cttacggccg aagtgacttc gctgctgcta 60
tgccgacacc cgatttccat acgctgctgt acacgacggc cgggccggtg gcctccatca 120
cgctcaaccg cccggaacag ctcaacacca tcgtcccgcc catgcccgac gagatcgagg 180
ccgctatcgg gttggtcgaa cgcgaccagg acatcaaggt catcntnctg cgcggtggcg 240
ggcgcgcctt ctccggcgg 259

<210> SEQ ID NO 298
<211> LENGTH: 369
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 298
caagcttaag ctggttccgg ccactccatg agccgtagtg caatggttcg tgcacggcga 60
ggccgaactt gccataaaca tccctgacga aagtctccgg caagccgatt gcttcttcgg 120
gccgcttctt gtggattgtc cgataacccg gtccctcatg ctggaagttg tgcgcactct 180
ttccttccgc gatgtgggct aacgactcgt cattgagcaa gaagtacgtg cacaggcatc 240
gtccgccggg cttcagcacg cgggagatct cgtccagata gtgctccacg tccggnggga 300
aacatgtggg tgaacaccga ggtnagaaac accncatcca acgacgcatc cgggatatgg 360
aaagcgaaa 369

<210> SEQ ID NO 299
<211> LENGTH: 387
<212> TYPE: DNA
<213> ORGANISM: Mycobacterium tuberculosis

<400> SEQUENCE: 299
tatggtcttc gtcgaccagt acgtcgtagg cgccatgagc cagcgactga agccgcgcca 60
tgcctgcacg gcccgctcat ccagcgaggc ggccatctcc cgcagatagc ctgccgcctc 120
ggcgcgcacg ctgtccggat cgcgtccgag ctcgtcggcc agcgcacgca gccgctcgtc 180
ataccatcgg gcatccagca gttgggtaac ctcaacgggg tcggtcgcta gcggcgtcat 240
tgattcagca acaataccga tgcgctgcag caactttcgc agtccgatgc ggcccacctc 300
ccgtgcagtc actggctagc ccccgtcatg ccggttgtgt cgatggcacg gcagcgggct 360
cgtaaacctg cggtctcagc tcgctgg 387

<210> SEQ ID NO 300
<211> LENGTH: 73
<212> TYPE: DNA
<213> ORGANISM: Mycobacterium tuberculosis -continued

<400> SEQUENCE: 300
gcttagcggt cttgctcgaa ccgacattgc gtgccactca tgagcgggtg gcggtcgcgg 60
tgcttacaca tct 73

<210> SEQ ID NO 301
<211> LENGTH: 156
<212> TYPE: DNA
<213> ORGANISM: Mycobacterium tuberculosis

<400> SEQUENCE: 301
gtatctggcg cctctcgaat atccttgaac gtcccgcggt gccacccaga tagatcgcag 60
cgccctgcaa tggagttccc tttatggcct ctctagcctc ccgcttgatc ggctcgaccc 120
gagagatgcc ctcgggcgtt gcgggatctc cctcca 156

<210> SEQ ID NO 302
<211> LENGTH: 394
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 302
cttcacgccg atccgcgacc gcgaacgcga cggtgacggt gggcgacaag gttcggttgg 60
tcgccgcggc gctgggcgat atcagctcac ccggtttcga ggtgttcggc gaccggacgg 120
tgctgcagac attcttgagc gtcctcgacc ggcccgattc ggccttcaac atcgtgacgc 180
cgtatttcgg cggtaccgct cggcgccgag tcgaaggcgg cctgagctaa agccgggcat 240
tgcgcgagtg gtaaacaagt tcggtgactt cggttgaccg actcgacggg ctcgatctgg 300
gcgcgctgga ccggtatctg cgttcgctgg ggatcgggcc naccgcnant tgcgttgcga 360
nctgattccg gtggagctcc aatctgactt ccgg 394

<210> SEQ ID NO 303
<211> LENGTH: 404
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 303
gcagctaccg accctagcga cgagtgtgtt cgcagcgtcg aatgtgaacg ttcggcgtga 60
ttcggcgcgc gggttcccgc tctcagcgca cgttcggcgc cgaggnggct agtccctggt 120
taagcaatgt ctcggtcgcc gccagcagcg cgcatgtcgc caacccgtcn accgcgttgc 180
gcatgtccgg taccgacgga aacgacggcg cgatccggat gttcttgtcg tccggatcct 240
ttcgatacgg gaacgacccc ccgcctcggt caccgcgata ccaacgtcct tagccaangc 300
tacngtccgg cgcgcggtcc cgggcaacac gtcgaagctg atgaantaac cacccttggg 360
ctcggtccaa gangcgatct tggactcctt aaccgctgat ncaa 404

<210> SEQ ID NO 304
<211> LENGTH: 479
<212> TYPE: DNA
<213> ORGANISM: Mycobacterium tuberculosis -continued
<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 304
tccccatcgg cgccggaccg tttgaaagtc caagcacggg tgggatggaa tcgacgacag 60
ttgagcgccg tcggtggccg tggtcagcag ctgttcgcga acgcaccagg tcacatccct 120
tcgacatctc accgacgtgg cacgggcgac atcaacagga agattgacga atccctcgca 180
ggcgcggcac gtccgcaggc caacgccaac tacggggcca ccagcgatcc tccgctcacg 240
caccagccca agccaggctc anccacccaa gtcggcccgc gctctccctc gccccctggt 300
ctccggggcc ttgttaaaca actaccggaa gtccaccaat cctcgctgca tctcgacacc 360
gtccgcctca ctcccttcct cccgcccctc tccacacnac acacctcttg cattaaggtc 420
acggagcggt cacttttcgt cggacgaaat tcgcaatccg gccgctcgcc gccagagat 479

<210> SEQ ID NO 305
<211> LENGTH: 260
<212> TYPE: DNA
<213> ORGANISM: Mycobacterium tuberculosis

<400> SEQUENCE: 305
cggaaagtgg atactcccag caggtagcag gtcgccacca cgctggtcag tgcgcgttca 60
gctcgcttgc ggcgctgcag cagccagtcc gggaaatagc tgccctggcg cagcttgggg 120
atcgcgacgt cgatggttgc ggcacgggtg tcgcaaatca cggtggcggt agccgttgcg 180
ctgattggac cgctcatcgc tgcgttcgcg gtagcccgcc ccgcacaggg cgtcggcttc 240
agcccccatc aaggcggcga 260

<210> SEQ ID NO 306
<211> LENGTH: 464
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 306
ggccgagtcc agcacttcgc actatgtgca gaccaaanac ccggtggtcg ccgcgctgcg 60
gcagcggctg gcaacggcgc cggtgatcac cgagtggtgc gnagttgccg accggcagtt 120
cgccgcgggc ttactacgag aagggcctgc gcgacgtcat caggtatcac gtgtcgatga 180
cgtcgagcgt taacttcccc gaccagacgg cgacctcgcc gatggacccc gcgttgtacc 240
tggtgtgggc gcaagctaac gccgccgcan gctatcggta ctcggtcgaa gcgcagccgg 300
ggtcgcaagc gctagcgggc aaggtcgcga cgatctcggt cacctggacc aactacggcg 360
ctgctgccgc caccgaatag tgngtgcccg gctaccggct ggtggattcc acgggacatg 420
tggttcggac ctgccggcag cggtggaact gaagangctg gtct 464

<210> SEQ ID NO 307
<211> LENGTH: 315
<212> TYPE: DNA
<213> ORGANISM: Mycobacterium tuberculosis
<220> FEATURE:
<221> NAME/KEY: unsure
<222> LOCATION: (various positions within the sequence)

-continued

<223> OTHER INFORMATION: applicants are uncertain of bases designated as "n"

<400> SEQUENCE: 307
agcttcaagg acatcgtcat cgcgaccaaa accgcgagct aggtcggcat ccgggaagca 60
tcgcgacacc gtggcgccga gcgccgctgc cggcaggccg attaggcggg cagattagcc 120
cgccgcggct cccggctccg attacggcgc cccgaatggc gtcaccggct ggtaaccacg 180
cttgcgcgcc tgggcggcgg cctgccggat caggtggtat atgccgacaa agcctgcgtg 240
atcggtcatc accaacggtg acagcagccg gttgtgcacc atcgcnaacg ccaccccggt 300
ctccgggtct gtcan 315

<210> SEQ ID NO 308
<211> LENGTH: 331
<212> TYPE: DNA
<213> ORGANISM: Mycobacterium tuberculosis

<400> SEQUENCE: 308
gctcgcggtc cagcagcaga cgtgtctgac cccgacgccc ggccgccggt accgaaaccg 60
gatcggcccg ccgatggccg cggccacggc gtctgcctta cccggcccgg ataccagcag 120
ccacacctcg cgggaacgct gaatcgccgg cagggtcaag gtgattcggc gtggcggcgg 180
tttcgcgaat cgtccaccgc caccaccatg cgggtgctct cgaagacgcg gggctgtgcg 240
ggaacagcga gttaatgtgg ccctcgggcc ccatgcccag caggtggacg tcgaaattcg 300
gcccgggtca cctggtgcgg cactggcggc c 331

<210> SEQ ID NO 309
<211> LENGTH: 286
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 309
agcttgtcga tcgtccggca gcgtccggcg agtcaagtcg aagccagtcc ggtctcctct 60
ccgactacgg ccaagaactg ggcgacggtg tcagtgcata ccagcggana ctggtggcgc 120
cctaggcgag cgaccgcctc acaaacggcg gtgaccgcgt tctggtcgtg caccatcgag 180
ccgtgcccat cccggccgcg tgccgtcagc cgcatccact ggatgccctt ctcggcggtt 240
tcaatcaggt acaggcgacg ttcgccanca tcgtgccggg gcangg 286

<210> SEQ ID NO 310
<211> LENGTH: 331
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 310
ttggtgatca tcgncccaac gaccccgagg cgatgttctt gcacaccgag gagtgtcgca 60
agctggggct ggccttcgcc gccgatccgt ctcagcagct ggcgaagctg tcggggtgag 120
gaaattcgca ggctcgtcaa cggtgctgct tacttgttca ccaacgacta ctaatgggat 180

-continued

```
ctgctgctgt ccaagaccgg ctggtcagan gccgatgtga tggcgcagat cgacctgcgg    240

gtgaccacat tgggtcctaa gggtgtcgat ttggtagaac ctgacgcacc accatccacg    300

tcggcgttgg tccccgaaac agccagaccg a                                   331
```

<210> SEQ ID NO 311
<211> LENGTH: 458
<212> TYPE: DNA
<213> ORGANISM: Mycobacterium tuberculosis

<400> SEQUENCE: 311

```
ggctcgtatg ttgtgtggaa ttgtgagcgg ataacaattt cacacaggaa acagctatga     60

ccatgattac gccaagctat ttaggtgaca ctatagaata ctcaagcttg attttgatca    120

tcatgatgat catcacccga agtgtggtag ccgcagtggt tatcgtgggt accgtcgtgc    180

tttccatggg cgcctctttc gggctttccg tattggtctg gcaggacatt ctgggtatcg    240

agttgtactg gatggtgttg gcgatgtcgg tgatcctgct cctggcggtg ggatccgact    300

acaatctgct gctgatttcc cggttgaaag aggaaattgg ggccggattg aacaccggaa    360

ttatccgtgc catggctggt accgggggag tggtgacggc tgccggcatg gtgttcgccg    420

ttaccatgtc gttgtttgtg ttcagcgatt tgcgaatt                            458
```

<210> SEQ ID NO 312
<211> LENGTH: 289
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 312

```
caggcatgca agcttggcgt gccgttccaa cccgaattgg ctttcggcgc catcggtgag     60

gacggcgtgc gggtgctcaa cgacgacgtc gtccgcggga cacacctcga tgctgccgcc    120

atggacgcgg tcgaacgcaa gcagctgatc gagctacaac gccgcgcgga acgcttccgc    180

cgcgggcgtg accgcatccc gttgaccggg cggatcgcgg tgatcgtcga tgacggcatc    240

gccaccggag cgacggccaa ggcggcgtgc caggtcnccc gggcgcacg                289
```

<210> SEQ ID NO 313
<211> LENGTH: 154
<212> TYPE: DNA
<213> ORGANISM: Mycobacterium tuberculosis

<400> SEQUENCE: 313

```
ggcatcttgg ccgccatgtt agccacactg ccaccggcta tagaagcgat gcgcaccgtc     60

ctgccagcac attgcggcgc tcctccctgg aaagcaagat aaccaagctc atgccgtggt    120

tgtgggtggc gtggtttggt ttgggtaact ttgg                                154
```

<210> SEQ ID NO 314
<211> LENGTH: 324
<212> TYPE: DNA
<213> ORGANISM: Mycobacterium tuberculosis

<400> SEQUENCE: 314

```
tcggctaata atcgtcgacg ccggcctcct ctgcaatcgc cttggcggtc gccgggttgt     60

caccggtgat catcacggtg cggatgctca ttcggcgcat ttcgtcgaat cgttcccgta    120
```

-continued

```
tgcccacctt gacgatgtcc ttcagatgga cgacgccgat ggcccgcgcg ctgctgttat    180

cggtccattc cgcaacgact aggggtgtcc cccgccggag ctgatgccgt cgacaatggc    240

acccacctcc tcggtggggt gggcaccgtg atcgcgaacc cacttcatca ccgcagccgc    300

ggcaccttgc ggattcgacg gatg                                           324
```

<210> SEQ ID NO 315
<211> LENGTH: 322
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 315

```
ctcaagcttg gaggcgtggc gatcgcggtc caaggcgcgc tctccgagca caacgagcga     60

agacngctcg gcgacggagc ctttatcgac ntccgttcgg gctggctgac ggcggcnaaa    120

taatgctgga ctcgttgttg tcgacggtgc cgtggcgagc cgagcgccgt cagatgtacg    180

accgggtggt ctatgtgccg cggttggtga gtttccacga cctgaccatc gaagatccgc    240

cgcatccgct gctggcgcgg atgcgccggt ggctcaacta attctacggc ggcgaactgg    300

gtnatccctt cnccaccgtc gg                                             322
```

<210> SEQ ID NO 316
<211> LENGTH: 404
<212> TYPE: DNA
<213> ORGANISM: Mycobacterium tuberculosis

<400> SEQUENCE: 316

```
cctaggtcaa ccgtaccgtc atcggatcgg ggtcgaccgc acagatggac tggagcttcg     60

gcgaggtcat cgcctatgcc tcgcgggggg tgacgctgac cccgggtgac gtgttcggct    120

cgggcacggt gcccacctgc acgctcgtcg aagcacctca ggccaccgga aatcattccc    180

gggctggctg cacgactgcg acgtggtcac cctccaggtc gaagggctgg gcgagacgat    240

gcagaccgtc cggacgagcg gcactccttt tccgttggct cttcggccga atccggacgc    300

cgaacccgac cggcgcgggg tcaacccggc accgacgcgg gtgccgttta cccgcgggct    360

gcacaaatcc cgacgggtat gggctttgac ctgccgacgg ggga                     404
```

<210> SEQ ID NO 317
<211> LENGTH: 346
<212> TYPE: DNA
<213> ORGANISM: Mycobacterium tuberculosis

<400> SEQUENCE: 317

```
agcttggcgt gacaccaaca cagggcactt aagatggcaa tgcgccgcct acctgcacgt     60

tttcgcgatg tcagaggatg ccgaggggag aacaatgcga gcacggccgc tgacgttgct    120

caccgctttg gcggcggtga cattggtggt ggttgcgggc tgcgaggccc gagtctaggc    180

cgaagcatat agcgcggccg accgcatttc gtctcgaccg caagcgcgac ctcagccgca    240

gccggtggag ctactgctgc gcgccatcac gccgcctagg gctccggcgg cgtcgccgaa    300

cgtcgggttt ggcgaactgc ctacccgggt ccggcaggca accgat                   346
```

<210> SEQ ID NO 318
<211> LENGTH: 333
<212> TYPE: DNA

-continued

<213> ORGANISM: Mycobacterium tuberculosis

<400> SEQUENCE: 318
tcatgccgtt ggaccgacca tcggagttag ttgccgaacc gcgggaccac cgcaagcacc 60
cggtcctggt cgcgcaccgc gtcggccaac cgcttgagca ccaccacgcc gcagccctcg 120
ccgcgcacga atccatccgc gttggcgtcg aagctgttgc atcggccggt cggtgacagc 180
gccgaccact tggacagcgc gatggcggtg aacggtgaca aggtgagctg caccccgccc 240
gccaatgcca cgtcggtttc acgcaggcga agctctgaca cgccaagtga attgccacca 300
gcgacgacga acaagcggta tctacggcga tgg 333

<210> SEQ ID NO 319
<211> LENGTH: 207
<212> TYPE: DNA
<213> ORGANISM: Mycobacterium tuberculosis

<400> SEQUENCE: 319
gggtcgactt tctgcaaggc gaggctacac cgtcgtcgtc gtggtatgcg atagccatcc 60
cgtcgggcta ctcgccatca ccgatcagct tcgccccgaa gccgccgtgg tgatttccgc 120
tgcgaccaaa ctgaacgggg ccaaaccggt attgcttacc ggcgacaacc gggccaccgc 180
cgatcggctc ggtgttcagg ttggcat 207

<210> SEQ ID NO 320
<211> LENGTH: 250
<212> TYPE: DNA
<213> ORGANISM: Mycobacterium tuberculosis

<400> SEQUENCE: 320
aatccgaaat cctgaccgat acttgaacct ggtctcgttc ggcaataact cgtcggcgtg 60
caggacgcgg cgcaaacgta cttcggcatc aacgcgtccg acctgaattg gcagcaagcg 120
gcgctgctgg ccggcatggt gcaatctaac agcacgctct tcccgtacac caaccccgac 180
ggcgcgctgg cccgggcgga acgtggtcct cgacaccatg atcgaaaaac cttcccgggg 240
aggcggatgc 250

<210> SEQ ID NO 321
<211> LENGTH: 365
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 321
ttccgaattt cgggtccngg tcatatgacc ctcatggaag aagaagcggc cgccccgcgc 60
ccgtgcgacg gcgaatgaaa accctcaccc aggccgcatt gaacgccgac aagacggtgg 120
agcaggtcga agacgtcctg gacggtctgg gtaagaccat ggccgagctg aacagctcgc 180
tgtcacagct gaacagcacc gtggagcgct tggaggacgg tctggaccat ctcgaaggta 240
ccctgcacag cctggacgat ctcgcgaaac ggctcatcgt gttggtcgag ccggtggaag 300
ccatcgtcga tcggatcgac tacatcgtga gcctcggcga aacggtgatg tcaccgctgt 360
cggtc 365

<210> SEQ ID NO 322

-continued

<211> LENGTH: 413
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 322

```
nctcgatctt ggggtacgtt cgatgaggct gctgaccaac aacccggcca agcgggtggg     60

actggatgga tacggattgc acatcatcga gcgcgtgccg ctgccggtgc gggccaacgc    120

ggaagaacat ccgttacctg atgaccaagc gtgacaaatt ggggcacgac ttggctgggt    180

tggacgattt tcacgaatcc gtgcatctgc ccggagaatt cggcggtgcc ttgtgaaggt    240

ggcgccgggg tgccggatct gccgtcgctg gatcgtctgg tgtgcggctg gcgattgtcg    300

ccagcagctg gcacggaaag atctgcgacg cgctgttgga cggcgcccgc aagtggccgc    360

cgggtgtggc ctcgatgacc gactgtggtt cgggtgctcc gcgcgatcga tat           413
```

<210> SEQ ID NO 323
<211> LENGTH: 364
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 323

```
tcatcccgac caaaacgcga gctaggtcgg catccgggaa gcatcgcgac accgtggcgc     60

cgagcgcgct gccggcaggc cgattaggcg ggcatattat cccgccgcgg ctcccggctc    120

cgagtacggc gccccgaatg gcgtcaccgg ctggtaaccg ctcttgcgcg cctgggcggc    180

ggcctgccgg atcaggtggt agatgccnac aaagcctgcg tgatcggtca tcaccaacgg    240

tgacagcagc cggttgtgca ccaagcgcga acgccacccc ggtctccggg tctgtccaac    300

cgatcgaccg cccaagccca catgaacaaa ccccggcatc acgttgccga tcggcatacc    360

gtga                                                                 364
```

<210> SEQ ID NO 324
<211> LENGTH: 488
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 324

```
ttggcgggtt ggcccagcag cccgccggtg acggcgacga tgctgggctg gttgcggccc     60

tgcgccaccg cggcttgcat gctggttggc tgtcttggga cgatcccgaa atagtccacg    120

cggatctggt gattttgcgg gctacccgcg attaccccgc gcggctcgac gagtttttgg    180

cctggactac ccgcgtggcc aatctgctga actcgcggcc ggtggtggcc tggaatgtcg    240

agcgccgtta cctacgtgac ctgatggatc gggggtgcc gaccgtgccc ggcgatgtgt    300

atgtgccggg anagccggtc cggttgccac gcaaaggcca tgtcttcgtc ggtccgacca    360

tcggtaccgg gacacggcgc tgtattgccc ggttcgctgc cgagttcgtc gcgcaactgc    420
```

-continued

```
acgcnggcgg gccagcggtg ctcgttcanc ccggaggttc cggtgacgat gatcgtgttg    480

gtctccct                                                             488


<210> SEQ ID NO 325
<211> LENGTH: 396
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 325

gtaggagaga acaaagaccg tcgataggac acgtgttacg ccggtagctg tcattggtat     60

ggggtgccgc tgccgggggg catctactca cccgatcggt tgtgggaggc gttgctgcgg    120

ggcgacaatc tggtcaccga gatccccgcc gaccgctggg acatctacga gtactacgac    180

cccgaacccg gcgtgcccgg acgcaccgac tgcaaatggg gcgcgtacct cgataacgtc    240

ggcgactttg atcccgagtt cttcgggatc ggggagaaag aaacgatagc gatcgatccg    300

cagcaccgct tgttgctgga aacctcctgg gaagccatgg aacacggcgg gctaacaccg    360

aaccatatgc ctcccgacan gggttttcgt ggggtt                              396


<210> SEQ ID NO 326
<211> LENGTH: 394
<212> TYPE: DNA
<213> ORGANISM: Mycobacterium tuberculosis

<400> SEQUENCE: 326

cgaactgagc ccatagaaag gcagcgacta attcgctggg caaataggaa gaccctttgt     60

cctgccacgt atatttgtcg acctcgttgc gaaggaagcg gctgcgattg gtgccctttt    120

ccctggagaa tctctgcccg gagcaggaag tcttatgagt tgacaagcag gggcgccgcc    180

ttcgccggaa atcacattct tggtctcgtg aaatgagagc gctcccaggt cgccgatgct    240

gccgagcgcc cgcccacgat acgacgccat cgcgccttgg gccgcgtctt cgaccaccgc    300

caggttgtgg tgcgtggcga tcttcatgat cgcgtccatc tcgcaggcca cccggcatag    360

tgaacgggga ccatggcctc ggttcgcggg tgaa                                394


<210> SEQ ID NO 327
<211> LENGTH: 140
<212> TYPE: DNA
<213> ORGANISM: Mycobacterium tuberculosis

<400> SEQUENCE: 327

cttagacgcc acctccgggc cgagctccac ggggtggata agtacggccg gatgtggccg     60

caatgggaag ttgttgcccg cttgactgtc cgggttaacg ccggattcca ccacatcccc    120

ttgcgaaagg ccgttgggtt                                                140


<210> SEQ ID NO 328
<211> LENGTH: 242
<212> TYPE: DNA
<213> ORGANISM: Mycobacterium tuberculosis

<400> SEQUENCE: 328

gatcgcgatc gtcgatgtgg ccatccggct tggcgtcgac ccgcgtaagg cagaccagat     60

ggttcgcggc acggtcaacc tgccacacgc actggtaaga ctgcccgcgt cgcggtattc    120
```

-continued

```
gcggttggtg aaaaggccga tgctgccgtt gccgcggggg ctgatgctgt cggatcgacg    180

atctgatcga gaggatcagg gcggctggct ggaattcgat gccgcgatcg cgataccgga    240

tt                                                                   242
```

<210> SEQ ID NO 329
<211> LENGTH: 220
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 329

```
agcttacgcc gctttcgctt cngatttggg acgccgcatc gaaagcgcag ttggaagcgc     60

ggcgcccggc tggtcgagct gctcaagcag ccgcaatccc agcccatgcc cgttgaggag    120

caagtggttt cgatcttcct gggcaccggc ggtcacctgg actcggtgcc cgtcaaggat    180

gtcggcggtt cgaaaccgaa ttactggacc acatgcgggc                          220
```

<210> SEQ ID NO 330
<211> LENGTH: 328
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 330

```
cgacgggacc tcgtcgcatc ttccatagcc cgccacacct tcagttgctc accggaatcc     60

aaccggtata aggtcggcga agcgctcggc attggtcatc gggatatgcc gctcgggacg    120

gtcagatgcc ctcgggtccn gccagcactc ctcaggcttc gtcggggtgg tcgcgaccgc    180

atgggccaca tcgcattcac caggtctgcg cgaatcacca gcacgtanac ggttcctttc    240

ctaagcaaca ccgaaatttc aggacccgaa tgctccggga aaacatgtca cggtaagtcc    300

ggtattccgg gtaccggttg agcattga                                       328
```

<210> SEQ ID NO 331
<211> LENGTH: 366
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 331

```
cggcatcggt ttgggctgtc accagcagtt ggtagttctt cactactgtt gttcgagcgt     60

cgagccgccg cgcgtgtcga ggtcgccgga cgcgtacccg ccaggccggt cagggtgccc    120

ttccagtcca cgcngctgtg gtcggctaac cgcttatctt caatcgagac natcgccagc    180

ttcatcgtgt tggcgatctt gtccgagggc acctcgaacc ggcgctgcga ntacagccac    240

gcgatcgtgt tgcccttcgc gtcgaccatc gtcgataccg caggcacttg cccctcgagc    300

agctgggccg atccgttggc aacgacctca gaggcacgat tggacatcag ccctagcccg    360

cctgcg                                                               366
```

-continued

<210> SEQ ID NO 332
<211> LENGTH: 407
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 332

```
ccgtcgangc cgccgacttg gcttgaccga caccaacatg gcctgagggt gttcaacaag     60

accgtggccg acgggctgaa catcaccatg agcggcatga gccacgccac cgagttcatc    120

atgttgatcg ccgaaaacca ttggcgggta gcggaagaac ggtcgaggtg ctctacaccg    180

agtattcgaa gtcgaaaggc caaccgctgc tcaacggcgt caacatcatt ttcgacgggt    240

ttctgcgagg gaggatgcca cgatgaactg gatccaggtg ctgttgatcg cgtcgatcat    300

cgggttgctg ttctacctgt tgcggtcgcg ccgaagcgcg cggtccgtgc ctgggtcaag    360

gtgggctatg tcttgttcgt gctcccggca tctatgccgt gctgaga                  407
```

<210> SEQ ID NO 333
<211> LENGTH: 473
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 333

```
ttacacgncc tgcttccggc tcgtatgttg tgtggaattg tgagcggata acaatttcac     60

acaggaaaca gctatgacca tgattacgcc aagctattta ggtgacacta tagaatactc    120

aagctttttg agcgtcgcgc ggggcagctt cgccggcaat tctactagcg agaagtctgg    180

cccgatncgg atctgaccga agtcgctgcg gtgcagccca ccctcattgg cgatggcgcc    240

gacnatggcg cctggaccga tcttgtgccg cttgccgacg gngacgcggt angtggtcaa    300

gtccggtcta cncttgggcc tttgcggacg gtcccgacgc tggtcgcggt tgcgccgcgg    360

aaagcggcgg gtcgggtgcc atcaggaatg cctcaccgcc gcggcactgn acggccagtg    420

ccgcggcgat gtcngccatc gggacatcat gctcgcgttc atactcctcg acc           473
```

<210> SEQ ID NO 334
<211> LENGTH: 305
<212> TYPE: DNA
<213> ORGANISM: Mycobacterium tuberculosis

<400> SEQUENCE: 334

```
caggcatgca agctttgtca caccaagtgt ttcgaccagg cgctccatcc ggcgagtgga     60

tactcccagc aggtagcagg tcgccaccac gctggtcagt gcgcgttcag ctcgcttgcg    120

gcgctgcagc agccagtccg ggaaatagct gccctggcgc agcttgggga tcgcgacgtc    180

gatggttgcg gcacgggtgt cgaaatcacg gtggcggtag ccgttgcgct gattggaccg    240

ctcatcgctg cgttcgcggt agcccgcccc gcacagggcg tcggcttcag cccccatcaa    300

ggcgg                                                                305
```

<210> SEQ ID NO 335
<211> LENGTH: 432

-continued

<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 335
agcttagcca gtttttctac tcttgggccc acacccacag tgcttcgacg gtacggtcac 60
ccatgatggc catccagttg gcatcggtga gctgataaat gccagctggt ttcgccaacc 120
cggtagcgat cttggcgcgc tgcttgttgt cactgatacc tatcgagcaa gacagcccgg 180
tttgcgacaa gatgactttt cggatctctt cggcgacttc gatggggtcg tcgggagtcc 240
cgggcgccac cgcgaggtaa gcctcgtccc agccccatac ctcgaccggg tatcccaggt 300
cgcgcaataa cgccaccacc tcctcggacg ccgcgttgta ggcggctggg ttcgacggca 360
agaagtggcc tcagggcatc gtcggcgcgg tcccaacggc ntgccggcgc gcacaccgta 420
ggcgcggggc tc 432

<210> SEQ ID NO 336
<211> LENGTH: 429
<212> TYPE: DNA
<213> ORGANISM: Mycobacterium tuberculosis

<400> SEQUENCE: 336
ccggcggaac tcagacgtgc tggtggtgcg gcatggcacc gcgggcagca aagcgcactt 60
ctccggggac gacagcaagc gaccgctaga caagaggggt cgtgcgcagg cagaagcgtt 120
ggtaccacag ctgctggcgt tcggcgccac cgatgtttat gccgccgacc gggtgcgctg 180
ccaccagacg atggagccac tcgccgcgga actgaacgtg accatacaca acgagcccac 240
cctgaccgaa gagtcctacg ccaacaaccc caaacgcggc cgacaccgag tgctgcagat 300
cgtcgagcaa gtaggcacac ccgtgatctg cacgcagggc aaggtcattc ccgatctgat 360
cacgtggtgg tgcgagcgcg accgtgtgcc cccgacagtc ccgcaatcgc aaaggcagca 420
cgttggtgt 429

<210> SEQ ID NO 337
<211> LENGTH: 94
<212> TYPE: DNA
<213> ORGANISM: Mycobacterium tuberculosis

<400> SEQUENCE: 337
gtatggtcag ctgtccatcc ggcgctgtcg gccgagctgc cagatctcgt cagccgtaac 60
cgggttgcgg gatccacgcg tgcgggttgt ctac 94

<210> SEQ ID NO 338
<211> LENGTH: 351
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 338
ccgactttcc gcgggtaccc gctcaacttt gtgtcnacct caacgccatt gccggcacct 60
actacgtgca ctccaactac ttcatcctga cgccggaaca aattgacgca gcggttccgc 120

-continued

```
tgaccaatac ggtcggtccc acgatgaccc agtactacat cattcgcacg gagaacctgc    180

cgctgctaga gccactgcga tcggtgccga tcgtggggaa cccactggcg aacctggttc    240

aaccaaactt gaaggtgatt gttaacctgg gctacgcgac ccggcctatg gttattcgac    300

ctcgccgccc aatgttgcga ctccgttcgg ttgttccaga angtcagccc g             351
```

<210> SEQ ID NO 339
<211> LENGTH: 152
<212> TYPE: DNA
<213> ORGANISM: Mycobacterium tuberculosis

<400> SEQUENCE: 339

```
gcaccgatgt cggcgagcac ttcgtcaact tccaggggtg cccgcaccaa gtatttcgac     60

gagtatttcc gtcgggccgc cgccgccggt gcgcggcagg tggtcatcct ggcggcgggg    120

ctgggactcg cgcgcgtacc ggctgcctcg gc                                  152
```

<210> SEQ ID NO 340
<211> LENGTH: 263
<212> TYPE: DNA
<213> ORGANISM: Mycobacterium tuberculosis

<400> SEQUENCE: 340

```
tgcacccaac ttactgagca tgctaacgct ggtcgtgcgg gtcttgttcc cgcgtgtcgg     60

cagggcacac gctcggggcg tagctgggag aggccccggt caagcccgga gagcagtgct    120

cagtccgcca gcttgaccga ctttcgatga gaacgcgctt ctcgccgtat tgaactggcg    180

tgctgacggt cgctgagcag cgctcgccga gtgcggccgc tgattctttc atcgagccag    240

gacgcgcatt cgtgttcggc cgc                                            263
```

<210> SEQ ID NO 341
<211> LENGTH: 249
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 341

```
agcttacggc cggtcgacgc gacgagtggt tcatgacacc acaaaccgtc aacgcctact     60

acaacccggg gatgaacgaa atcgtcttcc cgcagcgatt ttacagccac catttttcga    120

tccgcaggcc gacgaggccg ccaactacgg cgggatcggg gcgcgtgatc gggcacgatg    180

atcgggcacg gtttcgacga tagggcgcca aatacgangg cgacgcaatc tggtcnattg    240

gtggatcga                                                            249
```

<210> SEQ ID NO 342
<211> LENGTH: 269
<212> TYPE: DNA
<213> ORGANISM: Mycobacterium tuberculosis

<400> SEQUENCE: 342

```
atgtcgtcac gtcaccacaa tcgcgaggac ccaatcatgc cgcccagggc ggccaaccca     60

atggtggccg cgaagcggca gctcgatcgc agcgcggagg tgccggccgc cagttgattc    120

acgaacaggg tgaggtcata ggcgggcagg atagtgacga acgcaagacc tatatctgcc    180

gtcggagtaa gaatcgagta gccggtcgac caacggaagc gaaagtgtcc gcgatgttga    240
```

-continued tgagcgtcgc cggttgtggc ggcggtggc 269

<210> SEQ ID NO 343
<211> LENGTH: 336
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 343
agcttcacca gcgtgccgat gctgttcgcn acacctccct actatgcgca attcgccgac 60
acgggtggca tcaacacggg cgataaggtg gacatcgctg gggtgaacgt cgggctggtg 120
cgctcgctgg caatccgcgg caaccgcgtg ttgatcggat tctcgttgcc cggcaagaca 180
atcgggatgc aaagccgggc agcaattcgc accgacacca ttcttggccg taagaacctg 240
gaaatcgaac cccgcggttc ggagccgttg aaacccaacg gtttcctgcc gttggcgcag 300
aacactacgc cataccaaat ctatgacgcg ttcgtc 336

<210> SEQ ID NO 344
<211> LENGTH: 417
<212> TYPE: DNA
<213> ORGANISM: Mycobacterium tuberculosis

<400> SEQUENCE: 344
ctgccgcggt ggcggtcagc gcctggcaag tcaccgcacc gccgtccggt tcatcggcag 60
gctcccccga aaagggccct ggcaacagaa ggtgatcaat gagctcccgc agaccttcgc 120
cgatctggga ccgacatacg tgaagttcgg ccagatcatc gcgtccagcc cgggagcatt 180
cggtgagtcg ctgtcgcggg gaattccgcg gcctgctcga ccgggtgccg cccgcaaaaa 240
ccgacgaggt gcacaagctc ttcgtcgagg aactcggcga cgagccggcc cggctgttcg 300
cctccttcga ggaagaaccg ttcgcgtctg cgtccatcgc ccaagtgcac tacgcgacct 360
gcgcagcggc gaagaagtgt ggtcaagatc cacggccggg catccgccgc cgcgttt 417

<210> SEQ ID NO 345
<211> LENGTH: 405
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 345
gatcgtgccg gccccccggc ggcagtagca gatcagctcg tcgaaatcgc ggcaaccagt 60
ccagtcgatt tccatacggg cgccgtcaat caactctgcg aacatcgcga tcggcaccgg 120
aaaccggcga gccgcgtcag ccagcgcaac cagcaccggg atcggatgaa tcatcaatat 180
tatcaagtga tttcctgatg gcatcgagct cggtgatctt ggtctcgggg gccagctcgc 240
cgtcggcgac gtcgtcgatc cggcggccga gcgcatagac cgcaaatagt gccgctcgct 300
tttcgcgcgg caagagtcgg atgccgtaat atangtttct ggcggccgtg cgcgtgatcn 360
actcggtgat tcgatacgcc tgttcatctc ggtcatgccg tcctc 405

<210> SEQ ID NO 346
<211> LENGTH: 414

<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 346

```
ggtggcgcaa tgaccgaaac caccccagcc ccgcaaaccc cggcggcccc ggccgggccc     60

gcacaatcgt tcgtgttgga gcggcccatc cagaccgttg ggcgccgtaa ggaggccgtg    120

gtacgagtgc ggctggtgcc cggcaccggc aagttcgacc tcaacggccg cagcttggag    180

gactacttcc caaacaaggt gcaccagcag ttgatcaagg cacccctggt caccgtggat    240

cgggtggaaa gtttcgacat ctttgcccac ctgggcggcg gcggcccgtc gggtcatggc    300

cggcgcgctg cgcctgggta tcgcccgggc attgattctn gtatcgccgg atgaccggcc    360

cgcgctgaat aangccggct tcttgaccgt gatccacgcg ccaccgaacg caaa          414
```

<210> SEQ ID NO 347
<211> LENGTH: 331
<212> TYPE: DNA
<213> ORGANISM: Mycobacterium tuberculosis

<400> SEQUENCE: 347

```
cacaatagat tactcaagct tcgaaccagc ggccttatca cgtatccccg ctgagacctt     60

gacccttagg gccgaagtga cttcgctgct gctatgccga cacccgattt ccagacgctg    120

ctgttacacg acggccgggc cggtggccac catcacgctc aaccgcccgg aacagctcaa    180

caccatcgtc ccgcccatgc ccgacgagat cgaggccgct atcgggttgg ccgagcgcga    240

ccaggacatc aaggtcatcg tgctgcgcgg tgccggccgc gccttctccg gcggttacaa    300

cttcggcggc gggttccaac attgggggca t                                   331
```

<210> SEQ ID NO 348
<211> LENGTH: 386
<212> TYPE: DNA
<213> ORGANISM: Mycobacterium tuberculosis

<400> SEQUENCE: 348

```
tcaggacgct tatggttggc agatggtcgc cctggcgtcg aatacgcgcg agcgcatgag     60

ctcaccggtt cggaacaacg tatcgaagaa cgtcgcactg ctggcagatg gtatctccga    120

tgtggttgta atttgtatcc caactctaac tgtgctatcg gatcagcgtg aatatcgaga    180

tattgcgaat gcgatgacag gccgccattc ggtttattcg cttacgcttc ccgggttcga    240

ttcgtctgat gcactgccgc aaaacgcgga tatgattgtt gaaaccgtat ctaacgcaat    300

tattgatgtg gtaggcggca gctgccgttt tgtgctgtcg ggctattcat cgggtggggg    360

tgtttggcta tgccctctgc tcccat                                         386
```

<210> SEQ ID NO 349
<211> LENGTH: 187
<212> TYPE: DNA
<213> ORGANISM: Mycobacterium tuberculosis

<400> SEQUENCE: 349

```
cgcagctgtc gccgatctgg tccggaatac ctagctccag gttctgagtg gagatgagtg     60

cggccatcga agtgttgtca atgtactcca ggatgtcagg tgccaggccg ctggcgagga    120

tcttgggcac cgccgccatg acttggtcga agtcggcgaa cggggcgagc acgctggcgt    180
```

-continued

```
cgtggtc                                                             187


<210> SEQ ID NO 350
<211> LENGTH: 241
<212> TYPE: DNA
<213> ORGANISM: Mycobacterium tuberculosis

<400> SEQUENCE: 350

gtagttcgtt catccaaaca cagtgcggta ccggctcaag cggatcaccg acttcaccgg    60

gcgcgatccc acccagccac gcgatgccta tgtccttcgg gtggcggcca ccgtgggtca   120

actcaactat ccgacgccgc actgaagcat cgacagcaat gccgtgtcat agattccctc   180

gccggtcaga gggggtccag caggggcccc ggaaaagata ccaggggcgc cgtcggaccg   240

a                                                                   241


<210> SEQ ID NO 351
<211> LENGTH: 335
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 351

tccgctcgct tctccgagag gttgagtgcc aacgctctgc cgatgcccga agccggcccc    60

ggtgatgacg gcgaccttgc cttcgaatga gctcatttga ctactccccg tggttgtccc   120

tgcgattggt ggaggtggcc gcgcagcctt gccccgaggt cggcgatcgc gtctcgggct   180

tcggggagca gactgacctg cagatggaag tcgtgccaca tgcccgcgaa ccggcgatgc   240

tcgatgcttg ttttcgaagc ggcgcaggcg gtttcgatct tgtccgcgtc aacacngatc   300

ggatcgtcgc ccgcggtctg catgacgaat gggcg                              335


<210> SEQ ID NO 352
<211> LENGTH: 441
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 352

atgggaggcc accgattacc atcttgcaca caccgattcc gggctattga tgtccacgtt    60

cggtccgcga accgcgctgt ggctgctgct ggccaaaggc ggaggcgata ccgaagtcag   120

tgcccaagct tgggttccac gctcgcgcag ccacgccgtc acctttccac gagacctcac   180

ctgccgatcc gaaatggaat cggccgtgac ggaattggcg cagcgaacac tcaacgaggt   240

ggtggcttcg tcgcgaaccg tcacccgagt cgcggtcacc gtgcgcacgg cgacgttcta   300

cacccgcacc aagatccgaa agctgcaagc tcccagcacc gatcccgacg tcatcaccgc   360

tgccgcccgg cacgttcttg aacctattcg agctggaatc ggccgtccgg ttgctgggaa   420

ttgcngttaa gaactgggcc t                                             441


<210> SEQ ID NO 353
<211> LENGTH: 332
<212> TYPE: DNA
```

-continued

<213> ORGANISM: Mycobacterium tuberculosis

<400> SEQUENCE: 353
gctttgcgcg cttctccgag aggttggagt gccaacgctc tgccgatgcc cgagccggcc 60
ccggtgatga cggcgacctt gccttcgaat gagctcattt gactactccc cgtggttgtc 120
cctgcgattg gtggaggtgg ccgcgcagcc ttgccccgag gtcggcgatc gcgtcgcggg 180
cttcggggag caaactgacc tgcagatgga agtcgtgcca catgcccgcg aaccggcgat 240
gctcgatgct tgttttcgaa gcggcgcagg cggttcgatc ttgtccgcgt caacgcagat 300
cggatcgtcg cccgcgggtc tgcatgaaga at 332

<210> SEQ ID NO 354
<211> LENGTH: 334
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 354
ctcacgcagc cacgccgtca cctttccacg aagacctcac ctgccgatcc gaaatggaat 60
cggccgtgac ggaaattggc gcagcgaaac actcaacgag gtggtggctt cgtcgcgaac 120
cgtcacccga gtcgcggtca ccgtgcgcac ggcgacgttc tacacccgca ccaacatccg 180
aaagctgcaa gctcccagca ccgatcccga cgtcatcacc gctgccgccc ggcacgttct 240
tgacctattc gagctggatc ggcccgtccg gttgctggga gtgcggttag aaactggcct 300
agaaaccggc gggcacaccg cacctgggcg gggn 334

<210> SEQ ID NO 355
<211> LENGTH: 341
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 355
tgcttccggc tcgtatgttg tgtggaattg tgagcggata acaatttcac acaggaaaca 60
gctatgacca tgattacgcc aagctattta ggtgacacta tagaatactc aagcttgatg 120
ccgccgaaac cgagcgtgag cacgccgcca gccaccacnc gcgggtcggg cgccgggccc 180
gggtcgccan gctgctccgc tcggtgatgg cacgccaccg cgacaccacc cggctgcgct 240
acgtcgagcc ataccgggcg gagctacatc ggctcggccg cccagtgttc gggccctctt 300
tcgaagtcga agtcgatacc gattgcgcat ccgcngccgc a 341

<210> SEQ ID NO 356
<211> LENGTH: 259
<212> TYPE: DNA
<213> ORGANISM: Mycobacterium tuberculosis

<400> SEQUENCE: 356
caggcatgca agcttcacgt ccgtacggct cgggtacgct tcggtcgcag tgtgcgagtg 60
atagatgacg accgggacct cgtctgcatc ttccatagcc cgccacacct tcagttgctc 120
accggaatcc aaccggtaga aggtcggcga gcgctcggca ttggtcatcg ggatatgccg 180

-continued ctcgggacgg tcagaaccct cgggtccggc cagcactccg caggcttcgt cggggtggtc 240
gcgacgcgca tgggccacc 259

<210> SEQ ID NO 357
<211> LENGTH: 349
<212> TYPE: DNA
<213> ORGANISM: Mycobacterium tuberculosis

<400> SEQUENCE: 357
gcttgtctat cgtcccggcc aggtccggcc agtcaaggtc gaaggccagt ccggtctcct 60
ctccgactac ggccaagaac tgggcgacgg tgtcagtgca gaccagcgga aactggtggc 120
gccctaggcg agcgaccgcc tcacaaacgg cggtgaccgc gttctggtcg tgcaccatcg 180
agccgtgccc agcccggccg cgtgccgtca gccgcatcca ctggatgccc ttctcggcgg 240
tttcaatcag gtacaggcga cgttcgccac catcgtgccg gggcacggtt agcgagaaac 300
cgccgacttc acgattgcct cggtgatgcc gtcgaaacag atcgggcct 349

<210> SEQ ID NO 358
<211> LENGTH: 325
<212> TYPE: DNA
<213> ORGANISM: Mycobacterium tuberculosis

<400> SEQUENCE: 358
gcgcgccatg ttgaggttgt ccgacggtga cgacggtgaa ccacaactgt ttgacctgtc 60
cgcacacacc gtgtggatcg gcgagcggac ccgacaaatc gatggcgcgc acatcgcgtt 120
tgcccaggtg attgctaatc cggtcggggt caagttgggc cccaacatga ccccggaact 180
ggccgtggag tacgtcgagc ggctcgaccc gcacaataag ccgggccggc tgacttggtg 240
agcaggatgg gcaaccacaa ggtccgcgat ctgttgccac cgatcgtgga gaacgtccat 300
gccaccgggc atcaggtcat ctggc 325

<210> SEQ ID NO 359
<211> LENGTH: 191
<212> TYPE: DNA
<213> ORGANISM: Mycobacterium tuberculosis

<400> SEQUENCE: 359
ttgccttcca tgccgagcaa ggtcgactca gcgatgacga attgttcttc ttcgcgggtg 60
ttgctgctgg ttgcgggcta tgagagcact gctcatatga ttagcacatt gtttctgacg 120
ctggccgact atccagatca gctgacactc cttgcgcagc aaccagacct gatcccgccg 180
gcgatcgagg a 191

<210> SEQ ID NO 360
<211> LENGTH: 74
<212> TYPE: DNA
<213> ORGANISM: Mycobacterium tuberculosis

<400> SEQUENCE: 360
cgacgctggg cccaactgcg accaccaggt cctggtatgg caggacatgg ccgggttcag 60
cggcgccaat accg 74

<210> SEQ ID NO 361
<211> LENGTH: 312
<212> TYPE: DNA
<213> ORGANISM: Mycobacterium tuberculosis
<220> FEATURE:

-continued

<221> NAME/KEY: unsure
<222> LOCATION: (various positions within the sequence)
<223> OTHER INFORMATION: applicants are uncertain of bases designated as “n”

<400> SEQUENCE: 361
taacgactcg ggtccagcga ccgcgccaac acnaacggcc ggacnacgtg ggccagggtc 60
gcggcctccc ctacaaacag gatccgttgc ctgcgaacga caggctccgg tgcggcgttg 120
ggcgccgtgc tcgtcccagc gtccggtccc gggtcgccgg cgacgcttgt ttcctccata 180
ctcgccccct aatctcgagg cagcccgtac ccgcaggcaa cctcccaaaa atgcaatccc 240
ccaaaatgca atgcgtcnag ctatttctca caccgaccgc tagttgcgga tcanaaatcc 300
gttgggcgcg ga 312

<210> SEQ ID NO 362
<211> LENGTH: 335
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 362
cntggcggtg ggtgcggtgt cgaacacgac cacacttctt tgcggttcgg tgatctcgac 60
accggccgcg agccgaccac catgcgcgcg tagatcggcg atcagcgcgt cggctatcgc 120
ctgggtgccg cccaccggaa tcggccagcc gaccgaatgg gccagcgttg ccatcatcag 180
tccggcgccg gccgacacca gtgacggcaa cggtgaaatc ncgtgggcgg caacgccggt 240
gaacaacgcg cgggcatcct cgcccgccag cgaccgccag gcaggggtgc cctgggccag 300
catccgcagc ccgagacnca ggaccgancc cagtg 335

<210> SEQ ID NO 363
<211> LENGTH: 386
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 363
gcttttcnga tcgcagcgag tcgtacccgc gccggtcacc ttcgtggata tcgccggcct 60
ggtcaagggg gcgtccgagg gagccgggct gggtaacaag ttcctggctc atatccgcga 120
atgcnacgcc atttgtcagg tggtgcgggt gttcgtcaac aacnacttga ctcatgtcac 180
cggacgggtc gatccccant ccgacattga ggtcgtcgan accgagctga tcctggcana 240
tctgcaaacc ctggagcggg ccacgggccg gctggagaag gaancgcgca ccaacaaggc 300
gcgcaagccg gtctacgacg cggcactgcg tgcccagcag gtgctcgacg ccggcaanac 360
gctgttcgcc gcgggggtgg atgccg 386

<210> SEQ ID NO 364
<211> LENGTH: 386
<212> TYPE: DNA
<213> ORGANISM: Mycobacterium tuberculosis
<220> FEATURE:
<221> NAME/KEY: unsure
<222> LOCATION: (various positions within the sequence)

-continued

<223> OTHER INFORMATION: applicants are uncertain of bases designated as “n”

<400> SEQUENCE: 364

```
gtcgtacgcc attngtcggt gtgcgcatac cagtacgacg cgccgggcac ctgacgcggc     60

ggccgcgacc agtcggtggc catcgccatc gtctgccacc cggtcaacgg acgcaccttc    120

tcctggccga cgtagtgcgc ccacccgccg ccgttgcgtc ccatcnatcc ggtcaacatg    180

agcagcgcca acaccgagcg gtacatgaca tcgctgtgga accagtgaca gattccgccg    240

cccatgatga tcatcgaccg tcctccggat tcggtcgcgt tgcgggcgaa attccttggc    300

aaaccggatt gcctgcgcgg ccggcacacc ggtgatcgac tcctgccagg ccggggtgtt    360

ctgctgggtt cggtcgtggt accggt                                          386
```

<210> SEQ ID NO 365
<211> LENGTH: 335
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 365

```
gcgaggcggt atcgcttccc gtcgtaccgg cgaccgccag ccgagaagct cgttttccca     60

gtgttgctgg ggattctcac gctgctgctg antgcgtgcc anaccgcttc cgcttcgggt    120

tacaacgagc cgcggggcta cgatcgtgcg acgctgaant tggtgttctc catggacttg    180

gggatgtgcc tgaaccggtt cacctacnac tccaagctgg cgccgtctcg tccgcaggtc    240

gttgcttgcg atagccggga ggcccggatc cgcaatgacg gattccatgc caacgctccg    300

agttgcatgc ggatcgaata cnaattgatc accca                                335
```

<210> SEQ ID NO 366
<211> LENGTH: 396
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 366

```
tgggtcttgc cggcgagccc agcgaagtcg ctagcgtggc cgtgtttctt ggcttcggat     60

ctatcctcgt tacatgaccg gcaccgtgtt ggacgtgact ggcggccggt tcatatgaca    120

ccgagatcat tgccacggta cggcaattcg tcaagaagga aatctttccc natgcaccgg    180

ccctcgaacg tggcaacagc tacccgcaag aaatcgtcga tcggctgggt gttattggct    240

tgctcggtcg ccggctgcaa gggtatcgac accaccgagt tcattctcgg gcgtgccggc    300

gcattcgagc tggcggtgcg cgctgcccag caccgtcata agtacttgan gatggtcaaa    360

cgtcggacga accgccacca cgtcgctgcc gaacgg                               396
```

<210> SEQ ID NO 367
<211> LENGTH: 262
<212> TYPE: DNA
<213> ORGANISM: Mycobacterium tuberculosis
<220> FEATURE:
<221> NAME/KEY: unsure
<222> LOCATION: (various positions within the sequence)

-continued

<223> OTHER INFORMATION: applicants are uncertain of bases designated
as “n”

<400> SEQUENCE: 367
tagatgccca agcttgccnt tanagacctc gtcgaccaag cacggacgcg accgtcgaag 60
gtggcgaatc cgggcttggc gtcnacccgc gtaaggcaga ccagatggtt cgcggcacgg 120
tcaacctgcc acacggcact ggtaagactg cccgcgtcgc ggtattcgcg gttggtgaaa 180
aggccgatgc tgccgttgcc gcgggggcgg atgttgtcgg gagtgacgat ctgatcgaga 240
ggattcaggg cggctggctg ga 262

<210> SEQ ID NO 368
<211> LENGTH: 303
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as “n”

<400> SEQUENCE: 368
tctccacggc gtggatcaag gtaccggccg ggatgttgcg caatggcagg ttgttgcccg 60
gcttgatgtc tgcgttagcg ccggattcca ccacatcccc ttgcgaaaag tccgttgggt 120
gcaatgatgt agcgcttctc cccatcgaga tagtggagca acgcaatccg tgcggtacgg 180
ttcgggtcgt actcgatgtg cgcgaccttg gcgttgacac catctttgtc attgcggcga 240
aagtcgatca tccggtaagc gcgcttatga ccgccgcctt tgtgccgggt nggtaatccg 300
gcc 303

<210> SEQ ID NO 369
<211> LENGTH: 367
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as “n”

<400> SEQUENCE: 369
gcccggttcg atcgggcatg tccgcagtcg tcgttaccgg aggcggtcgt ggccgcgcta 60
atcggcgtcg gcgccgacaa gatgtgggat atccgcaatc ggggcgtcat ccctgcgggc 120
gcgctccccc gcgtccgagc cttcgtcgac gcaatcgagg caagtcacga cgcggatgag 180
gggcagcagt gaattacagc gaggtcgagc tgttgagtcg cgctcatcaa ctgttcgccg 240
gaaacagtcg gcgaccgggg ttggatgcgg gcaccacacc ctacggggga tctgctgtct 300
cgggctgccg acctgaatgt nggtgcgggc ancgccggta tcnactcccg tggaacacag 360
ccggggc 367

<210> SEQ ID NO 370
<211> LENGTH: 366
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as “n”

<400> SEQUENCE: 370

-continued

```
ctcggcgtgg atatcggtgt agccggcgcc ggtgaangtc ggctccttac gtccactcga     60

caacagctca tagcgatcca accagtangc aaccgccttc agcagtacaa ccgcgccggc    120

gaacactgcg agttgaacgc gagctgcctg ggtcagcatg cctctgccgg ttgtcagccg    180

aaggccgccg aacaggtaat gcgtcaacag gctcgctaga aacgccagaa ccacggccac    240

gaacagccag ttcagcaccg accggtagaa cggcagatcg aagacgaaaa aacccaatgt    300

catagccgaa ttcggggtcc acgatgccaa aggtgccccc gtgtacaaca actgaacctt    360

caccca                                                               366
```

<210> SEQ ID NO 371
<211> LENGTH: 455
<212> TYPE: DNA
<213> ORGANISM: Mycobacterium tuberculosis

<400> SEQUENCE: 371

```
tccggctcgt atgttgtgtg gaattgtgag cggataacaa tttcacacag gaaacagcta     60

tgaccatgat tacgccaagc tatttaggtg acactataga atactcaagc ttcacgtccg    120

tacggctcgg gtacgcttcg gtcgcagtgt gcgagtgata gatgacgacc gggacctcgt    180

cggcatcttc catagcccgc cacaccttca gttgctcacc ggaatccaac cggtagaagg    240

tcggcgagcg ctcggcattg gtcatcggga tatgccgctc gggacggtca gagccctcgg    300

gtccggccag cactccgcag gcttcgtcgg ggtggtcgcg acgcgcatgg gccaccatcg    360

cattcaccag gtctgcgcga atcaccagca cgtagacggt tcctttccta agcaacaccg    420

aagtttcagg accgaatgct ccgggaaaca tgtca                               455
```

<210> SEQ ID NO 372
<211> LENGTH: 196
<212> TYPE: DNA
<213> ORGANISM: Mycobacterium tuberculosis

<400> SEQUENCE: 372

```
caggcatgca agcttgatgc cgccgaaacc gagcgtgagc acgccgccag ccaccacgcc     60

cgggtcgggc gccgggcccg ggccgccagg ctgctccgct cggtgatggc acgccaccgc    120

gacaccaccc ggctgcgcta cgtcgagcca taccgggcgg agctccatcc gctcggccgc    180

cagtgtccgg gccctc                                                    196
```

<210> SEQ ID NO 373
<211> LENGTH: 443
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 373

```
cctgcatccg gctcgtatgt tgtgtggaat tgtgancgga taacaatttc acacaggaaa     60

cagctatgac catgattacg ccaagctatt taggtgacac tatagaatac tcaagcttcc    120

aatccccctg ccctgatacg cgtcggcaac cgtgaacgcg atctcggcga ccgtcggatc    180

ggtttcatcc cgcacaaaac gcgcgtcggc tacggggtcg cttccgtcgg tcaccaccca    240

gacgaagtgg tcgacgtagt cgacttccga caggtagtgc atcaacgccg gactgggaac    300

acnagccgac atgaaccgtc gatacagcgt ctcnccggag aactggatgt gtccgtgcac    360
```

-continued

```
ggtccgctcg cggtcaccgg gcagcacggg gcgtaacatc agttgagtcc cgtcggcaag    420

ccgtaccgga atcggggaga cga                                            443


<210> SEQ ID NO 374
<211> LENGTH: 445
<212> TYPE: DNA
<213> ORGANISM: Mycobacterium tuberculosis

<400> SEQUENCE: 374

caagatgatc gccggtgcca ccccgatccg tgcctcggtc agcgcgaacg tgctttccgg     60

tccggcgacc accatgtcgc acgcaccgac caggccgaac ccgccggccc gcacatgccc    120

gttgatggcg ccgaccaccg gcagcggcga ctcgacgatg gcgcgcaaca gcgccgtcat    180

ttcccgcgcc cgcgccaccg ccatccggta cggatcacca ccaccaccgc cggcctcgct    240

gaggtccgcg ccggcgcaga acgttccgcc ggtatgcccc agcacgacca gccgcaccgc    300

cggatctgct tcggccgcac tcagcccttg atgtagttgg ctgaccagcg tgctcgacag    360

cgcgttgcgg ttgtgcggag agttcagtgt cagcctggcg aaggggccgc cgcaggcggc    420

cgggccagcg tagtcgacgg ggctg                                          445


<210> SEQ ID NO 375
<211> LENGTH: 308
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as “n”

<400> SEQUENCE: 375

ctcaagcttc gatcgacagt actcccgcct tgggtctggt cttcgagctg gtcggtcatg     60

gtcggacctg ctggtagtgg ggatctaacg caacatggtc gggattcatc atggtgtacc    120

cgtgataccc attcgcagct gccggtgaaa ccccgcgatg ccgggatttc cagccgcact    180

aggatgtcta gccggccagc cgctgccgcc ggacttcggg atgttcggta taccaccgat    240

cggcaatctt gcntatccgc cgatgctcga acgctagcca ccccaaacca accactgtga    300

cnacaatc                                                             308


<210> SEQ ID NO 376
<211> LENGTH: 239
<212> TYPE: DNA
<213> ORGANISM: Mycobacterium tuberculosis

<400> SEQUENCE: 376

tgaatttccc gatcccacaa tctcggttca gatacaggtc gccatacccc ttacttcggc     60

aacgctgggc ggattggccc tgccgctgca gcagaccatc gacgccatcg aattgccggc    120

aatctcgttc agccaatcca tacccatcga cattccgccg atcgacatcc cggcctccac    180

tatcaacgga atttcgatgt cggaggtcgt gccgatcgat gtgtccgtcg acattccgg     239


<210> SEQ ID NO 377
<211> LENGTH: 431
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
```

-continued as "n"

<400> SEQUENCE: 377
tactcaagct tgaacgctgc gagcgagccc atgtagagcg tttggtacca aaccgatcgg 60
tgggccaact tgccatgggc tcacagcggc tatcgcgagc gtgtagccga tcatcggcca 120
ggcgacggtg gcctgagcgg caggggttgc cttatccatc ctcttgcggc atggttgccg 180
cagggagtgc cggtaagtct ggtcggcaac ctggcccgct gcgggttggg ttcggattcc 240
ctcggctagt aaggtgctcg cctggtgtta caacgaatcg ctagacagct cttatcggga 300
gtggccgtcg cgatcgttgc gctgccgctg gcgatcgcgt tcggcnttac cgccaccgga 360
acgtcccaag gtgcgctcat cgggctctac ggcgccatct tcgccggatt cttcccngcc 420
gtgttcggtg g 431

<210> SEQ ID NO 378
<211> LENGTH: 334
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 378
gcggtgtctg aacttcgccc gttccctcca gcgcattgag cttcagcccg accggcaggt 60
agggagtcgg catgcggtcc ttcgccccga ccccgctggc taaatagcca cccccgagcg 120
cggtcacggt ctttgcaccg ggacgacggc ataccggcag cgcgaacatc gccgcgggct 180
gcagcgtgaa cgtcgaatac gagtcgaaca gtgtcggcgc gtaaaaaccc gagccggcgg 240
tcgcttcggt aatcaacggc tcctgcgcaa ccagctgcaa ntcnccggtg ccaccggcgt 300
tgacaatctt gatntcggcg acctcgcgca ccan 334

<210> SEQ ID NO 379
<211> LENGTH: 302
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 379
tactcagctt cggctcaggt ggtgctgctg gtaaagttcn ctgaacggtg caggtttcga 60
caatgtggtg ccggttcggc gggtactgcc atcgagacac tggcgcaggc tatcgcaccc 120
gttatcggct acaaacaaat cgcggtatgc gttcttgagc atgagtcggc gaccgtcgtc 180
atggtcgaca cccacgacgg aaagacgcag atcgccgtca agcntgtgtg ccgcggatta 240
tcaggactga cctcctggct gaccggcntg tttggtcncg atgcctggcg cccggccggc 300
gt 302

<210> SEQ ID NO 380
<211> LENGTH: 240
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated -continued as “n”

<400> SEQUENCE: 380
catcacctgg ttcatgaaac tggaagcagc gcagcgcttc cttttcggcc gcaacatgag 60
ccagcctctc gtcggcggtc gggtgcaggt gctcgggcag ctcggccgcg acagccgcct 120
gaccctgaaa ccagcttcca tatcccgcga cgaacgacgc cagtccgcta cgtaacccct 180
ccgcgactgt ccatggacaa cancgcgttc tccaccgacc gggcccgggt gtggggtgtt 240

<210> SEQ ID NO 381
<211> LENGTH: 362
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as “n”

<400> SEQUENCE: 381
ctcaagcttc ccggcggcca gtaccgaaag cgcgaacagc tcgcggcagc ccacaacntg 60
ctgcgtcgga ttgccggcgg cganatcaat tccaggcagc tcccggacaa tgcggctctg 120
ctggcccgca acgaaggact cgaggtcacc ccggtgcccg gggtcgtggt gcacctgccg 180
atcgcacagg ttggcccaca accggccgct tgatgcccgg tcggcaagcc cggcagttgc 240
caaacccagc gtgatcaggc tcggctcgcg agttcggcga agaagtggct cgcctgatca 300
cctaccatcg gccaggatct gcgtgtcatc acnacgctcg ccaaggaggt tgttgtggtg 360
ct 362

<210> SEQ ID NO 382
<211> LENGTH: 411
<212> TYPE: DNA
<213> ORGANISM: Mycobacterium tuberculosis

<400> SEQUENCE: 382
gccacgtttc gcgccgcccg gcatacggcg gcgtaccgat ctccgcgtca tacacccgcg 60
ggtaatcgcc gacggtgccg gttcgcgagc cgaaggtgac gacgctgatt gaatcgagtt 120
ccaggtccag cgggtggcgc agcaacggcg cgagctcaac gacgtcaatc acgttgtcgc 180
tttctacggt caccgacccg gtgaccgtag tcgcccggtg cgctcggccg agaagttgca 240
ccgccaccac cgcgacaccg tcttgcacgc ggacgccacc cccggatcgg ttgttggcca 300
aggtaattgg gtcattccat ttgacgggac gccgaccccg cagccccagt accgcccacg 360
accacgccgg ctgaccccac cactgtacga acaccaaggc gacgccgacc a 411

<210> SEQ ID NO 383
<211> LENGTH: 331
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as “n”

<400> SEQUENCE: 383
ctcaagcttg atgccgccta aaccgaagcg tgagcacgcc gccacccacc acgcgcgggt 60
cgggcgccgg gcccgggccg ccaggctgct ccgctcggtg atggcacgcc accgcgacac 120
cacccggctg cgctacgtca agccataccg ggcggagcta catcggctcg gccgcccagt 180

-continued gttcgggccc tctttcgagg tcnaggtcna taccgatttg cgcatccgca gccgcaccct 240
ggacgacaga accgtgccct acgagtgctt gtcgggcggg gccaaagaac ancttggcat 300
cctggcgcga ttggccggcg cggtcctggt c 331

<210> SEQ ID NO 384
<211> LENGTH: 254
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 384
ctcgggtacg cttcggtcgc agtgtgcgag tgatagatga cgaccgggac ctcgtcggca 60
tcttccatag cccgccacac cttcagttgc tcaccggaat ccaaccggta naangtcggc 120
gagcgctcgg cattggtcat cgggatatgc cgctcgggac ggtcagagcc ctcgggtccg 180
gccagcactc cgcaggcttc gtcggggtgg tcgcgacncg catgggccac catcgcattc 240
accaggtctg cgcg 254

<210> SEQ ID NO 385
<211> LENGTH: 346
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 385
ctcaagcttc aattcctcca cgacgcgttc ccaaatgaat ttcccgatcc cacaatctcg 60
gttcagatac aggtcgccat accccttact tcggcaacgc tgggcggatt ggccctgccg 120
ctgcagcaaa ccatcgacgc catcgaattg ccggcaatct cgttcagcca atccataccc 180
atcgacattc cgccgatcga catcccggcc tccactatca acggaatttc gatgtcggag 240
gtcgtgccga tcgatntntc cgtcnacatt ccggnggtca ccatcaccgg caccagnatc 300
gacccgattc cgctgaactt cgacgttctc agcagcgccg gaacca 346

<210> SEQ ID NO 386
<211> LENGTH: 287
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 386
ttaacccccg tggcctctac gccgcctncg ggtcgaacat gcatcccgag canatgctcg 60
agcgcgcacc ccactcgccg atggccggaa ccggctggtt acccgggtgg cggctgacgt 120
tcggcggcga ggacatcggc tgggaagggg cgcttgccac cgtcgtcgaa gacccagatt 180
cgaaggtgtt cgtcgtgctc tacgacatga ccccggcgga cgagaagaac cttgaccggt 240
gggaaggctc cgagttcggc atccaccana agatccgatg ccgcgtt 287

<210> SEQ ID NO 387
<211> LENGTH: 370
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 387
ctcaagcttg attttgatca tcatggatga tcatcacccg aagtgtggta gccgcagtgg    60
ttatcgtggg taccgtcgtg ctttccatgg gcgcctcttt cgggctttcc gtattggtct   120
ggcaggacat tctgggtatc gagttgtact ggatggtgtt ggcgatgtcg gtgatcctgc   180
tcctggcggt gggatccgac tacaatctgc tgctgatttc ccggttgaaa aangaaattg   240
gggccggatt gaacaccgga attatccgtg ccatggctgg taccggggga gtggtgacgg   300
ctgccggcat ggtgttcgcc gttaccatgt cgttgtttgt gttcagcgat ttgcgaatta   360
ttggtcagat                                                          370

<210> SEQ ID NO 388
<211> LENGTH: 330
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 388
cgnccaaccc gaattggttt tcggcgccnt cggtgaggac ggcgtgcggg tgctcaacga    60
cgacgtcgtc cgcgggacac acctcgatgc tgccgccatg gacgcggtcg aacgcaagca   120
gctgatcgag ctacaacgcc gcgcggaacg cttccgccnc nggcgttacc gcatcccgtt   180
gaccgggcgg atcgcggtga tcgtcgatga cggcatcgcc accggagcga cggccaaggc   240
ggcgtgccag gtcgcccggg cgcacggtgc ggacaaggtg gtgctggcgg tcccgatcgg   300
cccanacgac atcgtggcga gattcgccgg                                    330

<210> SEQ ID NO 389
<211> LENGTH: 346
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 389
cgtgactgcc accggggcca ctccgcagaa tctgtacccg accaagatct acaccatcga    60
atacgacggc gtcgccgact ttccgcggta cccgctcaac tttgtgtcna ccctcaacgc   120
cattgccggc acctactacg tgcactccaa ctacttcatc ctgacgccgg aacaaattga   180
cncagcggtt ccnctgacca atacggtcgg tcccacgatg acccantact acntcattcg   240
cacgganaac ctgccgctgc tagagccact gcgatcggtg ccgatcgtgg ggaacccact   300
ggcgaacctg gttcaaccaa acttgaaggt gattgttaac ctgggg                  346

<210> SEQ ID NO 390
<211> LENGTH: 355

-continued

<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 390

```
tcgctcaagc gcntgaggcc gaancggctg gttacgactc cctgtttgtg atggaccact     60

tctaccaact gcccatgttg gggacgcccg accagccgat gctggaggcc tacacggccc    120

ttggtgcgct ggccacggcg accgagcggc tgcaactggg cgcgttggtg accggcaata    180

cctaccgcag cccgaccctg ctggcaaaga tcatcaccac gctcgacgtg gttagcgccg    240

gtcgagcgat cctcggcatt ggagccggtt ggtttgagct ggaacaccgc cagctcggct    300

tcgagttcgg cactttcagt gaccggttca accggctcga aaaggcgcta canat         355
```

<210> SEQ ID NO 391
<211> LENGTH: 403
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 391

```
atactcaagc ttccgctggg gcctgttcaa ccatggcgat cccgttggtc ccggacatcc     60

cgaacgagga caccgcgacc cncttcggtg tgtgatcatt accgttgggc cactgcgtaa    120

ccgcttgcgg cacaaagagc ccggtctcga cgtcggaaag ctcatcgggc acccgattga    180

aatgcagcag cggcggcacc accccgtgcc gcagtgacag aattgccttg atcagcccga    240

cggtccccgc cgatgccgtg ctgtgcccca tgttgctctt ggccgatcca agcgcgcagg    300

gggtgcccgc gccatacacc cgcgccaggc tgcggtactc aatcgggtcg ccgattggcg    360

taccggtgcc gtgcgcctcc accacaccga ccgtttcggg ctg                      403
```

<210> SEQ ID NO 392
<211> LENGTH: 440
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 392

```
caacagcgtt ccagcggcat accaccgcac atgccgtgca cccggcgccg ggcggagtcg     60

ccgcataaca cangtacacc ttgggaatcg gtgtgcgcca gggattcnac cgcggggtgg    120

ggccggcgat cgcgcgccag gtcgagttgg cgccgaccgt gatntcaccg ccgacgtagt    180

tggcgttgtg gtccgccatc cgcgcggcgg gcacggcgcg ggccgccacc acgatgtcac    240

ggaagccggg ggcgaacgct cgacgacctg gttaccgtct cngtcgcntc nancgtggac    300

ccgacngcac gtgggcatat gtccanaacg gacgnggccg gtttcntcga tgcngccggg    360

gtccgcgacn tgcggacncn cngncacacc atccgccagt ccgcgtggcg tcccgccgcg    420

actctgcctc ggccgcgcca                                                440
```

-continued

<210> SEQ ID NO 393
<211> LENGTH: 353
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 393

```
ctcaagcttt gncgacgatc gggcgatgtc gatganagga aaccccagcg cacaaccgac     60

nattttggcg tagccggcgg acntctgctc gattccgatc acgtcggcgc tcgcatcgag    120

catggcgccg gcgacggcta gcagcgatcc gccgtcgtcg aggaacacga cacgagccgt    180

acgcccggcc gtaagccgcg cccaggattc ggcgaaaaac cgttctacgt ggcgggtgta    240

ctgggtgtcc aatgattcgt ggggtgcgta ggcgtcgctg caatcgtcga cataaatgcc    300

gtcggcccgc atcgcgtcaa caactcccgg gtgagtggaa tancacttgc cga           353
```

<210> SEQ ID NO 394
<211> LENGTH: 340
<212> TYPE: DNA
<213> ORGANISM: Mycobacterium tuberculosis

<400> SEQUENCE: 394

```
tccaacgcgg tgacagattt gtctatcctg gacctgacgg tgaggtcgaa gttttccagg     60

aattcggcaa aatcggtaag agcctgaaga attcggtatc gccggacgaa atctgcgacg    120

catacggggc agatacgctt cgggtttacg agatgtcgat ggggccgctg gaggcttcac    180

gtccatgggc cacaaaggat gttgtcggcg cgtaccgttt tctgcagcgg gtgtggcgct    240

tggtcgtcga cgagcacacc ggcgaaactc gggtggctga cggcgtggaa ctcgacatcg    300

atacgctacg ggcgttgcac cgcaccatcg tcggcgtgtc                          340
```

<210> SEQ ID NO 395
<211> LENGTH: 362
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 395

```
ctcgtccttg actacgccca gtatcgaaan cctcctgtgc cggtncgcta aacacccggc     60

ggacactcan acggtgctgg tggtgcggca tggcaccgcg ggcagcaaag cgcacttctc    120

cggggacgac agcaagcgac cgctagacaa gaggggtcgt gcgcaggcag aagcgttggt    180

accacagctg ctggcgttcg gcgccaccga tgtttatgcc gccgaccggg tgcgctgcca    240

ccanacnatg gagccactcg ccgcggaact gaacgtgacc atacacaacg agcccnccct    300

gaccgaagag tcctacgcca acaaccccaa acgcggccga caccgagtgc tgcagatctt    360

cg                                                                   362
```

<210> SEQ ID NO 396
<211> LENGTH: 356
<212> TYPE: DNA
<213> ORGANISM: Mycobacterium tuberculosis
<220> FEATURE:
<221> NAME/KEY: unsure
<222> LOCATION: (various positions within the sequence)

-continued

<223> OTHER INFORMATION: applicants are uncertain of bases designated as "n"

<400> SEQUENCE: 396
gtatcgcctc cncctttggc caccagcagc cacagcgcgg ttcgcggacc gaacgtggac 60
atcaatagcc cggaatcggt gtgtgcaagt tggtaaacgg tgttgatccc aagctttgcc 120
agccttttcg tagtcttggg ccccacaccc cacagtgctt cgacggtacg gtcacccatg 180
atggccatcc agttggcatc ggtgagctga tagatgccag ctggtttcgc caacccggta 240
gcgatcttgg cgcgctgctt gttgtcactg atacctatcg agcaagacag cccggtttgc 300
gacaagatga cttttcggat ctcttcngcg aacttccaat gggggtctcc gggant 356

<210> SEQ ID NO 397
<211> LENGTH: 350
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 397
ctcaagcttt tggtctagcc ggccgagcac gatacgggtg tccttggcca ccggcggcgg 60
ctgtccggga aatggcgggt ccccggtggt tttgctgang antgctgaac cgtagtcgaa 120
gtgggcggcg tcagactcca cccagccagc aggcagcgcg aagctgaatc ctccaaccgg 180
gttgtcgatc cggacaggtt ggggtgcgtt tggggcaatg acaggtggcg gcggtgcgtt 240
cgggtcggcc ggcggaggtg ctgcgttggg atcncccggc tgggcattcg gcntnttggc 300
ggcggccggt ggtggggggg caacangtgt cccggtgcgg gtggcgctgc 350

<210> SEQ ID NO 398
<211> LENGTH: 355
<212> TYPE: DNA
<213> ORGANISM: Mycobacterium tuberculosis

<400> SEQUENCE: 398
atctgtaccc gaccaagatc tacaccatcg aatacgacgg cgtcgccgac tttccgcggt 60
acccgctcaa ctttgtgtcg accctcaacg ccattgccgg cacctactac gtgcactcca 120
actacttcat cctgacgccg gaacaaattg acgcagcggt tccgctgacc aatacggtcg 180
gtcccacgat gacccagtac tacatcattc gcacggagaa cctgccgctg ctagagccac 240
tgcgatcggt gccgatcgtg gggaacccac tggcgaacct ggttcaacca aacttgaagg 300
tgattgttaa cctgggctac ggcgacccgg cctatggtta ttcgacctcg ccgcc 355

<210> SEQ ID NO 399
<211> LENGTH: 360
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 399
ctcaagcttg caatgcgggt cgggatgccc atggttggaa natggtcgcc ctggcgtcna 60
atacgcgcga gcgcatgagc tcaccggttc ggaacaacgt atcgaaaaac gtcgcactgc 120

-continued

```
tggcagatgg tatctccgat gtggttgtaa tttgtatccc aactctaact gtgctatcgg    180

atcagcgtga atatcganat attgcgaatg cgatgacagg ccgccattcg gtttattcgc    240

ttacgcttcc cgggttcgat tcgtctgatg cactgccgca aaacgcggat atgattgttg    300

aaaccgtatc taacgcaatt attgatgtgg taggcggcag ctgccgtttt gtgctgtcgg    360


<210> SEQ ID NO 400
<211> LENGTH: 272
<212> TYPE: DNA
<213> ORGANISM: Mycobacterium tuberculosis

<400> SEQUENCE: 400

caaatacacg ccggacgcac aggcggacat cgccatcccg agcacaccca aaacgggata     60

caggatggag gccaacgcca cggccgcgcc caggatcacc aaccacaccg gcttggtcag    120

cttgtcggcg gcggtatagg catcgggccg ctgcaacgca gcatgcacaa acgcgtacac    180

cgctgtcacc aagacggcga ccagcaatac cagcatgacg gtacccacga ggtggctcac    240

gcattcagac tatgcggttt gcatccaaca cg                                 272


<210> SEQ ID NO 401
<211> LENGTH: 306
<212> TYPE: DNA
<213> ORGANISM: Mycobacterium tuberculosis

<400> SEQUENCE: 401

ctcgtccttc ggcctcgctg caggagtggg agccgcaggg ctggaaatcc gaaaaacgag     60

ccggtgatcg cactgtcgcc gatcggcgcc gcacctggtt ggtgttacgg atgaatccgc    120

agcgaaatgt ggctgcggtg gcgtgtcgtg actcgttggc gtcgacgctg gtggcagcca    180

ccgagcggtt ggtccaggat ctggatgggc aaagttgtgc ggcccggccg gtgacggccg    240

atgagctgac cgaggtcgac agcgccgtgt tggctgactt ggaaccgaca tggagtcgcc    300

ccggtt                                                              306


<210> SEQ ID NO 402
<211> LENGTH: 300
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 402

gtctagnccg ccgaacacga tacgggtgtc attggccacc ggcggcggct gtccgggaaa     60

tggcgggtcc ccggtggttt tgctgaagan tgctgaaccg tagtcgaagt gggcggcgtc    120

agactccacc cagccagcag gcagcgcgaa gctgaatcct ccaaccgggt tgtcgatccg    180

gacaggttgg ggtgcgtttg gggcaatgac aggtggcggc ggtgcgttcg ggtcggccgg    240

cggaagtgct gcgttgggat cgcccggctg ggcattcggc gtgttggcgg cggccggtgg    300


<210> SEQ ID NO 403
<211> LENGTH: 396
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"
```

-continued

<400> SEQUENCE: 403
actcaagctt gagattggcg tcaacgggtg tcggcaccgg cgtcctgcag ttggtaggcc 60
tgcagtttgt gcatcaggcc gatgccgcgg ccctcgtggc cacgcatgta cancaccacg 120
ccgcgcccct cacgggcgac catcgccagc gcggcgtcca gctgaggccc gcaatcgcag 180
cggcgtgacc caaacacatc gccggtcaag cactccgaat gcacccggac cagcacgtcg 240
tcaccgtcgg cgttgggccc ggcgatctcg ccgcggacca gcgcgacatg ttccacgtcc 300
tcgtaaatgc tggtgtancc gatggcgcga aactccccat gacaantcgg aatcccgcgc 360
ctcggcgacc ccgctcaatg ttgcttctcn tgcttg 396

<210> SEQ ID NO 404
<211> LENGTH: 352
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 404
tcgacnagca ttcttgacng ttgttttggc tcggcatggt tagccaaggt tctgcggtcc 60
caccagatca tcttggtccg gtagcgctcg tccgggtatg ctgccgccgg gattctcgct 120
gctattactc cccccgaaga acgccaccgg tccagcgcgt gggccgccgc ggtccccatc 180
acaaactgaa cccccaacag gggacatgct tagcggtagg gcgcgcgcca aggcggcagc 240
aatcgcatca ctgcgctgcg cgtcactatt aacccacccg gacttcactt ccacgacccc 300
gaatggcgcc cggtcattga tcatcttgcg caccgcggat aatccgggat tg 352

<210> SEQ ID NO 405
<211> LENGTH: 420
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 405
accggggcca ctccgcacaa tctgtacccg accaanatct acaccatcga atacgacggc 60
gtcgccgact ttccgcggta cccgctcaac tttgtgtcna ccctcaacgc cattgccggc 120
acctactacg tgcactccaa ctacttcatc ctgacgccgg aacaaattga cgcngcggtt 180
ccgctgacca atacggtcgg tcccacnatg acccantact acatcattcg cacgganaac 240
ctgccgctgc taaagccact gcgatcggtg ccgatcgtgg ggaacccact ggcgaacctg 300
gttcaaccaa acttgaaggt nattgttnac ctgggctacg gcganccggc ctntggttat 360
tccacctcnc cgcccaatgt ttgcnactcc cgttcggggt tgttcccnna aggtcaaccc 420

<210> SEQ ID NO 406
<211> LENGTH: 328
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

-continued

<400> SEQUENCE: 406
cgctcaagcg cntgaggccg aancggctgg ttacgactcc ctgtttgtga tggaccactt 60
ctaccaactg cccatgttgg ggacgcccga ccagccgatg ctggaggcct acacggccct 120
tggtgcgctg gccacggcga ccgagcggct gcaactgggc gcgttggtga ccggcaatac 180
ctaccgcagc ccgaccctgc tggcaaagat catcaccacg ctcgacgtgg ttagcgccgg 240
tcgagcgatc ctcggcattg gagccggttg gtttganctg gaacaccgcc agctcggctt 300
cgagttcggc actttcagtg accggttc 328

<210> SEQ ID NO 407
<211> LENGTH: 315
<212> TYPE: DNA
<213> ORGANISM: Mycobacterium tuberculosis

<400> SEQUENCE: 407
ctcaagcttg cgttcgatga agtagtcgtc ggtcagcgcc gcctcttcga gctccttggc 60
gatgcccagc aaggagtcat cgccgccgag cttggccagg atcttgtcgg cctgttcctt 120
gacgatgcgg gcccgcggat cgtagttctt gtagacacga tgaccgaaac ccatcaattt 180
gaccccggcc tcgcggttct tgaccttgcg tacaaactcg ctgacgtcgt cgccgctgtc 240
gcgaatgccc tcgagcatct ccaggacagc ctgattggcg ccgccatgaa gcggacccca 300
tagtgcgttg atgcc 315

<210> SEQ ID NO 408
<211> LENGTH: 329
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 408
ggtcaggccg agcaggcgcg aggaacgacg aacccaacaa gccatggtgg ttggcgccgt 60
cgagaggtcg gcggtcgcca caacgggaag atcgccttga gcgtcgctcg accgccgcct 120
cgagttgggt cataacgaag tagctgatgc cgatcatgtc gacgtttccg tcgcatcagc 180
gtgcagcggc gacccactcn acgaggtctc ggtgccgccg cggccagggc accagcagtg 240
acgagtccag gcgccgtcgg gccaagcagt cgcggtgcca nccgtggtgg gtcgggcgat 300
ggttgggtgt gctcatttcg ggaacgcca 329

<210> SEQ ID NO 409
<211> LENGTH: 294
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 409
ctcgaagctt taacagcatc aaccccgccc cgcaccagca ccgacacnat gtcgatgcca 60
tcgaggtgaa tgtcgaactg gcgcaaacca tcggcgaccg cgaccaccgg caacatgggt 120
accggcgatt tccggtgcca atgccgaccc gacgggccgc tctcaccgca ggtgacctcg 180

-continued

```
atcaccgaga ccanccggcc gttntnntca cgcaccccta ccgtgtcacg cccaaaacgg    240

cgctggtggt cgattgccgg agtgcacccc ncacccagtg tcgtgcccgg atcc          294


<210> SEQ ID NO 410
<211> LENGTH: 288
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 410

tgatgccgca cccgatcgac ggtcgttggt cggggttgac tggccgcccg gcgaagcagg     60

gcgtcgaccg cggcccggac gtcggcggcc gtcaccggtc ggccattgcc cgggcgggag    120

tcgtcgagct gaccacggta gacaagtcgg cgctggccgt cgaagacnaa cgtgtcgggt    180

gtgcaggccg cggagaaggc gcgggcgacn tcttgggttt cgtcgtanag atacgggaac    240

gtccagccgt ggcggcgggc ctcggcgacc atctgatcgg gcccgtcc                 288


<210> SEQ ID NO 411
<211> LENGTH: 420
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 411

tttcgggcga ggcggtatan cttcccntcg taccggcgac cgccagccga naagctcgtt     60

ttcccagtgt tgctggggat tctcacgctg ctgctgantg cgtgccaaac cgcttccgct    120

tcgggttaca acgagccgcg gggctacnat cgtgcgacgc tgaagttggt gttctccatg    180

gacttgggga tgtgcctgaa ccggttcacc tacnactcca agctggcgcc gtctcgtccg    240

caggtcgttg cttgcgatag ccgggaggcc cggatccgca atgacggatt ccntgccanc    300

gctccgagtt gcntgcggat cgactacnaa ttgatcaccc anaaccatcg ggcgtnttac    360

tgcctgaagt acctggtgcg ggtcggatac tgctatccgg cggtgacaac cccggcaagc    420


<210> SEQ ID NO 412
<211> LENGTH: 378
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 412

gttttggctc ggcatggtta gccaaggttc tgcggtccca ccagatcatc ttggtccggt     60

agcgctcgtc cgggtatgct gccgccggga ttctcgctgc tattactccc cccgaagaac    120

gccaccggtc cagcgcgtgg gccgccgcgg tccccatcac aaactgaacc cccaacaggg    180

acatgcttag cggtagggcg cgcgccaagg cggcagcaat cgcatcactg cgctgcgcgt    240

cactattaac ccacccggac ttcacttcca cgaccccgaa tggcgcccgg tcattgatca    300

tcttgcgcac cgcggataat ccgggattgc cagcccattc nactaccgca tgcgagtcat    360
```

-continued cggctgaccg cagcggtc 378

<210> SEQ ID NO 413
<211> LENGTH: 347
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 413
tcgcctaggc gggcttcccc ttccgtccga gcngtcagaa gctcctatga caatgcacta 60
cccgagacna tcaacggcct atgcaatacc nagctgatca aacccggcaa gccctggcgg 120
tccatcgagg atgtcgagtt ggccaccgcg cgctgggtcg actggttcaa ccatcgccgc 180
ctctaccggt actgcggcga catcccgccg gtctaactcg acgccgcctc actacgctca 240
acgccagaga ccanccgccg gctgacgtct cagatcagag agtctccgga ctcaccgggg 300
cggttcatcc ccactgtcga tagcgtctgt ggataacttt gtctgca 347

<210> SEQ ID NO 414
<211> LENGTH: 165
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 414
gcgcgtngaa ctgataggtg cggcccggct cgagcangcc ggccatttgt tcgatgcggt 60
taccgaagat ctcttcggtg acctgcccgc cgccggccag ctcggcccag tgcccggcgt 120
tggccgccgc ggcgacaatc ttggcgtcca cggtggtctg ggtca 165

SEQ ID NO 415

<211> LENGTH: 317
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 415
ctcaagcttc aatacagagt tataaactgt gataatcaac cctcatcaat gatgacnaac 60
taacccccga tatcaggtca catgacgaag ggaaagagaa ggaaatcaac tgtgacaaac 120
tgccctcaaa tttggcttcc ttaaaaatta cagttcaaaa agtatgagaa aatccatgca 180
ggctgaagga aacagcaata actgtgacaa attaccctca gtaggtcaga acaaatgtga 240
cgaaccaccc tcaaatctgt gacagataac cctcagacta tcctgtcgtc atggaagtga 300
tatcgcggaa ggaaaat 317

<210> SEQ ID NO 416
<211> LENGTH: 379
<212> TYPE: DNA
<213> ORGANISM: Mycobacterium tuberculosis
<220> FEATURE:
<221> NAME/KEY: unsure -continued
<222> LOCATION: (various positions within the sequence)
<223> OTHER INFORMATION: applicants are uncertain of bases designated
as "n"

<400> SEQUENCE: 416
ctcaagcttc gatcgacatt actcccgcct tgggtctggt ctccgagctg gtcggtcatg 60
gtcggacctg ctggtagtgg ggatctaacg caacatggtc gggattcatc atggtgtacc 120
cgtgataccc attcgcagct gccggtgaaa ccccgcgatg ccgggatttc cagccgcact 180
aggatgtcta gccggccagc cgctgccgcc ggacttcggg atgttcggta taccancgat 240
cggcaatctt gcgtatccgc cgatgctcga acgctancca cgccaaacca accactgtga 300
cnacaatcgc caccacacca aaggtcatgc cctcggcgtg atgtccggtg ccgaaagccg 360
caagagctcc gacgccgcc 379

<210> SEQ ID NO 417
<211> LENGTH: 420
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 417
cattcccaat tgaatttccc natcccacaa tctcggttca gatacaggtc gccatacccc 60
ttacttcggc aacgctgggc ggattggccc tgccgctgca gcanaccatc gacgccatcg 120
aattgccggc aatctcgttc agccaatcca tacccatcga cattccgccg atcgacatcc 180
cggcctccac tatcaacgga atttcgatgt cggaggtcgt gccgatcgat gtgtccgtcg 240
acattccggc ggtcaccatc accggcacca ggatcgaccc gattccgctg aacttcgacg 300
ttctcagcag cgccggaccc atcaacatct cgatcatcga cattccggcg ctgccgggct 360
ttggcaactc gaccgagctg ccgtcgtcgg gcttcttcaa caccggcggc ggtggcggct 420

<210> SEQ ID NO 418
<211> LENGTH: 255
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 418
ctcaagcttt cggcggagac ggacannttg cgaacattga tgacaaaata gaaatcattg 60
atggtttgag tcaccaggcc gatcaagcct tcgccgagcc aaattccaat caagaggccc 120
aagcccgtac caatcagccc ggcaacgagg gattccgtca ttatcagcca aaataactgc 180
tctcgggtta cacccaaaca gcgcaatatg gcgaaaaacg gtcgccgttg cacgacatta 240
aatgtcacgg tattg 255

<210> SEQ ID NO 419
<211> LENGTH: 359
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated -continued as "n"

<400> SEQUENCE: 419
agcttaactg ctccctaata cctggggctg tgcctgcggt gtatgcacgg catacggaca 60
tccntcccct gagacccncg gtctaatcag ccacgtgtcc accatcaggg gtcaaccccg 120
gccaagggcg acggcacccc aagttcgccg accgttaacc tattgctgtg agcttcattt 180
gctgcgagca aaacagttgg tcggccgtta ggaactgaat tgacactcaa ccgatttggt 240
gccnccgtag gtgtcctggc tgcgggtgcg ctggtgttgt ccgcgtgtgg taacgaccac 300
aatgtgaccg ggggaggtgc aaccactggc cacgcgtccg cgaatgtcta ttgcggggg 359

<210> SEQ ID NO 420
<211> LENGTH: 314
<212> TYPE: DNA
<213> ORGANISM: Mycobacterium tuberculosis

<400> SEQUENCE: 420
ctcaagcttg ggtggcgct gtcggtcggt gtgcttggcg gcgtcggtat caacaccgcc 60
cacgaaatgg ggcacaagaa ggattcgctg gagcggtggc tgtccaaaat caccctcgcc 120
cagacctgct acgggcactt ctacatcgag cacaaccgtg gccatcacgt ccgggtgtcc 180
acaccggagg acccggcgtc ggcgcggttc ggcgaaacgt tgtgggagtt cctgccccgc 240
agtgttatcg gcggcttgcg ctcggccgtt catttggagg cccaacggct gcgtcggctc 300
ggcgtcagcc ccct 314

<210> SEQ ID NO 421
<211> LENGTH: 280
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 421
gcaccaaggc cccacacgtc accctgtgac ctcctgcgcc gaccccgccc gaggtcctgg 60
ccgttaccac ctgaacgggc gagccgggag tctggtacgc atcgaacaaa gagcaaggtg 120
catgggcgga gttgttccgc cacttcgtcg atgacggggt cnatccattc gaggtccgtc 180
gccgcgtcgg tcgagtggcg gtcacactcc aggtactcga cctcacagac gagaggactc 240
gatcccatct aggtgtggac gaaacagatc ttctgtccga 280

<210> SEQ ID NO 422
<211> LENGTH: 230
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 422
tcgcctccgc atatgggtcg acgccaagcg ggtccggatt tctgggcttc atcgctcgcg 60
ccgtcgcgac aaacagcgcg gtcgaaccga cactcgttgt gatgtcccag ctatcacctt 120
cggtacgcac ccaatcgacc ctacncggct atctcagccg cgatctccag gctccgccga 180
gccaggtgca tcccggtccg gatcccacta acccggcacc attggcgtcn 230

-continued

<210> SEQ ID NO 423
<211> LENGTH: 272
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 423
gtcctcgagt gccgccgtcg ncacncccag cgcccgcgcg gccacttgga tgcgacccgt 60
ttcaagtccc ttcatcatct gcgaaaagcc ttgacccatg gctccgccca ggatcgccga 120
gaccggcacc cggaggttgt cgaacgacag ctcgcaggat tcgacgccct tgtaacccaa 180
cttcggcaag tcccgcgaca ccgtgagtcc cggcccgggt tcgacgagca cgatcgacat 240
gccttggtgc cgcggtgtgg cgttcgggtc gg 272

<210> SEQ ID NO 424
<211> LENGTH: 423
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 424
ggcataccaa tgtggacttc tgctcaccca cgatatccgt ggtctgatcc gctgctgcgg 60
cgggctgcna cctgcntctc ngcggcaccc gtnactacat ggcncgcgcc gcacgcatac 120
gtcgcggcgg gacccactcc nactggtcga cggtgctggc cgcgtgtccg cangtcccna 180
acccggccgc accgacgaaa ccggccgccg tccgttctgg accaacgctc atgtgccgtc 240
ggggtccatg ctcgacgcca tcgagaccgt aaccagcgtc ctcgagcggt tcgcctccgg 300
cttccgtgac atcttcgtgg ctgctcgcgc cgtgccgccg cgcggatggt cgaccacaac 360
gccaaccacc tcggcggtga catcaccgtc cgcgccactc gacctggcgc gcgatcgcgg 420
ccc 423

<210> SEQ ID NO 425
<211> LENGTH: 315
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 425
gtgagcagac ctacgccncc tggttgcgcc aactcggtac cgatcatggc gcgcngcctg 60
tcgtcaccga tacccagcga acaagacagc ccggtccgcg acaagatgac tttcccgatc 120
tcttcggcga cttccatggg gtcgtccgga gtcccgggcg ccaccgcgag gtaaccctcg 180
tctcagtccc atacgcgacc gggtatccac gtcgcgcaac aacgccacca cctccccaga 240
cgccncgttg tacgcggctg ggttccacng caataagtgg cctcanggca tcgtccggcg 300
gcggtccnca acgca 315

-continued

```
<210> SEQ ID NO 426
<211> LENGTH: 335
<212> TYPE: DNA
<213> ORGANISM: Mycobacterium tuberculosis

<400> SEQUENCE: 426

ctcaagcttg aggttaactt tgaacggatc gagctggacg ttcgagacgg tgatcgggcc     60

gaacctgaat tgtccggtaa tgcccaacgc aaaaagcagg gtggtggccg gggcggtgaa    120

accggcgtcg gcggcaccgt cgaaatctat gtggattgcc ggaatgggga tgtccggcac    180

ggcgaaaccg tagttcgctt gtcccgtgag gcccaggtgg atggggggaa agatcctggt    240

gtccgggata ataatggggc cgatgccgcc ggttgaagtc cactggatcg ggaattccgg    300

aatcttgatc cgacgttcag gccgaacagg ccctc                               335


<210> SEQ ID NO 427
<211> LENGTH: 346
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 427

cggcgacgtc gcgatacgcc gagcagttgg gaatcgctct gcagcaaacc aatattctgc     60

gcgacgttcg agaggacttt ttgaatggac ggatctacct gccgcgcgac gagctggacc    120

gattaggcgt acgcctccgc ctggacgaca ccggggcact cgatgacccc gacggacggc    180

tcgcggcnct gctgcggttc agtgccgacc gcgccgcaga ctggtnttcg ctgggactgc    240

ggctgattcc acacctcgac cgccgcagcg ctgcctgctg tgcggccatg tctggcatct    300

accgccgtca gctcgccttg atcagagcat cgccggcggt cgtcta                   346


<210> SEQ ID NO 428
<211> LENGTH: 332
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 428

ctataaaata ctcaagcttg atgccgccga aaccgagcgt gagcacgccg ccagccacca     60

cgcgcgggtc gggcgccggg cccgggccgc caggctgctc cgctcggtga tggcacgcca    120

ccgcgacacc acccggntgc gctacgtcna gccataccgg gcggagctac atcggctcgg    180

ccgcccagtg ttcgggccct ctttcgaggt cnaggtcnat accgatttgc gcatccgcag    240

ccgcaccctg aacnacanaa ccgtgcccta ctattgcttg tcnggcgggg ccaaaaaaca    300

gcttggcatc ctggcccnat tggccggcgc gg                                  332


<210> SEQ ID NO 429
<211> LENGTH: 276
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"
```

-continued

<400> SEQUENCE: 429
cttcggtcgc agtgtgcgag tgatagatga cgaccgggac ctcgtcggca tcttccatag 60
cccgccacac cttcagttgc tcaccggaat ccaaccggta gaaggtcggc gagcgctcgg 120
cattggtcat cgggatatgc cgctcgggac ggtcagagcc ctcgggtccg gccagcactc 180
cgcaggcttc gtcggggtgg tcgcgacgcg catgggccac catcgcattc accaggtctg 240
cgcgaatcnc cancacgtan acngttcctt tcctaa 276

<210> SEQ ID NO 430
<211> LENGTH: 420
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 430
ctggcaccaa ggccccacac gtcaccctgt gacctcctgc gccgaccccg cccgaggtcc 60
tggccgttac caccgaacgg gcgagccggg agtctggtnc gcatcgaaca aanagcaagg 120
tgcatgggcg gagttgttcc gccacttcgt cgatgacggg gtcnatccat tcgaggtccg 180
tcgccgcgtc ggtcnagtgg cggtcacact ccaggtactc gacctcacag acnaaaggac 240
tcnatcccat ctaggtgtgg acnaaacaga tcttctgtcc gacnactaca ccaccaccca 300
ggccatcgcc gccgcccgcg atgccaactt cgacgccgta ctggccccgg cggggggcgc 360
tccccggttg tcaacacttg ccgtgttcnt tcacgcnctg ccccacatcc aaccccaacg 420

<210> SEQ ID NO 431
<211> LENGTH: 130
<212> TYPE: DNA
<213> ORGANISM: Mycobacterium tuberculosis

<400> SEQUENCE: 431
gttcttgggc ccatgcggag gtatcgccgt ttccaccacg cggtcggggt ggcgttgcat 60
tagctcaccg atggtgcgct tgtgcaggcc gccgggatac cccgagtgcc ggtaaaccat 120
cttgtgctgc 130

<210> SEQ ID NO 432
<211> LENGTH: 215
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 432
caatactcaa gcttggcgtg ccgttccaac ccgaattggc tttcggcgcc atcggtgagg 60
acggcgtgcg ggtgctcaac nacnacgtcg tccgcgggac acacctcgat gctgccgcca 120
tggacgcggt cgaacgcaag cagctgatcg agctacaacg ccgcgcggaa cgcttccgcc 180
gcgggcgtga ccgcatcccg ttgaccgggc ggatc 215

<210> SEQ ID NO 433
<211> LENGTH: 360
<212> TYPE: DNA

-continued

<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 433
cntcatgatg atcatcaccc gaagtgtggt agccgcagtg gttatcgtgg gtaccgtcgt 60
gctttccatg ggcgcctctt tcgggctttc cgtattggtc tggcaggaca ttctgggtat 120
cgagttgtac tggatggtgt tggcgatgtc ggtgatcctg ctcctggcgg tgggatccga 180
ctacaatctg ctgctgattt cccggttgaa agaggaaatt ggggccggat tgaacaccgg 240
aattatccgt gccatggctg gtaccggggg agtggtgacg gctgccggca tggtgttcgc 300
cgttaccatg tcgttgtttg tgttcagcga tttgcgaatt attggtcaga tcggtaccac 360

<210> SEQ ID NO 434
<211> LENGTH: 265
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 434
atactcaagc ttttacggtg atcgcncatc acctggttca tgaactggaa gcagcgcagc 60
gcttcctttt cggccgcaac atgagccagc ctctcgtcgg cggtcgggtg caggtgctcg 120
ggcagctcgg ccgcnacagc cgcctgaccc tgaaaccagc ttccatatcc cgcgannaac 180
gacgccagtc cgctacgtna cccctccgcg actgtccatg gacaacagcg cgttctccac 240
cgaccgggcc cgggtgtggg gtntt 265

<210> SEQ ID NO 435
<211> LENGTH: 264
<212> TYPE: DNA
<213> ORGANISM: Mycobacterium tuberculosis

<400> SEQUENCE: 435
gctggtagag tcgctgaccg gtgcaggttt cgacaatgtg gtgccggttc ggcggctacg 60
tgccatcgag acactggcgc aggctatcgc acccgttatc ggctacgagc aaatcgcggt 120
atgcgttctt gagcatgagt cggcgaccgt cgtcatggtc gacacccacg acggaaagac 180
gcagatcgcc gtcaagcatg tgtgccgcgg attatcagga ctgacctcct ggctgaccgg 240
catgtttggt cgcgatgcct ggcg 264

<210> SEQ ID NO 436
<211> LENGTH: 335
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 436
gctttccgcc gatacccgcc atgtcncgca catccaggac ttctgggggg atccgctgac 60
agcggcggga tcccaaagtg cggatgatcg ggccgcctac gtcgtggtgt acctcgtcgg 120

-continued

```
taacaacgaa accgaagcgt atgactcggt ccacgcggtg cggcacatgg tggacaccac    180

accgccaccg cacggggtga aggcctatgt caccggtccg gcancactca atgccgacca    240

ggccgaggcc gganacaaaa ntatcgctaa ggtcaccgcg atcacnagca tggtgatcgc    300

agcaatgttg ctagtgatct atcgctccgt aatta                               335
```

<210> SEQ ID NO 437
<211> LENGTH: 304
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 437

```
cttccaaccc gaattggctt tcggcgccat cggtgaggac ggcgtgcggg tgctcaacga     60

cgacgtcgtc cgcgggacac acctcgatgc tgccgccatg gacgcggtcg aacgcaagca    120

gctgatcgag ctacaacgcc gcgcggaacg cttccgccgc gggcgtgacc gcatcccgtt    180

gaccgggcgg atcgcggtga tcgtcgatga cggcatcgcc accggagcga cggccaaggc    240

ggcgtgccan gtcgcccggg cgcacggtgc ggacaaggtg gtgctggcgg tcccgatcgg    300

ccca                                                                 304
```

<210> SEQ ID NO 438
<211> LENGTH: 223
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 438

```
tactcaagct tcgcgagatc cggatggcac tcacgctgga caagaccttc acaaaatctg     60

aaatcctgac ccgatacttg aacctggtct cgttcggcaa taactcgttc ggcgtgcagg    120

acgcggcgca aacgtncttc ggcatcaacg cgtccganct gaattggcag caagcggcgc    180

tgctggccgg catggtgcaa tcnaccagca cgctcaaccc gta                      223
```

<210> SEQ ID NO 439
<211> LENGTH: 263
<212> TYPE: DNA
<213> ORGANISM: Mycobacterium tuberculosis

<400> SEQUENCE: 439

```
cccacgactt tctcctcgat cagttggatt tgtacgaaga ggcaacgaaa gcagtgatcc     60

tcgggatggt cgacgcctac atcgacccgc cgttcacgcc gcacagcctg ctagatgcgc    120

tgggcgagca ggtcccacag ttcgccgcta aggcacggcg tctgttcccg tccggatcgc    180

cattcggcct cggcgtcctg ctcccattcg atcaataggg ctggcagctc cgtcggcagg    240

ggcctacgcc tcaccccgtc acg                                            263
```

<210> SEQ ID NO 440
<211> LENGTH: 301
<212> TYPE: DNA
<213> ORGANISM: Mycobacterium tuberculosis
<220> FEATURE:
<221> NAME/KEY: unsure -continued
<222> LOCATION: (various positions within the sequence)
<223> OTHER INFORMATION: applicants are uncertain of bases designated as "n"

<400> SEQUENCE: 440
ctcaagctta tgcgcgccgg ccgaggtctg ctcacggcaa cccctgaagt ttaggggacn 60
acctactcag cgcaaaattt cgctaatgtg agtccgcccc accaggggna natcaaccca 120
tgtcgatcat gatctacccg gataccggat tggcggtagc gcccacgatc gtcnaaatnt 180
ccgcctgaat catcggatag ctgatccggc gtcaacgcgt tttganttca ccgcgcaaca 240
gccgccaggc cggcccgcan cganccgatc tcntcgggcc gcatgggccc caatcttntc 300
g 301

<210> SEQ ID NO 441
<211> LENGTH: 90
<212> TYPE: DNA
<213> ORGANISM: Mycobacterium tuberculosis

<400> SEQUENCE: 441
gtgtgtggtg gaacccatct gagcagtgtg ccaaaccggg gcagacagct cccaattgac 60
gtgagcccgc tcacttgctg ggtaagcgtc 90

<210> SEQ ID NO 442
<211> LENGTH: 183
<212> TYPE: DNA
<213> ORGANISM: Mycobacterium tuberculosis

<400> SEQUENCE: 442
ctttacactt cctgcatccg gctcgtatgt tgtgtggaat tgtgagcgga taacaatttc 60
acacaggaaa cagctatgac catgattacg ccaagctatt taggtgacac tatagaatac 120
tcaagcttgg gcgtgacggc caccggggcc actccgcacc atctgtaccc gaccaagatc 180
tac 183

<210> SEQ ID NO 443
<211> LENGTH: 348
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 443
caggcatgca agctttagct gcccgaatgc gtcaccccga tgcgcccaga tcggggcttc 60
gcagataaag cacgaacagg cgggcaaaac gtcnatctcg gagccggaag ggcaatcagc 120
cgaccgtcga cgaacgacac cggcgagacc acttaggcag tgacggccgg cccgaacatt 180
acgcgctcgt tgattaggcg ttcggtctcg tccgcggtca tgccgagcag cttgcggcag 240
atctgaacgc tgtcctgtcc gggcagcggc gccgggcgtt ggggtgcctg cccgaatgtg 300
acgaaacgga gccggacccg tctcggcggg ccgcggacgg cgatccgc 348

<210> SEQ ID NO 444
<211> LENGTH: 335
<212> TYPE: DNA
<213> ORGANISM: Mycobacterium tuberculosis
<220> FEATURE:
<221> NAME/KEY: unsure
<222> LOCATION: (various positions within the sequence)

-continued

<223> OTHER INFORMATION: applicants are uncertain of bases designated as “n”

<400> SEQUENCE: 444
cncaagcttg cggatgttac ccctgacagc ctgaactatg tcnaaacaca cggcaccgga 60
acggtgttgg gggaccccat cganttcgag tcgctggcgg ccacttatgg cctgggtaaa 120
ggccagggcn anagcccgtg cgcattgggg tcggtcaaaa ccaacatcgg ccacctggag 180
gcggccgccg gtgtggctgg atncatcaag gcggtgctgg cggtgcaacg tgggcacatt 240
ccccgcaact tgcacttcac ccggtggaac ccggccatcn acgcgtcggc nacgcggctg 300
ttcgtgccna ccnaaaaccc cccgtggccg gcggc 335

<210> SEQ ID NO 445
<211> LENGTH: 289
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 445
ggaaccggta accagatcag ctcgtcgacc tcactgccgg gggtgaattc cccaccggtg 60
ctgcgcgctg cccagtagtg caccttcttg acgcctcgaa aaggggagtc ggtcgggtag 120
gtcaccgtca ggagccgcct acccaggttg gcgcnatagc cggtctcctc gagtatctcc 180
cgcaccgccc ccaccggtgc ggtctcaccc anatccactt tgcccttggg cagcgaccag 240
tcgtcgtanc nggggcggtg aatgacaacg atctcgaccg gcccttccn 289

<210> SEQ ID NO 446
<211> LENGTH: 263
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 446
tactcaagct tcagaacagg cctgttgtgg gcncacccgg ctcgccgagt tctgcacgca 60
ccgcctcaag tgcggcccgc accgccggca tctcccggtc acgcagggcc gcggcccgcg 120
ccgcagcgac ggcgtgttcg cgcagttcgc cgtcaatgat gctgacctga tcggccaccc 180
gggcgttctc ggcgtcgtcg cgttcactaa tcgcggtgct cagcagcgtc tcgacagcca 240
ccacccgagt ggcgaccagc tgc 263

<210> SEQ ID NO 447
<211> LENGTH: 279
<212> TYPE: DNA
<213> ORGANISM: Mycobacterium tuberculosis

<400> SEQUENCE: 447
taatgtcttg ccaacgtcac cacaatcgcg atgaattcaa tcatgccgcc cagggcggcc 60
aacccaatgg tggccgcgag cggcagctcg atcgcagcgc ggaggttgcc ggccgccagt 120
tgattcacga acagggtgag gtcataggcg ggcaggatag tgacgaaggc aagacctata 180
tctgccgtcg gaagaagaat cgagtagccg gtcgacacaa cggaagcgaa agtgtccgcg 240

-continued atgttgatga gcgtcgccgg ttgtggcggc ggtggcggc 279

<210> SEQ ID NO 448
<211> LENGTH: 295
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 448
tactcaagct ttcgtcagtt catcgcgcca gcagaccaac aagagcatcg ggacatacgg 60
agtcaactac ccggccaacg gtgatttctt ggccgccgct gacggcgcga acgacgccag 120
cgaccacatt cagcanatgg ccagcgcgtg ccgggccacg aggttggtgc tcggcggcta 180
ctcccagggt gcggccgtga tcgacatcgt caccgccgca ccactgcccg gcctcgggtt 240
cacgcagccg ttgccgcccg cagcgganna tcacatcgcc gcgatcgccc tgttc 295

<210> SEQ ID NO 449
<211> LENGTH: 280
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 449
ccacccgtgt aatttgggat gggcnaaaag gcnaagcacc gcgtggccac gaacgccggg 60
agggacaatc tcgggcggct agggcttctc gcgggaaggc ccgaacgtac ggcgtttcaa 120
cacgtcgcgt cgccctccga ccgcgaacat tcggggatgg cagcaacctg gtagcaccct 180
ggccgggcga tgatctgcag cgtcgccgcg ggtagtcgcc gcccgggcgg ctacagtctg 240
aaacgcgatg accatcgatg tgtggatgca gcatccgacg 280

<210> SEQ ID NO 450
<211> LENGTH: 320
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 450
tcaagcttta gctgcccgaa tccgtcancc cgatgcnccc agatcggggc ttcgcanata 60
aagcacnaac aggcgggcaa aacgtcnatc tcggagccgg aagggcaatc anccgaccgt 120
cnacaaacga caccggcgan accacttagg cagtgacggc cggcccgaac attacncgct 180
cgttgattag gcgttcggtc tcgtccgcgg tcatgccgag cagcttgcgg canatctgaa 240
cgctgtcctg tccgggcagc ggcgccgggc gttggggtgc ctgcggaatg tgacnaaacg 300
gagccggacc cntctcggcg 320

<210> SEQ ID NO 451
<211> LENGTH: 203
<212> TYPE: DNA
<213> ORGANISM: Mycobacterium tuberculosis
<220> FEATURE:

-continued

<221> NAME/KEY: unsure
<222> LOCATION: (various positions within the sequence)
<223> OTHER INFORMATION: applicants are uncertain of bases designated as "n"

<400> SEQUENCE: 451
ccggggccac tccgcacaat cngtaccnna ccaanatcta caccatcgaa tacgacggcg 60
tcgccgantt tccgcggtac ccgctcaact ttgtgtcgac cctcaacgcc attgccggca 120
cctactacgt gcactccaac tacttcatcc tgacgccgga acaaatngac gcntcggttc 180
cgctgaccaa tacggtcggt ccc 203

<210> SEQ ID NO 452
<211> LENGTH: 287
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 452
nctggccttt ggtccacact aanacaatac tcaagcttcc ggccgcagag ccgccaactc 60
acgatatcgt taaccgatat cccgagccga tagctggcgg gctcgggtgg tggccagcgg 120
cgctgcgacn aaaggtgtga ccgtcatgaa acagacacca ccggcggccg tcggccgtcg 180
tcacctgctc ganatctcag catccgcagc cggtgtgatc gcgctttcgg cgtgtngtgg 240
gtcnccgccc gagcccggca aaggccggcc cgacacaacc ccggaac 287

<210> SEQ ID NO 453
<211> LENGTH: 272
<212> TYPE: DNA
<213> ORGANISM: Mycobacterium tuberculosis

<400> SEQUENCE: 453
catctgccca ccacacggac cgcggtgcgg acgcggctga cgcgcctggt ggtcagcatc 60
gtggccggtc tgctgttgta tgccagcttc ccgccgcgca actgctggtg ggcggcggtg 120
gttgcgctcg cattgctggc ctgggtgctg acccaccgcg cgacgacacc ggtgggtggg 180
ctgggctacg gcctgctatt cggcctggtg ttctacgtct cgttgttgcc gtggatcggc 240
gagctggtgg gccccgggcc ctggttggca ct 272

<210> SEQ ID NO 454
<211> LENGTH: 364
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 454
gacaatactc aagcttgact ggccacccac cggcatgacc accgacaggc ccgactggtc 60
gtaccactcg aacgccgggg tgttgatgtc ccagccgctg aantcgtcct gcgcgcgcag 120
gccgtcnaac aggtacaggg cgggcgaatt ggcaccacca ctttggaatt ggaccttgat 180
gtcacggccc atcgacggcg acggcacctg caggtactcc accggcaagc ccggccggga 240
aaatgccccc gcggtcnccg tgccaccgac ggcgccganc aaacccgaca ctagggccgc 300

-continued gccnacggcc ccgaccacna ntcnacgcga catacccgtg acggcgccac naaccctgtc 360
aaca 364

<210> SEQ ID NO 455
<211> LENGTH: 360
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated

<400> SEQUENCE: 455
cctccaactc ggcggggaag cgacnccagc ctaccgagct tggagtccan gacgccagcg 60
gcggcgtcgg tctgcgtcgt ggtgccgccg gggtggcgtt ggctggcaac gatctccacc 120
cagccggtcg ggttacccac gatctcggca tanacgcggg ccgaggccgg tgcgataccg 180
tattgcgtca attgggacgc ggttgtgcat tcggctagct cggttgccac acccgtcagg 240
ggttcgacgt tggcgggttc ggcgggcccc ancaccgctg tcaccatgcc cgccaagccg 300
acctgcggcg ccaccaactg cagcaccanc atgtcgccgt cgcgcgccgc gatcacatgg 360

<210> SEQ ID NO 456
<211> LENGTH: 311
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 456
ctcaagcttt ttgagcgtcg cgcggggcan cttcgccggc aattctacta ncgagaantc 60
tggcccgata cggatctgac cgaantcgct gcggtgcanc ccaccctcat tggcgatggc 120
gccgacnatg gcgcctggac cgatcttgtg ccgcttgccg acggcgacgc ggtaggtggt 180
caagtccggt ctacgcttgg gcctttgcgg acggtcccga cgctggtcgc ggttgcgccg 240
cnaaagcggc gggtcgggtg ccatcaggaa tgcctcnccg ccgcggcact gcacggccag 300
tgccgcggcg a 311

<210> SEQ ID NO 457
<211> LENGTH: 288
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 457
cnccagcttg attggtctgg ttgcattggc cagctgcgcg agcctggctc acttcaacta 60
cgacgaccgc aaacaattgc cgccttcgga tccgagttcg gttgggtacg cggcaatgga 120
gcaccatttc tcggtgaatc agactattcc tgagtacttg atcatccact ctgcacacga 180
cctgcgaacc ccgcgcggcc ttgccgacct ggagcagctg gcgcaacgtg tgagccagat 240
cccaggcgtt gccatggttc gcggtgtgac ccggccaaac ggggaaac 288

<210> SEQ ID NO 458
<211> LENGTH: 256

-continued

<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 458
caatactcaa gcttgactgg gcccgcacct tcggcgccac ccacaccgtc aacgcccgcg 60
aagtcnacgt cgtccaggcc atcggcggcc tcacggatgg attcggcgcg gacgtggtga 120
tcgacgccgt cggccgaccg gaaacctacc agcaggcctt ctacgcccgc gatctcgccg 180
gaaccgttgt gctggtgggt gttccnacgc ccgacatgcg cctggacatg ccgctggtcn 240
acttcttctc tcacgg 256

<210> SEQ ID NO 459
<211> LENGTH: 327
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 459
tcgacggttt ggcggcctta aatgcactga ggtcgtcaat tgaccccaca gcggaaatgc 60
cgactattcg caggcctcct tcgccttggc tgccggagag gggctccgcg ggaaccgcat 120
gcaggtatat gacctcggtt tctcgggtgc taccgcgtgc cttgtntang atnanctcgg 180
cgttggaatt gtccagccgg cccaattcat cgagcgcana ttcgtacacn tggccggcgg 240
cgacatacgc ttcaccgtgg atctgctcca cacggaccgc cctgtcggga tcctgctcac 300
gggtaangga acttacgtgg cactcgg 327

<210> SEQ ID NO 460
<211> LENGTH: 100
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 460
gaccacgcca ggctaatcac gtgacgctac cgaataccct ncctagtggt gcaggctccc 60
gctggaaatg gccctgtacc aactcgcgca ccggtgccag 100

<210> SEQ ID NO 461
<211> LENGTH: 114
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 461
cggcacccga cccctttgag ccgtccgccg tggccgcggt ggaactggcc gacgagggac 60
tgatcgtgct gggcaaattg gtcgatggca cgctggccgc cgatctgaag gtcn 114

<210> SEQ ID NO 462
<211> LENGTH: 287
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 462
ctcaagcttg ccgttacccc gacttccgga gggacaccat gagcaccgcc agccgagcac      60
gaggccaaac tccgccgacg caggccggtt ggacttgtcg tgctggacaa ggggtttagc     120
cgccgaagca gtgacgtaca tcggcgaaaa gcagttcgcc tgtcgaccga cggngcnnac     180
cgtgaggcta gggaagcgag gagcacatgg ccgccgaccc gcaatgtaca cgctgcaagc     240
aaaccatcga acccggatgg ctatncntca ccgcccatcg ccgcggt                   287

<210> SEQ ID NO 463
<211> LENGTH: 288
<212> TYPE: DNA
<213> ORGANISM: Mycobacterium tuberculosis

<400> SEQUENCE: 463
catgtcgcgc acatccagga cttctggggg gatccgctga cagcggcggg atcccaaagt      60
gcggatgatc gggccgccta cgtcgtggtg tacctcgtcg gtaacaacga aaccgaagcg     120
tatgactcgg tccacgcggt gcggcacatg gtggacacca caccgccacc gcacggggtg     180
aaggcctatg tcaccggtcc ggcagcactc aatgccgacc aggccgaggc cggagacaaa     240
agtatcgcta aggtcaccgc gatcacgagc atggtgatcg cagcaatg                 288

<210> SEQ ID NO 464
<211> LENGTH: 255
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 464
atactcaagc ttcggtacgg tggcgggccg tgctgctggc cgcggtcgcg gcgtgcgcgg      60
cctgcggtct cgtttacnag ctcgcgctgc tgacactggc ggcnagcctg aacggcggcg     120
ggatcgtggc cacctccctg atcgtcgcgg gctacatagc cgcgctggga gcaggcgcct     180
tgctgatcaa gccgctactt gcacacgcgg ccatcgcgtt catcgccgtg gaggcggtgc     240
tgggcatcat cggcg                                                       255

<210> SEQ ID NO 465
<211> LENGTH: 288
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 465
tgtcaagtcc tttcagatct cntttttatg acatgactgg agatctgtct agattgcagc      60

-continued tcctgtgagc gtgggtaccg gattcaagcc ggtcggtcac gccgcggtgg taccggcttt 120
gcggcagtgc tcggcctcga gttcggcgat cgcgcgcgaa gtgcgttcgc gcagcaagat 180
cgcggccgta atgccggcga tgaccgcgat gaccagcgcg atccaggaga accgttccaa 240
ccagtgctgg gcggccatcc cggcgaagta gaccagtgca gtggtgcc 288

<210> SEQ ID NO 466
<211> LENGTH: 224
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 466
caatactcaa gcttcaaaac aggcctgttg tgggcgcacc cggctcgccg agttctgcac 60
gcaccgcctc aantgcggcc cgcaccgccg gcatctcccg gtcacgcagg gccgcggccc 120
gcgccgcanc gacggngtgt tcgcgcagtt cgccgtcaat gatgctgacc tgatcggcca 180
cccgggcgtt ctcggcgtcg tcncgttcac taatcgcggt gctc 224

<210> SEQ ID NO 467
<211> LENGTH: 320
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 467
tacgctggcg ctggagggag ccanntacaa catccacgcc aatgctcttg ccccgatcgc 60
ggcgaccagg atgacccagg acatcctgcc gcccgaagta ctggaaaagc tcacacccga 120
gttcgtcgca ccggtggtgg cctacctgtg caccgaggag tgtgccgaca acgcatcggt 180
gtacgtcgtc ggtggtggca aggtgcagcg agttgcgctg tttggcaacg acggcgccaa 240
cttcgacaaa ccgccgtcgg tacaagatgt tgcggcgcgg tgggccgaga tcaccgatct 300
gtccggtgcg aaaattgctg 320

<210> SEQ ID NO 468
<211> LENGTH: 303
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 468
gcttttcccg tccgtcnncg ctcaaccgcg tgaggccgaa gcggntggtt acgactccct 60
gtttgtgatg gaccacttct accaactgcc catgttgggg acncccgacc agccgatgct 120
ggaggcctac acggcccttg gtgcgctggc cacggcgacc gancggctgc nnntgggcgc 180
gttggtgacc ggcaatacct accgcagccc gaccctgctg gcaaanatca tcaccacgct 240
cgacgtggtt agcgccggtc gagcgatcct cggcattgga gccggttggt ttganctgga 300
aca 303

-continued

<210> SEQ ID NO 469
<211> LENGTH: 391
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 469

```
cngcttttta atggccttga cntgggcgng ccggccaccg gggccactcc gcacaatctg     60

tacccgacca agatctacac catcgaatac gacggcgtcg ccgactttcc gcggtacccg    120

ctcaactttg tgtcgaccct caacgccatt gccggcacct actacgtgca ctccaactac    180

ttcatcctga cgccggaaca aattgacgca gcggttccgc tgaccaatac ggtcggtccc    240

acgatgaccc agtactacat cattcgcacg gagaacctgc cgctgctaga gccactgcga    300

tcggtgccga tcgtggggaa cccactggcg aacctggttc aaccaaactt gaaggtgatt    360

gttaacctgg gctacggcga cccggcctat g                                   391
```

<210> SEQ ID NO 470
<211> LENGTH: 343
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 470

```
ctcaagcttg ccgggagggt gcatggccga ctcggattta cccaccangg ggcgccaacg     60

cggtgtccgc gccgtcnagc tgaacgttgc tgcccgcctg gagaacctgg cgctgctgcg    120

caccctggtc ggcgccatcg gcaccttcga ggacctggat ttcgacgccg tggccgacct    180

gaggttggcg gtggacgagg tgtgcacccg gttgattcgc tcggccttgc cggatgccac    240

cctgcgcctg gtggtcgatc cgcgaaaana cgaanttgtg gtggaggctt ctgctgcctg    300

cgacacccac nacgtggtgg caccgggcag ctttagctgg cat                      343
```

<210> SEQ ID NO 471
<211> LENGTH: 303
<212> TYPE: DNA
<213> ORGANISM: Mycobacterium tuberculosis

<400> SEQUENCE: 471

```
ccgacgccgt cgtggccacc aacaccgcga ccagcaccgt gacccggacc ggggtgccgc     60

gcgaaccggt cttggccaat tgccgcggca ccaagccgtc gcgcgccatg gcgaacagca    120

cgcggcattg cccgagcatc aacaccatca ccaccgtggt aagcccggcc agcgcgccga    180

cggagatgat gccgctggcc cagtacaccc cgttggcctg gaacgcggtg gccagatttg    240

ccggcccgcg gcccggtacg gtccgcagtt gggtgtatgg aaccatgccc gacagcacca    300

ccg                                                                  303
```

<210> SEQ ID NO 472
<211> LENGTH: 264
<212> TYPE: DNA
<213> ORGANISM: Mycobacterium tuberculosis
<220> FEATURE:
<221> NAME/KEY: unsure
<222> LOCATION: (various positions within the sequence)

-continued

<223> OTHER INFORMATION: applicants are uncertain of bases designated as “n”

<400> SEQUENCE: 472
ttnactggcc tttggtccac actagacaat actcaagctt ccaggacatc gtcatcgcga 60
ccaaaaccgc gagctaggtc ggcatccggg aagcatcgcg acaccgtggc gccgagcgcc 120
gctgccggca ggccgattag gcgggcaaat tagcccgccg cggctcccgg ctccgantac 180
ggcgccccga atggcgtcac cggctggtaa ccacgcttgc gcgcctgggc ggcggcctgc 240
cggatcaggt ggtaaatgcc gaca 264

<210> SEQ ID NO 473
<211> LENGTH: 280
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 473
ngacgtcttc catccgcgcg tcgttttggc gggttggcca cagcagcccg ccggtgacgg 60
cgacgatgct gggctggttg cggccctgcg ccaccgcggc ttgcatgctg gttggctgtc 120
ttgggacgat cccgaaatag tccacgcgga tctggtgatt ttgcgggcta cccgcgatta 180
ccccgcgcgg ctcgacgagt ttttggcctg gactacccgc gtggccaatc tgctgaactc 240
gcggccggtg gtggcctgga atgtcgagcg ccgttaccta 280

<210> SEQ ID NO 474
<211> LENGTH: 153
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 474
cttcctcctg agtaccnccc gtntactttg ggatgggtaa aaaggcgaat cnccgtttgg 60
tcacgaacgc cgggagggac aatctcgggc ggctggggcc tctcgcggga angcccgaat 120
gtacggtgtc tcgacacttc ccntccccct ccg 153

<210> SEQ ID NO 475
<211> LENGTH: 247
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 475
gagcatcggg acntacggag tcaactaccc ggccaacggt gatttcttgg ccgccgctga 60
cggcgcgaac gacgccngcg accacattca gcagatggcc agcgcgtgcc gggccacgag 120
gttggtgctc ggcggctact cccagggtgc ggccntgatc nacatcgtca ccgccgcacc 180
actgcccggc ctcgggttca cgcagccgtt gccgcccnca gcggacgatc acntcgccgc 240
gatcgcc 247

<210> SEQ ID NO 476
<211> LENGTH: 264
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 476
tactcatgan catcctttaa tcanngcttt gcgttttttt attaaatctt gcaatttact 60
gcaaagcaac aacaaaatcg caaagtcatc aaaaaaccgc aaagttgttt aaaataagag 120
cancactaca aaaggagata agaagagcac atacctcagt cacttattat cactagcgct 180
cgccgcagcc gtgtaaccga gcatagcgag cgaactggcg aggaagcaaa gaagaactgt 240
tctgtcagat agctcttacg cnca 264

<210> SEQ ID NO 477
<211> LENGTH: 264
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 477
ctcaagcttc aggtcaatgt gcnccaagcc ctgacgctgg ccgaccaggc caccgccgcc 60
gganacnctg ccaaggccac cgaatacaac aacgccgccg aggcgttcgc ancccagctg 120
gtgaccgccg agcanancgt caaaaacctc aagacgctgc atgaccaggc gcttancncc 180
gcanctcagg ccaagaaggc cgtcnaacga aatgcgatgg tgctgcacca naagatcgcc 240
gagcgaacca agctgctcag ccng 264

<210> SEQ ID NO 478
<211> LENGTH: 352
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 478
catggtggca ctgtagcgac gtgctgcaat caaggtcatg cccgactctg gtcagctcgg 60
anccgctgac accccgctaa ggctgctcag ctcggtgcat tacctcaccg acggcgaact 120
cccccagctt tacgactatc cggatgacgg cacctggttg cgggcgaact tcatcatcag 180
cttggacggc ggcgctaccg tcgatggcac cagcggggcg atggccgggc ccggcgaccg 240
attcgtcttc aacctgttgc gtgaacttgc cgacgtcatc gtggtcggcg tgggcaccgt 300
gcgcattgag ggctactccg gcgtccggat gggtgtcgtc cagcgccagc ac 352

<210> SEQ ID NO 479
<211> LENGTH: 207
<212> TYPE: DNA
<213> ORGANISM: Mycobacterium tuberculosis
<220> FEATURE:
<221> NAME/KEY: unsure -continued
<222> LOCATION: (various positions within the sequence)
<223> OTHER INFORMATION: applicants are uncertain of bases designated as "n"

<400> SEQUENCE: 479
tactcaagct tgcgggtgat cgccttggtc aacggcaccg tgatcggatc ggggtcnacc 60
gcacaaatgg actggagctt cggcgaantc atcgcctatg cctcgcgggg ggtgacgctg 120
accccgggtg acntgttcgg ctcgggcacg gtgcccacct gcacgctcgt ctatcacctc 180
nggccaccgg aatcattccc gggctgg 207

<210> SEQ ID NO 480
<211> LENGTH: 256
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 480
gttggngcct cgtcggcgaa cagttctcgc acgatttccg gattagcggg actggtcacc 60
agttgggtat gcgggaaggc gctgacgttc gccgcgatta gctgtttgat ggacgcggtg 120
gtgatgttct gatcacggaa ctggctgtaa tagcccaggg tcgccacgct ttcatccggg 180
cccggacccg gcgcaccgag cgtgtcgcgc aggtatgcga cgtgattttc gctgaagtcc 240
ccgtacccgg agaact 256

<210> SEQ ID NO 481
<211> LENGTH: 397
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 481
tgcttccggc tcgtatgttg tgtggaattg tgancggata acaatttcac acaggaaaca 60
gctatgacca tgattacgcc aagctattta ggtgacacta tagaatactc aagctccagg 120
tcaatgtgcg ccaagccctg acgctggccg accaggccac cgccgccgga gacgctgcct 180
ttgtcaccga atacaacaac gccgccgagg cgttcgcagc ccagctggtg accgccgagc 240
agagcgtcga agacctcaag acgctgcatg accaggcgct tagcgccgca gctcaggcca 300
agaatgccgt cgaacgaaat gcgatggtgc tgcggcataa gatcgccgag cgaaccaagc 360
tgctcagcca gctcgagcag gcgaagatgc acgagca 397

<210> SEQ ID NO 482
<211> LENGTH: 379
<212> TYPE: DNA
<213> ORGANISM: Mycobacterium tuberculosis

<400> SEQUENCE: 482
caggcatgca agcttcggag gcagacccgt gcatggtggc actgtagcga cgtgctgcaa 60
tcaaggtcat gcccgactct ggtcagctcg gagccgctga caccccgcta aggctgctca 120
gctcggtgca ttacctcacc gacggcgaac tcccccagct ttacgactat ccggatgacg 180
gcacctggtt gcgggcgaac ttcatcagca gcttggacgg cggcgctacc gtcgatggca 240

-continued

```
ccagcggggc gatggccggg cccggcgacc gattcgtctt caacctgttg cgtgaacttg    300

ccgacgtcat cgtggtcggc gtgggcaccg tgcgcattga aggctactcc ggcgtccgga    360

tgggtgtcgt ccatcgcca                                                 379
```

<210> SEQ ID NO 483
<211> LENGTH: 264
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 483

```
tactcaagct tggggtggcg ctgtcggtcg gtgtgcttgg cggcgtcggt atcaacaccg     60

cccacgaaat ggggcacaag aaggattcgc tggagcggtg gctgtccaaa atcaccctcg    120

cccanacctg ctacgggcac ttctacatcg agcacaaccg tggccatcac gtccgggtgt    180

ccacaccgga ggacccggcg tcggcgcggt tcggcnaaac gttgtgggan ttcctgcccc    240

gcantgttat cggcggcttg cgct                                           264
```

<210> SEQ ID NO 484
<211> LENGTH: 351
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 484

```
ggccatcgcc accgcnccgc ggcgaacgct caaaggcacc tactggcacc aaggccccac     60

acgtcaccct gtgacctcct gcgccgaccc cgcccgaggt cctggccgtt accaccgaac    120

gggcgagccg ggagtctggt acgcatcgaa caaagagcaa ggtgcatggg cggagttgtt    180

ccgccacttc gtcgatgacg ggtcgatcc attcgaggtc cgtcgccgcg tcggtcgagt     240

ggcggtcaca ctccangtac tcgacctcac agacgagagg actcgatccc atctaggtgt    300

ggacgaaaca gatcttctgt ccgacgacta caccaccacc caggccatcg c             351
```

<210> SEQ ID NO 485
<211> LENGTH: 328
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 485

```
gcttgcgggt gatcgccttg gtcaacggca ccgtgatcgg atcggggtcn accgcncaga     60

tggactggan cttcggcgaa ntcntcgcct atgcctcgcg gggggtgacc ctgaccccgg    120

gtgacntgtt cggctcgggc acggtgccca cctgcacgct cgtcaagcac ctcnggccac    180

cggaatcatt cccgggctgg ctgcacnacg gcgacntggt cnccctccag gtcgaagggc    240

tgggcnaaac aangcagacc gtccggacaa ncggcactcc ttttccgttg gctcttcggc    300

cgaatccgga cgccnaaccc gaccggcg                                       328
```

<210> SEQ ID NO 486
<211> LENGTH: 344
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 486

```
gttctcgcac gatttccgga ttagcgggac tggtcaccag ttgggtatgc gggaaggcgc     60

tgacgttcgc cgcgattagc tgtttgatgg acgcggtggt gatgtnctga tcacggaact    120

ggctgtaata ncccagggtc gccncgcttt catccgggcc cggacccggc gcaccgagcg    180

tgtcgcgcag gtatgcgacg tgattttcgc tgaagtcccc gtacccggag aactcgaaca    240

cgctgaggcg ctcgtcaccg tcgtnncggc gaccaagcgc ggcgagcaac tgcgcaaaat    300

cgttaagana ggtcgaatcg ttgaaattcg gcaccacctg cacc                     344
```

<210> SEQ ID NO 487
<211> LENGTH: 285
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 487

```
cacaagacaa tactcaagct tcaggtcaat gtgcnccaag ccctgacgct ggccgaccag     60

gccaccgccg ccggganacgc tgccaaggcc accgaataca acaacgccgc cgaggcgttc    120

gcagcccagc tggtgaccgc cgagcananc gtcnaaaacc tcaagacgct gcatgaccag    180

gcgcttancg ccncagctca ggccaagaag gccgtcgaac gaaatgcgat ggtgctgcag    240

canaanatcg ccgancgaac caagctgctc agccagctcg agcag                    285
```

<210> SEQ ID NO 488
<211> LENGTH: 280
<212> TYPE: DNA
<213> ORGANISM: Mycobacterium tuberculosis

<400> SEQUENCE: 488

```
ccacccgtgc atggtggcac tgtagcgacg tgctgcaatc aaggtcatgc ccgactctgg     60

tcagctcgga gccgctgaca ccccgctaag gctgctcagc tcggtgcatt acctcaccga    120

cggcgaactc ccccagcttt acgactatcc ggatgacggc acctggttgc gggcgaactt    180

catcagcagc ttggacggcg gcgctaccgt cgatggcacc agcggggcga tggccgggcc    240

cggcgaccga ttcgtcttca acctgttgcg tgaacttgcc                          280
```

<210> SEQ ID NO 489
<211> LENGTH: 160
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 489

-continued gctttccgcc gatacccncc atgtcccgca catccaggac ttctgggggg atccgctgac 60
agcggcggga tcccaaagtg cggatgatcg ggccgcctac gtcgtggtgt acctcgncgg 120
taacaacgaa accgaancgt atgactcngt ccacgcggtg 160

<210> SEQ ID NO 490
<211> LENGTH: 176
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 490
caacccgant tggctttcgg cgccntcggt gaggacggcg tgcgggtgct caacgacgac 60
gtcgtccgcg ggacacacct cgatgctgcc gccatggacg cggtcgaacg caagcagctg 120
atcgatctac nacgccgngn ggaacgcttc ngccgcgggc gtgaccgcnt cccgtt 176

<210> SEQ ID NO 491
<211> LENGTH: 216
<212> TYPE: DNA
<213> ORGANISM: Mycobacterium tuberculosis

<400> SEQUENCE: 491
gggatgggca aaaaggcgaa gcaccgcgtg gccacgaacg ccgggaggga caatctcggg 60
cggctagggc ttctcgcggg aaggcccgaa cgtacggcgt ttcaacacgt cgcgtcgccc 120
tccgaccgcg aacattcggg gatggcagca acctggtagc accctggccg ggcgatgatc 180
tgccagcgtc cccgcgggta gtcgccgccc gggcgg 216

<210> SEQ ID NO 492
<211> LENGTH: 163
<212> TYPE: DNA
<213> ORGANISM: Mycobacterium tuberculosis

<400> SEQUENCE: 492
cagcagacca acaagagcat cgggacatac ggagtcaact acccggccaa cggtgatttc 60
ttggccgccg ctgacggcgc gaacgacgcc agcgaccaca ttcagcagat ggccagcgcg 120
tgccgggcca cgaggttggt gctcggcggc tactcccacg gtt 163

<210> SEQ ID NO 493
<211> LENGTH: 80
<212> TYPE: DNA
<213> ORGANISM: Mycobacterium tuberculosis

<400> SEQUENCE: 493
ctcaagcttg actggccacc caccggcatg accaccgaca ggcccgactg gtcgtaccac 60
tcgaacgccg gggtgtttga 80

<210> SEQ ID NO 494
<211> LENGTH: 248
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 494
ttggtgcccg gaatggcgag tcccatttan tcgctgattt gtttgaacag cgacgaaacc 60
ggtgttgaaa atgtcgcctg ggtcggggat tccctctcca agcaagagta actggcccca 120
aataaagtta ctcgtcgtct tgcaaagacc gctacccgat gccatttatg tgtttcctta 180
cgctcnnnnt tccggtgcgc catcattatc tgcacctttg cactgcacat tgagcttagc 240
agcgctcg 248

<210> SEQ ID NO 495
<211> LENGTH: 341
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 495
gaattngctt tcggcgccat cggcccagga ccgcgtgcgg gtgctcaacg acgacgtcgt 60
ccgcgggaca cacctcgatg ctgccgccat ggacgcggtc gaacgcaagc agctgatcga 120
gctacaacgc cgcgcggaac gcttccgccg cgggcgtgac cgcatcccgt tgaccgggcg 180
gatcgcngtg atcgtcgatg acggcatcgc caccggagcg acggccaagg cggcgtgcca 240
ggtcgcccgg gcgcacggtg cggacaaggt ggtgctggcg gtcccgatcg gcccagacga 300
catcgtggcg agattcgccg ggtacgccga tgaagtggtg t 341

<210> SEQ ID NO 496
<211> LENGTH: 420
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 496
taaagctttc gtcagttcat ngngcccccg gaccaacaaa agcatcggga catacggagt 60
caactacccg gccaacggtg atttcttggc cgccgctgac ggcgcnaacg acgccagcga 120
ccacattcag cagatggcca gcgcgtgccg ggccacgagg ttggtgctcg gcggctactc 180
ccagggtgcg gccgtgatcn acatcgtcac cgccgcacca ctgcccggcc tcgggttcac 240
gcagccgttg ccgcccgcag cggacgatca cntcgccgcg atcgccctgt tcgggaatcc 300
ctcgggccgc gctggcgggc tgatgagcgc cctgacccct caattcgggt ccaanaccat 360
cnacctctgc aacaacggcg acccgatttg ttcggacggc aaccggtggc gancgcacct 420

<210> SEQ ID NO 497
<211> LENGTH: 135
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 497
ccgggaggga ccatcncggg cggctncggc ttctctccgg aaggttctan ngtnnngcgt 60

-continued ttcnacnctt cccgtcgccc tgcgaccgcc gaacattcgg ggtatggnng cancctgtna 120
gcatccnggc cgggc 135

<210> SEQ ID NO 498
<211> LENGTH: 277
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 498
ctcaagcttc cgcatcagat cgctatagaa ccggtgcgcg tccccaccga gtggctggtc 60
gccttccagc acgatcgtta ccgcgttatc ggaatcaaac tcnccgaaca cctgaccaac 120
gcgcttgatc gcctgaatcg atgcggcgtc gctggggctc atcgataccg agtgtgcttt 180
tccgaccact tccagttgcg gtacggcgag attgacaaag gcggtgaagc ccagccagag 240
caggacgatc accnccgcaa accggcggat ttgcccg 277

<210> SEQ ID NO 499
<211> LENGTH: 323
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 499
gcttggcagc ctgcggctgg gcgccctnga gctcttcgat ctggatctcc ggactcgaga 60
tgctcacttg cccggccgtg gacgtaccca ttgcggccgg gaccccagcg ccccaggtga 120
ccagcgagtt gggctgcacg ctgaccggcc cgtcggggtc gacgccggta acggtcagca 180
gctccgangt ccnnctgatc ccgaccgcag ctgccaatgc gcggctggca gccgacgtgg 240
atgtgccggg gcctagatcg cggggcagca gcgagaccgc gtcaccgacg gtcatcacct 300
tgccgagttt nggcctgccg can 323

<210> SEQ ID NO 500
<211> LENGTH: 148
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 500
gcttccggct cgtatgttgt gtggaattgt gagcggataa caattncaca caggaaacag 60
ctatgaccat gattacgcca agctatctag gtgacactat agaatactca agcttgagcc 120
atcgggctat cagctggttg atgtcccg 148

<210> SEQ ID NO 501
<211> LENGTH: 242
<212> TYPE: DNA
<213> ORGANISM: Mycobacterium tuberculosis

<400> SEQUENCE: 501

-continued caggcatgca agcttgtcgt ctatcacatc cgaccaccaa ccgcccgacg gctcggcaga 60
acgcctccgc atatgggtcg acgaccagcg ggtcggactt ctgggctgcc agcgctcgcg 120
ccgtcgcgac aaacagcgcg gtcgaaccga cactccttgt gatgtcccac ctatcacctt 180
cggtacgcac ccaatcgacc ctacgcggct agctcagccc cgatcttcca gagctccgcc 240
cg 242

<210> SEQ ID NO 502
<211> LENGTH: 230
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 502
gctttttgag cgtcgcgcgg ggcggcttcc ccggcaattc tactagcgag aagtctggcc 60
cgatacggat ctgaccgaag tcgctgcggt gcagcccacc ctcattggcg atggcgccga 120
cnatggcgcc tggaccgatc ttgtgccgct tgccgacggc gacgcggtag gtggtcaatt 180
ccggtctacg cttgggcctt tgcggacggt cccgacgctg gtcgcggttg 230

<210> SEQ ID NO 503
<211> LENGTH: 235
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 503
cgancctgtt cgacggctac ctgaatcacc ccgatnccac cgccgcggcg ttcgacgccg 60
acagctggta ccgcaccggc gacgtcgcgg tggtcgacgg cagtgggatg caccgcatcg 120
tgggacgcga gtcggtcgac ttgatcaagt cgggtggata ccgggtcggc gccggtgaaa 180
ttgaaacggt gctgctcggg catccggacg tggcggaggc ggcagtcgtc ggggt 235

<210> SEQ ID NO 504
<211> LENGTH: 152
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 504
naagctttgt cacaccaagt gtttcnacca gncgctccat ccggcgaagt ggatactccc 60
agcaggtagc aggtcgccac cacgctggtc agtgcgcgtt cagctcgctt gcggcgctgc 120
agcagccagt ccgggaaata gctgccctgg cg 152

<210> SEQ ID NO 505
<211> LENGTH: 192
<212> TYPE: DNA
<213> ORGANISM: Mycobacterium tuberculosis
<220> FEATURE:
<221> NAME/KEY: unsure
<222> LOCATION: (various positions within the sequence)

-continued

<223> OTHER INFORMATION: applicants are uncertain of bases designated as “n”

<400> SEQUENCE: 505
cgctggncgc cggcgctggg ctgcggtaac caattaccac aacacttttc ggtagccgaa 60
cagcggcgcg taccagcgaa atggcacagc caccgcagtc gccgacatcc cgcgaagatg 120
tggcagattt tcgtgcggtc gagccggcga aggcctagcg tcattgttgc ctggcaaggt 180
tgctgggccc gg 192

<210> SEQ ID NO 506
<211> LENGTH: 312
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 506
ctcaagcttc ttctgcccct tgccgttncg gatnacatcc cgcagcgact cggcttcggc 60
gtcgatgtcg aagttctcga tcagcttctg gatcgactcc gcgcccatgg caccggtgaa 120
gtactcgccg tagcggtcga cnagttcgcg gtagaggttt tcgtcnacna tcagctgctt 180
gggcgccanc ttggtgaaag tgctccaaat gtcctccaac cggtccagct cacgctgcgc 240
gcggtcacgg atctggcgca tctcgcgctc gccgccgtcg cgaacttgcg ccgcgcatcg 300
gccttggggc cc 312

<210> SEQ ID NO 507
<211> LENGTH: 296
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 507
gttcacacct acctactatg ccncaattcn ccgacacggg tggcatcaac acgggcgata 60
aggtggaaat cgctggggtg aacgtcgggc tggtgcgctc gctggcaatc cgcggcaacc 120
gcgtgttgat cggattctcg ttgcccggca agacaatcgg gatgcaaagc cgggcagcaa 180
ttcncnccna caccattctt ggccgtaaga acctggagat cgaaccccgc ggttcggagc 240
cgttgaaacc caacggtttc ctgccgttgg cgcanaccac tacgccatac caaatc 296

<210> SEQ ID NO 508
<211> LENGTH: 208
<212> TYPE: DNA
<213> ORGANISM: Mycobacterium tuberculosis

<400> SEQUENCE: 508
ctcaagcttt acgccgacgc cggcctacac aacaccaagg aaacgattgc ctactgccga 60
atcggggaac ggtcctcgca cacctggttc gtgttgcggg aattactcgg acaccaaaac 120
gtcaagaact acgacggcag ttggacagaa tacggctccc tggtgggcgc cccgatcgag 180
ttgggaagct gatatgtgct ctggaccc 208

<210> SEQ ID NO 509

-continued

<211> LENGTH: 278
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 509
tcccncatgg gataacgggt ttagatttcn acaacggcac cgtgtttctc aacaagccgg 60
tcatcagctg ggccggcgac aacggtatct acttcacccg ctttcgcccg tacaagaaaa 120
accactaggc caccatcgag tccaagaaca accacctggt ccgcaagtac gcgttctact 180
accgctatga caccgccgag gaacgcgccg tgctcaaccg gatgtggaag ctggtcaacg 240
accgcctcaa ctacctcacc ccgaccatca aaccgatc 278

<210> SEQ ID NO 510
<211> LENGTH: 177
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 510
ctcaagcttg ggtgttgccg atcaccggaa gccncatgat cagccacgtt tcgcgccgcc 60
cggcatacgg cggcgtaccg atctccgcgt catacacccg cgggtaatcg ccgacggtgc 120
cggttcgcga gccgaaggtg acaacgctga ttgaatcnag ttccangtcc agcgggt 177

<210> SEQ ID NO 511
<211> LENGTH: 296
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 511
tnaacagctc gcggcagccc acgacctgct gcgtcggatt gccggcggcg agatcaattc 60
caggcagctc ccggacaatg cggctctgct ggcccgcaac gaangactcg aggtcacccc 120
ggtgcccggg gtcgtggtgc acctgccgat cgcacaggtt ggcccacaac cggccgcttg 180
atgnnnngtc ggcaagcccg gcagtngcca aacccagcgt gatcangctc ggctcgcgag 240
ttcggcgaan aagtggctcg cctgatcacc taccatcggc cangatctgc gtgtca 296

<210> SEQ ID NO 512
<211> LENGTH: 223
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 512
gccanccggc ttggcgtcga ctcccgttcn gcacatcata cggtccccgg tactgtccaa 60
ctgcgccggt gcgctagcca aacgtcacga ctctcagtga tcccagttcg tgatccggcc 120

-continued ggtggcgccg ctgcggcggg ggctnatnta cttcggactn attatctcat ccaaaggaca 180
ccgggccggt ggctggaatc ccatggtgcg atcggccaca can 223

<210> SEQ ID NO 513
<211> LENGTH: 147
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 513
ccgacctggt atcttccgat agcgcgcgtt gatatccggt ctgatctcct gcccttaacg 60
ccggatctca gcaggtcccc atgcaaagat ccgaggtgtc ccngatctag gggtcctcgt 120
cctccagatg atggagcaag tcggccc 147

<210> SEQ ID NO 514
<211> LENGTH: 149
<212> TYPE: DNA
<213> ORGANISM: Mycobacterium tuberculosis

<400> SEQUENCE: 514
ctcaagcttc ggctcaggcg gcgctgccgg taacgtcgct gaccggtgca ggtttcgaca 60
atgtggtgcc ggttcggcgg ctacgtgcca tcaagacact ggcgcaggct atcgcacccg 120
ttatcggcta caaacaaatc gcggtatgc 149

<210> SEQ ID NO 515
<211> LENGTH: 238
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 515
catcacctgn ttcatgaact ggaagcaccg cagcgcttcc ttttcggccg caacatgagc 60
cagcctctcg tcggcggtcg ggtgcaggtg ctcgggcagc tcggccgcga cagccgcctg 120
accctgaaac cagcttccat atcccgcgac gaacgacgcc agtccgctac gtaacccctc 180
cgcgactgtc catggacaac agcgcgttct ccaccgaccg ggcccgggtg tggggtgt 238

<210> SEQ ID NO 516
<211> LENGTH: 175
<212> TYPE: DNA
<213> ORGANISM: Mycobacterium tuberculosis

<400> SEQUENCE: 516
agcttagctt cccgccccgg caatagggct ccagctcatc cggtgtgacc agataggggc 60
ccagggtgat accgctgtct ttgcccttgg cctgtccgat gcgcagctgg ccctccagca 120
tctgcaggtc ccgtgcggac cagtcgttga aaatggtata gccgatgatc gaccg 175

<210> SEQ ID NO 517
<211> LENGTH: 144
<212> TYPE: DNA
<213> ORGANISM: Mycobacterium tuberculosis
<220> FEATURE:

-continued

<221> NAME/KEY: unsure
<222> LOCATION: (various positions within the sequence)
<223> OTHER INFORMATION: applicants are uncertain of bases designated as “n”

<400> SEQUENCE: 517
ccngaacaga agcggnggtt cctaccgcgg tgtgcggccg gcgcgatatc ggccttttta 60
ctaaccgaac ccgatgtggg ctccgatccg gcgcgcatgg catcgacggc gacgccgatc 120
gatgaccgcc aggcttacca cctt 144

<210> SEQ ID NO 518
<211> LENGTH: 174
<212> TYPE: DNA
<213> ORGANISM: Mycobacterium tuberculosis

<400> SEQUENCE: 518
ctcaagcttg cgcgactcga caagcattct tgacagttgt tttggctcgg catggttagc 60
caaggttctg cggtcccacc agatcatctt ggtccggtag cgctcgtccg ggtatgctgc 120
cgccgggatt ctcgctgcta ttactccccc cgaagaacgc caccggtcca gcgc 174

<210> SEQ ID NO 519
<211> LENGTH: 187
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 519
gcnaggcggt atagcttccc gtcgtaccgg cgaccgccag ccgagaagct cgttttccca 60
gtgttgctgg ggattctcac gctgctgctg agtgcgtgcc agaccgcttc cgcttcgggt 120
tacaacgagc cgcggggcta cgatcgtgcg acgctgaagt tggtgttctc catggacttg 180
gggatgt 187

<210> SEQ ID NO 520
<211> LENGTH: 215
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 520
gtgtggaacc gtgagcggat aacaatttca cacaggaaac agctntgacc ttgattacgc 60
caagctattt aggtgaggct atattaatac tcaagattgc ggtcgagcac atcggcccaa 120
gaaccgccga aggcacggcg gaacgcctgc ggcacatggg gcgacgacca gcgggtcgga 180
cttctgggct gtccagccgg atcgcgccgt cgcga 215

<210> SEQ ID NO 521
<211> LENGTH: 406
<212> TYPE: DNA
<213> ORGANISM: Mycobacterium tuberculosis

<400> SEQUENCE: 521
cactgtcagt acatatgcgc cgctcctcct catcgctgcg ctcggcatcg tcgccggcgg 60

-continued tcatggcgtc accctaccca agccgaacgc gaaacgagaa cgtgttccat tattagggtg 120
tgagcaccaa taccagattg ctcaccagga actcacgcag caccgggacg gatgtcagcc 180
accacgccca tctggggtgg tagcggggaa atacggctaa cgcggctccg gtgccggcag 240
cccagcgcag accctcggcg gcggacacgg caaacaacga cgacccatag ttgttctttg 300
ccggatggcc gtgtttgcgg acatatcggg cggcggcgcg ggcgccgccg aggtagtggc 360
tgaggcccat ctcgtgcccg ccgaatggcc ccagccaaac cgtgta 406

<210> SEQ ID NO 522
<211> LENGTH: 180
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 522
ctcaagcttt tacggtgatc gcgcatcacc tggttcatga actggaagca gcgcagcgct 60
tccttttcgg ccgcaacatg agccancctc tcgtcggcgg tcgggtgcag gtgctcgggc 120
agctcggccg cgacagccgc ctgaccctga aaccagcttc catatcccgc gacnaacgac 180

<210> SEQ ID NO 523
<211> LENGTH: 69
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 523
ctcagaagcc gctagctggt agagtcgctg accggtgcac gtggcgncaa tgtgcgctgc 60
cggttcgcg 69

<210> SEQ ID NO 524
<211> LENGTH: 168
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 524
ctcaagcttg cgctcatcaa gcgcgaacag cagggcggtc ggctggtcgc catgacgggt 60
gacgggacca atgacgcacc cgcgctcgcg caagccgatg tcggggtggc natnaatacc 120
ggcacccagg cggcccggga agccggcaac atggtcnatc tccactcc 168

<210> SEQ ID NO 525
<211> LENGTH: 83
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 525

-continued actttctattt cgactggtgt gctgtggcgc gatccgactg ccggcgtggt caaggccggc 60
cagttgtggg atnccacagg cac 83

<210> SEQ ID NO 526
<211> LENGTH: 173
<212> TYPE: DNA
<213> ORGANISM: Mycobacterium tuberculosis

<400> SEQUENCE: 526
gcttgtcgta ttccgtggca ctgtcagaca tatgcgccgc tcctcctcat cgctgcgctc 60
ggcatcgtcg ccggcggtca tggcgtcacc ctacccaagc cgaacgcgaa acgagaacgt 120
gttccattat tagggtgtga gcaccaatac cagattgctc accaggaact cac 173

<210> SEQ ID NO 527
<211> LENGTH: 38
<212> TYPE: DNA
<213> ORGANISM: Mycobacterium tuberculosis

<400> SEQUENCE: 527
cgatattcgt cggccgcgtt gtctcgactg ggtcgcgt 38

<210> SEQ ID NO 528
<211> LENGTH: 136
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 528
gacctcggcc accaagccgg acgcgaccgt cgaggtggcg atccggcttg gcgtcgaccc 60
gcgtaaggca gaccacatgg tccgcggcac ggccancctg ccacacggca ctggtaagac 120
tgcccgcgtc gcggcn 136

<210> SEQ ID NO 529
<211> LENGTH: 114
<212> TYPE: DNA
<213> ORGANISM: Mycobacterium tuberculosis

<400> SEQUENCE: 529
ccggaagtct aggggacgac ctactcagcg caaaatgtcg ctaatgtgag tccgccccac 60
cagggcagat caacccatgt cgatgatgac ctacccggat accggattgg cggt 114

<210> SEQ ID NO 530
<211> LENGTH: 119
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 530
agcttcagtt cctccacgac gcgttcccaa atgaatttcc cgatcccaca atctcggttc 60
agatacaggt cgccataccc cttacttcgg naacgctggg cggattggcc ctgccgctg 119

<210> SEQ ID NO 531

-continued

<211> LENGTH: 99
<212> TYPE: DNA
<213> ORGANISM: Mycobacterium tuberculosis

<400> SEQUENCE: 531
ccgcctacgg gtcgaacatg catcccgaga ccgatgctcg agcgcgcacc ccactcgccg 60
atggccggaa ccggctggtt acccgggtgg cggctgacc 99

<210> SEQ ID NO 532
<211> LENGTH: 308
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 532
gcggctggtt acgactccct gtttgtgatg gaccacttct accaactgcc catgttgggg 60
acgcccgacc agccgatgct ggaggcctac acggcccttg gtgcgctggc cacggcgacc 120
gagcggctgc aactgggcgc nttggtnacc ggcaatacct accgcagccc gaccctgctg 180
gcaaagatca tcaccacgct cgacgtggtt agcgccggtc gagcgatcct cggcattgga 240
gccggttggt ttgagctgga acaccgccag ctcggcttcg agttcggcac tttcagtgac 300 cggttcan 308

<210> SEQ ID NO 533
<211> LENGTH: 328
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 533
gcctttccgc acaatctgta ccccaggacc ntctaaaaaa tcgaatacga cggcgtcgcc 60
gactttccgc ggtacccgct caactttgtg tcgaccctca acgccattgc cggcacctac 120
tacgtgcact ccaactactt catcctgacg ccggaacaaa ttgacgcagc ggttccgctg 180
accantnntg tcggtcccac gatgacccag tactacatca ttcgcacgga gaacctgccg 240
ctgctagagc cactgcgatc ggtgccgatc gtggggaacc cactggcgaa cctggttcaa 300
ccaaacttga aggtgattgt taacctgg 328

<210> SEQ ID NO 534
<211> LENGTH: 75
<212> TYPE: DNA
<213> ORGANISM: Mycobacterium tuberculosis

<400> SEQUENCE: 534
gcagaccaac aagatgcatc gggatcatac gccgtcaact acccggccaa cggtgatttc 60
ttggccgccg cccac 75

<210> SEQ ID NO 535
<211> LENGTH: 319
<212> TYPE: DNA
<213> ORGANISM: Mycobacterium tuberculosis
<220> FEATURE:
<221> NAME/KEY: unsure -continued
<222> LOCATION: (various positions within the sequence)
<223> OTHER INFORMATION: applicants are uncertain of bases designated as "n"

<400> SEQUENCE: 535
ctcaagcttg ccaaagagac ctcgtccacc aagcnggacg cgaccgtcna ggtggcgatc 60
cggcttggcg tccacccgcg taaggcanac canatggttc gcggcacggt caacctgcca 120
cacggcactg gtaanactgc ccgcgtcgcg gtattcgcgg ttggtgaaaa ggccgatgct 180
gccgttgccg cgggggcgga tgttgtcggg agtgacaatc tgatcganag gattcagggc 240
ggctggctgg aattcgatgc cgcgatcgcg acaccggatc agatggccaa agtcggtcnc 300
atcgctcggg tgctgggtc 319

<210> SEQ ID NO 536
<211> LENGTH: 312
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 536
ccacggcgtg gatcaaggta ccggccggga tgttgcgcaa tggcaggttg ttgcccggct 60
tgatgtcggc gttagcgccg gattccacca catccccttg cgaaagtccg ttgggtgcaa 120
tgatgtagcg cttctcccca tcgagatagt ggagcaacgc aatccgtgcg gtacggttcg 180
ggtcntactc gatgtgcgcg accttggcgt tgacaccatc tttgtcattg cggcgaaagt 240
cgatcatccg gtaagcgcgc ttatgaccgc cgcctttgtg ccgggtggta atccggccat 300
gcgcgttgcg tc 312

<210> SEQ ID NO 537
<211> LENGTH: 105
<212> TYPE: DNA
<213> ORGANISM: Mycobacterium tuberculosis

<400> SEQUENCE: 537
ggcggctgcg tcggcgagat gatcgcccgg tgccaccccg atccgtgcct cggtcagcgc 60
caacgtgctt tccggtccgg cgaccaccat gtcgcatgcg ccgac 105

<210> SEQ ID NO 538
<211> LENGTH: 144
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 538
gcaatcgcct tggcggtcgc cgggttgtca ccggtgatca tcncggngcg gatgctcatn 60
cggcgcattt cgtcnaatcg ttcccgtatg cccaccttga cgatgtcctt catatggacc 120
acgccgatgg cccncgcgct nctg 144

<210> SEQ ID NO 539
<211> LENGTH: 431
<212> TYPE: DNA
<213> ORGANISM: Mycobacterium tuberculosis -continued

<400> SEQUENCE: 539
ccggctcgta tgttgtgtgg aattgtgagc ggataacaat ttcacacagg aaacagctat 60
gaccatgatt acgccaagct atttaggtga cactatagaa tactcaagct tccacatcgg 120
tatgccaaag cattgcgccg ctatcgattt cgcgctggca tcgccaaggt ggacttcttg 180
ctcagcgacg agatcccgtg gtcggatccg cggctgcggc gggctgcgac cctgcatctc 240
ggcggcaccc gtgaccagat ggcgcgcgcc gaggcagacg tcgcggcggg acgccacgcc 300
gactggccga tggtgctggc cgcgtgtccg cacgtcgccg accccggccg catcgacgaa 360
accggccgcc gtccgttctg gacctatgcc cacgtgccgt cggggtccac gctcgacgcg 420
accgagaccg t 431

<210> SEQ ID NO 540
<211> LENGTH: 462
<212> TYPE: DNA
<213> ORGANISM: Mycobacterium tuberculosis

<400> SEQUENCE: 540
cgcgtccacc gcagcgtgag attggtggcg ccattcgtcg tggtgtagct gctgttggcg 60
gcgtcgccgt attgtgcggg ccagccttgt gcgggggccg cttctaccca cgagtcggca 120
cttccgcaac cgcccagctc gaccgcgatt acggcggccg caacggccgc cggaaggcgt 180
ctcgcaagcg ccttatcctt tcgcaggttc ccagatcctt ccgctacgtg ggtcgctcat 240
cggcgggccc ggccgaatga gtacaggtga gggtaaccgc tacaaatgaa gttggtcagt 300
gctggccaac tgtgtaatgg ttgcccggct cgggtcacca cgtacattct ggcaaggcgg 360
gcgagattcg gttcctcgcg tccttggccg gtggcggttc ccggttgtcc gtgggcgtgt 420
cgtgtacgtg gtgtaagtgt cgtgaactcc tcagtttggg ct 462

<210> SEQ ID NO 541
<211> LENGTH: 307
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 541
ctcaagcttg cgctggatct ggcggctgag cctgttcttg ggcaacatgc cgagggatcg 60
ccttttccac cacgcggtcg gggtggcgtt gcattagctc accgatggtg cgcttgtgca 120
ggccgccggg ataccccgag tgccggtaaa ccatcttgtg ctgcagtttg tcgccgctga 180
tggcgacctt gtcggcgttg atcacnatga cnaagtcacc gccatcgaca ttgggggcga 240
acgtcggctt gtgcttgccg cgcagcaggt tggccgccgc gacggcaagg cggccaanca 300
ccacgtc 307

<210> SEQ ID NO 542
<211> LENGTH: 333
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

-continued

<400> SEQUENCE: 542
tttgggatgg gcaaaaaggc gaagcnccgc gtggccacga acgccgggag ggacaatctc 60
gggcggctag ggcttctcgc gggaaggccc gaacgtacgg cgtttcaaca cgtcgcgtcg 120
ccctccgacc gcgaacattc ggggatggca gcaacctggt agcaccctgg ccgggcgatg 180
atctgcagcg tcgccgcggg tagtcgccgc ccgggcggct acagtctgaa acgcgatgac 240
catcgatgtg tggatgcagc atccgacgca acggttccta cacggcgata tgttcgcctc 300
gctgcgccgg tggaccggtg ggtctatccc gga 333

<210> SEQ ID NO 543
<211> LENGTH: 234
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 543
ctcaagcttc gtcataagac catggtgcgc tttctttcac ccgtccanag tcgggggcat 60
ccgcaccggc tcgcatcgca tcatcctccc acgacgggcc gctcatcagc ttgggccatt 120
tcaatgtact tgataccccg cgctgcgggt aggccactgc nacaattcaa acacggtgtc 180
acacggtgaa tantgtcnan atgggctctg atcaaccgtc ncaaacccgg tttc 234

<210> SEQ ID NO 544
<211> LENGTH: 440
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 544
gaattctgcg tgcaccgcta tgggttgcag cagcggctgg cgccgcacac cccactggcc 60
cgggtgtttt cgcccccgaac ccggatcatg gtgagcgaaa aggagattcg cctgttcgat 120
gctgggattc gccaccgcga ggccatcgac cgattactcg ccaccggggt gcgagaggtg 180
ccgcagtccc gctccgtcga cgtctccgac gatccatccg gcttccgccg tcgggtggcg 240
gtagccgtcg atgaaatcgc tgccggccgc taccacaagg tgattctgtc ccgttgtgtc 300
gaagtgcctt tcgcgatcga ctttccgttg acctaccggc tggggcgtct gcacaacacc 360
ccggtgaggt cgtttttgtt gcagttgggc ggaatccgtg ctctgggtta cagccccgaa 420
ctcgtcncgg cggtgcgcgc 440

<210> SEQ ID NO 545
<211> LENGTH: 425
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 545
gcagttggga atcgctctgc agcaaaccan tattctgcgc gacgttcgag aggactnttt 60

-continued

```
gaatggacgg atctacctgc cgcgcgacga gctggaccga ttaggcgtac ncctccgcct    120

ggacgactcc ggggcactcg atgaccccga cggacggctc gcggcactgc tgcggttcan    180

tgccnaccgc gccgcanact ggtattcgct gggactgcgg ctgattccac acctcgaccg    240

ccgcagcgct gcctgctgtg cggccatgtc tggcatctac cgccgtcngc tcgccttgat    300

cagaccatcg ccggcggtcg tctaccatcg gcgaatctct ctgttcggga ctgaanaang    360

cccaagtggc ggcggcagca ctggnctctt cggtaacctg cngaccgccc attggaccgc    420

taccg                                                                425
```

<210> SEQ ID NO 546
<211> LENGTH: 401
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 546

```
ttgatctgga cgtctgagac ggtgatcggn ccgaacctga attgtccggt aatgcccagc     60

gcagaaagca nggtggtggc cggggcggtg aanccggcgt cggcggcacc gtcgaagtcg    120

atgtggattg ccggaatggg gatgtccggc acggcgaagc cgtagttcgc ttgtcccgtg    180

aggcccangt ggatgggggg aaggatcgtg gtgtccggga tgataatggg gccgatgccg    240

ccggttgaag tccagtggat cgggaattcg ggaatcgtga tgccgacgtt caggccgaac    300

aggccctcca agttgcctcg ccacnagatg ccgttgctga agttgcccga catgagggcg    360

ccggtgtcca cattgcccga attggcgacg ccggtgttgg c                        401
```

<210> SEQ ID NO 547
<211> LENGTH: 391
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 547

```
cacgtaggcg ccgtccataa atnactccgc cgcgcttcgc acatcctcgt ancgatcctt     60

ggcgagcagg tcaaccgggc gctgcccgtc naggagccgg tttttggcgt gcagccactg    120

gccgacacct cggggggtaa gcgaatccga gagcaggagg acnaggtcac gaanctgcgc    180

cagccggtcg taccgctcag ggcggatgtc gccggtccgc cacccgcgta ccgcccgatc    240

ggacacctgt atgaccgcgg cgacntcgac ctgggtgacg ccgaagggtt tcagggcatc    300

nacnatctcg ctggcctcga ccgcccggtc cagggtgacc gccatcgtgg ttcctccgca    360

acttccggtt ctactaccgt aaacgctacc g                                   391
```

<210> SEQ ID NO 548
<211> LENGTH: 369
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

-continued

<400> SEQUENCE: 548
cggggaacgg tcctcgcaca cctggttcgt gttgcgggaa ttactcggac ancaaaacgt 60
caagaactac gacggcagtn ggacagaana cggctccctg gtgggcgccc cgatcgagtt 120
gggaagctga tatgtgctct ggacccaagc aaggactgac attgccggcc agcgtcgacc 180
tggaaaaaga aacggtgatc accggccgcg tagtggacgg tgacggccag gccgtgggcg 240
gcgcgtttcg tgcggctgct gggacncctc cgacgagttc accgccggga ggtcgtcgcg 300
tcggccaccg ggcgaatttc cggttcttcg ccgcgccccg ggatcctggg accgcnggcg 360
cgcgctgtt 369

<210> SEQ ID NO 549
<211> LENGTH: 85
<212> TYPE: DNA
<213> ORGANISM: Mycobacterium tuberculosis

<400> SEQUENCE: 549
ctcaagcttt gtccgacaag cgttcccggg cggtcagcaa gcgaacgtcg gttggcccac 60
tgcgggtcga tattgccgcc aggga 85

<210> SEQ ID NO 550
<211> LENGTH: 101
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 550
cgtcagcacg gcgacgtcgc gntacgccga gcagttacac aatcgctctg cagcaaacca 60
atattctgcg cgacgttcga gaggacttct tgattggact g 101

<210> SEQ ID NO 551
<211> LENGTH: 458
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 551
ctgcatccgg ctcgtatgtt gtgtggaatt gtgagcggat aacaatttca cacaggaaac 60
agctatgacc atgattacgc caagctattt aggtgacact atagaatact caagcttcgc 120
gcagcggcgg gttgacccgg ttcacgccgt catagctggc caatctggca tcgtcgatca 180
ncatgtggtg gggggtgacc tcggcggtga tcgaaatacc ctggtcctta tcccatttca 240
ggatttcgac ggtgcccgcg gccgacgcgt gacagatgtg cacccgggcg ccggcgtcac 300
gggccagcaa ggcgtcgcgg gcgacgatcg attcctcggc ggcccgcggc catcccgcca 360
ggcccagccg cgccgccatg ggtccctcgt gcgcgacggc gccgaccgtc agccggggct 420
cctcggcgtg ctgggcgatc agcacgccca aaccggtg 458

<210> SEQ ID NO 552
<211> LENGTH: 463
<212> TYPE: DNA
<213> ORGANISM: Mycobacterium tuberculosis -continued

<400> SEQUENCE: 552
ccgacgcgca ctacgtgctg gtgtccaccc gcgacccgca ccggcacgag ctacgcagct 60
accgcatcgt cgatggcgct gtcaccgagg aacctgtcaa tgtcgtcgag cagtactgaa 120
ccgttccgag aaaggccagc atgaacgtca ccgtatccat tccgaccatc ctgcggcccc 180
acaccggcgg ccagaagagt gtctcggcca gcggcgatac cttgggtgcc gtcatcagcg 240
acctggaggc cagctattcg ggcatttccg agcgcctgat ggacccgtct tccccaggta 300
agttgcaccg cttcgtgaac atctacgtca acgacgaaga cgtgcggttc tccggcggct 360
tggccaccgc gatcgctgac ggtgactcgg tcaccatcct ccccgccgtg gccggtgggt 420
gagcggacac atgacacgat acgactcact gttgcatgcc ttg 463

<210> SEQ ID NO 553
<211> LENGTH: 453
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 553 gcttccggc tcgtatgttg tgtggaattg tgagcggata acaatttcac acaggaaaca 60
gctatgacca tgattacgcc aagctattta ggtgacacta tagaatactc aagcttgccg 120
ggagggtgca tggccgactc ggatttaccc accaaggggc gccaacgcgg tgtccgcgcc 180
gtcgagctga acgttgctgc ccgcctggag aacctggcgc tgctgcgcac cctggtcggc 240
gccatcggca ccttcgagga cctggatttc gacgccgtgg ccgacctgag gttggcggtg 300
gacgangtgt gcacccggtt gattcgctcg gccttgccgg atgccaccct gcgcctggtg 360
gtcgatccgc gaaaagacga agttgtggtg gaggcttctg ctgcctgcga cacccacgac 420
gtggtggcac gggcagcttt agctggcatt cct 453

<210> SEQ ID NO 554
<211> LENGTH: 466
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 554
ggaaacaccg ncgccgtcgt ggccaccaac accgcgacca gcaccgtgac ccggaccggg 60
gtgccgcgcg aaccggtctt ggccaattgc cgcggcacca agccgtcgcg cgccatggcg 120
aacagcacgc ggcattgccc gagcatcaac accatcacca ccgtggtaag cccggccagc 180
gcgccgacgg agatgatgcc gctggcccag tacaccccgt tggcctggaa cgcggtggcc 240
agatttgccg gcccgcggcc cggtacggtc cgcagttggg tgtatggaac catgcccgac 300
agcaccaccg ataccgcgac gtagagaagg gtcacgaccc ccagcgacgc gagaatccct 360
cgagggacgt ctcgttgagg acgcttggtc tcctcggcca tggtggccac gatgtcaaac 420
ccgataaacg cgaagaacac gatcgatgcc cggccagcac gccgta 466

<210> SEQ ID NO 555

-continued

<211> LENGTH: 466
<212> TYPE: DNA
<213> ORGANISM: Mycobacterium tuberculosis

<400> SEQUENCE: 555
cctgcttccg gctcgtatgt tgtgtggaat tgtgagcgga taacaatttc acacaggaaa 60
cagctatgac catgattacg ccaagctatt taggtgacac tatagaatac tcaagcttgt 120
cctcgggcgt ggcctcggcc aagaaatcgt cgacgccggc ctcctgtgca atcgccttgg 180
cggtcgccgg gttgtcaccg gtgatcatca cggtgcggat gctcattcgg cgcatttcgt 240
cgaagcgttc ccgtatgccc accttgacga tgtccttcag atggacgacg ccgatggccc 300
gcgcgctgct gttatcggtc cattccgcaa cgactagggg tgtccccccg ccggagctga 360
tgccgtcgac aatggcaccc acctcctcag tggggtggcc accgtgatcg caaaaccact 420
tcatcaccgc agccgcggca ccttgcggat ccgaacggat gcgctc 466

<210> SEQ ID NO 556
<211> LENGTH: 467
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 556
ttcgttcgat ggcgccgccc cggctacggt ttgacctgtg ggtgtcgaat tggggtcaaa 60
ttccgaggtc ggcgcgctaa gagtggtcat cctgcaccgc ccgggggccg aactgcgccg 120
gctcacaccg cgcaacaccg accagctgct gttcgacggc ctgccctggg tatcccgcgc 180
gcatgacgag cacgacgaat tcgccgagct gctggcttcc cgcggtgcgg aagtgctgtt 240
gctgtcggac ctgttgactg aggcactaca tcacagcggg gccgcccgca tgcaggggat 300
cgccgctgcc gtcgacgcac cgcggctggg actgccgctg gcgcaagaac tttcggccta 360
cctgcgtatc tcgacccaag cangttggcg catgtgctga cgccggcatg acttcaacga 420
actcccntcc gacacgccga acgaagtgtc gttggtgttg cgtatgc 467

<210> SEQ ID NO 557
<211> LENGTH: 142
<212> TYPE: DNA
<213> ORGANISM: Mycobacterium tuberculosis

<400> SEQUENCE: 557
gcggcgagtg tggtgggtgc cgaacacgaa tccaacgacg cactggcgga gagataccac 60
ttgctgtact ggaagcacgt gctgatgatc tcccgtggaa tgtgcctcgc cgccgtctat 120
cgaaaacagt gagcatgctg cg 142

<210> SEQ ID NO 558
<211> LENGTH: 217
<212> TYPE: DNA
<213> ORGANISM: Mycobacterium tuberculosis

<400> SEQUENCE: 558
caaccgcgct cggcgcgtct gggccttccg ccggctccgc cgacaattct atctctggat 60
cagcggggct ctccgggccg gcctccgcga actcaacagg ccgcgccttc cggccgaaac 120
attccctagc catatatgat cgcacctcga tacacgatct ggcggcaaca ccgcaaagcg 180

-continued

```
tccgacgggc ccaacctccg caattcaggt atccggg                          217


<210> SEQ ID NO 559
<211> LENGTH: 147
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as “n”

<400> SEQUENCE: 559

gaaggtcggc gaaggtgtgg ctggntgccg atcacgaatc caatgatgca gtggtcggaa     60

gatattagcc acttgctgtt ctggagacag gtgctgatga tctcccgtgg aatgtccctc    120

gactccgtct atcgaaatct gtgaaca                                        147


<210> SEQ ID NO 560
<211> LENGTH: 177
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as “n”

<400> SEQUENCE: 560

tcctgcgctc tgggccattc tcgggtctgc cgacaattct atctctggat ctgtggggct     60

ctcttggccg gcctcngcga tctcttcang gcgcgccttc cggccgaaac attccctatc    120

catatatgat cgcacctcta tacaccgttt ggcggcaaca ccgcaaagtg tctgtcg       177


<210> SEQ ID NO 561
<211> LENGTH: 128
<212> TYPE: DNA
<213> ORGANISM: Mycobacterium tuberculosis

<400> SEQUENCE: 561

agctttacgc tggcgtatca gcgttggggc cgctgccatt tcggtcgccc aacgcgttgc     60

cagctccctg cgctgtcagg gcttgcgcgc caaactggcc accgcaacaa acttggctga    120

gcttgatc                                                             128


<210> SEQ ID NO 562
<211> LENGTH: 142
<212> TYPE: DNA
<213> ORGANISM: Mycobacterium tuberculosis

<400> SEQUENCE: 562

ctctatctgg cgtcacattc gcaatcttta gattgcagat atcgataaaa tcacccgcgc     60

gacaagaccg ccatgtcatc ctttcgatgt tatttcgccg gcctggggaa agcgcaacga    120

cgttgcctac acgttccgcc gt                                             142


<210> SEQ ID NO 563
<211> LENGTH: 406
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as “n”
```

-continued

<400> SEQUENCE: 563
agctttncct tgcatctgca ccccgatcca cgtcagccac gtcggcgttc tccaccaaga 60
agttgcgggc attctccttg ccctggccga gctgctcgcc ctcgtaggtg aaccaggcac 120
ccgacttgcg gatgaggccc tgatccacac ccatgtcgat cagcgagccc tccctgctga 180
ttcccttgcc gtagaggatg tcgaactcgg cctgcttgaa ggggggcgaa cagttgtgca 240
cgacaacccc ttcggcgacg agggtgtgca gttcctcgac ctcgaggtcg aacgttcgtg 300
cccgccgcgt tggcagcact tctcggatca cggaatagcg ganttcttcc gccagcatgt 360
cgtgcaggaa tttgtcatcc agggcatccg cgagcgcctg cacgcg 406

<210> SEQ ID NO 564
<211> LENGTH: 311
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 564
actgtcnagg gaatgcttcg cagcatctac ctgcagtcgc ttgtgcataa gcggacggcc 60
cnacctgttc gtgttccggg acaccagacg cgggagcacc ggcagtacgg cgaaaggttt 120
gagcggaagg agttgcgcaa atcggggcgc cccaacaccc gtccgcaaga cgcggtcaac 180
gacctgtttc aggcgatcag ggtcaccgac tcacctgcac tgagaacaag cgatctgctg 240
atctgccaga agatggacat gaatgtccac ggcaagcctg atggcctgcc gctcttccgg 300
gaatgtttgg c 311

<210> SEQ ID NO 565
<211> LENGTH: 310
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 565
tgaattatga tcccgacaca actgcatcan tttagccgcg tcgngatgct atccgccgac 60
ggtttgganc nggtccgtgt cgttcgtgtt gatctcaccc gaagttgtgt ccgccgccgc 120
cggggatcta gcgaacgtgg gatcgacaat cagcgccgcc aacaaggcgg cagcggctgc 180
gaccacgcag gtgctggccg cgggcgccga tnaggtgtca gcgcgcatcg cggcgctgtt 240
tggtatgtac ggcctgnaat atccggcgat cagtgcgcaa gttgccgcgt atcaccanca 300
gtccgtgcag 310

<210> SEQ ID NO 566
<211> LENGTH: 326
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 566

-continued

```
aacggggacc ncaagaaacc attcaanaac gaggggtcgt caccaacgtc gaaaccgacg     60

gttgccagcc ggcccacgat attgcgtgct cgagggtccg ctgtaccctc accgaacgtg    120

agtcccacac cgcggaggcg ggcgactctg gcgtcgttag cagccgagct caaggtgtcc    180

cgcaccactg tctcgaatgc ttttaaccga ccggatcagc tctccgccga tctacgtgaa    240

cgagtgcttg ccacggccaa gcgactgggc tatgccggac cggatccggt ggcgcgatcg    300

ttgcggaccc gcaaagccgg tgcggt                                         326
```

```
<210> SEQ ID NO 567
<211> LENGTH: 374
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 567

agctttggag ccncnccgan ccnccggtac gccccgccac cgccgtaccc ggcacccgac     60

ccctttgagc cgttcgccgt ggccgcggtg ganctggccg acgagggact gatcgtgctg    120

ggcaaagtgg tcgatggcac gctggccgcc gatctgaagg tcggcatgga gatggagctg    180

acgaccatgc cgctgttcgc cgacnacgac ggtgtgcagc gcatcgtcta cgcgtggcgg    240

atcccatcgc gcgccggcga cnatgcanag cgcancgatg ctgaggagcg gcgccgatga    300

ggatgagcgc gccggaaccc gtttacntcc tgggtgccgg tatgcacccg tgggggaaat    360

ggggtaatga cttc                                                      374
```

```
<210> SEQ ID NO 568
<211> LENGTH: 422
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 568

ttctcncatc gttcgtactn ngatgggacg ctgctgcccg aggcgatcct ggccaaccgg     60

ctctcgccgg cgctgacctt cggcggggcg aacctgaact tctttccgat gggcgcttgg    120

gccaaacgta ccggggctat cttcattcgg cgtcagacga aagatattcc cgtctaccgc    180

ttcgtattac gtgcttacgc cgcgcagctg gtgcaaaacc atgtcaacct cacctggtcg    240

atcgaagggg gtcggaccag aacgggcaag ctacggccac cggtgttcgg gatcctgcgt    300

tacatcaccg atgcggtcga cgaaatcgac ggtcccgaag tgtatttggt gccgacctcg    360

atcgtgtacg aacagctgca cgaagtggaa gccatgacca ccgaagccta tggcgccgtg    420

aa                                                                   422
```

```
<210> SEQ ID NO 569
<211> LENGTH: 300
<212> TYPE: DNA
<213> ORGANISM: Mycobacterium tuberculosis

<400> SEQUENCE: 569

ttcttccggg taccgctgat cggcggcacc atcacgcacc cggtgcaggg cgaggcggcc     60

gccggtgtgg tgttgctacg gccggccagc ccgggtaccg gtgtgatcgc cggtggtgcg    120
```

-continued gcccgcgcgg tgctggaatg tgcgggggtg cacgacatct tggccaagtc gctgggcagt 180
gacaacgcga tcaatgtggt gcacgccacc gtggccgcgc tcaagctgct gcaccgtccg 240
gaggaggtgg cggcgcgccg cggtttgcca atagaagacg tccccccggc cgggatgctg 300

<210> SEQ ID NO 570
<211> LENGTH: 343
<212> TYPE: DNA
<213> ORGANISM: Mycobacterium tuberculosis

<400> SEQUENCE: 570
gtcgaaagtg accatctcta ccttgagtgc cataccgccc gaccctatgc ctcggatagc 60
tcggcggaaa gaaacgcttg cagtgccgcc gaataggcgg ctacgtcgtg agcgcccatc 120
aactctcgcg cggagtgcat cgccagctgg gcggcgccga cgtcgaccgt ggggattccg 180
gtgcgcgccg cggccaacgg cccgatcgtc gacccgcacg gcagatcggc gcgatgttcg 240
taacgctgca taggcactcc cgcgcgctgg caggccagtt gcgaaacgcc cccgccgggt 300
gccttccgtc ggttggcttt accgcaaatt tggggttgcc cct 343

<210> SEQ ID NO 571
<211> LENGTH: 220
<212> TYPE: DNA
<213> ORGANISM: Mycobacterium tuberculosis

<400> SEQUENCE: 571
aaagccacgg aaacgattgc ctactgccga atcggggaac ggtcctcgca cacctggttc 60
gtgttgcggg aattactcgg acaccaaaac gtcaagaact acgacggcag ttggacagaa 120
tacggctccc tggtgggcgc cccgatcgag ttgggaaact gatatgtgct ctggacccaa 180
gcaaggactg acattgccgg ccagcgtcta cctggaaaaa 220

<210> SEQ ID NO 572
<211> LENGTH: 254
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as “n”

<400> SEQUENCE: 572
tttcgccacc gcnaggtcgt gcgcgttcca gaaaagcgtg gtttcgccgg gcgcgaggat 60
tcgacggtcc aactgaccag ccggtcccgc cacccgttag gcaggatcgc ggtgtctata 120
tgttcgccct cggcataaac gccattgctg cggtgaaaat cggacatctc gccgattgcc 180
acgtctacat gatccgcttt gtcccgcgcc gggtcgttga caaacgcgat gtcngcctcc 240
tgggaagcgg tggc 254

<210> SEQ ID NO 573
<211> LENGTH: 329
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as “n”

<400> SEQUENCE: 573

-continued

```
tcgccaagtg gattcgtgct caccnacgag atccgtggtc ggatccgcng ctgcggcggg      60

ctgcgaccct gcatctcggc ggcacccgtg accaaatggc gcgcgccgaa gcagacgtct     120

cggcgggacg ccacgccgac tggccgatgg tgctggccgc gtgtccgcnc gtcnccgacc     180

ccggccgcat cnaccaaacc ggccgccgtc cgttctggac ctatcccacg tgccntcggg     240

gtccacgctc gacgcgaccg anaacgtaac cagcgtcctc gancggttcg cccccggctt     300

ccgtgacatc gtggtggcgg ccgcgccgt                                        329
```

<210> SEQ ID NO 574
<211> LENGTH: 297
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 574

```
gtaccgtcac catgatcgcc cccatcggca tcggtgagct gatagatccc agccggtttc      60

gccaaccccg gagcgatctt ggcgcgctgc tngtngtcnc tganacntag ccaccaacag     120

agcccggtgt gcgacaagan gactgatcgg atctctccgg acacntcgag ggggtcntca     180

ggagnccggg cgccaccccg aggtaagcct ccgcccagcc tcacaccgcg accgggtatc     240

ncaagtcgcg caataanccc accacctcct cggaccccac gttgtatgcg gctgggt       297
```

<210> SEQ ID NO 575
<211> LENGTH: 401
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 575

```
atactcaagc ttagacctca ctgatgtggc gggacgcggg agataaccgc ggttcgagcc      60

gttcaacagt ggtggttccc acaccagttg tttgcctttg cgaagtaaag cgattcgatt     120

tgctcgaaaa gagggctggc tgctcgtgag ggacatccat ggccgatacc tcagcgatct     180

caacggtcaa gcgactgcat gtttggcgca aggtatcgct aagcataggt tcgtgacgga     240

tttgacagca agagctttcc aaagattgct gtccacatan tgattcgcat ctctacacct     300

cttcgccggt gctgtcaaga gccattcgaa tcagttatct cgctcgtgct tggaanaaat     360

tttcccagcc tgcgttggac aaaccgcgtc gccaaagcgg t                         401
```

<210> SEQ ID NO 576
<211> LENGTH: 453
<212> TYPE: DNA
<213> ORGANISM: Mycobacterium tuberculosis

<400> SEQUENCE: 576

```
agcttcccga gaaacagtgc attccctaag cagcccgttg tcacgccgat gagtgaagag      60

tgcacgcaat cgccggaatc cggcaaagcc ctgcacaagc gaaatcaacc cggaggctga     120

caaggcaacg tcggtgatcc gtaccgcctg gttggacaaa cggcagaagg cggcctcgtc     180

cggtccatct acgccgagca cactggtgat agcgcgcatc ggcatcggtg cggccacggt     240

ggagacgacg tccgcgggcg tctgggtcag taacccgccg accagttctc gggcaagctg     300
```

-continued

```
gtcgaccatc gggcgccacg tctccaacgc gccacgcgcc atacctggtg ccagttgctt    360

gcgcatccgg gtgtgcgccg gcggatcgga cgtcgcagaa acgcagccac cccgtgagaa    420

gtgacccacg gcgctggaca cgtgtctggt tac                                 453
```

<210> SEQ ID NO 577
<211> LENGTH: 474
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 577

```
cggccgggat gtgcgcaatg gcaggttgtc gcccggcttg atgtcggcgt tagcgccgga     60

ttccaccaca tccccttgcg aaagtccgtt gggtgcaatg atgtancgct tctccccatc    120

gagatagtgg agcaacgcaa tccgtgcggt acggttcggg tcgtactcga tgtgcgcgac    180

cttggcgttg acaccatctt tgtcatggcg gcgaaagtcg atcatccggt aagcgcgctt    240

atgaccgccg cctttgtgcc nggtggtaat ccggccatgc gcgttgcgtc caccgcgacc    300

gtgcagcggg cgcaccagcg acntctccgg ggttgaccgg gtgatctcgg cgaaatcaga    360

tacgctggcg ccgcgacgac caggcgtcgt gggcttgtac ttgcgaattg ccatggtcta    420

atcaggtctt tctctcacct ctcgtcgccg ggctagggcg cattgcctgc tcct          474
```

<210> SEQ ID NO 578
<211> LENGTH: 357
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 578

```
tagcggtgta accaactccc gggtcaccac ccgcaaacct cttgcggcaa cagcaccgtc     60

gacgcgtcaa ccgggctgcc cggaatcctg tggatgggca tcgagtgcat ggtcacgacg    120

tccccgacgc ggccggtggc aacgacaagt ggcccggatg caccacaaat gacggccgca    180

caccggtggg gacggccagc acgagagccg tgtcgccgaa gtcgacgcta atgccgtagg    240

cattggccgt cacaacaggc gacgccccgc gtaccaccga gtccacggng gttgggcggt    300

ctcctcggcc aaccaggcgt gaacccggcg gatccgaatg cagcaagacc cgtgggc       357
```

<210> SEQ ID NO 579
<211> LENGTH: 269
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 579

```
ccattggtcg gtgtgcgcat accantacna cgcgccgggc acctgacgcg gcggccgcaa     60

ccattcggtg gccatcgcca tcgtctgcca cccggtcaac ggacgcacct tctcctggcc    120

gacctagtgc gcccacccgc cgccgttgcg tcccatcgat ccggtcaaca tgagcagcgc    180
```

-continued caacaccgag cggtacatga catctgctgt ggaaccagtg acanattccg ccgcccatga 240
tgatcntcga ccgtcctccg gattcggtc 269

<210> SEQ ID NO 580
<211> LENGTH: 272
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 580
gccggcctgg tcaaaggggc gtccgaagga nccgggctgg gtaacaagtt cctggctcat 60
atccgcgaat gcgacgccat ttgtcaggtg gtgcgggtgt tcgtcgacga cnacgtgact 120
catgtcaccg gacgggtcga tccccagtcc gacattgagg tcgtcgagac cgagctgatc 180
ctggcagatc tgcaaaccct ggagcgggcc acgggccggc tggagaanga agcncgcacc 240
aacaaggcgc gcaagccggt ctacgacccg gc 272

<210> SEQ ID NO 581
<211> LENGTH: 373
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 581
gatccactga ccacgatgac atatcgaaat gctcgacgat tccgatggcg atcaaggcca 60
cgatgccctg gccgttgggc ggtatctggt ggatggtgta cccgcggtag gttcccgtga 120
tcgtgtcgac ccagtccacg cgatgggcgg cgaggtcgtc ggcacgcatc accccgccgt 180
ntgccgccga gtgcgcctcg agtttggcgg ccagctctcc ccggtagaac tctcaccgtt 240
ggtcgccgcg atcttctcta ncgtcgccgc gtggtcagga aaggtaaaca gctcaccggg 300
tttcggcgct cgtccgccgg gcatgaacgc atctgcgaat ccgggctggg atgcgaacaa 360
cggacctgtg ccg 373

<210> SEQ ID NO 582
<211> LENGTH: 314
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 582
tctactgccg aatcggggaa cggtcctcgc ccaccnggtt cgtgttgccg gaattactca 60
ggacaccgaa acgtcgagaa ctacgagcgg agttggacan aataccgctc ccnggtgggc 120
gcccccatcg anttgggaag cngaaatgtg ctctggaccc cacccaagaa tgacattgcc 180
ggccgccctc caactggaaa tagaaacngt gatcacccgc cgcgttcttg gaaggaatgg 240
catgccctgg gccgggcgtt ccttccgctg ccggactcct cccaccaatt caccgccgaa 300
ggcgtcccgt ctgc 314

<210> SEQ ID NO 583
<211> LENGTH: 135
<212> TYPE: DNA
<213> ORGANISM: Mycobacterium tuberculosis

<400> SEQUENCE: 583
atactcaagc ttctgtcacc gaaatcccgc atgggataac gggtttagat ttcgacaacg 60
ggaccgtgtt tctcaacaag ccggtcatca gctgggccgg cgacaacggt atctacttca 120
cccgctttcg cccgt 135

<210> SEQ ID NO 584
<211> LENGTH: 221
<212> TYPE: DNA
<213> ORGANISM: Mycobacterium tuberculosis

<400> SEQUENCE: 584
ctggctcaag cgctcggcgc gcaggtgaac tcggaccggc tcgacgtcgc cgaacgcgag 60
gcggtgctgg cccacgccga cgccgtcgtc gcacatatcg gcaccgtgca caagtctaca 120
acaacgccgg catcgcgtac aacggcaacg tcgacaagtc ggagttcaag gacatcgagc 180
gcatcatcga cgtcgacttc tggggcgtcc tccacgggcc c 221

<210> SEQ ID NO 585
<211> LENGTH: 70
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 585
ccgccctccg cattatgggt caagaaccat cgggtcggac ttctgggctt ccaacgctcg 60 cgccgtcccn 70

<210> SEQ ID NO 586
<211> LENGTH: 241
<212> TYPE: DNA
<213> ORGANISM: Mycobacterium tuberculosis

<400> SEQUENCE: 586
ccgtggcact gtcagacata tgcgccgctc ctcctcatcg ctgcgctcgg catcgtcgcc 60
ggcggtcatg gcgtcaccct acccaagccg aacgcgaaac gagaacgtgt tccattatta 120
gggtgtgagc accaatacca gattgctcac caggaactca cgcagcaccg ggacggatgt 180
cggccaccac gcccatctgg ggtggtagcg gggaaatacc gctaacgcgg ctccggtgcc 240
g 241

<210> SEQ ID NO 587
<211> LENGTH: 492
<212> TYPE: DNA
<213> ORGANISM: Mycobacterium tuberculosis

<400> SEQUENCE: 587
tactcaagct tgtccaaata tcgaagcgtc gggtcgcgag gctcggtcgg cagctccagc 60
aaaacccgct ccacccctag atgccggtat ccctcaaggt ctttatccgc cgcttcaccc 120
cactggcaca cggtcaccgg cacgtcgccc ccggccatgg cgcgcaaccg ctgaagcgga 180

-continued

```
cccgacagcc gctgcggtga tggactgatc gcgatccacc cggcattgag ccgggctatc    240

cgcgggaagt tcgccggtcc cccgcccaca tacagcggag gatagggctt tgtcaccggc    300

ttcggccagc agtagatcgg atcgaagtcc acatatgtcc catggaattc cgcctgctcc    360

tgcgttcaga tctcgattat cgcgcgcaac cgctcatcga tcacacgtcc gcgcaccgca    420

gggtccacac catggttggc gacttcttcg cgcaaccagc cacacccacg ccgaaacgaa    480

accgtccctg cg                                                        492


<210> SEQ ID NO 588
<211> LENGTH: 313
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 588

caggcatgca agcttggcca actcctcatc ggacttgaag gtgccgtcct cgttggcggc     60

cctgctccac ggcacgttga tggcaccagg aatgtgtccg ggccgctggc tttgttcctg    120

cggcaggtgc gcgggggcca ggatcttgcc ggagaactcg tcgggagagc gcacgtcgat    180

gaggttcttg acgttgatgg ccgccaggac ctcgtcgcgg aatgcccgaa tcgtgttatc    240

cggcggggan gcggtgtagg aagtcaccgg ccggctgacc gggtcgctgg acagcgggcg    300

tccgtcgagc tcc                                                       313


<210> SEQ ID NO 589
<211> LENGTH: 305
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 589

atactcaagc ttcaaaacag gcctgttgtg ggcgcacccg gctcgccgag ttctgcacgc     60

accgcctcaa gtgcggcccg caccgccggc atctcccggt cacgcagggc cgcggcccgc    120

gccgcagcga cggcgtgttc gcgcagttcg ccgtcaatga tgctgacctg atcggccacc    180

cgggcggtct cggcgtcgtc ccgttcacta atcgcggtgc tcagcagcgt ctcgacagcc    240

accacccgag tggagaccag atgcnccacc acggaccgca gcgatgccag tcacctcacc    300

cgtcc                                                                305


<210> SEQ ID NO 590
<211> LENGTH: 394
<212> TYPE: DNA
<213> ORGANISM: Mycobacterium tuberculosis

<400> SEQUENCE: 590

caggcatgca agctttgcag ttgctgagta atgtcggcca acgtcaccac aatcgcgatg     60

aattcaatca tgccgcccag ggcggccaac ccaatggtgg ccgcgagcgg cagctcgatc    120

gcagcgcgga ggttgccggc cgccagttga ttcacgaaca gggtgaggtc ataggcgggc    180

aggatagtga cgaaggcaag acctagatct gccgtcggaa gaagaatcga gtatccggtc    240
```

-continued

```
gacacaacgg aagcgaaagt gtccgcgatg ttgatgagcg tcgccggttg tggcggcggt    300

ggcggcggta gcaccgtccg cacataccgc gggaacgcgg gcatccgaat ttggggcagg    360

gtgttcaagg cggctggcaa ctcaccatga atct                                394


<210> SEQ ID NO 591
<211> LENGTH: 457
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 591

ccggctcgta tgttgtgtgg aattgtgacc ggataacaat ttcacacagg aaacagctat     60

gaccatgatt acgccaagct atttaggtga cactatagaa tactcaagct tggccgcagg    120

gccgagtcga ttggtcgcgg tcgcctcgac agttagctta tgcaatgcta acttcggggc    180

aaagttcagg cggatcggcc gatggcgggc gtaggtgaag gagacagcgg aggcgtggag    240

cgtgatgaca ttggcatggt ggccgcttcc cccgtcgcgt ctcgggtaaa tggcaaggta    300

gacgctgacg tcgtcggtcg atttgccacc tgctgccgtg ccctgggcat cgcggtttac    360

cagcgtaaac gtccgccgga cctggctgcc gcccggtctg gtttcgccgc gctgacccgc    420

gtcgcccatg acagtgcgac cctgnaccgg gctggcc                             457


<210> SEQ ID NO 592
<211> LENGTH: 438
<212> TYPE: DNA
<213> ORGANISM: Mycobacterium tuberculosis

<400> SEQUENCE: 592

gtgtgctgtc aattcagagc tgagcctgat gcactcaact tactgagcat gctaacgctg     60

gtcgtgcggg tcttgttccc gcgtgtcggc agggcacacg ctcggggcgt agctgggaga    120

ggccccggtc aagcccggag agcagtgctc agtccgccag cttgaccgac tttcgatgag    180

aacgcgcttc tcgccgtatt gaactggcgt gctgacggtc gctgagcagc gctcgccgag    240

tgcggccgct gattctttca tcgagccagg aggcgcattc gtgttcggcc gcctgcgggt    300

cggccccatc gtcgacgcga tccgtcaccc actcctcgat caggtctgcc tcatcgaacg    360

ggccaacggt gctgtcggag taagtgtgcg tgggcacgcg agccgggtgc tgtggtacac    420

ccaccgttgc atgaacaa                                                  438


<210> SEQ ID NO 593
<211> LENGTH: 220
<212> TYPE: DNA
<213> ORGANISM: Mycobacterium tuberculosis

<400> SEQUENCE: 593

atactcaagc ttcaccaggc gccggcgggc cgcggcgcca agccaggcag ccgcgctcgg     60

cgcgtcgggg ccttccgccg gctcggccga cagttcgatc tctggatcgg cggggctctc    120

cgggccggcc tcggcgacct cagcgggccg cgccttccgg ccgaaccatt ccctagccat    180

agataaccgc acctcaatgc acggtttggc ggcaacccgg                          220


<210> SEQ ID NO 594
<211> LENGTH: 266
<212> TYPE: DNA
```

-continued

<213> ORGANISM: Mycobacterium tuberculosis

<400> SEQUENCE: 594
agcttccgtc acgacccgcc ctcgccggtg ccggcgccat cggtcatcgg atctcatgac 60
gacgtcacgt aggcccgcta gccgcgagcg ggcgcggtca actggcgagg cggcggcgac 120
gtgactgagc tggccgagct ggaccggttc accgcggaac taccgttctc gctcgacgac 180
tttcagcagc gggcttgcag cgcgctggaa cgcggccacg gtgttgctgg tgtgcgcgcc 240
gaccggcgct ggcaagacgg tggtcg 266

<210> SEQ ID NO 595
<211> LENGTH: 105
<212> TYPE: DNA
<213> ORGANISM: Mycobacterium tuberculosis

<400> SEQUENCE: 595
atactcaagc ttgccgggac cgcggaacag aaccggcggt tcctaccgcg gtgtgcggcc 60
ggcgcgatat cggcctcccg actaaccgaa cccgatgtgg gctcc 105

<210> SEQ ID NO 596
<211> LENGTH: 141
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as “n”

<400> SEQUENCE: 596
acgttggctc tgccggaacg tatttccagc ggcacgcatt cggcgtgggt gccgggcgcc 60
gagttgcgtc gctgggatca cgcagcagtc gccggcggct gccgtcgggc tatgaattgc 120
accgagccgg aaaatccnca c 141

<210> SEQ ID NO 597
<211> LENGTH: 234
<212> TYPE: DNA
<213> ORGANISM: Mycobacterium tuberculosis

<400> SEQUENCE: 597
atactcaagc ttgtcgtatt ccgtggcact gtcagacata tgcgccgctc ctcctcatcg 60
ctgcgctcgg catcgtcgcc ggcggtcatg gcgtcaccct acccaagccg aacgcgaaac 120
gagaacgtgt tccattatta gggtgtgagc accaatacca gattgctcac caggaactca 180
cgcagcaccg ggacggatgt cagccaccac ccccatctgg ggtggtagcg ggga 234

<210> SEQ ID NO 598
<211> LENGTH: 184
<212> TYPE: DNA
<213> ORGANISM: Mycobacterium tuberculosis

<400> SEQUENCE: 598
cgttggtagc ccgatatgca tagtgtatct tactgaacat gatttccatt atggagcccg 60
gggtgccggc agcgcgaacg gtgcgccgtc agacgcgggc ggcactgacc agggtgttgc 120
gggcgaacat cggcccggct tcggattccg gtccgggtac cgggcgaccc accgcttcga 180
ggta 184

<210> SEQ ID NO 599

-continued

<211> LENGTH: 351
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 599
atactcaagc ttggccaact cctcatcgga cttgaaggtg ccgtcctcgt tggcggccct 60
gctccacggc acgttgatgg caccaggaat gtgtccgggc cgctggcttt gttcctgcgg 120
caggtgcgcg ggggccatga tcttgccgga aaactcgtcg ggagagcgca cgtcgatgag 180
gttcttgacg ttgatggccg ccaggacctc gtcgcggaat gcccgaatcg tgttatccgg 240
cggggaggcg gtgtatgagg tcaccggccg gctgaccggg tcgctggaca gcgggcgtcc 300
gtccagctcc cacttcttgc gggcgccgtc caacnacttg acttctcctg g 351

<210> SEQ ID NO 600
<211> LENGTH: 438
<212> TYPE: DNA
<213> ORGANISM: Mycobacterium tuberculosis

<400> SEQUENCE: 600
atatcttaag cgtcgggtcc cgaggctcgg tcggcagctc cagcaaaacc cgctccaccc 60
ctagatgccg gtatccctca aggtctttag ccgccgcttc accccactgg cacacggtca 120
ccggcacgtc gcccccggcc atggcgcgca accgctgaag cggacccgac agccgctgcg 180
gtgatggact gatcgcgatc cacccggcat tgagccgggc tatccgcggg aagttcgccg 240
gtcccccgcc cacatacagc ggaggatagg gctttgtcac cggcttcggc cagcagtaga 300
tcggatcgaa gtccacatat gtcccatgga attccgcctg ctcctgcgtc cagatctcga 360
ttatcgcgcg caaccgctca tcgatcacac gtccgcgcac cgcagggtcc acaccatggt 420
tggcgacttc ttcgcgca 438

<210> SEQ ID NO 601
<211> LENGTH: 410
<212> TYPE: DNA
<213> ORGANISM: Mycobacterium tuberculosis

<400> SEQUENCE: 601
atactcaagc ttgtcgcggt aaacccgcag cagggcggtg ggtgcggtgt caaaaacaac 60
cacacttctt tgcggttcgg tgatctcgac accggccgcg agccgaccac catgcgcgcg 120
taaatcggcg atcagcgcgt cggctatcgc ctgggtgccg cccaccggaa tcggccagcc 180
gaccgaatgg gccagcgttg ccagcatcag tccggcgccg gccgacacca gtgacggcaa 240
cggtgaaatc gcgtgggcgg caacgccggt gaacaacgcg cgggcatcct cgcccgccag 300
cgaccgccag gcaggggtgc cctgggccag catccgcagc ccgagacgca ggaccgagcc 360
cagtgcagta ggcaaagacc gcttgtcgga gacatgaact ccacgaccgt 410

<210> SEQ ID NO 602
<211> LENGTH: 456
<212> TYPE: DNA
<213> ORGANISM: Mycobacterium tuberculosis

<400> SEQUENCE: 602
agcttattga accgcgggtc gcaggcaaag tggacctcat aacgactcgg gtccagcgac 60

-continued

```
cgcgccaaca cgaacggccg gacgacgtgg gccagggtcg cggcctcccc tacaaacagg    120

atccgttgcc tgcgagcgac aggctccggt gcggcgttgg gcgccgtgct cgtcccagcg    180

tccggtcccg ggtcgccggc gacgcttgtt tcctccatac tcgcccccta atctcgaggc    240

agcccgtacc cgcaggcaac ctcccaaaaa tgcaatcccc caaaatgcaa tgcgtcgagc    300

tatttctcac accgaccgct agttgcggat cagaaatccg ttgggcgcgg aagtccagcc    360

gaatttgttc tcccgctccg catcatgctt gtaatcgttt ggaaattcat cctcatatgc    420

ctcgatcgct tcatagggtc caggccaaac cgggca                              456
```

<210> SEQ ID NO 603
<211> LENGTH: 217
<212> TYPE: DNA
<213> ORGANISM: Mycobacterium tuberculosis

<400> SEQUENCE: 603

```
cttccggctc gtatgttgtg tggaattgtg agcggataac aatttcacac aggaaacagc     60

tatgaccatg attacgccaa gctatttagg tgacactata gaatactcaa gcttggccac    120

ctcgcggtgt gtggtggaac ccatctgagc agtgtgccaa accggggcag acagctccca    180

attgacgtga gcccgctcac ttgctgggta agcgtcg                             217
```

<210> SEQ ID NO 604
<211> LENGTH: 478
<212> TYPE: DNA
<213> ORGANISM: Mycobacterium tuberculosis

<400> SEQUENCE: 604

```
tagcgccccc tcccgggcgg agctccacgg cgtggatcaa ggtaccggcc gggatgttgc     60

gcaatggcag gttgttgccc ggcttgatgt cggcgttagc gccggattcc accacatccc    120

cttgcgaaag tccgttgggt gcaatgatgt agcgcttctc cccatcgaga tagtggagca    180

acgcaatccg tgcggtacgg ttcgggtcgt actcgatgtg cgcgaccttg gcgttgacac    240

catctttgtc attgcggcga aagtcgatca tccggtaagc gcgcttatga ccgccgcctt    300

tgtgccgggt ggtaatccgg ccatgcgcgt tgcgtccacc gcgaccgtgc agcgggcgca    360

ccagcgactt ctccggggtt gaccgggtga tctcggcgaa atcagatacg ctggcgccgc    420

gacgaccaag cgtcgtgggc ttgttcttgc gaattgcatg tctaatcagg tctttctc      478
```

<210> SEQ ID NO 605
<211> LENGTH: 459
<212> TYPE: DNA
<213> ORGANISM: Mycobacterium tuberculosis

<400> SEQUENCE: 605

```
tgaaactata taatactcaa gcttgccaaa gaagacctcg tcgaccaagc aggacgcgac     60

cgtcgaggtg gcgatccggc ttggcgtcga cccgcgtaag gcaaaccaga tggttcgcgg    120

cacggtcaac ctgccacacg gcactggtaa gactgcccgc gtcgcggtat tcgcggttgg    180

tgaaaaggcc gatgctgccg ttgccgcggg ggcggatgtt gtcgggagtg acgatctgat    240

cgaaaggatt cagggcggct ggctggaatt cgatgccgcg atcgcgacac cggatcagat    300

ggccaaagtc ggtcgcatcg ctcgggtgct gggtccgcgc ggcctgatgc ccaacccgaa    360

aaccggcacc gtcaccgccg acgtcgccaa ggccgtcgcg gacatcaagg gcggcaagat    420

caacttccgg gttgacaagc aggccaacct gcacttctc                           459
```

-continued

<210> SEQ ID NO 606
<211> LENGTH: 464
<212> TYPE: DNA
<213> ORGANISM: Mycobacterium tuberculosis

<400> SEQUENCE: 606
gctgagctcc acggcgtgga tcaaggtacc ggccgggatg ttgcgcaatg gcaggttgtt 60
gcccggcttg atgtcggcgt tagcgccgga ttccaccaca tccccttgcg aaagtccgtt 120
gggtgcaatg atgtagcgct tctccccatc gagatagtgg agcaacgcaa tccgtgcggt 180
acggttcggg tcgtactcga tgtgcgcgac cttggcgttg acaccatctt tgtcattgcg 240
gcgaaagtcg atcatccggt aagcgcgctt atgaccgccg cctttgtgcc gggtggtaat 300
ccggccatgc gcgttgcgtc caccgcgacc gtgcagcggg cgcaccagcg acttctccgg 360
ggttgaccgg gtgatctcgg cgaaatcaga tacgctggcg ccgcgacgac caggcgtcgt 420
gggcttgtac ttgcgaattg ccatgtctaa tcaggtcttt ctct 464

<210> SEQ ID NO 607
<211> LENGTH: 205
<212> TYPE: DNA
<213> ORGANISM: Mycobacterium tuberculosis

<400> SEQUENCE: 607
atactcaagc ttgttggtga cctcgccggc gaacagttct cgcacgattt ccggattagc 60
gggactggtc accagttggg tatgcgggaa ggcgctgacg ttcgccgcga ttagctgttt 120
gatggacgcg gcggtgatgt cctgatcacg gaactggctg taatagccca gggtcgccac 180
gcttccatcc gggcccggac ccggc 205

<210> SEQ ID NO 608
<211> LENGTH: 244
<212> TYPE: DNA
<213> ORGANISM: Mycobacterium tuberculosis

<400> SEQUENCE: 608
gatgatcgcc ggtgccaccc cgatccgtgc ctcggtcagc gcgaacgtgc tttccggtcc 60
ggcgaccacc atgtcgcacg caccgaccag gccgaacccg ccggcccgca catgcccgtt 120
gatggcgccg accaccggca gcggcgactc gacgatggcg cgcaacagcg ccgtcatttc 180
ccgcgcccgc gccaccgcca tccggtacgg atcaccacca cctccgccgg cctcgctgag 240
gtcc 244

<210> SEQ ID NO 609
<211> LENGTH: 289
<212> TYPE: DNA
<213> ORGANISM: Mycobacterium tuberculosis

<400> SEQUENCE: 609
atactcaagc ttgccgcaat cgaaaccaac ctgtttgtgc cgcaagaaat tacgccgtgg 60
cccggcgccg atcaagaaac gccccggcgc gcggcggtgt cgtcgtatgg catgacgggc 120
accaatgtgc acgccattgt cgagcaggca ccggtgccag cccccgaatc cggtgcacca 180
ggcgacaccc cggccacacc cggtatcgac ggcgcgctgc tgttcgcgct gtcggccagc 240
tcgcaggacg cgctgcggca aaccgccgcg cggctggccg attgggtct 289

<210> SEQ ID NO 610
<211> LENGTH: 282
<212> TYPE: DNA

-continued

<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as “n”

<400> SEQUENCE: 610
ttggcgggtt ggccacanca ncccgccggt gacggcgacg atgctgggct ggttgcggcc 60
ctgcgccacc gcggcttgca tgctggttgg ctgtcttggg acgatcccga aatagtccac 120
gcggatctgg tgattttgcg ggctacccgc gattaccccg cgcggctcga cgagtttttg 180
gcctggacta cccgcgtggc caatctgctg aactcgcggc cggtggtggc ctggaatgtc 240
cancgccgtt cacctacgtg accttgatgg gatccggggg nt 282

<210> SEQ ID NO 611
<211> LENGTH: 312
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as “n”

<400> SEQUENCE: 611
ncgtggacac cggtgtcgan cgccaccagc cgcatgtctg cangtcnatt ccgtcctcgg 60
caacatcttg aatgccgagc agcgcctggg cgtgatcggc aaccggggat gaccgctcgc 120
cgatccgctc gacaatcccg gcggcacgtg acatgccggc ggacggctcg acgagctgga 180
acttcagcga cgacgatccg gaattgatca ccagcacggt gctactcatg gacccctgcg 240
cctgaatccc gtgatggcca cggtgttgac tattcgtcga cagtgcaccc gagatagtct 300
tcacggctgc gt 312

<210> SEQ ID NO 612
<211> LENGTH: 349
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as “n”

<400> SEQUENCE: 612
catgtattgc cgtgctcacg gcgccacgct cgatggtttc tcgaagtctc cgggctggtg 60
tacagcttct cgttgatctc gttcgccacg ccgtcctctt cccgccgacg acccgatctc 120
gatctccana atgatcttgg cggccgccgc cgccttgagc agctcctggg cgatggccag 180
gttctcatcg atgggcactg ccgaccgtcc cacatgtgcg acggaacaaa gatgtcacct 240
tgctcacgcg tgcgcnagat cncanaaggg ccggacatac tgtcnacttg tccttgggca 300
gtggtccgtg tcagcccacg tgacgggtac ttggcgcgat aacgtggtg 349

<210> SEQ ID NO 613
<211> LENGTH: 350
<212> TYPE: DNA
<213> ORGANISM: Mycobacterium tuberculosis

<400> SEQUENCE: 613
gccaccacga cccggccgta actctgctca cggaaatgcg gccaggccgc gcgtagcacg 60

-continued

```
tggtatccgc cataaaggtg caccttaagc acggcgtccc aattctcgaa cgacatcttg    120

tggaaggtgc cgtcgcgcaa gatcccggcg ttgctcacca caccgtgcac ggcgccgaat    180

tcgtcaagcg cggtcttgat gatgttcgct gcgccgtcct cggtggcgac gctgtcctta    240

gttggcgacc gcccggcccc ccttgtcgcg aatctcggcg acgacctcat cggccatcgc    300

cgaacggcgc ccgtgcccgt cgcgggcgcc accgaggtcg ttgaccacga               350
```

<210> SEQ ID NO 614
<211> LENGTH: 126
<212> TYPE: DNA
<213> ORGANISM: Mycobacterium tuberculosis

<400> SEQUENCE: 614

```
caggcatgca acctttgtcc acacggcgtc tactccgtgc aaggtccgac cgcttccacg     60

tcccgccgtg acggtgctcc atctccctca gcaacgcgtg aagtggtccg atcccgcggc    120

ttcagg                                                               126
```

<210> SEQ ID NO 615
<211> LENGTH: 395
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 615

```
gttgagacgc aaccagcgca caacgacgat ttggcgtagc ggcggacgtc tgctcgattc     60

gatcacgtcg cgctcgcatc gagcatggcc cgcgacgcta cacgatcgcc gtcgtcgatg    120

acacgaccga gccgtacgcc ggccgtaagc cgcgccagga ttcggcgaaa aacgtctacg    180

tggcgggtgt actgggtgtc gaatgattcg tggggtgcgt atgcgtcctg caatcgtcga    240

catagatccg tcgccgcatc gcgtcgacaa ctccgggtga gtggaataca cttgccgatc    300

acgcgacgtg cgcggatcga tgccgaccga aatacgacca catggctctt gttgcncagt    360

gttggcggca tcaaataccc tcagtgccgt ccgac                               395
```

<210> SEQ ID NO 616
<211> LENGTH: 371
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 616

```
ttnccgcctt nacgcctact ccnagacgat gctcgacgcg tgtgagcaca cggcgctgct     60

gtagacggca cggcgcagct ggatcgcgct tggtgcaccc aagcctctac gcgcgtcgct    120

gcgtcgtcat cgggtaccga acatattccg gtcgttgcgc agagtgtgca tgtgcggctc    180

ttgtgaacga acatagcaaa gcgtatatgt ctgtggcggc tctgcagata tcgcgataat    240

acgtatatac ataaggtggc gcgcgatcta tcggtatatc cgttatggcg gacgtgcgtg    300

agcgtgagtc gcggcgcatc gcgcacttcg cgatcgcgtg actggtcctc gcgactgcgc    360

gcatgcgtag c                                                         371
```

-continued

<210> SEQ ID NO 617
<211> LENGTH: 423
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 617
ggtgatgacg cacttgcttc gaatgagtca ttgactactc ccgtggttgt cctgcgatgg 60
tggagtgccg cgcagccttg cccgangtcg cgatcgcgtc gcgggcttcg gggagcagac 120
tgacctgcag atggaagtcg tgccacatgc ccgcgaacgg cgagctcgat gcttgttttc 180
gaagngcgca ngcggtttcg atcttgtccg cgtcaacgca gatcggatct cgccgcggtc 240
tgcatgacga tgggcgcagg cccgctcatg tcccgtagac ggggagatac gggcagccgc 300
ggatcgagac ctacgtagcg cggcgcccat cgtgccatcg acgaagaatg acggatcgcg 360
cagcgccgtc gcgtcgcttc gatgtcacgc gagatcgcca cggcagatca gcgatgcgcg 420
ggc 423

<210> SEQ ID NO 618
<211> LENGTH: 354
<212> TYPE: DNA
<213> ORGANISM: Mycobacterium tuberculosis

<400> SEQUENCE: 618
cggtacgccg gcaacaaacg ccttgtgacg agcgcgtccg agcggtcatc ggcctccacc 60
gtcatgcaca gctccttctc caggtctacg ccgacgtcgc ggtccacatt ggtgagcttg 120
gcgaatgcct cggcaacctc gtcgaaatgc gcctccgcgt ccgcatcgaa ggtcgccatg 180
tcaaagatca actcgacgta gtagctagtt accgcatcag gtcagtgttt gctggcctcg 240
gagtccggcc gaacaatggc catttcccgc gactctagaa tccagtcatc gtctcggtga 300
cgacgccttg ccgatcacat agctcgaccg gatcggagag aatctggttc tcgt 354

<210> SEQ ID NO 619
<211> LENGTH: 128
<212> TYPE: DNA
<213> ORGANISM: Mycobacterium tuberculosis

<400> SEQUENCE: 619
atactcaagc ttaagcgcag cagtaccggc ggtgcctggg catcccagca aaacggggag 60
ctcaacgaac gattcctgaa cgaagggtcg tccaccaacc tccaaaccga acggttgcca 120
gccccggc 128

<210> SEQ ID NO 620
<211> LENGTH: 295
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 620
gcaagtccgc tcaatgtggt tgtgatcaca ngactacgtc gcctcaatca gctcaaacgt 60
caccccgtgg cgtgctgcgc agcatgaagg tcggcgcccg cacgatgtgg gcgaagcaac 120

-continued

```
aggtaataac tggtcggcat gggtcaaccc tcattgggcc gttgcggatc gggtgcacgc    180

ccggagtgcc ggtcgaactc aacaccgcct tcaccgatct tttcgtcgaa aatggcggtc    240

gtgtcggggt atacgtccgc gatcccacga ggcggaatcc gctgagccgc actga         295
```

<210> SEQ ID NO 621
<211> LENGTH: 361
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 621

```
atactcaagc ttcgcgccct caagcggctg aaggtggttc cggcgtncca acngtcgggc     60

aactcgccga tgggcatggt gctcgacncc gtcccggtga tcccgccgga gctgcgcccg    120

atggtgcagc tcgacggcgg ccggttcgcc ncgtccgact tgaacgacct gtaccgcagg    180

gtgatcaacc gcnacnncnn gntgaaaagg ctgatcgatc tgggtgcgcc ggaaatcatc    240

gtcaacaacn agaancggat gctgcnggaa tccgtggacg cgctgttcga caatggccgc    300

cgcggccggc ccgtcaccgg gccgggcaac cgtccgctca agtcgctttc cgatctgctc    360

a                                                                    361
```

<210> SEQ ID NO 622
<211> LENGTH: 361
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 622

```
tgcgcatggc agttgttgcc ggcttgagtc gcgttagcgc ggattccacc acatcccttg     60

cgaagtcgtg ggtgcaatga tgtagcgctt ctcccatcga gatagtggag caacgcaatc    120

cgtgcgtacg ttgggtcgta ctcgagtgcg cancttggcg ttgacaccat ctttgtcatt    180

gcggcgaagt cgatcatccg gtaagcgcgc ttatcgacgc cgcctctgtg ccgggtggta    240

atccggccat gcgcttgcgt ccaccgcgac gtgcagcggg cgcacaccga cttctccggg    300

tgacgggtga tctcggcgaa tcagaacctg gcgcgcgaca cagcgtcgtg gctgtacttg    360

c                                                                    361
```

<210> SEQ ID NO 623
<211> LENGTH: 312
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 623

```
tgggtgatca gatactggct agttggtcgg gtggggtgat cgaagatcgc ggtggccggc     60

agcgttactg cggtgacgct gttaagcggt tacgtactcc acggcactca angaattana    120

tcccgaatcg gcaaaccctg gccagcgtcg agtccgcagc gccgtcgcgc cccccaccgc    180
```

-continued

```
tgcggcatgc tcacatacca cctcgatcgc tgcgggagtt gctcgtcggc cgaccgaccg    240

gccagccggg cggcaaaccg gaggacccaa gattcagcac caccatcgct agcccgatct    300

ggccgcgcgt gg                                                        312
```

<210> SEQ ID NO 624
<211> LENGTH: 454
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 624

```
tcgtagcggt tgcgaccant ccgcggacag ctccgccacg cgacgggtcg ggatcaccgc     60

ggtcaaacca ccgagcggcg aggatctctg gccgtcgacg tgaccgcgca cggccgcggt    120

gatggccagt cccgaccgcc gttccacttg gcgtacgcgc tggatgtgtt gtgccgcaac    180

ggaatcccac ctcaattatg acctcgttgt gggcgagcgc ggtatcgtac gcccgaccag    240

gaatcgtcga tgctatctca cgtcaccgaa ggcctctccc agcacaccgc atccagaacg    300

tgcacacngt cgacatgtct cggcggatcc gcctgcagaa cgaacgccan gtgcgctgtg    360

cgacacgggt cgcgatcacc gctcgcacgc ggagatcggc acacgcgcag cgcatcgatc    420

ataatctctc gatgcggtct ccaccaccga acag                                454
```

<210> SEQ ID NO 625
<211> LENGTH: 366
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 625

```
atactcaagc ttcgctgagg tggtggggca cgatcacgtc accgcaccgc tgtcggtggc     60

gctggatgcc ggccggatca accacgcgta cctgttctct gggccgcgtg gctgcggaaa    120

gacgtcgtca gcgcgtatcc tggcncggtc gttgaactgt gcgcagggcc ctaccgccaa    180

cccgtgcggg gtctgcgaat cctgcgtttc gttggcgccc aacgcccccg gcagcatcga    240

cgtggtagag ctggatgccg ccagccacgg cggcgtggac gacacccgcg agctgcggga    300

ccgcgcgttc tatgcgccgg tccactcacg gtaccgggta tttatcgtcg acgaggcgca    360

catggt                                                               366
```

<210> SEQ ID NO 626
<211> LENGTH: 363
<212> TYPE: DNA
<213> ORGANISM: Mycobacterium tuberculosis

<400> SEQUENCE: 626

```
gcactcacgc tggtacaaga ccttcacaaa atctgaaatc ctgacccgat acttgaacct     60

ggtctcgttc ggcaataact cgttcggcgt gcaggacgcg gcgcaaacgt acttcggcat    120

caacgcgtcc gacctgaatt ggcagcaagc ggcgctgctg gccggcatgg tgcaatcgac    180

cagcacgctc aacccgtaca ccaaccccga cggcgcgctg gcccggcgga acgtggtcct    240

cgacaccatg atcgagaacc ttcccgggga ggcggaggcg ttgcgtgccg ccaaggccga    300
```

-continued tccgctgggg gtactgccgc agcccaatga gttgccgcgc ggctgcatcg cggccggcga 360
ccg 363

<210> SEQ ID NO 627
<211> LENGTH: 367
<212> TYPE: DNA
<213> ORGANISM: Mycobacterium tuberculosis

<400> SEQUENCE: 627
atactcaagc ttgtataaaa agatcggtga gcgcatcgat tcgctccgcc gggtttgccg 60
ctgcggcggc ggagctgccg tgaccgtcta tttgggtgat cagatactgg gctagttcgg 120
tcggggtggg gtgatcgaag atcgcggtgg ccggcagcgt tactgcggtg acggctgtta 180
agcggttacg tacctccacg gcactcaagg aattaaatcc cgaatcggca aacgcctggc 240
cagcgtcgaa tccggcagcg ccgtcgcgcc ccagcaccgc tgcggcatgc tcacatacca 300
cctccatcgc tgcggcgaat tgctcgtcgg ccgaccgacc ggccagccgg gcggcaaacc 360
cggaaga 367

<210> SEQ ID NO 628
<211> LENGTH: 518
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 628
cctcatcata tgccgataga gctctacata ttcaggagat caccatggct cgtgcggtcg 60
ggatcgactc gggaccacca actccgtcgt ctcggttctg gaangtggcg accnggtcgt 120
cgtcgccaac tccggagggc tccaggacca cccgtcaatt gtcgcgttcg cccgcaacgg 180
tgaggtgctg gtcngccagc ccgccaagaa caggcagtga ccaacgtcga tcgcaccgtg 240
cgctcggtca agcgaccatg ggcagcgact ggtccataga gattgacgca agaaatacac 300
gcccggagat ctcgccgcat tctgatgaac tgaacgcgac ccgaggctac tcggtganga 360
catnacgacg cgttatcaca ccccgcctnc ttcaatgacc ccacgtcngg caccaaggac 420
ccggcaatcg cggctcactt gngcgatngt cnacaaccaa cgcgncgcct ggctacgggc 480
tcaacaaggc anaagacaca atccgctctc gattggtg 518

<210> SEQ ID NO 629
<211> LENGTH: 435
<212> TYPE: DNA
<213> ORGANISM: Mycobacterium tuberculosis

<400> SEQUENCE: 629
atactcaagc ttatcgaggc ggcgcatacc gaagcgtggg aaatccagac cgaataccgc 60
gacgtgctgg acactttggc cggcgagctg ctggaaaagg agaccctgca ccgacccgag 120
ctggaaagca tcttcgctga cgtcgaaaag cggccgcggc tcaccatgtt cgacaacttc 180
ggtggccgga tcccgtcgga caaaccgccc atcaagacac ccggcgagct cgcgatcgaa 240
cgcggcgaac cttggcccca gccggtcccc gagccggcgt tcaaggcggc gattgcgcat 300
gctacccaag ccgctgaggc cgcccggtcc gacccggcca aaccgggcac ggcgccaacg 360
gttcgcccgc cggcaccacc ggtccggtga ccgcagtacg gtccccccag cctgactacc 420

-continued

```
gtgccccggc gggct                                                 435


<210> SEQ ID NO 630
<211> LENGTH: 398
<212> TYPE: DNA
<213> ORGANISM: Mycobacterium tuberculosis

<400> SEQUENCE: 630

tggccgggct ggtagcccgc gtatggcaag gttccgctca atgtggttgt gatgcagcag     60

gactacgttc gcctcaatca gctcaaacgt cacccccgtg gcgtgctgcg cagcatgaag    120

gtcggcgccc gcacgatgtg ggcgaaggca acaggtaaga acctggtcgg catgggtcga    180

gccctcattg ggccgttgcg gatcgggttg cagcgcgccg gagtgccggt cgaactcaac    240

accgccttca ccgatctttt cgtcgaaaat ggcgtcgtgt ccggggtata cgtccgcgat    300

tcccacgagg cggaatccgc tgagccgcag ctgatccggg ctcgccgcgg cgtgatcctg    360

gcctgtggtg gtttcgagca taacgagcag atgcgaat                            398


<210> SEQ ID NO 631
<211> LENGTH: 464
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 631

gtccagtcaa gcatcggtcc tctccgacta cgccaagant ggcgacgtgt cagtgcanac     60

agcgganatg gtggcgccta tgcgtcgacg ctcacaaacn gcggtgancg cgttctggtc    120

gtgcaccatc gagccgtgcc agcccggccg cgtgccgtca gccgcatcca ctggatgcct    180

tctcggngtt tcaatcangt acangcgacg ttcgccacca tcgtgccggg gcacggttag    240

cgagaaaccg ccgacttcac cgattgcctc ggtgatgccg tcgaacagat cgggcctatt    300

gtcgacagcc agtgtgatnc gtatttgccg ccgtgctcct cgtcgcaacg atgcgaacac    360

agatccgtgg nggacgatag cggctgacaa ngtgggggca acacaatcac atgccacatt    420

tcttcatttc acgcccacaa cccagacttc gtctcgatgn gccg                     464


<210> SEQ ID NO 632
<211> LENGTH: 499
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 632

cacgcggtct ggcccgatcc gaagatccct ttgccggcgt ggcggctctg ctcggcggtg     60

ttgtacactt ctcgaacacc tcggcaccga caccaccacc gtngcttgaa caccgccaac    120

atcggcagca gatcttgatg gtcctggtga atcccacggt gactttggag tggaaggcgc    180

catactgatc gccgcgccag cacatgagct agcggcagga aaaccagcag ccgctcacct    240

tgcgcagcag cgtcnggtga tatgcctggc gcccttaatc tcgtgaacca gttggattgg    300

gtcaactggc agccttgggt ctccggtggt gccgangtgt anataagctc ccgggtccgt    360
```

-continued

```
caacgtantg cgcaggcggc ggttactcgg cgggtcaacg agccccgctc gtgagcnatc    420

agcctttgga ccgaacggga ttcatactcc gcaggcggcc ctccgaaatc ggcacatgtc    480

ctttgatcgt tcgcaacan                                                 499
```

<210> SEQ ID NO 633
<211> LENGTH: 343
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 633

```
ggccatgtca catcggtggt acaggtaaac cgcgccgtgt gcgcggtctc ggagatcaga     60

acgtggtcgc agttgaaccg cgggctttca gccagtcgcg ataatcggcg gaagtcggcg    120

cctgccgccc caactagcgc gactcgccac ctagcacacc gatggcgaag gccatgtntc    180

cggccacgcc gccgcggtgc atcaccaagt catcgactag gaagctaagc gacancttgt    240

gcaggtgttc gggcagtagc tgctcggaaa atcggctgga aaccgcatca aatggtcggt    300

ccaatcgaac cggttacccg atcgtcacaa aaatctccgt cct                      343
```

<210> SEQ ID NO 634
<211> LENGTH: 192
<212> TYPE: DNA
<213> ORGANISM: Mycobacterium tuberculosis

<400> SEQUENCE: 634

```
gggtctacaa ccaccgggtc tgacttctgg gcttccaccg ctcgcgccgt cgcgacaaac     60

agcgcggtcg aaccgacact cgttgtgatg tcccagctat cacctccggt aggcacccaa    120

tcgaccctac ccggctatct cacccccgat ctccaggctc cgccgatcca tgcgcatccc    180

ggtccggatc cc                                                        192
```

<210> SEQ ID NO 635
<211> LENGTH: 376
<212> TYPE: DNA
<213> ORGANISM: Mycobacterium tuberculosis

<400> SEQUENCE: 635

```
caggcatgca agcttgtcgt attccgtggc actgtcagac atatgcgccg ctcctcctca     60

tcgctgcgct cggcatcgtc gccggcggtc atggcgtcac cctacccaag ccgaacgcga    120

aacgagaacg tgttccatta ttagggtgtg agcaccaata ccagattgct caccaggaac    180

tcacgcagca ccgggacgga tgtcagccac cacgcccatc tggggtggta gcggggaaat    240

acggctaacg cggctccggt gccggcagcc cagcgcagac cctcggcggc ggacacggct    300

aacaacgacg acccatagtt gttctttgcc ggatggccgt gtttgctgac atatcgggcg    360

cggcgccggc gccgcc                                                    376
```

<210> SEQ ID NO 636
<211> LENGTH: 83
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

-continued

<400> SEQUENCE: 636
nctacgctgc tgaatgttgt gcgccggagg anctcaagac ccacgcggtt gtacgcggac 60
ntgcgacatg ttcaaccgcc gga 83

<210> SEQ ID NO 637
<211> LENGTH: 319
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 637
ctaaccaaca agccatggtg gttggcgccg tcgagaggtc ggcggtcgcc acaacgggaa 60
gatcgccttg agcgtcgctc gaccgccgcc tcgagttggg tcataacgaa gtactgatgc 120
cgatcatgtc gacgtgtccg tcgcatcagc gtgcagcggc gacccctcga cgagcctcgg 180
tgccgccgcg gccagggcac cagctgtttt agcgcattgt gctccgccgg taataaagga 240
ngtcggtcgc ctccgctgct gtggttgcgg aataacatct tcccttcctg caacaggatg 300
agaatggttt taattgctc 319

<210> SEQ ID NO 638
<211> LENGTH: 94
<212> TYPE: DNA
<213> ORGANISM: Mycobacterium tuberculosis

<400> SEQUENCE: 638
ctaagctttc gggtccgccg ccactagtac cgcgttgccg gccccgccga cctagaatgt 60
tccgcccatt gccgtttcct cccgccgccg ggtt 94

<210> SEQ ID NO 639
<211> LENGTH: 122
<212> TYPE: DNA
<213> ORGANISM: Mycobacterium tuberculosis

<400> SEQUENCE: 639
tctggtgccg ggtgtgccga cgggtccgtc cgcctctgct tcagtgattc tgtgatgcga 60
ccggcaacgt cctcgttgtt cggtgtctat gtggtccgtc tctccttgtt ccgcatacga 120
tt 122

<210> SEQ ID NO 640
<211> LENGTH: 210
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 640
gcgatcgntn accacaaggg cgcaaccgtt cgcgcgtcga ctgaacgtgc tgccgcctgg 60
agaactggcg ctgctgccac ctggtcggcg catcggcact tcgaggactg gatttcgacg 120
cgtggcccga cctgangtng gcggtggacn ngtgtgcacc cggttgattc ctcggccttg 180
ccgggatgcc acctgcgcct ggtggtcgat 210

-continued

<210> SEQ ID NO 641
<211> LENGTH: 328
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 641
cgtgaccgga cggggtgccg cgcgaaccgg tcttggccaa ttgccgggga ctggggctgg 60
agtataaagc gggcctgttg ccggaagata aagtcaaagc ggtgaccgag ctgaatcaac 120
atgcgccgct ggcgatggtc ggtgacggta ttaacgaccg ccagcgatga aagctgccgc 180
catcgggatt gcaatgggta gcggcacaga ctggcgctgg aaaccgccga cgcacattaa 240
ccataaccac ctgcgcggct ggtgcaaatg attgaactgg cacgnccact cacgccaata 300
tccgccagaa catcactatt gcgctggg 328

<210> SEQ ID NO 642
<211> LENGTH: 553
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 642
atactcaagc ttcttaccca nagcatgaac cccgccgtcc aatgccgcca ccgtggtgct 60
gtcggccggc cgggtgcggg cacaatcgcc gagttcggcg aacagatcct cgaaggtctt 120
cacggccagc gattgttgca cgtgtcagcc agccaagtca cggtggtttg acgccacacg 180
ttcgccaccg ccgcgccgcg cattagggca tcctaatata ggttaggcta ccctanttat 240
tcctgtggtc naaggaggca gccgaacgtg accttcccga tgtggttcgc agttccgccg 300
gaagtgccgt cagcatggct gtccaccggc atgggccccg gtccgctgct ggccgcggcc 360
agggcgtggc acgcgctggc cgcgcaatac accgaaattg caacggaact cgcaagcgtg 420
ctcgctgcgg tgcaggcaac tcgtggcagg ggcccagcgc cgacggttcg tcntccccat 480
caaccgttcc gtattggcta accacctgca cggtggcacc gcacaacgcc gccacaaacg 540
cgccccggta tac 553

<210> SEQ ID NO 643
<211> LENGTH: 486
<212> TYPE: DNA
<213> ORGANISM: Mycobacterium tuberculosis

<400> SEQUENCE: 643
ggccgaactt aatcggttgt tggcggctgc cgagttgggt cactcggggg gtgtgcactg 60
gcacatggtg ggccggattc aacgcaacaa agccgggtcg ctggctcgct gggcgcacac 120
cgctcactcg gtggacagct cgcggttggt gaccgcgctg gatcgggcgg ttgttgcggc 180
gctggccgaa caccgtcgtg gcgagcggct gcgggtttac gtccaggtca gcctcgacgg 240
tgacggatcc cggggcggcg tcgacagcac gacgcccggc gccgtagacc ggatttgcgc 300
gcaggtgcag gagtcagagg gcctcgaact ggtcgggttg atgggcattc cgccgctgga 360
ttgggacccg acgaagcctt tgaccggctg caatcggagc acaaccgggt gcgtgcgatg 420

-continued ttcccgcacg cgatcggtct gtcgcgggca tgtccaacaa cttgaaatcc cgtcaacatg 480
gtcgac 486

<210> SEQ ID NO 644
<211> LENGTH: 146
<212> TYPE: DNA
<213> ORGANISM: Mycobacterium tuberculosis

<400> SEQUENCE: 644
gcttcccctg atactcgacc agccccactc gggccaatac gtgaatgtcc tagcattttt 60
cacccgttca cgggctagtc gagtagtaga cgattgatta gcctgaacgt acctccgacg 120
gccagctgac gaacgggttt gacgga 146

<210> SEQ ID NO 645
<211> LENGTH: 204
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 645
tcagctgtct gtagaagggc tggcgatact gtgcactgtc tgatatcgcn ncgtngtggg 60
actatncagn ccatnangat gcggttcngn nnntgcagag natcctggna cacatncggt 120
tcacgttaat cancatcgcg anttnctncg tnttcgatta nttctgctaa cgnntctnnn 180
agtgcctgcg ggtcgactct agag 204

<210> SEQ ID NO 646
<211> LENGTH: 209
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 646
nctctgccgg gcnagagcgc agagtcggac ggcttcgtcg atcgtgaagc gaccntgcga 60
tgancagata tcgntnacac tgctcanaaa cttcggatca tcgntgatac acaggccaac 120
gggtagcggt tgtccaaccg cttcgtcaac ganatgggat cgtgacganc ctacgctcgc 180
aggatatgtc gcngaccngn tctaganan 209

<210> SEQ ID NO 647
<211> LENGTH: 183
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 647
cacttcatgc tcgtgcgttg gcntcgattt gcncgagngg ttagctcctc gagtgngtga 60
cgtatcactc cggcngacta nccgtatcng cgtcccgcac cggtcaactg gtctagccac 120
accggggaga atncncgacc ggngctatcg accnatcacg gcttgtcgnn aagatagnca 180

-continued gcc 183

<210> SEQ ID NO 648
<211> LENGTH: 154
<212> TYPE: DNA
<213> ORGANISM: Mycobacterium tuberculosis

<400> SEQUENCE: 648
atactcaagc ttgccaaccg ccaccctgca tccggggggc gagcactgct ccgccgacca 60
gtacgaacca acctgcggtg cccaggccat tgacaatgtg ctggtcggcg cccgcgagtt 120
ctagcacagc aacgccgcgg ccaccacagg ggcg 154

<210> SEQ ID NO 649
<211> LENGTH: 219
<212> TYPE: DNA
<213> ORGANISM: Mycobacterium tuberculosis

<400> SEQUENCE: 649
cggtcggtgt gcttggcggc gtcggtatca acaccgccca cgaaatgggg cacaagaagg 60
attcgctgga gcggtggctg tccaagatca ccctcgccca gacctgctac gggcacttct 120
acatcgagca caaccgtggc catcacgtcc gggtgtccac accggaagac ccggcgtcgg 180
cgcggttcgg caaaactttg tgggatttcc cgccccccc 219

<210> SEQ ID NO 650
<211> LENGTH: 307
<212> TYPE: DNA
<213> ORGANISM: Mycobacterium tuberculosis

<400> SEQUENCE: 650
aatactcaag cttcgcggag gtggtggggc aggagcacgt caccgcgccg ctgtcggtgg 60
cgctggatgc cggccggatc aaccacgcgt acctgttctc tgggccgcgt ggctgcggaa 120
agacgtcgtc agcgcgtatc ctggcgcggt cgttgaactg tgcgcagggc cctaccgcca 180
acccgtgcgg ggtctgcgaa tcctgcgttt cgttggcgcc caacgccccc ggcagcatcg 240
acgtggtaga gctggatgcc gccagccacg gcggcgtgga gcaaccccgc gagctgcggg 300
accgccc 307

<210> SEQ ID NO 651
<211> LENGTH: 252
<212> TYPE: DNA
<213> ORGANISM: Mycobacterium tuberculosis

<400> SEQUENCE: 651
gatggcactc acgctggaca agaccttcac aaaatctgaa atcctgaccc gatacttgaa 60
cctggtctcg ttcggcaata actcgttcgg cgtgcaggac gcggcgcaaa cgtacttcgg 120
catcaacgcg tccgacctga aattggcagc aaaccggcgc tgctgggccg ggcatggtgc 180
aatccgaaca agcacgctca acccgtacac caaccccgaa gggccgctgg cccggcggaa 240
ccttgtcctc ca 252

<210> SEQ ID NO 652
<211> LENGTH: 402
<212> TYPE: DNA
<213> ORGANISM: Mycobacterium tuberculosis
<220> FEATURE:
<221> NAME/KEY: unsure
<222> LOCATION: (various positions within the sequence)

-continued

<223> OTHER INFORMATION: applicants are uncertain of bases designated as "n"

<400> SEQUENCE: 652
aacagctatg accatgatta cgccaagcta tttaggtgac actatagaat actcaagctt 60
ctgggcgtcg tggtgcccgg cctgccggtg caggaactgg attttactgc catctctcgc 120
gaccctgagg tggtccaggc ttacaacacc gacccactcg tgcaccacgg acgggttccg 180
gccgggattg gccgcgcgct gctgcangtg ggcgagacca tgccgcggcg ancaccggca 240
ttgaccgcgc cgctgctagt gctgcacggc accgatgacc ggctgatccc catcgaaggc 300
agccgtcgcc tggtcnaatg tntnggatcn gccgacgtgc anctgaanga ntatccccgg 360
ctgtnccacn aggtgttcaa cgaaccggan cgcaaccaag tg 402

<210> SEQ ID NO 653
<211> LENGTH: 429
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 653
caaggcatac gccaagaccc aagggatcgc agtcacctcc gtcaacggcc tggtcgccgg 60
ccacgggtcc gtgcaggaga cgtggctggc catgcaaagc gccgccgcct tatcaggaac 120
gccccggctt gtcggctttt cctgcatcga cacatttccg gaggtgttgt ggttggcgca 180
ncgcgcgaga caggcctggg atggcgtgcg catcgtcatc gggaatgcga tggcaacact 240
gaactacgag cgcatcctgc gccagcatga ctgtttcgac tacgtcgtcg ttggcgacgg 300
ggangtagcg ttcaccaagc tggccttggc cctggcgaat gacctgcggt tgacgactcc 360
cgggactaac ccgccgtant gagcaaggac agattctgcg cacaccctcc tcgctggtcg 420
accttgaca 429

<210> SEQ ID NO 654
<211> LENGTH: 353
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 654
aacagctatg accatgatta cgccaagcta tttaggtgac actatagaat actcaagctt 60
gccggtgatc tgggtggcca actcggcggg caccatctcc atcacgacng caaacgctcc 120
ggcttcggcg acagcgatcg cgtctgcgat ngtttgttcg gcggcgtctc cgcggccctg 180
cacccggaag ccgcccaagg tgttgacnct ttgcggggtg aagccgatgt gtgccatcac 240
cgggatnccc gccgcggtca gacangcgat ttgctcggcc acccgctcac cgccctcgan 300
cttgacngca tgtgcgccgc cgtccttgaa gaaaccggtg gcggnggcaa ccc 353

<210> SEQ ID NO 655
<211> LENGTH: 464
<212> TYPE: DNA
<213> ORGANISM: Mycobacterium tuberculosis
<220> FEATURE:

-continued

<221> NAME/KEY: unsure
<222> LOCATION: (various positions within the sequence)
<223> OTHER INFORMATION: applicants are uncertain of bases designated
as "n"

<400> SEQUENCE: 655
cgttgagatc cagctgcgca ctgtgcagcg cctcggtggt ctgctcggcc tgccgggata 60
actcgttgag cttggccagc gcgtcgtcgg ccggatcagc cagcacattc gcggccagga 120
cgccggagga gacggtgaag ctcgcaaaga aacctatggc ggaccgcatg attacacgcg 180
cgatcaacca cctctggtcg agcctcaaaa tttgcttcct taaacgggcc atcgacggat 240
gacgtcgagc tggtttaggt ctcaaacagg ttacgaaacg atctcggaat tgtccaaaag 300
gggaagttaa gaaaatggat agatttctac catttcgctg tggacgatcg tacttctgct 360
atagggctcc aggggcatcg acacgcaacg accttacgcg acaccggatc cgcgctggcg 420
gcggaacggc accangcgca accgaagggc caatccgaca tcgg 464

<210> SEQ ID NO 656
<211> LENGTH: 515
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 656
atactcaagc ttatctaggc gccagcttga ttggtctggt tgcattggcc agctgcgcga 60
gcctggctca cttcaactac aacaaccgca aacaattgcc gccttcggat ccgagttcgg 120
ttgggtacgc ggcaatggan caccatttct cggtgaatca gactattcct gagtacttga 180
tcatccactc tgcacacgac ctgcgaaccc cgcgcggcct tgccgacctg gagcagctgg 240
cgcaacgtgt gagccanatc ccaggcgttg ccatggttcg cggtgtgacc cggccaaacg 300
gggaaaccct tgaacaggcc cgggcgacat accaagccgg ccaagttggc aaccggctgg 360
gcggcgcgtc gcgaatgatc gatgagcgca ccggcgacct gaatcggctg gcatcgggtg 420
ccaacctgtt ggccgacaat ctcggtgact tcgcggtcaa gtcagccggg ccgttgcggg 480
tgtccgcagc cttgtccagc ccctcgctta ctcca 515

<210> SEQ ID NO 657
<211> LENGTH: 403
<212> TYPE: DNA
<213> ORGANISM: Mycobacterium tuberculosis

<400> SEQUENCE: 657
caggcatgca agctttttga gcgtcgcgcg gggcagcttc gccggcaatt ctactagcga 60
gaagtctggc ccgatacgga tctgaccgaa gtcgctgcgg tgcagcccac cctcattggc 120
gatggcgccg acgatggcgc ctggaccgat cttgtgccgc ttgccgacgg cgacgcggta 180
ggtggtcaag tccggtctac gcttgggcct ttgcggacgg tcccgacgct ggtcgcggtt 240
gcgccgcgaa agcggcgggt cgggtgccat caggaatgcc tcaccgccgc ggcactgcac 300
ggccagtgcc cgcggcgatt cagccatcgg gacatcatgc tcgcttcata ctcctcgacc 360
agtcggcgga acagctcgat tcccggaacg cccacgcatg gtg 403

<210> SEQ ID NO 658
<211> LENGTH: 444

-continued

<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 658
aacagctatg accatgatta cgccaagcta tttaggtgac actatagaat actcaagctt 60
gtagaaaaag atcggtgagc gcatcgattc gctccgccgg gtttgccgct gcggcggcgg 120
agctgccgtg accgtctatt tgggtgatca gatactgggc tagttcggtc ggggtggggt 180
gatcgaagat cgcggtggcc ggcagcgtta ctgcggtgac agctgttaag cggttacgta 240
tctccacggc actcaaggaa ttaaatcccg aatcggcaaa cgcctggcca gcgtcnagtc 300
cggcagcgcc gtcncgcccc agcaccgctg cggcatgctc acataccacc tcgatcgctg 360
cggcganttg ctcgtcngcc gaccgaccgg ccanccgggc ggcaaacccn gaagacccaa 420
gaattcatca ccaccatcgc tagc 444

<210> SEQ ID NO 659
<211> LENGTH: 437
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 659
ccttcttgac acccacctcg ccatcgacct tgagcactcc gtcgtagttg gtgaacatgt 60
gaccggcgat cgggcgggtg aacgcgtact gggtgtcggt gtcgacgttc atcttcacca 120
cgccgtagcg cagcgcctcc tcgatctccg acttaagcga acccgagccg ccgtggaaca 180
cgaaatcnaa cggcttggcg tcngccggca gtccgagctt ggccgccgcc acctgttgcc 240
cttgcgcaag gatgtcnggg cgaancttga cgttgccggg cttgtanacg ccatgcacgt 300
tgccgaacgt cncggccagc angtatttgc cgtgctcacc ggcgcccanc gcctcgatgg 360
ttttctcgaa gtcctccggg ctggtgtaca gcttctcgtt gatctcgttc gccacgccgt 420
cctcttcgcc gccgacg 437

<210> SEQ ID NO 660
<211> LENGTH: 422
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 660
aacagctatg accatgatta cgccaagcta tttaggtgac actatagaat actcaagctt 60
ggaaaggaga tccccgggaa cctggtggca accccgccat tggggttgtt gggattgccg 120
atcagcgtga angaaagctc gtctggagac agcgggtcgg ccgaagccgc aagattggcc 180
atcactagtg acganatcgt ggcgctctgc gagtanccna agacagtgac gttgttnccg 240
gcggcaattt gctgccgaat cgcactttcg agaatgacng caccctgcgc caccgangaa 300
tcnaaagtga ggttcttgat cacgaccacc gggtngagcc cttggggcgt gaagancgcc 360
tgcgcnataa cacccgggac gctgccactc atgtncagcg cgttcgcgan ctcnacatat 420
ct 422

<210> SEQ ID NO 661
<211> LENGTH: 412
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 661
tcctggtgat cganggccgc ggttccggcc gaaaatccgg ttcgggttcg ggtcgcggtt 60
ccaacttgan cgcggtccgc agctgattca ccgtggcaac gccggccaac tgcgcataat 120
gcgcatccga accctcaccc gcccgccccg cgatcacccc aacctgatcc aacgacaacc 180
gcccctcccg catacccegg gcgcagcgcg gaaactccgg caaccgccgc gccaccgtgg 240
cgatcgtgtg ggcgttgcct gacgaacanc ccatcttcca ggccaccaac cccgccaccg 300
accgcgcccc cgtcacaccc cacaacccgt cgcgatccag ctcagccacg atctccacaa 360
tgcgcccatc aatcgcattg cgctgaacgg gcaactccgc caactcctcc aa 412

<210> SEQ ID NO 662
<211> LENGTH: 467
<212> TYPE: DNA
<213> ORGANISM: Mycobacterium tuberculosis

<400> SEQUENCE: 662
aacagctatg accatgatta cgccaagcta tttaggtgac actatagaat actcaagatc 60
tggtacccat ccgtgataca ttgaggctgt tccctggggg tcgttacctt ccacgagcaa 120
aacacgtagc cccttcagag ccagatcctg agcaagatga acagaaactg aggttttgta 180
aacgccacct ttatgggcag caaccccgat caccggtgga aatacgtctt cagcacgtcg 240
caatcgcgta ccaaacacat cacgcatatg attaatttgt tcaattgtat aaccaacacg 300
ttgctcaacc cgtcctcgaa tttccatatc cgggtgcggt agtcgccctg ctttctcggc 360
atctctgata gcctgagaag aaaccccaac taaatccgct gcttcaccta ttctccagcg 420
ccgggttatt ttcctcgctt ccgggctgtc atcattaaac tgtgcaa 467

<210> SEQ ID NO 663
<211> LENGTH: 452
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 663
aacagctatg accatgatta cgccaagcta tttaggtgac actatagaat actcaagctt 60
ancgccacct cccgggcgga actccacggc gtggatnaag gtaccggccg ggatgttgcg 120
caatggcagg ttgttgcccg gcttgangtc cgcgttagcg ccggattcca ccacatcccc 180
ttgcgaaant ccgttgggtn cnatgatgtn ncgcttctcc ccntcnanat aatggancaa 240
cgcnatccgt gcggtacggt tcgggtcnta ctccatgtnc gcgaccttgg cgttganacc 300

-continued

```
atctttgtca ttgcggcgaa agtcnatcat ccggtnagcn cgcntatgan cgccgccttt      360

gtgccgggtg gtaatccggc catgcgcntt gcgtccaccg cgaacgtgca acgggggcnc      420

caacganttc tccngggttg aaccggtnat ct                                   452
```

<210> SEQ ID NO 664
<211> LENGTH: 93
<212> TYPE: DNA
<213> ORGANISM: Mycobacterium tuberculosis

<400> SEQUENCE: 664

```
tgtgtgtggt ggtaacccat ctgagcagtg tgccaaaccg gggcagccag ctcccaattg       60

acgtgagccc gctcacttgc tgggtaagcg tcg                                   93
```

<210> SEQ ID NO 665
<211> LENGTH: 352
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 665

```
aacagctatg accatgatta cgccaagcta tttaggtgac actatanaat actcaagctt       60

gcgggtnatn gccttggtca acggcaccgt gatcggatcn gggtctaccg cacacatnga      120

ctggagcttc ggcgaantca tcgcctatgc ctcgcggggg gtgacgctga ncccnggtga      180

cntgttcngc tcnggcacgg tgcccacctg cacgctcntc naacacctca ngccaccgga      240

atcattcccn ggctggctgc acganagcga nnttgtcncc ctccaagtct aaaggctggg      300

cgananaagc anaacgtccc gacnaacggc actccttttc cntttgctct tc              352
```

<210> SEQ ID NO 666
<211> LENGTH: 448
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 666

```
gaaatcattg atggtttgag tcaccaggcc gatcaagcct tcgccgagcc aaattccaat       60

caagaggccc aagcccgtac caatcagccc ggcaacgagg gattccgtca ttatcagcca      120

aaataactgc tctcgggtta cacccaaaca gcgcaatatg gcgaaaaacg gtcgccgttg      180

cacgacatta aatgtcacgg tattgtagat taaaaagata cccaccaaca angcaatcaa      240

actgagagcg gttaaattga ccgtaaaagc gtccgtcatc tgtttgacng tgtcccgttg      300

ggtatccgac gtttccatac gcacaccggc cggcagtctt tgttggatgc gtnttgcaat      360

ggcctcatct ttgatgatca aatcgatgtn gctcagtctt ccgggcatat ggaacaactc      420

ttgggccgtg gaaatatcag caatgata                                         448
```

<210> SEQ ID NO 667
<211> LENGTH: 386
<212> TYPE: DNA
<213> ORGANISM: Mycobacterium tuberculosis
<220> FEATURE:
<221> NAME/KEY: unsure -continued
<222> LOCATION: (various positions within the sequence)
<223> OTHER INFORMATION: applicants are uncertain of bases designated as "n"

<400> SEQUENCE: 667
ctttcgccca ggccggcgcg gatgtcctca tcgcttcacg aacatcatcc gagcttgacg 60
ctgtcgccga acagatccgc gctgccggcc gccgcgccca caccgttgcc gccgatctgg 120
cccatcccga ggtgaccgcg cagctggctg gtcaggccgt cggagctttc gggaagctcg 180
acatcgtcgt caacaacgtt ggcggcacca tgcccaacac gctgctaagc acctcgacca 240
angacctcgc ggacgccttc gccttcaacg tgggcaccgc ccacgcgctg accgtcgcgg 300
cggtgccgtt gatgctggaa cactccggcg gcggcagcgt gatcaacatc agctccacca 360
tgggccggct ggcggcgcgg ggtttc 386

<210> SEQ ID NO 668
<211> LENGTH: 378
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 668
tgtgggctcc gatccggcgc gcatggcatc gacggcgacg ccgatcgatg acggccaggc 60
ttacgagctt gagggtgtga agttgtggac caccaacggt gtggtagcgg acctgctagt 120
ggttatggcg cgggtaccgc gcagtgaagg gcnccgaggg ggaatcancg cctttgtcgt 180
cgaggctgat tcgcccggga tcaccgtgga gcggcgcaac aagttcatgg gactgcgtgg 240
catcgaaaac ggcgtgaccc ggcttcntcg cgtcagggtg cccaaagaca acttgatcgc 300
anggaagcga cggtctgaag atcgcgctga ccacactcaa cgccggacgg ctgtccctac 360
cggcgatcca accggagt 378

<210> SEQ ID NO 669
<211> LENGTH: 344
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 669
gagctggccg agctggaccg gttcaccgcg gaactaccgt tctcgctcga cgactttcag 60
cagcgggctt gcagcgcgct ggaacgcggc cacggtgtgc tggtgtgcgc gccgaccggc 120
gctggcaaga cagtggtcgg cgagttcgcc gtgcacctgg cgctggcggc cggcagtaaa 180
tgtttctaca ccacgccgct gaaagccctg agcaaccaaa agcacaccga tctcacagca 240
cgctacggcc gtgaccagat ctggctgctg accggtgacc tgtcngtcaa cggcaaccgc 300
cggtggtggt gatgaccacc gaaatgctgc gcaacatgct ctac 344

<210> SEQ ID NO 670
<211> LENGTH: 411
<212> TYPE: DNA
<213> ORGANISM: Mycobacterium tuberculosis
<220> FEATURE:
<221> NAME/KEY: unsure -continued
<222> LOCATION: (various positions within the sequence)
<223> OTHER INFORMATION: applicants are uncertain of bases designated as "n"

<400> SEQUENCE: 670
gatctctgga tcggcggggc tctccgggcc ggcctcggcg acctcagcgg gccgcgcctt 60
ccggccgaac cattccctag ccatagatga ccgcacctcg atgcacggtt tggcggcaac 120
gcggcaaggc gtcngtcggg cccagccgcg gcaatgcggg tacccgggag cgcgggtcng 180
tanaccancg ctggactgcg tcgcgcggtg cgtcnacntc aaagtccccg gcgtcccata 240
tcgcgtatga cgcgggcgcg cccggcacca ngggtgccga tccggccgtc tcgaacacca 300
ccggcccgcc agccgccgcg ggtccggcag cnaacccgcc cgcgccgata cccgctgccc 360
gcgtgcgtga ttgaccgccg cgcgcacgct ggccanggat caaagcccgt g 411

<210> SEQ ID NO 671
<211> LENGTH: 473
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 671
ggacgcgtag cccgccaggc cggtcagggt gcccttccag tccacgccgc tgtggtcggc 60
gaaccgctta tcttcaatcg agacgatcgc cagcttcatc gtgttggcga tcttgtccga 120
gggcacctcg aaccggcgct gcgagtncag ccacgcgatc gtgttgccct tcgcgtcgac 180
catcgtcgat accgcaggca cttgcccctc gagcagctgg gccgagccgt tggcaacgac 240
ctcagangca cgattggaca tcagccctag cccgcctgcg aacgggaacg tcagcgcagt 300
ggcgacgaca ctggccaaca gacagcaccc agccagcttc agaacggtga tcgcggccgg 360
gaagcgctcg ggcatgcgtn ctacagtagc gacctcctgt cactccacgt gccgctcggt 420
ccaatagaat ctttccgcgg gcgggtgaat ctctgcngga tcggggcngg cgc 473

<210> SEQ ID NO 672
<211> LENGTH: 357
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 672
gctcgttgcc ggcggcgatc tcgtcgagct cgtcttccat cgccgcggtg aagtcgtagt 60
cgacgagccg accgaaatgc tgctcgagca gaccggttac cgcgaacgcc acccatgacg 120
gcaccagtgc actgcccttc ttgtgcacgt ngccgcgatc ctggatggtc ttgatgatcg 180
acgantaggt cgacgggcgg ccgatgccca gctcctcgag cgctttgacc agcgacgcct 240
cngtgtnncg ggccggcggg ttggtggcat ggccgtctgg ggtcaactcg acnatgtcca 300
accgttgacc cggggtcaga tggggcagtc gccgctcggc atcgtcagcc tcgccgc 357

<210> SEQ ID NO 673
<211> LENGTH: 402
<212> TYPE: DNA
<213> ORGANISM: Mycobacterium tuberculosis -continued
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 673
gtctttcgat ggctgcttct tcggcgctga cgctggcgat ctatcacccc cagcagttcg 60
tctacgcggg agcgatgtcg ggcctgttgg acccctccca ggcgatgggt cccaccctga 120
tcggcctggc gatgggtgac gctggcggct acaaggcctc cgacatgtgg ggcccgaagg 180
aggacccggc gtggcagcgc aacgacccgc tgttgaacgt cnggaanctg atcgccaacn 240
acacccncgt ctgggtgtac tgcggcaacn gcaagccgtc ggatctgggt ggcaacaacc 300
tgccggccaa gttcctcgag ggcttcgtgc ggaccatcaa catcaagttc caagacgcct 360
acaacgccng tggcggccac aaccgcgtgt tcgacttccc gg 402

<210> SEQ ID NO 674
<211> LENGTH: 336
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 674
gccaggtcga ggtcccatgc gcgtgggcca ttgatgctga tcgccaggac gtcaaanatt 60
tggtccggcg tcagctgggc gaaaaacgtg ggccccagga cttgcccgga gctgcccggg 120
ttcccgtcgc gcagctcggc ggccccggtc agaaanaaat tgcgccaggt cgcacactcc 180
gcgccgtang ccagctgctc cagggtgtcg gcatagagcc cgcgggccgc agcgtgctcg 240
ctgtcggcga acaccgcatg gtcgagaagc gttgccgccc aacggaaatc acctgcgtcn 300
aangcttcgc gggccaactc cagcactcgg tcgatg 336

<210> SEQ ID NO 675
<211> LENGTH: 405
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 675
naaacgttcc ggcttnggtg ccgggcgctt atttgcgtct ctgggatcac nctcagtcgc 60
cggcggctgc cgttgggcta tnanttgcac cganccggaa aatccgcacn anaactgcna 120
gtagcggcct gcagaantgc atcctcggcg aancngacta ccggtggaca ncnacaagcg 180
ccgccgaaca acgcactggc ccgagggatn ggcgtctatc ggccccgccc gtcgaactng 240
gaacagacng tgcggttcta ccgtgatctg gtgggaatgc tcnaccanac cttcccnann 300
gctacggaac nacggcgcga tattcngccn tcccanctcg agcctgacnc tngatatcgt 360
cgannctcac catcncgatc ngctgtgccg gtnttgctcg gactn 405

<210> SEQ ID NO 676
<211> LENGTH: 389
<212> TYPE: DNA
<213> ORGANISM: Mycobacterium tuberculosis -continued
<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 676
cgaacgacga acnccncaag ccatggtggt tggcgccgtc aaaaggtccg cggtcgccac 60
tactggaaaa tcgccttgag cgtcnctcga ccnccgcctc gagttgggtc ntaacgaaat 120
acctgatgcc gatcangtcn acgtctccgt cgcnncaacg tgcagcggcg acccactcta 180
cnangtctcg gtnccgccnc ggccagngca ccaccagtga cnaatccntg cgccntcggg 240
ccnagcantc ccggtgcnac cgnggtgggt ccggcgatgg tngggtgtnc tcnntacngg 300
aacgccagcg cnatcancat cggcanactc ncgtcgatgt gccgcggcgc aaccatcccc 360
cacaatgatc nggtgcgtct gatcaggcn 389

<210> SEQ ID NO 677
<211> LENGTH: 135
<212> TYPE: DNA
<213> ORGANISM: Mycobacterium tuberculosis

<400> SEQUENCE: 677
ttaggcgtga cggccaccgg ggccactccg cacaatctgt acccgaccaa gatctacacc 60
atcgaatacg acggcgtcgc cgactttccg cggtacccgc tcaactttgt gtcgaccctc 120
aacgccattg ccggc 135

<210> SEQ ID NO 678
<211> LENGTH: 140
<212> TYPE: DNA
<213> ORGANISM: Mycobacterium tuberculosis

<400> SEQUENCE: 678
cgtcaccccg atgcgcccag atcggggctt cgcagataaa gcacgaactg gcgggcaaaa 60
cgtcgatctc ggagccggaa gggcaatcag ccgaccgtcg acgaacgaca ccggcgagac 120
cacttaggca gtgacggcct 140

<210> SEQ ID NO 679
<211> LENGTH: 272
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 679
cttttcncga tgtctcatga tnccnangga gaacnntgcn ancncngccg ctgacntngc 60
ncaccgctnt ggcngnggtg acattggtgg tggttgcggg ctgcnacgcc cgactcgang 120
ccganccatn tnttgcggcc gaccgcntnt cgtctcnacc gcanncccna tctcngccgc 180
ncccggtgga nctacngctn cttcgccatc tctcgccnat ggctccngcg nntcgcncaa 240
cgtntggttt ggtnanctgc ctacctggtc nt 272

<210> SEQ ID NO 680
<211> LENGTH: 507
<212> TYPE: DNA
<213> ORGANISM: Mycobacterium tuberculosis
<220> FEATURE:

-continued

<221> NAME/KEY: unsure
<222> LOCATION: (various positions within the sequence)
<223> OTHER INFORMATION: applicants are uncertain of bases designated as "n"

<400> SEQUENCE: 680
gctgcgccag tcgttcggtg cggtcatgcc gttggaccna ccatcggagt tagttgccga 60
accgcggacc accgcaagca cccggtcctg gtcgcgcacc gcgtcggcca accgcttgag 120
caccaccacg ccgcagccct cgccgcgcac gaatccatcc gcgttggcgt cnaanctgtn 180
gcatcggtcg gtcggtgaca gcgccgacca cttggacagc gcgatggcgg tgaacggtna 240
ntaggtgacc tgccnccncg cccgccaatg cccacctccg cttcacncat gcgaatggtc 300
tgacacgccn agtgaattgc caccagcgac aacaaaaatc ggtatctncn gcgacggcgg 360
acacgcnatc ccnactgata ctcgatccgc cccaccgctt gnanctccgg gttccngtgc 420
tcatgtaccn tcatgtcggt ctgcgcncga tattgacgat cgtgtttccc acgannanag 480
ancctcatca cgccggttcg agtgccg 507

<210> SEQ ID NO 681
<211> LENGTH: 470
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 681
ctgtgtgcgg ncggcgcgat atcggccttt ttactaaccg aacccgatgt gggctccgat 60
ccggcgcgca tggcatctac ngcgacgccg atcgatgacg gccaggctta cgagcttgag 120
ggtgtgaant tgtggaccnc caacggtgtg gtagcggacc tgctantggt tatggcgcgg 180
gtaccgcgca gtgaanggca ccgaggggga atcancgcct ttgtcgtcta ngctgattct 240
cccgggatca ccntggagcg cnccncnant tcatgggact gcgtggcatc caanacggcg 300
tgaccggctt catccntcng ggtgcccaaa gacaacttga tcngcnngga agcgacgtct 360
gaanatcgcg ctgatcncac tcaacgccgg acgctgtcct accggcgatc gcaccggant 420
tgccaanccg cgctnannat ncgcgngaat gnccgtccac nantgcatgg 470

<210> SEQ ID NO 682
<211> LENGTH: 346
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 682
tggggtgccg ggcgccgagt tgcgtccctg ggatcacgca gagtcgccgg cggctgccgt 60
tgggctatga attgcaccga gccggaaaat ccgcancaaa actgcgagta gcggcctgca 120
gaagtgcanc ctcggcgaaa cggagtacgg tggacaacga aaagcgccgc cgaacnacgc 180
actggcccga gggattggcg tcaatcggcc ccgcccgtcg aacttggaag anacantgcg 240
gttctaccgt gatctggtgg gaatgctcca acnnaccttc nccgaaagct acggaagcna 300
cggcgcgatn ttcggccttc ccagctcgac ctgacgctgg aaatcg 346

-continued

<210> SEQ ID NO 683
<211> LENGTH: 453
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 683
nggcngggaa gttaatgccc tactggttcn atgctcncac ntcnccngtg acnncctgcn 60
ccgacccgcc gaggtcctgn ccgtnaccac cgancnggcg atccgggact ctngtacgca 120
tccaacanng ancaacgtgc acgggcggag tngtnccgcc acttcgncna tgacggggtc 180
gatccnttcg acgtccgtcg ccgcgtcggt cgagtggcgg tcacnctccn ngtactcgac 240
cncacngacg agaggactcg ancccatcta cgtgtggacg aaacanatct tctgtccnac 300
gactacacca ccacccaggc catcgccgnc gcccgcgang ccccttcgac gccntactgg 360
tccngnggng gcgctctccg gttgtctnnc ncntgncgtg ttccttcacn cactgcccna 420
catcganccc gagcnatncn angtccgtca atc 453

<210> SEQ ID NO 684
<211> LENGTH: 382
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 684
ggacactgtt cgcgtgcccc tcgtcaaagc cggagtggtc gtgctgcgcc ggacccgacc 60
cgaccttcag cgggggttca cagctccgtg ggtgccgtta cttccgatcg ccgcagtgtg 120
cgcgtgcctg tggctgatgc tgaacctcac cgcgttgact tggatccggt tcgggatctg 180
gctggtggcc ggaaccgcga tttatgtcng ctacgggcgc cggcactcgg cgcatggcct 240
tcggcaagcn cnananaacg cgacccggag gtgttgaact agcttcgccg cgtatttaca 300
aattgcntta tatgtctaca cataagacgc aaactgctct attgtcaant cccancgtgg 360
tgtggcncat gaagatgttt gg 382

<210> SEQ ID NO 685
<211> LENGTH: 408
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 685
tccttctcgg tatcggtttg ggctgtcacc ancagttggt agttcttcac gtnctgttgt 60
tcgagcgtcn agccgtcgcg cgtgtcnang tcnccggacg cgtatcccgc caggccggtc 120
anggtgccct tccantccac gccgctgtgg tcggcgaacg ctnatcttca atcgagacca 180
tcgccagctt catcntgttg gcgatcttgt cnnacggcac ctcnaaccgg cgctnctagt 240
acnccacncn atcntgttnc cttcncgtcn acatcctcga tnccncntgc actttccctc 300

-continued

```
gancncctgg gccgagccgt tggcantnac ctcngagccc cattggacat cancccancc    360

cgcctgcgaa cgggaacgtc agcncnctgg cgacaacctg gccaacan                 408


<210> SEQ ID NO 686
<211> LENGTH: 372
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 686

cacnccgtga tcgcnagccc cngtagaaat ngttgagcca gttggtgcgg cgctcgttgc     60

cggcggtnat ctcgtcgagc tcntcttcca tcgccgcggt gaagtcgtac tcgacnagcc    120

gaccnaaatg ctgctcnagc agaccggtta ccnnnaacnc cncctcntga cngcaccagt    180

gcnctgccct tcttgtgcac gtacccgcna tcctggatgg tcttgatgat cnactantnt    240

gtcgacgggc ggccgatgcc catctcctcn agcgctttga ccagcgacnc ctcggtgtat    300

cgggccggcg ggttngtggc atggccgtct ggggtcanct cnacnatntt canccgttga    360

cccggggtca ca                                                        372


<210> SEQ ID NO 687
<211> LENGTH: 403
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as
      "n"

<400> SEQUENCE: 687

tggccttctt gncangggcn nacatnngct atngcgagcg tgtaaccgat catcntccng     60

gcgactgtgg cctgancggc aagggtngcc tnattcntcc tcctgnggca tggttnccac    120

acggaatgnc ggtaagtctg gtcggcaacc tggcccgctg cgggttgggt tcggattcgc    180

tcggctanta aggtgctcgc ctggtgtnac nactaatcnc natatacnct tancgggagt    240

ngncgtcccg atcctngccc tgccgcnggc gatcncgttc gcancaccgc caccggaact    300

cncaangtgc gctcatcggg ctctacgcgc catcttcccc ggattcttcg cggcngngtn    360

ccgngggacc ccggactgtg acnggcccaa cggctcatca tcg                      403


<210> SEQ ID NO 688
<211> LENGTH: 356
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 688

ccggatagcg gtgtctgaac ttcgcccgtt ccctccancg cattgagctt cagcccgacc     60

ggcaggtnng gagtcggcat gcggtccttc gccccgaccc cgctggctaa atanccaccc    120

ccgagcgcgg tcacggtctt tgcaccggga cgacgcatac cggcagcgcg aacatcnccg    180

cgggctgcag cntgaacgtc caataccant cnaacagtgt ccgcgcgtna aaacccganc    240
```

-continued cggcggtcgc ttcngtaatc aacggctcct gcgcaaccag ctgcaagtcg ccggtgccac 300
cggcgttgac gatcttgatg tctgcganct cgcgcaccag ctcgacggcc cgggca 356

<210> SEQ ID NO 689
<211> LENGTH: 439
<212> TYPE: DNA
<213> ORGANISM: Mycobacterium tuberculosis

<400> SEQUENCE: 689
cctcccgacc acatacaggc aaagtaatgg cattaccgcg agccattact cctacgcgcg 60
caattaacga atccaccatc ggggcagctg gtgtcgataa cgaagtatct tcaaccggtt 120
gagtattgag cgtatgtttt ggaataacag gcgcacgctt cattatctaa tctcccagcg 180
tggtttaatc agacgatcga aaatttcatt gcagacaggt tcccaaatag aaagagcatt 240
tctccaggca ccagttgaag agcgttgatc aatggcctgt tcaaaaacag ttctcatccg 300
gatctgacct ttaccaactt catccgtttc acgtacaaca ttttttagaa ccatgcttcc 360
ccaggcatcc cgaatttgct cctccatcca cggggactga gagccattac tattgctgta 420
tttggtaagc aaaatacgt 439

<210> SEQ ID NO 690
<211> LENGTH: 442
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 690
cttcacntcc gtacggctcg ggtacgcttc ggtcncattg tgcgagtgat agatgacgac 60
cgggacctcg tcggcatctt ccatagcccg ccacaccttc agttgctcac cggaatccaa 120
ccggtanaag gtcggcganc gctcngcatt ggtcatcggg atatgccgct cgggacggtc 180
anagccctcg ggtccggcca gcactccgca ggcttcgtcg gggtggtcgc gacgcgcatg 240
ggccaccatc gcattcacca ggtctgcgcg aatcaccagc acgtanacgg ttcctttcct 300
aagcaacacc gaantttcag gacccgaatg ctccgggaaa catgtcacgg taggtcggta 360
ttccggctac cggctganca ttgagcacgc cggccagcac cgcacgaacc aggcaatcag 420
ccgccgccgc acccgaccgc gg 442

<210> SEQ ID NO 691
<211> LENGTH: 365
<212> TYPE: DNA
<213> ORGANISM: Mycobacterium tuberculosis

<400> SEQUENCE: 691
caggcatgca agcttgatgc cgccgaaacc gagcgtgagc acgccgccag ccaccacgcg 60
cgggtcgggc gccgggcccg ggccgccagg ctgctccgct cggtgatggc acgccaccgc 120
gacaccaccc ggctgcgcta cgtcgagcca taccgggcgg agctacatcg gctcggccgc 180
ccagtgttcg ggccctcttt cgaggtcgag gtcgataccg atttgcgcat ccgcagccgc 240
accctggacg acagaaccgt gccctacgaa ttgcttgtcg ggcggggcca aagaacagct 300
tggcatcctg gcgcgattgg ccggcgcggc gctggtcgcc aaggaagacc cgttccggtg 360
ctgat 365

<210> SEQ ID NO 692
<211> LENGTH: 307
<212> TYPE: DNA
<213> ORGANISM: Mycobacterium bovis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 692
aagntcgggt ttccacacgc gcggtttgac cctagtcata tgtaatcatg tgtaccatgt 60
gcgggcgctt ttcgacggcc gcgaaccacc gganatttcc tgtgatttca ctgcatgcgt 120
accatctggc acaattgagc anttgtctnt cgcggtggtc ggncgggttg cgtgccgcct 180
gctgcganat gcaccantaa gcccgaaccc accggcttgg tgaccaccgc acgctgcgtg 240 tgggggtaa ccactccgcg accccaagga tggtcatttc caatgaaccg gctggacttc 300 gtccana 307

<210> SEQ ID NO 693
<211> LENGTH: 414
<212> TYPE: DNA
<213> ORGANISM: Mycobacterium bovis

<400> SEQUENCE: 693
gtcgcggttc gatcgacccg atcttcacct cgtaacctcg atgcttagca ggatccagct 60
tgaccgcgtt tggctctacc cactctttga gtggcgccgt cgcctgtgcc ccatcggtgt 120
tcatgacgaa cgcttcgaaa gacttcctct tgtgagccgg aatgtctgcg taaagaagtt 180
ccatgtccgg gaagtagacc cggtcgccct ccacgtggta ctccttcgag gtccgcttct 240
cgccggatcc gataaacacc ggccccaggc accgcagcgt gagttcgaac ggcttcaggt 300
aggtgttcat gcggcggact ccgggagtgc gagaaatagc ggtcgcgcgt agctgtagac 360
cggatggttt ccgcccaggc tgacgtcgaa gatgcctcct tggaaggggc gcga 414

<210> SEQ ID NO 694
<211> LENGTH: 256
<212> TYPE: DNA
<213> ORGANISM: Mycobacterium bovis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 694
aactcaagtt tttacggtga tcgcgcatca cctggttcat gaactggaag cagcgcagcg 60 cttcctttc ggccgcaaca tgagccagcc tctcgtcggc ggtcgggtgc aggtgctcgg 120
gcagctcggc cgcgacagcc gcctgaccct gaaaccagct tccatatccc gcgacnaacg 180
acgccagtcc gctacgtaac ccctccgcga ctgtccatgg acaacagcgc gttctccacc 240
gaccgggccc gggtgt 256

<210> SEQ ID NO 695
<211> LENGTH: 328
<212> TYPE: DNA
<213> ORGANISM: Mycobacterium bovis
<220> FEATURE:
<221> NAME/KEY: unsure
<222> LOCATION: (various positions within the sequence)
<223> OTHER INFORMATION: applicants are uncertain of bases designated -continued as "n"

<400> SEQUENCE: 695
gtgcaggttt cgacaatgtg gtgccggttc ggcggctacg tgccatcgag acactggcgc 60
angctatcgc acccgttatc ggctgcgagc aaatcgcggt atgcgttctt gagcatgagt 120
cggcgaccgt cgtcatggtc gacacccacg acggaaagac gcagatcgcc gtcaagcatg 180
tgtgccgcgg attatcagga ctgacctcct ggctgaccgg catgtttggt cgcgatgcct 240
ggcgcccggc cggcgtggtc gtggtcggct cggatagcga ggtcagcgaa ttctcgtggc 300
agctcgaaag ggtcctgccg gtgccggt 328

<210> SEQ ID NO 696
<211> LENGTH: 278
<212> TYPE: DNA
<213> ORGANISM: Mycobacterium bovis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 696
ttcgagtcat gcgcccgcct cgaccacgaa natgcacgtc gnggttcgat cgacccgatc 60
ttcacctcgt aacctcgatg cttagcagga tccagcttga ccgcgtttgg ctctacccac 120
tctttgagtg gcgccgtcgc ctgtgcccca tcggtgttca tgacgaacgc ttcgaaagac 180
ttcctcttgt gagccggaat gtctgcgtaa agaagttcca tgtccgggaa gtagacccgg 240
tcgccctcca cgtggtactc cttcgaggtc cgcttctc 278

<210> SEQ ID NO 697
<211> LENGTH: 264
<212> TYPE: DNA
<213> ORGANISM: Mycobacterium bovis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 697
gtcatgtgta ccatttgcgg gcgcttttcg acggccgcga aacaccggag atttcctgtg 60
atttcactgc atgcgtaccg tctggcacaa ttgagcagtt gtctgtcgcg gtggtcggcc 120
gggttgcgtg ccgcctgctg cgagatgcac caataagccc gaacccaccg gcttggtgac 180
caccgcacgc tgcgtgtggg gggtaaccac gccgcgaccc caaggatggt catttccaat 240
gaaccggctg gacttcntca acaa 264

<210> SEQ ID NO 698
<211> LENGTH: 169
<212> TYPE: DNA
<213> ORGANISM: Mycobacterium bovis

<400> SEQUENCE: 698
aacagcgcgg ttgaactgat aggtgcggcc cggctcgagc aggccgggcc atttgttcga 60
tgcggttacc gaaagatctc ttcggtgacc tgcccgccgc cggccagctc ggcccagtgc 120
ccggcgttgg ccgccgcggc gacgatcttg gcgtccacgg tggtcgggg 169

<210> SEQ ID NO 699
<211> LENGTH: 256

-continued

<212> TYPE: DNA
<213> ORGANISM: Mycobacterium bovis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 699
gcatctgggc tggcggtggt tcgccgctcc gaagccgtcg aacaccatcg ccagcgcggc 60
ttccacatca acgaccattt cggccagctt gcggcgcatc agcggcttgt cgatgagcgc 120
cccaccgaat gcccgccgct gcccggcgta ncacagcgat tcgaccagcg cgcggcgcgc 180
gttgccgagg gcgaacgaag cggtgcccaa ccgcaatctg ttggtcagct ccatcatgcg 240
ggtgagtccc ttgccg 256

<210> SEQ ID NO 700
<211> LENGTH: 291
<212> TYPE: DNA
<213> ORGANISM: Mycobacterium bovis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 700
atcggtttcc agcaacagcc gatcgacggc ttcgcccagg ccgctcccgg gcgacccgac 60
cattgctgtc gccgcgtaac gccatcacgg atgacgcgca gttcgtcgct gtctagctcc 120
accatcgcct gcacaccggc ggccagnacc cattggccgt cgcactcgta nagcaggtaa 180
tcctcgtcga cggactcggt aaccaccgcc gccagctccg ctgccaggtc ggcggggttg 240
acaccggcgg gcatcgggat ggacgacgac gcggtgctga cggcgcctgt c 291

<210> SEQ ID NO 701
<211> LENGTH: 315
<212> TYPE: DNA
<213> ORGANISM: Mycobacterium bovis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 701
agcggtttcc cangcgggat gtgctgtgag cgccgcacca ccagcgccga cgctaaggat 60
ggaacgcacg gcatcttctg acgcgtaacc gcgttgtgat cgcgagctga ggagacggta 120
tgggggaggg ttctcggagg ccatctggga tgttgatgtc tgtcgatctt gagccggtgc 180
aactcgtcgg cccggacggt acgccgacgg ccgaacgccg ctaccaccgt gaccttcctg 240
aggaaacgct gcgttggctc tacgagatga tggtggtcac ccgcgagctg gataccgaat 300
tcgtcaatct gcacg 315

<210> SEQ ID NO 702
<211> LENGTH: 328
<212> TYPE: DNA
<213> ORGANISM: Mycobacterium bovis
<220> FEATURE:
<221> NAME/KEY: unsure
<222> LOCATION: (various positions within the sequence)
<223> OTHER INFORMATION: applicants are uncertain of bases designated as "n"

-continued

<400> SEQUENCE: 702
caagcttcca caggtaggga tcgaggaaca gcgcgttgaa ctgataggtg cggcccggct 60
cgagcaggcc ggccatttgt tcgatgcggt taccgaaaat ctcttcggtg acctgcccgc 120
cgccggccag ctcggcccag tgcccggcgt tggccgccgc ggcaacgatc ttggcgtcca 180
cggtggtcgg ggtcatgccc gcgagcagga tcggcgagcg gccggtcagc cgggtgaact 240
tcgtcgaaag cttgaccctg ccgtcgggga ggcgaaccac ggtcggtgcg tanctccacc 300
aagcccgggc aacctcgggg gtggcgcc 328

<210> SEQ ID NO 703
<211> LENGTH: 352
<212> TYPE: DNA
<213> ORGANISM: Mycobacterium bovis

<400> SEQUENCE: 703
tggacctcat gacaacgcgg cggcgattac ccccgctacc gccagcagca tgacggcggt 60
agcgaacacc gccggatgca gcgcaggtgc gtcgatgtgc tcacggaatc gccccggcac 120
cgcgatctcg aggatcacca gtgccacccc ctgcagcgcg acaccgacga ttccgtacac 180
cgccacgccg atcaggccct gggccagctg gcgtatatgg cggcgatggt gacgatggcc 240
agcgccacat acattgtggc ggccagaacc acggcgttgg ggcggcggtc gatgaacact 300
aggcgacgca gatcgcccgg ggtcaacagg ttgaccatca gaaagcctgc ga 352

<210> SEQ ID NO 704
<211> LENGTH: 315
<212> TYPE: DNA
<213> ORGANISM: Mycobacterium bovis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 704
tttggtgcgg ccggcaatca acttcngctc ncagcggttt cccaggcggg atgtgctgtg 60
agcgccgcac caccagcgcc gacgctaagg atggaacgca cggcatcttc tgacgcgtaa 120
ccgcgttgtg atcgcgagct gaggagacgg tatgggggag ggttctcgga ggccatctgg 180
gatgttgatg tctgtcgatc ttgagccggt gcaactcgtc ggcccggacg gtacgccgac 240
ggccgaacgc cgctaccacc gtgaccttcc tgaggaaacg ctgcgttggc tctacgatat 300
gatggtggtc acccg 315

<210> SEQ ID NO 705
<211> LENGTH: 390
<212> TYPE: DNA
<213> ORGANISM: Mycobacterium bovis

<400> SEQUENCE: 705
cgcccagggc cgctcccggg cgacccgacc attgctgtcg ccgcgtaacg ccatcacgga 60
tgacgcgcag ttcgtcgctg tctagctcca ccatcgcctg cacaccggcg gccaggaccc 120
attggccgtc gcactcgtag agcaggtaat cctcgtcgac ggactcggta accaccgccg 180
ccagctccgc tgccaggtcg gcggggttga caccggcggg catcgggatg gacgacgacg 240
cggtgctgac ggcgcctgtc gcgacgctga gctcggacac agctagtaaa tgtagcctaa 300
cctacttaat gggtcgcagc cccccggggt cgtcgcatgt ccaacgttgc tcgactggaa 360

-continued

```
gaaaatgctc gtcggggagc aaatggcacc                                    390


<210> SEQ ID NO 706
<211> LENGTH: 322
<212> TYPE: DNA
<213> ORGANISM: Mycobacterium bovis

<400> SEQUENCE: 706

aatactcaat cttgatcggt ttccagcaac agccgatcga cggcttcgcc cagggccgct    60

cccgggcgac ccgaccattg ctgtcgccgc gtaacgccat cacggatgac gcgcagttcg   120

tcgctgtcta gctccaccat cgcctgcaca ccggcggcca ggacccattg gccgtcgcac   180

tcgtagagca ggtaatcctc gtcgacggac tcggtaacca ccgccgccag ctccgctgcc   240

aggtcggcgg ggttgacacc ggcgggcatc gggatggacg acgacgcggt gctgacggcg   300

cctgtcgcga ctctgagctc gg                                            322


<210> SEQ ID NO 707
<211> LENGTH: 398
<212> TYPE: DNA
<213> ORGANISM: Mycobacterium bovis

<400> SEQUENCE: 707

ggatgtgctg tgagcgccgc accaccagcg ccgacgctaa ggatggaacg cacggcatct    60

tctgacgcgt aaccgcgttg tgatcgcgag ctgaggagac ggtatggggg agggttctcg   120

gaggccatct gggatgttga tgtctgtcga tcttgagccg gtgcaactcg tcggcccgga   180

cggtacgccg acggccgaac gccgctacca ccgtgacctt cctgaggaaa cgctgcgttg   240

gctctacgag atgatggtgg tcacccgcga gctggatacc gaattcgtca atctgcagcg   300

ccagggggaa gctggcgttg tacacgccct gtcgcgggca ggaagccgcg caggtgggtg   360

cggcggcttg cctacgcaaa accgactggt tgttcccc                            398


<210> SEQ ID NO 708
<211> LENGTH: 175
<212> TYPE: DNA
<213> ORGANISM: Mycobacterium bovis
<220> FEATURE:
<221> NAME/KEY: unsure
<222> LOCATION: (various positions within the sequence)
<223> OTHER INFORMATION: applicants are uncertain of bases designated
      as “n”

<400> SEQUENCE: 708

atcacgacaa cagcgacggt gtgtcggatc agcggccccc gttgccgggc aatgttgagg    60

cgtttctgcg tctggttgag gccggctggg acnccgaggt ggctcgtcgg ccacatgggc   120

agcacaccac cgtggtgatg catctagacg tgcaggaccg tgccgctggc ctgca         175


<210> SEQ ID NO 709
<211> LENGTH: 210
<212> TYPE: DNA
<213> ORGANISM: Mycobacterium bovis

<400> SEQUENCE: 709

gcggctacgt gccatcgaga cactggcgca ggctatcgca cccgttatcg gctgcgagca    60

aatcgcggta tgcgttcttg agcatgagtc ggcgaccgtc gtcatggtcg acacccacga   120

cggaaagacg cagatcgccg tcaagcatgt gtgccgcgga ttatcaggac tgacctcctg   180

gctgaccggc atgtttggtc gcgatgcctg                                    210
```

-continued

<210> SEQ ID NO 710
<211> LENGTH: 312
<212> TYPE: DNA
<213> ORGANISM: Mycobacterium bovis

<400> SEQUENCE: 710
tacaagcggc acctcgccgg tgaactgacc gttcgcacgc tgcgcaccgc cgccgggcgc 60
gtgctcggcg cgccggcggc ccccgaggcc tgagagggga accaaccatg caggtgaaca 120
tgacggtaaa cggcgagccc gtcaccgccg aggtcgaacc ccggatgctg ctggtccatt 180
ttctccgtga tcagctgcgg ctcaccggaa ctcactgggg ctgtgatacc agcaactgcg 240
ggacatgcgt ggtggaggtc gacggcgtgc cggtgaaatc ctgcacgatg ctcgccgtga 300
tggcctccgg gc 312

<210> SEQ ID NO 711
<211> LENGTH: 255
<212> TYPE: DNA
<213> ORGANISM: Mycobacterium bovis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 711
agcggctggt tacgactccc tgtttgtgat ggaccacttc taccaactgc ccatgttggg 60
gacgcccgnc cntccgatgc tggaagccta cactgccctt ggtgcgctgg ccncngcgac 120
cgagcggctg caactgggcg cnttggtgac cngcaatacc taccgcaccc cnaccctgct 180
ggncaaanat catcaccacg ctcgacttgg ttagcgccgg tcgancgatc ctcggcattg 240
gaaccggttg gtttn 255

<210> SEQ ID NO 712
<211> LENGTH: 304
<212> TYPE: DNA
<213> ORGANISM: Mycobacterium bovis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 712
acgcgcgccg atcatatctg ctatggatgt acaattcagc tcttgctgtt ataccagtat 60
atggtgtact atttgatcta tgctgacgtg tgagatgcgg gaatcggccc tggctcgact 120
cggccgggct ctggctgatc cgacgcggtg ccggattctg gtggcgttgc tggatggcgt 180
ttgctatccc ggccagctag ctgcgcacct cgggttgacc cgatcgaatg tgtccaacca 240
tctgtcgtgt ttgcggggct gcgggctggt antcccaacc tatgagggcc ggcaggttcg 300
gtat 304

<210> SEQ ID NO 713
<211> LENGTH: 352
<212> TYPE: DNA
<213> ORGANISM: Mycobacterium bovis

<400> SEQUENCE: 713
ccgcgctgct gctgacgtcg gtcgaacgtg cgacacgtct gcgaataccg gccgaacgct 60
gggtttatcc acaggctggc accgacgccc acgacacacc ggccgtcgcc gaccgccacc 120

-continued gactgcatcg gtcgacggcc attcggatcg ccggtgcccg ggcgctggaa ctggctgggc 180
tggggctcga tgacatcgaa tacgtcgacc tgtattcgtg ctttccctcc gctgtccaag 240
tcgccgcaat cgaactcggc ctggacaccg acgatcctgc ccgcccgctg accgtcaccg 300
ggggcctgac cttcgccggc gggccgtgga gcaattacgt cacgcactcc at 352

<210> SEQ ID NO 714
<211> LENGTH: 233
<212> TYPE: DNA
<213> ORGANISM: Mycobacterium bovis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 714
caggcgtgca atgacctgca ctgcgccgga nantccctaa cccactaaac cggggccgct 60
cacaagccgt gcagctcggt cagcgtcagg tgcgcgacca ggaantaaat gagcagaccc 120
gtgccgtcaa cgatggtggc gatcatcggc cccgaaacga tggccgggtc natgcgcaac 180
ttcttcagca gcggcggaag gacggcancc accagcgacn accacaccac gat 233

<210> SEQ ID NO 715
<211> LENGTH: 335
<212> TYPE: DNA
<213> ORGANISM: Mycobacterium bovis

<400> SEQUENCE: 715
gcgaacactt cgtcaacttc cagggctgcc cgcaccaagt atttcgacga gtatttccgt 60
cgggccgccg ccgccggcgc gcggcaggtg gtcatcctgg cggcggggct ggactcgcgc 120
gcgtaccggc tgccttggcc cgacgggacc acggtttttg agctggaccg cccgcaggtc 180
cttgatttca agcgcgaggt gctcgccagc cacggtgccc aaccgcgcgc cctgcgccgc 240
gagatcgccg tcgacctgcg tgacgattgg ccacaagcct tgcgggacag tggtttcgat 300
gcggctgcac cgtcggcatg gattgccgaa gggct 335

<210> SEQ ID NO 716
<211> LENGTH: 274
<212> TYPE: DNA
<213> ORGANISM: Mycobacterium bovis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 716
ttgggcnttg cccncaatan ggccccaatc aaaagccgag caggtggaac ctanncgcat 60
tcgcctcntc gtntgtgcac ccgagccatc gcacgcgcgg gaattcccgg atntcnccgt 120
attctccggc ggccgggcta acccatccca ngccgaacgg ttggctcntg ccgtgggtcc 180
cgtgttggcc gatcggggcg tcaccggggg tgctcgggtg cggntgacca tggcnaactg 240
ccccnatggg ccgaccctgg tgcagataaa cctg 274

<210> SEQ ID NO 717
<211> LENGTH: 327
<212> TYPE: DNA
<213> ORGANISM: Mycobacterium bovis
<220> FEATURE:

-continued

<221> NAME/KEY: unsure
<222> LOCATION: (various positions within the sequence)
<223> OTHER INFORMATION: applicants are uncertain of bases designated
as "n"

<400> SEQUENCE: 717
tggtggaggt ccccaccaan acccggccgt aactctgctc acggaaatgc ggncaggccg 60
cgcgtagcac gtggtatccg ccataaaggt gcaccttaag cacggcgtcc caattctcga 120
acgacatctt gtggaaggtg ccgtcgcgca agatcccggc gttgctcacc acaccgtgca 180
cggcgccgaa ttcgtcaagc gcggtcttga tgatgttcgc tgcgccgtcc tcggtggcga 240
cgctgtcggt anttggcgac cgcccggccc cccttgtcgc gaaatctcgg cgacgacctc 300
atcggccatc gccgaaccgg gcgcccg 327

<210> SEQ ID NO 718
<211> LENGTH: 344
<212> TYPE: DNA
<213> ORGANISM: Mycobacterium bovis
<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 718
gccggccaaa ctggccggcg gggttgctgt cntcaaggtg ggttccgcca ccaanaccnc 60
actcaaggat cgcaaggaaa gcntcaagga tgcggtcgcg gccgccaagg ccgcggtcaa 120
ggagggcatc gtccctggtg ggggancctc cctcatccac caggcccgca aggcgctgac 180
cgaactgcnt gcgtcncnga ccggtgacaa ngtcctcggt gtccacgtgt nctccgaagc 240
ccttgccgct ccgttgttct ggatcnccnc caacnctggc ttggacggct cngtggtggt 300
caacaaggtc agcgagctac ccgccgggca tgggctgaac gtga 344

<210> SEQ ID NO 719
<211> LENGTH: 271
<212> TYPE: DNA
<213> ORGANISM: Mycobacterium bovis
<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 719
cgaacctnaa ttgtcctgta atgcccagct caccaangca tggctggtgg ccggggcggt 60
gaagccggcg tctgcggcac cgtccaactc natgtggatn gccggaatgg ggatgtccgg 120
nacggcgaat ccgtanttcg cttgtcccgt gaggcccagg tggatggggg gaaggatcnt 180
ggtgtccggg atgatnatgg ggccgatgcc gccggttgaa gtccactgga tcgggaattc 240
gggaatcgtg atnccgacgt tcaggccgaa c 271

<210> SEQ ID NO 720
<211> LENGTH: 302
<212> TYPE: DNA
<213> ORGANISM: Mycobacterium bovis
<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 720

-continued

```
ctaacggaat gaaagccctg gtggccgtnt cggcggtggc cgtcgtcgca ctgctcggtg     60

tatcttccgc ccaagctgat cccgaggcgg atcccggcgc aggtgaggcc aactatggtg    120

gccccccaag ttccccacgt cttgtcgatc acaccgaatg ggcgcantgg ggaattctgc    180

ccagcctccg ggtctacccg tcccaagttg ggcgtacanc ctcccgccgc ctcgggatgg    240

ccgctgccga cccggcctgg gccnaggttc tcgcgctgtc accggaagcc gacactgccg    300

gc                                                                   302


<210> SEQ ID NO 721
<211> LENGTH: 303
<212> TYPE: DNA
<213> ORGANISM: Mycobacterium bovis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 721

ccgcgggaca cncctcnatg ctgccgccat ggacgcggtc gaacgcaagc agctgatcga     60

gctacaacgc cgcgcggaac gcttccgccg cgggcgtgac cgcatcccgt tgaccgggcg    120

gatcgcggtg atcgtcgatg acggcatcgc caccggagcg acggccaagg cggcgtgcca    180

ggtcgcccgg gcgcacggtg cggacaaggt ggtgctggcg gtcccgatcg gcccanacga    240

catcgtggcg aagattcgcc gggtacgccg atgatgtggt gtgtttggcg acgccggcgt    300

tgt                                                                  303


<210> SEQ ID NO 722
<211> LENGTH: 280
<212> TYPE: DNA
<213> ORGANISM: Mycobacterium bovis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 722

ctctgggacc ggccacggtg ccnccggcgt tcccggacgt gctgcgccag gtgtccggcg     60

gccgcgtgca tggtgttccc ggatcggccg ctggccagag cccaccggtg aatctggcgc    120

ctggccgacc accgtgcgcc gtaggcttgc gatcgtgcag cgctggcgtg gccaggacga    180

gatcccgacg gattggggca gatgcgtgct caccatcggg gtatttgacg gcgtgcaccg    240

cgggcacgcc gaactgatcg cgcacgcggt caaaggcggc                          280


<210> SEQ ID NO 723
<211> LENGTH: 333
<212> TYPE: DNA
<213> ORGANISM: Mycobacterium bovis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 723

aatactcaag ctttcgtcag ttcattgcgc cagcagacca acaanagcat cgggacatac     60

ggantcaact acccggccaa cggtgatttc ttggccgccg ctgacggcgc gaacgacgcc    120

agcgaccacn ttcagcaaat ggccancgcg tgccgggcca cgaggttggt gctcggcggc    180
```

tactcccagg gtgcggccgt gatcnacatc ntcaccgccg caccactgcc cggcctcggg 240
ttcacgcagc cgttgccgcc cgcagcggac natcacatcg ccgcgatcgc cctgttcggg 300
aatccctcng gccgcgctgg cgggctgatt aac 333

<210> SEQ ID NO 724
<211> LENGTH: 320
<212> TYPE: DNA
<213> ORGANISM: Mycobacterium bovis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 724
tgccgcggat ttggctggct gcccaatatt cagaatcggg cctttctttt tgcgcgacaa 60
taaggtcaca gtaaaccctc gttttgtgag atgcggggcg ggccgggcga antcgacctc 120
gagtgaatgg atctcgagtg aatggacagg gcatcgccta cgagtcgcat ccccatccaa 180
cagaccggtg ctcttgcatc ggaccctgaa ggtcccgcac ggagggtgtg gttgccggcg 240
cggggtcacg gtgcggtagc gacgtagtgt ttgaacgaat ttcttgatgc tccaacctgt 300
ttggtgttca atccagttct 320

<210> SEQ ID NO 725
<211> LENGTH: 296
<212> TYPE: DNA
<213> ORGANISM: Mycobacterium bovis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 725
aancttgcgc gctcggccgg gtcnagcatc cagctgctcg gcaaggaggc cagctacncn 60
tcgctgcgta tgcccagcgg tgagatccgc cgggtcnacg tccgctgccg cgcgaccgtc 120
ggcgaagtgg gcaatgccga gcaggcaaac atcaactggg gcaaggccgg tcggatgcgg 180
tggaagggca agcgcccgtc ggtccggggc gtggtgatna acccggtcna ccacccgcac 240
ggcggtggtg agggtaaaac ctccggcggc cgtcacccgg ttagcccgtg gggcaa 296

<210> SEQ ID NO 726
<211> LENGTH: 304
<212> TYPE: DNA
<213> ORGANISM: Mycobacterium bovis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 726
antcgaaagt gaccatctct accttgagtg ccataccgcc cgaccctatg cctcggatag 60
ctcggcggaa agaaacgctt gcagtgccgc cgaataggcg gctacgtcgt gagcgcccat 120
caactctcgc gcggagtgca tcgccagctg ggcggcgccg acgtcgaccg tggggattcc 180
ggtgcgcgcc gcggccaacg gcccgatcgt cgacccgcac ggcagatcgg cgcgatgttc 240
gtaacgctgc ataggcactc ccgcgcgctg gcaggccagt gcgaacgccg ccgcggtgcg 300
tccg 304

-continued

<210> SEQ ID NO 727
<211> LENGTH: 318
<212> TYPE: PRT
<213> ORGANISM: Mycobacterium sp.

<400> SEQUENCE: 727

Pro Thr Gln Thr Leu Thr Gly Arg Pro Leu Ile Gly Asn Gly Thr Pro
1 5 10 15

Gly Ala Val Gly Ser Gly Ala Thr Gly Ala Pro Gly Gly Trp Leu Leu
20 25 30

Gly Asp Gly Gly Ala Gly Gly Ser Gly Ala Ala Gly Ser Gly Ala Pro
35 40 45

Gly Gly Ala Gly Gly Ala Ala Gly Leu Trp Gly Thr Gly Gly Ala Gly
50 55 60

Gly Ala Gly Gly Ser Ser Ala Gly Gly Gly Gly Ala Gly Gly Ala Gly
65 70 75 80

Gly Ala Gly Gly Trp Leu Leu Gly Asp Gly Gly Ala Gly Gly Ile Gly
85 90 95

Gly Ala Ser Thr Val Leu Gly Gly Thr Gly Gly Gly Gly Gly Val Gly
100 105 110

Gly Leu Trp Gly Ala Gly Gly Ala Gly Gly Ala Gly Gly Thr Gly Leu
115 120 125

Val Gly Gly Asp Gly Gly Ala Gly Gly Ala Gly Gly Thr Gly Gly Leu
130 135 140

Leu Ala Gly Leu Ile Gly Ala Gly Gly Gly His Gly Gly Thr Gly Gly
145 150 155 160

Leu Ser Thr Asn Gly Asp Gly Gly Val Gly Gly Ala Gly Gly Asn Ala
165 170 175

Gly Met Leu Ala Gly Pro Gly Gly Ala Gly Gly Ala Gly Gly Asp Gly
180 185 190

Glu Asn Leu Asp Thr Gly Gly Asp Gly Gly Ala Gly Gly Ser Ala Gly
195 200 205

Leu Leu Phe Gly Ser Gly Gly Ala Gly Gly Ala Gly Gly Phe Gly Phe
210 215 220

Leu Gly Gly Asp Gly Gly Ala Gly Gly Asn Ala Gly Leu Leu Leu Ser
225 230 235 240

Ser Gly Gly Ala Gly Gly Phe Gly Gly Phe Gly Thr Ala Gly Gly Val
245 250 255

Gly Gly Ala Gly Gly Asn Ala Gly Trp Leu Gly Phe Gly Gly Ala Gly
260 265 270

Gly Val Gly Gly Ser Ala Gly Leu Ile Gly Thr Gly Gly Asn Gly Gly
275 280 285

Asn Gly Gly Thr Gly Ala Asn Ala Gly Ser Pro Gly Thr Gly Gly Ala
290 295 300

Gly Gly Leu Leu Leu Gly Gln Asn Gly Leu Asn Gly Leu Pro
305 310 315

<210> SEQ ID NO 728
<211> LENGTH: 334
<212> TYPE: PRT
<213> ORGANISM: Mycobacterium sp.

<400> SEQUENCE: 728

Pro Thr Gln Thr Leu Thr Gly Arg Pro Leu Ile Gly Asn Gly Thr Pro
1 5 10 15

-continued

```
Gly Ala Val Gly Ser Gly Ala Thr Gly Ala Pro Gly Gly Trp Leu Leu
            20                  25                  30

Gly Asp Gly Gly Ala Gly Gly Ser Gly Ala Ala Gly Ser Gly Ala Pro
        35                  40                  45

Gly Gly Ala Gly Gly Ala Ala Gly Leu Trp Gly Thr Gly Gly Ala Gly
    50                  55                  60

Gly Ile Gly Gly Ala Ser Thr Val Leu Gly Gly Thr Gly Gly Gly Gly
65                  70                  75                  80

Gly Val Gly Gly Leu Trp Gly Ala Gly Gly Ala Gly Gly Ala Gly Gly
                85                  90                  95

Thr Gly Leu Val Gly Gly Asp Gly Gly Ala Gly Gly Ala Gly Gly Thr
            100                 105                 110

Gly Gly Leu Leu Ala Gly Leu Ile Gly Ala Gly Gly Gly His Gly Gly
        115                 120                 125

Thr Gly Gly Leu Ser Thr Asn Gly Asp Gly Gly Val Gly Gly Ala Gly
    130                 135                 140

Gly Asn Ala Gly Met Leu Ala Gly Pro Gly Gly Ala Gly Gly Ala Gly
145                 150                 155                 160

Gly Asp Gly Glu Asn Leu Asp Thr Gly Gly Asp Gly Gly Ala Gly Gly
                165                 170                 175

Ser Ala Gly Leu Leu Phe Gly Ser Gly Gly Ala Gly Gly Ala Gly Gly
            180                 185                 190

Phe Gly Phe Leu Gly Gly Asp Gly Gly Ala Gly Gly Asn Ala Gly Leu
        195                 200                 205

Leu Leu Ser Ser Gly Gly Ala Gly Gly Phe Gly Gly Phe Gly Thr Ala
    210                 215                 220

Gly Gly Val Gly Gly Ala Gly Gly Asn Ala Gly Trp Leu Gly Phe Gly
225                 230                 235                 240

Ala Gly Gly Ile Gly Gly Ile Gly Gly Asn Ala Asn Gly Gly Ala Gly
                245                 250                 255

Gly Asn Gly Gly Thr Gly Gly Gln Leu Trp Gly Ser Gly Gly Ala Gly
            260                 265                 270

Val Glu Gly Gly Ala Ala Leu Ser Val Gly Asp Thr Gly Gly Ala Gly
        275                 280                 285

Gly Val Gly Gly Ser Ala Gly Leu Ile Gly Thr Gly Gly Asn Gly Gly
    290                 295                 300

Asn Gly Gly Thr Gly Ala Asn Ala Gly Ser Pro Gly Thr Gly Gly Ala
305                 310                 315                 320

Gly Gly Leu Leu Leu Gly Gln Asn Gly Leu Asn Gly Leu Pro
                325                 330
```

<210> SEQ ID NO 729
<211> LENGTH: 650
<212> TYPE: DNA
<213> ORGANISM: Mycobacterium sp.

<400> SEQUENCE: 729

```
gcggccgcaa ggggttcgcg tcagcgggtg ttggcgggtg tcggggctgg cttaactatg     60

cggcatcaga gcagattgta ctgagagtgc accatatgcg gtgtgaaata ccgcacagat    120

gcgtaaggag aaaataccgc atcaggcgcc attcgccatt caggctgcgc aactgttggg    180

aagggcgatc ggtgcgggcc tcttcgctat tacgccagct ggcgaaaggg ggatgtgctg    240

caaggcgatt aagttgggta acgccagggt tttcccagtc acgacgttgt aaaacgacgg    300
```

-continued

```
ccagtgaatt gtaatacgac tcactatagg gcgaattcga gctcggtacc cggggatcct    360

ctagagtcga cctgcaggca tgcaagcttg agtattctat agtgtcacct aaatagcttg    420

gcgtaatcat ggtcatagct gtttcctgtg tgaaattgtt atccgctcac aattccacac    480

aacatacgag ccggaagcat aaagtgtaaa gcctggggtg cctaatgagt gagctaactc    540

acattaattg cgttgcgctc actgcccgct ttccagtcgg gaaacctgtc gtgccagctg    600

cattaatgaa tcggccaacg cgaacccctt gcggccgccc gggccgtcga                650
```

```
<210> SEQ ID NO 730
<211> LENGTH: 8
<212> TYPE: PRT
<213> ORGANISM: Mycobacterium sp.
<220> FEATURE:
<221> NAME/KEY: Unsure
<222> LOCATION: (1-8)
<223> OTHER INFORMATION: applicants are uncertain of residues designated
      as "xaa"

<400> SEQUENCE: 730

Asn Xaa Gly Xaa Gly Asn Xaa Gly
  1               5


<210> SEQ ID NO 731
<211> LENGTH: 9
<212> TYPE: PRT
<213> ORGANISM: Mycobacterium sp.
<220> FEATURE:
<221> NAME/KEY: Unsure
<222> LOCATION: (1-9)
<223> OTHER INFORMATION: applicants are unsure of residues designated as
      "xaa"

<400> SEQUENCE: 731

Gly Xaa Xaa Ser Val Pro Xaa Xaa Trp
  1               5


<210> SEQ ID NO 732
<211> LENGTH: 29
<212> TYPE: PRT
<213> ORGANISM: Mycobacterium sp.

<400> SEQUENCE: 732

Gly Gly Ala Gly Gly Ala Gly Gly Ser Ser Ala Gly Gly Gly Gly Ala
  1               5                  10                  15

Gly Gly Ala Gly Gly Ala Gly Gly Trp Leu Leu Gly Asp
             20                  25


<210> SEQ ID NO 733
<211> LENGTH: 45
<212> TYPE: PRT
<213> ORGANISM: Mycobacterium sp.

<400> SEQUENCE: 733

Gly Ala Gly Gly Ile Gly Gly Ile Gly Gly Asn Ala Asn Gly Gly Ala
  1               5                  10                  15

Gly Gly Asn Gly Gly Thr Gly Gly Gln Leu Trp Gly Ser Gly Gly Ala
             20                  25                  30

Gly Val Glu Gly Gly Ala Ala Leu Ser Val Gly Asp Thr
         35                  40                  45


<210> SEQ ID NO 734
<211> LENGTH: 21
<212> TYPE: DNA
```

-continued

<213> ORGANISM: Mycobacterium sp.

<400> SEQUENCE: 734
agttagctca ctcattaggc a 21

<210> SEQ ID NO 735
<211> LENGTH: 21
<212> TYPE: DNA
<213> ORGANISM: Mycobacterium sp.

<400> SEQUENCE: 735
ggatgtgctg caaggcgatt a 21

<210> SEQ ID NO 736
<211> LENGTH: 27
<212> TYPE: DNA
<213> ORGANISM: Mycobacterium sp.

<400> SEQUENCE: 736
aaacagctat gaccatgatt acgccaa 27

<210> SEQ ID NO 737
<211> LENGTH: 24
<212> TYPE: DNA
<213> ORGANISM: Mycobacterium sp.

<400> SEQUENCE: 737
tcctctagag tcgacctgca ggca 24

<210> SEQ ID NO 738
<211> LENGTH: 18
<212> TYPE: DNA
<213> ORGANISM: Mycobacterium sp.
<220> FEATURE:
<221> NAME/KEY: variation
<222> LOCATION: (1-18)
<223> OTHER INFORMATION: bases designated as "n" may be A,T,C or G

<400> SEQUENCE: 738
tctagannnn nntccggc 18

<210> SEQ ID NO 739
<211> LENGTH: 18
<212> TYPE: DNA
<213> ORGANISM: Mycobacterium sp.
<220> FEATURE:
<221> NAME/KEY: variation
<222> LOCATION: (1-18)
<223> OTHER INFORMATION: bases designated as "n" may be A, T, C or G

<400> SEQUENCE: 739
tctagannnn nngggccc 18

<210> SEQ ID NO 740
<211> LENGTH: 20
<212> TYPE: DNA
<213> ORGANISM: Mycobacterium sp.
<220> FEATURE:
<221> NAME/KEY: variation
<222> LOCATION: (1-20)
<223> OTHER INFORMATION: bases designated as "n" may be A, T, C, or G

<400> SEQUENCE: 740
cgtttaaann nnnwaggccg 20

-continued

```
<210> SEQ ID NO 741
<211> LENGTH: 21
<212> TYPE: DNA
<213> ORGANISM: Mycobacterium sp.
<220> FEATURE:
<221> NAME/KEY: variation
<222> LOCATION: (1-21)
<223> OTHER INFORMATION: bases designated as "n" may be A, T, C, or G

<400> SEQUENCE: 741

ggtactagtn nnnnwtccgg c                                              21


<210> SEQ ID NO 742
<211> LENGTH: 22
<212> TYPE: DNA
<213> ORGANISM: Mycobacterium sp.

<400> SEQUENCE: 742

acgacctcat attccgaatc cc                                             22


<210> SEQ ID NO 743
<211> LENGTH: 23
<212> TYPE: DNA
<213> ORGANISM: Mycobacterium sp.

<400> SEQUENCE: 743

gcatctgttg agtacgcact tcc                                            23
```

METHOD FOR ISOLATING A POLYNUCLEOTIDE OF INTEREST FROM THE GENOME OF A MYCOBACTERIUM USING A BAC-BASED DNA LIBRARY APPLICATION TO THE DETECTION OF MYCOBACTERIA

I. BACKGROUND OF THE INVENTION

The present invention pertains to a method for isolating a polynucleotide of interest that is present in the genome of a mycobacterium strain and/or is expressed by said mycobacterium strain and that is absent or altered in the genome of a different mycobacterium strain and/or is not expressed in said different mycobacterium strain, said method comprising the use of at least one clone belonging to a genomic DNA library of a given mycobaterium strain, said DNA library being cloned in a bacterial artificial chromosome (BAC). The invention concerns also polynucleotides identified by the above method, as well as detection methods for mycobacteria, particularly *Mycobacterium tuberculosis*, and kits using said polynucleotides as primers or probes. Finally, the invention deals with BAC-based mycobacterium DNA libraries used in the method according to the invention and particularly BAC-based *Mycobacterium tuberculosis* and *Mycobacterium bovis* BCG DNA libraries.

Radical measures are required to prevent the grim predictions of the World Health Organisation for the evolution of the global tuberculosis epidemic in the next century becoming a tragic reality. The powerful combination of genomics and bioinformatics is providing a wealth of information about the etiologic agent, *Mycobacterium tuberculosis*, that will facilitate the conception and development of new therapies. The start point for genome sequencing was the integrated map of the 4.4 Mb circular chromosome of the widely-used, virulent reference strain, *M. tuberculosis* H37Rv and appropriate cosmids were subjected to systematic shotgun sequence analysis at the Sanger Centre.

Cosmid clones (Balasubramanian et al., 1996; Pavelka et al., 1996) have played a crucial role in the *M. tuberculosis* H37Rv genome sequencing project. However, problems such as under-representation of certain regions of the chromosome, unstable inserts and the relatively small insert size complicated the production of a comprehensive set of canonical cosmids representing the entire genome.

II. SUMMARY OF THE INVENTION

In order to avoid the numerous technical constraints encountered in the state of the art, as described hereabove, when using genomic mycobacterial DNA libraries constructed in cosmid clones, the inventors have attempted to realize genomic mycobacterial DNA libraries in an alternative type of vectors, namely Bacterial Artificial Chromosome (BAC) vectors.

The success of this approach depended on whether the resulting BAC clones could maintain large mycobacterial DNA inserts. There are various reports describing the successful construction of a BAC library for eucaryotic organisms (Cai et al., 1995; Kim et al., 1996; Misumi et al., 1997; Woo et al., 1994; Zimmer et al., 1997) where inserts up to 725 kb (Zimmer et al., 1997) were cloned and stably maintained in the *E. coli* host strain.

Here, it is shown that, surprisingly, the BAC system can also be used for mycobacterial DNA, as 70% of the clones contained inserts in the size of 25 to 104 kb.

This is the first time that bacterial, and specifically mycobacterial, DNA is cloned in such BAC vectors.

In an attempt to obtain complete coverage of the genome with a minimal overlapping set of clones, a Bacterial Artificial Chromosome (BAC) library of *M. tuberculosis* was constructed, using the vector pBeloBAC11 (Kim et al., 1996) which combines a simple phenotypic screen for recombinant clones with the stable propagation of large inserts (Shizuya et al., 1992). The BAC cloning system is based on the *E. coli* F-factor, whose replication is strictly controlled and thus ensures stable maintenance of large constructs (Willets et al., 1987). BACs have been widely used for cloning of DNA from various eucaryotic species (Cai et al., 1995; Kim et al., 1996; Misumi et al., 1997; Woo et al., 1994; Zimmer et al., 1997). In contrast, to our knowledge this report describes the first attempt to use the BAC system for cloning bacterial DNA.

A central advantage of the BAC cloning system over cosmid vectors used in prior art is that the F-plasmid is present in only one or a maximum of two copies per cell, reducing the potential for recombination between DNA fragments and, more importantly, avoiding the lethal overexpression of cloned bacterial genes. However, the presence of the BAC as just a single copy means that plasmid DNA has to be extracted from a large volume of culture to obtain sufficient DNA for sequencing and it is described here in the examples a simplified protocol to achieve this.

Further, the stability and fidelity of maintenance of the clones in the BAC library represent ideal characteristics for the identification of genomic differences possibly responsible for phenotypic variations in different mycobacterial species.

As it will be shown herein, BACs can be allied with conventional hybridization techniques for refined analyses of genomes and transcriptional activity from different mycobacterial species.

Having established a reliable procedure to screen for genomic polymorphisms, it is now possible to conduct these comparisons on a more systematic basis than in prior art using representative BACs throughout the chromosome and genomic DNA from a variety of mycobacterial species.

As another approach to display genomic polymorphisms, the inventors have also started to use selected H37Rv BACs for "molecular combing" experiments in combination with fluorescent in situ hybridization (Bensimon et al., 1994; Michalet et al., 1997). With such techniques the one skilled in the art is enabled to explore the genome of mycobacteria in general and of *M. tuberculosis* in particular for further polymorphic regions.

The availability of BAC-based genomic mycobacterial DNA libraries constructed by the inventors have allowed them to design methods and means both useful to identify genomic regions of interest of pathogenic mycobacteria, such as *Mycobacterium tuberculosis*, that have no counterpart in the corresponding non-pathogenic strains, such as *Mycobacterium bovis* BCG, and useful to detect the presence of polynucleotides belonging to a specific mycobacterium strain in a biological sample.

By a biological sample according to the present invention, it is notably intended a biological fluid, such as plasma, blood, urine or saliva, or a tissue, such as a biopsy.

Thus, a first object of the invention consists of a method for isolating a polynucleotide of interest that is present in the genome of a mycobacterium strain and/or is expressed by said mycobacterium strain and that is absent or altered in the genome of a different mycobacterium strain and/or is not expressed in said different mycobacterium strain, said method comprising the use of at least one clone belonging to a genomic DNA library of a given mycobaterium strain, said DNA library being cloned in a bacterial artificial chromosome (BAC).

The invention is also directed to a polynucleotide of interest that has been isolated according to the above method and in particular a polynucleotide containing one or several Open Reading Frames (ORFs), for example ORFs encoding either a polypeptide involved in the pathogenicity of a mycobacterium strain or ORFs encoding Polymorphic Glycine Rich Sequences (PGRS).

Such polynucleotides of interest may serve as probes or primers in order to detect the presence of a specific myobacterium strain in a biological sample or to detect the expression of specific genes in a particular mycobacterial strain of interest.

The BAC-based genomic mycobacterial DNA libraries generated by the present inventors are also part of the invention, as well as each of the recombinant BAC clones and the DNA insert contained in each of said recombinant BAC clones.

The invention also pertains to methods and kits for detecting a specific mycobacterium in a biological sample using either at least one recombinant BAC clone or at least one polynucleotide according to the invention, as well as to methods and kits to detect the expression of one or several specific genes of a given mycobacterial strain present in a biological sample.

III. BRIEF DESCRIPTION OF THE DRAWINGS

In order to better understand the present invention, reference will be made to the appended figures which depicted specific embodiments to which the present invention is in no case limited in scope with.

Figure 1B:
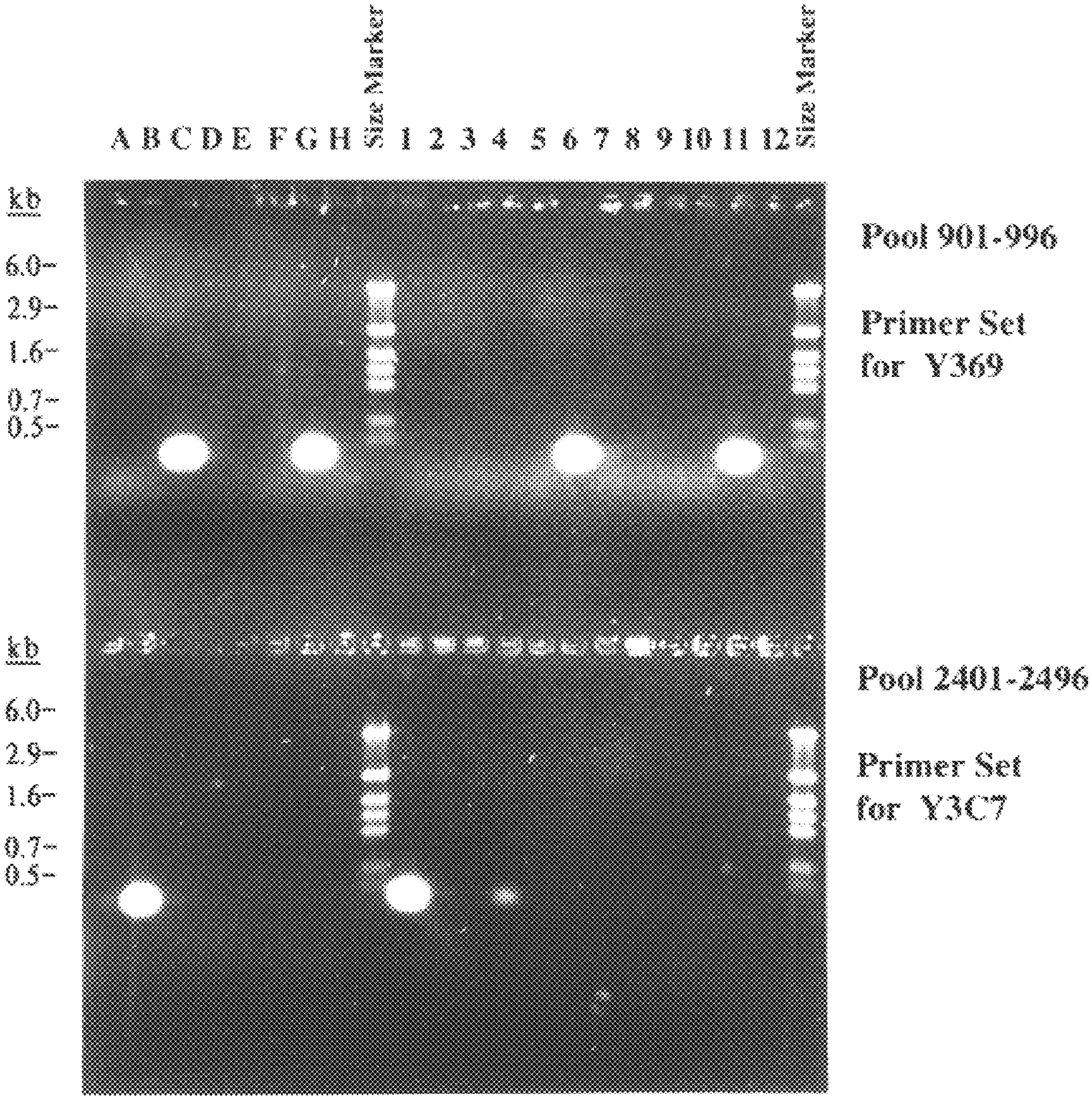

FIGS. 1A and 1B: PCR-screening for unique BAC clones with specific primers for 2 selected genomic regions of the H37Rv chromosome, using 21 pools representating 2016 BACs (Panel A) and sets of 20 subpools from selected positive pools (Panel B).

Figure 2:
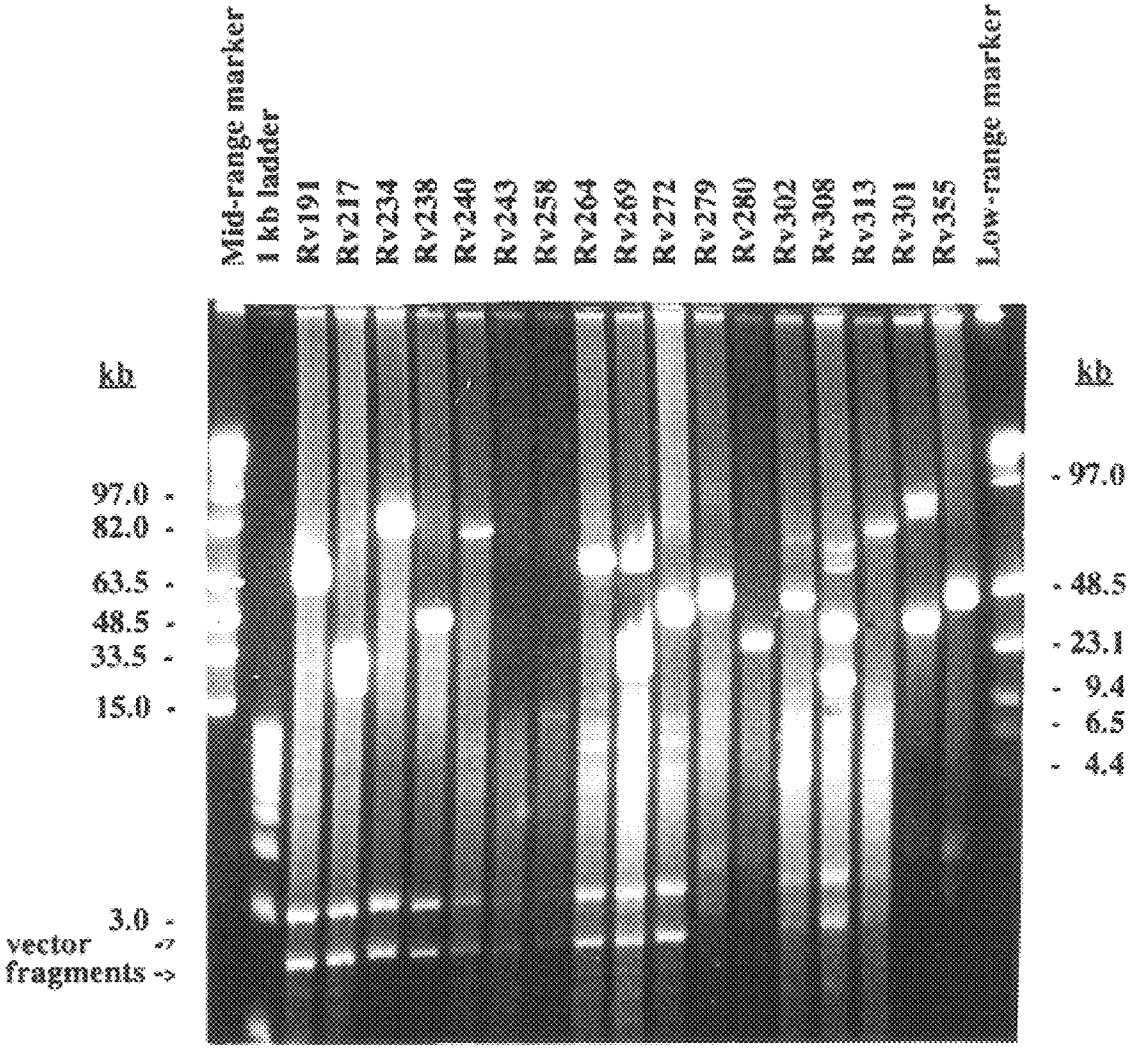
Figure 3A:
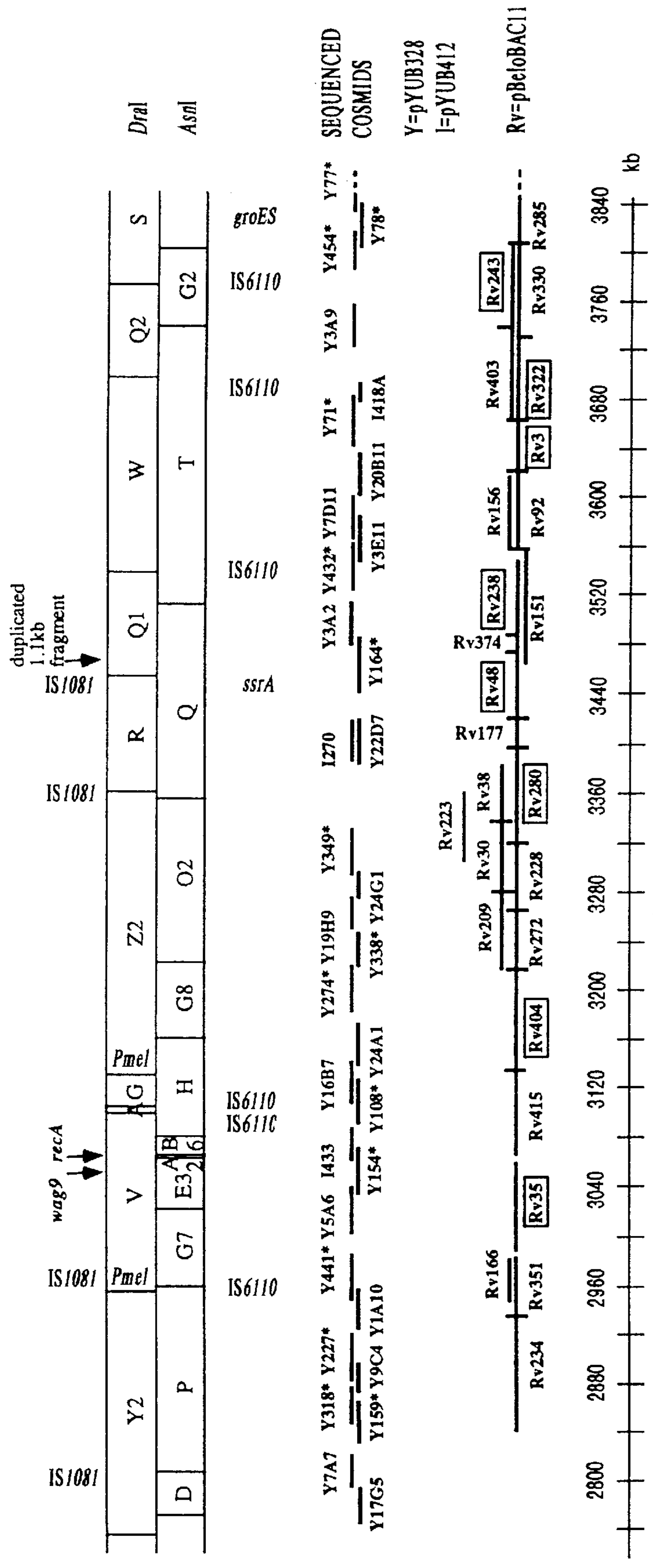
Figure 3B:
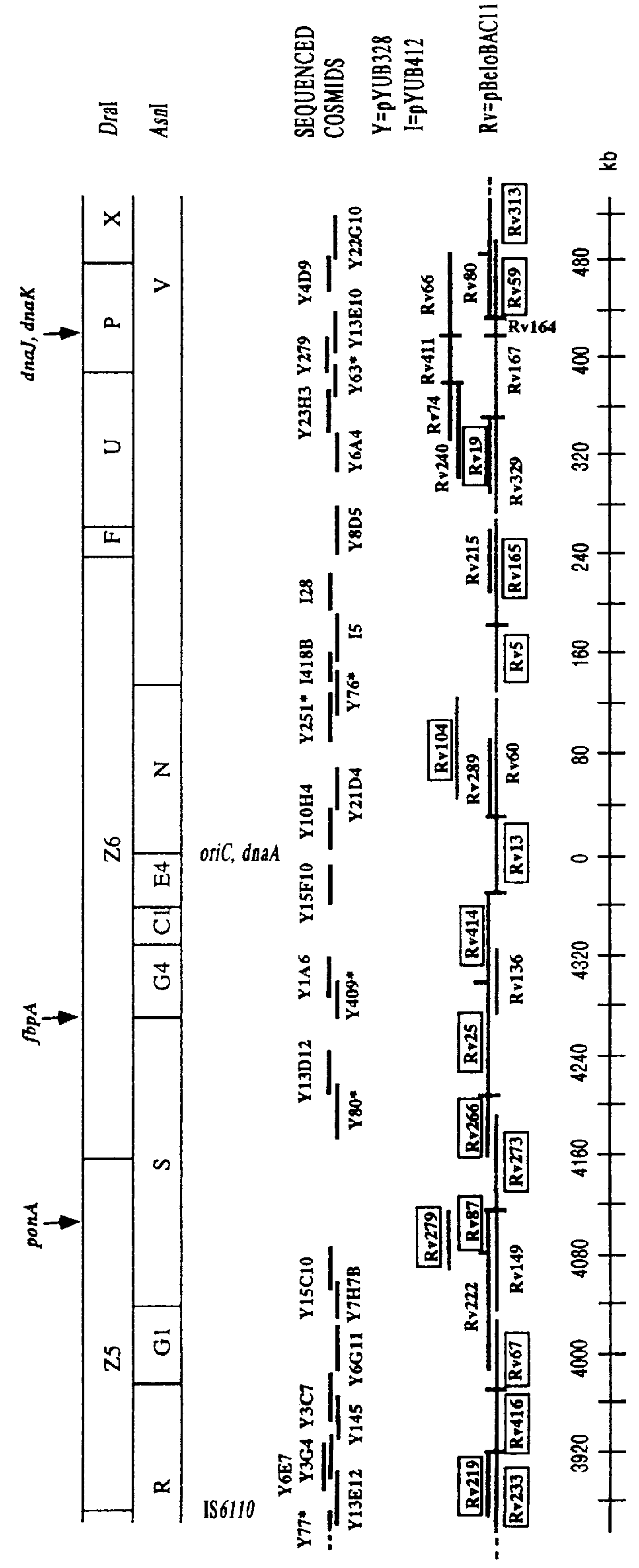
Figure 3C:
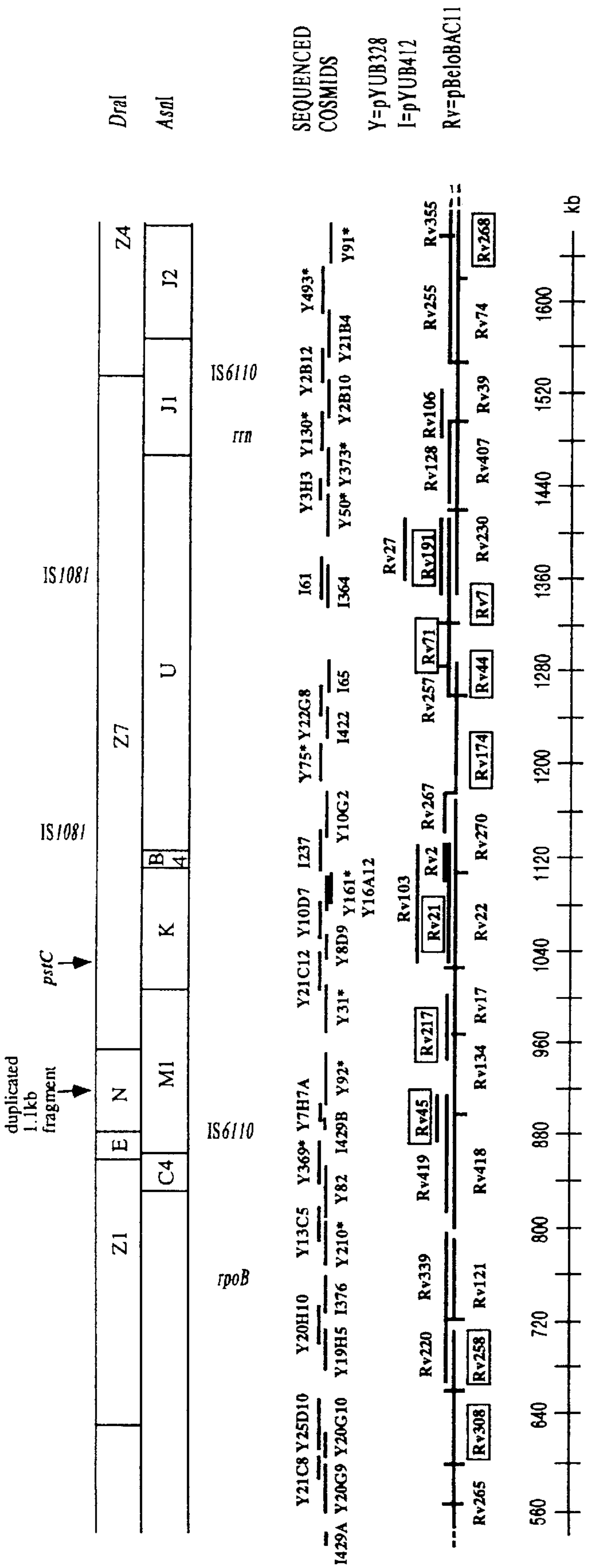
Figure 3D:
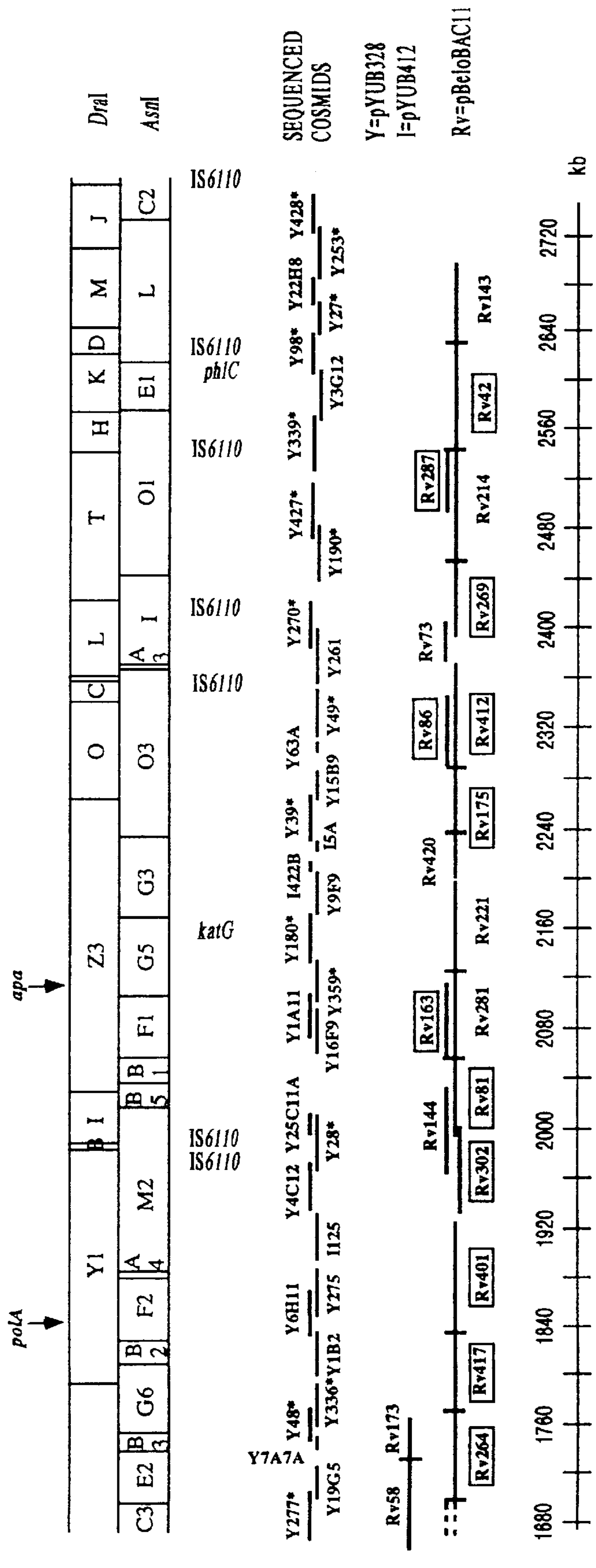

FIG. 2: Pulsed-field gel electrophoresis gel of DraI-cleaved BAC clones used for estimating the insert sizes of BACs.

FIG. 3: Minimal overlapping BAC map of *M. tuberculosis* H37Rv superimposed on the integrated physical and genetic map established by Philipp et al. (18). Y- and I-numbers show pYUB328 (2) and pYUB412 (16) cosmids which were shotgun sequenced during the H37Rv genome sequencing project. Y-cosmids marked with * were shown in the integrated physical and genetic map (18). Rv numbers show the position of representative BAC clones relative to sequenced Y- and I-clones. Squared Rv numbers show BACs which were shotgun sequenced at the Sanger Centre.

Figure 4A:
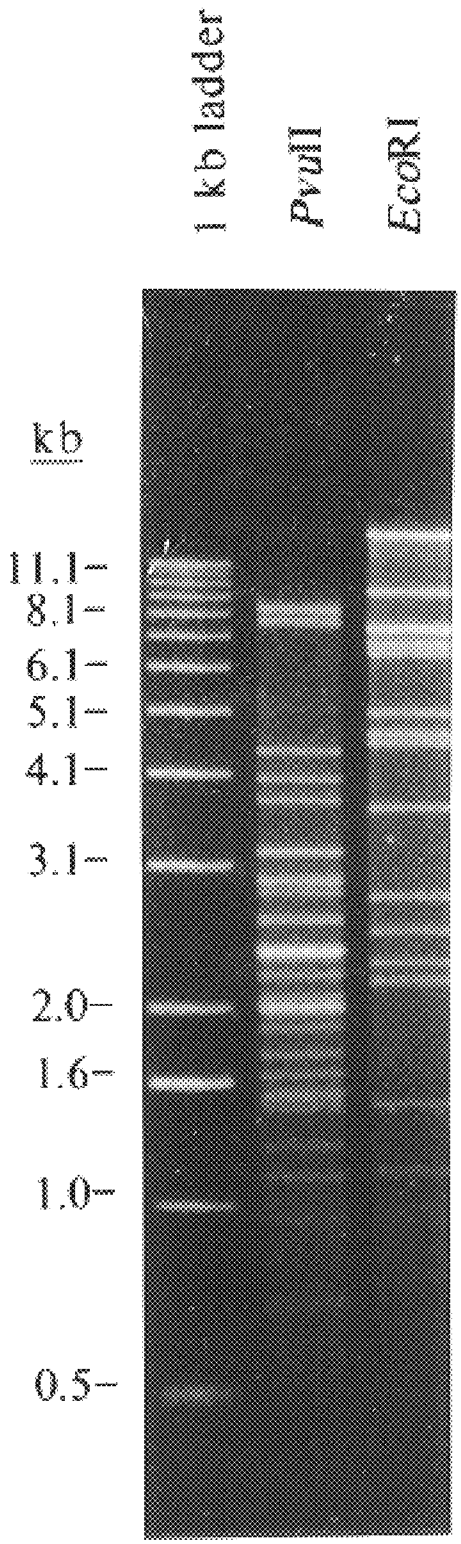
Figure 4B:
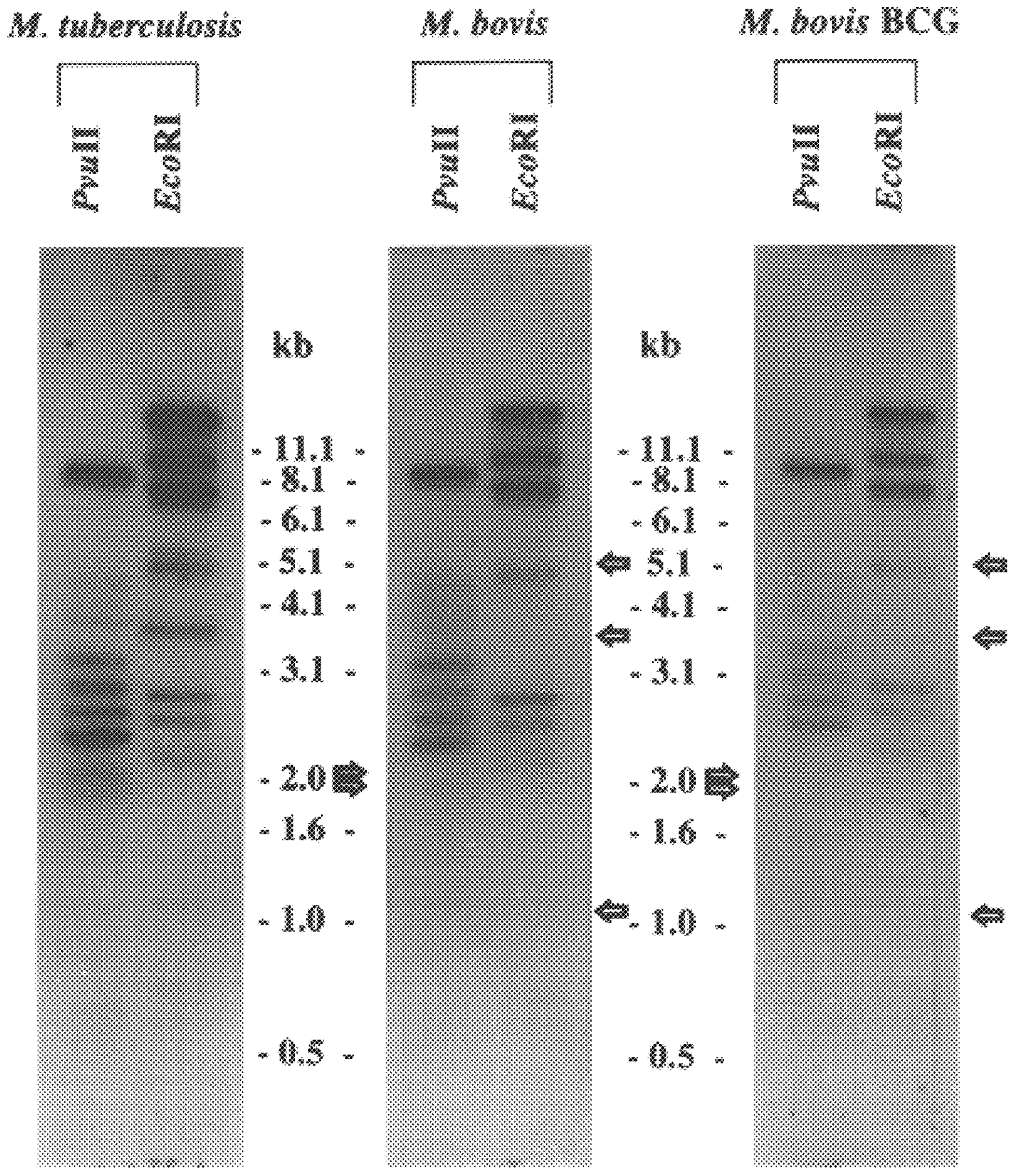

FIGS. 4A and 4B: Ethidium bromide stained gel (Panel A) and corresponding Southern blot (PanelB) of EcoRI and PvuII digested Rv58 DNA hybridized with $^{32}P$ labeled genomic DNA preparations from *M. tuberculosis* H37Rv, *M. bovis* ATCC 19210 and *M. bovis* BCG Pasteur.

Figure 5:
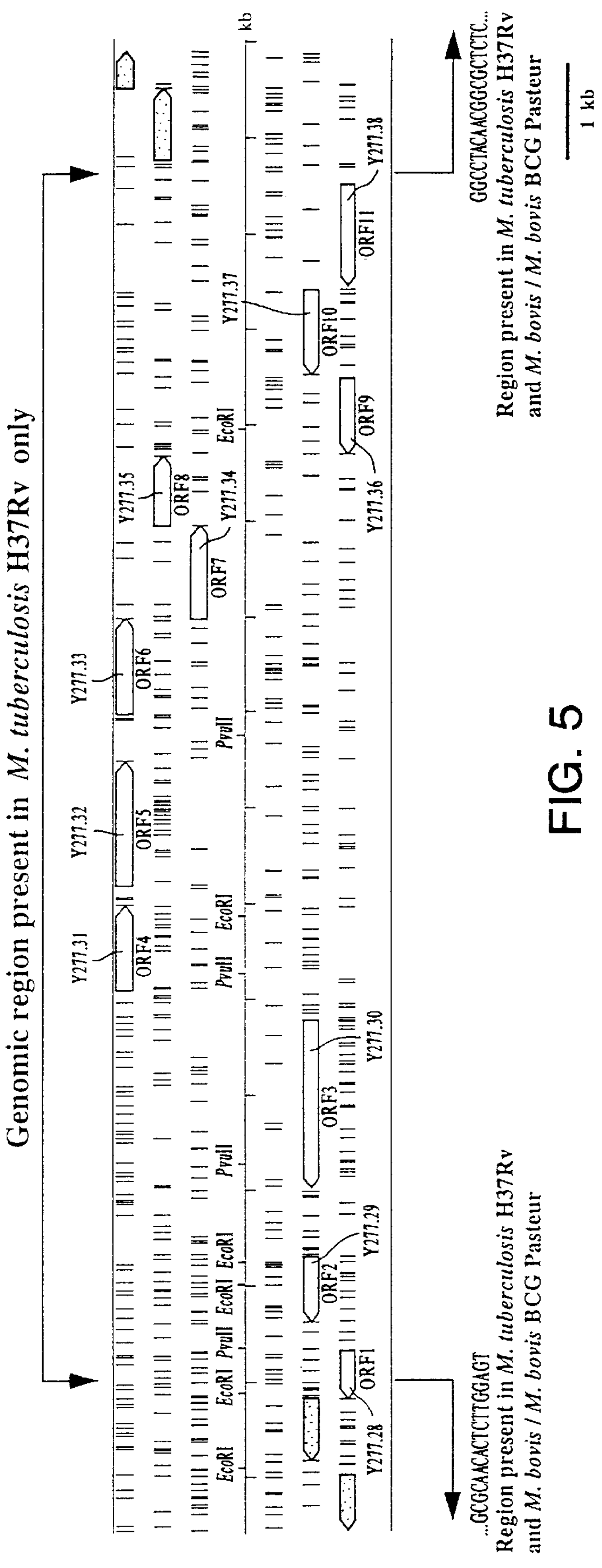

FIG. 5: Organisation of the ORFs in the 12.7 kb genomic region present in *M. tuberculosis* H37Rv but not present in *M. bovis* ATCC 19210 and *M. bovis* BCG Pasteur. Arrows show the direction of transcription of the putative genes. Positions of EcoRI and PvuII restriction sites are shown. Vertical dashes represent stop codons. The 11 ORFs correspond to the ORFs MTCY277.28 to MTCY277.38/accession number Z79701-EMBL Nucleotide Sequence Data Library. The junction sequences flanking the polymorphic region are shown.

FIG. 6: Variation in the C-terminal part of a PE-PGRS open reading frame in *M. tuberculosis* strain H37Rv relative to *M. bovis* BCG strain Pasteur. The numbers on the right side of the Figure denote the position of the end nucleotides, taking as the reference the *M. tuberculosis* genome.

FIG. 7: Polynucleotide sequence next to the HindIII cloning site in the BAC vector pBeloBAC11 (Kim et al., 1996) used to clone the inserts of the BAC-based myobacterial genomic DNA library according to the invention. NotI: location of the NotI restriction sites.

Primer T7-BAC1: nucleotide region recognized by the T7-BAC1 primer shown in Table 1.

T7 promoter: location of the T7 promoter region on the pBeloBac11 vector.

Primer T7-Belo2: nucleotide region recognized by the T7-Belo2 primer shown in Table 1.

Hind III: the HindIII cloning site used to clone the genomic inserts in the pBeloBAC11 vector.

SP6-Mid primer: nucleotide region recognized by the SP6 Mid primer shown in Table 1.

SP6-BAC1 primer: nucleotide region recognized by the SP6 BAC1 primer shown in Table 1.

SP6 promoter: location of the SP6 promoter region on the pBeloBac11 vector.

IV. DETAILED DESCRIPTION OF THE PREFERRED EMBODIMENTS

As already mentioned hereinbefore, the present invention is directed to a method for isolating a polynucleotide of interest that is present in the genome of a mycobacterium strain and/or is expressed by said mycobacterium strain and that is absent or altered in the genome of a different mycobacterium strain and/or is not expressed in said different mycobacterium strain, said method comprising the use of at least one clone belonging to a genomic DNA library of a given mycobaterium strain, said DNA library being cloned in a bacterial artificial chromosome (BAC).

For this purpose, the inventors have constructed several BAC-based mycobacterial genomic DNA libraries that may be used in order to perform the above described method.

Because it is the first time that mycobacterial genomic DNA has been successfully cloned in BAC type vectors, and because these DNA libraries are then novel and nonobvious, an object of the present invention consists in a myobacterial genomic DNA library cloned in such a BAC type vector.

As an illustrative example, a BAC-based DNA library of *Mycobacterium tuberculosis* has been realized. Forty-seven cosmids chosen from the integrated map of the 4.4 Mb circular chromosome (Philipp et al., 1996a) were shotgun-sequenced during the initial phase of the H37Rv genome sequence project. The sequences of these clones were used as landmarks in the construction of a minimally overlapping BAC map. Comparison of the sequence data from the termini of 420 BAC clones allowed us to establish a minimal overlapping BAC map and to fill in the existing gaps between the sequence of cosmids. As well as using the BAC library for genomic mapping and sequencing, we also tested the system in comparative genomic experiments in order to uncover differences between two closely related mycobacterial species. As shown in a previous study (Philipp et al., 1996b), *M. tuberculosis, M. bovis* and *M. bovis* BCG, specifically BCG Pasteur strain, exhibit a high level of global genomic conservation, but certain polymorphic regions were also detected. Therefore, it was of great interest to find a reliable, easy and rapid way to exactly localize polymorphic regions in mycobacterial genomes using selected BAC clones. This approach was validated by determining the exact size and location of the polymorphisms in the genomic region of DraI fragment Z4 (Philipp et al., 1996b), taking advantage of the availability of an appropriate BAC clone covering the polymorphic region and the H37Rv genome sequence data. This region is located approximately 1.7 Mb from the origin of replication.

The Bacterial Artificial Chromosome (BAC) cloning system is capable of stably propagating large, complex DNA inserts in *Escherichia coli*. As part of the *Mycobacterium tuberculosis* H37Rv genome sequencing project, a BAC library was constructed in the pBeloBAC11 vector and used for genome mapping, confirmation of sequence assembly, and sequencing. The library contains about 5000 BAC clones, with inserts ranging in size from 25 to 104 kb, representing theoretically a 70 fold coverage of the *M. tuberculosis* genome (4.4 Mb). A total of 840 sequences from the T7 and SP6 termini of 420 BACs were determined and compared to those of a partial genomic database. These sequences showed excellent correlation between the estimated sizes and positions of the BAC clones and the sizes and positions of previously sequenced cosmids and the resulting contigs. Many BAC clones represent linking clones between sequenced cosmids, allowing full coverage of the H37Rv chromosome, and they are now being shotgun-sequenced in the framework of the H37Rv sequencing project. Also, no chimeric, deleted or rearranged BAC clones were detected, which was of major importance for the correct mapping and assembly of the H37Rv sequence. The minimal overlapping set contains 68 unique BAC clones and spans the whole H37Rv chromosome with the exception of a single gap of ~150 kb. As a post-genomic application, the canonical BAC set was used in a comparative study to reveal chromosomal polymorphisms between *M. tuberculosis, M. bovis* and *M. bovis* BCG Pasteur, and a novel 12.7 kb segment present in *M. tuberculosis* but absent from *M. bovis* and *M. bovis* BCG was characterized. This region contains a set of genes whose products show low similarity to proteins involved in polysaccharide biosynthesis. The H37Rv BAC library therefore provides the one skilled in the art with a powerful tool both for the generation and confirmation of sequence data as well as for comparative genomics and a plurality of post-genomic applications.

The above described BAC-based *Mycobacterium tuberculosis* genomic DNA library is part of the present invention and has been deposited in the Collection Nationale de Cultures de Microorganismes (CNCM) on Nov. 19, 1997 under the accession number I-1945.

Another BAC-based DNA library has been constructed with the genomic DNA of *Mycobacterium bovis* BCG, Pasteur strain, and said DNA library has been deposited in the Collection Nationale de Cultures de Microorganismes (CNCM) on June 30, 1998 under the accession number I-2049.

Thus, as a specific embodiment of the above described method for isolating a polynucleotide of interest said method makes use of at least one BAC-based DNA library that has been constructed from the genomic DNA of *Mycobacterium tuberculosis*, more specifically of the H37Rv strain and particularly of the DNA library deposited in the accession number I-1945.

In another specific embodiment of the above described method for isolating a polynucleotide of interest said method makes use of at least one BAC-based DNA library has been constructed from the genomic DNA of *Mycobacterium bovis* BCG, more specifically of the Pasteur strain and particularly of the DNA library deposited in the accession number I-2049.

In more details, the method according to the invention for isolating a polynucleotide of interest may comprise the following steps:

a) Isolating at least one polynucleotide contained in a clone of a BAC-based DNA library of mycobacterial origin;

b) Isolating:

at least one genomic or cDNA polynucleotide from a mycobacterium, said mycobacterium belonging to a strain different from the strain used to construct the BAC-based DNA library of step a); or alternatively at least one polynucleotide contained in a clone of a BAC-based DNA library prepared from the genome of a mycobacterium that is different from the mycobacterium used to construct the BAC-based DNA library of step a);

c) Hybridizing the at least one polynucleotide of step a) to the at least one polynucleotide of step b);

d) Selecting the at least one polynucleotide of step a) that has not formed a hybrid complex with the at least one polynucleotide of step b);

e) Characterizing the selected polynucleotide.

Following the above procedure, the at least one polynucleotide of step a) may be prepared as follows:

1) Digesting at least one recombinant BAC clone by an appropriate restriction endonuclease in order to isolate the polynucleotide insert of interest from the vector genetic material;

2) Optionally amplifying the resulting polynucleotide insert;

3) Optionally digesting the polynucleotide insert of step 1) or step 2) with at least one restriction endonuclease.

The above method of the invention allows the one skilled in the art to perform comparative genomics between different strains or species of mycobacteria cells, for example between pathogenic strains or species and their non pathogenic strains or species counterparts, as it is the illustrative case for the genomic comparison between *Mycobacterium tuberculosis* and *Mycobacterium bovis* BCG that is described herein in the examples.

Restriction digests of a given clone of a BAC library according to the invention may be blotted to membranes, and then probed with radiolabeled DNA form another strain or another species of mycobacteria, allowing the one skilled in the art to identify, characterize and isolate a polynucleotide of interest that may be involved in important metabolical and/or physiological pathways of the mycobacterium under testing, such as a polynucleotide functionally involved in the pathogenicity of said given mycobacteria for its host organism.

More specifically, the inventors have shown in Example 6 that when restriction digests of a given clone of the BAC library identified by the CNCM accession number I-1945 are blotted to membranes and then probed with radiolabeled total genomic DNA from, for example, *Mycobacterium bovis* BCG Pasteur, it is observed that restriction fragments that fail to hybridize with the *M. bovis* BCG Pasteur DNA are absent from its genome, hence identifying polymorphic regions between *M. bovis* BCG Pasteur and *M. tuberculosis* H37Rv.

Thus, a further object of the present invention consists in a polynucleotide of interest that has been isolated according to the method described herein before.

In Example 6, a polynucleotide of approximately 12.7 kilobases has been isolated that is present in the genome of *M. tuberculosis* but is absent of the genome of *M. bovis* BCG. This polynucleotide of interest contains 11 ORFs that may be involved in polysaccharide biosynthesis. In particular, two of said ORFs are of particular interest, namely ORF6 (MTCY277.33; Rv1511) that encodes a protein that shares significant homology with bacterial GDP-D-mannose dehydratases, whereas the protein encoded by ORF7 (MTCY277.34; Rv1512) shares significant homology with a nucleotide sugar epimerase. As polysaccharide is a major constituent of the mycobacterial cell wall, these deleted genes may cause the cell wall of *M. bovis* BCG to differ from that of *M. tuberculosis*, a fact that may have important consequences for both the immune response to *M. bovis* BCG and virulence. Detection of such a polysaccharide is of diagnostic interest and possibly useful in the design of tuberculosis vaccines.

Consequently, the polynucleotide of interest obtained following the method according to the invention may contain at least one ORF, said ORF preferably encoding all or part of a polypeptide involved in an important metabolical and/or physiological pathway of the mycobacteria under testing, and more specifically all or part of a polypeptide that is involved in the pathogenicity of the mycobacteria under testing, such as for example *Mycobacterium tuberculosis*, and more generally mycobacteria belonging to the *Mycobacterium tuberculosis* complex.

The *Mycobacterium tuberculosis* complex has its usual meaning, i.e. the complex of mycobacteria causing tuberculosis which are *Mycobacterium tuberculosis, Mycobacterium bovis, Mycobacterium africanum, Mycobacterium microti* and the vaccine strain *Mycobacterium bovis* BCG.

An illustrative polynucleotide of interest according to the present invention comprises all or part of the polynucleotide of approximately 12.7 kilobases that is present in the genome of *M. tuberculosis* but is absent from the genome of *M. bovis* BCG disclosed hereinbefore. This polynucleotide is contained in clone Rv58 of the BAC DNA library I-1945.

Generally, the invention also pertains to a purified polynucleotide comprising the DNA insert contained in a recombinant BAC vector belonging to a BAC-based mycobacterial genomic DNA library, such as for example the I-1945 BAC DNA library.

Advantageously, such a polynucleotide has been identified according to the method of the invention.

Such a polynucleotide of interest may be used as a probe or a primer useful for specifically detecting a given mycobacterium of interest, such as *Mycobacterium tuberculosis* or *Mycobacterium bovis* BCG.

More specifically, the invention then deals with a purified polynucleotide useful as probe or a primer comprising all or part of the nucleotide sequence SEQ ID NO.1:

```
ACCTGCGCTT GCAGAGATCA AATAGGGCGC ATGGGTCAGC ATAGTACAGG TCGTCGCGCA      60
TCTTTGATGC ATCGGAATAA GATGTCAGGC AATTAAAAGA GAAGCCACGG CGACTCGCGG     120
CATTCAGCAT GTCGAGCGTC GCTTCGATGT GAGCGCACCA TTCCGTGTCC AACGATTTCA     180
GACGAACATT GAATATTCCA CTCGCGACGC TATAGTCCGC CTCCCGATCT ATGCGCGCCG     240
CGCAGATGAA GTCTGCGTTC GCCCGACCTT CGAAACGTAG TGCGGCCGCG CGCACCATTT     300
CGGGGGAGAC GTCGATGCCG GTGTAATCAG TTTTGAAGCC ACGCGCATCT AGGTAGTCCA     360
GTAGAGCCCC ATAGCCACAG CCTAGATCGT TGATCGAAAA TGGGTCCGCC GCATTGACAA     420
TGCGCACCAG CTGGTCAAAG CGCAACGCCT GCCCGGCTTC GCCGTTCCAA TCGACGCCGC     480
GCGGGTGCCG TGTGCTTCGA GTTTCGATGC GTAGTAACGG GCCACGTCAG CGAGCATGGT     540
CGTTGCGTCT TCCGCCATGA AGCTGCCTCA CGATTTGTGT GTGTGGGCGT CGGTGCGTGG     600
GTCCGAGACT ATACCTTCAA CAGTTGCATG CCGAGGCTGC GGCGGGCAAT GACCCAAAAA     660
CCCGCCGGCA CGGTTCGCCG AGCAAGGAAG CGTGGAGACG ATAGATAATT TCACTGGCGA     720
CAGTACCTCA AATAGTCCGG AGCCTCGGCT CCGACGTTAA AGAGCAGATC CAGAATCGAC     780
ACGGCGGGCT CGAACCCTCC CCACAATTGC TTATAATCGC GdTAGCCGTC ATAATCGAAC     840
CAAGTTACCC GGATGCTAAG TTCGTCGAAC ACGCGCTCAT CGACATACGA ACGGGCTGAG     900
GGGCCAGAGA CATATTCGGT CGCTGCGGCC TGTTGGCAGA GGTTGGCCAG TCTCTCGGTC     960
TTGCCGTCGG CTAATTCGTA GTCCCACGAA TTTGCCAGTC GCGTGCTGAT ACCGAGATAA    1020
CTGCAAATCG CATTCAATAG ACGCCTGTTG AGTAAGGAAA GATTCGTGTG CTGTTCTTCG    1080
AGGTAAATCG GCGCGAGCCA GTCAGCGATC TCCGCAAAAT GAGCGGCCGC GCTGTAGTTG    1140
AATTCTAGTG CCCGCCAGTG CGCTTTCGCC CAATCGGTGC CGTCGATCAG CGTCTCACGT    1200
ATCTTTTGAT GGAAACGTCC CTTCACCTGG ACGGGAACAG TTATCCACTG TAACCCCTGG    1260
CTCGTTTTGA TCCGATTTCT GTTTCGCCAA TCACGCTTGG TATATTGCAT GTCATCATAG    1320
ATGATGAATT CATCGACGAA TGCAATCAGG TCAAAATATC CTCGCCAAGG TATGTAATTT    1380
```

-continued

```
GATTGAACAA TCGCGACTTT CTTCAACGCG GTGTCTCCAA TTTAGAATAA CAAATACGTC    1440
GCGCCCGCGA CAGCTCCGCT GGAGCGAGTT CAAGCGATTC TGCGACATAT TCAATATGGT    1500
GCTCGGGAAG GCCAGGATGG GCCGCGACCC GGGGCGTCCG GTGCGCGATG AACGTCGCAT    1560
CGTCTCCTGT GAGATAATTG CATCCGATCA TATAGGGCTG GCTGCGGCTA GGTTGCTGGC    1620
AAAAAGATAT CGCGGCCGAT CCGTTTCTGG TTTTGTCTTG ATGATCAAAT CCGCTTCCGT    1680
TCACGAGATC GATTCCTGGT CTTCCCCCAG CGTCGCGATG TCGATAGGTG TCGCGCTTTG    1740
TTCGTACCCG CACTACGCGG CGGCGAGAAC CTCGCCACCG AATCGGGATT GGGGGGAGGA    1800
TACCACTCGG TCGAGGCCCG TCACCGGCCT TCTAGCGGGT TGACCATCAG TGTTTGCAGG    1860
GCCCTATCCC GGTATGGCGC ACCACGGGAT CGGCAGCGTT CCGGTTGCTG GCGTGGTACC    1920
TCGTTGTGGC GCCGTGGTCC ATGTCGATTG AGTGCGTGGA TCAGTGTAAA CCGTTGCGCG    1980
CCATGTTCTG TAGGCACTGG TTCGGGTTGT GGTTAGGCTG CACGGTTGGC AGGTTACCAA    2040
CCACTGAGCC CCTGGGCGGA TGTGAGCTCG GACTCCGCCT ATGGGGTGTA ATTTTGGCAG    2100
ATTGGGCCGG GTCCCCGTGG TGAGGACTCC TCAACCGGAT TGGGTAAGCA TGAGGTGGTG    2160
CTGGCAGCGG TGTCCTGGTC GCTCTCCCGA GTAGGCCCGT TGTGACTGTC ATGTGGGCGA    2220
GCGGGTTTGC GCGCGTAGGA GACGATGATT ACTACGCACG TGACCAACCA CAAGAACGGT    2280
GCCCATGTCA CCGTGGTGAA AACGAGTGGC GTGGTACCGA CTACCCCTTT GGCTCCCAGC    2340
TGTCCATAGA GCGGCACGTA GAACGGCTGG CCCGGGACCG CGACGTTGAC GATGCTCAGC    2400
GCCACGGCCA AACTCACGCA GACGCCGACC GCGCGGCGGC GGTCTCCATG GGCTGCGAGT    2460
TGGTCGAATA TCCCAGCACC AGGAGGCCCG TTGGGGTCTC GGGCTACCAG TGCAGCGATT    2520
GGCAAGACGA AAACGAGATA GTAGAAGGCG ACGTCCGCGG GGGAGAAGGT GGCGGTGGCG    2580
AGCAACACAA TCCCCACCAT GACAGGCGGG ATACGGCGTC CGAGCGCCAG CACGGCGACC    2640
ACGACTATGA CTAGGACAGC AAACCCGATC TGCGTTCGCG GACCAGTGAG GAAACCCTCT    2700
GGGATCTTGC CCGATTGATA GTTCTTGATG CTATCGGGGA TCAGCAGGAG TGCCTTGCCA    2760
AAGGACACGT TCCGCGGGTC TCGAAGCCCT CCGAACGAAC TATTGAACTT GATGATGCCG    2820
TGGATCGACT GTGCGATCGT CCCCGGGAAG CCTCGTGGCC ACAACAGAAA GGCTGCGATA    2880
TTGGACACCA CCACGCCGGT GATCCCGATA CCAGCCCACC GCCATTGTCG AGCCGCCAAC    2940
AACACCACGC CGAGAACGAC GAACTGCGGC TTTACCAGGA CGGCCAAGAT CACCGTGATG    3000
GTGGCGAGGC CCCACCGCTG TCGGGACAAC GCCACGAAGT AAGCCAGCGC GATCGGTACC    3060
ACGAACCCTG TCGAGTTGCC TCGATCGATG ACCCCCCACG CCGGGATGGC CGCGGCGCCC    3120
AGTGTCACGA AGATGACCAC TCGCTCCAGA CCACGTGCCC CCCGGGCCGC CCAGATGGCG    3180
GGAGATATGA CCGCCATCGT TAGGGCGACC AGGTAACAGA TCAGCCCCAA GCGCGGCGCA    3240
CCCAGCCAAT GGCTGGGTAG TCCGAAAATC GCATACGGTA TGCGGGCGGG GGCCCATGCA    3300
GCAACCGCGG TCGGCTGGTA ATCGGCGGGT AGCGAGATCA GGTAGTCCGC GGGATTGGGT    3360
TGAATCCCGG CGGCGGCGAC CATGGCGTAG TCGCTGAAGC AGTGCCGACC GATATTCATG    3420
CCCCAATCAA GCCAACAGTC CCCAGGGACT ACCAAAAGAG TGGAAAAGAC GTCGACCGCG    3480
TACCACTGAC TGAGGGCGTA CGCCGTCGCC GCCGAAATCA CCGACGCCAG CAGGATGGTG    3540
CCGAGCATGA GGGTGCGCTC GGATTGGGAG CCGATCGCCC AGAGCCGCTC CCGGCTCGCG    3600
GTCACGGCAC CGCGCAACAC CTCCGGGGGT CGCTTCATCT GGATTCTCCT CGGTTCTGCG    3660
CGAAACGGTA GCAGAGCGCC ATGGTTGCCA ACGCGGTCGC CGGGCAGTCT AGACCGGATC    3720
TTCCTCGTGG CAACCGACAA CAGGACGTCG TTGCCGAAAG GGCGCTGGGC ACCGACATCT    3780
```

-continued

```
AGGATGAACC CACAGCCACG CCCCGACGTT ATGCCATGGC GAAGAGCGAC CGGCAGGAGC    3840
GGGAACCCAG TGAAGCGAGC GCTCATCACC GGAATCACAG GACCGGACGG CTCGTATCTC    3900
GCTAAGCTCC CGCTGAAGGG ATATGTGGCC GCTGGTAGCC CGGCCGAGGT CTATTTCTGC    3960
TGGGCGACAC GGAATTATCG CGAATTGTAT GGGTTGCTCG CGGTCAACAG CATCTGGTTC    4020
AATCACGAAT CACCGCGTCA CGGCGAGACA TTCATGACTC GTAATCCTGC ACCATATCGC    4080
GGTCGGCAAC GAGGCGCTGA TCGATGCGCA GACGCTGATG CGCCGGCCCA CCCGGATAGG    4140
TATCAGTATT GGGGCGTTCC GGCCAGCGTA CGAGGCGTGA TCGACCGCGC AATGGGTGTT    4200
TGCGTTGAGT AATAATCTGA ACCGTGTGAA CGCATGCATG GATGGATTCC TTGCCCGTAT    4260
CCGCTCACAT GTTGATGCGC ACGCGCCAGA ATTGCGTTCA CTGTTCGATA CGATGGCGGC    4320
CGAGGCCCGA TTTGCACGCG ACTGGCTGTC CGAGGACCTC GCGCGGTTGC CTGTCGGTGC    4380
AGCATTGCTG GAAGTGGGCG GGGGGGTACT TCTGCTCAGC TGTCAACTGG CGGCGGAGGG    4440
ATTTGACATC ACCGCCATCG AGCCGACGGG TGAAGGTTTT GGCAAGTTCA GACAGCTTGG    4500
CGACATCGTG CTGGAATTGG CTGCAGCACG ACCCACCATC GCGCCATGCA AGGCGGAAGA    4560
CTTTATTTCC GAGAAGCGGT TCGACTTCGC CTTCTCGCTG AATGTGATGG AGCACATCGA    4620
CCTTCCGGAT GAGGCAGTCA GGCGGGTATC GGAAGTGCTG AAACCGGGGG CCAGTTACCA    4680
CTTCCTGTGC CCGAATTACG TATTCCCGTA CGAACCGCAT TTCAATATCC CAACATTCTT    4740
CACCAAAGAG CTGACATGCC GGGTGATGCG ACATCGCATC GAGGGCAATA CGGGCATGGA    4800
TGACCCGAAG GGAGTCTGGC GTTCGCTCAA CTGGATTACG GTTCCCAAGG TGAAACGCTT    4860
TGCGGCGAAG GATGCGACGC TGACCTTGCG CTTCCACCGT GCAATGTTGG TATGGATGCT    4920
GGAACGCGCG CTGACGGATA AGGAATTCGC TGGTCGCCGG GCACAATGGA TGGTCGCTGC    4980
TATTCGCTCG GCGGTGAAAT TGCGTGTGCA TCATCTGGCA GGCTATGTTC CCGCTACGCT    5040
GCAGCCCATC ATGGATGTGC GGCTAACGAA GAGGTAATGA CATGGCGCAA GCGACATCGG    5100
GCATTCGCGC GGCACTTTCG CAACCTGCTG TGTATGAGGC GTATCAGCGG ATTGCGGGCG    5160
CTAAAAGCGG GCTTGCGTGG ATCACAACCG ACCCCATCCA GTCGTTGCCA GGCATGCGTA    5220
CTCTCGACCT CGGTTGCTGG CCAGCGGTGA TACACAGCTC CCCGCCAGTG GACGTGACAT    5280
GTACGAGAGA CGGCATGAGC GCGGAATGTG CGACCGTGCC GTCGAGATGA CCGACGTCGG    5340
CGCTACGGCA GCCCCCACCG GACCTATCGC GCGGGGCAGC GTCGCTCGGG TCGGCGCGGC    5400
GACCGCGTTG GCCGTTGCCT GCGTCTACAC GGTCATCTAT CTGGCGGCCC GCGACCTACC    5460
CCCGGCTTGT TTTTCGATAT TCGCGGTGTT TTGGGGGGCG CTCGGCATTG CCACCGGCGC    5520
CACCCACGGC CTCCTGCAAG AAACGACCCG CGAGGTCCGC TGGGTGCGCT CCACCCAAAT    5580
AGTTGCGGGC CATCGTACCC ATCCGCTGCG GGTGGCCGGG ATGATTGGCA CCGTCGCGGC    5640
CGTCGTAATT GCGGGTAGCT CACCGCTGTG GAGCCGACAG CTATTCGTCG AGGGGCGCTG    5700
GCTGTCCGTG GGGCTACTCA GCGTTGGGGT GGCCGGGTTC TGCGCGCAGG CGACCCTGCT    5760
GGGCGCGCTG GCCGGCGTCG ACCGGTGGAC ACAGTACGGG TCACTGATGG TGACCGACGC    5820
GGTCATCCGG TTGGCGGTCG CCGCGGCAGC GGTTGTGATC GGATGGGGTC TGGCCGGGTA    5880
CTTGTGGGCC GCCACCGCGG GAGCGGTGGC GTGGCTGCTC ATGCTGATGG CCTCGCCCAC    5940
CGCGCGCAGC GCGGCCAGCC TGCTGACGCC CGGGGGAATC GCCACGTTCG TGCGCGGTGC    6000
CGCTCATTCG ATAACCGCCG CGGGTGCCAG CGCGATTCTG GTAATGGGTT TCCCAGTGTT    6060
GCTCAAAGTG ACCTCCGACC AGTTAGGGGC AAAGGGCGGA GCGGTCATCC TGGCTGTGAC    6120
CTTGACGCGT GCGCCGCTTC TGGTCCCACT GAGCGCGATG CAAGGCAACC TGATCGCGCA    6180
```

-continued

TTTCGTCGAC CGGCGCACCC AACGGCTTCG GGCGCTGATC GCACCGGCGC TGGTCGTCGG 6240

CGGCATCGGT GCGGTCGGGA TGTTGGCCGC AGGGCTTACC GGTCCCTGGT TGCTGCGTGT 6300

TGGATTCGGC CCCGACTACC AAACTGGCGG GGCGTTGCTG GCCTGGTTGA CGGCAGCGGC 6360

GGTAGCTATC GCCATGCTGA CGCTGACCGG CGCCGCCGCG GTCGCGGCCG CACTGCACCG 6420

GGCGTATTTG CTGGGCTGGG TCAGCGCGAC GGTGGCGTCG ACGCTGTTGC TGCTGCTGCC 6480

GATGCCGCTG GAGACGCGCA CCGTGATCGC GCTGTTGTTC GGTCCAACGG TGGGAATCGC 6540

CATCCATGTG GCCGCGTTGG CGCGGCGACC CGACTGATTT GTGCCCCAGG TCGACAAATC 6600

ACGCCGTCTC GTCAGTGAGC ACTCCGTCCT CGGGTCCGAT CCTTCCAGGA GACGTTGCAA 6660

CCTGATTTGG CTCAAATTGG TGCGCACCGA GGGTCGGGCA CATCGTAGGG TCGCAACAGT 6720

CACATGTGTC ACTGCACCGG GCGACACCCG ATGTCCCGGC TCTCAGCGAC AGCTGTCTGA 6780

CCTGTGGTTT TGTTCCCAAG TTGGTCGTGG CTGTGCGGGA TTGGAGGTGG CGTGGGGGTC 6840

GCGTCGTATG GATTCTCCTC CTCGGTTCCG CGCGAAACGG CCGCAGGCGC AATGGTCACC 6900

AACTTGGCCG CGGTGGAGTC TAGCCTCACA TTTTCCTGGT CGCCCCCGAC AACCAGGAGG 6960

TCGCTGCAGA ACGGGCGTTC CCTACCCACA TCTACTATGA AGCGACAGCG GCGCCCCGCT 7020

GTGATGGCTG AGCATGACCG ACAGAGGCGG GAAGACAGTG AAGCGAGCGC TCATCACCGG 7080

AATCACCGGC CAGGACGGCT CGTATCTCGC CGAACTGCTG CTGGCCAAGG GGTATGAGGT 7140

TCACGGGCTC ATCCGGCGCG CTTCGACGTT CAACACCTCG CGGATCGATC ACCTCTACGT 7200

CGACCCGCAC CAACCGGGCG CGCGGCTGTT TCTGCACTAT GGTGACCTGA TCGACGGAAC 7260

CCGGTTGGTG ACCCTGCTGA GCACCATCGA ACCCGACGAG GTGTACAACC TGGCGGCGCA 7320

GTCACACGTG CGGGTGAGCT TCGACGAACC CGTGCACACC GGTGACACCA CCGGCATGGG 7380

ATCCATGCGA CTGCTGGAAG CCGTTCGGCT CTCTCGGGTG CACTGCCGCT TCTATCAGGC 7440

GTCCTCGTCG GAGATGTTCG GCGCCTCGCC GCCACCGCAG AACGAGCTGA CGCCGTTCTA 7500

CCCGCGGTCA CCGTATGGCG CCGCCAAGGT CTATTCGTAC TGGGCGACCC GCAATTATCG 7560

CGAAGCGTAC GGATTGTTCG CCGTTAACGG CATCTTGTTC AATCACGAAT CACCGCGGCG 7620

CGGTGAGACG TTCGTGACCC GAAAGATCAC CAGGGCCGTG GCACGCATCA AGGCCGGTAT 7680

CCAGTCCGAG GTCTATATGG GCAATCTGGA TGCGGTCCGC GACTGGGGGT ACGCGCCCGA 7740

ATACGTCGAA GGCATGTGGC GGATGCTGCA GACCGACGAG CCCGACGACT TCGTTTTGGC 7800

GACCGGGCGC GGTTTCACCG TGCGTGAGTT CGCGCGGGCC GCGTTCGAGC ATGCCGGTTT 7860

GGACTGGCAG CAGTACGTGA AATTCGACCA ACGCTATCTG CGGCCCACCG AGGTGGATTC 7920

GCTGATCGGC GACGCGACCA AGGCTGCCGA ATTGCTGGGC TGGAGGGCTT CGGTGCACAC 7980

TGACGAGTTG GCTCGGATCA TGGTCGACGC GGACATGGCG GCGCTGGAGT GCGAAGGCAA 8040

GCCGTGGATC GACAAGCCGA TGATCGCCGG CCGGACATGA ACGCGCACAC CTCGGTCGGC 8100

CCGCTTGACC GCGCGGCCCG GGTCTACATC GCCGGGCATC GCGGCCTGGT CGGGTCCGCG 8160

CTGCTACGCA CGTTTGCGGG CGCGGGGTTC ACCAACCTGC TGGTGCGGTC ACGCGCCGAG 8220

CTTGATCTGA CGGATCGGGC CGCGACGTTC GACTTCGTTC TCGAGTCGAG GCCGCAGGTC 8280

GTCATCGACG CGGCGGCCCG GGTCGGCGGC ATCCTGGCCA ACGACACCTA CCCGGCCGAT 8340

TTCCTGTCGG AAAACCTCCA GATCCAGGTC AACCTGCTGG ATGCCGCCGT GGCGGCGCGG 8400

GTGCCGCGGC TGCTGTTCCT GGGCTCGTCG TGCATCTACC CGAAACTCGC CCCGCAGCCG 8460

ATCCCGGAGA GCGCGCTGCT CACCGGTCCG TTGGAGCCGA CCAACGACGC GTACGCGATC 8520

GCCAAAATCG CCGGCATCCT TGCGGTCCAG GCGGTGCGCC GCCAACATGG CCTGCCGTGG 8580

-continued

```
ATCTCGGCGA TGCCCACCAA CCTGTACGGG CCAGGCGACA ACTTTTCGCC GTCCGGCTCG    8640
CATCTGCTGC CGGCACTCAT CCGCCGCTAT GACGAGGCCA AAGCCAGTGG CGCGCCCAAC    8700
GTGACCAACT GGGGCACCGG CACGCCCCGA CGGGAGTTGC TGCACGTCGA CGACCTGGCG    8760
AGCGCATGCC TGTATCTGCT GGAACATTTC GACGGGCCGA CCCATGTCAA CGTGGGAACC    8820
GGCATCGACC ACACCATCGG CGAGATCGCC GAGATGGTCG CCTCGGCGGT AGGCTATAGC    8880
GGCGAAACCC GCTGGGATCC AAGCAAACCG GACGGAACAC CACGCAAACT GCTGGATGTT    8940
TCGGTGCTAC GGGAGGCGGG ATGGCGGCCT TCGATCGCGC TGCGCGACGG CATCGAGGCG    9000
ACGGTGGCGT GGTATCGCGA GCACGCGGGA ACGGTTCGGC AATGAGGCTG GCCCGTCGCG    9060
CTCGGAACAT CTTGCGTCGC AACGGCATCG AGGTGTCGCG CTACTTTGCC GAACTGGACT    9120
GGGAACGCAA TTTCTTGCGC CAACTGCAAT CGCATCGGGT CAGTGCCGTG CTCGATGTCG    9180
GGGCCAATTC GGGGCAGTAC GCCAGGGGTC TGCGCGGCGC GGGCTTCGCG GGCCGCATCG    9240
TCTCGTTCGA GCCGCTGCCC GGGCCCTTTG CCGTCTTGCA GCGCAGCGCC TCCACGGACC    9300
CGTTGTGGGA ATGCCGGCGC TGTGCGCTGG GCGATGTCGA TGGAACCATC TCGATCAACG    9360
TCGCCGGCAA CGAGGGCGCC AGCAGTTCCG TCTTGCCGAT GTTGAAACGA CATCAGGACG    9420
CCTTTCCACC AGCCAACTAC GTGGGCGCCC AACGGGTGCC GATACATCGA CTCGATTCCG    9480
TGGCTGCAGA CGTTCTGCGG CCCAACGATA TTGCGTTCTT GAAGATCGAC GTTCAAGGAT    9540
TCGAGAAGCA GGTGATCGCG GGTGGCGATT CAACGGTGCA CGACCGATGC GTCGGCATGC    9600
AGCTCGAGCT GTCTTTCCAG CCGTTGTACG AGGGTGGCAT GCTCATCCGC GAGGCGCTCG    9660
ATCTCGTGGA TTCGTTGGGC TTTACGCTCT CGGGATTGCA ACCCGGTTTC ACCGACCCCC    9720
GCAACGGTCG AATGCTGCAG GCCGATGGCA TCTTCTTCCG GGGCAGCGAT TGACGCGCCG    9780
GCGCGTCAAT CTATTTCGAC ATTCGCGTGA AGACGTTTTC CCAGAATCGA CTGTTGTAGG    9840
CGTAGAACTC CCGGCCGCGT AGGTAGGCAT GTGATATTCG CCTTCCCCCG AACGGGTAGC    9900
GGCGATGAAG GTCGCCCATG CGGCGCAGAT CACCGAAGAC CGCGCTTGGT TCCCGGTGCG    9960
AGCCGACGCC CGTGGTGTCG AACTCGCACA GCACACACCG AATCGTGACC GGCTCGCATA   10020
CCAGCGCGGC CCGCAATATG AATTCCTGGT CGGCGGCGAT CCCGAAATCA AGGTCGTAGC   10080
CACCGATCTT GGCCACCAGC GATGATCCGA AGAACGATGC TTGATGCGGA ACAACCTGCT   10140
TGCCGGCCAG GAATTTGCGC AGGCTGAAAG GTATCGGGCC GCGCACCCGA TCGAGCCCGA   10200
CGAGACGATC CATCCCGAAG CCCCACAATT CGGACACCGG TCCCTTGCCG GATAGCGCCT   10260
CCACGGCCTG GGCTACCACG TCGGGCCCGG AAAAACGATC GGCGGAGTGC AAGAACCACA   10320
ACAGATCACC CGATGCGTGC GCGATGCCCT GGTTCATCGC GTCGTACCGC CCGCCGTCGG   10380
GCTCGGACTG CCAATACGCG AAGCCTGGTT CACACCCGGA CAGGTATGCC ACCACGTCGT   10440
CGCCGCTGCC ACCGTCGATT ACGATGTGCT CGATGCGTCC CCGGTAGCGT TGCGCCCGCA   10500
CACTTTTCAC CGTGCGCTGC AACCCGTCGA GGTCGTTGAA CGAGATCGTT ATCACCGAGA   10560
CGGTCGGAGC AGACGTCACC GAGTTCCCCT AGGTTGCTGG CGGCGATTGT GGATCACCGG   10620
GTCTTGATAC CGATGAAGGT GCCTCGAAGA TTCGCCGCAT AGGAACCTCC GAGCAACGAC   10680
TCGGCGATGC TTGGTTCCAA GTTGTCGTAC TCCTCCATCA CCAGGTCGAC GCCGACGTCT   10740
TTGATGGCCT GAAGTAGGTG CTCGCGTTGA ATCCAGAATG ACCGGCGATT GTCCCAGGAC   10800
GCCCATTTTG CGGTGTCGCG CTGGCCAAAC GAGCGGTCGT CGGAAAACTC GGTAAACCAC   10860
CTACCGGGAA GTCCCTCATG TTCGGTGGGC GCCGAGAGCA TGAACTTCAC CGGCGCCGGC   10920
CGCCGCAGCA ACCGATCGGT CAATTGTCGT GCCGTCGTGG GCAACCGGAG CCATTTATCG   10980
```

-continued

```
CTCCGGTTGA TGATCGAGAA GTGCGTCTGG AGAATCAGCA GCTTGTTCGT TACCGACGAG    11040

AGGGTTTCCA GGTATTGCTT CGGATTCTCC AGGTGGTAGA AGAGGCCGCA GCAGAAGACG    11100

GTATCGAAGA GCCCGTGGTT GGCGATGTTG AGGGCGTTGT CGTGGACGAA CCGGAGATTC    11160

GGCAGGTTGG TCTTCGATTT GATGTAGTTG CAGGCCGCCA TGTTCAGCTC GCGAACCTCG    11220

ATCCCGAGGA CCTGAAATCC CATGCGCGCG AACCCGACCG CGTACCCGCC TTCCAAGCAG    11280

CCGACATCGG CCAGGCGTAG GTGGCTCTTG TCCCCGGGAA AGACGGTTTC CAGAATCCCG    11340

CGCGCCGAGA TGAACCAGGA CGATTCGTCT AACGTGCGCG AGGACTCCGG TATCGTCAAG    11400

GTTCCGTCGT CGAGGCGAAC GTTGTGGGCG GTGAATTGTA CCGCGCCGGC CGAATGTTCC    11460

TGTGCCATCA CTTGGTTAGC CCCTTCGGCT GGTCCTGGGT TTGTCGACAT GGTCAGGCTC    11520

GACAGCCGCG TCGGAGCCGG GAGGGCCACA CATCCACGAG CCCCCTGCGG CTCGGCGTCG    11580

CGGCGGCGAG CTTGCGCCAC TGGGTCTTGA GCCGCCGCGC GGGTGTCGCC CCGCGGTGCT    11640

GCAGCGCCAG CATGGCGATC CGGGGATGGC GCGCGATGGT TTCCTGCAGC GCGGCGCGCC    11700

CCTCCGGGCC TGGAACGTTG GCGATCTGGC GAAGGATCCA GTCGGCCATG ACGGCGATGA    11760

GCTCCTCGCG CGCGGGGTCT CCCGGGAACA GGTCGAGCAT CGCGTCAAAC GTCGCCGCAT    11820

GCCCCGGACC CTGCGTCAAC CAGAACTTTG GCGGGTCCAC CACCTGGTTG TGCCACATGC    11880

CTTGGGCGTG GCGGCGATAC ACGGCCATGG TGTCGGGCAA CATGGCGATG TCGCCATGCA    11940

CCGCGTGCCG GACGTGCAGA TACCAGTCCA GGGGCATGAC GTCGGCAGGA ATGTCGTCGT    12000

AGCGCTCGAG GCGACGGTAC ACGGCCGAGT TGGTCTGGAT GAAGTTCATC AAGATCAACG    12060

CATCCAGGCT CAAGTTGCCC CGCACCCGAA CCGGGGGGAA CTTCGAGTCC TTGGCATGGC    12120

CGTCCTCCCA TATCACTCGG ACGGGATGGA AGCACACCGT CGTCTTGGGG TGCCGGTCGA    12180

GGAATGCGAC CTGTTTGCTT AGCTTCAGCG GATCGATCCA GTAGTCGTCC GCCTCGCACA    12240

ACGCGACGTA CTCGCCGCGA GCGGCCGACA GGGCGCCGGT CAGGTTCCCA TTGAGGCCGA    12300

GGTTTTCGGT CCTGAAGATC GGCCGGAACA CGTGCGGGTA CCGCTCGGCG TACTCACGGA    12360

TGATCGCCGG GGTGGCATCG GTCGACGCGT CGTCGGCGAC GATGATCTCC ACCGGGAAGT    12420

CGGTTTGCTG GTCGAGAAAG CTGTCGAAGG CCTGACGGGC GTAGCCCGCC TGGTTGTGAG    12480

TGGTCGAGAC GATGCTCACC TTGGGGCAAA GCTGGGGACT CACCGTCGGC CCTTTTCCTG    12540

CGCGGCCGCA AGGGTATTGC GATGGCGAAC GTGAATCGCC TGTGCCCGCC GGCCGTCGGC    12600

CGTCGTGGCC TGGTGGTCGG CGGACGTACG GCACACGCTG GCGAAGTATA GCGAGGGTGC    12660

ACTGACGTTG GGCTCGAACC GCGTGGCGCG CGGTGTGGGC GCACCGTCTC GAGTCGGTGC    12720

TGGTTGGCTC GC                                                       12732
```

The location, on the *Mycobacterium tuberculosis* chromosome, of the above polynucleotide of sequence SEQ ID NO.1 has now been ascribed to begin, at its 5' end at nucleotide at position nt 1696015 and to end, at its 3' end, at nucleotide at position nt 1708746.

For diagnostic purposes, this 12.7 kb deletion should allow a rapid PCR screening of tubercle isolates to identify whether they are bovine or human strains. The primers listed in Table 1 are flanking the deleted region and give a 722 bp amplicon in *M. bovis* or *M. bovis* BCG strains, but a fragment of 13,453 bp in *M. tuberculosis* that is practically impossible to amplify under the same PCR conditions. More importantly, assuming that some of the gene products from this region represent proteins with antigenic properties, it could be possible to develop a test that can reliably distinguish between the immune response induced by vaccination with *M. bovis* BCG vaccine strains and infection with *M. tuberculosis* or that the products (e.g. polysaccharides) are specific immunogens.

The invention also provides for a purified polynucleotide useful as a probe or as a primer, said polynucleotide being chosen in the following group of polynucleotides:

a) a polynucleotide comprising at least 8 consecutive nucleotides of the sequence SEQ ID NO.1.

b) a polynucleotide whose sequence is fully complementary to the sequence of the polynucleotide defined in a);

c) a polynucleotide that hybridizes under stringent hybridization conditions with the polynucleotide defined in a) or with the polynucleotide defined in b).

For the purpose of defining a polynucleotide or oligonucleotide hybridizing under stringent hybridization conditions, such as above, it is intended a polynucleotide that hybridizes with a reference polynucleotide under the following hybridization conditions:

The hybridization step is realized at 65° C. in the presence of 6×SSC buffer, 5×Denhardt's solution, 0,5% SDS and 100 μg/ml of salmon sperm DNA.

For technical information, 1×SSC corresponds to 0.15 M NaCl and 0.05M sodium citrate; 1×Denhardt's solution corresponds to 0.02% Ficoll, 0.02% polyvinylpyrrolidone and 0.02% bovine serum albumin.

The hybridization step is followed by four washing steps:

two washings during 5 min, preferably at 65° C. in a 2×SSC and 0.1% SDS buffer;

one washing during 30 min, preferably at 65° C. in a 2×SSC and 0.1% SDS buffer, one washing during 10 min, preferably at 65° C. in a 0.1×SSC and 0.1% SDS buffer A first illustrative useful polynucleotide that is included in the polynucleotide of sequence SEQ ID NO.1 is the following polynucleotide of sequence SEQ ID NO.2 that corresponds to the Sp6 endsequence of SEQ ID NO.1:

```
ATACTCAAGC TTGCCGCAAT CGAAACCAAC CTGTTTGTGC CGCAAGAAAT TACGCCGTGG   60
CCCGGCGCCG ATCAAGAAAC GCCCCGGCGC GCGGCGGTGT CGTCGTATGG CATGACGGGC  120
ACCAATGTGC ACGCCATTGT CGAGCAGGCA CCGGTGCCAG CCCCCGAATC CGGTGCACCA  180
GGCGACACCC CGGCCACACC CGGTATCGAC GGCGCGCTGC TGTTCGCGCT GTCGGCCAGC  240
TCGCAGGACG CGCTGCGGCA AACCGCCGCG CGGCTGGCCG ATTGGGTCT              289
```

A second illustrative useful polynucleotide that is included in the polynucleotide of sequence SEQ ID NO.1 is the following polynucleotide of sequence SEQ ID NO.3 that corresponds to the T7 endsequence of SEQ ID NO.1, located on the opposite strand:

```
TTGGCGGGTT GGCCACACAC CCGCCGGTGA CGGCGACGAT GCTGGGCTGG TTGCGGCCCT   60
GCGCCACCGC GGCTTGCATG CTGGTTGGCT GTCTTGGGAC GATCCCGAAA TAGTCCACGC  120
GGATCTGGTG ATTTTGCGGG CTACCCGCGA TTACCCCGCG CGGCTCGACG AGTTTTTGGC  180
CTGGACTACC CGCGTGGCCA ATCTGCTGAA CTCGCGGCCG GTGGTGGCCT GGAATGTCCA  240
CGCCGTTCAC CTACGTGACC TTGATGGGAT CCGGGGGT                          278
```

The polynucleotide of sequence SEQ ID NO.1 contains 11 ORFs, the respective locations of which, taking into account the orientation of each ORF on the chromosome, on the sequence of the *Mycobacterium tunerculosis* chromosome, is given hereafter:

The location of ORF1 is comprised between nucleotide at position nt 1695944 and nucleotide at position nt1696441.

The location of ORF2 is comprised between nucleotide at position nt 1696728 and nucleotide at position nt1697420.

The location of ORF3 is comprised between nucleotide at position nt 1698096 and nucleotide at position nt1699892. ORF3 probably encodes a protein having the characteristics of a membrane protein.

The location of ORF4 is comprised between nucleotide at position nt 1700210 and nucleotide at position nt1701088.

The location of ORF5 is comprised between nucleotide at position nt 1701293 and nucleotide at position nt1702588. ORF5 encodes a protein having the characteristics of a membrane protein.

The location of ORF6 is comprised between nucleotide at position nt 1703072 and nucleotide at position nt1704091. ORF6 encodes a protein having the characteristics of a GDP-D-mannose dehydratase.

The location of ORF7 is comprised between nucleotide at position nt 1704091 and nucleotide at position nt1705056. ORF7 encodes a protein having the characteristics of a nucleotide sugar epimerase involved in colanic acid biosynthesis.

The location of ORF8 is comprised between nucleotide at position nt 1705056 and nucleotide at position nt1705784.

The location of ORF9 is comprised between nucleotide at position nt 1705808 and nucleotide at position nt1706593. ORF9 encodes a protein having the characteristics of colanic acid biosynthesis glycosyl transferase.

The location of ORF10 is comprised between nucleotide at position nt 1706631 and nucleotide at position nt1707524.

The location of ORF11 is comprised between nucleotide at position nt 1707530 and nucleotide at position nt1708648. ORF11 encodes a protein similar to a spore coat polysaccharide biosynthesis.

A polynucleotide of interest obtained by the above-disclosed method according to the invention may also contain at least one ORF that encodes all or part of acidic, glycine-rich proteins, belonging to the PE and PPE families, whose genes are often clustered and based on multiple copies of the polymorphic repetitive sequences. The names PE and PPE derive from the fact that the motifs ProGlu (PE, positions 8, 9) and ProProGlu (PPE, positions 7 to 9) are found near the N-terminus in almost all cases. The PE protein family all have a highly conserved N-terminal domain of ~110 amino acid residues, that is predicted to have a globular structure, followed by a C-terminal segment which varies in size, sequence and repeat copy number. Phylogenetic analysis separated the PE family into several groups, the larger of which is the highly repetitive PGRS class containing 55 members whereas the other groups share very limited sequence similarity in their C-terminal domains. The predicted molecular weights of the PE proteins vary considerably as a few members only contain the ~110 amino acid N-terminal domain while the majority have C-terminal extensions ranging in size from 100 up to >1400 residues. A striking feature of the PGRS proteins is their exceptional glycine content (up to 50%) due to the presence of multiple tandem repetitions of GlyGlyAla or GlyGlyAsn motifs or variations thereof.

Like the PE family, the PPE protein family also has a conserved N-terminal domain that comprises ~180 amino acid residues followed by C-terminal segments that vary considerably in sequence and length. These proteins fall into at least three groups, one of which constitutes the MPTR class characterised by the presence of multiple, tandem copies of the motif AsnXGIyXGlyAsnXGly (SEQ ID NO. 730). The second subgroup contains a characteristic, well-conserved motif around position 350 (GlyXXSerValProXXTrp) (SEQ ID NO. 731), whereas the other group contains proteins that are unrelated except for the presence of the common 180-residue PPE domain. C-terminal extensions may range in size from 00 up to 3500 residues One member of the PGRS sub-family, the WHO antigen 22T (Abou-Zeid et al., 1991), a 55 kD protein capable of binding fibronectin, is produced during disease and elicits a variable antibody response suggesting either that individuals mount different immune responses or that this PGRS-protein may not be produced in this form by all strains of *M. tuberculosis*. In other words, at least some PE_PGRS coding sequences encode for proteins that are involved in the recognition of *M. tuberculosis* by the immune system of the infected host Therefore, differences in the PGRS sequences could represent the principal source of antigenic variation in the otherwise genetically and antigenically homogeneous bacterium.

By performing the method of the invention using the *M. tuberculosis* BAC based DNA library I-1945, the inventors have discovered the occurence of sequence differences between a given PGRS encoding ORF (ORF reference on the genomic sequence of *M. tuberculosis* Rv0746) of *M. tuberculosis* and its counterpart sequence in the genome of *M. bovis* BCG.

More precisely, the inventors have determined that one ORF contained in BAC vector NO. Rv418 of the *M. tuberculosis* BCG I-1945 DNA library carries both base additions and base deletions when compared with the corresponding ORF in the genome of *M. bovis* BCG that is contained in the BAC vector N° X0175 of the *M. bovis* BCG I-XXXX DNA libary. The variations observed in the base sequences correspond to variations in the C-terminal part of the aminoacid sequence of the PGRS ORF translation product.

As shown in FIG. 6, an amino acid stretch of 9 residues in length is present in this *M. tuberculosis* PGRS (ORf reference Rv0746) and is absent from the ORF counterpart of *M. bovis* BCG, namely the following amino acid sequence:

$NH_2$-GGAGGAGGSSAGGGGAGGAGGAGGWLLGD-COOH (SEQ ID NO. 732).

Furthermore, FIG. 6 shows also that an amino acid stretch of 45 residues in length is absent from this *M. tuberculosis* PGRS and is present in the ORF counterpart of *M. bovis* BCG, namely following amino acid sequence:

$NH_2$-GAGGIGGIGGNANGGAGGNGGTGGQLWGSGGAGVEGGAALSVGDT-COOH (SEQ ID NO. 733).

Similar observations were made with PPE ORF Rv0442, which showed a 5 codon deletion relative to a *M. bovis* amino acid sequence.

Given that the polymorphism associated with the PE-PGRS or PEE ORFS resulted in extensive antigenic variability or reduced antigen presentation, this would be of immense significance for vaccine design, for understanding protective immunity in tuberculosis and, possibly, explain the varied responses seen in different BCG vaccination programmes.

There are several striking parallels between the PGRS proteins and the Epstein-Barr virus-encoded nuclear antigens (EBNA). Both polypeptide families are glycine-rich, contain Gly-Ala repeats that represent more than one third of the molecule, and display variation in the length of the repeat region between different isolates. The Gly-Ala repeat region of EBNA1 has been shown to function as a cis-acting inhibitor of antigen processing and MHC class I-restricted antigen presentation (Levitskaya et al., 1995). The fact that MHC class I knock-out mice are extremely suscepible to *M. tuberculosis* underlines the importance of MHC class I antigen presentation in protection against tuberculosis. Therefore, it is possible that the PE/PPE protein family also play some role in inhibiting antigen presentation, allowing the bacillus to hide from the host's immune system.

As such the novel and nonobvious PGRS polynucleotide from *M. bovis* which is homolog to the *M. tuberculosis* ORF Rv0746, and which is contained in the BAC clone N° X0175 (See Table 4 for SP6 and T7 endsequences of clone n° X0175) of the I-2049 *M. bovis* BCG BAC DNA library is part of the present invention, as it represents a starting material in order to define specific probes or primers useful for detection of antigenic variability in mycobacterial strains, possible inhibition of antigen processing as well as to differentiate *M. tuberculosis* from *M. bovis* BCG.

Thus, a further object of the invention consists in a polynucleotide comprising the following sequence SEQ ID NO.4:

| | |
|---|---|
| CCGACCCAGA CACTGACCGG GCGACCGCTG ATCGGCAACG GCACCCCCGG GGCGGTCGGC | 60 |
| AGCGGGGCCA CCGGGGCCCC CGGTGGGTGG CTGCTCGGCG ACGGCGGGGC CGGCGGGTCC | 120 |
| GGCGCGGCGG GCTCGGGCGC GCCCGGCGGG GCGGGCGGGG CTGCCGGGCT GTGGGGTACC | 180 |
| GGCGGGGCCG GCGGGATCGG CGGAGCCAGC ACCGTACTCG GCGGCACCGG CGGGGGAGGC | 240 |
| GGGGTCGGTG GGCTGTGGGG CGCCGGTGGG GCCGGCGGGG CCGGTGGAAC CGGCCTTGTT | 300 |
| GGTGGCGACG GCGGGGCCGG TGGGGCCGGC GGGACCGGCG GACTGCTGGC CGGGCTGATC | 360 |
| GGTGCCGGCG GAGGTCACGG CGGGACCGGC GGGCTCAGCA CTAATGGCGA CGGCGGGGTT | 420 |
| GGCGGGGCCG GCGGGAATGC CGGAATGCTC GCCGGGCCGG GCGGCGCCGG CGGAGCCGGC | 480 |

-continued

```
GGTGACGGCG AAAACCTGGA CACCGGTGGG GACGGCGGGG CCGGCGGTAG CGCAGGGCTG    540

CTGTTCGGCA GCGGCGGCGC CGGCGGCGCC GGCGGATTTG GTTTCCTCGG TGGGGACGGC    600

GGGGCCGGTG GCAACGCCGG GCTGCTGTTG TCCAGCGGCG GGGCCGGCGG GTTCGGCGGG    660

TTCGGCACCG CCGGTGGGGT CGGTGGGGCC GGCGGCAATG CCGGCTGGCT GGGCTTCGGC    720

GGGGCCGGGG GCATCGGCGG AATCGGCGGT AACGCTAACG GGGGCGCCGG TGGGAACGGC    780

GGCACCGGCG GTCAGTTATG GGGTAGCGGC GGCGCCGGCG TCGAAGGCGG CGCAGCCTTA    840

AGCGTCGGCG ACACCGGCGG GGCCGGTGGC GTCGGCGGCA GCGCCGGGCT GATCGGCACC    900

GGCGGCAACG GCGGCAACGG CGGCACCGGC GCCAACGCCG GCAGCCCCGG AACCGGCGGC    960

GCCGGCGGGT TGCTGCTGGG CCAAAACGGG CTCAACGGGT TGCCGTAGCC GGGCGGCACG   1020

GCATGGCTTC CGGGCGTCAA CCACTCGCCG GTGATGCAGA TCGGCTGCGG AGCGGGCCGC   1080

CAAAATGGGG GCCGCCGCGC CAGGTATCTC GGCGAAGATC CCCGGCGCTC GAGCGCTTTG   1140

TCAGAGGCCC GTCGCGGGTC GTCGTGACGA CGGCTATCCG GGCGGTGCGG GTTTCGCGGC   1200

GCGCCCTGTG CCCGGCACCG CCGCCCGTTT GTCGGCAACG CCGCCGCGAC CCGTGAGCCG   1260

TCCAGCAGCT GGCGCCTGCG                                               1280
```

Polynucleotides of interest have been defined by the inventors as useful detection tools in order to differentiate *M. tuberculosis* from *M. bovis* BCG. Such polynucleotides are contained in the 45 aminoacid length coding sequence that is present in *M. bovis* BCG but absent from *M. tuberculosis*. This polynucleotide has a sequence beginning (5' end) at the nucleotide at position nt 729 of the sequence SEQ ID NO.4 and ending (3' end) at the nucleotide in position nt 863 of the sequence SEQ ID NO.4.

Thus, part of the present invention is also a polynucleotide which is chosen among the following group of polynucleotides:

a) A polynucleotide comprising at least 8 consecutive nucleotides the following nucleotide sequence SEQ ID NO.5:

```
GGGCATCGGC GGAATCGGCG GTAACGCTAA CGGGGGCGCC GGTGGGAACG GCGGCACCGG    60

CGGTCAGTTA TGGGGTAGCG GCGGCGCCGG CGTCGAAGGC GGCGCAGCCT TAAGCGTCGG   120

CGACACC                                                             127
```

b) A polynucleotide which sequence is fully complementary to the sequence of the polynucleotide defined in a);

c) A polynucleotide that hybridizes under stringent hybridization conditions with the polynucleotide defined in a) or with the polynucleotide defined in b).

The stringent hybridization conditions for the purpose of defining the above disclosed polynucleofide are defined herein before in the specification.

The invention also provides for a BAC-based *Mycobacterium tuberculosis* strain H37Rv genomic DNA library that has been deposited in the Collection Nationale de Cultures de Microorganismes on November 19, 1997 under the accession number I-1945.

A further object of the invention consists in a recombinant BAC vector which is choosen among the group consisting of the recombinant BAC vectors belonging to the BAC-based DNA library I-1945.

Generally, a recombinant BAC vector of interest may be choosen among the following set or group of BAC vectors contained in the BAC-based DNA library I-1945:

Rv101; Rv102; Rv103; Rv104; Rv105; Rv106; Rv107; Rv108; Rv109; Rv10; Rv110; Rv111; Rv112; Rv113; Rv114; Rv115; Rv116; Rv117; Rv118; Rv119; Rv11; Rv120; Rv121; Rv122; Rv123; Rv124; Rv126; Rv127; Rv128; Rv129; Rv130; Rv132; Rv134; Rv135; Rv136; Rv137; Rv138; Rv139; Rv13; Rv140; Rv141; Rv142; Rv143; Rv144; Rv145; Rv146; Rv147; Rv148; Rv149; Rv14; Rv150; Rv151; Rv152; Rv153; Rv154; Rv155; Rv156; Rv157; Rv159; Rv15; Rv160; Rv161; Rv162; Rv163; Rv164; Rv165; Rv166; Rv167; Rv169; Rv16; Rv170; Rv171; Rv172; Rv173; Rv174; Rv175; Rv176; Rv177; Rv178; Rv179; Rv17; Rv180; Rv181; Rv182; Rv183; Rv184; Rv185; Rv186; Rv187; Rv188; Rv18; Rv190; Rv191; Rv192; Rv193; Rv194; Rv195; Rv196; Rv19; Rv1; Rv201; Rv204; Rv205; Rv207; Rv209; Rv20; Rv214; Rv215; Rv217; Rv218; Rv219; Rv21; Rv220; Rv221; Rv222; Rv223; Rv224; Rv225; Rv226; Rv227; Rv228; Rv229; Rv22; Rv230; Rv231; Rv232; Rv233; Rv234; Rv235; Rv237; Rv240; Rv241; Rv243; Rv244; Rv245; Rv246; Rv247; Rv249; Rv24; Rv251; Rv252; Rv253; Rv254; Rv255; Rv257; Rv258; Rv259; Rv25; Rv260; Rv261; Rv262; Rv263; Rv264; Rv265; Rv266; Rv267; Rv268; Rv269; Rv26; Rv270; Rv271; Rv272; Rv273; Rv274; Rv275; Rv276; Rv277; Rv278; Rv279; Rv27; Rv280; Rv281; Rv282; Rv283; Rv284; Rv285; Rv286; Rv287; Rv288; Rv289; Rv28; Rv290; Rv291; Rv292; Rv293; Rv294; Rv295; Rv296; Rv29; Rv2; Rv301; Rv302; Rv303; Rv304; Rv306; Rv307; Rv308; Rv309; Rv30; Rv310; Rv311; Rv312; Rv313; Rv314; Rv315; Rv316; Rv317; Rv318; Rv319; Rv31; Rv32; Rv322; Rv327; Rv328; Rv329; Rv32; Rv330; Rv331; Rv333; Rv334; Rv335; Rv336; Rv337; Rv338; Rv339; Rv33; Rv340; Rv341; Rv343; Rv344; Rv346; Rv347; Rv348; Rv349; Rv34; Rv350; Rv351; Rv352; Rv353; Rv354; Rv355; Rv356; Rv357; Rv358; Rv359; Rv35;

Rv360; Rv361; Rv363; Rv364; Rv365; Rv366; Rv367; Rv368; Rv369; Rv36; Rv370; Rv371; Rv373; Rv374; Rv375; Rv376; Rv377; Rv378; Rv379; Rv37; Rv381; Rv382; Rv383; Rv384; Rv385; Rv386; Rv387; Rv388; Rv389; Rv38; Rv390; Rv391; Rv392; Rv393; Rv396; Rv39; Rv3; Rv40; Rv412; Rv413; Rv414; Rv415; Rv416; Rv417; Rv418; Rv419; Rv41; Rv42; Rv43; Rv44; Rv45; Rv46; Rv47; Rv48; Rv49; Rv4; Rv50; Rv51; Rv52; Rv53; Rv54; Rv55; Rv56; Rv57; Rv58; Rv59; Rv5; Rv60; Rv61; Rv62; Rv63; Rv64; Rv65; Rv66; Rv67; Rv68; Rv69; Rv6; Rv70; Rv71; Rv72; Rv73; Rv74; Rv75; Rv76; Rv77; Rv78; Rv79; Rv7; Rv80; Rv81; Rv82; Rv83; Rv84; Rv85; Rv86; Rv87; Rv88; Rv89; Rv8; Rv90; Rv91; Rv92; Rv94; Rv95; Rv96; Rv9.

The end sequences of the polynucleotide inserts of each of the above clones corresponding respectively to the sequences adjacent to the T7 promoter and to the Sp6 promoter on the BAC vector are shown in Table 3.

It has been shown by the inventors that the minimal overlapping set of BAC vectors of the BAC-based DNA library I-1945 contains 68 unique BAC clones and practically spans almost the whole H37Rv chromosome with the exception of a single gap of approximately 150 kb.

More specifically, a recombinant BAC vector of interest is choosen among the following set or group of BAC vectors from the BAC-based DNA library I-1945, the location of which vector DNA inserts on the chromosome of *M. tuberculosis* is shown in FIG. 3:

Rv234; Rv351; Rv166; Rv35; Rv415; Rv404; Rv209; Rv272; Rv30; Rv228; Rv233; Rb38; Rv280; Rv177; Rv48; Rv374; Rv151; Rv238; Rv156; Rv92; Rv3; Rv403; Rv322; Rv243; Rv330; Rv285; Rv233; Rv219; Rv416; Rv67; Rv222; Rv149; Rv279; Rv87; Rv273; Rv266; Rv25; Rv136; Rv414; Rv13; Rv289; Rv60; Rv104; Rv5; Rv165; Rv215; Rv329; Rv240; Rv19; Rv74; Rv411; Rv167; Rv56; Rv80; Rv164; Rv59; Rv313; Rv265; Rv308; Rv220; Rv258; Rv339; Rv121; Rv419; Rv418; Rv45; Rv217; Rv134; Rv17; Rv103; Rv21; Rv22; Rv2; Rv270; Rv267; Rv174; Rv257; Rv44; Rv71; Rv7; Rv27; Rv191; Rv230; Rv128; Rv407; Rv106; Rv39; Rv255; Rv74; Rv355; Rv268; Rv58; Rv173; Rv264; Rv417; Rv401; Rv144; Rv302; Rv81; Rv163; Rv281; Rv221; Rv420; Rv175; Rv86; Rv412; Rv73; Rv269; Rv214; Rv287; Rv42; Rv143.

The polynucleotides disclosed in Table 3 may be used as probes in order to select a given clone of the BAC DNA library I-1945 for further use.

The invention also provides for a BAC-based *Mycobacterium bovis* strain Pasteur genomic DNA library that has been deposited in the Collection Nationale de Cultures de Microorganismes on June 30, 1998 under the accession number I-2049.

A further object of the invention consists in a recombinant BAC vector which is chosen among the group consisting of the recombinant BAC vectors belonging to the BAC-based DNA library I-2049. This DNA library contains approximately 1600 clones. The average insert size is estimated to be ~80 kb.

Generally, a recombinant BAC vector of interest may be chosen among the following set or group of BAC vectors contained in the BAC-based DNA library I-2049.

X0001; X0002; X0003; X0004; X0006; X0007; X0008; X0009; X000; X0012; X0013; X0014; X0015; X0016; X0017; X0018; X0019; X0020; X0021; X0175.

The end sequences of the polynucleotide inserts of each of the above clones corresponding respectively to the sequences adjacent to the T7 promoter and to the Sp6 promoter on the BAC vector are shown in Table 4.

The polynucleotides disclosed in Table 4 may be used as probes in order to select a given clone of the BAC DNA library I-2049 for further use.

Are also part of the invention the polynucleotide inserts that are contained in the above described BAC vectors, that are useful as primers or probes.

These polynucleotides and nucleic acid fragments may be used as primers for use in amplification reactions, or as nucleic probes.

PCR is described in the U.S. Pat. No. 4,683,202. The amplified fragments may be identified by an agarose or a polyacrylamide gel electrophoresis, or by a capillary electrophoresis or alternatively by a chromatography technique (gel filtration, hydrophobic chromatography or ion exchange chromatography). The specificity of the amplification may be ensured by a molecular hybridization using, for example, one of the initial primers as nucleic probes.

Amplified nucleotide fragments are used as probes in hybridization reactions in order to detect the presence of one polynucleotide according to the present invention or in order to detect mutations in the genome of the given mycobacterium of interest, specifically a mycobacterium belonging to the *Mycobacterium tuberculosis* complex and more specifically *Mycobacterium tuberculosis* and *Mycobacterium bovis* BCG.

Are also part of the present invention the amplified nucleic fragments (<<amplicons>>) defined herein above.

These probes and amplicons may be radioactively or non-radioactively labeled, using for example enzymes or fluorescent compounds.

Other techniques related to nucleic acid amplification may also be used and are generally preferred to the PCR technique.

The Strand Displacement Amplification (SDA) technique (Walker et al., 1992) is an isothermal amplification technique based on the ability of a restriction enzyme to cleave one of the strands at his recognition site (which is under a hemiphosphorothioate form) and on the property of a DNA polymerase to initiate the synthesis of a new strand from the 3'OH end generated by the restriction enzyme and on the property of this DNA polymerase to displace the previously synthesized strand being localized downstream. The SDA method comprises two main steps:

a) The synthesis, in the presence of dCTP-alpha-S, of DNA molecules that are flanked by the restriction sites that may be cleaved by an appropriate enzyme.

b) The exponential amplification of these DNA molecules modified as such, by ezyme cleavage, strand displacement and copying of the displaced strands. The steps of cleavage, strand displacement and copy are repeated a sufficient number of times in order to obtain an accurate sensitivity of the assay.

The SDA technique was initially realized using the restriction endonuclease HincII but is now generally practised with an endonuclease from *Bacillus stearothermophilus* (BSOBI) and a fragment of a DNA polymerase which is devoid of any 5'→3' exonuclease activity isolated from *Bacilllus cladotenax* (exo- Bca) [=exo-minus-Bca]. Both enzymes are able to operate at 60° C. and the system is now optimized in order to allow the use of dUTP and the decontamination by UDG. When using this technique, as described by Spargo et al. in 1996, the doubling time of the target DNA is of 26 seconds and the amplification rate is of $10^{10}$ after an incubation time of 15 min at 60° C.

The SDA amplification technique is more easy to perform than PCR (a single thermostated waterbath device is necessary) and is faster than the other amplification methods.

Thus, another object of the present invention consists in using the nucleic acid fragments according to the invention (primers) in a method of DNA or RNA amplification according to the SDA technique. For performing SDA, two pairs of primers are used: a pair of external primers (B1, B2) consisting of a sequence specific for the target polynucleotide of interest and a pair of internal primers (S1, S2) consisting of a fusion oligonucleotide carrying a site that is recognized by a restriction endonuclease, for example the enzyme BSOBI.

The operating conditions to perform SDA with such primers are described in Spargo et al, 1996.

The polynucleotides of the invention and their above described fragments, especially the primers according to the invention, are useful as technical means for performing different target nucleic acid amplification methods such as:

TAS (Transcription-based Amplification System), described by Kwoh et al. in 1989;

SR (Self-Sustained Sequence Replication), described by Guatelli et al.in 1990.

NASBA (Nucleic acid Sequence Based Amplification), described by Kievitis et al. in 1991.

TMA (Transcription Mediated Amplification).

The polynucleotides according to the invention are also useful as technical means for performing methods for amplification or modification of a nucleic acid used as a probe, such as:

LCR (Ligase Chain Reaction), described by Landegren et al. in 1988 and improved by Barany et al. in 1991 who employ a thermostable ligase.

RCR (Repair Chain Reaction) described by Segev et al. in 1992.

CPR (Cycling Probe Reaction), described by Duck et al. in 1990.

Q-beta replicase reaction, described by Miele et al. in 1983 and improved by Chu et al. in 1986, Lizardi et al. in 1988 and by Burg et al. and Stone et al. in 1996.

When the target polynucleotide to be detected is a RNA, for example a mRNA, a reverse transcriptase enzyme will be used before the amplification reaction in order to obtain a cDNA from the RNA contained in the biological sample. The generated cDNA is subsequently used as the nucleic acid target for the primers or the probes used in an amplification process or a detection process according to the present invention.

The non-labeled polynucleotides or oligonucleotides of the invention may be directly used as probes. Nevertheless, the polynucleotides or oligonucleotides are generally labeled with a radioactive element ($^{32}P$, $^{35}S$, $^{3}H$, $^{125}I$) or by a non-isotopic molecule (for example, biotin, acetylaminofluorene, digoxigenin, 5-bromodesoxyuridin, fluorescein) in order to generate probes that are useful for numerous applications.

Examples of non-radioactive labeling of nucleic acid fragments are described in the french patent N° FR-7810975 or by Urdea et al. or Sanchez-Pescador et al., 1988.

In the latter case, other labeling techniques may be also used such as those described in the french patents FR-2,422,956 and 2,518,755. The hybridization step may be performed in different ways (Matthews et al., 1988). The more general method consists of immobilizing the nucleic acid that has been extracted from the biological sample onto a substrate (nitrocellulose, nylon, polystyrene) and then to incubate, in defined conditions, the target nucleic acid with the probe. Subsequently to the hybridization step, the excess amount of the specific probe is discarded and the hybrid molecules formed are detected by an appropriate method (radioactivity, fluorescence or enzyme activity measurement).

Advantageously, the probes according to the present invention may have structural characteristics such that they allow the signal amplification, such structural characteristics being, for example, branched DNA probes as those described by Urdea et al. in 1991 or in the European patent No. EP-0225,807 (Chiron).

In another advantageous embodiment of the probes according to the present invention, the latters may be used as <<capture probes>>, and are for this purpose immobilized on a substrate in order to capture the target nucleic acid contained in a biological sample. The captured target nucleic acid is subsequently detected with a second probe which recognizes a sequence of the target nucleic acid which is different from the sequence recognized by the capture probe.

The oligonucleotide probes according to the present invention may also be used in a detection device comprising a matrix library of probes immobilized on a substrate, the sequence of each probe of a given length being localized in a shift of one or several bases, one from the other, each probe of the matrix library thus being complementary to a distinct sequence of the target nucleic acid. Optionally, the substrate of the matrix may be a material able to act as an electron donor, the detection of the matrix positions in which an hybridization has occurred being subsequently determined by an electronic device. Such matrix libraries of probes and methods of specific detection of a targer nucleic acid is described in the European patent application No. EP-0713,016 (Affymax technologies) and also in the U.S. Pat. No. 5,202,231 (Drmanac).

Since almost the whole length of a mycobacterial chromososme is covered by a BAC-based genomic DNA libraries according to the present invention (i.e. 97% of the *M. tuberculosis* chromosome is covered by the BAC library I-1945), these DNA libraries will play an important role in a plurality of post-genomic applications, such as in mycobacterial gene expression studies where the canonical set of BACs could be used as a matrix for hybridization studies. Probing such matrices with cDNA probes prepared from total mRNA will uncover genetic loci induced or repressed under different physiological conditions (Chuang et al., 1993; Trieselman et al., 1992). As such, the H37Rv BAC library represents a fundamental resource for present and future genomics investigations.

The BAC vectors or the polynucleotide inserts contained therein may be directly used as probes, for example when immobilized on a substrate such as described herein before.

The BAC vectors or their polynucleotide inserts may be directly asdorbed on a nitrocellulose membrane, at predetermined locations on which one or several polynucleotides to be tested are then put to hybridize therewith.

Preferably, a collection of BAC vectors that spans the whole genome of the mycobacterium under testing will be immobilized, such as, for example, the set of 68 BAC vectors of the I-1945 DNA library that is described elsewhere in the specification and shown in FIG. 3.

The immobilization and hybridization steps may be performed as described in the present Materials and Methods Section.

As another illustrative embodiment of the use of the BAC vectors of the invention as polynucleotide probes, these vectors may be useful to perform a transcriptional activity analysis of mycobacteria growing in different environmental conditions, for example under conditions in which a stress response is expected, as it is the case at an elevated temperature, for example 40° C.

In this specific embodiment of the invention, Genescreen membranes may be used to immobilize the restriction endonuclease digests (HindIII digests for the BAC DNA library I-1945) of the BAC vectors by transfer from a gel (Trieselman et al., 1992).

Alternatively, the BAC vectors may be immobilized for dot blot experiments as follows. First, the DNA concentration of each BAC clone is determined by hybridization of blots of clone DNAs and of a BAC vector concentration standard with a BAC vector specific DNA probe. Hybridization is quantified by the Betascope 603 blot analyzer (Betagen Corp.), which colects beta particles directly from the blot with high efficiency. Then, 0.5 $\mu g$ of each clone DNA is incubated in 0.25 M NaOH and 10 mM EDTA at 65° C. for 60 min to denature the DNA and degrade residual RNA contaminants. By using a manifold filtration system (21 by 21 wells), each clone DNA is blotted onto a GeneScreen Plus nylon membrane in the alkaline solution. After neutralization, the blots are baked at 85° C. for 2 h under vacuum. Positive and negative controls are added when necessary. In order to perform this procedure, it may be referred to the article of Chuang et al. (1993).

For RNA extractions, cells grown in a suitable volume of culture medium may, for example, be immediately mixed with an equal volume of crushed ice at −70° C. and spun at 4° C. in a 50 ml centrifugation tube. The cell pellet is then suspended in 0.6 ml of ice-cold buffer (10 mM KCl, 5 mM MgCl, 10 mM Tris; pH 7.4) and then immediately added to 0.6 ml of hot lysis buffer (0.4 M NaCl, 40 mM EDTA, 1% beta-mercaptoethanol, 1% SDS, 20 mM Tris; pH 7.4) containing 100 $\mu l$ of water saturated phenol. This mixture is incubated in a boiling water bath for 40 s. The debris are removed by centrifugation. The supernatant is extracted with phenol-chloroform five times, ethanol precipitated, and dried. The dried RNA pellet is dissolved in water before use.

Then labeled total cDNA may be prepared by the following method. The reaction mixture contains 15 $\mu g$ of the previously prepared total RNA, 5 $\mu g$ of pd($N_6$) (random hexamers from Pharmacia Inc.), 0.5 mM dATP, 0.5 mM dGTP and 0.5 mM DTTP, 5 $\mu M$ dCTP, 100 $\mu Ci$ of [$\alpha$-$^{32}P$] dCTP (3,000 Ci/mmol), 50 mM Tris-HCl (pH 8.3), 6 mM $MgCl_2$, 40 mM Kcl, 0.5 U of avian myeloblastosis virus reverse transcriptase (Life Science Inc.) in a total volume of 50 $\mu l$. The reaction is allowed to continue overnight at room temperature. EDTA and NaOH are then added to final concentrations of 50 mM and 0.25 M, respectively, and the mixture is incubated at 65° C. for 30 min to degrade the RNA templates. The cDNA is then ready to use after neutralization by adding Hcl and Tris buffer.

The hybridization step may be performed as described by Chuang et al. (1993) and briefly disclosed hereinafter. The DNA dot blot is hybridized to $^{32}P$-labeled total cDNA in a solution containing 0.1% polyvinylpyrrolidone, 0.1% Ficoll, 0.1% sodium $P_{pi}$, 0.1% bovine serum albumin, 0.5% SDS, 100 mM NaCl, and 0.1 mM sodium citrate, pH 7.2, at 65° C. for 2 days and then washed with a solution containing 0.1% SDS, 100 mM NaCl, and 10 mM Na-citrate, pH 7.2. The same dot blot is used for hybridization with both control and experimental cDNAs, with an alkaline probe stripping procedure (soaked twice in 0.25M NaOH-0.75 M NaCl at room temperature, 30 min each, neutralized, and completely dried at 65° C. for at least 30 min) between the two hybridizations. Quantification may be done with the Betascope 603 blot analyzer (Betagen Corp.).

As it flows from the above technical teachings, another object of the invention consists in a method for detecting the presence of mycobacteria in a biological sample comprising the steps of:

a) bringing into contact the recombinant BAC vector or a purified polynucleotide according to the invention with a biological sample.

b) detecting the hybrid nucleic acid molecule formed between said purified polynucleotide and the nucleic acid molecules contained within the biological sample.

The invention further deals with a method for detecting the presence of mycobacteria in a biological sample comprising the steps of:

a) Bringing into contact the recombinant BAC vector or a purified polynucleotide according to the invention that has been immobilized onto a substrate with a biological sample.

b) Bringing into contact the hybrid nucleic acid molecule formed between said purified polynucleotide and the nucleic acid contained in the biological sample with a labeled recombinant BAC vector or a polynucleotide according to the invention, provided that said polynucleotide and polynucleotide of step a) have non-overlapping sequences.

Another object of the invention consists in a method for detecting the presence of mycobacteria in a biological sample comprising the steps of:

a) Bringing into contact the nucleic acid molecules contained in the biological sample with a pair of primers according to the invention.

b) Amplifying said nucleic acid molecules;

d) detecting the nucleic acid fragments that have been amplified, for example by gel electrophoresis or with a labeled polynucleotide according to the invention.

In one specific embodiment of the above detection and/or amplification methods, said methods comprise an additional step wherein before step a), the nucleic acid molecules of the biological sample have been made available to a hybridization reaction.

In another specific embodiment of the above detection methods, said methods comprise an additional step, wherein, before the detection step, the nucleic acid molecules that are not hybridized with the immobilized purified polynucleotide are removed.

Also part of the invention is a kit for detecting mycobacteria in a biological sample comprising:

a) A recombinant BAC vector or a purified polynucleotide according to the invention;

b) Reagents necessary to perform a nucleic acid hybridization reaction.

The invention also pertains to a kit for detecting a mycobacteria in a biological sample comprising:

a) A recombinant BAC vector or a purified polynucleotide according to the invention that is immobilized onto a substrate.

b) Reagents necessary to perform a nucleic acid hybridization reaction.

c) A purified polynucleotide according to the invention which is radioactively or non-radioactively labeled, provided that said polynucleotide and the polynucleotide of step a) have non-overlapping sequences.

Moreover, the invention provides for a kit for detecting mycobacteria in a biological sample comprising:

a) A pair of purified primers according to the invention;

b) Reagents necessary to perform a nucleic acid amplification reaction;

c) Optionally, a purified polynucleotide according to the invention useful as a probe.

The invention embraces also a method for detecting the presence of a genomic DNA, a cDNA or a mRNA of mycobacteria in a biological sample, comprising the steps of:

a) Bringing into contact the biological sample with a plurality of BAC vectors according to the invention or purified polynucleotides according to the invention, that are immobilized on a substrate;

b) Detecting the hybrid complexes formed.

The invention also provides a kit for detecting the presence of genomic DNA, cDNA or mRNA of a mycobacterium in a biological sample, comprising:

a) A substrate on which a plurality of BAC vectors according to the invention or purified polynucleotides according to the invention have been immobilized;

b) Optionally, the reagents necessary to perform the hybridization reaction.

Additionally, the recombinant BAC vectors according to the invention and the polynucleotide inserts contained therein may be used for performing detection methods based on <<molecular combing>>. Said methods consist in methods for aligning macromolecules, especially DNA and are applied to processes for detecting, for measuring intramolecular distance, for separating and/or for assaying a macromolecule, especially DNA in a sample.

These <<molecular combing>> methods are simple methods, where the triple line S/A/B (meniscus) resulting form the contact between a solvent A and the surface S and a medium B is caused to move on the said surface S, the said macromolecules (i.e. DNA) having a part, especially an end, anchored on the surface S, the other part, especially the other end, being in solution in the solvent A. These methods are particularly fully described in the PCT Application n° PCT/FR 95/00165 files on Feb. 11, 1994 (Bensimon et al.).

When performing the <<molecular combing>> method with the recombinant BAC vectors according to the inventions or their polynucleotide inserts, the latters may be immobilized (<<anchored>>) on a suitable substrate and aligned as described in the PCT Application n° PCT/FR 95/00165, the whole teachings of this PCT Application being herein incorporated by reference. Then, polynucleotides to be tested, preferably under the form of radioactively or non radioactively labeled polynucleotides, that may consist of fragments of genomic DNA, cDNA etc. are brought into contact with the previously aligned polynucleotides according to the present invention and then their hybridization position on the aligned DNA molecules is determined using any suitable means including a microscope or a suitable camera device.

Thus, the present invention is also directed to a method for the detection of the presence of a polynucleotide of mycobacterial origin in a biological sample and/or for physical mapping of a polynucleotide on a genomic DNA, said method comprising:

a) Aligning at least one polynucleotide contained in a recombinant BAC vector according to the invention on the surface of a substrate;

b) Bringing into contact at least one polynucleotide to be tested with the substrate on which the at least one polynucleotide of step a) has been aligned;

c) detecting the presence and/or the location of the tested polynucleotide on the at least one aligned polynucleotide of step a).

The invention finally provides for a kit for performing the above method, comprising:

a) a substrate whose surface has at least one polynucleotide contained in a recombinant BAC vector according to the invention;

b) optionally, reagents necessary for labeling DNA;

c) optionally, reagents necessary for performing a hybridization reaction.

In conclusion, it may be underlined that the alliance of such BAC-based approaches such as described in the present specification to the advances in comparative genomics by the availability of an increased number of complete genomes, and the rapid increase of well-characterized gene products in the public databases, will allow the one skilled in the art an exhaustive analysis of the mycobacterial genome.

MATERIALS AND METHODS

1. DNA-preparation. Preparation of *M. tuberculosis* H37Rv DNA in agarose plugs was conducted as previously described (Canard et al., 1989; Philipp et al., 1996b). Plugs were stored in 0.2 M EDTA at 4° C. and washed 3 times in 0.1% Triton X-100 buffer prior to use.

2. BAC vector preparation. pBeloBAC11 was kindly provided by Dr. Shizuya, Department of Biology, California Institute of Technology (Pasadena, Calif.). The preparation followed the description of Woo et al., 1994 (Woo et al., 1994).

3. Partial digestion with HindIII. Partial digestion was carried out on plugs, each containing approximately 10 μg of high molecular weight DNA, after three one hour equilibration steps in 50 ml of HindIII 1×digestion buffer (Boehringer Mannheim, Mannheim, Germany) plus 0.1% Triton X-100. The buffer was then removed and replaced by 1 ml/plug of ice-cold HindIII enzyme buffer containing 20 units of HindIII (Boehringer). After two hours incubation on ice, the plugs were transferred to a 37° C. water bath for 30 minutes. Digestions were stopped by adding 500 μl of 50 mM EDTA (pH 8.0).

4. Size selection. The partially digested DNA was subjected to contour-clamped homogenous electric field (CHEF) electrophoresis on a 1% agarose gel using a BioRad DR III apparatus (BioRad, Hercules, Calif.) in 1×TAE buffer at 13° C., with a ramp from 3 to 15 seconds at 6 V/cm for 16 hours. Agarose slices from 25 to 75 kb, 75 to 120 kb and 120 to 180 kb were excised from the gel and stored in TE at 4° C.

5. Ligation and transformation. Agarose-slices containing fractions from 25 to 75 kb, 75 to 120 kb and 120 to 180 kb were melted at 65° C. for 10 minutes and digested with Gelase (Epicentre Technologies, Madison, Wis.), using 1 unit per 100 μl gel-slice. 25–100 ng of the size-selected DNA was then ligated to 10 ng of HindIII digested, dephosphorylated pBeloBAC11 in a 1:10 molar ratio using 10 units of T4 DNA ligase (New England Biolabs, Beverly, Mass.) at 16° C. for 20 hours. Ligation mixtures were heated at 65° C. for 15 minutes, then drop-dialysed against TE using Millipore VS 0.025 mM membranes (Millipore, Bedford, Mass.). Fresh electrocompetent *E. coli* DH10B cells (Sheng et al., 1995) were harvested from 200 ml of a mid-log (($OD_{550}$=0.5) culture grown in SOB medium. Cells were washed three times in ice-cold water, and fmally resuspended in ice-cold water to a cell density of $10^{11}$ cells/ml ($OD_{550}$=150). 1 μl of the ligation-mix was used for electroporation of 30 μl of electrocompetent DH10B *E. coli* using a Eurogentec Easyject Plus electroporator (Eurogentec, Seraing, Belgium), with settings of 2.5 kV, 25 μF, and 99½, in 2 mm wide electroporation cuvettes. After electroporation, cells were resuspended in 600 μl of SOC medium, allowed to recover for 45 minutes at 37° C. with gentle shaking, and then plated on LB agar containing 12.5 μg/ml chloramphenicol (CM), 50 μg/ml X-gal, and 25 μg/ml IPTG. The plates were incubated overnight and recombinants (white colonies) were picked manually to 96 well plates. Each clone was inoculated 3 times (2×200 μl and 1×100 μl of 2YT/12.5 μg/ml CM per clone) and incubated overnight. One of the microtiter plates, containing 100 μl culture per well, was maintained as a master plate at −80° C. after 100 ml of 80% glycerol were added to each well, while minipreps (Sambrook et al., 1989) were prepared from the remaining two plates to check for the presence of inserts. Clones containing inserts were then designated "Rv" clones, repicked from the master plate to a second set of plates for storage of the library at −80° C.

6. Preparation of DNA for sizing, direct sequencing and comparative genomics. A modified Birnboim and Doly protocol (Birnboim et al., 1979) was used for extraction of plasmid DNA for sequencing purposes. Each Rv clone was inoculated into a 50 ml Falcon polypropylene tube containing 40 ml of 2YT medium with 12.5 μg/ml of CM and grown overnight at 37° C. with shaking. Cells were harvested by centrifugation and stored at −20° C. The frozen pellet was resuspended in 4 ml of Solution A (50 mM glucose, 10 mM EDTA, 25 mM Tris, pH 8.0) and 4 ml of freshly prepared solution B (0.2 M NaOH, 0.2% SDS) was then added. The solution was gently mixed and kept at room temperature for 5 minutes before adding 4 ml of ice-cold solution C (3M Sodium Acetate, pH 4.7). Tubes were kept on ice for 15 min, and centrifuged at 10,000 rpm for 15 min. After isopropanol precipitation, the DNA pellet was dissolved in 600 μl RNase solution (15 mM Tris HCl pH 8.0, 10 μg/ml RNase A). After 30 minutes at 37° C. the DNA solution was extracted with chloroform:isoamylalcohol (24:1) and precipitated from the aqueous phase using isopropanol. The DNA pellet was then rinsed with 70% ethanol, air-dried and dissolved in 30 μl distilled water. In general, DNA prepared by this method was clean and concentrated enough to give good quality results by automatic sequencing (at least 300 bp of sequence). For a few DNA preparations, an additional polyethylene glycol (PEG) precipitation step was necessary, which was performed as follows. The 30 μl of DNA solution were diluted to 64 μl, mixed gently and precipitated using 16 μl 4M NaCl and 80 μl of 13% PEG 8000. After 30 min on ice the tubes were centrifuged at 4° C., the pellet carefully rinsed with 70% ethanol, air-dried and diluted in 20 μl of distilled water.

7. Sizing of inserts. Insert sizes were determined by pulsed-field gel electrophoresis (PFGE) after cleavage with DraI (Promega). 100–200 ng of DNA was DraI-cleaved in 20 μl total reaction volume, following the manufacturer's recommendations, then loaded onto a 1% agarose gel and migrated using a pulse of 4 s for 15 h at 6.25 V/cm at 10° C. on an LKB-Pharmacia CHEF apparatus. Mid-range and low-range PFGE markers (New England Biolabs) were used as size standards. Insert sizes were estimated after ethidium bromide staining of gels.

8. Direct sequencing. For each sequencing reaction 7 μl BAC DNA (300–500 ng), 2 μl primer (2 μM), 8 μl reaction mix of the Taq DyeDeoxy Terminator cycle sequencing kit (Applied Biosystems) and 3 μl distilled water were used. After 26 cycles (96° C. for 30 sec; 56° C. for 15 sec; 60° C. for 4 min) in a thermocycler (MJ-research Inc., Watertown, Mass.) DNA was precipitated using 70 μl of 70% ethanol/0.5 mM $MgCl_2$, centrifuged, rinsed with 70% ethanol, dried and dissolved in 2 μl of formamide/EDTA buffer. SP6 and T7 samples of 32 BAC clones were loaded onto 64 lane, 6% polyacrylamide gels and electrophoresis was performed on a Model 373A automatic DNA sequencer (Applied Biosystems) for 12 to 16 hours. The sequences of oligonucleotides used as primers are shown in Table 1.

9. DOP-PCR. As an alternate procedure we used partially degenerate oligonucleotides in combination with vector-specific (SP6 or T7) primers to amplify insert ends of BAC clones, following a previously published protocol for P1 clones (Liu et al., 1995). The degenerate primers Deg2, Deg3, Deg4, Deg6 (Table 1) gave the best results for selected amplification of insert termini.

TABLE 1:

Primers used for PCRs and sequencing

Vector specific Primers for DOP PCR- first amplification step:

SP6-BAC1: AGT TAG CTC ACT CAT TAG GCA (SEQ ID NO. 734)

T7-BAC1: GGA TGT GCT GCA AGG CGA TTA (SEQ ID NO. 735)

Vector specific Primers (direct sequencing, nested primer for second PCR step)

SP6 Mid: AAA CAG CTA TGA CCA TGA TTA CGC CAA (SEQ ID NO. 736)

T7-Belo2: TCC TCT AGA GTC GAC CTG CAG GCA (SEQ ID NO. 737)

Degenerate Primers:

Deg2: TCT AGA NNN NNN TCC GGC (SEQ ID NO. 738)

Deg3: TCT AGA NNN NNN GGG CCC (SEQ ID NO. 739)

Deg4: CGT TTA AAN NNN NWA GGC CG (SEQ ID NO. 740)

Deg6: GGT ACT AGT NNN NNW TCC GGC (SEQ ID NO. 741)

Primers used for the amplification of *M. bovis* DNA in polymorphic chromosomal region of Rv58:

Primer 1: ACG ACC TCA TAT TCC GAA TCC C (SEQ ID NO. 742)

Primer 2: GCA TCT GTT GAG TAC GCA CTT CC (SEQ ID NO. 743)

10. Screening by pooled PCR. To identify particular clones in the library which could not be detected by random end-sequencing of the 400 BAC clones, PCR-screening of DNA pools was performed. Primers were designed for regions of the chromosome where no BAC coverage was apparent using cosmid-or H37Rv whole genome shotgun sequences. Primers were designed to amplify approximately 400–500 bp. Ninety-six-well plates containing 200 μl 2YT/12.5 μg/ml CM per well were inoculated with 5 μl of −80° C. glycerol stock cultures each from the master plates and incubated overnight. The 96 clones of each plate were pooled by taking 20 μl of culture from each well and this procedure was repeated for 31 plates. Pooled cultures were centrifuged, the pellets were resuspended in sterile water, boiled for 5 minutes, centrifuged and the supernatants kept for PCRS. As an initial screening step, the 31 pools of a total of 2976 BACs, representing about two thirds of the library were tested for the presence of a specific clone using appropriate PCR primers. PCR was performed using 10 ∞l of supernatant, 5 μl of assay buffer (100 mM b-mercaptoethanol, 600 mM Tris HCl (pH 8.8), 20 mM $MgCl_2$, 170 mM $(NH_4)_2SO_4$), 5 μl of Dimethylsulfoxide (DMSO), 5 μl of dNTPs (20 mM), 5 μl of water, 10 μl primer (2 μM), 10 μl inverse primer (2 μM) and 0.2 units of taq DNA polymerase (Boehringer). 32 cycles of PCR (95° C. for 30 s, 55° C. for 1 min 30 s, 72° C. for 2 min) were performed after an initial denaturation at 95° C. for 1 min. An extension step at 72° C. for 5 min finished the PCR. If a pool of 96 clones yielded an appropriate PCR product (FIG. 1A), subpools were made to identify the specific clone. Subpools representative for lane A of a 96 well plate were made by pooling clones 1 to 12 from lane A into a separate tube. Subpools for lanes B to H were made in the same way. In addition, subpools of each of the 12 rows (containing 8 clones each) were made, so that for one 96 well plate, 20 subpools were obtained. PCR with these 20 subpools identified the specific clone (FIG. 1B, lower gel portion). If more than one specific clone was present among the 96 clones of one plate (FIG. 1B, upper gel portion), additional PCR reactions had to be performed with the possible candidates (data not shown).

11. Genomic comparisons. DNA from the BAC clone Rv58 was digested with the restriction endonucleases EcoRI and PvuII, and resolved by agarose gel electrophoresis at low voltage overnight (1.5 V/cm). DNA was transferred via the method of Southern to nitrocellulose membranes (Hybond C extra, Amersham) following standard protocols (Sambrook et al., 1989), then fixed to the membranes at 80° C. for 2 hours. The blot was hybridized with $^{32}P$ labelled total genomic DNA from *M. tuberculosis* H37Rv, *M. bovis* type strain (ATCC 19210) or *M. bovis* BCG Pasteur. Hybridization was performed at 37° C. overnight in 50% formamide hybridization buffer as previously described (Philipp et al., 1996b). Results were interpreted from the autoradiograms.

12. Computer analysis. Sequence data from the automated sequencer ABI373A were transferred as binary data to a Digital Alpha 200 station or Sun SparcII station and analysed using TED, a sequence analysis program from the Staden software package (Dear et al., 1991). Proof-read sequences were compared using the BLAST programs (Altschul et al., 1990) to the *M. tuberculosis* H37Rv sequence databases of the Sanger Centre, containing the collected cosmid sequences (TB.dbs) and whole-genome shotgun reads (TB_shotgun_all.dbs) (http://www.sanger.ac.uk/). In addition, local databases containing 1520 cosmid endsequences and the accumulating BAC endsequences were used to determine the exact location of end-sequenced BACs on the physical and genetic map. MycDB (Bergh et al., 1994) and public databases (EMBL, Genbank) were also used to compare new sequences, but to a lesser extent. The organization of the open reading frames (ORFs) in the polymorphic region of clone Rv58 was determined using the DIANA software established at the Sanger Centre.

EXAMPLES

Example 1

Construction of a pBeloBAC11 Library of *M. tuberculosis* H37Rv

Partial HindIII fragments of H37Rv DNA in the size range of 25 to 180 kb were ligated into pBeloBAC11 and electroporated into strain *E. coli* DH10B. While cloning of fractions I (25 to 75 kb) and II (75 to 120 kb) gave approximately $4\times10^4$ transformants (white colonies), cloning of fraction III (120 to 180 kb) repeatedly resulted in empty clones. Parallel cloning experiments using partial HindIII digests of human DNA resulted in stable inserts for all three fractions (data not shown), suggesting that the maximum size of large inserts in BAC clones is strongly dependent on the source of the DNA. Analysis of the clones for the presence of inserts revealed that 70% of the clones had an insert of the appropriate size while the remaining 30% of white colonies represented empty or lacZ'-mutated clones. Size determination of randomly selected, DraI-cleaved BACs via PFGE showed that the insert sizes ranged for the majority of the clones between 40 kb and 100 kb with an average size of 70 kb. Clones with inserts of appropriate size were designated with "Rv" numbers, recultured and stored at −80° C. for further use.

Example 2

Direct DNA Sequence Analysis of BACs

To characterize the BAC clones, they were systematically subjected to insert termini sequencing. Two approaches, direct sequencing of BAC DNA and PCR with degenerate oligonucleotide primers (DOP), adapted to the high G+C content of mycobacterial DNA, were used. In a first screening phase, 50 BAC clones designated Rv1 to Rv50 were analysed using both methods in parallel. Except for two clones, where the sequences diverged significantly, the sequences obtained by the two methods only differed in length. Sequences obtained directly were on average about 350 bp long and for 95% of the clones both the SP6 and T7 endsequences were obtained at the first attempt. Sequences obtained by DOP-PCR were mostly shorter than 300 bp. For 40% of the BACs we obtained only very short amplicons of 50 to 100 base pairs from one end. In two cases the sequence obtained with the DOP-PCR differed from the sequences obtained by direct sequencing, and in these cases *E. coli* or vector sequences were amplified (data not shown). Taking the advantages and disadvantages of both methods into account, we decided to use direct termini sequencing for the systematic determination of the SP6 and T7 end-sequences.

Example 3

Representativity of the Library

After having determined the end-sequences of 400 BACs a certain redundancy was seen. The majority of clones were represented at least 3 to 4 times. Maximum redundancy was seen in the vicinity of the unique rrn operon, as 2.5% of the clones carried identical fragments that bridge the cosmids Y50 and Y130 (FIG. 3, approximate position at 1440 kb). The majority of clones with identical inserts appeared as two variants, corresponding to both possible orientations of the HindIII fragment in pBeloBAC11. This suggests that the redundancy was not the result of amplification during library construction, but due to the limited number of possible combinations of partial HindIII fragments in the given size-range of 25 to 120 kb. To detect rare BAC clones, a pooled PCR protocol was used. Primers were designed on the basis of the existing cosmid sequences and used to screen 31 pools of 96 BAC clones. When positive PCR products of the correct size were obtained, smaller subpools (of 8 or 12 clones each) of the corresponding pool were subsequently used to identify the corresponding clone (FIG. 1). With this approach 20 additional BACs (Rv401–Rv420) were found for the regions where no BACs were found with the initial systematic sequencing approach. The endsequences of these BACs (Rv401–420) were determined by direct sequencing, which confirmed the predicted location of the clones on the chromosome. A 97% coverage of the genome of H37Rv with BAC clones was obtained. Only one region of ~150 kb was apparently not represented in the BAC library as screening of all pools with several sets of specific primers did not reveal the corresponding clone. This was probably due to the fact that HindIII fragments of mycobacterial DNA larger than 110 kb are very difficult to establish in *E. coli* and that a HindIII fragment of ~120 kb is present in this region of the chromosome (data not shown).

Example 4

Establishing a BAC Map

Using all endsequence and shotgun-sequence data from the H37Rv genome sequencing project, most of the BAC clones could then be localized by sequence comparison on the integrated map of the chromosome of *M. tuberculosis* strain H37Rv (Philipp et al., 1996b) and an ordered physical map of the BAC-clones was established. PCR with primers from the termini sequences of selected BACs were used for chromosomal walking and confirmation of overlapping BACs (data not shown). The correct order of BACs on the map was also confirmed more recently, using 40,000 whole genome shotgun reads established at the Sanger Centre. In addition, pulsed-field gel electrophoresis of DraI digests of selected BACs was performed (FIG. 2) in order to see if the approximate fragment size and the presence or absence of DraI cleavage sites in the insert were consistent with the location of the BACs on the physical map (FIG. 3). Comparison of the sequence-based BAC-map with the physical and genetic map, established by PFGE and hybridization experiments (Philipp et al., 1996b), showed that the two maps were in good agreement. The positions of 8 genetic markers previously shown on the physical and genetic map were directly confirmed by BAC-endsequence data (Table 2, FIG. 3). The position of 43 from 47 Y-clones (91%) shown on the physical and genetic map, which were later shotgun sequenced, was confirmed by the BAC endsequences and shotgun sequence data. Four clones (Y63, Y180, Y251, and Y253) were located to different positions than previously thought and this was found to be due to book keeping errors or to chimeric inserts. Their present approximate location relative to the oriC is shown in FIG. 3: Y63 at 380 kb, Y63A at 2300 kb, Y180 at 2160 kb, Y251 at 100 kb, and Y253 at 2700 kb. A total of 48 BACs, covering regions of the chromosome, not represented by cosmids were then shotgun sequenced (Cole et al., 1997), and these are squared in FIG. 3. No chimeric BACs were found, which is consistent with the observations of other research groups for other BAC libraries (Cai et al., 1995; Zimmer et al;, 1997). The absence of chimeric BACs was of particular importance for the correct assembly of the *M. tuberculosis* H37Rv sequence. The exact position of the BAC termini sequences on the chromosome will be available via the world wide web (http://www.pasteur.fr/MycDB).

TABLE 2

Identities of genetic markers previously shown on the integrated and genetic map of H37Rv (Phlipp et al., 1996b) which showed perfect sequence homology with BAC end sequences.

| Locus | BAC end sequence | Description of genetic marker | Organism | GenBank Accession n° |
|---|---|---|---|---|
| apa | Rv163SP6 | Secreted alanine-proline-rich antigen | *M. tuberculosis* | X80268 |
| dnaJ, dnaK | Rv164T7 | DnaJ hsp | *M. leprae* | M95576 |
| fop-A | Rv136T7 | Fibronectin binding protein | *M. tuberculosis* | M27016 |
| polA | Rv401T7 | DNA polymerase I | *M. tuberculosis* | L11920 |
| ponA | Rv273T7 | Penicillin binding protein | *M. leprae* | S82044 |
| pstC | Rv103T7 | Putative phosphate transport receptor | *M. tuberculosis* | Z48057 |
| recA | Rv415SP6 | Homologous recombination | *M. tuberculosis* | X58485 |
| wag9 | Rv35SP6 | 35-kDa antigen | *M. tuberculosis* | M69187 |

Example 5

Repetitive Endsequences

Repetitive sequences can seriously confound mapping and sequence assembly. In the case of the BAC endsequences, no particular problems with repetitive sequences were observed. Although nine clones with one end in an IS1081 (Collins et al., 1991) sequence were identified, it was possible to correctly locate their position on the map using the sequence of the second terminus. Moreover, these BACs were used to determine the exact locations of IS1081 sequences on the map. Five copies of this insertion sequence, which harbors a HindIII cleavage site, were mapped on the previous physical and genetic map. In contrast, BAC endsequence data revealed an additional copy of IS1081 on the *M. tuberculosis* H37Rv chromosome. The additional copy was identified by six clones (Rv27, Rv118, Rv142, Rv160, Rv190, Rv371) which harbored an identical fragment linking Y50 to I364 (FIG. 3, at ~1380 kb). This copy of IS1081 was not found by previous hybridization experiments probably because it is located near another copy of IS1081, localized on the same DraI fragment Z7 and AsnI fragment U (FIG. 3, at ~1140 kb). Furthermore, the position of a copy of IS1081 previously shown in DraI fragment Y1 (FIG. 3, at ~1840 kb) had to be changed to the region of Y349 (FIG. 3, at ~3340 kb) according to the endsequences of BAC Rv223. The positions of the four other IS1081 copies were confirmed by the sequence data and therefore remained unchanged. In total 6 copies of IS1081 were identified in the H37Rv genome in agreement with the findings of others (Collins et al., 1991).

In addition, a sequence of 1165 bp in length containing a HindIII site was found in two copies in the genome of H37Rv in different regions. The endsequences of BAC clones Rv48 and Rv374, covering cosmid Y164, as well as Rv419 and Rv45, that cover cosmid Y92, had perfect identity with the corresponding parts of this 1165 bp sequence (FIG. 3, at ~3480 kb and ~900 kb). Analysis of the sequence did not reveal any homology with insertion sequences or other repetitive elements. However, as each of the two locations showed appropriate BAC coverage, chimerism of the sequenced cosmids Y164 and Y92 can be ruled out as the probable cause.

Example 6

Using BAC Clones in Comparative Genomics

The minimal overlapping set of BAC clones represents a powerful tool for comparative genomics. For example, with each BAC clone containing on average an insert of 70 kb, it should be possible to cover a 1 Mb section of the chromosome with 15 BAC clones. Restriction digests of overlapping clones can then be blotted to membranes, and probed with radiolabelled total genomic DNA from, for example, *M. bovis* BCG Pasteur. Restriction fragments that fail to hybridize with the *M. bovis* BCG Pasteur DNA must be absent from its genome, hence identifying polymorphic regions between *M. bovis* BCG Pasteur and *M. tuberculosis* H37Rv. The results of such an analysis with clone Rv58 (FIG. 3, at –1680 kb) are shown here. This clone covers a previously described polymorphic genomic region between

*M. tuberculosis* and *M. bovis* BCG strains (Philipp et al., 1996a). EcoRI and PvuII digests from clone Rv58, fixed on nitrocellulose membranes, were hybridized with $^{32}$P-labelled total genomic DNA from *M. tuberculosis* H37Rv, *M. bovis* (ATCC 19120), and *M. bovis* BCG Pasteur. FIG. 4 presents the results of this analysis, where it is clear that several restriction fragments from clone Rv58 failed to hybridize with genomic DNA from either *M. bovis* or *M. bovis* BCG Pasteur. On the basis of the various missing restriction fragments, a restriction map of the polymorphic region was established and compared to the H37Rv sequence data. The localization of the polymorphism could therefore be estimated, and appropriate oligonucleotide primers (Table 1) were selected for the amplification and sequencing of the corresponding region in *M. bovis*. The alignment of *M. bovis* and *M. tuberculosis* H37Rv sequences showed that 12,732 bp were absent from the chromosomal region of the *M. bovis* type strain and *M. bovis* BCG Pasteur strain. The G+C content of the polymorphic region is 62.3 mol %, which is the same as the average genome G+C content of the *M. tuberculosis* genome, hence indicating that this region is not a prophage or other such insertion. Subsequent PCR studies revealed that this segment was also absent from the Danish, Russian, and Glaxo substrains of *M. bovis* BCG, suggesting that this polymorphism can be used to distinguish *M. bovis* from *M. tuberculosis*. Analysis of this sequence showed that 11 putative open reading frames (ORFs) are present in *M. tuberculosis*, corresponding to ORFs MTCY277.28 to MTCY277.38/accession number Z79701 -EMBL Nucleotide Sequence Data Library (FIG. 5). FASTA searches against the protein and nucleic acid databases revealed that the genes of this region may be involved in polysaccharide biosynthesis. Among these putative genes, the highest score was seen with ORF 6 (MTCY277.33), whose putative product shows a 51.9% identity with GDP-D-Mannose dehydratase from Pseudomonas aeruginosa (accession number U18320-EMBL Nucleotide Sequence Data Library) in a 320 amino acid overlap. The novel *M. bovis* sequence of the polymorphic region was deposited under accession number AJ003103 in the EMBL Nucleotide Sequence Data Library.

As it appears from the teachings of the specification, the invention is not limited in scope to one or several of the above detailed embodiments; the present invention also embraces all the alternatives that can be performed by one skilled in the same technical field, without deviating from the subject or from the scope of the instant invention.

TABLE 3

End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character << - >> denotes an uncertain base residue.

Clone Rv101 (SEQ ID NO. 6)

```
::::::::::::::Rv101SP6.seq:::::::::::::
AATACTCAAGCTTGCCCAGCCGTCGATGACAAGAAATATGTCCGCAAAAGACTCAGCGGCCGACTTTGCT
CGCAGCTGGCGGTACCGCGCCACCGATTCTATGCCGTGGTCGCGGAAAAATGCCTCCCGAAATCGCACGG
CCGACTCCAGTTCGGCGAGCATCCGCGATGCCAGCTGCGGCTGCGCCCTGCCGGCCACGGCACCCACATG
CGGCAGTTCGTCCACCTGGGCCAGCGCCCCGCCGCCGAATTCCAAACAATAGAACTGCACCCGGCCCGCA
TCGTGGGTAACAGCCAACGCCATGATCAGCGTCCGCAGCGCGGTTGACTTGCCCGTTTGCGGTGCACCTA
CGAACGCGACATTGCCTGCGGCCCCGGACAAGTCGATCGTGCGCGGCACCCGTGACTGCTCTAACGGGCG
ATTGAAATTCCGAT
```

(SEQ ID NO. 7)

```
::::::::::::::Rv101T7.seq:::::::::::::
CCACCCGTGTAATTTGGGATGGGCAAAAAGGCGAAGCACCGCGTGGCCACGAACGCCGGGAGGGACAATC
TCGGGCGGTTAGGGCTTCTCGCGGGAAGGCCCGAACGTACGGCGTTTCAACACCTCGCGTCGCCCTCCGA
CCGCGAACATTCGGGGATGGCAGCAACCTGCTGGCACCCTGGCCGGGCGATGATCTGCAGCGTCGCCGCG
GGTAGTCGCCGCCCGGGCGGCTACACTCTGAAACGCGATGACCATCGATGTGTGGATGCAGCATCCCGAC
GCAACGGTTCCTACACCGCGATATGTTCGCCTCGCTGCCCCGGTGGACCGGT
```

Clone Rv102 (SEQ ID NO. 8)

```
::::::::::::::Rv102SP6.seq:::::::::::::
AATACTCAAGCTTTCCGCCGATACCCGCCATGTCGCGCACATCCAGGACTTCTGGGGGGATCCGCTGACA
GCGGCGGGATCCCAAAGTGCGGATGATCGGGCCGCCTACGTCGTGGTGTACCTCGTCGGTAACAACGAAA
CCGAAGCGTATGACTCGGTCCACGCGGTGCGGCACATGGTGGACACCACACCGCCACCGCACGGGGTGAA
GGCCTATGTCACCGGTCCGGCAGCACTCAATGCCGACCAGGCCGAGGGCGGAGACAAAAGTATCGCTAAG
GTCACCGCGATCACCAACATGGTGATCGCAGCAATGTTGCTAGTGATCTATCGCTCCGTAATTACCGCGG
TTCT
```

(SEQ ID NO. 9)

```
::::::::::::::Rv102T7.seq:::::::::::::
GTGCCGTTCCAACCCGAATTGGCTTTCGGCGCCATCGGTGAGGACGGCGTGCGGGTGCTCAACGACGACG
TCGTCCGCGGGACACACCTCGATGCTGCCGCCATGGACGCGGTCGAACGCAAGCAGCTGATCGAGCTACA
ACGCCGCGCGGAACGCTTCCGCCGCGGGCGTGACCGCATCCCGTTGACCGGGCGGATCGCGGTGATCGTC
GATGACGGCATCGCCACCGGAGCGACGGCCAAGGCGGCGTGCCAGGTCGCCCGGGCGCACGGTGCGGACA
AGGTGGTGCTGGCGGTCCCGATCGGCCCAGACGACATCGTGGCGAGATTCGCCGGGTACGCCGATGAGGT
GGT
```

Clone Rv103 (SEQ ID NO. 10)

```
::::::::::::::Rv103SP6.seq:::::::::::::
AATACTCAAGCTTTCGGCGGAAACGGACACATTGCGAATATTGATGACAAAATAAAAATCATTGATGGTT
TGAGTCACCAGGCCGATCAAGCCTTCGCCGAGCCAAATTCCAATCAAGAGGCCCAAGCCCGTACCAATCA
GCCCGGCAACGAGGGATTCCGTCATTATCAGCCAAAATAACTGCTCTCGGGTTACACCCAAACAGCGCAA
TATGGCGAAAACGGTCGCCGTTGCACGACATTAAATGTCACGGTATTGTAGATTAAAAGATACCCAC
```

TABLE 3-continued

End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character << - >> denotes an uncertain base residue.

:::::::::::::Rv103T7.seq::::::::::::: (SEQ ID NO. 11)
TGCTCCCGAAACCTGGGGGTGTGCCTGCTCTGTATGCACGGCATACGGACATCCTTCCCCTGAGACCCGC
GGTCGAACCAGCCACGTGTCCATCATAGNGGGTCAACCCCGGCCAAGGGCGACGGCACGCCAAGTTCGCC
GACCGTTAACCTAGTGCTGTTAGCTTCATTTGCTGCGATCAAAACAGCTGGTCGGCCGTTAGGAACTGAA
TTGAAACTCAACCGATTTGGTGCCGCCGTAGGTGTCCTGGCTGCGGGTGCGCTGGTGTTGTCCGCGTGTG
GTAACGACGACAATGTGACCGGGGGAGGTGCAACCACTGGCCAGGCGTCGGCAAAGGTCGATTGCGGGGGG
AAGAAGACACTCAAAGCCAGTGGGT Clone Rv104 (SEQ ID NO. 12)
:::::::::::::Rv104SP6.seq::::::::::::
ATACTCAAGCTTTGCCGACGAGCGGGCGATGTTGATGACGGGAAACCCCAGCGCACAACCGACGATTTTG
GCGTAGCCGGCGGACGTCTGCTCGATTCCGATCACGTCGGCGCTCGCATCGAGCATGGCGCCGGCGACGG
CTAGCAGCGATCCGCCGTCGTCGAGGAGCACGACACGAGCCGTACGCCCGGCCGTAAGCCGCGCCCAGGA
TTCGGCGAAAAACCGTTCTACGTGGCGGGTGTACTGGGTGTCGAATGATTCGTGGGGTGCGTAGGCGTCG
CTGCAATCGTCGACATAGATGCCGTCGGGCCGCATCGCGTCGACAACTCCGGGTGAGTGGAATAGCACTT
GCCGATCACCGCGACGTTGCGCGGATGAGGCCGAACCCGAATA :::::::::::::Rv104T7.seq:::::::::::: (SEQ ID NO. 13)
TCCTATGTCCCTGCCGAGCANGTGATCGAACGCGGTGACAGATTTGTCTATCCTGGACCTGACGGTGAGG
TCGAAGTTTTCCAGGAATTCGGCAAAATCGGTAAGAGCCTGAAGAATTCGGTATCGCCGGACGAAATCTG
CGACGCATACGGGGGCATATACGCTTCGGGTTTACGAGATGTCGATGGGGCCGCTGGAGGCTTCACGTCC
ATGGGCCACAAAGGATGTTGTCGGCGCGTACCGTTTTCTGCAGCGGGTGTGGCGCTTGGTCG Clone Rv105 (SEQ ID NO. 14)
:::::::::::::Rv105SP6.seq::::::::::::
ATACTCAAGCTTGATTCCGCCGAAACCGACCGTGAGCACCCCGCCAGCCACCACGCTCGGGTCGGGCGCC
GGGCCCGGGCCGCCAGGCTGCTCCGCTCGGTGATGGCACGCCACCGCGACACCACCCGGCTGCGCTACGT
CTAACCATTCCAGGCGGAGCTACATCAGCTCGGCCGCCCAGTGTTCGGGCCCTCTTTCCAGGTCGAAGTC
TATACCGATATGCGCATCCGCAGCCGCCACCCTGGAGAACAGAACGATGCCCTACTAATGCTTGTCTGGC
GGGGCC :::::::::::::Rv105T7.seq:::::::::::: (SEQ ID NO. 15)
GGTACGCTTCGGTCGCAGTCTGCGAGTGATGCATGACGACCGGGACCTCGTCGGCATCTTCCATAGCCCG
CCACACCTTCAGTTGCTCACCGGAATCCAACCGGTAGAAGGTCGGCGAGCGCTCGGCATTGGTCATCGGG
ATATGCCGCTCGGGACGGTCAGAGCCCTCGGGTCCGGCCAGCACTCCGCAGGCTTCGTCGGGGTGGTCGC
GACGCGCATGGGCCACCATCGCATTCACCAGGTCTGCGCGAATCACCAGCACGTAGACGGTTCCTTTCCT
AAGCAACACCGAAGTTTCAGGACCCGAATGCTCCGGGAAACATGTCACGGTAGGTCGGTATTCCGGCTAC
CGGCTGA Clone Rv106 (SEQ ID NO. 16)
:::::::::::::Rv106SP6.seq::::::::::::
GGCGTCAACGGTGTCGGAACCCGCGTCAAGCAATTGGTAGGCCTGCAGTCTGTGAATCAGGCCGACGCTG
TGGCCGCCGCGGC :::::::::::::Rv106T7.seq:::::::::::: (SEQ ID NO. 17)
GGCTNGCGTACCCGGTACCGGCCGCGGGCCTACCACGTGCCGGAACTGGAAGCGCAGTAAGCCCTCAACG
CGCCACCGCTTTGGCCCGCGCGCCCGGCGTAGGCGCATCGGCGGTGGCCGTGGGGCGGCGCACTGCGACC
TCACCAGCGGCTTTCGAGCTTTGTTCGATCAACCGGCCAGCATGGTCGANGATGCATTCGAGACCATATT
CGAAATTGGTTTCATCGGGGGCCCCGATCCGATGCCCCCTCCCAGTTGCGTGAGCAANCAGCGGAGTCNT
CGCGGGATCGATGGCCACGGGGTGTTCAATGGCGGATGGTCCGCTGCCCGCCGACTGGCTCTTGCGGGAG
AACCGATCTAGCACCACCGATCCGCGCACGTNG Clone Rv107 (SEQ ID NO. 18)
:::::::::::::Rv107T7D4.seq::::::::::::
CGTAATNTCGCGCACANCCANGACTTCTGGGGGGATCNGCTGACAGTGGTNGGATCCCAAATTGCGGATG
ATCGGGCCGCCNACGTCGTTGTGTACCTCNTCNGTCACAACNAANCCGAANCGTATGACTCGGTCCACGC
GGTGCGGCACATGGTGGACACCACACCGCCACCGCNCGGGGTGAAGGCCTATGTCACCGGTCCGGCAACA
CTCAATGCCGACCAGGCCGANGCCGGACACNANAGTATCNCTAACGTCACCGCGATCACGAGCATGGTGA
TGATCGNNCAATGTTNCTANTGATCTATCGCTCCGTAATTACCGCGGTTCTCGTCTTGATCATGGTCGCA
NCGAACTCCGGCGCAATCCGCGGATTCATCGNCTTGCTCGCCGATCACATATTTTCAGCCTTTCACATTG
CAACNAACCTGCTCGTCTCATGGNGATGCGGCGACACGGACTACCGATATCATGCTCGCCGTTACACAAT
CNCGCCACGCCGCGAAGACNGGAAACGCTTCTACACAATNTTCNCGGGACGCCACTNAACTTGGTTCNGG
TTTGACATTGCCGCGCATGTNTGCCCAGCTTTGCCGGCTCCCCTTA Clone Rv108 (SEQ ID NO. 19)
:::::::::::::Rv108T7D4.seq::::::::::::
TGAATTTCCCGATCCCACAATCTCGGTTCAGATACAGGTCGCCATACCCCTTACTTCGGCAACGCTGGGC
GGATTGGCCCTGCNGCTGCAGCANACCATCGACGCCATCGAATTGCCGGCAATCTCGTTCAGCCAATCCA
TACCCATCGACATTCCGCCGATCGACATCCCGGCCTTCNCCCTTTAACGG TABLE 3-continued End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character << - >> denotes an uncertain base residue.

Clone Rv109 (SEQ ID NO. 20)
:::::::::::::Rv109SP6.seq:::::::::::::
AACAGCTATGACCATGNTTACGCCAAGCTATTTAGGTAACACTATANAATACTCAAGCTTTTACGGTGAT
CGCGCATCACCTGGTTCATGAACTGGAAGCAGCGCANCGCTTCCTTTTCGGCCGCAACATGAGCCAGCCT
CTCGTCCGCGGTCNGGTGCAGGTGCTCGGGCAGCTCGGCCGCGACAGCCGCCTGACCCTGAAACCAGCTT
CCATATCCCGCGACNAACNACNCCAGTCCGCTACGTAACCCCTCCGCGACTGTCCATGGACAACAGCGCG
TTCTCCACCGACCGGGCCCGGGTGTGGGGTGTTTCGGCGACCGGCAGCCAGGTGGTCCACACTGCCGACG
GGCGCCGCGAGCCGTTCACCGACCAAGCCGCCGAACAAGTCCGCCCGATCGCATACTCCAACCGGTTGCG
GTACTGCAGGTCAGCTGGCGTACCTCCTCNTCNCGCTCGGCGAAGTCTTGCTCCANCACGTCGCAGAACG
GCAAGGAACACGTTCA :::::::::::::Rv109T7.seq::::::::::::: (SEQ ID NO. 21)
GACCGNNCCATGTTTCCACAATGTGGTGCCAGTNCGGNGGCTACGTGCCATCNANACACTGGCGCAGGCT
ATCGCACCCGTTATCNGCTACGAACAAATCNCGGTATGCGTTCTTTANCATGAGTCGGCGACCGNCGATC
ATGGTCGACACCCACGACNGAAATACGCAGATCGCCNTCNAGCNTGTGCCGCGGATTATCANGACTGA
CCTCCTGGCTGACCGGNNTGTNTGGTCGCGATGCCTGGCGCCCGGCCGGCGTGNTCGTGGTCGGCTCGGA
TAGCGAAGTCAGCTAATTCTCGTGGCAGCTCGAAAGGGTCCTGCCGGTGCCGGTCTTTGCGCAAACCATG
CNCATGTTACGGTCCCTCGGGTGCGGCCTGGCGGCGGC Clone Rv10 (SEQ ID NO. 22)
:::::::::::::Rv10SP6D2.seq:::::::::::::
GGGATGGGCGGGCCCGCTAAACTCTTCGTGTTCCACTAACTCCGGGAGGGNCAATCTCGGGCCGTTATGG
CTCACGTCGCGTCGCCCTCCGACCGCGAACATTCGGAGTTGGCAGCAACCTGGTAGCACCCTGGCCGG :::::::::::::Rv10T7D4.seq::::::::::::: (SEQ ID NO. 23)
NCCGTCGTTGACAAGTAAATATGTCCGCAAAAGTCTCAGCGGCCGACTTTGCTCGCAGGTGGCGGTACCG
CGCCACCGAGTCGATGCCGTGGTCGCGGAAGAATGCCTCCCGAAATCGCACGGCCTTCCCNNTTTAAACG
GA Clone Rv110 (SEQ ID NO. 24)
:::::::::::::Rv110SP6.seq:::::::::::::
TTTAGGTGACACTATAGAATACTCAAGCTTTTGGTCTAGCCGGCCGAGCACGATACGGGTGTCATTGGCC
ACCGGCGGCGGCTGTCCGGGAAATGGCGGGTCCCCGGTGGTTTTGCTGATGAGTGCTGAACCGTANTCGA
AGTGGGCGGCGTCAGACTCCACCCANCCAGCAGGCAGCGCGAAGCTGAATCCTCCAACCGGGTTGTCNAT
CCGGACAAGTTGGGGTGCGTTTGGGGCAATGACAGGTGGCNGCGGTGCGTTCGGGTCCGCCGGCGGAAGT
GCTGCGTTGGGATCNCCCGCTGGGCATTCGGCNTTTTTGCGGCGGCCGGTGGTNGGGGGGCAACAGGTNT
CCCNGTGCGGGTGGCGCTCAACGGTCNACGGCGCAAGCCGCCGTTGTTGGTACCNGGGGCGCTGGCTCCG
GATCGCGTTGGCGGTCNCCGG :::::::::::::Rv110T7.seq::::::::::::: (SEQ ID NO. 25)
CTACACCATCGAATACGACGGCGTCGCCNACTTTCCGCGGTACCCGCTCAACTTTGTGTCGACCCTCAAC
GCCATTGCCGGCACCTACTACGTGCACTCCAACTACTTCATCCTGACGCCGGAACAAATTGACGCAGCGG
TTCCGCTGACCAATACGGTCGGTCCCACGATGACCCAGTACTACATCATTCGCACGGANAACCTGCCGCT
GCTAGAGCCACTGCGATCGGTGCCGATCGTGGGGAACCCACTGGCGAACCTGGTTCAACCAAACTTGAAN
GTGATTGTTAACCTGGGCTACNGCGACCCGGCCTATGGTTATTCNACCTCNCCGCCCAATGTTGCGACTC
CGTTCGGGTTGTTCCCANAAGTCNNCCCGGTCGTCATCGCCGAANCTCTCNTCCCGGGACCCACAGGGAA
TCNGCNATTTCNCCTACAAATCANCCACCTCCA Clone Rv111 (SEQ ID NO. 26)
:::::::::::::Rv111T7.seq:::::::::::::
GCATGATCGGCCACCTTTCGGGCCGCCCGGCATACGGCGGCGTACCGATCTCCGCGTCATACACCCGCGG
GTAATCGCCGACGGTGCCGGTTCGCGAGCCGAAGGTGACGACTCTGATTGAATCGAGTTCCAGGTCCAGC
GGGTGGCGCACCAACGGCGCGAGCTCAACGACGTCAATCNCGTTGTCGCTTTCTACGGTCACCGACCCTG
GTGACCGTAGTTCNCCCG Clone Rv112 (SEQ ID NO. 27)
:::::::::::::Rv112SP6.seq:::::::::::::
GACACTATAGAATACTCAAGCTTGCCAACCGCCAGCCTGCATCCGGCGGCGANCACTGCTCCGCCGACCA
GTACGAACCAACCTGCGGTGCCCAGGCCATTGACGATGTGCTGGTCGGCGCCCGCGAGTCCGCGCACCAT
CAACGCCGCGGGCACCACCANGGCGGCCCCACCCTGCACGGCGACGATCATTCCGGCGCCGCTCACGGCG
GGCGGGGCTCGAACANGCACAGCATCAACGTNGTCACCCGGCCGTGACCGGCCCGCATCGTCACACCACC
CAAGCCCATTGCCGTCCTCCTCAACNGGGCGACCCGGCCCGCATCGTCACACGGNCTAAGGCCATTGCCG
TCCTCCT :::::::::::::Rv112T7.seq::::::::::::: (SEQ ID NO. 28)
TCGGCGCCATCGGCACCTTCGAGGACCTGTATTTCGACGCCGTGGCCNACCTGAGGTTGGCGGTGGACNA
AGTGTGCACCCGGTTGATTCGCTCGGCCTTGCCGGATGCCACCCNGCGCCTGGTGGTCGATCCGCNAANA
GACAANTTGTGGTGGANGCTTCTGCTGCCTGCGACACCCACNACGTGGTGGCACCGGGCAGCTTTAGCTG
GCATGTCCTGACCGCGCTGGCCGACNACTCCAGACNTTCCACNAANGGTCGCCNNCCCAATGTNCCGNAN
TGTCTCCGGNTCCCTTTACCNCCCAATGGGCNGNTTCCACNGGTTACGGGCCCCNTNCCGGCGGGTCTNC
CTCCCAANCTACCAAATACGCCCGACNTTCCGGA TABLE 3-continued

| End sequences of the polynucleotide inserts cloned in the named recombinant BAC vectors contained in the I-1945 *M. tuberculosis* H37Rv genomic DNA library. RvXXXSP6 corresponds to the SP6 endsequence of the clone RvXXX; RvXXXT7 corresponds to the T7 endsequence of the clone RvXXX. RvXXXIS 1081 corresponds to a region located close to a copy of the IS1081 repetitive sequence (Insertion element) The character << - >> denotes an uncertain base residue. |
|---|

Clone Rv113 (SEQ ID NO. 29)
::::::::::::Rv113SP6.seq::::::::::::
ATACTCAAGCTTTTATGGTGATCGCGCATCACCTGGTTCATGAACTGGAAGCAGCGCAGCGCTTCCTTTT
CGGCCGCAACATGAGCCAGCCTCTCGTCGGCGGTCGGGTGCAGGTGCTCGGGCAGCTCGGCCGCGAACAG
CCCGGCTTGAACCCTGAAAACCNGCTTTCCATATCCCGCGACGAAAGAACGCCAGTTCCGCTACTTAACC
CCTCCGCGAACCGTCCATGGACAACAGCGCGTTCTCCACCAACCGGGCCCGGGTGT ::::::::::::Rv113T7.seq:::::::::::: (SEQ ID NO. 30)
TCGGCTCAGGCCGCGCTGCTGGTAGAGTCGCTGACCGGTGCAGGTTTCGACAATGTGGTGCCGGTTCGGC
GGCTACGTGCCATCGAGACACTGGCGCAGGCTATCGCACCCGTTATCGGCTACGAAGCAAATCGCGGTAT
GCGTTCTTGAGCATGAGTCGGCGACCGTCGTCATGGTCGACACCCACGACGGAAAGACGCAGATCGCCGT
CAAGCATGTGTGCCGCGGATTATCAGGACTGACCTCCTGGCTGACCGGCATGTTTGGTCGCGATGCCTGG
CGCCCGGCCGGCGTGGTCGTGGTCGGCTCGGATAGCGAGGTCAGCGAATTCTCGTGGCAGCTCGAAAGGG
TCCTGCCGGTGCCGGTCTTTGCGCAAACAATAGCGCAGGTTACGGTCGCGCGGGGTGCGGCCTGGCGGCG
GCC Clone Rv114 (SEQ ID NO. 31)
::::::::::::Rv114SP6.seq::::::::::::
CAAGCTATTTAGGTGACACTATAGAATACTCAAGCTTCGCGTCTACGCCGGCCCGGAGCATCCGCACAGC
GCTCAGCAGCCGGTTCCGTACGANCTCAAGCAGGTGGCGCAATGACCGAAACCACCCCAGCCCCGCAAAC
CCCGGCGGCCCCGGCCGGGCCCGCACAATCGTTCGTGTTGGAGCGGCCCATCCANACCGTTGGGCGCCGT
AAGGANGCCGTGGTACGAATGCGGCTGGTGCCCGGCACCGGCAAGTTCGACCTCAACGGCCGCAGCTTGG
ANGACTACTTCCCAAACAAGGTGCACCAGCAGTTGATCAAGGCACCCCTGGTCACCGTGGATCGGGTGGA
AAGTTTCGACATCTTTGCCCACCTGGGCGGCGGCGGCCGTCCGGTCAGGCCGGGCCTGCCCTGGGTATCG
CCCGGGCATTGATTCTGGTATCCCCNGAAGAACCG ::::::::::::Rv114T7.seq:::::::::::: (SEQ ID NO. 32)
CGGTTGGCCACCGCTTCTGCGGTGCCGCCGCCGTCGACAATGACCGTGTCGTCCTTGCTGACCACCACGC
GTCGGGCCGAGCCCAGCACCTCCAAGCCCACCTCGCGCAGCACCATGCCGGCGTCGGGGTTGACCACCTG
GCCACCCGTCACCACCGCCAGGTCCTCAAGGAAACGCCTTACGGCGGTCACCGAAGTACGGCCCCTTGAC
CGCGACCGCTTTCAACGTCTTGCGAATCGCGTTGACGACCAGCGTCGCCAACGCTTCGCCCTCCACGTCT
TCAGCCACGATCAGTAGTGGCTTACCCGTTCCTGCAACCTTTTCCAGCAATGGCAACAGATCGGGAAGCG
ANCTGATCTTGTCTTGGTGCN Clone Rv115 (SEQ ID NO. 33)
::::::::::::Rv115SP6.seq::::::::::::
CCAAGCTATTTAGGTGACACTATAGAATACTCAAGCTTTTGGCTGGGTCGCCTTCGAATTCNGCGTGCAC
CGCTATGGGTTGCANCAGCGGCTGGCGCCGCACACCCCACTGGCCCGGGTGTTTTCGCCCCGAACCCGGA
TCATGGTGAGCGAAAAGGANATTCNCCTGTTCGATGCTGGGATTCGCCACGCCAAGGCATCTANCGATTA
CTCTCCNCGGGGTGGGAAAAGTGCCCAATCCCCCTCCCTCCAACTTTCCNAACAATCATTCCGGTTCCNC
CNTCCGGTTGGNGGTAACCNNCCAATAAAACCCCTGCCCG :::::::::::::Rv115T7.seq::::::::::::: (SEQ ID NO. 34)
GCCCGCNCATGGCCAATCCCCGAAGACATCATTGGCCAGTGGCCGGGCGCTAACAGGTTCCAGCCCCCCA
CCANTGCCGCTCGAACATGCGGTGCAACCCATTCGCAGGCCGGCAGGGAAAGCACCGCGGAAGCCGCAAA
GGGCTGCAGTTCCGCGCCCAATAATGTCGTCCGCAACCAGATGCGCTCNAAAACCNCNCCGGCAGTCAGC
GCACCCGACGCGANGTCGAAAGACGTCNTCAGCGCGCCCACATGGGGTGCCAATCGGCACGGCAGGTATG
CCGCGCGCAACCCGAGCGCGTGGTGCATGCCCACGGTCCGCANGANGCGCANCACCCGCCAATGCCGAAN
CCCACGAAACATCGGGCGCATCCACCTTCAACC Clone Rv116 (SEQ ID NO. 35)
::::::::::::Rv116SP6.seq::::::::::::
ATACTCAAGCTTGCCCAGCCGTCGATGACAAGAAATATGTCCGCAAAAGACTCAGCGGCCGACTTTGCTC
GCAGCTGGCGGTACCGCGCCACCGAGTCGATGCCGTGGTCGCGGAAGAATGCCTCCCGAATTCGCACGGC
CAATTCCATTCCGGGAAGCATCCGCAATGCCAGCTGCGGTTGCCCCCTGCCGGCCACGGCACCCACTTGC
GGCATTGCGTCCACCTGGGCCAGCGCCCCGCCGCCAAATTCCAAACAATAAAATTGCACCCGGC ::::::::::::Rv116T7.seq:::::::::::: (SEQ ID NO. 36)
CCACCCGTGTATTTTGGGATGGGCAAAAAGGCGAAGCACCGCGTGGCCACGAACGCCGGGAGGGACAATC
TCGGGCGGCTAGGGCTTCTCGCGGGAAGGCCCGAACGTACGGCGTTTCAACACGTCGCGTCGCCCTCCGA
CCGCGAACATTCGGGGATGGCAGCAACCTGGTAGCACCCTGGCCGGGCGATGATCTGCAGCGTCGCCGCG
GGTAGTCGCCGCCCGGGCGGCTACAGTCTGAAACGCGATGACCATCGATGTGTGGATGCAGCATCCGACG
CAACGGTTCCTACACGGCGATATGTTCGCCTCCCTGCCCCGT Clone Rv117 (SEQ ID NO. 37)
:::::::::::::Rv117SP6D2.seq:::::::::::::
CTGCCCATGTTTGGGGACGCCCGACCAGCCGATGCTGGAGGCCTACACGGCCCTTGGTGCGCTGGCCACG
GCGACCGAGCGGCTGCAACTGGGCGCGTTGGTGACCGGCAATACCTACCGCAGCCNGACCCCTNTCNCAA
NAGGATNTTGTTCGCCGGACCCCNCTC TABLE 3-continued End sequences of the polynucleotide inserts cloned in the named recombinant BAC vectors contained in the I-1945 *M. tuberculosis* H37Rv genomic DNA library. RvXXXSP6 corresponds to the SP6 endsequence of the clone RvXXX; RvXXXT7 corresponds to the T7 endsequence of the clone RvXXX. RvXXXIS 1081 corresponds to a region located close to a copy of the IS1081 repetitive sequence (Insertion element) The character << - >> denotes an uncertain base residue.

::::::::::::Rv117T7D4.seq:::::::::::: (SEQ ID NO. 38)
CCGACTTTCCGCGGTACCCGCTCAACTTTGTGTCGACCCTCAACGCCATTGCCGGCACCTACTACGTGCA
CTCCAACTACTTCATCCTGACGCCGGAACAAATTGACGCAGCGGTTCCGCTGACCAATACGGTCGGTCCC
ACGATGACCCAGTACTACATCATTCGCACGGAGAACCTGCCGCTGCTAGAGCCACTGCGATCGGTGCCGA
TCGTGGGGAACCCACTGGCGAACCTGGTTCAACCAAACTTGAAGGTGATTGTTAACCTGGGCTACGCGAC
CGCCTTT Clone Rv118 (SEQ ID NO. 39)
::::::::::::Rv118SP6.seq::::::::::::
ATACTCAAGCTTTGTCACACCAAGTGTTTCGACCAGGCGCTCCATCCGGCGAGTGGATACTCCCAGCAGG
TAGCAGGTCGCCACCACGCTGGTCAGTGCGCGTTCAGCTCGCTTGCGGCGCTGCAGCAGCCATTCGGGGA
AATACCTGCCCTGGCGCAGCTGGGGGATCCCAACTTCAATGGTTGCGGCACGGGTGTCAAATTCACGGTG
GCGGTAGCCGTTGCCCTAATTGGACCGCTCATCGCTGCTTTCGCGGTACCCCGCCCCGCACAGGGCTTCG
GCTTCAGCCCCCATCAGGGCGGCAATAAACTTCAAGAGCACC ::::::::::::Rv118T7.seq:::::::::::: (SEQ ID NO. 40)
GAGGCAGCTTCGCCGGCAATTCTACTAGCGAGAAGTCTGGCCCGATACGGATCTGACCGAAGTCGCTGCG
GTGCAGCCCACCCTCATTGGCGATGGCGCCGACGATGGCGCCTGGACCGATCTTGTGCCGCTTGCCGACG
GCGACGCGGTAGGTGGTCAAGTCCGGTCTACGCTTGGGCCTTTGCGGACGGTCCCGACGCTGGTCGCGGT
TGCGCCGCGAAAGCGGCGGGTCGGGTGCCATCAGGAATGCCTCACCGCCGCGGCACTGCACGGCCAGTGC
CGCGGCGATGTCAGCCATCGGGACATCATGCTCGCGTTCATACTCCTCGACCAGTCGGCGGAACAGCTCG
ATTCCCGGACCGCCCAGCGCATTGGTGATGGAATCGGCGAACTTGGCCACCCGCTGGGTGTTGACATCCT
CGACGGTGGGCAATTGCGCCTCGGTAAGCTTTGCCGCGTAGCCTTTTCATC Clone Rv119 (SEQ ID NO. 41)
::::::::::::Rv119SP6.seq::::::::::::
ATACTCAAGCTTCACTGACAAGGGACGAATTCGTCGGCCGCCTGTTCGACTGGGTGGTGGCCGAGCTGGT
CGCCACCACTCAGGCCGCGGTCACGGCGGTACCGGCGCGGGAGCAAACTCGCGCGGGCATGGCCAACTTC
TTGCGGACCATCACCGCAGACGCCCGCTTCGGACCCCTGCTGTCCACCACACAGTTGGCCAACGCATTAA
TCACCCGCAAGCTTGCGGAATCCACCGCCCTGTTCGC ::::::::::::Rv119T7.seq:::::::::::: (SEQ ID NO. 42)
TCCATCACCCGATGTGGCNGGAGCACTGCCATGTCGATCTCAACTACCACCTCCGGCCGTGGCGGTTGCG
CGCCCCGGGGGGTCCGCGCGAACTCGACGAGGCGGTCGGAGAAATCGCCANCACCCCGCTGAACCGCGAC
CACCCGCTGTGGGAGATGTACTTCGTTGAGGGGCTTGCCAACCACCGGATCGCGGTGGTTGCCAAAATTC
ACCATGCGTTGGCTGACGGTGTTGCCTCGGCAAACATGATGGCACGGGGGATGGATCTGCCGCCGGGACC
GGAGGTCGGCCGCTATGTGCCTGACCCCGCTCCTACCAAGCGGCA Clone Rv11 (SEQ ID NO. 43)
::::::::::::Rv11SP6.seq::::::::::::
AGCTTTGCAGTTGCTGAGTAATGTCGGCCAACGTCACCACAACCGCGATGAATTCAATCATGCCGCCCAG
GGCGGCCAACCCAATGGTGGCCGCGAGCGGCAGCTCGATCGCAGCGCGGAGGTTGCCGGCCGCCAGTTGA
TTCACGAACAGGGTGAGGTCATAGGCGGGCAGGATAGTGACGAAGGCAAGACCTCCATCTGCCGTCGGAA
GAAGTATCGAG ::::::::::::Rv11T7.seq:::::::::::: (SEQ ID NO. 44)
AGCTTCAGAACAGGCCTGTTGTGGGCGCACCCGGCTCGCCGAGTTCTGCACGCACCGCCTCAAGTGCGGC
CCGCACCGCCGGCATCTCCCGGTCACGCAGGGCCGCGGCCCGCGCCGCAGCGACGGCGTGTTCGCGCAGT
TCGCCGTCAATGATGCTGACCTGATCGGCCACCCGGGCGTTCTCGGCGTCGTCGCGTTCACTAATCGCGG
TGCTCAGCAGCGTCTCGACAGCCACCACCCGAGTGGCGACCAGCTGCTCCACCACGGACCGCAGCGATGC
CCGTC Clone Rv120 (SEQ ID NO. 45)
::::::::::::Rv120SP6.seq::::::::::::
ATACTCAAGCTTCAGTTCCTCCACGACGCGTTCCCAAATGAATTTCCCGATCCCACAATCTCGGTTCAGA
TACAGGTCGCCATACCCCTTACTTCGGCAACGCTGGGCGGATTGGCCCTGCCGCTGCACCAAACCATCAA
CGCCTTCAAATTGCCGGCAATCTCGTTCAGCCAATCCAT ::::::::::::Rv120T7.seq:::::::::::: (SEQ ID NO. 46)
GCTCTACGCCGCCTACGGGTCGAACATGCATCCCGAGCAGATGCTCGAGCGCGCACCCCACTCGCCGATG
GCCGGAACCGGCTGGTTACCCGGGTGGCGGCTGACGTTCGGCGGCGAGGACATCNGCTGGGAAGGGGCGC
TTGCCACCGTCGTCNAAGACCCAAATTCGAAGGTGTTCGTCGTGCTCTACGACATGACCCCGGCGGACGA
GAAGAACCTTGACCGGTGGGAAGGCTCCGAGTTCGGTATCCACCAGAAGATCCGATGCCGCGTGGAGCGC
ATTTCCTCGGACACCACAACGGGATCCCGTCCTCG Clone Rv121 (SEQ ID NO. 47)
::::::::::::Rv121SP6.seq::::::::::::
ATACTCAAGCTTGCCAAAGAGACCTCGTCCACCAAGCAGGACGCGACCGTCGAGGTGGCGATCCGGCTTG
GCGTCGACCCGCGTAAGGCAAACCAGATGGTTCGCGGCACGGTCAACCTGCCCACACCGGCACTGGTTAA
GAACTGCCCGCGTCGCGGTTTTCGCGGTTGGTGAAAAGGCCAATGCCTGCGTTTGCCGTGGGGGCGGATG
TTGTCGGGAGTGACAATCTGATCAAAAGGATTCAGGGCGGTTGGCTGGAATTCAATGCCGCAATCGCGAC TABLE 3-continued End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character << - >> denotes an uncertain base residue.

ACCGG

:::::::::::::Rv121T7.seq:::::::::::: (SEQ ID NO. 48)
CCACGGCGTGGATCAAGGTACCGGCCGGGATGTTGCGCAATGGCAGGTTGTTGCCCGGCTTGATGTCGGC
GTTAGCGCCGGATTCCACCACATCCCCTTGCGAAAGTCCGTTGGGTGCAATGATGTAGCGCTTCTCCCCA
TCGAGATAGTGGAGCAACGCAATCCGTGCGGTACGGTTCGGGTCGTACTCGATGTGCGCGACCTTGGCGT
TGACACCATCTTTGTCATTGCGGCGAAAGTCGATCATCCGGTAAGCGCGCTTATGACCGCCGCCTTTGTG
CCGGGTGGTAATCCGGCCATGCGCGTTGCGTCCACCGCGACGTGCAGCGGGCGCACCAGCGACTTCTCCG
GGGTTGACCGGGTNATCTC Clone Rv122 (SEQ ID NO. 49)
:::::::::::::Rv122SP6D2.seq:::::::::::::
GCAGCATGACGGCGGTAGCGAACACCGCCGGATGCAGCGCAAGTAGCGTCGATGTGCTCACGGAATCGCC
CCGGCACCGCGATCTCGANGATCACCAGTGCCACCCCCTGCAGCGCNACACCGACGATTCCGTACACCGC
CACGCCGATCAGGCCCTGGGCCATCTGATTGGAGCTGGCGTANATGGCGGCGATGGTGACGATGGCCAGC
GCCACATACATTGTGGCGGCCAGAACCACGGCGTTGGGGCGGCGGTCGATGAACACTAGGCGACGCAGAT
CGCCCGGGGTCAACAGGTTGACCATCAGAAAGCCTGCG ACTAGCACGGCGGCGCCACTAGGAAGTACAA
GAANGTGGCCACCACCCCATGCAGGATCGGGGTAAGGCTGATGGTCCCGAAATCGACTCCGGCCTAATAC
ATGACTCTCTCCTTTGCGTCATCGCCTTACTTGTGCGCGGAA Clone Rv (SEQ ID NO. 50)
:::::::::::::Rv123SP6D2.seq:::::::::::::
GGGACACACCTCGATGCTGCCGCNATGGACGCGGTCGAACGCAAGCAGCTGATCGAGCTACAACGCCGCG
CGGAACGCTTCCGCCGCGGGCGTGACGCATCCCGTTGACCGGCCGGANCNCTCTCTA :::::::::::::Rv123T7D4.seq:::::::::::: (SEQ ID NO. 51)
TGGGCGCCTCTTTCGGCCTTCCCNNTTTAAACGNAGCANGACATTCTGGGTATCGAGTTGTACTGGATGG
TGTTGGCGATGTCGGTGATCCTGCTCCTGGCGGTGGGATCCGACTACAATCTGCTGCTGATTTCCCGGTT
GAAAGAGGAAATTGGGGCCGGATTGAACACCGGAATTATCCGTGCCATGGCTGGTACCGGGGGAGTGGTG
ACGGCTGCCGGCATGGTGTTCGCCGTTACCATGTCGTTGTTTGTGTTCAGCGATTTGCGAATTATTGGTC
AGATCGGTACCACCATCGCCTTCCC Clone Rv124 (SEQ ID NO. 52)
:::::::::::::Rv124SP6D2.seq:::::::::::::
CCGATCGGCGCCGCANCTGGTTGGTGTTNCGGATGAATCCGCAGCGAAAATGTAGCTGCGGTGGCGTGTC
GTGACTCGTNGGCGTCGACGCTCGTGGCAGCCACCGANCGGTTGGTCCAGGATCTGGATGGGCAAAGTTG
TGCGGCCCGGCCGGTGACGGCCGATGAGCTGACCGAGGTCGACAGCGCCGTGTTGGCTGACTTGGAACCG
ACATGGAGTCGCCCCGGTTGGCGTCACCTCAAGCATTTCAATGGTTATGCGACCAGTTTTTGGGTTACGC
CGTCAGACATCACGTCGGAGACTTGGATGAGCTGTGTCTGCCAGATAGCCCCGAATCGGGACGACCGTGG
TCACGGTGCGTCTGACCACTCGGGTCGGGTCGCCCGCGCTATCGGCATGGGTGCGTNATCACAGCGACAC
GCGCCTGCCCAAGGANGTNCGGNCGGACC :::::::::::::Rv124T7D4.seq:::::::::::: (SEQ ID NO. 53)
CGGGTTGCGGATCCACGCGTGCGGGTTGTCAGCAGCTACGGCACTGAACCGCGCCCACAGCTCGCCGATC
CGCTTTCGGTGGTTCTCGATCGACTCGCCGTAGGCGATGCGCAGCGCCTGCTCGAATATCGGGTACACGT
AGGCCGGCCTTCCCNCTTTA Clone Rv126 (SEQ ID NO. 54)
:::::::::::::Rv126SP6.seq::::::::::::
CTTGATTTTGATCATCATGACGATCATCACCCTAATTTTGCTACCCGCACTGGTTATCGTGGGTACCGTC
GTGCTTTCCATGGGCGCCTCTTTCGGGCTTTCCGTATTGGTCTGGCAGGACATTCTGGGTATCGATTTGT
ACTGGATGGTGTTGGCGATGTCGGTGATCCTGCTCCTGGCGGTGGGATCCGACTACAATCTGCTGCTGAT
TTCCCGGTTGAAAAAGGAAATTGGGGCCGGATTGAACACCGGAATTATCCGTGCCATGGCTGGTACCGGG
GGAGTGGTGACGGCTGCCGGCATGGTGT :::::::::::::Rv126T7.seq:::::::::::: (SEQ ID NO. 55)
GGGGATCCCTAGATCGACCTGCAGGCATGCAAGCTTGGCGTGTCGTTCCAACCCGAATTGGCTTTCGGCG
CCATCGGTGAGGCGGGACACACCTCGATGCTGCCGCCATGGACGCGGTCGAACGCAAGCAGCTGATCGAG
CTACAACGCCGCGCGGAACGCTTCCGCCGCGGGCGTGACCGCATCCCGTTGACCGGGCGGATCGCGGTGA
TCGTCGATGACGGCATCGCCACCGGAGCNACTGTCAAGGCGGCGTGCCAGGTCGCCCGGGCGCACGGTGC
GGACAAGGTGGTGCTGGCGGTCCCGATCGGCCCAGACGACATCGTGGCGAGATTCGNCGGGTACGCCGAT
GAGGTGGTGTGTTTGGCGACGCCGGCGTNGTTCTTCGCCGNCGGGCANGGTTACCGCAACTTCACCCAGA
CCTCCGACGACGAGGTGGTGGCGTCTCCTGGATCGTGCTC Clone Rv127 (SEQ ID NO. 56)
:::::::::::::Rv127SP6.seq::::::::::::
AAGGCTGCAGGTCGAAGCGGNTGGTTACGACTCCCTGTGTGTGATGGACCAGTTCTACTATCTGCGTCTA
CACGGCCCTTGGTGCGCTGGCCACGGCGACCGAGCGGCTGCAACTGGGCGCGTTGGTGACCGGCAATACC
TACCGCAGCCCCGACCCTGCTGGCAAAGATNATCACCACGCTCGACGTGGTTAGCGCCGGTCGAGCGATC
CTCGGCATTGGAGCCGGCGGGTTTGAACTGGAACACCGCCAGCTCGGCTTCGAGTCCGGCACTTCCAGTG
ACCGGTTCAACCGGCTCGA TABLE 3-continued End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character << - >> denotes an uncertain base residue.

::::::::::::Rv127T7.seq::::::::::: (SEQ ID NO. 57)
CTTTCCGCGGTACCCGCTCAACTTTGTGTCGACCCTCAACGCCATTGCCGGCACCTACTACGTGCACTCC
AACTACTTCATCCTGACGCCGGAACAAATTGACGCNGCGGTTCCGCTGACCAATACGGTCGGTCCCACGA
TGACCCAGTACTACATCATTCGCACGGAGAACCTGCCGCTGCTACAGCCACTGCGATCGGTGCCGATCGT
GGGGAACCCACTGGCGAACCTGGTTCAACCAAACTTGAAGGTGATTGTTAACCTGGGCTACGGCGACCCG
GCCTATGGTTATTCGACCTCGCCGNCCAATGTTGCGACTCCGTTCGGGTTGTTCCAGANGTCAGCCCGGT
CGTCATCGCCGACGCTCTCGTCN Clone Rv128 (SEQ ID NO. 58)
::::::::::::Rv128SP6.seq::::::::::::
CGGTCATAGCCCTCGGGTCCGGCCAGCACTCCGCAGGCTTCGTCGGGGTGGTCGCGACGCGCATGGGCCA
CCATCGCATTCACCAGGTCTGCGCGAATCACCAGCACGTAGACGGTTCCTTTCCTAAGCAACACCGAAGT
TTCACGACCCGAATGCTCCGGGAAACATGTCACGGTAGGTCGGTATTCCGGCTACCGGCTGAGCATTGAG
CACGCCGGCCAGCACCGCACGAGCCAGGCAATCAGCCGCCGCCGCACCGATCGCGGTGACCAGCTGAGTC
TCCGGAGACAATGCGGCCGGCACGCCGGNCTCCGGCGGCACCGCTACNGCGCCCGTGG ::::::::::::Rv128T7.seq::::::::::: (SEQ ID NO. 59)
GTGATGGCACGCCACCGCGACACCACCCGGCTGCGCTACNTCGAGCCATACCGGGCGGAGCTACATCGGC
TCGGCCGCCCAGTGTTCGGGCCCTCTTTCGAGGTCGAGGTCGATACCGATTTGCGCATCCGCANCCGCNC
CCTGGACGACAGAACCGTGCCCTACGAGTGCTTGTCGGGCGGGGCCAAAGAACAGCTTGGCATCCTGGCG
CGATTGGCCGGCGCGGCGCTGGTCGCCAAGGACGACGCCGTTCCGGTGCTGATCGACGACGCGCTGGGGT
TCACCGATCCGGAGCGACTATCAAGATGGGGGAGGTCTCTGACACCATCGGCCCCNACGGACATGTGATC
GTGCCGACGTGCAGTCCCACCCCG Clone Rv129 (SEQ ID NO. 60)
::::::::::::Rv129SP6.seq::::::::::::
GCGAAAGTCCGTTGGGTGCAATGATGTAGCGCTTCTCCCCATCGAGATAGTGGAGCAACGCAATCCGTGC
GGTACGGTTCGGGTCGTACTCGATGTGCGCGACCTTGGCGTTGACACCATCTTTGTCATTGCGGCGAAAG
TCGATCATCCGGTNNGCGCGCTTATGACCGCCGCCTTTGTGCCGGGTGGTAATCCGGCCATGCGCGTTGC
GTCCACCGCGACCGTGCAGCGGGCGCACCAGCGACTTCTCCGGGGTTGACCGGGTGATCTCGGCGAAATC
AGATACGCTGGCGCCGCGACGACCAGGCGTCGTGGGCTTGTNCTTGCGAATTGNCATGTCTAATCANGTC
TTTCTCTCACGCTCTCGTCGCCGGGCTAGGCCGCATTGCCCTGCTCCTCCTCATCGCTTCGCTCTGCATC
GTCCCCGGGCTAAGCCCGTGCCCCGAAA ::::::::::::Rv129T7.seq::::::::::: (SEQ ID NO. 61)
GATGGTTCGCGGCACGGTCAACCTGCCACACGGCACTGGTAAGACTGCCCGCGTCGCGGTATTCGCGGTT
GGTGAAAAGGCCGATGCTGCCGTTGCCGCGGGGGCGGATGTTGTCGGGAGTGACGATCTGATCGAGAGGA
TTCAGGGCGGCTGGCTGGAATTCGATGCCGCGATCGCGAACACCGGATCAGAATGGCCAAAGTCGGTCGC
ATCGCTCGGGTGCTGGGTCCGCGCGGCCTGATGCCCAACCCGAAAACCGGCACCGTCACCGCCGACTCCC
CATGGCGTCCCGGATATCAAGGGCCGGCAAATCAACTTCCCGGTTGATCAGCAAGGCAACCTGCCTCCNC
CTCCGG Clone Rv130 (SEQ ID NO. 62)
::::::::::::Rv130SP6.seq::::::::::::
ATACTCAAGCTTCGTCATAAGACCATGGTGCGCTTTCTTTCACCCGTCCAGAGTCGGGGGCATCCGCACC
GGCTCGCATCGCATCATCCTCCCACGACGGGCCGCTCATCAGCTTGGGCCATTTCAATGTACTTGATACC
CCGCGCTGCGGGTAGGCCACTGCGACAATTCAAACACGGTGTCACACGGTGAATAGTGTCGAGATGGGCT
CTGATCAACCGTCGCAAACCCGGTTTCGCATCAATAGCGGAATCCCACCGGGTTGCATGGAGGCTGCTGA
CCTTGGAAAACAAAATTTTTTCATTACAACAAAACAACCGCCNCGGAAACTTTGCA ::::::::::::Rv130T7.seq::::::::::: (SEQ ID NO. 63)
CGAATTCGGCGTGCACCGCTATGGGTTGCAGCAGCGGCTGGCGCCGCACACCCCACTGGCCCGGGTGTTT
TCGCCCCGAACCCGGATCATGGTGAGCGAAAAGGAGAATTCGCCTGTTCGATGCTGGGATTCGCCACCGC
GAGGCCATCGACCGATTACTCGCCACCGGGTGCGAGAGGTGCCGCAGTCCCGCTCCGTCGACGTCTCCCA
CGATCCATCCGGCTTCCGCCGTCGGGTGGCGGTAGCCGTCGATGAAATCGCTGCCGGCCGCTACCTGCAA
GGTGATTCTGTCCCGTTGTGTCGAAGTGCCTTTCGCGATCGACTTTCCGTTGACCTACCGGCTGGGGCGT
CGGCACAACACCCCGGTGAGGTCGTTTTTGTTGCAGTTGGGCGGAATCCGTGCTCTGGGTTACAGCCCCG
AACTCGTCACGGCGGTGCGCGCCGACGGAGTTGTTATCACCGATCCGTTGGCCGTACCGCGCCTTGGGC Clone Rv132 (SEQ ID NO. 64)
::::::::::::Rv132SP6.seq::::::::::::
TCAGACTCCACCCAGCCAGCAGGCAGCGCGAAGCTGAATCCTCCAACCGGGTTGTCGATCCGGACAGGTT
GGGGTGCGTTTGGGGCAATGACAGGTGGCGGCGGTGCGTTCGGGTCGGCCGGCGGAGGTGCTGCGTTGGG
ATCGCCCGGCTGGGCATTCNGCGTGTTGGCGGCGGCCGGTGGTGGGGGGGCAACAGGTGTCGCCGGTGCG
GGTGGCGCTGCAGCGGTCGACGGCGGCGAAGCGGCCGTTGTGGGTACCGGGGGCGCTGGCTCCGGATCGG
CGTTGGCGGTCGCGGGCACCGCAACGGTCACCAAGCTGGCGCTGGCCATCGCCGCGATAGCCAGTGCCGC
CAATCGTCCCTTGCGACGTGTCAAGTNGGGGTCCACCTGATGCATGGCCAAAGAACCTCAAGTGTTAACG
GCNCAACNCAAGGACCGCGCCGGTCGCN ::::::::::::Rv132T7.seq::::::::::: (SEQ ID NO. 65)

TABLE 3-continued

End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character << - >> denotes an uncertain base residue.

TTTCCGCGGTACCCGCTCAACTTTGTGTCNACCCTCAACGCCATTGCCGGCACCTACTACGTNCACTCCA
ACTACTTCATCCTGACGCCGGAACAAATTGACGCAGCGGGTCCGCTGAACAATTCGGTCCGTCCCACGAA
AGAACCAGTTTTNCNTCTTTCNCACGGAGAACCTGCCGCTGCTAGAGCCACTGCGATCGGTGCCGATCGT
GGGGAACCCACTGGCGAACCTGTGTTTCAACCAACACTTAGAGTGTAATTGTAAACCTGGGCTAGGGGAA
ACCGGCTCTAGTTTTTCCACCNTCTCCGCCCCNTGTTTCGAATACTCCGTTCGGGTTGTCCCCAAA

Clone Rv134 (SEQ ID NO. 66)
:::::::::::::Rv134SP6.seq:::::::::::::
GCTTCCGGCTCGTATGTTGTGTGGAATTGTGACCGGATACCAATTTCACACAGGAAACAGCTATGACCAT
GATTACGCCAAGCTAGTTAGGTGACACTATACAATACTCAAGCTTGCCGGCTGGTGGGCCGACCACTTCG
ATGGCACGACCCGTGAACTGCTGCCCGGCCAATTCTTCTTGGTCGCCCGGACCGATGGACCGCGGCTGGG
ATTCCAGAAGGTGCCCGATCCCGCCCCTGGGAAAAACCGCGTGCACCTCTACTTCACGACCAACGAC :::::::::::::Rv134T7.seq::::::::::::: (SEQ ID NO. 67)
CCGATCGACTGATGCGCCGACAACCACGCCCCAACAACTGGAATGAACCGTCGTGACCATCATCAGCACG
CGGTTGTAGGCGACTTGCGACATGTTCAACCCGCCGTACTCGGACGGAATCTTCAAACCGAAACAGCCCA
GCTCGGCCAGGCCTTTCACGTACTCGTCGGGGATCTGGGCACCACGCTCGAGGACGCTGCCGTCCACGGT
GTCTAGGAATTCCCGCAGTTTGACCAGAAACGCCTCGGTTCGGGCCTCCTCGGCGTCCGACGGCTTGGGA
AATGGGTGTATGAGCCCTACGGGAAACCGGCCCACAAAGAGTTCTTTGGCGAAGGACGGTTTATCCCAAC
CACTTTCGCGAGATTCCTCGGCAAGGGCCCGCGCTTGCTCCTCGGTGACCTGAGTTTGCTGTGCCATCGC
CGCCTCCTCCCTGA Clone Rv135 (SEQ ID NO. 68)
:::::::::::::Rv135SP6.seq:::::::::::::
TGCATCCGGCTCGTATGTTGTGTGGAATTGTGAGCGGATAACAATTTCACACAGGAAACAGCTATGACCA
TGATTACGCCAAGCTATTTAGGTGACACTATAGAATACTCAAGCTTTTACGGTGATCGCGCATCACCTGG
TTCATGAACTGGAAGCAGCGCAGCGCTTCCTTTTCGGCCGCAACATGAGCCAGCCTCTCGTCGGCGGTCG
GGTGCAGGTGCTCGGGCAGCTCGGCCGCGACAGCCGCCTGACCCTGAAACCAGCTTCCATATCCCGCGAC
GAACGACGCCAGTCCGCTACGTAACCCCTCCGCGACTGTCCATGGACAACAGCGCGTTCTCCACCGACCG
GGCCCGGGTGTGGGGTGTTTCGGCGACCGGCAGCCAGGTGGTCCACACTGCCGACGGGCGCCGCGAGCCG
TTCACCGACCAGGCCGCCGAGCAAGTCCGCCCGATCGCATACTCC :::::::::::::Rv135T7.seq::::::::::::: (SEQ ID NO. 69)
GGGGGCGCTGCTGGTATAGTCGCTGACCGGTGCAGGTTTCGACAATGTGGTGCCGGTTCGGCGGCTACGT
GCCATCGAGACACTGGCGCAGGCTATCGCACCCGTTATCGGCTACGAGCAAATCGCGGTATGCGTTCTTG
AGCATGAGTCGGCGACCGTCGTCATGGTCGACACCCACGACGGAAAGACGCAGATCGCCGTCAAGCATGT
GTGCCGCGGATTATCAGGACTGACCTCCTGGCTGACCGGCATGTTTGGTCGCGATGCCTGGCGCCCGGCC
GGCGTGGTCGTGGTCGGCTCGGATAGCGAGGTCAGCGAATTCTCGTGGCAGCTCGAAAGGGTCCTGCCGG
TGCCGGTCTTTGCGCAAACGATGGCGCAGGTTACGGTCGCGCGGGGTGCGGCCTGGCGGCGGCCAGAGCA
CGAGTTCACCGATGCGCAGCTAGTGGCGACAGCGTCAGCCAAC Clone Rv136 (SEQ ID NO. 70)
:::::::::::::Rv136SP6.seq:::::::::::::
TGCTTCCGGCTCGTATGTTGTGTGGAATTGTGAGCGGATAACAATTTCACACAGGAAACAGCTATGACCA
TGATTACGCCAAGCTATTTAGGTGACACTATACAATACTCAAGCTTCCGTACAGGTCGCCTCCAACACGG
CGGGGAAGCGACACCAGCCTACCGAGCTTGGAGTCCAGGACGCCAGCGGCGGCGTCGGTCTGCGTCGTGG
TGCCGCCGGGGTGGCGTTGGCTGGCAACGATCTCCACCCAGCCGGTCGGGTTACCCACGATCTCGGCATA
GACGCGGGCCGAGGCCGGTGCGATACCGTATTGCGTCAATTGGGACGCGGTTGTGCATTCGGCTAGCTCG
GTTGCCACACCCGTCAGGGGTTCGACGTTGGCGGGTTCGGCGGGCCCCAGCACCGCTGTCACCATGCCCG
CCAAGCCGACCTGCGGCGCCACCAACT :::::::::::::Rv136T7.seq::::::::::::: (SEQ ID NO. 71)
CGGCATGACCACCGACAGGCCCGACTGGTCGTACCACTCGAACGCCGGGGTGTTGATGTCCCAGCCGCTG
AAGTCGTCCTGCGCGCGCAGGCCGTCGAGCAGGTACAGGGCGGGCGAGTTGGCACCACCACTTTGGAATT
GGACCTTGATGTCACGGCCCATCGACGGCGACGGCACCTGCAGGTACTCCACCGGCAAGCCCGGCCGGGA
AAATGCCCCCGCGGTCGCCGTGCCACCGACGGCGCCGACCAGACCCGACACTAGGGCCGCGCCGACGGCC
CCGACCACGAGTCGACGCGACATACCCGTGACGGCGCCACGAACCCTGTCAACAAGCTGCATTCTTGCTT
CCCTCATCCTCATCTCAACGCATCCATGCATGTTTGGGCGCATCCTGAATTANGTCAGACTGCAGGCGCT
GGGCCGGCAGTGCTCGTGTATCAACCACAACTTCGGGCGT Clone Rv137 (SEQ ID NO. 72)
:::::::::::::Rv137SP6.seq:::::::::::::
TTCCAACCCTAATTGGCTTTCGGCCCCATCCGTGAGGACGGGGTGCGGGTGCTCAACAACAACGTCGTCC
GCGGGACACACCTCTATGCTGCCGCCATGGACGCGGTCCAACGCAAGCAGCTGATCGAGCTACAACCCCG
CGCGGAACGCTTCCGCCGCGGGCGTGACCGCATCCCGTTGACCGGGCGGATCGCGGTGATCGTCGATGAC
GGCATCGCCACCGGAGCGACGGCCAAGGCGGCGTGCCACGTCGCCCGGGCGCACGGTGCGGACAAGGTGG
TGCTGGCGGTCCCGATCGGCCCAAACGACATCGTGGCGAGATTCGCCGGGTACGCCGATGAGGTGGTGTG
TCTGGCGACGCCGGCGTTGTTCTTCGCCCTCGGGCAGGGTTACCGCAACTTCAC :::::::::::::Rv137T7.seq::::::::::::: (SEQ ID NO. 73)
CAGGCATGCAAGCTTTCCGCCGATACCCGCCATGTCGCGCACATCCAGGACTTCTGGGGGGATCCGCTGA TABLE 3-continued End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character << - >> denotes an uncertain base residue.

CAGCGGCGGGATCCCAAAGTGCGGATGATCGGGCCGCCTACGTCGTGGTGTACCTCGTCGGTAACAACGA
AACCGAAGCGTATGACTCGGTCCACGCGGTGCGGCACATGGTGGACACCACACCGCCACCGCACGGGGTG
AAGGCCTATGTCACCGGTCCGGCAGCACTCAATGCCGACCAGGCCGAGGCCGGAGACAAAAGTATCGCTA
AGGTCACCGCCGATCACNAGCATGGTGATCGCAGCAATGTTGCTAGTGATCTATCGCTCCGTAATTACCG
CGGTTCTCGTCTTGATCATGGTCGGCATCGACTCGGCCAATCCGCGGATTCATCGCCTTGCTCGCCGAAC
ACAACATTTTCACCTTTCACATTTGCACCAACCTGCTCTTCTCAT

Clone Rv138 (SEQ ID NO. 74)
::::::::::::Rv138P6.seq::::::::::::
CACTACTCAAGCTCTCTCNTCATTACCACCCCTGTAATTTGGGATGGGCAAAAGGCGAAGCACCGCTTG
GCCACNAACGCCGGGAGGGACAATCTCGGGCGGCTATGGCTTCTCCCGGGAAGGCCCCAACGTACGGCGT
TTCAACACGTCGCGTCGCCCTCCGACCGCGAACATTCGGGGATTGGCACCAACCTGNTACCACCCTGGCC
GGGCGATGATCTGCAGCGTCGCCGCGGGTAGTCCCCGCCCGGGCGGCTACAGTCTGAAACCCCGATGACC
ATCGATGTGTGGATGCAGCATCCGACGCAACGGTTCCTACACGGCGGATATGTTCTCCTCGCTGCGCCGG
TGGACCGGTGGGTCTATCCCCTGAAACCGACATCCCN ::::::::::::Rv138T7.seq:::::::::::: (SEQ ID NO. 75)
CAGGCATGCAAGCTTTCGTCAGTTCATTGCGCCAGCAGACCAACAAGAGCATCGGGACATACGGAGTCAA
CTACCCGGCCAACGGTGATTTCTTGGCCGCCGCTGACGGCGCGAACGACGCCAGCGACCACATTCAGCAG
ATGGCCAGCGCGTGCCGGGCCACGAGGTTGGTGCTCGGCGGCTACTCCCAGGGTGCGGCCGTGATCGACA
TCGTCACCGCCGCACCACTGCCCGGCCTCGGGTTCACGCAGCCGTTGCCGCCCGCAGCGGACGATCACAT
CGCCGCGATCGCCCTGTTCGGGAATCCCTCGGGCCGCGCTGGCGGGCTGATGAGCGCCCTGACCCCTCAA
TTCGGGTCCAAGAACATCAACCTCTGCAACAACGGCGACCCATTTGTTCGGACGGCAACCGGTGGCAACG
CACCTAAGCTACTTGCCCGGGATGA Clone Rv139 (SEQ ID NO. 76)
::::::::::::Rv139SP6.seq::::::::::::
GTTTATGCACTGGTTAGGTGTTTCCATGAGTTTCATTCTGAACATCCTTTAATCATTGCTTTGCGTTTTT
TTATTAAATCTTGCAATTTACTGCAAAGCAACAACAAAATCGCAAAGTCATCAAAAAACCGCAAAGTTGT
TTAAAATAAGAGCAACACGTACACAAGGAGATAAGAAGAGCACATACCTCAGTCACTTATTATCACTAGC
GCCCGCCGCAGCCGTGTAACCGAGCATAGCGAGCGAACTGGCGAGGAAGCAAAGAAGAACTGTTCTGTCA
GATAGCTCTTACGCTCAGCGCAAGAAGAAATATCCACCGTGGGGAAAAACTCCAGGTAGAGGTAC Clone Rv13 (SEQ ID NO. 77)
::::::::::::Rv135P6.seq::::::::::::
ATACTCAAGCTTGGGTGTAGCCGATCACCGGAAGTCNCATGATCAGCCACGTTCCGCGCCGCCCGGCATA
CGGTGGTGTACCGATCTCCGCGTCATACACCCGCGGGTAATCGCCGACGGTGCCGGTTCGCGAGCCGAA ::::::::::::Rv13T7.seq:::::::::::: (SEQ ID NO. 78)
AGCTTTATCGAAAGCGCGAACAGCTCGCGGCGGCCCACGACGTGCTGCGTCGGATTGCCGGCGGCGAGAT
CAATTCCAGGCAGCTCCCGGACAATGCGGCTCTGCTGGCCCGCAACGAAGGACTCGAGGTCACCCCGGTG
CCCGGGGTCGTGGTGCACCTGCCGATCGCACAGGTTGGCCCACAACCGGCCGCTTGATGCCCGGTCGGCA
AGCCCGGCAGTTGCCAAACCCATCGTGATCAGGCTCGGCTCGCGAGTTCGGCGAAGAAATGGTTCGCCTG
ATCACCTACCATCGGCCA Clone Rv140 (SEQ ID NO. 79)
::::::::::::Rv140SP6.seq::::::::::::
TCAACACGCCGCCAGCCACCACGCGCGGGTCGGGCGCCGGGCCCGGGCCTCCAGGCTNCTCCGCTCGGTG
ATGGCACGCCACCGCGACACCACCCGGCTGCGCTACGTCGAGCCATACCGGGCGGAGCTACATCGGCCCG
GCCGCCCAGTGTTCGGGCCCTCTCGCCCAGGTCGAGGTCGACACCGATTTGCGCATCCGCAGCCGCACCC
TGCGACGACAGAACCGCGGCCCTACCCACTGCTTGTCGGGCGGGGGCCAAAGAACCAGCTTGNCATCCTG
CCACAATTGGCCGGCGCCCG ::::::::::::Rv140T7.seq:::::::::::: (SEQ ID NO. 80)
CAGGCATGCAAGCTTCACGTCCGTACGGCTCGGGTACGCTTCGGTCGCAGTGTGCGAGTGATAGATGACG
ACCGGGACCTCGTCGGCATCTTCCATAGCCCGCCACACCTTCAGTTGCTCACCGGAATCCAACCGGTAGA
AGGTCGGCCAGCGCTCGGCATTGGTCATCGGGATATGCCGCTCGGGACGGTCAGAGCCCTCGGGTCCGGC
CAGCACTCCGCAGGCTTCGTCGGGGTGGTCGCGACGCGCATGGGCCACCATCGCATTCACCAGGTCTGCG
CGAATCACCAGCACGTAGACGGTTCCTTTCCTAAGCAACAC Clone Rv141 (SEQ ID NO. 81)
::::::::::::Rv141SP6.seq::::::::::::
AATATTCAAGCTTTCGGCGGAAACGGACNCCTTGCGAACATTGATAACAAAATAGAAATCATTGATGGTT
TGAGTCACCAGGCCGATCAAGCCTTCGCCGAGCCAAATTCCAATCAAGAGGCCCAAGCCCGTACCAATCA
GCCCGGCAACGAGGGATTCCGTCNTTATCAGCCNAAATAACTGCTCTCGGGTACCACCCAAACAGCGCAA
TATGGCGAAAAACGGTCGCCGTTGCACAACATTAAATGTCTCGGTATTGTTGATTAAAAAGATACCCACC
ACCAGGGCAATCCAACTGAGAGCGGTTAAATTGACCGTAAAAACCTCCCGTCATCTGTTT ::::::::::::Rv141T7.seq:::::::::::: (SEQ ID NO. 82)
CAGGCATGCAAGCTTGCTGCATCTTCCTGTGACTGCTCCCGAAACCTGGGGGTGTGCCTGCTGTGTATGC
ACGGCATACGGACATCCTTCCCCTGATACCCGCGGTCGAACCAGCCACGTGTCCATCATCAGGGGTCAAC TABLE 3-continued End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character << - >> denotes an uncertain base residue.

CCCGGCCAAGGGCGACGGCACGCCAAGTTCGCCGACCGTTAACCTAGTGCTGTTAGCTTCATTTGCTGCG
AGCAAAACAGCTGGTCGGCCGTTAGGAACTGAATTGAAACTCAACCGATTTGGTGCCGCCGTAAGTGTCC
TGTCTGCGGGTGCGCTGGTGTTGTCCGCGTGTGGTAACGACGACAATGTGACCGGGGGAGGTGCAACCAC
TGGCCAGGCGTCCGCGAAAGTCCATTGCNGGGGGAAGAAGACAC

Clone Rv142 (SEQ ID NO. 83)
::::::::::::Rv142IS1081.seq::::::::::::
GAAAGTGCCCCAAGGTGTTGGTGAAACTCGCTGGACGGTCCCCAGGATGTTGGCAGCACATTCACCGGAC
ATGACCGGAGCAAGACCGGACATCCTCCCATACCGTCGTCGCCGTGTACATCCGTAGCCCGTCCTGGCAG
GTGCTGGGTTGAACAAAATCAGCCCAACACCTGCCACGACGAAGAAGCGGGTTGCGCTGGCATGTCTTGT
CGGCTCGGCGATCGAATTCTACGAATTCCTTATCTACGGGACCGCTGCGGCGCTGGTGTTTCCCACCGTG
TTCTTCCCACACCTGGATCCCACGGTGGCCGCCGTGGCCTCCAAGGGGACATTTGCTGTGGCGTTCCTAT
CCCGGCCGTTCGGCGCGGCCGTCTTTGGATACTTTGGAGACCGCCTCGGCCGCCAGAAGACCCTGGTCGC
CACACTGTTGATCATGGGCCTGGCAACCGTGACTGTTGGGCTGGTTCCACGACAGTGGCCATCGCGC ::::::::::::Rv142SP6.seq:::::::::::: (SEQ ID NO. 84)
ATATTCAAGCTTTGTCACACCAAGTGTTCCGACCAANCGCTCCATCCGGCGAGTGGATACTCCCAGCAGG
TAGCAGGTCGCCACCACGCTGGTCAGTGCGCGTTCATCTCGCTTGCGGCGCTGCAGCAGCCAGTCCGGGA
AATAGCTGCCCTGGCGCAGCTTGGGGATCGCGACGTCGATGGTTGCGGCACGGGTGTCGAAATCACGGTG
GCGGTAGCCGTTGCGCTGATTGGACCGCTCATCGCTGCGTTCGCGGTAGCCCNCCCCGCACAGGGCGTCG
GCTTCAGCCCCCATCCAAGGCGGCGATGAACGTCGAGAGCAGCCCGCGCAGCAAATCCGGGCTCGCCTGT
GCGAGTTGGTCAGCCAGAAGCTGCTCGGTGTCATAAGATGAGAAGAGGTCAGTGCGTCCTTTCCTTCG ::::::::::::Rv142T7.seq:::::::::::: (SEQ ID NO. 85)
CAGGCATGCAAGCTTTTTGAGCGTCTCGCGGGGCAGCTTCGCCGGCAATTCTACTAGCGAGAAGTCTGGC
CCGATACGGATCTGACCGAAGTCGCTGCGGTGCAGCCCACCCTCATTGGCGATGGCGCCGACGATGGCGC
CTGGACCGATCTTGTGCCGCTTGCCGACGGCGACGCGGTAGGTGGTCAAGTCCGGTCTACGCTTGGCCT
TTGCGGACGGTCCCGACGCTGGTCGCGGTTGCGCCGCCAAAGCGGCGGGTCGGGTGCCATCATGAATGCC
TCACCGCCGCCGCACTGCACGGCCAGTGCCCCGGCGATGTCAGCCATCGGGACATCATGCTCGCGTTCAT
ACTCCTCGACCAGTCCGCGGAACAGCTCCATTCCCGGACCGCCCAACGC Clone Rv143 (SEQ ID NO. 86)
::::::::::::Rv143SP6.seq::::::::::::
ATACTCAAGCTTTTGGCTGGGTCGCCTTCCAATTCAGCGTGCACCGCTATGGGTTGCAGCAGCGGCTGGC
NCCGCACACCCCACTGGCCCGGGTGTTTTCGCCCCGAACCCGGATCATGGTGAGCGAAAAGGAGATTCNC
CTGTTCGATGCTGGGATTCGCCACCGCGAGGCCATCGACCGATTACTCGCCACCGGGGTGCGAGAGGTGC
CGCAGTCCCGCTCCGTCGACGTCTCCGACGATCCATCCGGCTTCCGCCGTCGGGTGGCGGTAGCCGTCGA
TGAAATCGCTGCCGGCCGCTACCACAAGGTGATTCTGTCCCGTTGTGTCCAAGTGCCTTTCGCGATCGAC
TTTCCGTTGACCTACCGGCTGGGGCGTCGGCACAACACCCCGGTGAGGTCGTTTTTGTTGCAGTTGGGCG
GAATCCGTGCTCTGGGTTACAGCCCCGAACTCGTCACGGCGGTGCGCCGCCGAC ::::::::::::Rv143T7.seq:::::::::::: (SEQ ID NO. 87)
CAGGCATGCAAGCTTCAACCTATTGACGCATTGTGCGAACTGACGGCGCCCGCGCATGGCCAATCCGGAA
GACCATCATTGGCCAGTGGCCGGGCGCTAACAGGTTCCAGCCCCCCACCAGTGCCGCTCGAACATGCGGT
GCAACCCATTCGCAGGCCGGCAGGGAAAGCACCGCGGAAGCCGCAAAGGGCTGCAGTTCCGCGCCCAATA
GTGTCGTCCGCAACCAGATGCGCTCGAAAACCGCCGCCGGCAGTCAGCGCACCCGACGCGAGGTCGAGAG
ACGTCGTCAGCGCGCCCACATGGGGTGCCAATCGGCACGGCAGGTAGGCCGCGCGCAACCCCAACGCGTG
GTGCATGCCACGGTCCGCAGGAGGCCACCACCC Clone Rv144 (SEQ ID NO. 88)
::::::::::::Rv1448P6.seq::::::::::::
ATACTCAAGCTTCCCGGCCGCAGGTGACGGCGCGGCCTAGCGCCACTTGATGCCGCACCCGATCGACGGN
CGTTGGTCGGGGTTGACTGGCCGCCCGGCGAGCAGGGCGTCAACCGCGGCCCGGACGTCGGCGGCCGTCA
CCGGTCGGCCATTGCCCGGGCGGGAGTCGTCGAGCTGACCACGGTAGACAAGTCGGCGCTGGCCGTCGAA
GACAAACGTGTCGGGTGTGCAGGCCGCGGAGAAGGCGCNGGCGACGTCTCGGGTTTCGTCGTAGAGATAC
GGGAACGTCCAGCCGTGGCGGCGGGCCTCGGCGACCATCTGATCGGGCCCGTCCTGCGGGTAGGTGACCA
CGTCCTTACTGGAGATACCGACCATCGGGACCCTTTGATCGGCGAGGTCCCGGCCGACCGTGGCCAATCC
GGCGGCGACGTGTCGCCCGTACCGGCCAGTGGTTC ::::::::::::Rv144T7.seq:::::::::::: (SEQ ID NO. 89)
CAGGCATGCAAGCTTTANCANCATCAACCCCGCCCCGCACCAGCACCGACACGATGTCGATGCCATCGAG
GTGAATGTCGAACTGGCNCAAACCATCTGGCGACCGCGACCACCGGCAACATGGGTACCGGCGATTTCCG
GTGCCAATGCCGACCCGACGGGCCGCTCTCACCGCAGGTGACCTCGATCACCGAGACCAGCCGGCCGTTA
TACTCACGCACCCCTACCGTGTCACGCCCAAAACGGCGCTGGTGGTCGATTGCCGGAGTGCACCCCGCAC
CCAGTGTCGTGCCCGGATCCGCCGACCAATCCCGCACCCACGTCGCCAAACCCGAAATCACCGTGATGCC
GTGGTAACTGACCACCGACAGTAACGTCACTACGGCCGCCACGCCGACGCCGAACCACCACGCACATGAT
GATCGGCTG Clone Rv145 (SEQ ID NO. 90)
::::::::::::Rv145SP6.seq::::::::::::
ATATTCAACCTTGCACACATTGACGATACCTTGGTCACGAGACCCCAAAAGCTGGCCTCCACCGCGCGCC TABLE 3-continued End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character << - >> denotes an uncertain base residue.

GGGGACCACGGTCATACCTTGANNCNGCTTTCGATCGTTGATGCTGCGTCTTGGTCCGCGGAAACCGCAG
GCTGGCATATGCACGTGGGCGCACTGGCGATCTGCGATCCCCACCGATTCGCCCGAATACAGCTTTCAGC
GGCTCCCCAAGTTGATCATCGACCGGCTGCCGGATATCCCGCACTTGCGGTGGCGGGTCACCGGCGCCCC
GCTCGGACTGGACCGGCCGTGGTTCGTCGAGGACCACGAAC

::::::::::::Rv145T7.seq::::::::::: (SEQ ID NO. 91)
CAGGCATGCAAGCTTCATGCCCGCGGCATGATAGCCACATGCACGCAATCGAACTCAGCGAAACCGGCGG
GCCAGGCGTCTTACGCCACCTCACCAGCGCGCAACCTCAACCCGGCCACGGAGACCTCCTGATC Clone Rv146 (SEQ ID NO. 92)
::::::::::::Rv146SP6.seq::::::::::::
ATACTCAAGCTTGATTTTGATCATCATGATGATCATCACCCGAATTGTGGTAGCCGCAGTGGTTATCGTG
GGTACCGTCGTGCTTTCCATGGGCGCCTCTTTCGGGCTTTCCGTATTGGTCTGGCAGGACATTCTGGGTA
TCGAGTTGTACTGGATGGTGTTGGCGATGTCGGTGATCCTGCTCNTGGCGGTGGGATCCGACTACAATCT
GCTGCTGATTTCCCGGTTGAAAGAGGAAATTGGGGCCGGATTGAACACCGGAATTATCCGTGCCATGGCT
GGTACCGGGGGAGTGGTGACGGCTGCCGGCATGGTGTTCGCCGTTACCATGTCGTTGTTTGTGTTCAGCG
ATTTGCGAATTATTGGTCAGATCGGTACCACCATCGGCCTGGGCTTGCTGTTCGACACCCTCGTCGTGCC
TCGTTCATGAAACCGTCCATTGCTGCCCTGCTGGGACCTGGTTCTGGTGGCCGCTACGGGTGCGCCCGCG
CCCGGCAGTCAAATCTTCCGCCG ::::::::::::Rv146T7.seq::::::::::: (SEQ ID NO. 93)
CAGGCATGCAAGCTTGGCGTGCCGTTCCAACCCGAATTGGCTTTCGGCGCCATCGGTGAGGACGGCGTGC
GGGTGCTCAACGACGACGTCGTCCGCGGGACACACCTCGATGCTGCCGCCATGGACGCGGTCGAACGCAA
GCAGCTGATCGAGCTACAACGCCGCGCGGAACGCTTCCGCCGCGGGCGTGACCGCATCCCGTTGACCGGG
CGGATCGCGGTGATCGTCGATGACGGCATCGCCACCGGAGCGACGGCCAAGGCGGCGTGCCAGGTCGCCC
GGGCGCACGGTGCGGACAACGTGGTGCTGGCGGTCCCCATCGGCCCAGACGACATCGTGGCGAGA Clone Rv147 (SEQ ID NO. 94)
::::::::::::Rv147SP6.seq::::::::::::
ATACTCAAGCTTTTACGGTGATCGCGCATCACCTGGTTCATGAACTGGAAGCAGCGCAGCGCTTCCTTTT
CGGCCGCAACATGAGCCAGCCTCTCGTCGGCGGTCGGGTGCAGGTGCTCGGGCAGCTCGGCCGCGACAGC
CGCCTGACCCTGAAACCAGCTTCCATATCCCGCGACGAACGACGCCAGTCCGCTACGTAACCCCTCCGCG
ACTGTCCATGGACAACAGCGCGTTCTCCACCGACCGGGCCCGGGTGTGGGGTGTTTCGGCGACCGGCAGC
CANGTGGTCCACACTGCCGAAG ::::::::::::Rv147T7.seq::::::::::: (SEQ ID NO. 95)
TAGTCGCTGACCGGTGCAGGTTTCGACNATGTGGTGCCGGTTCGGCGGCTACGTGCCATCGAGACACTGG
CGCAGGCTATCGCACCCGTTATCGGCTACGAGCAAATCGCGGTATGCGTTCTTGAGCATGAGTCGGCGAC
CGTCGTCATGGTCGACACCCACGACGGAAAGACGCAGATCGCCGTCTANCNTGTGTGCCGCGGATTATCA
GGACTGACCTCCTGGCTGACCGGCATGTTTGGTCGCGATGCCTGGCGCCCGGCCGGCGTGGTCGTGGTCG
GCTCGG Clone Rv148 (SEQ ID NO. 96)
::::::::::::Rv148SP6.seq:::::::::::
ATACTCAAGCTTTCCGCCGATACCCGCCATGTCGCGCACATCCAGAACTTCTGGGGGGATCCGCTGACAG
CGGCGGGATCCCAAAGTGCGGATGATCGGGCCGCCTACGTCGTGGTGTACCTCGTCGGTAACAACGAAAC
CGAAGCGTATGACTCGGTCCACGCGGTGCGGCACATGGTGGACACCACACCGCCACCGCACGGGGTGAAG
GCCTATGTCACCGGTCCGGCAGCACTCAATGCCGACCAGGCCGAGGCCGGAGACAAAAGTATCGCTAAGG
TCACCGCGATCACGAGCATGGTGATCGCAGCAATGTTGCTAGTGATCTATCGCCCCGTAATTACCGCGGT
TCTCGTCTTGATCATGGTCGGCATCGACCTCGGCGCAATCCGCGGATTCNTCGCCTTGCTCGCCGACCAC
AACATTTTCAGCCTTTCAACATTTGCGACAACCTGCTCGTTCTCATGGCGATTGCNGCGAAC ::::::::::::Rv148T7.seq::::::::::: (SEQ ID NO. 97)
CAGGCATGCAAGCTTGGCGTGCCGTTCCAACCCGAATTGGCTTTCGGCGCCATCGGTGAGGACGGCGTGC
GGGTGCTCAACGACGACGTCGTCCGCTGGACACACCTCGATGCTGCCGCCATGGACGCGGTCGAACGCAA
GCAGCTGATCGAGCTACAACGCCGCGCGGAACGCTTCCGCCGCGCGCGTGACCGCATCCCGTTGACCGGG
CGGATCGCGGTGATCGTCGATGACGGCATCGCCACCGGAGCGACGGCCAAGGCGGCGTGCCAGGTCGCCC
GGGCGCACGGTGCGGACAAGGTGGTGCTGGCGGTCCCGATCGGCCCAGACGACATCGTGGCGAGATTCGC
CGGGTACGCCGATGAAGTGGTGTTGTTTGGCGACCCGGCGTTGTT Clone Rv149 (SEQ ID NO. 98)
::::::::::::Rv149SP6.seq::::::::::::
ATACTCAAGCTTTGGCATTGTGCACATTTTCCACCCGTGCTCTATTAATGCTGAGCCGCTAATTGTGACC
CCAGTCGGGAAACACGCGGAGCACCAAATTCACCGCAGCGGCCGGGGCGGTTCAACTCACCATGGATCGC
TCTCGTCGTCTGGTGCTGGACAATCGTCGCTGTAGCGCGTCGCGAACACCTCAGCTTCTGCTGCCGCGGC
TTCTTCCGGCGATGGTAACCCCCAGGTTTCGCCCACGGTCTTACGTAGCAGTGCGACGCGGTGTTCATCT
GCATCGACCTGTTGACTCATCCTGTCAAGGATGAAGGCGTACTGGGCCGACTGCGCCTTCTGCCGCGCCA
GGTCGGCAATCACCAGGATCTCAGAAACGAGCTGCGACTCACTCTTCCAGGCCACCCTGGCCGAAAGCTC
GACATGGTCAATCCGGCCG ::::::::::::Rv149T7.seq::::::::::: (SEQ ID NO. 99)

TABLE 3-continued

End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character << - >> denotes an uncertain base residue.

CAGGCATGCAAGCTTGCGGGCCGGAGTGGTTTCGACGGCCGCTCGCTTCTCGGCATCGGTTTGGGCTGTC
ACCAGCAGTTGGTAGTTCTTCACGTACTGTTGTTCGAGCGTCGAGCCGCCGCGCGTGTCGAGGTCGCCGG
ACGCGTATCCCGCCAGGCCGGTCAGGGTGCCCTTCCAGTCCACGCCGCTGTGGTCGGCGAACCGCTTATC
TTCAATCGAGACGATCGCCAGCTTCATCGTGTTGGCGATCTTGTCCGAGGGCACCTCGAACCGGCGCTGC
GAGTACAGCCACGCGATCGTGTTGCCCTTCGCGTCGACCATCGTCGATACCGCAGGCACTTGCCCCTC

Clone Rv14 (SEQ ID NO. 100)
::::::::::::Rv14SP6.seq:::::::::::
ATACTCAAGCTTCCCGGCGGCCAGTACCGAAAGCGCGAACAGCTCGCGGCAGCCCACGACGTGCTGCGTC
GGATTGCCGGCGGCGAAATCAATTCCAGGCAGCTCCCGGACAATGCGGCTCTGCTGGCCCGCAACGAAGG
ACTCGAGGTCACCCCGGTGCCCGGGGTCGTGGTGCACCTGCCGATCGCACAGGTTGGCCCACAACCGGCC
GCTTGATGCCCGGTCGGCAAGCCCGGCAGTTGCCAAACCCAGCGTGATCAGGCTCGGCTCGCGAGTTCGG
CGAAGAAGTGGCTCGCCTGATCACCTACCATCGGCCAGGATCTGCGTGTCATCACAACGCTCGCCAAGGA
GGTTGTTGTGGTGCTATCGACGGCCTTTAGCCAGATGTTCGGAATCGACTATCCGATAGTGTCCGCGCCA
ATGGACTTGATCGCCG ::::::::::::Rv14T7.seq::::::::::: (SEQ ID NO. 101)
AGCTTCGGTGTAGCCGATCACCGGAAGCCGCATGATCAGCCACGTTTCGCGCCGCCCGGCATACGGCGGC
GTACCGATCTCCGCGTCATACACCCGCGGGTAATCGCCGACGGTGCCGGTTCGCGAGCCGAAGGTGACGC
ACGCTGATTGAATCGAGTTCCAGGTCCAGCGGGTGGCGCAGCAACGGCGCGAGCTCAACGACGTCAATCA
GTTGTCGCTTTCTACGGTCACCGACCCGGTGACCGTAGTCGCCCGGTGCGCTCGGCCGAGAAGTTGCACC
GCCACCACCGCGACACCGTCTTGCACGCGGACGCCACCCCCGGATCGGTTGTTGGCCAAGGTAATTGGGT
CATTCCATTTGACGGGACGCCGACCCCGCAGCCCCAGTACCGCCCACGACCACGCCGGCTGACCCACCAC
TGTACGAACACCAAGGCGACGCCGA Clone Rv15 (SEQ ID NO. 102)
::::::::::::Rv150SP6.seq::::::::::::
ATACTCAAGCTTCGGTGGCTTCGCCCGCCCTGCCGGGTGGACTTCATGACAACGCGGGGGCGATTACCCC
CGCTACCGCCAGCAGCATGACGGCGGTACCTAACACCGCCCGGATGCCTCGCACGTGCCTCGATGTGCTC
ACGGAATCGCCCCGGCACCGCGATCTCGAGGATCACCAGCGTTACCCCCGGCAGCGCGACACCGACAATT
CCGTACACCGCCACGCCGATCCGGCCCTGGGCCAGCTGATTGGAGCTGGCG ::::::::::::Rv150T7.seq::::::::::: (SEQ ID NO. 103)
CAGGCATGCAAGCTTCCACATGTACGGATCCACGAACATCCCGTTGAACTGACAGGTGCGGCCCGGCTCG
ATCAGGCCGGCCACTTGTTCTACGCGGTTACCGAAGATCTCTTCGGTGACCTGCCCGCCGCCGGCCAGCT
CGGCCCAGTGCCCGGCGTTGGCCGCCGCGGCGACGATCTTGGCGTCCACGGTGGTCCGGGTCTTGCCCGC
TAGCACGATCCGCGAGTCGGCCGGTCACCCGGGT Clone Rv151 (SEQ ID NO. 104)
::::::::::::Rv151SP6.seq::::::::::::
ATACTCAAGCTTTCCAAGTCCCAAGTGTCGATCATGGCCAAAGAGCTCGACAAAGCCGTAGAGGCGTTTC
GGACCCGCCCGCTCGATGCCGGCCCGTATACCTTCCTCGCCGCCGACGCCCTGGTGCTCAAGGTGCGCGA
GGCAGGCCGCGTCGTCGGGGTGCACACCTTGATCGCCACCGGCGTCAACGCCGAGGGCTACCGAAAGATC
CTGGGCATCCAGGTCACCTCCGCCGAAGACGGGGCCGGCTGGCTGGCGTTCTTCCGCGACCTGGTCGCCC
GCGGCCTGTCCGGGGTCGCGCTGGTCACCAGCGACGCCCACGCCGGCCTGGTGGCCGCGATCGGGGCCAC
CCTGCCCGCAGCGGCCTGGCAGCGCT ::::::::::::Rv151T7.seq:::::::::::: (SEQ ID NO. 105)
CAGGCATGCAAGCTTCACACGTAGGCGCCGTCGATAAATGACTCCGCCGCGCTTCGCACATCCTCGTAGC
GATCCTTGGCGAGCAGGTCAACCGGGCGCTGCCCGTCGAGGAGCCGGTTTTTGGCGTGCAGCCACTGGCC
GACACCTCGGGGGGTAAGCGAATCCGAGAGCAGGAGGACGAGGTCACGAAGCTGCGCCAGCCGGTCGTAC
CGCTCAGGGCGGATGTCGCCGGTCCGCCACCCGCGTACCGCCCGATCGGACACCTGTATGACCGCGGCGA
CGTC Clone Rv152 (SEQ ID NO. 106)
::::::::::::Rv152SP6.seq::::::::::::
CGCGGCGGCGCATTACCCCCGCTACCGTCAGCAGCTTGACGGCGGTAGCGAACACCGCCGGATGCAGCGC
AGGTGCGTCTATGTGCACACGGAATCGCCCCGGCACCGCGATCTCGAGGATCACCAGTGCCCGCCCCCTG ::::::::::::Rv152T7.seq:::::::::::: (SEQ ID NO. 107)
GGGATCGAGGAACAGCGCGTTGAACTGATAGGTGCGGCCCGGCTCGAGCAGGCCGGCCATTTGTTCGATG
CGGTTACCGAAGATCTCTTCGGTGACCTGCCCGCCGCCGGCCAGCTCGGCCCAGTGCCCGGCGTTGGCCG
CCGCGGCGACGATCTTGGCGTCCACGGTGGTCGGGGTCATGCCCGCGAGCAGGATCGGCGAGCGGCCGGT
CAGCCGGGTGAACTTCGTCGAGAGCTTGACCCTGCCGTCGGGGAGGCGAACCACGGTCGGTGCGTATCTC
GACCAGGCCCGGGCAACCTCGGGGGTGGCGCCGACGGTGAACAGGTTGCGCTGGCCACCGCGGGTAGCCG
CCGGCACTATGCCGATGCCCAGGCCGCGGATCACCGGTGCGGTCAGTCGGGTCAGGATGTCGCCCGGCCC
CAGGTCGAAGATCCAGCGGGCGCCGGCCGCGTGGACACNGGTGATCTCGTCCACCATCGACTTTCTGATC
A Clone Rv153 (SEQ ID NO. 108)
::::::::::::Rv153SP6.seq::::::::::::

TABLE 3-continued

End sequences of the polynucleotide inserts cloned in the named recombinant BAC vectors contained in the I-1945 *M. tuberculosis* H37Rv genomic DNA library. RvXXXSP6 corresponds to the SP6 endsequence of the clone RvXXX; RvXXXT7 corresponds to the T7 endsequence of the clone RvXXX. RvXXXIS 1081 corresponds to a region located close to a copy of the IS1081 repetitive sequence (Insertion element) The character << - >> denotes an uncertain base residue.

TAACTCAAGGCTTGCGTTGAGGCCCCAGGCCCATCGACGGTTTGGCGGCCTTAAATGCACTGAGGTCGTC
AATTGACCCCACAGCGGAAATGCCGACTATTCGCAGGCCTCCTTCGCCTTGGCTGCCGGAGAGGGGCTCC
GCGGGAACCGCATGCAGGTATATGACCTCGGTTTCTCGGGTGCTACCGCGTGCCTTGTCGAGGATGAACT
CGGCGTTGGAATTGTCCAGCCGGCCCAATTCATCGAGCGCAGATTCGTACACATGGCCGGCGGCGACATA
CGCTTCACCGTGGATCTGCTCCACACGGACCGCCCTGTCGGGATCCTGCTCACGGGTAAAGGAACTTACN
TGGCNCTCGGTGCC

::::::::::::Rv153T7.seq:::::::::::: (SEQ ID NO. 109)
CCTTCTGCGCCACCCACACCGTCAACGCCCGCGAAGTCGACGTCGTCCAGGCCATCGGCGGCCTCACGGA
TGGATTCGGCGCGGACGTGGTGATCGACGCCGTCGGCCGACCGGAAACCTACCAGCAGGCCTTCTACGCC
CGCGATCTCGCCGGAACCGTTGTGCTGGTGGGTGTGCCGACGCCCGACATGCGCCTGGACATGCCGCTGG
TCGACTTCTTCTCTCACGGCGGTGCGCTGAAGTCGTCGTGGTACGGCGATTGCCTGCCCGAAAGCGACTT
CCCCACGCTGATCGACCTTGACCTGCATGGCCGGCTGCCGCTGCAGCGGTTCGTTTCCGAACGCATCGGG
CTCGAAGACGTCGAGGAGGCGTTCCACAAGATGCATGGCGGCAAGGTATTGCGTTCGGTGGTGATGTTGT
GATGGCCGCCATCGAGCGCGTCATCACCCACGG Clone Rv154 (SEQ ID NO. 110)
::::::::::::Rv154SP6.seq::::::::::::
ATACTCAAGCTTGATTTTGATCATCATGATGATCATCACCCGAAGTGTGGTAGCCGCAGTGGTTATCGTG
GGTACCGTCGTGCTTTCCATGGGCGCCTCTTTCGGGCTTTCCGTATTGGTCTGGCAGGACATTCTGGGTA
TCGAGTTGTACTGGATGGTGTTGGCGATGTCGGTGATCCTGCTCCTGGCGGTGGGATCCGACTACAATCT
GCTGCTGATTTCCCGGTTGAAAAAAGAAATTGGGGCCGGATTGAACACCGGAATTATCCGTGCCATGGCT
GGTACCGGGGGAGTGGTTACCGCTGCCGGCATGGTGTTCGCCGTTACCA ::::::::::::Rv154T7.seq:::::::::::: (SEQ ID NO. 111)
ATTGNCTTTCGGCGCCATCGGTGAGGACGGCGTGCGGGTGCTCAACGACGACGTCGTCCGCGGGACACAC
CTCGATGCTGCCGCCATGGACGCGGTCGAACGCAAGCAGCTGATCGAGCTACAACGCCGCGCGGAACGCT
TCCGCCGCGGGCGTGACCGCATCCCGTTGACCGGGCGGATCGCGGTGATCGTCGATGACGGCATCGCCAC
CGGAGCGACGGCCAAGGCGGCGTGCCAGGTCGCCCGGGCGCACGGTGCGGACAAGGTGGTGCTGGCGGTC
CCGATCGGCCCAGACGACATCGTGGCGAGATTCGCCGGGTACGCCGATGAGGTGGTGTGTTTGGCGACGC
CGGCGTTGTTCTTCGCCGTCGGGCAGGGTTACCGCAACTTCACCCAGACCTCCGACGAAGAAGTGGTGGC
GTTTTCTGGATCGTGCTC Clone Rv155 (SEQ ID NO. 112)
::::::::::::Rv155SP6.seq::::::::::::
ATACTCAAGCTTTTCCCGTCCGTCATCGCCCAAGCGCGTGAGGCCGAAGCGGCTGGTTACGACTCCCTGT
TTGTGATGGACCACTTCTACCAACTGCCCATGTTGGGGACGCCCGACCAGCCGATGCTGGAGGCCTACAC
GGCCCTTGGTGCGCTGGCCACGGCGACCGAGCGGCTGCAACTGGGCGCGTTGGTGACCGGCAATACCTAC
CGCAGCCCGACCCTGCTGGCAAAGATCATCACCACGCTCGACGTGGTTAGCGCCGGTCGAGCGATCCTCG
GCATTGGAGCCGGTTGGTTTGAGCTGGAACACCGCCAGCTCGGCTTCGAGTTCGGCACTTTCAGTGACCG
GTTCAACCGGCTCGAANAGGCGCTACAGATCCTCGAGCCAATGGTCAAGGGTGAGCGCCAACGTTTTTCG
GCGATTGGTACCCACCGA ::::::::::::Rv155T7.seq:::::::::::: (SEQ ID NO. 113)
CGGCCACCGGGGCCACTCCGCACAATCTGTACCCGACCAAGATCTACACCATCGAATACGACGGCGTCGC
CGACTTTCCGCGGTACCCGCTCAACTTTGTGTCGACCCTCAACGCCATTGCCGGCACCTACTACGTGCAC
TCCAACTACTTCATCCTGACGCCGGAACAAATTGACGCAGCGGTTCCGCTGACCAATACGGTCGGTCCCA
CGATGACCCAGTACTACATCATTCGCACGGAGAACCTGCCGCTGCTAGAGCCACTGCGATCGGTGCCGAT
CGTGGGGAACCCACTGGCGAACCTGGTTCAACCAAACTTGAAGGTGATTGTTAACCTGGGCTACGGCGAC
CCGGCCTATGGTTATTCGACCTCGCCGCCCAATGTTGCGACTCCGTTCGGGTTGTTCCCAGAGGTCAGCC
CGGTCGTCATCGCCGACGCTCTCGTCGCCGGGACCAGCAGGGAATCGGCGATTTCGCCTACA Clone Rv156 (SEQ ID NO. 114)
::::::::::::Rv156SP6.seq::::::::::::
ATACTCAAGCTTGGGGTGGCGCTGTCGGTCGGTGTGCTTGGCGGCGTCGGTATCAACACCGCCCACGAAA
TGGGGCACAAGAAGGATTCGCTGGAGCGGTGGCTGTCCAAAATCACCCTCGCCCAGACCTGCTACGGGCA
CTTCTACATCGAGCACAACCGTGGCCATCACNTCCGGGTGTCCACACCGGAGGACCCGGCGTCGGCGCGG
TTCGGCGAAACGTTGTGGGAGTTCCTGCCCCGCAGTGTTATCGGCGGCTTGCGCTCGGCCGTTCATTTGG
AGGCCCAACGGCTGCGTCGGCTCGGCGTCAGCCCCTGGAATCCCATGACGTATCTGCGCAACGACGTGCN
CAACNCGTGGCTGATGTCNGTGGTGTTGTGGGGTGGGC ::::::::::::Rv156T7.seq:::::::::::: (SEQ ID NO. 115)
TCGCCACCGCACCGCGGCGAACGCTCAAAGGCACCTACTGGCACCAAGGCCCCACACGTCACCCTGTGAC
CTCCTGCGCCGACCCCGCCCGAGGTCCTGGCCGTTACCACCGAACGGGCGAGCCGGGAGTCTGGTACGCA
TCGAACAAAGAGCAAGGTGCATGGGCGGAGTTGTTCCGCCACTTCGTCGATGACGGGGTCGATCCATTCG
AGGTCCGTCGCCGCGTCGGTCGAGTGGCGGTCACACTCCAGGTACTCGACCTCACAGACGAGAGGACTCG
ATCCCATCTAGGTGTGGACGAAACAGATCTTCTGTCCGACGACTACACCACCACCCAGGCCATCGCCGCC
GCCCGCGATGCCAACTTCGACGCCGTACTGGCCCCGGCGGCGGCGCTCCCCGGTTGTCAAACACTTTGCC
GTGTTCGTTCACGCACTGCCCAACATCGAGCCCGA Clone Rv157 (SEQ ID NO. 116)

TABLE 3-continued

End sequences of the polynucleotide inserts cloned in the named recombinant
BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081
repetitive sequence (Insertion element)
The character << - >> denotes an uncertain base residue.

:::::::::::::Rv157SP6.seq:::::::::::::
ATGAAATAAGAAGAGCACATCCCTCAGTCGGTTATCATCACTAGCGCTCGCCGCACCCGTGTAACCGATC
ATAGCGAGCGAACTGGCGAGGAAGCAAAGAATATCTGTTCTGTCAGATAGCTCTTACGCTCAGCGCAAGA
AGAAATATCCCCCGCGGGAACAACTCCAGGTAGAGGTACACACGCGGATAGCCAATTCAGAGTAATAAAC
TGTGACACTCACACCCTCATCAATGATGACGAACTACACCCCGATATCCGGTCACATGACGAAGGGAAAG
AGAAGGATATCATCTGTGACAAACTGCCCTCAAATTTGGCTTCCTTAA Clone Rv159 (SEQ ID NO. 117)
:::::::::::::Rv159SP6.seq:::::::::::::
ATACTCAAGCTTGTCGAACTCCTTCTTGAATACCGGCCGGCCATCCACAGATGCCCGGAAGAACTTCCAG
GTACCCATGGCGGCTGGATCAGGGGGCGGCACAGTTGGTCTTGTCCTGCCTCGAGTGGCGTCGTTGTCCG
GCTTGGACGGGGCTCCGACGGTACCGGAGGGCAGCGACAAAACACTTATGCACTTGGGCGACCCGCCGAG
ACGGTGCGACACCCATCCCGACGGCACAAGCTCAGCCGCGGCCGCTCTTGTTCTTCGTCGGATCGACATT
CACCCACTTCTGACCGGGCTTGGGCGAAGGAAGCAGAA :::::::::::::Rv159T7.seq::::::::::::: (SEQ ID NO. 118)
GGTATAGTCGCTGACCGGTGCAGGTTTCGACAATGTGGTGCCGGTTCGGCGGCTACGTGCCATCGAGACA
CTGGCGCAGGCTATCGCACCCGTTATCGGCTACGAGCAAATCGCGGTATGCGTTCTTGAGCATGAGTCGG
CGACCGTCGTCATGGTCGACACCCACGACGGAAAGACGCAGATCGCCGTCAAGCATGTGTGCCGCGGATT
ATCAGGACTGACCTCCTGGCTGACCGGCATGTTTGGTCGCGATGCCTGGCGCCCGGCCGGCGTGGTCGTG
GTCGGCTCGGATAGCGAGGTCAGCGAATTCTCGTGGCAGCTCGAAAGGGTCCTGCCGGTGCCGGTCTTTG
CGCAAACGATGGCGCAGGTTACGGTCGCGCGGGGTGCGGCCCTGGCGGCGGCCCA Clone Rv15 (SEQ ID NO. 119)
:::::::::::::Rv15SP6D2.seq:::::::::::::
GACACTATATNATACTCAAGCTTCAGGTCAATGTGCGCCAAGCCCTGACGCTGGCCGACCAGGCCACCGC
CGCCGGANCCCTNTCTAGA :::::::::::::Rv15T7.seq::::::::::::: (SEQ ID NO. 120)
CTGTAGCCACCTGTTGCCATCCCCGTCATGCCCGACTCTGGTCATCTCGGATCCGCTGACACCCCGCTAA
GGCTGCTCCTCTCGGTGCATTACCTCACCGACGGCGAACNCCCCCAGCTTTACGACTATCCGGATGACGG
CACCTGGTTGCCGGCTAACTTCACCGTCAGCTTGGACGGCGGCGCTACCGTCGATGGCGCCAGCGGGGCG
ATGGCCGGGCCCGGCGACCGATTCGTCNTCANCCTGTCGCGTGAACTTGCCGACGTCATCGTGGTCGGTG
TGGGCACCGTGCGCATTGAGGGCTACTCCGGCGTCCGGATGGGTGTCGTCAAGCGCCCGCACCGGCAGGC
CCGA Clone Rv160 (SEQ ID NO. 121)
:::::::::::::Rv160SP6.seq:::::::::::::
ATACTCAAGCTTCGCACGCTCGGCGCGCGGTACCGCCCAGGTCGCCCAACAGATCGTCGATGTTCGCG
TCGTCCGCCTCGCGCACGTGGTCTGTCACCAGTCAACGTTAACGCCGCCGCACATGTCCTGCGGCCGGGC
AAAAACGTGAAAAACGAGCGGGCGACTGCNATGTCATGACACCGACGGCCGCCGATGGGCCCAGGGTCTG
GCAAATTCGATCTGTGCGGCCAGTGCCAGCAGCGTCGCCTCGTCATACGGCCGGCCGACGAGTTGAACCG
ACATGGGCAGGCCGTCGCCGTCGAAGTCCCACGGCACCACGGGCGCGGGCTGGCCGGTCAGATTCCAAAA
TTGAAAGTACGGAACCGCTGCACCACCAA :::::::::::::Rv160T7.seq::::::::::::: (SEQ ID NO. 122)
ATCGTTTCGACCAGGCGCTCCATCCGGCGAGTGGATACTCCCAGCAGGTAGCAGGTCGCCACCACGCTGG
TCAGTGCGCGTTCAGCTCGCTTGCGGCGCTGCAGCAGCCAGTCCGGGAAATAGCTGCCCTGGCGCAGCTT
GGGGATCGCGACGTCGATGGTTGCGGCACGGGTGTCGAAATCACGGTGGCGGTAGCCGTTGCGCTGATTG
GACCGCTCATCGCTGCGTTCGCGGTAGCCCGCCCCGCACAGGGCGTCGGCTTCAGCCCCCATCAAGGCGG
CGATGAACGTCGAGAGCAGCCCGCGCAGCAGATCCGGGCTCGCCTGTGCGAGTTGGTCAGCCAGAAGCTG
CTCGGTGTCGATAAGATGANAAGAAGTCATTGCGTTATTTCCT Clone Rv161 (SEQ ID NO. 123)
:::::::::::::Rv161SP6.seq:::::::::::::
ATACTCAAGCTTGGGTGTTGCCGATCACCGGAAGCCGCATGATCAGCCACGTTTCGCGCCGCCCGGCATA
CGGCGGCGTACCGATCTCCGCGTCATACACCCGCGGGTAATCGCCGACGGTGCCGGTTCGCGAGCCGAAG
GTGACGACGCTGATTGAATCGAGTTCCAGGTCCAGCGGGTGGCGCAGCAACGGCGCGAGCTCAACNACGT
CAATCACGTTGTCGCTTTCTACGGTCACCGACCCGGTGACCGTAGTCGCCCGGTGCGCTCGGCCGAGAAG
TTGCACCGCCACCACCGCGACAACGTCTTGCACGCGGACGCCACCCCCCGGAT :::::::::::::Rv161T7.seq::::::::::::: (SEQ ID NO. 124)
GCGCNAACAGCTCGCGGCAGCCCACGACGTGCTGCGTCGGATTGCCGGCGGCGAGATCAATTCCAGGCAG
CTCCCGGACAATGCGGCTCTGCTGGCCCGCAACGAAGGACTCGAGGTCACCCCGGTGCCCGGGGTCGTGG
TGCACCTGCCGATCGCACAGGTTGGCCCACAACCGGCCGCTTGATGCCCGGTCGGCAAGCCCGGCAGTTG
CCAAACCCAGCGTGATCAGGCTCGGCTCGCGAGTTCGGCGAAAAAGTGGCTCGCCTGATCACCTACCATC
GGCCAGGATCTGCGTGTCATCACGACGCTCGCCAAGGAGGTTGTTGTGGTGCTATCGACGGCCTTTAGCC
AGATGTTCGGAATCGACTATCCGATAGTGTCCGCGCCAATGGACTTGATCGCCGGCGGTGAGCTGGCTGC
CGCNGT Clone Rv162 (SEQ ID NO. 125)

TABLE 3-continued

End sequences of the polynucleotide inserts cloned in the named recombinant BAC vectors contained in the I-1945 *M. tuberculosis* H37Rv genomic DNA library. RvXXXSP6 corresponds to the SP6 endsequence of the clone RvXXX; RvXXXT7 corresponds to the T7 endsequence of the clone RvXXX. RvXXXIS 1081 corresponds to a region located close to a copy of the IS1081 repetitive sequence (Insertion element) The character << - >> denotes an uncertain base residue.

::::::::::::Rv162SP6.seq::::::::::::
ATACTCAAGCTTTCTCCGATACCCGCCATGTCGCGCACATCCAGGACTTCTGGGGGGATCCGCTGACAGC
GGCGGGATCCCAAAGTGCGGATGATCGGGCCGCCTACGTCGTGGTGTACCTCGTCGGTAACAACGAAACC
GAAGCGTATGACTCGGTCCACGCGGTGCGGCACATGGTGGACACCACACCGCCACCGCACGGGGTGAAGG
CCTATGTCACCGGTCCGGCAGCACTCAATGCCGACCAGGCCGAGGCCGGAAACAAAAGTATCGCTAAGGT
CACCGCGATCACGAACATGGTGATCGCAGCAATGTTGCTAGTGATCTATCGCTCCG ::::::::::::Rv162T7.seq:::::::::::: (SEQ ID NO. 126)
CCATGAGCACCGCCAGCCGAGCACGAGGCCAAACTCCGCCGACGCAGGCCGGTTGGACTTGTCGTGCTGG
ACAAGGGGTTTAGCCGCCGAAGCAGTGACGTACATCGGCGAAGAGCAGTTCGCCTGTCGACCGACGGCGC
AAACCGTGAGGCTAGGGAAGCGAGGAGCACATGGCCGCCGACCCGCAATGTACACGCTGCAAGCAAACCA
TCGAACCCGGATGGCTATACATCACCGCCCATCGCCGCGGTCAAGCCGGGATCGTCGATGACGGCGCAGT
ACTGATTCACGTGCCCGGTGAATGCCGCACCCCGGGGAGCACTTTCCGCCAAAACTAACCCGGTTGG Clone Rv163 (SEQ ID NO. 127)
::::::::::::Rv163SP6.seq::::::::::::
CGGGTGTCATTGGCCACCGGCGGCGGCTGTCCGGGAAATGGCGGGTCCCCGGTGGTTTTGCTGAGGAGTG
CTGAACCGTAGTCGAAGTGGGCGGCGTCAGACTCCACCCAGCCAGCAGGCAGCGCGAANCTGAATCCTCC
AACCGGGTTGTCNATCCGGACAGGTTGGGGTGCGTTTGGGGCAATNACAGGTGGCGGCGGTGCGTTCGGG
TCGGCCGGCGGAGGTGCTGCNTTGGGATCCCCGGCTGGGCATTCGGCNTGTTGGCGGCGGCCGGTGGTGG
GGGGGGCAACACGTGTCNCCGGTGCGGGTGGCCCT ::::::::::::Rv163T7.seq:::::::::::: (SEQ ID NO. 128)
CCAAGATCTACACCATCGAATACGACGGCGTCGCCGACTTTCCGCGGTACCCGCTCAACTTTGTGTCGAC
CCTCAACGCCATTGCCGGCACCTACTACGTGCACTCCAACTACTTCATCCTGACGCCGGAACAANTTGAC
GCAGCGGTTCCGCTGACCAATACGGTCGGTCCCACGATGACCCAGTACTACATCATTCGCACGGAGAACC
TGCCGCTGCTAGAGCCACTGCGATCGGTGCCGATCGTGGGGANACCCACTGGCGAACCTGGGTTCAACCA
AACTTGAAGGTGATTGTTAACCTGGGCTACGGCGACCCGGCCTATGGTTATTCGACCTCGCCGCCCAAAT
GTTG Clone Rv164 (SEQ ID NO. 129)
::::::::::::Rv164SP6.seq::::::::::::
AGCTTCCCGAGTTCGGCTTTGGATCAAGACCCCAGTCCGCGGGCGCGATCCGGCNGCTCGGTGACTACAT
CAAGCCACAAATCGACGGCTTTCGGGGTGCCGATACCGATGACGTGGCGGATGTCGAGTGTTGAGTTCTC
GGCGGGGCGGATGCTCACCTGGCGATCACCTGCCTCTCGTTGACGATCGATCGTCTATGCCGCCGTCTCT
GCGGGAACAGGCCNCCAGTACATCGCCACAGACGGGATCCACCCGCATTTCGGCTACGGTTGCTCGTTTC
GGTGTTCGGACTAGTCGGTCCTGGTGACGTGCCGGTGATGCGGACCGGTCCTAGCACTGACCAATGGCCA
AAATGCGGGC ::::::::::::Rv164T7.seq:::::::::::: (SEQ ID NO. 130)
CGGGGGGCCTCTTAATAGTGTAGGAAAGAAGCTCTACATATTCAGGAGGATTCACCATGGCTCGTGCGGT
CGGGATCGACCTCGGGACCACCAACTCCGTCGTCTCGGTTCTGGAAGGTGGCGACCCGGTCGTCGTCGCC
AACTCCGAGGGCTCCAGGACCACCCCGTCAATTGTCGCGTTCGCCCGCAACGGTGAGGTGCTGGTCTGCC
AGCCCGCCAAGAACCAGGCAGTGACCAACGTCGATCGCACCGTGCGCTCGGTCAAGCGACACATGGGCAG
CGACTGGTCCATAGAGATTGACGGCAAGAAATACACCGCGCCGGAGATCAGCGCCCGCATTCTGATGAAG
CTGAAGCGCGACGCCGAGGCCTACCTCGGTGAGGACATTACCGACGCGGTTATCACGACGCCCGCCTACT
TCAATGACGCCCAGCGTCAGGCCACCAAGGACCCGGCCAGATCGCCGGTCTCACGTGCTGCGG Clone Rv165 (SEQ ID NO. 131)
::::::::::::Rv165SP6.seq::::::::::::
ATACTCAAGCTTCATAACAGGCCTGTTGTGGGCGCACCCGGCTCGCCGAGTTCTGCACGCACCGCCTCAA
GTGCGGCCCGCACCGCCGGCATCTCCCGGTCACGCAGGGCCGCGGCCCGCGCCGCGCCGCAGCGACGGCGTGTTC
GCGCAGTTCGCCGTCAATGATGCTGACCTGATCGGCCACCCGGGCGTTCTCGGCGTCTTCGCGTTCACTA
ATCGCGGTGCTCAGCAGCGTCTCGACAGCCACCACCCGAGTGGCGACCAGCTGCTCCACCACGGACCGCA
GCGATGCCGTCACCTCACCCGTCCAGCGGTCCACCACGACACGGTCGTGCACCAGCGCGCGGGCATTCAC
CACCCAGGCGGTCACCGCCAGGCCGATCGCCACACCCGCCACCATCCCCGATGCAGCCAGGCCGGGAGTA
AGA ::::::::::::Rv165T7.seq:::::::::::: (SEQ ID NO. 132)
CTGGTGCTGGACGGAGCCTAGTACAACTTCCTCTCCAATGCTCTTGCCCCGATCGCGGCGACCAGGATGA
CCCAGGACATCCTGCCGCCCGAAGTACTGGAAAAGCTCACACCCGAGTTCGTCGCACCGGTGGTGGCCTA
CCTGTGCACCGAGGAGTGTGCCGACAACCCATCGGTGTACGTCGTCAGTGGTGGTTAGGTGCAGCGAGTT
GCGCTGTTTGGCAACGACGGCGCCAACTTCGACAAACCGCCGTCNGTACAAGATGTTGCGGCGCGGTGGG
CCGAGATCNCCGATCTGTCCGGTGCGAAAATTGCTGGATTCAAGTTGTAGAACTAAAT Clone Rv166 (SEQ ID NO. 133)
::::::::::::Rv166SP6.seq::::::::::::
ATACTCAAGCTTTTCCGGCGTCGTCCACCTGACCCAAAAAGCGCAGGTGCGCCGCCAAACGGCCCGCCTG
GCCGCGCAACTGGTCGGCGTCGCCGTGGCCGACAATCAGTAGCTGGACATCCGGAAACCGCTGCACCACC
TTCGGCAGCGCGTCAAGCAAAAACGGCCATTCC TABLE 3-continued End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character << - >> denotes an uncertain base residue.

::::::::::::Rv166T7.seq:::::::::::: (SEQ ID NO. 134)
TTTCAGATCTCATTTTTATGACATGACTGGAGATCTGTCTAGATTGCAGCTCCTGTGAGCGTGGGTACCG
GATTCAAGCCGGTCGGTCACGCCGCGGTGGTACCGGCTTTGCGGCAGTGCTCGGCCTCGAGTTCGGCGAT
CGCGCGCGAAGTGCGTTTCGCGCACCAAGATCGCGGCCTAATGGCCGGCGATGACCGCGATGACCAGCGC
GATCCAGGAAAAACCGTTCCAACCAGTGCTGGGCGGCCATCCCCG Clone Rv167 (SEQ ID NO. 135)
::::::::::::Rv167SP6.seq::::::::::::
ATACTCAAGCTTCCCGACCACAAGTTGAACAGCACCGATTTCGGCGAGCACTTCGTCAACTTCCAGGGTG
CCCGCACCAAGTATTTCGACAAGTATTTCCGTCGGGCCGCCGCCGCCGGCGCGCGGCAGGTGGTCATCCT
GGCGGCGGGGCTGGACTCCCGCGCGTACCGGCTGCCTTGGCCCGACGGGACCACGGTTTTTGAGCTGGAC
CGCCCGCAGGTCCTTGATTTCAAGCGCGAGGTGCTCGCCAGCCACGGTGCCCAACCGCGCGCCCTGCGCC
CGCGA ::::::::::::Rv167T7.seq:::::::::::: (SEQ ID NO. 136)
GTGTGCTGTCAATTCAGAGCTGAGCCTGATGCACTCAACTTACTGAGCATGCTAACGCTGGTCGTGCGGG
TCTTGTTCCCGCGTGTCGGCAGGGCACACGCTCGGGGCGTAGCTGGGAGAGGCCCCGGTCAAGCCCGGAG
AGCAGTGCTCAGTCCGCCAGCTTGACCGACTTTCGATGAGAACGCGCTTCTCGCCGTATTGAACTGGCGT
GCTGACGGTCGCTGAGCAGCGCTCGCCGAGTGCGGCCGCTGATTCTTTCATCGAGCCAGGAGGCGCATTC
GTGTTCGGCCGCCTGCGGGTCGGCCCCATCGTCGACGCGATCCGTCACCCACTCCTCGATCAGGTCTGCC
TCATCGAACGGGCCAACGGTGCTGTCGGAGTATGTGTGCGTGGGCACGGCGAGCCGGGTGCTGTGGTACA
CCCACCGTTGCATGACCAAGTTGACGCCTGACTGGCTGAGCACCGCGATCCGCTCACAGGTCGGAACGTT
GGTG Clone Rv169 (SEQ ID NO. 137)
::::::::::::Rv169SP6.seq::::::::::::
ATACTCAAGCTTTTGGTCTAGCCGGCCGAGCCCGATACAGGTGTCATTGGCCACCGGCGGCGGCTGTCCG
GGAAATGGCGGGTCCCCGGTGGTTTTGCTGAGGAGTGCTGAACCGTATGCGAAGTGGGCGGCGTCAGACT
CCACCCAGCCAGCAGGCAGCGCGAAACTGAATCCTCCAACCGGGTTGTCGATCCGGACAGGTTGGGGTGC
GTTTGGGGCAATGACAGGTGGCGGCGGTGCGTCCGGGTCGGCCGGCGGAAGTGCTGCGTTGGGATCGCCC
GGCTGGGCATTCTGCGTGTTGGCGGCGGCCGGTGGTGGGGGGGCAACAGGTGTCTCCGGTGCGGGTGGCG
CTGCACC ::::::::::::Rv169T7.seq:::::::::::: (SEQ ID NO. 138)
GGGGCCACTCCGCACAATCTGTACCCGACCAAGATCTACACCATCGAATACGACGGCGTCGCCGACTTTC
CGCGGTACCCGCTCAACTTTGTGTCGACCCTCAACGCCATTGCCGGCACCTACTACGTGCACTCCAACTA
CTTCATCCTGACGCCGGAACAAATTGACGCAGCGGTTCCGCTGACCAATACGGTCGGTCCCACGATGACC
CAGTACTACATCATTCGCACGGAGAACCTGCCGCTGCTAGAGCCACTGCGATCGGTGCCGATCGTGGGGA
ACCCACTGGCGAACCTGGTTCAACCAAACTTGAAGGTGATTGTTAACCTGGGCTACGGCGACCCGGCCTA
TGGTTATTCGACCTCGCCGCCCAATGTTGCGACTCCGTTCGGGTTGTTCCCAGAGGTCAGCCCGGTCGTC
ATCGCCGACGCTCTCGTCGCCGGGACCCAGCACGGAAT Clone Rv16 (SEQ ID NO. 139)
::::::::::::Rv16SP6.seq::::::::::::
TTCTNTCTTCCCNNATTCGTNNNTCTCNTACTACCNGGGCCNCAAAACACCTTGGCNAACGCTCAAAGGC
GNTACNGGCACCAAGGCCCCACACGTCACCCTGTGACCTCCTGCGCCGACCCCGCCCGAGGTCCTGGCCG
TTACCACTGAACGGGCGAGCCGGGAGTCTGGTACGCATCGAACAAAGAGCAAGGTGCATGGGCGGAGTTG
TTCCGCCNCTTTTTTTATGACGGGGTCGATCCATTCGAGGTCCGTCGCCGCGTCGGTCGAGTGGCGGTCA
CACTCCAGGTACTCGACCTCNCAGACGAGAGGACTCGATCCCATCTANGTGTGGACNAAACAGATCTTCT
GTCCGACGACTACACACCACCCAGGCCATCGCCGCCGCCCGCGATGCCAACTTCNACNCCGTNCTGGCCC
CGGCGGCGGCGCTCCCCGGTTGTCAAACACCTGCCGTGTTCGTTCACNCACTGCCCAACATCNAGCCCGA
NCNATCCNAGGTCCGTCCAACGCCTCCGCGGCTCNCCAACCTNCTCCCNCTGATCNTCCGCACCAAACAC
ATGCCCGACTCCNTGCNCCNATTGCTTGNATCCCT ::::::::::::Rv16T7.seq:::::::::::: (SEQ ID NO. 140)
CCGCTATCGGTCGGTGTGCTTGGCGGCGTCGGTATCAACACCGCCCACGAAATGGGGCACAAGAAGGATT
CGCTGGAGCGGTGGCTGTCCAAGATCACCCTCGCCCAGACCTGCTACGGGCACTTCTACATCGAGCACAA
CCGTGGCCATCACGTCCGGGTGTCCACACCGGAGGACCCGGCGTCGGCGCGGTTCGGCGAGACGTTGTGG
GAGTTCCTGCCCCGCAGTGTTATCGGCGGCTTGCGCTCGGCCGTTCATTTGGAGGCCCAACGGCTGCGTC
GGCTCGGCGTCAGCCCCTGGAATCCCATGACGTATCTGCGCAACGACGTGCTCAACGCGTGGCTGATGTC
GGTGGTGTTGTGGGGTGGGCTGATCGCGGTCTTCGGCCCGGCGCTGATCCCGTTCGTCATCATCCAGGCA
GTCTTCGGCTTCAG Clone Rv170 (SEQ ID NO. 141)
::::::::::::Rv170SP6.seq::::::::::::
ATACTCATGCTTGCCGAAGTTCCGATGGGTCGCGCCGGCGANCCCAGCGAAGTCGCTAGCGTGGCCGTGT
TCTTGGCTTCGGATCTATCCTCGTACATGACCGGCACCGTGTTGGACGTGACTGGCGGCCGGTTCATATG
ACACCGAGATCATTGCCACGGTACGGCAATTCGTCAAGAAGGAAATCTTTCCCAATGCACCGGCCCTCGA
ACGTGGCAACAGCTACCCGCAAGAAATCGTCGATCGGCTGGGTGTTATTGGCTTGCTCGGTCGCCGGCTG
CAAGGGTATCGACACCACCGAGTTCATTCTCCGGGCGTGCC TABLE 3-continued End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character << - >> denotes an uncertain base residue.

::::::::::::Rv170T7.seq:::::::::::: (SEQ ID NO. 142)
GGCGTCAACGGTGTCGGCACCGGCGTCCTGCAGTTGGTAGGCCTGCAGTTTGTGCATCAGGCCGATGCCG
CGGCCCTCGTGGCCACGCATGTACAGCACCACGCCGCGCCCCTCACGGGCGACCATCGCCAGCGCGGCGT
CCAGCTGAGGCCCGCAATCGCAGCGGCGTGACCCAAACACATCGCCGGTCAAGCACTCCGAATGCACCCG
GACCAGCACGTCGTCACCGTCGGCGTTGGGCCCGGCGATCTCGCCGCGGACCAGCGCGACATGTTCCACG
TCCTCGTAGATGCTGGTGTAGCCGATGGCGCGAATCTCCCATGACGAGTCGGAATCCGCGCCTCGGCG Clone Rv171 (SEQ ID NO. 143)
::::::::::::Rv17JSP6.seq::::::::::::
ATACTCAAGCTTCGGCCTCGCTGCAGGAGTGGGAGCCGCAGGGCTGGAAATCCGAAAAACGAGCCGGTGA
TCGCACTGTCGCCGATCGGGGCCGCACCTGGTTGGTGTTACCGATGAATCCGCACCCAAAATGTGGCTGC
GGTGGCGTTTCTTGACTCCTTGGCGTCGACTCTTGTGGCAGCCACCGAGCGGTTGGTCCAGGATCTGGAT
GGGCAAAGTTGTGCGGCCCGGCCGGTGACGGCCGATGAGCTGACCGAGGTCGACAGCGCCGTGTTGGCTG
ACTTGGAACCGACATGGATTCGCCCCGGTTGGCGTCACCTCAAGCATTTCAATGGTTAT ::::::::::::Rv171T7.seq:::::::::::: (SEQ ID NO. 144)
ATGCGTCACCCCGATGCGCCCAGATCGGGGCTTCGCAAATAAAGCACGAACAGGCGGGCAAAACGTCTAT
CTCGGAGCCGGAAGGGCAATCAGCCGACCGTCGACGAACGACACCGGCGATAACCACTTAGGCGTTGAAC
GGCCGGCCCAAACATTACGCCTCCGTTGATAAGGCTTTCGGTCTCTTCCCCGGTCATCCCAAGCACCTTG
CGGCAAATTTGAACGCTTTCCTGTCCGGGCACCGGCCCCGGGCTTTGGGGTCCNTCCGA Clone Rv172 (SEQ ID NO. 145)
::::::::::::Rv172SP6.seq::::::::::::
ATACTCAAGCTTCAATCGCGCCGCCACAATCCAAATATGCGTCTAGCGTCTCGATGAGCGTCGGTCCGGC
ATCGGCTAGGGGCCGCATCACGTCGGTATGCAGGGCCACGATCGCCCAAGGCGTCGCCCATCAAGGGCGC
GTTCGGGCAAAAATTCCCCTATCCAGCACGGGCCGCGGCGCTCCGCNCCAGCCGGCGACGGCGTTCATCC
CGGAGATCGCCTCGCTAGCGCTGCGGTGCGCCGCGGTCAGCATGGGCGCCGTGGGGCCGATGACCACCGG
GGCGT ::::::::::::Rv172T7.seq:::::::::::: (SEQ ID NO. 146)
TTCGGCGGGTCTGTAGATTGCGGTCGGCCACCCCACAGGCACTCATGAACCGCAGCCCACGATCGATCTC
GGTGG Clone Rv173 (SEQ ID NO. 147)
::::::::::::Rv173SP6.seq::::::::::::
GCGCACCATCGCCAGTAGGTGCCCGTGGTCGGGCGCGTCGAGCCACCCGAGCGGAAACGCGAGTCCGAAC
AGCAACAGCAGGACGGGCGCAACCAGGGCGGTGACCATGCCCCCGGCGCTGAACATCAACCACAGGAAGG
GCTCCGCCGAGCGTCCGCGCGACC ::::::::::::Rv173T7.seq:::::::::::: (SEQ ID NO. 148)
CATCGTCGAACTTCGGTCCGGGTTGNTAGNACCGCAGCACCAAACGCACCCACCGACCCCCACGCTTCAC
GCCAACCCTTTAGTTCATTGGCGTGAACAGCAGCGTAGCCGGTTGCCCCGATATATGTGGAAAAATCGTT
CGGACGTACAAAAAAAGTTCCTGACGCTGGCGTCAACTCGAAACTGCCTCGGAAGTCAATGATGATCCAT
CAGTCAATATTAAAGTCG Clone Rv174 (SEQ ID NO. 149)
::::::::::::Rv174SP6.seq::::::::::::
ATACTCAAGCTTGTCTGCTGCCTCAGCGTATGCATCCAACAGCGCATCGCGATCAACGATCAGGCGCGCC
GATTTCGGGCCGCGGGCAGTGGCACTGGCCAGATGGCCGTTTTTTTCGAGAAACTTCAACGCCTGAGCGC
TGCTTCCCATCGAGAGACCGGTGGCCTCTACAACCGATGCGACAGTTGGACCGGCGATGTTCGCCAGCAG
CGCTTCACATACGGCAAGTNTGGCGCGG ::::::::::::Rv174T7.seq:::::::::::: (SEQ ID NO. 150)
TTGTCCAGGCGGGGAATCGGGCAGGGAGACGACACCTTCGTTCGGTTCGATCGTCGCGAACGGGTAGTTG
GCCGCGACCACGTTGTTTCGGGTCAGCGCGTTGAAAAGTGTCGACTTGCCGACGTTGGGCAGGCCCACGA
TCCCCAGGCTCAAGCTCACAGA Clone Rv175 (SEQ ID NO. 151)
::::::::::::Rv175SP6.seq::::::::::::
ATACTCATGCTTGGCGCCTGGGTGGCAGCCCACCTGCCCACCACACGGACCGCGGTGCGGACGCGGCTGA
CGCGCCTGGTGGTCAGCATCGTGGCCGGTCTGCTGTTGTATGCCAACTTCCCGCCGCGCAACTGCTGGTG
GGCGGCGGTGGTTGCGCTCGCATTGCTGGCCTGGGTGCTGACCCNCCGCNCNACAACACCGGTGGGTGGG
CTGGGCTACGGCCTGCTATTCGGCCTGGTGTTCTACGTCTCGTTGTTGCCGTGGATCGGCGAGCTGGTGG
GCCCCGGGCCCTGGTTGGCACTGGCGACGACGTNCGCGCTGTTCCCCGGCATCTTCGGTCTGTTCGCCGT
CGTGGTACCCTGTTGCCGGGTTGGCCC ::::::::::::Rv175T7.seq:::::::::::: (SEQ ID NO. 152)
CGCCAATTCACGATATCGTTAACCGATATCCCGAGCCGATAGCTGGCGGGCTCGGGTGGTGGCCAGCGGC
GCTGCGACGAAAGGTGTGACCGTCATGAAACAGACACCACCGGCGGCCGTCGGCCGTCGTCACCTGCTCG
AGATCTCAGCATCCGCAGCCGGTGTGATCGCGCTTTCGGCGTGTAGTGGGTCGCCGCCCGACCCCGGCAA
AGGCCGGCCCGACACAACCCCGGAACAGGAAGTCCCGGTCACCGCGCCCGAAGNACTTGATGCGCGAACN TABLE 3-continued End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character << - >> denotes an uncertain base residue.

CGGAGTGCTCCAAACGCATCCTGCTGAT

Clone Rv176 (SEQ ID NO. 153)
::::::::::::Rv176SP6.seq::::::::::::
ATACTCAAGCTTGGGCACTGACTTCGGTACCCCCTCCGCCTTTGGCCAGCAGCAGCCACAGCGCGGTTCG
CGGACCGAACGTGGACATCAATAGCCCGGAATCGGTGTGTGCAAGTTGGTAAACGGTGTTGATCCCAAGC
TTTGCCAGCCTTTTCGTAGTCTTGGGCCCCACACCCCACAGTGCTTCGACGGTACGGTCACCCATGATGG
CCATCCAGTTGGCATCGGTGAGCTGATAAATGCCAGCTGGTTTCGCCAACCCGGTAGCGATCTTGGCGCG
CTGCTTGTTGTCACTGATACCTATCGAGCAAGACAGCCCGGTTTGCGACAAAATGACTTTTCGGATCTCT
TCGGCGACTTCGATGGGGTCGTCGGGA ::::::::::::Rv176T7.seq:::::::::::: (SEQ ID NO. 154)
AAAGTCCTGTGCCGGTTCGCTAAACACCCGGCGGACACTCAGACGGTGCTGGTGGTGCGGCATGGCACCG
CGGGCAGCAAAGCGCACTTCTCCGGGGGACGACAGCAAGCGACCGCTAGACAAGAGGGGTCGTGCGCAGG
CAGAAACGTTGGTACACAGCTGCTGGCGTTCGGCGCCACCGATGTTTATGCCGCCGACCGGGTGCGCTGC
CACCAGACGATGGAGCCACTCGCCGCGGAACTGAACGTGACCATACACA Clone Rv177 (SEQ ID NO. 155)
::::::::::::Rv177SP6.seq::::::::::::
ATACTCAAGCTTGGGTTCCACGCCCGCGCAGCCACGCCGTCACCTTTCCACGAGACCTCACCTGCCGATC
CGAAATGGAATCGGCCGTGACGGAATTGGCGCACCGAACACCCAACGAGGTGGTGGCTTCGTCGCGAACC
GTCACCCGAGTCGCGGCCACCGTGCGCACGGCGACGTTCTACACCCGCACCAAGATCCGAAAGCTGCAAG
CTCCCAGCACCGATCCCGACGTCATCACCGCTGCCGCCCGGCACGTCCTTGACCTATTCGAGCTGGATCG
GCCCGTCCGGTTGCTGGGAGTGCGGTTAGAACTGGCCTAGAACCGGCGGGCACACCGCNCCTGGGCGGGG
CGAATTCTTGACCGCNCCGGCC ::::::::::::Rv177T7.seq:::::::::::: (SEQ ID NO. 156)
CGCGGTTGGCGTAGTTGGACGGGTCGCCCTCCGAGGCCAATGATGACGATGACCACGCCGATCACGATGG
CCACCGAGAGGGACAACAACAGAAAGCTGACGAATCCCTCCTTGGCGGCCGGGGCTTTGTGGTCGCCGGT
CGCGATGGGCGCGAATTTACGGCCCGCTCCCCCAGGCCGCCGCGAAGCAGGGTCCCCAGCCAGTTGGCGT
AGGCGGAATTAACGATCAGCGCCACCGCGATAACCTGCCATGCCTCGGGCATATCGATGTGCGGCCAGAA
CAGGCCGAAC Clone Rv178 (SEQ ID NO. 157)
::::::::::::Rv178SP6.seq::::::::::::
CCAACAAGAGCATCGGGACATACGGAGTCAACTACCCGGCCAACGGTGATTTCTTGGCCGCCGCTGACGG
CGCGAACGACGCCAGCGACCACATTCAGCAGATGGCCAGCGCGTGCCGGGCCACGAGGTTGGTGCTCGGC
GGCTACTCCCAGGGTGCGGCCGTGATCGACATCGTCACCGCCGCACCACTGCCCGGCCTCGGGTTCACGC
AGCCGTTGCCGCCCGCAGCGGACGATCACATCGCCGCGATCGCCCTGTTCGGGAATCCCTCGGGCCGCGC
TGGCGGGCTGATGAGCGCCCTGACCCCTCAATTCGGGTCCAAGACCATCANCCTCTGCAACAACGGCGAC
CCGATTTGTTCNGACGGCAACCGGTGGCGAGCGCACCTAGGCTACGTGCCCGGGATGACCAACCAGGCGG
CGCGTTTCGTCGCGAGCAGGATCTAACCGCGAGCCGCCCATAGATTCCCG ::::::::::::Rv178T7.seq:::::::::::: (SEQ ID NO. 158)
TAANACCCGTGTAATTTGGGATGGGCAAAAAGGCCAAGCACCGCGTGGCCACGAACGCCGGGAGGGACAA
TCTCGGGCGGCTAGGGCTTCTCGCGGGAAGGCCCGAACGTACGGCGTTTCAACACGTCGCGTCNCCCTCC
GACCGCGAACATTCGGGGATGGCAGCAACCTGGTAGCNCCCTGGCCGGGCGATGATCTGCAGCGTCGCCG
CGGGTAGTCGCCGCCCGGGCGGCTACAGTCTGAAACGCGATGACCATCGATGTGTGGATGCAGCATCCGA
CGCAACGGTTCCTACACGGCGATATGTTCGCCTCGCTGCGCCGGTGGACCGGTGGGTCTATCCCGGAGAC
CGACNTCCCGATCGAAGCGACCGTCTCCTCGATGGACGCCGGCGGCGTCACCCTGGGTTTGCTCACCGCC
TGGCGTGGCCCCAA Clone Rv179 (SEQ ID NO. 159)
::::::::::::Rv179SP6.seq::::::::::::
GTCCGCAAAAGACTCAGCGGCCGACTTTGCTCGCAGCTGGCGGTACCGCGCCACCGATTCGATGCCGTGG
TCGCGGAAGAATGCCTCCCGAAATCGCACGGCCGACTCCAGTTCGGCGAGCATCCGCGATGCCAGCTGCG
GCTGCGCCCTGCCGGCCACGGCACCCACATGCGGCAGTTCGTCCACCTGGGCCAGCGCCCCGCCGCCGAA
GTCCAAACAATAGAACTGCACCCGGCCCGCATCGTGGGTAGCAGCCAACGCCATGATCAGCGTCCGCAGC
GCGGTTGACTTGCCCGTTTGCGGTGCACCTACGACCGCGACATTGCCTGCGGCCCCGGACAAGTCGATCG
TCAGCGGCACCCN ::::::::::::Rv179T7.seq:::::::::::: (SEQ ID NO. 160)
CGTGGCCACGAACGCCGGGAGGGACANTCTCGGGCGGCTAGGGCTTCTCGCGGGAAGGCCCGAACGTACG
GCGTTTCAACACGTCGCGTCGCCCTCCGACCGCGAACATTCGGGGATGGCAGCAACCTGGCAGCTACCTG
GCCGGGCGATGATCTGCAGCGTCGCCGCGGGTAGTCGCCGCCCGGGCGGCTACAGTCTGAAACGCGATGA
CCATCGATGTGTGGATGCATCATCCGACGCAACGGTTCCTACACGGCGATATGTTCNCCTCGCTGCGCCG
GTGGACCGGTGGGTCTATCCC Clone Rv17 (SEQ ID NO. 161)
::::::::::::Rv17SP6.seq::::::::::::
ATACTCAAGCTTTGCGGCGGGCGCCGAAATGTGAACGCACCAAACCCGCCCGCTGCGGGTCGGCGGGCCA TABLE 3-continued End sequences of the polynucleotide inserts cloned in the named recombinant
BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081
repetitive sequence (Insertion element)
The character << - >> denotes an uncertain base residue.

CTCGACCTCGAATTTCGCCGCCGTGACCATCCAGCCCGACGGCAGTTGGGCACCCGGCCCCCCGGTCGCG
GCATAACTGTTGGCGTCGCCGTCATAAAGCTCGAACAGCACCGAAACCGACTCCACCACCGGCCGGTGCG
CCTCAAAATCCACGCCGATCTCCACATACCGGGAAAACGTCGGTGTCCCATCGGGTTTCGGCTTGCCCGC
CAGCTGCACACCACCGGTGGCCTCGGCCACCTTCGCGGCCTGAGCGCAGCTACNCATCCTGACGATCATC
ACCCCGCCCCCGGCTCACGCTTGGCCTCCGTGACCGCACGCATCGCCCGGTTGCGCGCACCGCGACGCCC
GTACAGCCGCGCGCAC

::::::::::::::Rv17T7.seq:::::::::::::: (SEQ ID NO. 162)
AGCTTGCCGGGACTGCGGAACAGAAGCGGCGGTTCCTACCGCGGTGTGCGGCCGGCGCGATATCGGCCTT
TTTACTAACCGAACCCGATGTGGGCTCCGATCCGGCGCGCATGGCATCGACGGCGACGCCGATCGATGAC
GGCCAGGCTTACGAGCTTGAGGGTGTGAAGTTGTGGACCACCAACGGTGTGGTAGCGGACCTGCTAGTGG
TTATGGGCGCGGGTACCGCGCAGTGAAGGGCACCGAGGGGGAATCAGCGCCTTTGTCGTCGAGGCTGATT
CGCCCGGGATCACCGTGGAGCGGCGCAACAAGTTCATGGGACTGCGTGGCATCNAAAACGGCGTGACCCG
GCTTCATCGCGTCNGGGTGCCCAAAGACAACTTGATCGGCA Clone Rv180 (SEQ ID NO. 163)
:::::::::::::::Rv180SP6.seq:::::::::::::
CTCAAGCTTGGCGATGCGGGCTGGCCAAAACTGGCCGGGCGGGGGTTGGCTTGTTCAATCAAGGGTGGGT
TGCCG ::::::::::::::Rv180T7.seq:::::::::::::: (SEQ ID NO. 164)
CCGAAGGCCCGTTCCCGGGCGTTCAGCAAGCGATCGTCGGTTGGCCCACTGCGGGTCGAATCTTGCGGCC
GCGCCGGTCGTGGAACGCCCAGGTCACCCGGCGGCGTACC Clone Rv181 (SEQ ID NO. 165)
::::::::::::::Rv181SP6.seq::::::::::::::
ATACTCAAGCTTTTTTCTGCTCATGAAGGTTAGATGCCTGCTGCTTAAGTAATTCCTCTTTATCTGTAAA
GGCTTTTTGAAGTGCATCACCTGACCGGGCAAATAGTTCACCGGGGTGAGAAAAAAGAGCAACAACTGAT
TTAGGCAATTTGGCGGTGTTGATACAGCGGGTAATAATCTTACGTGAAATATTTTCCGCATCAGCCAGCG
CAGAAATATTTCCAGCAAATTCATTCTGCAATCGGCTTGCATAACGCTGACCACGTTCATAAGCACTTGT
TGGGCGATAATCGTTACCCAATCTGGATAATGCAGCCATCTGCTCATCATCCAGCTCGCCAACCAGAACA
CGATAATCACTTTCGGTAAGTGCAGCAGCTTTACGACGGCGACTCCCATCGGCAATTTCTATGACACCAG
ATACTCTTCGACCGAACGCCGGTGTCTGTTGACCA Clone Rv182 (SEQ ID NO. 166)
::::::::::::::Rv182SP6.seq::::::::::::::
CTCAAGCTTGGTGCCGACATGGCCGGGCTGGAGCCCGCGTATGGCAAGGTTCCGCTCAATGTGGTTGTGA
TGCAGCAGGACTACGTTCGCCTCAATCAGCTCAAACGTCACCCCCGTGGCGTGCTGCGCAGCATGAAGGT
CGGCGCCCGCACGATGTGGGCGAAGGCAACAGGTAAAAACCTGGTCGGCATGGGTCGAGCCCTCATTGGG
CCGTTGCGGATCGGGTTGCACCGCGCCGGAGTGCCGGTCGAACTCAACACCGCCTTCACCGATCTTTTCG
TCAAAAATGGCGTCGTGTCCGGGGTATAC ::::::::::::::Rv182T7.seq:::::::::::::: (SEQ ID NO. 167)
CCGAAGCGTGGGAAATCCTGACCGAATACCGCGACGTGCTGGACACTTTGGCCGGCGAGCTGCTGGAAAA
GGAGACCCTGCACCGACCCGAGCTGGAAAGCATCTTCGCTGACGTCTAAAAGCGGCCGCGGCTCACCATG
TTCGACGACTTCGGTGGCCGGATCCCGTCGGACAAACCGCCCATCAAGACACCCGGGGGAGATCGCGATC
GAAACGCGGCGAAACTTGGGCC ::::::::::::::Rv183SP6.seq:::::::::::::: (SEQ ID NO. 168)
CGACTCGACAAGCATTCTTGACAGTTGTTTTGGCTCGGCATGGTTAGCCAAGGTTCTGCGGTCCCACCAG
ATCATCTTGGTCCGGTAGCGCTCGTCCGGGTATGCTGCCGCCGGGATTCTCGCTGCTATTACTCCCCCCG
AAAAACGCCACCGGTCCAGCGCGTGGGCCGCCGCGGTCCCCATCACAAACTGAACCCCCAACAGGGGACA
TGCTTAGCGGTAGGGCGCGCGCCAAGGCGGCAGCAATCGCATCACTGCGCTGCGCGTCACTATTAACCCA
CCCGGACTTCACTTCCACGACCCCGAATGGCGCCCGGTCATTGATCATCTTGCGCACCGCGGATAATCCG
GGATTGCCAGCCCATTCGACTACCGCATGCGAGTCATCGGCTGACCGCAGCGGTCCGATTACCCGAGCGC
CCCGANTACATCTCCTCCAATATCAATGGGCGCAA Clone Rv183 (SEQ ID NO. 169)
::::::::::::::Rv183T7.seq::::::::::::::
GCGGTNTAGCTTCCCGTCGTACCGGCGACCGCCAGCCGAGAAGCTCGTTTTCCCAGTGTTGCTGGGGATT
CTCACGCTGCTGCTGAGTGCGTGCCAGACCGCTTCCGCTTCGGGTTACAACGAGCCGCGGGGCTACGATC
GTGCGACGCTGAAGTTGGTGTTCTCCATGGACTTGGGGATGTGCCTGAACCGGTTCACCTACGACTCCAA
GCTGGCGCCGTCTCGTCCGCAGGTCGTTGCTTGCGATAGCCGGGAGGCCCGGATCCGCAATGACGGATTC
CATGCCAACGCTCCGAGTTGCATGCGGATCGACTACGAATTGATCACCCAGAACCATCGGGCGTATTACT
GCCTGAAGTACCTGGTGCGGGTCGGATACTGCTATCCGGCGGTGACGACCCCCGGCAAGCCGCCATCCGT
GCTGCTGT Clone Rv184 (SEQ ID NO. 170)
::::::::::::::Rv184SP6.seq::::::::::::::
CTCAAGCTTGGGCGTGACGGCCACCGGGGCCACTCCGCACAATCTGTACCCGACCAAGATCTACACCATC
GAATACGACGGCGTCGCCGACTTTCCGCGGTACCCGCTCAACTTTGTGTCGACCCTCAACGCCATTGCCG TABLE 3-continued End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character << - >> denotes an uncertain base residue.

GCACCTACTACGTGCACTCCAACTACTTCATCCTGACGCCGGAACAAATTGACGCAGCGGTTCCGCTGAC
CAATACGGTCGGTCCCACGATGACCCAGTACTACATCATTCGCACGGAGAACCTGCCGCTGCTAAAGCCA
CTGCGATCGGTGCCGATCGTGGGGAACCCACTGGCGAACCTGGTTCAACCAAACTTGAAGGTGATTGTTA
ACCTGGGCTACGGCGACCCGGCCTATGGTTATTCC

::::::::::::Rv184T7.seq::::::::::: (SEQ ID NO. 171)
CGGGTGTCATTGGCCACCGGCGGCGGCTGTCCGGGAAATGGCGGGTCCCCGGTGGTTTTGCTGAGGAGTG
CTGAACCGTAGTCGAAGTGGGCGGCGTCAGACTCCACCCAGCCAGCAGGCAGCGCGAAGCTGAATCCTCC
AACCGGGTTGTCGATCCGGACAGGTTGGGGTGCGTTTGGGGCAATGACAGGTGGCGGCGGTGCGTTCGGG
TCGGCCGGCGGAGGTGCTGCGTTGGGATCGCCCGGCTGGGCATTCGGCGTGTTGGCGGCGGCCGGTGGTG
GGGGGGCAACANGTGTCGCCGGTGCGGGTGGCGCTGCA Clone Rv185 (SEQ ID NO. 172)
::::::::::::Rv185SP6.seq:::::::::::
NCTTGATATTGGCGTCAACGGTGTCGGCACCGGCGTCCTGCAGTTGGTAGGCCTGCAGTTTGTGCATCAG
GCCGATGCCGCGGCCCTCGTGGCCACGCATGTACAGCACCACGCCGCGCCCCTCACGGGCGACCATCGCC
AGCGCGGCGTCCAGCTGAGGCCCGCAATCGCAGCGGCGTGACCCAAACACATCGCCGGTCAAGCACTCCG
AATGCACCCGGACCAGCACGTCGTCACCGTCGGCGTTGGGCCCGGCGATCTCGCCGCGGACCAGCGCGAC
ATGTTCCACGTCCTCGTAGATGCTGGTGTAGCCGATGGCGCGAAACTCCCCATGACGAGTCGGAATCCGC
GCCTCGGCGACCCGCTCAATGTGCTTCTCGTGCTTGCGCCGCCATTCGATCAAGTCAGCAATGGTGATCA
GCGCCAGACCGTGCTCNTCGGCG ::::::::::::Rv185T7.seq::::::::::: (SEQ ID NO. 173)
CATAAGGGCCGGCGTACCCGGTACCGGCCGCGGGCCTACCACGTGCCGGAACTGGAAGCGCAGTAAGCCC
TCAACGCGCCACCGCTTTGGCCCGCGCGCCCGGCGTAGGCGCATCGGCGGTGGCCGTGGGGCGGCGCACT
GCGACCTCACCAGCGGCTTTCGAGCTTTGTTCGATCAACCGGCCAGCATGGTCGAGGATGCATTCGAGAC
CATATTCGAAATTGGTTTCATCGGGGGCCCCGATCCGATGCCCCCTCCCAGTTGCGTGAGCAAGCAGCGG
AGTCGTCGCGGGATCGATGGCCACGGGGTGTTCAATGGCGGATGGTCCGCTGCCCGCCGACTGGCTCTTG
CGGGAGAGCCGATCTAGCACCACCGATCCGCGCACGTGGACCGAAACCGCCGAGTAGATGTCGAAAGCGT Clone Rv186 (SEQ ID NO. 174)
::::::::::::Rv186SP6.seq:::::::::::
CGTCCTTTTCCCGAAGATAGAAAGGCAGGAGAGTGTCTTCTGCATGAATATGAAGATCTGGTACCCATCC
GTGATACATTGAGGCTGTTCCCTGGGGGTCGTTACCTTCCACNAGCAAAACACGTAGCCCCTTCAGAGCC
NNATCCTGAGCAANATGAACAGAAACTGAGGTTTTGTAAACGCCACCTTTATGGGCAGCAACCCCGATCA
CCGGTGGAAATACGTCTTCAGCACGTCGCAATCGCGTACCAAACACATCACGCATATGATTAATTTGTTC
AATTGTATAACCAACACGTTGCTCAACCCGTCCTCGAATTTCCATATCCGGGTGCG Clone Rv187 (SEQ ID NO. 175)
::::::::::::Rv187SP6.seq:::::::::::
CTCAAGCTTCATGTCCGTACGGCTCGGGTACGCTTCCGTCGCAGTGTGCGAGTGATAAATGACGACCGGG
ACCTCGTCGGCATCTTCCATAGCCCGCCACACCTTCAGTTGCTCACCGGAATCCAACCGGTAGAAGGTCG
GCGAGCGCTCGGCATTGGTCATCGGGATATGCCGCTCGGGACGGTCAGAGCCCTCGGGTCCGGCCAGCAC
TCCGCAGGCTTCGTCGGGGTGGTCGCGACACGCATGGGCCACCATCGCATTCAC ::::::::::::Rv187T7.seq::::::::::: (SEQ ID NO. 176)
NCGCCGCCAGCCACCACGCGCGGGTCGGGCGCCGGGCCCGGGCCGCCAGGCTGCTCCGCTCGGTGATGGC
ACGCCACCGCGACACCACCCGGCTGCGCTACGTCGAGCCATACCGGGCGGAGCTACATCGGCTCGGCCGC
CCAGTGTTCGGGCCCTCTTTCGAGGTCGAGGTCGATACCGATTTGCGCATCCGCAGCCGCACCCTGGACG
ACAGAACCGTGCCCTACGANTGCTTGTCGGGCGGGGCCAAAGAACAGCTTGGCATCCTGGCGCGATTGGC
CGGCGCGGCGCTGGTCTCCAAAGAAGACGCCCTTCCGGTGCTGAT Clone Rv188 (SEQ ID NO. 177)
::::::::::::Rv188SP6.seq:::::::::::
CGCCACGTTCATGGGCAACAACCCCGATCACCGGTGGAAATACGTCTTCAGCACGTCGCAATCGCGTACC
AAACACATCACGCATATGATTAATTCGTCCAATTGTATAACCAACACGTTGCTCAACCCGTCCTCGAATT
TCCATATCCGGGTGCGGTAGTCGCCCTGCTTTCTCGGCATCTCTGATAGCCTGAGAAGAAACCCCAACTA
AATCCGCTGCTTCNCCTATTCTCCAGCGCCGGG Clone Rv189 (SEQ ID NO. 178)
::::::::::::Rv18SP6.seq:::::::::::
ATACTCAAGCTTCAACCGATTGACGCATTGTGCGAACTGACGGCGCCCGCGCATGGCCAATCCGGAAGAC
CATCATTGGCCAGTGGCCGGGCGCTAACAGGTTCCAGCCCCCCACCAGTGCCGCTCGAACATGCGGTGCA
ACCCATTCGCAGGCCGGCAGGGAAAGCACCGCGGAAGCCGCAAAGGGCTGCAGTTCCGCGCCCAATAGTG
TCGTCCGCAACCAGATGCGCTCGAAAACCGCGCCGGCAGTCAGCGCACCCGACGCGAGGTCGAGAGACGT
CGTCAGCGCGCCCACATGGGGTGCCAATCGGCACGGCAGGTAGGCCGCGCGCAACCCGAACGCGTGGTGC
ATGCCCACGGTCCGCAGGAGGCGCAGCACCCGCCAATGCCGAAGCCCACGAAACATCGGGCGCATCCACG
CTTCAACCTC Clone Rv18 (SEQ ID NO. 179)
::::::::::::Rv18T7.seq:::::::::::

TABLE 3-continued

End sequences of the polynucleotide inserts cloned in the named recombinant BAC vectors contained in the I-1945 *M. tuberculosis* H37Rv genomic DNA library. RvXXXSP6 corresponds to the SP6 endsequence of the clone RvXXX; RvXXXT7 corresponds to the T7 endsequence of the clone RvXXX. RvXXXIS 1081 corresponds to a region located close to a copy of the IS1081 repetitive sequence (Insertion element) The character << - >> denotes an uncertain base residue.

AGCTTTTGGCAGGGTCTCCTTCGAATTCGGCGTGCACCGCTATGGGTTGCAGCAGCGGCTGGCGCCGCAC
ACCCCACTGGCCCGGGTGTTTTCGCCCCGAACCCGGATCATGGTGAGCGAAAAGGAGATTCGCCTGTTCG
ATGCTGGGATTCGCCACCGCGAGGCCATCGACCGATTACTCGCCACCGGGGTGCGAGAGGTGCCGCAGTC
CCGCTCCGTCGACGTCTCCGACGATCCATCCGGCTTCCGCCGTCGGGTGGCGGTAGCCGTCGATGAAATC
GCTGCCGGCCGCTACCACAAGGTGATTCTGTCCCGTTGTGTCGAAGTGCCTTTCGCGATCGACTTTCCGT
TGACCTACCGGCTGGGGCGTCGGCACAACACCCCGGTGAGGTCGTTTTTGTTGCAGTTGGGCGGAATCCG
TGCTCTGGGTTACAGCCCGAATCGTCAC

Clone Rv190 (SEQ ID NO. 180)
::::::::::::Rv190SP6.seq::::::::::::
ATACTCAAGCTTTGTCACACCAACTGTTTCCACCAGGCGCTCCATCCGGCGAGTGGATACTCCCAGCAGG
TAGCAGGTCGCCACCACGCTGGTCAGTGCGCGTTCAGCTCGCTTGCGGCGCTGCAGCAGCCAGTCCGGGA
AATAGCTGCCCTGGCGCAGCTTGGGGATCGCGACTTCTATGGTTGCGGCACGGGTGTCGAAATCACGGTG
GCGGTAGCCGTTGCGCTGATTGGACCGCTCATCGCTGCGTTCGCGGTAGCCCGCCCCGCACAGGGCGTCG
GCTTCAGCCCCCATCAAGGCGGCGATGAACGTCGAGAGCAGCCCGCGCAGCAGATCCGGGCTCGCCTGTG
CGAGTTGGTCAGCCAGAACCTGCTCGGTGT ::::::::::::Rv190T7.seq:::::::::::: (SEQ ID NO. 181)
CCTTAAGCCCCGCAGGGCCCGGCACGCGCGGTACCGCCCAGGTCGCCCAACAGATCGTCGATGTTCGCGT
CGTCCGCCTCGCGCACGTGGTCTGTCACCAGTCAACGTTAACGCCGCCGCACATGTCCTGCGGCCGGGCA
AAAACGTGAAAAACGAGCGGGCGACTGCAATGTCATGACACCGACGGCCGCCGATGGGCCCAGGGTCTGG
CAGATTCGATCTGTGCGGCCAGTGCCAGCAGCGTCGCCTCGTCATACGGCCGGCCGACGAGTTGAACCGA
CATGGGCAGGCCGTCGCCGTCGAAGTCCCACGGCACCACGGCCGCGGGCTGGCCGGTCAGATTCCAGACT
TGAAAGTACGGAACCCGCTGCACCACCAGCAGCAACGTCGAAACTGCACCCCGGCGTTGGTAGGCGCCGA
TGCGGGACGGGCCGGTCGCGGCGCCTGGCGTCACAACTACGTCGACATCGTCGAAGATCGACTGGATCGG
CTGCTCACACCACTCGGCGGCCGCAGGCCGCCATCCGCCGTC Clone Rv191 (SEQ ID NO. 182)
::::::::::::Rv191SP6.seq::::::::::::
AGCTTTTTGAGCGTCGCGCGGGGCAGCTTCGCCGGCAATTCTACTAGCGAGAAGTCTGGCGCGATACGGA
TCTGACCGAAGTCGCTGCGGTGCAGCCCACCCTCATTGGCGATGGCGCCGACGATGGCGCCTGGACCGAT
CTTGTGCCGCTTGCCGACGGCGACGCGGTGGGTGGTCAAGTCCGGTCTACGCTTGGGCCTTTGCGGACGG
TCCCGACGCTGGTCGCGGTTGCGCCGCGAAAGCGGCGGGTCGGGTGCCATCAGGAATGCCTCACCGCCGC
GGCACTGCACGGCCAGTGCCGCGGCGATGTCAGCCATCGGGACATCATGCTCGCGTTCATACTCCTCGAC
CAGTCGGCGGAACAGCTCGATTCCCGGACCGCCCAGCGCATTGGTGATGGAATCGGCGAACTTGGCCACC
CGCTGGGTGTTGACATCCTCGACGGTGGGCAATTGCCCCCGGTAACGTTTGCCGCCT ::::::::::::Rv191T7.seq:::::::::::: (SEQ ID NO. 183)
CGGTCCGACCCTGTTCGACGGCTACCTGAATCAACCCGATGCCACCGCCGCGGCGTTCGACGCCGACAGC
TGGTACCGCACCGGCGACGTCGCGGTGGTCGACGGCAGTGGGATGCACCGCATCGTGGGACGCGAGTCGG
TCGACTTGATCAAGTCGGGTGGATACCGGGTCGGCGCCGGTGAAATTGAAACGGTGCTGCTCGGGCATCC
GGACGTGGCGGAGGCGGCAGTCGTCGGGGTGCCCGACGATGATCTAGGCCAGCGGATCGTTGCCTACGTA
GTCGGCTCAGCGAATGTCGATGCGGACGGGCTTATCAACTTTGTTGCCCAACAACTTTCGGTGCACAAGC
GCCCGCGCGAGGTGCGTATCGTANATGCGCTGCCGCGCAACGCCTTGGGGAAAGTGCTCCAGAACATTGC
TGTCAGAAGCTGANCTACGCGAATTATCGTGTTACGCTGGA Clone Rv192 (SEQ ID NO. 184)
::::::::::::Rv192SP6.seq::::::::::::
ATACTCAAGCTTGCCGAAGTTCCGATGGGTCGCGCCGGCGAGCCCAGCGAAGTCGCTACCGTGGCCGTGT
TCTTGGCTTCGGATCTATCCTCGTTCATGACCGGCACCGTGTTGGACGTGACTGGCGGCCGGTCCATATG
ACACCGAGATCATTGCCACGGTACGGCAATTCGTCAAGAAGGAAATCTTTCCCAATGCACCGGCCCTCGA
ACGTGGCAACAGCTACCCGCAAGAAATCGTCGATCGGCTGGGTGTTATTGGCTTGCTCGGTCGCCGGCTG
CAAGGGTATCGACACCACCGAGTTCATTCTCGGGCGTGCCGGCGGATTCGAGCTGGCGGTGCGCGCTGCC
CAGCACCGTCATAGGTACTTGACGATGGTCCACGTCGGACGAGCGCCTCCACGTCGCTGCCGAACGGTAT
GCATGGCGGCTACGATTCTC ::::::::::::Rv192T7.seq:::::::::::: (SEQ ID NO. 185)
CGGTGTCGGCACCGGCGTCCTGCAGTTGGTAGGCCTGCAGTTTGTGCATCAGGCCGATGCCGCGGCCCTC
GTGGCCACGCATGTACAGCACCACGCCGCGCCCCTCACGGGCGACCATCGCCAGCGCGGCGTCCAGCTGA
GGCCCGCAATCGCAGCGGCGTGACCCAAACACATCGCCGGTCAAGCACTCCGAATGCACCCGGACCAGCA
CGTCGTCACCGTCGGCGTTGGGCCCGGCGATCTCGCCGCGGACCAGCGCGACATGTTCCACGTCCTCGTA
GATGCTGGTGTAGCCGATGGCGCGAAACTCCCCATGACGAGTCGGAATCCGCGCCTCGGCGACCCGCTCA
ATGTGCTTCTCGTGCTTGCGCCGCCATTCGATCAAGTCAGCAATGGTGATCAGCGCCAGACCGTGCTCAT
CGGCGAACACCGCAATTCATCGGTGTTGCGCCATCGAGCCCTCATCTTTTTGGCTGACGATCTCGCAAAT
CGCCCCCGCGGGTTGCAGCCGGCAT Clone Rv193 (SEQ ID NO. 186)
::::::::::::Rv193SP6.seq::::::::::::
ATACTCAAGCTTTGGGTGAAAGCCGATCACCGGAAGCCGCATGATCAGCCACGTTTCGCGCCGCCCGGCA
TACGGCGGCGTACCGATCTCCGCGTCATACACCCGCGGGTAATCGCCGACGGTGCCGGTTCGCGAGCCGA
AGGTGACGACGCTGATTGAATCGAGTTCCAGGTCCAGCGGGTGGCGCAGCAACGGCGCGAGCTCAACGAC TABLE 3-continued End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character << - >> denotes an uncertain base residue.

GTCAATCACGTTGTCGCTTTCTACGGTCACCGACCCGGTGACCGTNCTCGCCCGGTGCGCTCGGCCGATA
AGTTGCACCGCCACCACCGCGACACCGTCTTGCACGCGGACCCACCCCCGGATCCGTTGTTGGCC

::::::::::::Rv193T7.seq::::::::::: (SEQ ID NO. 187)
AGCTTGCTGGCATCCGCTCCAGTAGCGCCCCGCGCGTGGCTTCCAGCGCCCGCAGATGCTCCATGAGCCG
GCCGGTCGAGTCGGCGCCGGCGTTCACCGCCACCCGCCAGGAGCTGGCGGCCAGCATCTCCGCCTTCACG
CATTGCGCGATCACAGAGAGAATATACGTCTCATATTCGTTGGAGGTCGTCGCAGGCAATCGGTCGATGA
CGGATTTGATGGCATCGAGCTGTGCTTCGGCGTAGCCCTCCAGCACGTCGGTATCGCTGTGGCGGTCCAC
GACGACCGCACCGGCGCGGCGGACAGCCGTCGGGTTGGACGNTGTGCGGCGATCAGTCCGGCCAGCTCCG
CCTCGGGATCAGCGGC Clone Rv194 (SEQ ID NO. 188)
::::::::::::Rv194SP6.seq::::::::::::
ATACTCAAGCTTGCTGCAGCTTCCTATGACTGCTCCCGAAACCTGGGGGTGTGCCTGCTGTGTATGCACG
GCATACGGACATCCTTCCCCTGAGACCCGCGGTCGAACCAGCCACGTGTCCATCATCAGGGGTCAACCCC
GGCCAAGGGCGACGGCACGCCAAGTTCGCCGACCGTTAACCTAGTGCTGTTAGCTTCATTTGCTGCGAGC
AAAACAGCTGGTCGGCCGTTAGGAACTGAATTGAAACTCAACCGATTTGGTGCCGCCGTAGGTGTCCTGG
CTGCGGGTGCGCTGGTGTTGTCCGCGTGTGGTAACNACNACAATGTGACCGGGGGAGGTGCAACCACTGG
CCAGGCGTCGGCGAAGGTCGATTGCGGGGGGAAGAAGAACTCAAAGCCAGTGGGTCGACGCGCAGGCCAA
CGC ::::::::::::Rv194T7.seq::::::::::: (SEQ ID NO. 189)
AGCTTGACGCGGAGACGGACACATTGCGAACATTGATGACAAAATAGAAATCATTGATGGTTTGAGTCAC
CAGGCCGATCAAGCCTTCGCCGAGCCAAATTCCAATCAAGAGGCCCAAGCCCGTACCAATCAGCCCGGCA
ACGAGGGATTCCGTCATTATCAGCCAAAATAACTGCTCTCGGGTTACACCCAAACAGCGCAATATGGCGA
AAAACGGTCGCCGTTGCACGACATTAAATGTCACGGTATTGTAGATTAAAAAGATACCCACCAACAAGGC
AATCAAACTGAGAGCGGTTAAATTGACCGTAAAAGCGTCCGTCATCTGTTTGACGGTGTCCCGTTGGGTA
TCCGACGTTTCCATACGCACACCGGCCGGCAGTCTTTGTTGGATGCGTGTTGCAGTGGCCTCATCTTTGA
TGATCAAATCGATGTGGCTCAGTCTTCCGGGCA Clone Rv195 (SEQ ID NO. 190)
::::::::::::Rv195SP6.seq::::::::::::
ATACTCAAGCTTCGGCTCAGGCGGCGCTGCTGGTAAAGTCGCTGACCGGTGCAGGTTTCGACAATGTGGT
GCCGGTTCGGCGGCTACGTGCCATCGAGACACTGGCGCAGGCTATCGCACCCGTTATCGGCTACGAGCAA
ATCGCGGTATGCGTTCTTGAGCATGAGTCGGCGACCGTCGTCATGGTCGACACCCACGACGGAAAGACGC
AGATCGCCGTCAAGCATGTGTGCCGCGGATTATCAGGACTGACCTCCTGGCTGACCGGCATGTTTGGTCG
CGATGCCTGGCGCCCGGCCGGCGTGGTCGTGGTCCGCTCGGATAGCGAGGTCAGCGAATTCNCNTGGCAG
CTCCAAAGGGTCCTGCCGGTGCCGGTCTTTGCGCAAACNAAGGCNCAGGTTA ::::::::::::Rv195T7.seq:::::::::::: (SEQ ID NO. 191)
TGATCGCGCATCACCTGCTTCATAAACTGGAAGCAGCGCAGCGCTTCCTTTTCGGCCGCAACATGAGCCA
GCCTCTCGTCGGCGGTCGGGTGCAGGTGCTCGGGCAGCTCGGCCGCGACAGCCGCCTGACCCTGAAACCA
GCTTCCATATCCCGCGACGAACGACGCCAGTCCGCTACGTAACCCCTCCGCGACTGTCCATGGACAACAG
CGCGTTCTCCACCGACCGGGCCCGGGTGTGGGGTGTTTCGGCGACCGGCAGCCAGGTGGTCCACACTGCC
GACGGGCGCCGCGAGCCGTTCACCGACCAGGCCGCCGAGCAAGTCCGCCCGATCGCATACTCCAACCGGT
TGCGGTACTGCAGGTTCAGCTGGCGTACTCCTCGTCGCGCTCGGCGAGGTCTTGCTCCAGCACGTCGCAN
ACGGCAG Clone Rv196 (SEQ ID NO. 192)
::::::::::::Rv196SP6.seq::::::::::::
CAAAGCGCGAACTGCTCGCGGCAGCCCACGACGTGCTGCGTCGGATTGCCGGCGGCGAAATCAATTCCAG
GCAGCTCCCGGACAATGCGGCTCTGCTGGCCCGCAACGAAGGACTCGAGGTCACCCCGGTGCCCGGGGTC
GTGGTGCACCTGCCGATCGCACAGGTTGGCCCACAACCGGCCGCTTGATGCCCGGTCGGCAAGCCCGGCA
GTTGCCAAACCCAGCGTGATCAGGCTCGGCTCGCGAGTTCCGGGAAGAAGTGGCTCCGCCTGATCACCTA
CCATCCGCCAGGATCTGCGTGTCTTCACCACGCCCGCCAAGGAGGTTGTTGTGGTGCTATCGACCGN ::::::::::::Rv196T7.seq:::::::::::: (SEQ ID NO. 193)
CCGGAAGCCGCATGATCAGCCAAGTTTCGCGCCGCCCGGCATACGGCGGCGTACCGATCTCCGCGTCATA
CACCCGCGGGTAATCGCCGACGGTGCCGGTTCGCGAGCCGAAGGTGACGACGCTGATTGAATCGAGTTCC
AGGTCCAGCGGGTGGCGCAGCAACGGCGCGAGCTCAACGACGTCAATCACGTTGTCGCTTTCTACGGTCA
CCGACCCGGTGACCGTNGTCGCCCGGTGCGCTCGGCCGAAAANTTGCACCGCCACCACCGCGAAACCGTC
TTGCACNCCGGAAGCCACCCCCGATCCGTTGTTGGGCCAGGTTATTGGGT Clone Rv19 (SEQ ID NO. 194)
::::::::::::Rv19SP6.seq::::::::::::
CCGGAACCGCCGACGGCACGGTATAACGCCTCCGCATATGGGTCGACAACCAGCGGGTCGGACTTCTGGG
CTTCTAGCGTTCGCGCNGTCGCGACAAACAGCGCGGTCGAACCGACACTCGTTGTGATGTCCTAGCTATC
ACGTTCGGTACGCACCCAATCGAGTCTAGCGCGGGTAGNTCAGCCCCGATCTCCANGCTCCGCCGAGCCA
GGCGC ::::::::::::Rv19T7.seq::::::::::: (SEQ ID NO. 195)

TABLE 3-continued

End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character << - >> denotes an uncertain base residue.

CTGGTTTATGTCCCGTTCAAGTTCCATCACCCGATGTGGCGGGAGCACTGCCAGGTCGATCTCAACTACC
ACATCCGGCCGTGGCGGTTGCGCGCCCCGGGGGGTCGGCGCGAACTCGACGAGGCGGTCGGAGAAATCGC
CAGCACCCCGCTGAACCGCGACCACCCGCTGTGGGAGATGTACTTCGTTGAGGGGCTTGCCAACCACCGG
ATCGCGGTGGTTGCC

Clone Rv1 (SEQ ID NO. 196)
:::::::::::::Rv1SP6D2.seq:::::::::::::
CCGAGCAGTTGGGAATCGCTCTGCANCAAACCAATATTCTGCGCGACGTCGCGCGACGAGCTGGACCGAT
TAGGCGTACGCCTCCGNCTGGACGACACCGGGGCAC TCGATGACCCCGACGCCTACGCTCGCAGGATAT
TGTTCGCCGGACCCCTCTCTAG :::::::::::::Rv1T7.seq::::::::::::: (SEQ ID NO. 197)
TATATAATACTCAAGCTTGCCGACGCCAACGCTCGCGCGATGTTGTTAGCCCGACCCGGCTCTTACATGG
CACCGGTGCCCCACACGTCAGCCTGTGACGTCCTGCACCGCGACTCTTTACATAGAATGTGGATTGCCGG
ATTGGGGATGTCCGGCATCGCTCAATCTGTAGTCCGCGTTGTCCCGCGAGGGCCATGTGGATGGGGGGAA
GGATCCGTGGCGTCCGGGATCACCATGGGG Clone Rv201 (SEQ ID NO. 198)
:::::::::::::Rv201SP6.seq:::::::::::::
ATACTCAAGCTTGCCGAAGTTCCGATGGGTCGCGCCGGCGAGCCCAACGAAATCGCTAGCGTGGCCGTGT
TCTTGGCTTCGGATCTATCCTCGTACATGACCGGCACCGTGTTGGACGTGACTGGCGGCCGGTTCATATG
ACACCGAGATCATTGCCACGGTACGGAAATTCGTCCAGAAGGAAATCTTTCCCAATGCACCGGCCCTCGA
ACGTGGCAACAGCTACCCGCAAGAAATCGTCAATCGGCTGGGTGTTATTGGCTTGCTCGGTCGCCGGCTG
CGAGGGTTTCTACACCACCGAGTTCATTCTCGGGCGTGCCGGCGCATTCGAACTGGCGGTGCGCGCTG :::::::::::::Rv201T7.seq::::::::::::: (SEQ ID NO. 199)
GCACCGGCGTCCTGCAGTTGGTAGGCCTGCAGTTTGTGCATCAGGCCGATGCCGCGGCCCTCGTGGCCAC
GCATGTACAGCACCACGCCGCGCCCCTCACGGGCGACCATCGCCAGCGCGGCGTCCAGCTGAGGCCCGCA
ATCGCAGCGGCGTGACCCAAACACATCGCCGGTCAAGCACTCCGAATGCACCCGGACCAGCACGTCTTCA
CCGTCGGCGTTGGGCCCGGCGATCTCGCCGCGGACCAACGCGACATGTTCCACGTCCTCGTAGATGCTGG
TGTAGCCGATGGCGCGAAACTCCCCANGACAAGTCGGAATCCGCGCCTCGGCGAACCGCTCAATGTGCCT
CTCGTGCTTGCGCCGCCATTC Clone Rv204 (SEQ ID NO. 200)
:::::::::::::Rv204SP6.seq:::::::::::::
TGGTCCGTGTGCGCATACCAATACAACGCGCCGGGCACCTGACGCGGCGGCCGCAACCAATCGGTGGCCA
TCGCCATCTTCTGCTACCCGGTCAACGGACGCACCTTCTCCTGGCCGACGTAGTGCGCCCACCCGCCGCC
GTTGCGTCCCATCGATCCGGTCAAC Clone Rv205 (SEQ ID NO. 201)
:::::::::::::Rv205SP6.seq:::::::::::::
GGCGTGTTGGCCACCGGGGCCACTCCGCACAATCTGTACCCGACCAAGATCTACACCATCGAATACGACG
GCGTCGCCGACTTTCCGCGGTACCCGCTCAACTTTGTGTCGACCCTCAACGCCATTGCCGGCACCTACTA
CGTGCACTCCAACTACTTCATCCTGACGCCGGAACAAATTGACGCAGCGGTTCCGCTGACCAATACGGTC
GGTCCCACGATGACCCAGTACTACATCATTCGCACGGAGAACCTGCCGCTGCTAAAGCCACTGGCGATCG
GTGCCGATCGTGGGGAACCCACTGGCGAACCTGGTTCAACCAAACTTGAAGGTGATTGTTTACCTGGGCT
ACGGCGACCCGGCCTATGGTTATTCGACCTCCCCGCCCAA :::::::::::::Rv205T7.seq::::::::::::: (SEQ ID NO. 202)
CGTCCGTGNCCCCTCAANCGCGTGNNGCCGAAGCGGCTGGTTACGACTCCCTGTTTGTGATGGACACTTC
TACCAACTGCCCATGTTGGGGACGCCCGACCAGCCGATGCTGGAGGCCTACACGGCCCTTGGTGCGCTGG
CCACGGCGACCGANCGGCTGCAACTGGGCGCGTTGGTGACCGGCAATACCTACCGCAGCCCGACCCTGCT
GGCAAAGATCATCACCACGCTCGACGTGGTTAGCGCCGGTCGAGCGATCCTCGGCATTGGAGCCGGTTGG
TTTGAGCTGGAAACACCGCCAGCTCGGCTTCGAGTTCGGCACTTTCAGTGACCGGTTCAACCGGCTCGAA
GAGGCGCTACAGATCCTCCAGCCAATGGTCAAGGGTGAGCGCCCAACGTTTTTCGGCGATTGGTACACCA
CCGAATC Clone Rv207 (SEQ ID NO. 203)
:::::::::::::Rv207SP6.seq:::::::::::::
CCGCTTCCGTGTAACCGAGCANNGCGAGCGANCTGGCGAGGAAGCAAAGAAGAACTGTTCTGTCAGATAG
CTCTTACGCTCAGCGCAAGAAGAAATATCCACCGTGGGAAAAACTCCAGGTAGAGGTACACACGCGGATA
GCCAATTCAGAGTAATAAACTGTGATAATCAACCCTCATCAATGATGACGAACTATCCCCCGATATCAGG
TCACATGACGAAGGGAAAGAGAAGGAAATCAACTGTGACAAACTGCCCTCAAATTTGGCTTCCTTAAAAA
TTACAGTTCAAAAAGTATGAGAAAATCCATGCAGGCTGAAGGAAACAGCAAAACTGTGACAAATTACCCT
CAGTAGGTCAGAACAAATGTGACGAACCNCCCTCAAATCTGTGACAGATAACCCTCAGACTATCCTGTCG
TCATGGAAGTGATATCGCGGAAGGAAAATACGATNTGAGTCGTCTGGCGGCCTTTCTTTTTCTCAATGTA
TGAGAGCG Clone Rv209 (SEQ ID NO. 204)
:::::::::::::Rv209SP6.seq:::::::::::::
TGACACCCAACAGAGGGCACTTAAGATGGCAATGCGGCCGCCTACCTGCACGTTTTCGCGATGTCAGAGG TABLE 3-continued End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character << - >> denotes an uncertain base residue.

ATGCCGAGGGAGAACAATGCGAGCACGGCCGCTGACNTTGCTCACCGCTTTGGCGGCGGTGACATTGGTG
GTGGTTGCGGGCTGCNAGGCCCGANTCNAGGCCGAAGCATATAGCGCGGCCGACCGCATTTCGTCTCGAC
CGCAAGCGCGACCTCAGCCGCAGCCGGTGGAGCTACTGCTGCGCGCCATCACGCC

::::::::::::Rv209T7.seq:::::::::::: (SEQ ID NO. 205)
ACGGGCGACGCTGAGGTGGGCCCGCGGCTATTCATGCTGTCGTCCACGTCCAGCGACGCACTGCGCCAGA
CGGCCCGCCAACTAGCCACCTGGGTGGAAGAACACCAGGACTGCGTGGCGGCCTCGGATCTGGCCTACAC
GCTGGCGCGTGGCCGCGCGCACCGGCCGGTGCGCACCGCGGTGGTTGCCGCCAACCTGCCGGAGCTCGTC
GAGGGTTTGCGCGAGGTGGCCGACGGTGACCCCTCTATGACGCGGCGGTGGGACACTGTGATCTAAGACC
GGTCTGGGTCTTCTCCGGGCAAGGGTCTCAGTGGGCGGCGATGGGCACCCAATTGCTCGCCAGCGAACCA
GTGTTCGCGGCCACCATCG Clone Rv20 (SEQ ID NO. 206)
::::::::::::Rv20SP6.seq::::::::::::
ATACTCAAGCTTCGCGAGATCCGGATGGCACTCACGCTGGACAAGACCTTCACAAAATCTGAAATCCTGA
CCCGATACTTGAACCTGGTCTCGTTCGGCAATAACTCGTTCGGCGTGCAGGACGCGGCGCAAACGTACTT
CGGCATCAACGCGTCCGACCTGAATTGGCAGCAAGCGGCGCTGCTGGCCGGCATGGTGCAATCGACCAGC
ACGCTCAACCCGTACACCAACCCCGACGGCGCGCTGGCCCGGCGGAACGTGGTCCTCGACACCATGATCN
AAAACTTCCCGGGGAGGCGGAGGCGTTGCGTGCCGCCCAGGGCGAACCGCTGGGGGTTCTGCCGCAGCCC
AATGATTGCCGCGCGGCTGCATCGCGGGCGGCGACCGCCATTCTTCTGCGAATACGTCCAGGAGTACTGT
CTCGGGGC ::::::::::::Rv20T7.seq:::::::::::: (SEQ ID NO. 207)
AGCTTATGTGGCCGCCCACCTACCTTATCTAGCCTAGCTAACTAAATCCAGTGCCGACAGTGCGCGGCTG
GCCACCCAGCATGAGGTTATGACCACGGCATATGCCAGCGCGCTGGCGGCGATGCCGACGCTGACCGAGT
TGGCCGCTAATCACACCAGCCATGCGGTGTTGCTGGGAACGAATTTCTTTGGAATCAATACGATCCCGAT
CGCGCTCAATGAGGCCGACTATGCGCGGATGTGGATTCAGGCGGCCACCACGATGAGTATCTATGAGGGC
ACCTCCGATGCGGCGCTGGCGTCNGCACCGCAAACCACACCGGCTCCGGTACTGTTCAACGGCGGTGCTG
GCGTTTGCCAGCGCCTGCCGGCGATCTC Clone Rv214 (SEQ ID NO. 208)
::::::::::::Rv214SP6.seq::::::::::::
ATACTCAAGCTTGCCACCCATGCCGAGCAAGGTCGACTCAGCGATGACGAATTGTTCTTCTTCGCGGTGT
TGCTGCTGGTTGCGGGCTATGAGAGCACTGCTCATATGATTAGCACNTTGTTTCTGACGCTGGCCGACTA
TCCAGATCAGCTGACACTCCTTGCGCAGCAACCAGACCTGATCCCGTCGGCGATCGAGGAGCACCTCCGC
TTTATATCGCAATCCAAAACATCTGCCGCACAACGCGCGTCGACTATTCGGTCGGTCAAGCGGTCATCCC
GGGA ::::::::::::Rv214T7.seq:::::::::::: (SEQ ID NO. 209)
CCGGGGTAGAACGATGCGATCTGGGCCATGTCGACATCGGTGGTACAGGTAAACCGCGCCGTGTGCGCGG
TCTCGGAGATCAGAACGTGGTCGCAGTTGACACCGCGGGCTTTCAGCCAGTCGCGATAATCGGCGAAGTC
GGCGCCTGCCGCCCCAACTAGCGCGACCTCGCCACCTAGCACACCGATGGCGAAGGCCATGTTTCCGGCC
ACGCCGCCGCGGTGCATCATCAACTC Clone Rv215 (SEQ ID NO. 210)
::::::::::::Rv215SP6.seq::::::::::::
ATACTCAAGCTTGGCGGCAACGCCACTACCGGGCTCACCAGGTCCTGTGCCGCCACCGCCGGCGCCGAAA
GCACCATCAGGTCGTAGTTGTCTGGACGTTCGACACCGTAAGCGAACACAATGCCGCCGCCCATGCTGTG
CCCGAGCACGATGCGCTTGCACCCGGGATATTCCCGGGTGGCGATCCCAACGAGGGTGTCGAAGTCAGCG
GTGTATCTGAGATGTCTCTCACTATCATCCGTTTGGCACCCGAGCGGGCATGCCCGCGGGGGGTCAAC ::::::::::::Rv215T7.seq:::::::::::: (SEQ ID NO. 211)
GTCGACGGCATCAAGGTCCGCAGTGATGGTGTTCATCTCACCCAGGAAGGCGTGAAGTGGCTGATACCGT
GGCTTGAGGATTCGGTGCGGCTCGCCAGTTAATCCGCCGTGTGCTCCGGATGAGCGCGACGGTAACCCTG
GAATTGTGCTGTGTGCTGGCTGTGTCGTTGTGATGAGCCTGTCTAAGTGGTGCGTAACCGTTTGACGAGC
CGCGGCCTCGCTGCAAACATTGAAGCCCGCACGTCTGGGTTTGTATTTACACAACGAGGGCGCTCCCCGA
TCTGGCGCGCGCAACGAGGTGCNCACTATCCATTCGAGGTGAACTGGACTCCTTGATGCTCATGCCGGTG
CGGTTTTGTC Clone Rv217 (SEQ ID NO. 212)
::::::::::::Rv217SP6.seq::::::::::::
ATACTCAAGCTTGCGTTCGATGAAGTAGTCGTCGGTCAGCGCCGCCTCTTCGAGCTCCTTGGCGATGCCC
AGCAAGGAGTCATCGCCGCCGAGCTTGGCCAGGATCTTGTCGGCCTGTTCCTTGACGATGCGGGCCCGCG
GATCGTAGTTCTTGTAGACACGATGACCGAAACCCATCAATTTGACCCCGGCCTCGCGGTTCTTGACCTT
GCGTTACAAACTCGCTGACGTCGTCGCCGCTGTCGCGAATGCCCTC ::::::::::::Rv217T7.seq:::::::::::: (SEQ ID NO. 213)
NGTCAAGCCGAGCATGCGCGAGGNAACGACGAACCCAACAAGCCATGGTGGTTGGCGCCGTCGAGAGGTC
GGCGGTCGCCACAACGGGAAGATCGCCTTGAGCGTCGCTCGACCGCCGCCTCGAGTTGGGTCATAACGAA
GTAGCTGATGCCGATCATGTCGACGTTTCCGTCGCATCAGCGTGCAGCGGCGACCCACTCGACGAGGTCT
CGGTGCCGCCGCGGCCAGGGCACCAGCAGTGACGATTCCAGGCGCCGTCGGG TABLE 3-continued End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character << - >> denotes an uncertain base residue.

Clone Rv218 (SEQ ID NO. 214)
:::::::::::::Rv218SP6.seq:::::::::::::
CGATAATCGCTTCCGGTAAGTGCAGCAGCTTTACGACGGCGACTCCCATCGGCAATTTCTATGACACCAG
ATACTCTTCGACCGAACGCCGGTGTCTGTTGACCAGTCAGTAGAAAAGAAGGGATGAGATCTCCCCGTGC
GTCCTCAGTAAGCAGCTCCTGGTCGCGTTCATTACCTGACCATACCCGAGAGGTCTTCTCAACACTATCA
CCCCGGAGCACTTCTAGAGTAAACTTCCCATCCCGACCACATATAGGCTAAGGTAATGGGCATTACCGCG
AGCCATTACTCCTACGCGCGCAATTAACGAATCCACCATCGGGGCCGCTGGTGTCN Clone Rv219 (SEQ ID NO. 215)
:::::::::::::Rv219SP6.seq:::::::::::::
NAATACTCAAGCTTTCTCGTGATTACCACCCGTGTAATTTGGGATGGGCAAAAAGGCGAATCACCGCGTG
GCCACAAACGCCGGGAGGGACAATCTCGGGCGGCTAGGGCTTCTCGCGGGAAGGCCCGAACGTACGGCGT
TTCAACACGTCGCGTCGCCCTCCGACCGCGAACATTCGGGGATGGCAGCAACCTGGTATCACCCTGGCCG
GGCAATGATCTGCAGCGTCGCCGCGGGTAGTGNCCGCCCGGGCGGCTAC :::::::::::::Rv219T7.seq::::::::::::: (SEQ ID NO. 216)
CCAACTAGAGCATCGGGACATACGGAGTCAACTACCCGGCCAACGGTGATTTCTTGGCCGCCGCTGACGG
CGCGAACGACGCCAGCGACCACATTCAGCAGATGGCCAGCGCGTGCCGGGCCACGATGTTGGTGCTCGGC
GGCTACTCCCAGGGTGCGGCCGTGATCGACATCGTCACCGCCGCACCACTGCCCGGTCTCGGGTTCACGC
AGCCGTTGCCGCCCGCAGCGGACGATCACATCGCCGCGATCGCCCTGTTCGGGAATCCCTCGGGGCCGCG
CTGGCGGGCTGATGATCGCCCTGACCCCTCAATTCGGGTCCAAGA Clone Rv21 (SEQ ID NO. 217)
:::::::::::::Rv21SP6.seq:::::::::::::
ATACTCAAGCTTGCTGCAGCTTCCTGTGACTGCTCCCGAAACCTGGGGGTGTGCCTGCTGTGTATGCACG
GCATACGGACATCCTTCCCCTGAGACCCGCGGTCGAACCAGCCACGTGTCCATCATCAGGGGTCAACCCC
GGCCAAGGGCGACGGCACGCCAAGTTCGCCGACCGTTAACCTAGTGCTGTTAGCTTCATTTGCTGCGAGC
AAAACAGCTGGTCGGCCGTTAGGAACTGAATTGAAACTCAACCGATTTGGTGCCGCCCGTAAGTGTCCTG
GCTGCCGGTGCGCTGGTGTT :::::::::::::Rv21T7.seq::::::::::::: (SEQ ID NO. 218)
AGCTTGCGCGGCGTGGCGATCGCGGTTCAAGGCGCGCTCTTCGAGCACAACGAGCGAAGACAGCTCGGCG
ACGGAGCCTTTATCGACATCCGTTCGGGCTGGCTGACCGGCGGCGAAGAACTGCTGGACGCGTTGTTGTC
GACGGTGCCGTGGCGAGCCGAGCGCCGTCAGATGTACGACCGGGTGGTCGATGTGCCGCGGCTGGTGAGT
TTTCACGACCTGACCATCGAAGATCCGCCGCATCCGCAGCTGGCGCGGATGCGCC Clone Rv220 (SEQ ID NO. 219)
:::::::::::::Rv220SP6.seq:::::::::::::
AATACTCAAGCTTGCGCACGACCAGGACGTCGAGTGGCGCTTGCAGTGACTTGGCGACCTCAAAGGCCAC
CGGTACCCCGCCGCGCGGCAAGCCAAGGACNACNACGGCCTTGCCGGATAGCTGCGCCAGGCGTTGCGCC
AACTGGCGTCCAGCGTCGCCACGATCGTCAAAGAGCTTCATCTGCCGAGTGTGTCGCCATCTCATGGCTC
CAAATATGGAATTAGGTCCCTGGGCCGACTGACGACAGTCCCTCAGCGACCGGATTGCGCATCCCGCCTT
GTACGCTGCTCCGCAAATCCCGGGCTTGCGTCCGCGGAAGCGAACTCGGCGGCGCTACGGTGGTGGCTCA
CTTCGGCCGTGC :::::::::::::Rv220T7.seq::::::::::::: (SEQ ID NO. 220)
GGTTGGTGCGGTCCACCTTCGCGGCGGCGGCGCGATATGCCTTGCTGGTCTTGCTCATTTGATATCCAAT
CTATGGGTCGTGGTTACTCAGCGGGCCGAAGCTGGCCCTCCCACGGGTAGGGCCCTATTCGACGGTGATG
CCCATCGACCGAGCGGTACCGGCGATGATCTTGGCCGCAGCGTCGACGTCGTTGGCGTTGAGGTCCGTCT
TCTTGGTCTCGGCGATTTCGCGGACTTGATCCCAGGTGACTTTGGCGACCTTGGTCTTGTGCGGCTCCGC
CGAACCCTTCGCCACACCAGCGGCCTTAAGCAGCAGCTTGGCGGCGGGCGGCGTCTTCAGCGTGAAAGTG
AAGCTACGGTCTTCATAAACGGTGATCTCCACCGGGATGACGTTGCCGCGCTGGTTCTCCGTCGCGGCGT
TGTACGCCTTGCAGAACTCCATGATGTTGACCCGTGCTGACCGAACGCGGGGCCCACTGGCGGGGC Clone Rv221 (SEQ ID NO. 221)
:::::::::::::Rv221SP6.seq:::::::::::::
ATACTCAAGCTTTTCGACCCGCAAGCCGGCGGTGCCCCTCCTCGTTCCGCTGCCCGGTCTGCTCGATCGG
TTCGGGGTCGCCGCGCTAGGCCCAATTGCCCGGCTCCTCCTCGGGCCGTTCCACAACCCGCATCGTCGCC
GGGCTAGGTTCAAGCCATGCCGGTAAACCCCAGGACGCCAGTGCTGATCGGCTATGGACAGGTCAACCAC
CGAGGCGACATCGACGCCNAAAATCAGTCCATCGAACCCGTCGACCTGATGGCCNCCGCGGCCCGGAAAG
CCGCCGAGTCCACCGTGCTCGAAGCGGTGGATTCCATCCGTGTGGTGCACATGCTGTCGGCGCATTACCG
GAATTCCCGGGCGTCTCCTCGGC :::::::::::::Rv221T7.seq::::::::::::: (SEQ ID NO. 222)
NCCTGGTTCATGAACTGGAAGCAGCGCAGCGCTTCCTTTTCGGCCGCAACATGAGCCAGCCTCTCGTCGG
CGGTCGGGTGCAGGTGCTCGGGCAGCTCGGCCGCGACAGCCGCCTGACCCTGAAACCAGCTTCCATATCC
CGCGACGAACGACGCCAGTCCGCTACGTAACCCCTCCGCGACTGTCCATGGACAACAGCGCGTTCTCCAC
CGACCGGGGCCGGGTGTTGGGGTGTTCGGCAACGGCAACCAAGTTGGTCCACACTGCCGACGGGCGCCGC
AAATCCGTTCACCGAACCAGGCCGCCNAAACAATTCCGCCCGATCCCATAT TABLE 3-continued End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character << - >> denotes an uncertain base residue.

Clone Rv222 (SEQ ID NO. 223)
:::::::::::::Rv222SP6.seq::::::::::::
ATACTCAAGCTTGTCGGGATCAATCTCGAGGGCATCCACGCACGAAAAGTAAACTCTATCAAGCTTTTTG
ACGACACCCACGGACGCCCCATATATGTTCGGGTGGGCAAGAACGGTCCCTACCTGGAACGTTTGGTGGC
CGGCGACACCGGTGAGCCCACGCCGCAGCGGGCCAACCTCAGCGACTCGATTACCCCGGACGAACTGACT
CTACAGGTGGCCGGAAGAGCTCTTTGCCACACCGCAACAGGGACGGACTTTGGGCTTGGACCCAGAAACC
GGCCACGAAATCTTTGCCAGGGGAAGGCCGGTTTGGGCCTTATGTTACCTATATCCTGCCGGAACCTGCG
GCTGATGCGGCCGCGGCCGCTCAGGGAN :::::::::::::Rv222T7.seq:::::::::::: (SEQ ID NO. 224)
AGCAGCTAGCCGCGCTCGCCGCGCTGGTCGGTGCGTGCATGCTCGCAGCCGGATGCACCAACGTGGTCGA
CGGGACCGCCGTGGCTGCCGACAAATCCGGACCACTGCATCAGGATCCGATACCGGTTTCAGCGCTTGAA
GGGCTGCTTCTCGACTTGAGCCAGATCAATGCCGCGCTGGGTGCGACATCGATGAAGGTGTGGTTCAACG
CCAAGGCAATGTGGGACTGGAGCAAGAGCGTGGCCGACAAGAATTGCCTGGGCTATCGACGGTCCAGCAC
AGGAAAAGGTCTATGCCGGCACCGGGTGGACCGCTATGCGCGGCCAACGGCTGGATGACAGCATCGATGA
CTCCAAGAAACGCGACCACTACGCCATTCAAGCGGTCGTCGGCTTCCCGACCGCACATGATGCCGAAGAA
TTCTACAGCTCCTCCG Clone Rv223 (SEQ ID NO. 225)
:::::::::::::Rv223IS1081N1400.seq::::::::::::
CGCGACTGGCTCCCCGGNCGGCTGCTCGGGTCCGCCGATAGAGACCGGGATGTCGCCCGACGACGGGCAG
CCGGGTTGCGTGGGACGGGGCGGGGGTCGGGCAGCCCAAGCAACGGGCTAGTCCCCGAATCCTACGGAGC
CGTCACCTACGCCTACGTAATAGTAGCTATCAATAACAGTTGACATACGCAACGATCTGTGAGATCAATA
TTGCCTGACGCATGTCAAGACAGGCGTCAAGACAGGTGTCAATAATTCGCTCCGCTGGTGACGGTAACCG
GTCGTGCGGGTGTGTGACGCCTAAGGAAGGAGTGTGGGTGGTGACGCTGAGAGTGGTTCCTGAGGGTTTG
GCGGCCGCCAGTGCGGCGGTGGAGGCGTTGACCGCACGGCTGGCCGCCGCACACGCTGGCGCGGCGCCGG
CGATTACGGCGGTGGTGGCGCCCGCGGCGGATCCGGTGTCGTTGCAGAATGCGGTGGGGTTTAGCGCCTT
AAGTAGCCAGCATGCCGCGATCGCCGGCGAAAGGGTCCAAGAACTGGGT :::::::::::::Rv223SP6.seq:::::::::::: (SEQ ID NO. 226)
ATACTCAAGCTTATTGAACCGCGGGTCGCAGGCAAAGTGGACCTCATAACGACTCGGGTCCAGCGACCGC
GCCAACACGAACGGCCGGACGACGTGGGCCAGGGTCGCGGCCTCCCCTACAAACAGGATCCGTTGCCTGC
GAACGACAGGCTCCGGTGCGGCGTTGGGCGCCGTGCTCGTCCCAGCGTCCGGTCCCGGGTCGCCGGCGAC
GCTTGTTTCCTCCATACTCGCCCCCTAATCTCGAGGCAGCCCGTACCCGCAGGCAACCTCCCAAAAATGC
AATCCCGCAAAATGCAATGCGTCNAGCTATTTCTCACACCGACCGCTAGTTGCGGATCAGAAATCCGTTG
GGCGCGGAAGTCCAGCCGAATTTGTTCTCCCGCTCCGCATCATGCTTGTAATCGTTTGGAAATTCATCCT
CATATGCCTCGATCGCTTCATAGGGTCCAGGCCCAAACCCGGGCAGGACTGGGTGGCCGTTGATGTTGGA
ATCCTCCACTACTAGGTATTCACCGGC :::::::::::::Rv223T7.seq:::::::::::: (SEQ ID NO. 227)
GTCTCGATCATGGCCAAAGAGCTCGACGAAGCCGTAGAGGCGTTTCGGACCCGCCCGCTCGATGCCGGCC
CGTATACCTTCCTCGCCGCCGACGCCCTGGTGCTCAAGGTGCGCGAGGCAGGCCGCGTCGTCGGGGTGCA
CACCTTGATCGCCACCGGCGTCAACGCCGAGGGCTACCGAGAGATCCTGGGCATCCAGGTCACCTCCGCC
GAGGACGGGGCCGGCTGGCTGGCGTTCTTCCGCGACCTGGTCGCCCGCGGCCTGTCCGGGGTCGCGCTGG
TCACCGGCGACGCCCACGCCGGCCTGGTGGCCGCGATCGGCGCCACCCTGCCCGCAGCGGCCTGGCAGCG
CTGCAGAACCCACTACGCAGCCAATCTGATGGCAGCCACCCCGAAGCCCTCCTGGCCGTGGGTGCGCACC
CTGCTGCACTCCATCTACGACCAGCCCGACGCCGAATCAGTTGTTGCCAATATGATCGGGTTCTCGAC Clone Rv224 (SEQ ID NO. 228)
:::::::::::::Rv224SP6.seq::::::::::::
ATACTCAAGCTTTCGTCAGTTCATGGCGCCAGCAGACCAACAAGAGCATCGGCACATACGGAGTCAACTA
CCCGGCCAACGGTGATTTCTTGGCCGCCGCTGACGGCGCGAACGACGCCAGCGACCACATTCAGCAAATG
GCCAGCGCGTGCCGGGCCACGAGGTTGGTGCTCGGCGGCTACTCCCAGGCTGCGGCCGTGATCAAGATCT
TCACCGCCGCACCACTGCCCGGCCTCGGGTTCACGCATCCGTTTGGCCGCCGCC :::::::::::::Rv224T7.seq:::::::::::: (SEQ ID NO. 229)
GCCCCGTGTAATTTGGGATGGGCAAAAAGCGAAGCACCGCGTGGCCACGAACGCCGGGAGGGACAATCTC
GGGCGGCTAGGGCTTCTCGCGGGAAGGCCCGAACGTACGGCGTTTCAACACGTCGCGTCGCCCTCCGACC
GCGAACATTCGGGGATGGCAGCAACCTGGTAGCACCCTGGCCGGGCGATGATCTGCAGCGTCGCCGCGGC
TAGTCTCCGCCCGGGCCGC Clone Rv225 (SEQ ID NO. 230)
:::::::::::::Rv225SP6.seq::::::::::::
ATACTCAAGCTTCCTTTGACCGAACGCGTCCACCGCACCGTGAGATTGGTGGCGCCATTCGTCGTGGTGT
AGCTGCTGTTGGCGGCGTCGCCGTATTGTGCGGGCCAGCCTTGTGCGGGGGCCGCTTCTACCCACAAGTC
GGCACTTCCGCAACCGCCCAGCTCGACCGCGAATTACGGCGGCCGCAACGGCCGCCGGAAGGCGTCACGC
AATCGCTTATCCTTTCCAGGTTCCCAAATCCTCCGCTTACTTGGGTCCTTCATCGG :::::::::::::Rv225T7.seq:::::::::::: (SEQ ID NO. 231)
GGCAGCGGCGACAACCGGAACGTCCGCACGGTGCTCAATCACGGGTGCACGGTGTGCATCAGAATGGCGG
GGGTTCGTTGTCGCGGTGAGGCGTTCGGCGAGGAGGTAGTGTCTACCCCTTGCCCGCGGGTTCGTGCGGA TABLE 3-continued End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character << - >> denotes an uncertain base residue.

CTGAAAGGGATTTCATTGGGAACCCACGGCTGCGTATCGCAGGGCCTCGGTGACGTCTGCTTCCTCNAGC
TCAGGAAGTTCGGCGAGAATCTCGGTGGATGTTATTTGGTCCGCCTAC

Clone Rv226 (SEQ ID NO. 232)
:::::::::::::Rv226SP6.seq:::::::::::::
ATACTCAAGCTTTCTCGGCTTCTCTGATAGCCTGAGAAGAAACCCCAAGTTAATCCGCTGCTTCACCTAT
TCTCCAGCGCCGGGTTATTTTCCTCGCTTCCGGGCTGTCATCATTAAACTGTGCAATGGCGATAGCCTTC
GTCATTTCATGACCAGCGTTTATGCACTGGTTAAGTGTTTCCATGAGTTTCATTCTGAACATCCTTTATT
CATTGTTTTGCGTT Clone Rv227 (SEQ ID NO. 233)
:::::::::::::Rv227SP6.seq:::::::::::::
ATACTCAAGCCTGGTGACCGGCACCGCGATACGTTGCGGCAGGCATCTGGGCTGGCGGTGGTTCGCCGCT
CCGAAGCCGTCGAACACCATCGCCAGCGCGGCTTCCACATCAACGACCATTTCGGCCAGCTTGCGGCGCA
TCAGCGGCTTGTCGATGAGCGCCCCACCGAATGCCCGCCGCTGCCCGGCGTATCACATCGATTCGACCAT
CGCGCGGCGCGCGTTGCCGAGGGCGAACGAGGCGGTGCCCAACCGCAATCTGTTTGGTCAGCTCCCTCAT
GCGGGTTGATTCCTTGCCGTCCGGACGGGCCCGCGTCATGCGCTCGGTTCGCC :::::::::::::Rv227T7.seq::::::::::::: (SEQ ID NO. 234)
CCGTTGCGCAGCGTGAGCCGATAGTTGACATCCGGCTCGGTGAAGGTGAAATCGATGGCCAGGTCGAGGT
CCCATGCGCGTGGGCCATTGATGCTGATCGCCAGGACGTCAAAGATTTGGTCCGGCGTCAGCTGGGCGAA
AAACGTGGGCGCCGGGACTTGCCCGGAGCTGCCCGGGTTCCCGTCGCGCAGCTCGGCGGCCCCGGTCAGA
AAGAAATTGCGCCAGGTCGCACACTCCGCGCCGTAGGCCAGCTGCTCCAGGGTGTCGGCATAGAGCCCGC
GGGCCGCAGCGTGCTCGCTGTCGGCGAACACCGCATGGTCGAGAAGCGTTGCCGCCCAACGGGAAATCAC
CTGCGTCGAAAGCTTCGCGGGCCAGCTCCAGCACTCGGTCGATGCCACCCAACGCGT Clone Rv228 (SEQ ID NO. 235)
:::::::::::::Rv228SP6.seq:::::::::::::
ATACTCAAGCTTGCGGATGTTACCCCTGACAGCGTGAACTATGTCNAAACACACGGCACCGGAACGGTGT
TGGGGGACCCCATCGAGTTCGAGTCGCTGGCGGCCACTTATGGCCTGGGTAAAGGCCAGGGCGAGAGCCC
GTGCGCATTGGGGTCGGTCAAAACCAACATCGGCCACCTGGAGGCGGCCGCCGGTGTGGCTGGATTCATC
AAGGCGGTGCTGGCGGTGCAACGTGGGCACATTCCCCGCAACTTGCACTTCACCCGGTGGAACCCGGCCA
TCAACACGTCGGCGACGCGGCTGTTCGTGCCGACCGAAAGCGCCCCGTGGCCGGCGGCTGCCGGTCCACG
CAGGGCTGCGGTGTCATCGTTCGGCCTCAGCGGGACCAA :::::::::::::Rv228T7.seq::::::::::::: (SEQ ID NO. 236)
CCGGTAACCAGATCAGCTCGTCGACCTCACTGCCGGGGGTGAATTCCCCACCGGTGCTGCGCGCTGCCCA
GTAGTGCACCTTCTTGACGCCTCGAAAAGGGGAGTCGGTCGGGTAGGTCACCGTCAGGAGCCGCCTACCC
AGGTTGGCGCGGTGACCGGTCTCCTCGAGTATCTCCCGCACCGCCCCCACCGGTGCGGTCTCGCCCGGAT
CCACTTTGCCCTTGGGCAGCGACCAGTCGTCGTAACGGGGGCGGTGAATGACAGCGATCTCGACCGGCCC
TTCCGAATCGGCACTGCCGGGTCGCCAGAACACCGCACCGGCGGCGTACACAATCCGGCCCGCCGAGCGC
CGGCGGGCGGACGANTTCTGGATCGACACCTCAACTCCTGCAGGTCAATTCGGCCAAGCTGCTCGCGGTC
GTGGATGTGGTC Clone Rv229 (SEQ ID NO. 237)
:::::::::::::Rv229SP6.seq:::::::::::::
ATACTCAAGCTTGATGCCGCCGAAACCGAGCGTGAGCACGCCGCCACCCACCACGCGCGGGTCGGGCGCC
GGGCCCGGGCCGCCAGGCTGCTCCGCTCGGTGATGGCACGCCACCGCGACACCACCCGGCTGCGCTACGT
CGAGCCATACCGGGCGGAGCTACATCGGCTCGGCCGCCCAGTGTTCGGGCCCCTCTTTCGAGGTCGAGGTC
TATACCGATTTGCGCATCCGCAGCCGCACCCTGGTCGTCTCGTACCGTGCCCTACCTCTGCTTGTCGGGC
GGGGCCA :::::::::::::Rv229T7.seq::::::::::::: (SEQ ID NO. 238)
TCCGTACGGCCCGGGTACGCTTCGGTCGCAGTGTGCGAGTGATAGATGACGACCGGGACCTCGTCGGCAT
CTTCCATAGCCCGCCACACCTTCAGTTGCTCACCGGAATCCAACCGGTAGAAGGTCGGCGAGCGCTCGGC
ATTGGTCATCGGGATATGCCGCTCGGGACGGTCAGAGCCCTCGGGTCCGGCCAGCACTCCGCAGGCTTCG
TCGGGGTGGTCGCGACGCGCATGGGCCACCATCCATCCACCAGGTCTGCGCGAATCACCCGC Clone Rv22 (SEQ ID NO. 239)
:::::::::::::Rv22SP6.seq:::::::::::::
GGACACATTGCGAACATTGATGACAAAATAGAAATCATTGATGGTTTGAGTCACCAGGCCGATCAAGCCT
TCGCCGAGCCAAATTCCAATCAAGAGGCCCAAGCCCGTACCAATCAGCCCGGCAACGAGGGATTCCGTCA
TTATCAGCCAAAATAACTGCTCTCGGGTTACACCCAAACAGCGCAATATGGCGAAAAACGGTCGCCGTTG
CACGACATTAAATGTCACGGTATTGTAAATTAAAAAGATACCCACCAACAAGGCAATCAAACTGAGAGCG
GTTAAATTGACCGTAAAAGCGTCCGTCATCTGTTTGACGGTGTCCCGTTGGGTNTCCGACGTTTCCATAC
GCACACCGGCCGGCAGTCTTTGTTGGATGCGTGTTGCAGTGGCCTCATCTTTGATGATCA :::::::::::::Rv22T7.seq::::::::::::: (SEQ ID NO. 240)
GCCTGGCCCAGGTGAAGGCCGACCTCGACGCCAAAGCCGCTGATCCGGCACATGAGTCGGTGGACTGGGA
CTTGAAGTCGCTGCGATGGGCGTGGAACCGAGCCAAAGATGACGTGGCGCCGTGGTGGGCCGAGAATTCC
AAGGAGTGCTACTCGTCGGGGTTGGCCGATCTGGCCCAGGGCCTGGCTAATTGGAAAGCTGGCAAGAACG TABLE 3-continued End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character << - >> denotes an uncertain base residue.

GGACCCGCAAAGGCCGGCGGGTGGGCTTCCCGCGATTCAAATCCGGGCGGCGTGATCCTGGCAGGGTGCG
GTTCACCACCGGCACCATGCGCATAGAGGATGACCGGCGCACGATCACGGTCCCGGTGATCGGGCCGCTG
CGGGCCAAGGAGAACACCCGCCGGGTGCAACGCCACCTCGTGAGCGGGCGCGCGCAGATCCTGAACATGA
CCTTGTCGCAGCGGTGGGG

Clone Rv230 (SEQ ID NO. 241)
::::::::::::Rv230SP6.seq::::::::::::
TAACTCAAGCTTCAAGTCCGCNGTCCGACCCTGTTCGACGGCTACCTGAATCAACCCGATGCCCCGCCGC
GGCGTTCGACCCGACAGCTGGTACCGCACCGGCGACGTCGCGGTGGTCGACGGCAGTGGGATGCACCGCA
TCGTGGGACGCGAGTCGGTCGACTTGATCAAGTCGGGTGGATACCGGGTCGGCGCCGGTGAAATTGAAAC
GGTGCTGCTCGGGCATCCGGACGTGGCGGANGCGGCAGTCGTCGGGGTGCTCGACTATTATCTAGGCCAG
CGGATCGTTGCCTACGTAGTCGGCTCAGCGAATGTCGATGCGGACGGGCTTATCAACTTTGTTGCCCAAC
AACTTT ::::::::::::Rv230T7.seq:::::::::::: (SEQ ID NO. 242)
CCATGTCGCCCAACATATCGTCGATGTTCGCGTCGTCCGCCTCGCGCACGTGGTCTGTCACCAGTCAACG
TTAACGCCGCCGCACATGTCCTGCGGCCGGGCAAAAACGTGAAAAACGAGCGGGCGACTGCAATGTCATG
ACACCGACGCCGCCGATGGGCCCAGGGTCTGGCAGATTCGATCTGTGCGGCCAGTGCCAGCAGCGTCGCC
TCGTCATACGGCCGGCCGACGAGTTGAACCGACATGGGCATGCCGTCGCCGTCGAAGTCCCACGGCACCA
CGGCCGCGGGCTGGCCGGTCAGATTCCANACTTGAAAGTACTGAAGCCGCTGCACCACCAG Clone Rv231 (SEQ ID NO. 243)
::::::::::::Rv231SP6.seq::::::::::::
CGAAAGCGTGAAACAGCTCGCGGCAGCCCCCGACGTGCTGCGTCGGATAGCCGGCGGGCGAAGATCAATT
CCAGGGAGCTCCCGGACAATGCGGCTCTGCTGGCCCGCAACGAAGGACTCGAGGTCACCCCGGTGCCCGG
GGTCGTGGTGCACCTGCCGATCGCACAGGTTGGCCCACAACCGGCCGCTTGATGCCCGGTCGGCAAGCCC
GGCAGTTGCCAAACCCAGCGTGATCNTGCTCNGCTCTNTANTTCGGCGAAGAAGTGGCTCGCCTGATCAC
CTACCATCGGCCAGGATCTGCGTGTCATCACAACGCTC GCCAAGGAGGTTGTTGTG ::::::::::::Rv231T7.seq:::::::::::: (SEQ ID NO. 244)
TCCGCCACGCTTCGCGCCGCCCGGCATACGGCGCGTACCGATCTCCGCGTCATACACCGCGGGTAATCGC
CGACGGTGCCGGTTCGCGAGCCGAAGGTGACGACGCTGATTGAATCGAGTTCCAGGTCCAGCGGGTGGCG
CAGCAACGGCGCGAGCTCAACGACGTCAATCACGTTGTCGCTTTCTACGGTCACCGACCCGGTGACCGTA
GTCGCCCGGTGCGCTCGGCCGAGAAGCTGCACCGCCACCACCGCGACACCGTCTTGCACGCGGACCCACC
CCGGATCGGTTGTTGGCCAAGGTAATTGGGTCATTCCATTTGACGGGACGCCGACCC Clone Rv232 (SEQ ID NO. 245)
::::::::::::Rv232SP6.seq::::::::::::
CATTCTTTAACAGTTGTTTTGGGCTCGGCATGGTTAGCCAACGTTCTGCGGTCCACCATATCATCTTGGT
CCGGTAGCGCTCGTCCGGGGTATGCTGCCGCCGGGATTCTCGCTGCTATTACTCCCCCCGAAGAACCGCC
ACCGGTCCAGCGCGTGGGCCGNCGCGGTCCCATCACAAACTGAACCCCCAACAGGGACATGCTTATCGGT
AGGGCGCGCGCCAAGGCGGCAGCCATCGCATCACTGCGCTCTGCGCGTCACTATTAACCCACCCGGACTT
CACTTCCACCACCCCGAATGGCGCCCGGTCATTGATCATCTGGCGCACCGCGGATAA ::::::::::::Rv232T7.seq:::::::::::: (SEQ ID NO. 246)
CGGTGTCCTGCAGTTGGTAGGCCTGCAGTTTGTGCATCATGCCGATGCCGCGGCCTCGTGGCCACGCATG
TACAGCACCACGCCGCGCCCCTCACGGGCGAACATCGCCAGCGCGGCGTCCAGCTGAAGCCCGCAATCGC
AGCGGCGTGACCAAACACATCGCCGGTCAAGCACTCCGAATGCACCGGACCAGCACGTCGTCACCGTCGG
CGTTGGGCCCGGCGATCTCGCCGCGGACCATGCGCGACATGTTCCACGTCCTCGTANATGCTGGTGTAGC
CGATGGCGCGAAACTCCCCATGACGAGTCGGAATCCGCGCCTCGGCGACCCGCTCAATGTGCT Clone Rv233 (SEQ ID NO. 247)
::::::::::::Rv233SP6.seq::::::::::::
CGGCATCTGGCGGCTGAACCTGTTCTTGGGCAACATGCCGAGGATCGCCTCTTCCACCACGCGGTCGGGG
TGGCGTTGCATTACCTCACCGATGGTGCGCTTGTGCAGGCCGCCGGGATACCCCGAGTGCCGGTAAACCA
TCTTGTGCTGCAGTTTGTCGCCGCTGATGGCGACCTTGTCGGCGTTGATCACGATNACNAATCACCGCCA
NCGACATTGGGGGCGAACGTCGGCTCGTGCTTGCCGCGCAGCAGGCTGGCCGCCGCGACGCAAGGCGCCA
ACCACCACGTCCGTGGCGTCGATGACGTACCACCATCGCGTGGTGTCACCCGCCTTGGGC ::::::::::::Rv233T7.seq:::::::::::: (SEQ ID NO. 248)
GCGGCAAAAATTGAAGCACTCNTGGCCACTNCCGCCGGGAGGGACAATCTCGGGCGGCTAGGGCTTCTCG
CGGGAAGGCCCGAACGTACTGCGTTTCAACACGTCGCGTCGCCCTCCGACCGCGAACATTCTGGGATGGC
AGCAACCTGTTAGCACCCTGGCCGGGCGATGATCTGCAGCGTCGCCGCGGGTAGTCGCCCCCGGGCGGCT
ACAGTCTGAAACGCGATGACCATCGATGTGTGGACGCCGCATCCGACNCAACGGTTCCTACACTGTGATA
TGTTCGCCTCGCTGCGCCGGTGGACGGTGGGTCTATCCCGGA Clone Rv234 (SEQ ID NO. 249)
::::::::::::Rv234SP6.seq::::::::::::
CGCGTTGAACTGAAGGGGTGCCGCCCGGCTCGAGCAGGCAAGCCATTTGTTCGATGCGGTTACCGAAGAT
CTCTTCGGTGACTGCCCGCCGCCGGCCAGCTCGGCTCAGTGTCCGGCGTTGGTCGCCGCGGCGACAATCT
TGGCGTCCACGGTGGTCGGGGTCATGCCCGCGAGCAGGATTGGCGAGCGGNCGGTCAGCCGGGTGAACTT TABLE 3-continued End sequences of the polynucleotide inserts cloned in the named recombinant BAC vectors contained in the I-1945 *M. tuberculosis* H37Rv genomic DNA library. RvXXXSP6 corresponds to the SP6 endsequence of the clone RvXXX; RvXXXT7 corresponds to the T7 endsequence of the clone RvXXX. RvXXXIS 1081 corresponds to a region located close to a copy of the IS1081 repetitive sequence (Insertion element) The character << - >> denotes an uncertain base residue.

CGTCAAGAGCTGACGCTGCGGTTGGGGAGGCGAATCATGGTCGGTGCGTAGCCTCGACTAGGCCCGGG

:::::::::::::Rv234T7.seq::::::::::::: (SEQ ID NO. 250)
TGACAACGCGGCGGCGATTACCCCGCTACCGCAGCAGCATGACGCGGTAGCGAACACCGCCGGATGCAGC
GCAGGTGCGTCGATGTGCTCACGGAATCGCCCCGGCACCGCGATCTCGAGGATCACCAGTGCCACCCCCT
GCAGCGCGAGACCGACGATTCCGTACACCGCCACGCCGATCAGGCCCTGGGCCAGCTGATTGGAGCTGGC
GTATATGGCGGCGATGGTGACGATGGTCATCGCCTCTTACATTGTGGCGGCCAGAACCACGGCGTTGGGG
CGGCGGTCGATGAACACTAGGCGACCANATCCCCGGGGTCAACAGGTTGACCATCC Clone Rv235 (SEQ ID NO. 251)
:::::::::::::Rv235SP6.seq:::::::::::::
CGCGGACATCCCGAACGAGGACACGCGACCGCTTCGGTGTGTGATCTATCAGGGCTCGCACCACGCGCAA
CCGCTTCCGGCTACCTAGACGCGGT :::::::::::::Rv235T7::::::::::::: (SEQ ID NO. 252)
GCATGCGGGTGATGCCGTTCTCAGTGCGCAACAGCGTTCGACGCGGCATACCCAGCCGCACATGCCGTGC
ACGCCGGNGCCGGGGCGGGAATCT Clone Rv237 (SEQ ID NO. 253)
:::::::::::::Rv237SP6.seq:::::::::::::
CTCAAGCTTCAGNCCNTCTAAGCGGTCTGCGCGGCGATCGCAAAGATCGCCCTTTGCCGGCGTTGGGGGC
TTCTGCTCGGGGGTGTTGTACACCTTCTCGAACACCTCGGCACCGACACCACCACCGTCGGCTTGAACAC
CGCCAACATCGGCAGCANATCTTGATGTCCTGGTGAATCCACGGTGACTTTGGAGTGGAAGGCGGCCATA
CTGATCGCGCGCGCCACCACATGAGCTAGCGGCAGGAAAACCAGCAGCCGCTCACCCTTGCGCAGCAGCG
TCGGGTGATATGCCTGGCGCCC :::::::::::::Rv237T7.seq::::::::::::: (SEQ ID NO. 254)
AGTCGAANGTCAGTCCGGTCTCCTCTCCGACTACGGCCAAGAACTGGGGCGACGGTGTCAGTGCAGAACA
GCGGAAACTGGTGGCGCCCTAGGCGAGCGAACGCTCACAAACGGCGGTGACCGCTTCTGGTCGTGCACCA
TCGAGCCGTGCCCAGCCCGGCCGCGTGCCGTCAGCCGCATCCACTGGATGCCCTTCTCGGCGGTTTCAAT
CANGTACAGGCGACGTTCGCCACCATCGTGCCGGGGCACGGTTAGCGAGAAACGCCGACTTCACCGATTG
CCTCGGTGATGxxxxx Clone Rv23 (SEQ ID NO. 255)
::::::::::::::Rv23T7.seq:::::::::::::
AGCTTCGCGGCGTGGCGATCGCGGTTCAAGGCGCGCTCTTCGAGCACAACGAGCGAAGACAGCTCGGCGA
CGGAGCCTTTATCGACATCCGTTCGGGCTGGCTGACCGGCGGCGAAGAACTGCTGGACGCGTTGTTGTCG
ACGGTGCCGTGGCGAGCCGAGCGCCGTCAGATGTNCGACCGGGTGGTCGATGTGCCGCGGCTGGTGAGTT
TTCACGACCTGACCATCGAAGATCCGCCGCATCCGCAGCTGGCGCGGATGCGCCGGCGGCTCAACGACAT
CTACGGCGGCGAACTGGGTGAGCCCTTCACCACCGCCGGGCTGTGCTACTACCGCGACGGCTCTGACAGC
GTCGCCTGGCATGGCGACACCATTGGTCGCGGCAGCACTGAGGACACTATGGTGGCGATCGTCAGCCTCG
GCGCCACCCGCGTCTTCGCGCTGCGGCCGCGTGG Clone Rv240 (SEQ ID NO. 256)
:::::::::::::Rv240SP6.seq:::::::::::::
AGCTTCAGCTGATACTCGACCAGCCCCACTCGGGCCAATACGTGAATGTCTAGCATCTTCACCCGTTCAC
GGGCTANTCGAGTAGTAGACATTGATTAGCCTGAACGTACCTCCGACGCCAGCTGACGAACGGGTATGAC
GGATGGATTTCGTGGTGTCGCGCCCGAGGTCAATTCGTTACGGATGTATCTCGGGGCCGGATCGGGGCCG
ATGTTGGCGGCCGCGGCGGCCTGGGACGGACTATCCGACGAACTGGCGGTGGCGGCGTCGTGGTTTGGGT
CGGTGACCTCGGGCCTGGCGGATGCGGCGTGGCGCGGCCCGCGGCGGTTGCGATGGCNCGCGCGGT :::::::::::::Rv240T7.seq::::::::::::: (SEQ ID NO. 257)
CTGGTCATGGACGTTGCTCCGGTAGTGGCTCACTGCCGATCCTCCTCGTTGAGAGTGCCACCTCAGGGTT
GGGTAGGGTTGGGTACTCGAAACCAAGTTACCCACCAGTAACACCGTCAAAATATATCCGTTGCATAGGT
CAATGCAAGTTGATGTGAGCTACATTGCACCAACTAACTAACCAACCGGTTGGGTTAGCGGTGATCCTGG
CCGTGTCGGTCCTCTCACCTGCGGTGATAGCGATCAAATGAAGAATATGCGGAGTCTAGGGCGGCAGCGC
CTGGCANCGTAGATCATCGGCTCACGCGGATGCGGCCTCTTGGTACGGACATGCGCGCG Clone Rv241 (SEQ ID NO. 258)
:::::::::::::Rv241SP6.seq:::::::::::::
CTCGTGAGTAGCACCCCTGTAATTTGGGATCGGCAAAAAGGCGAATCACCGCGTGGCCACGACACGCCGG
GAGGGACNATCTCGGGCGGCTAGGGCTTCTCGCGGGAAGGCCCGAACGTACGGCGTTTCAACACGTCGCG
TCGCCCTCCGACCGCGAACATTCGGGGATGGCAGCAACCTGG :::::::::::::Rv241T7.seq::::::::::::: (SEQ ID NO. 259)
GGATCAACTACCGGCCAACGGTGATTCTTGGGCGCCGCTGACGCGCGAACGACCCAGCGACACATTCAGC
AGATGGCCAGCGCGTGCCGGGCCACGATGTTGGTGCTCGGCGGCTACTCCCATGGTGCGGCNCGTGATCG
ACATCGTCACCGCCGCACCACTGCCGGCCTCGGGTTCACGCAGCCGTTGCCGCCCGCAGCGGACGATCAC
ATC Clone Rv243 (SEQ ID NO. 260)

TABLE 3-continued

End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character << - >> denotes an uncertain base residue.

::::::::::::Rv243SP6.seq::::::::::::
AGGACCGTCAGCACGGCGACGTGCTACTCGCCGAGCAGTGGGAATCGCTCTGCAGCAAACCATTACTCTG
CGCGACGTTCGAGATGACCTTCTGAATGGACGGATCTACCTGCCGCGCGACGACCTGGACCGCGTATGCG
TCCGCCTCCGCCTGGACGACACCGGGGCACTCTATGACCCCGACGGACGGCTCGCGGTACTGCTGCGGTT
CACCGCCGACGCCCGCACGGTACGCGTCGGGACTGCGCTGAGTCCANCCTCGACGCCGTAGCGCTGCTGC
TGTGCGGCCATGTCTGGCATCTACCGCCGTCGCTCCCTTGA ::::::::::::Rv243T7.seq:::::::::::: (SEQ ID NO. 261)
CGACTCTGTTGGCCACTGCGGGTCGATCTTGCGGCCGCCCCGGTCGTGGAACGCCCAGGTCACCCGGCGG
CGCACCGCGGTCAGCGCGTCGTTGGCCAGCGTGGTCACATGGAAGTGGTCGACGACGAGCTTGGCGTTGG
GCAGCAGCCCGGGCGTGCGGATCGCCGAGGCGTATGCAGCGGCGGGGTCGATGGCCACCGTACTGGATGC
TCTCCCGGAACTGCGGTGTGCGCGCTTGCAGCCATGCCAGCACCGCCGCGCCGCCGCGGCCTTCATGCTG
CCCATAAACCCTGATACCGGCCAGGTCGACNAACCNGTATCCCACGGTCAACCC Clone Rv244 (SEQ ID NO. 262)
::::::::::::Rv244SP6.seq::::::::::::
CACACGGACGGCGGTGCGGACGGAGCTGACGCGCATGGTGGTCAGCATCGCGGCCGGTCTGCTGTTGTAT
GCCTACTTCGCGCCGCGCAAATGCTGGTGGGCGGCGGTGGTGGCGCTCGCATGGCTGGGCTGGGTGCTGA
CCCAACTCTCGAACCACACCGGTGGGTGGGCTGGGCTATGGCCTGCCATATCGGCCTGGTGTTCTACN ::::::::::::Rv244T7.seq:::::::::::: (SEQ ID NO. 263)
CCGATATCCGAGCCGATAGCTGGCGGGCTCGGGTGGTNGCCAGCGGCGCTGCGACGAAAGTGTGACCGTC
ATGAAACAGACACCACCGGCGGCCGTCGGCCGTCGTCACCTGCTCGAGATCTCAGCATCCGCAGCCGGTG
TGATCGCGCTTTCGGCGTGTAGTGGGTCGCCGCCCGAGCCCGGCAAACGCCGGCCCGACACAACCCCGGA
ACAGGAAGTCCGGTCACCGCGCC Clone Rv245 (SEQ ID NO. 264)
::::::::::::Rv245SP6.seq::::::::::::
GCTTCAGGACAAATTGNATCCCTATGCACCCGTTGTCACGCCGATGAGTGAAGACTGCACGCAATCGCCG
GAATCCGGCAAAACCCTGCACAAGCGAAATCAACCGGAGGCTGACAAGGCAACGTCGGTGATCCGTACCG
CCTGGTTGGACAAACGGCAGAAGGCGCCTCGTCCGGTCCATCTACGCCGAGCACACTGGTGATAGCGCCA
TCGGCATCGGTGCGGCCACGGTGGAGACGAACGTCCGCNGGCGTCTGGGTCAGTAACCCGCCGACCAGTT
CTCGGGCAAGCTGGTCAACATCGGGCGCCACGTCTCCAAC ::::::::::::Rv245T7.seq:::::::::::: (SEQ ID NO. 265)
GTTTGGCGGCCTTATTGCACTGAGGTCGTCAATTGACCCACAGCGGAAATGCCGACTATTCGCAGGCCTC
CTTCGCCTTGGCTGCCGGAGATGGGCTCCGCGGGAACCGCATGCAGGTATATGACCTCGGTTTCTCGGGT
GCTACCGCGTGCCTTGTCGAGGATGAACTCGGCGTTGGAATTGTCCAGCCGGCCCAATTCATCGAGCGCA
GATTCGTACACATGGCCGGCGGCGACATACCTTCACCGTGGATCTGCTCCACACGGACCGCCCTGTCGGG
ATCTGCTCACGGGTAAAGGAATTA Clone Rv246 (SEQ ID NO. 266)
::::::::::::Rv246SP6.seq::::::::::::
GCGCACTCCTCCTTATCGCTCCGCTCTGCATCGTCGCGGCGCGGTCAGGTGCAAACGCCTTCGGGGGTGG
GGGTCCTGCGGAGCACACCGGATACGGAGCGCAACGCGTCGCGTTGTGCGGGCAAACAAGTGTGCAGGNN
CCAATGCCATGTCCAGCAGCTTATCAGTGTCGAACGTGCGAACGTCGCGCCTTCGCCGGTGCCTGAATCT
CTACAAG ::::::::::::Rv246T7.seq:::::::::::: (SEQ ID NO. 267)
CGCTGAAAGCCACCATTCGCGGGTCGGGCGCCGGGCTCGGGCCGCCAGGCTGCTCCGCTCGGTGATGGCA
CGCCACCGCGACACCACCCGGCTGCGCTACGTCGAGCCATACCGGGCGGAGCTACATCGGCTCGGCCGCC
TAGTGTTCGGGNCCTCTTTCGAGGTCGAGGTCGA Clone Rv247 (SEQ ID NO. 268)
::::::::::::Rv247SP6.seq::::::::::::
TGTAATTTGGGATGGGCAAAAAGCAAANCACCGCGTGGCCACAAACGCGGGGAGGGACAATCTCGGGCGG
CTAGGGCTTCTCGCGGGAAGCCCGAAACGTACGGCGTTTCAACACGTCGCGTCGCCTCCGACGCGAAATT
CGGG ::::::::::::Rv247T7.seq:::::::::::: (SEQ ID NO. 269)
CTTGGGCAACATGCTGAGGATCGCCTTTTCACCACGCGGTCGGGGTGGCGTTGCATTAGCTCACCGATGG
TGCGCTTGTTGCAGGCCGCCGGGATACCCGAGTGCCGGTAAACCATCTTGTGCTGCAGTTTGTCCCGCTG
ATGGCGACCTTGTCGCGTTGATCACGATGACGAAGTCACCGCCATCGACATTGGGGGCGAACTCGGCTTG
TGCTTG Clone Rv249 (SEQ ID NO. 270)
::::::::::::Rv249SP6.seq::::::::::::
GCATGCTTCATTATCTAATCTCCAGCCGTGGTTTAATCAGACGATCGAAAATTCATGCAGACGGTCCCAA
ATAGAAAGACATTCTCCAGGCACCAGTTGAAGAGGTTGATCAATGGTCTGTTCAAAAACAAGTTCTCATC
CGGATTGAACTTTACCAACTTCATCCGTTTCATGTACAACATTTTTAGAANCATGCTTC TABLE 3-continued End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character << - >> denotes an uncertain base residue.

Clone Rv24 (SEQ ID NO. 271)
::::::::::::Rv245P6.seq::::::::::::
ATACTCAAGCTTGATGCCGCCGAAACCGAGCGTGAGCACGCCGCCAGCCACCACGCGCGGGTCGGGCGCC
GGGCCCGGGCCGCCAGGCTGCTCCGCTCGGTGATGGCACGCCACCGCGACACCACCCGGCTGCGCTACGT
CTATCCATACCGGGCGGAGCTACATCGGCTCGGCCGCCCATTGTTCNGGCCCTCTTTCGAGGTCGAGGTC
TATACCGATTTGCGCATCCG ::::::::::::Rv24T7.seq:::::::::::: (SEQ ID NO. 272)
TCCGTACTGGTCGGGTACGCTTCGGTCGCAGTGTGCGAGTGATAGATGACGACCGGGACCTCGTCGGCAT
CTTCCATAGCCCGCCACACCTTCAGTTGCTCACCGGAATCCAACCGGTAGAAGGTCGGCGAGCGCTCGGC
ATTGGTCATCGGGATATGCCGCTCGGGACGGTCAGAACCTCGGGTCCG Clone Rv251 (SEQ ID NO. 273)
::::::::::::Rv251SP6.seq::::::::::::
GTTCTCGCACGATTTCGGATTAGCGGGATGGTCTGAATTGGGTATGCGGGGAAGGCGCTGACATTCGCCG
CGATTAGCTGTTTGATGGACCGGGGGTGATTTTTGATCACGGAAATGGGTGTTTATNCAGGTCGCACGCT
TTCATCCGGGGCGGAACG ::::::::::::Rv251T7.seq:::::::::::: (SEQ ID NO. 274)
GGGTGTGCCTGCTGTGTATGCACGGCATACGGACATCCTTCCCCTGAAGACCCGCGGTCGAACAGCCACG
TGTCCATCATCANGGGGTCAACCCCGGCCAAGGGCGACGGCACGCCAAGTTCGCCGACCGTTAACCTAGT
GCTGTTAGCTTCATTTGCTGCGAGCAAAACAGCTGGTCGGNCGTTAGGAATGAATTGAAACTCAACCGAT
TTGGTGCCGCCGTAGGTGTCCTGGCTG Clone Rv252 (SEQ ID NO. 275)
::::::::::::Rv252T7.seq::::::::::::
ACTACCCGGCCAACGGTGATNTCTTGGCCGCCGCTGACNGCGCGAACGACGCCAGCGACCACATTCAGCA
GATGGCCAGCGCGTGCCGGGCCACGANGTTGGTGCTCGGCGGCTACTCCCANGGTGCGGNCGTGATCGAC
ATCNTCACCGCCGCACCACTGCCCGGCCTCGGGTTCACCAGCCGTTGCCGCCCGCAGCGGACGATCACAT
CGCTTTTATTTNNTNTTCNGGAATCCCTCGGGCCGCGCTGGCGGGCTGATGA Clone Rv253 (SEQ ID NO. 276)
::::::::::::Rv253SP6.seq::::::::::::
ACGTCGGGANACTGTTCGCGTTCATCCTCGTCTCGGCGGATTGGTCTGCTGCGCCGGACCGACCGATCTT
CAGCGGGGGGTCACGCTCCGTGGGGTGCCGTTACTTCCGATCGCCCAGTGTGCGCGTGCTGTGGCTGATG
CTGAACCTCACCGCGTTGANTTGGATCGGTTCGGGATCTGGCTGGTGGCCGGAACGCNATTTATGTCGCT
ACGGGCGCCGGC ::::::::::::Rv253T7.seq:::::::::::: (SEQ ID NO. 277)
GCTCAAAGGCACTACTGGCACCAAGGCCCACACGTCACCTGTGACTCCTGCGCCGACCCGCCCGAGGTCT
GGCCGTTACACCGAACGGGCGAGCCGGGAGTTGGTACCATCGAACAAGACAAGGTGCATGGGCGGAGTTG
TTCCGCCACTTCGTCGATGACGGGTC Clone Rv254 (SEQ ID NO. 278)
::::::::::::Rv254SP6.seq::::::::::::
CGATACCGGCTGCTTACCGAGACATCCACCATGCCACCCGAATCACCGCACGCGCCGAAATCGCACAACA
GCTTGACGCCTTGCAGGTTCCGCGATTGGAATTGCCGACGGTCTCTGACGGCGTCGACCTTGGCAGCCTC
TACGAGCTCTCGGAATCACTTGCCCAGCAGGGGGTTCGATGAGTGTCACACCGAAGACCTCGATATGGGC
GCAATCCTGGCCGACACATCCAACCGGGTGGTTGTGTGCTGCGGCGCCGGTGGGGTCNGCAANACACTAC
CGCGGCCGCGCTGGCGTTGCGCGCGGCCGAATATGGCCGCACTGTGGTCG ::::::::::::Rv254T7.seq:::::::::::: (SEQ ID NO. 279)
CGTCGTCGTCGTGGTATGCGATAGCCATCCCGTCGGGCTACTCGCCATCACCGATCAGCTTCGCCCCGAA
GCCGCCGCGGCGATTTCCGCTGCGACCAAACTGACCGGGGCCAAACCGGTATTGCTTACCGGCGACAACC
GGGCCACCGCCGATCGGCTCGGTGTACANGTTGGCATCGACGACGTACGGGCCGGGCTACTGCCGACGAC
AANGTCGCAGCCGTGCNGCNGCTGCAAGCTGGAGGTGCCAGATTGACCGTGGTCGGTGACGGTATCAACG
ACCTCCGGCCTTAGCGGCCGCGCATGTCGCATCGCCATGGGCAGCGCCCGAC Clone Rv255 (SEQ ID NO. 280)
::::::::::::Rv255SP6.seq::::::::::::
GCACGCAATCGAAGTCACCCAAACCGGGCGGGCCAGGCGTCTNACGCCACGTCNACCAGCCGCAACCTGA
ACCCGGCCACGGCGAGCTCCTGATCAAGGCCGAGGCCATCGGTGTCTACTTCATCGACACCTACTTCCGC
TCCGGGCAATATCCGCGCGAACTCCCGTTCGTCATCTGCTCCGAAGTATGCGGCACGGTGGANGCCGTCG
GCCAGGGGTTAC ::::::::::::Rv255T7.seq:::::::::::: (SEQ ID NO. 281)
TCGACTGTGTGGCCACAGATCACGCCCCGCATGCCGAGCACGAGAAATGCGTCGAATTCGCCGCGGGCCG
GCCGGCATGCTCGGGTTGCAGACGGCATTGTCGGTGGTGGTGCATACAATGGTGGCGCCGGCTTGTTGAN
TTNGGCGCGATATCGCGCGGGTGATGAGTGANAACCGGCGTGCA Clone Rv257 (SEQ ID NO. 282)

TABLE 3-continued

End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character << - >> denotes an uncertain base residue.

:::::::::::::Rv257SP6.seq::::::::::::
GAACCTGACACCCTGGTCACGGGTGAGCACGGACTTGATTTCTTCNCTATTGGTCGGCGCTGTTGAGCAC
ACCACGCCGCTGACGGCCGTCGCGTCCTCGCTGTGCTCGGTCTGGTGGAGCGCGCTGCCCGCGGCCNAAC
ATCNTAAATCAAGCGTATTCGTCAACAGATATCATCAATGTCGGCGCTGGACTATTCAAATCATCGATAT
ACTGGTGACCTGGTCCTTCGCCATCGATCAATGGCGATAGTCACGCAAATCGTCACGGACATCGTCGGCG
TCCCAGCTGGCCCGTGCCAACAGATGCTGCAACCCATCGGGGTGGTATCACCGCGGTGCTCGGCGATGGT
CCACAATTCTTGCGGTCCAAGCCCNAAACATCCCGGGCATGAATTCACCGGCATGCGCN :::::::::::::Rv257T7.seq:::::::::::: (SEQ ID NO. 283)
CTATCGTACCCGCGCCGGTCACCTTCTGGATATCGCCGGCCTGGTCAAGGGGGCGTCCGAGGGAGCCGGG
CTGGGTNACAAGTTCCTGGCTCATATCCGCGAATGCGACGCCATTTGTCAGGTGGTGCGGGTGTTCGTCG
ACGACGACGTGACTCATGTCACCGGACGGGTCGATCCCCAGTCCGACATTGAGGTCGTCGAGACCGAGCT
GATCCTGGCAGATCTGCAAACCCTGGAGCGGGCCACGGGCCGGCTGGAGAATGAAGCGCGCACCAACAAG
GCGCGCAAGCCGGTCTACGAAGCGGCACTGCGTGCCCAGCANGTGCTCGACGCCGGGCAAGACGCTGTTC
GCCGCGGGGGTGGATGCCGCCGCGTTGCGCGACTGAAACTGCTGACCACCAAGCCCTTCCTGT Clone Rv258 (SEQ ID NO. 284)
:::::::::::::Rv258SP6.seq::::::::::::
TACTCAAGCTTCAGGCCGCCACGTCCGCCGTCCGTCGGCGACGTGACCTCGAGCGCCGAGTTCGACTCGA
CATCGCCGCCGGCGCATGCCGACATGAACGCGGCACTCACCGCAAGCCCGTCGGACGTCAGGTCGATCGA
CTCCGCTTCAAGCACCGGATCGTCCGGGCAACTCGCGGCCTCGGCCTGTGCGAACGGCACACCCGTCGTG
GCGGCNCCCCGCGCGGAACTGGGCTCATCACGGTCGTTGCGAGCCGGTCGCGTCACCGCGTACCGACGCC
GTC :::::::::::::Rv258T7.seq:::::::::::: (SEQ ID NO. 285)
CCGACATCGAGTGGGCTCGCAGTGACTTGGCGACCTCCAAGCCACCGGTACCCGCCGCGCGGCAAGCCAA
GGACGACGACGGCCTTGCCGGATAGCTGCGCCAGGCGTTGCGCCAACTGGCGTCCAGCGTCGCCACGATC
GTCAAAGAGCTTCATCTGCCGAGTGTGTCGCCATCTCATGGCTCCAAATATGGAATTAGGTCCCTGGGCC
GACTGACGACAGTCCCTCAGCGACCGGATTGCGCATCCCGCCTTGTACGCTACTCCGCAAATCCCGGGCT
TGCGTCCGCGGAAGCGAACTCGGCGGCGCTACGTGGTGGTTCACTTCGGCCGTGCGCACTCGGATCGACG
GGCCGATGGTGGCCGGGCCCGCGCGCTTCTTGGTCATCCGATTGAGT Clone Rv259 (SEQ ID NO. 286)
:::::::::::::Rv259SP6.seq::::::::::::
ATACTCAAGCTTGTCGCGGTAAACCGCACGCAGGGCGGTGGGTGCGGTGTCAAAGACACCCACACTTCTT
TGCGGTTCGGTGATCTCGACACCGGCCGCGAGCCGACCACCATGCGCGCGTAGATCGGCGATCAGCGCGT
CGGCTATCGCCTGGGTGCCGCCCACCGGAATCGGCCAGCCGACCGAATGGGCCAGCGTTGCCAGCATCAG
TCCGGCGCCGGCCGACACCAGTGACGGCAACGGTGAAATCGCGTGGGCGGCAACGCCGGTGAACAACGCG
CGGGCATCCTCGCCCGCCAACGACCGCCAGGCAGGGTGCCTGGGCCATCATCCGCAGCCCGA :::::::::::::Rv259T7.seq:::::::::::: (SEQ ID NO. 287)
TGGACTCATAACGATCGGGTCAGCGACGCGCCAACACGAACGGCCGGACGAGTGGGCCAGGGTCGCGCCT
CCCCTACAAACAGGATCCGTTGCCTGCGAGCGACAGGCTCCGGTGCGGCGTTGGGCGCCGTGCTCGTCCC
AGCGTCCGGTCCCGGGTCGCCGGCGACGCTTGTTTCCTCCATACTCGCCCCCTAATCTCGAGGCAGCCCG
TACCCGCAGGCAACCTCCCAAAAATGCAATCCCCCAAAATGCAATGCGTCGAGCTATTTCTCACACCGAC
CGCTAGTTGCGGATCAGAAATCCGTTGGGCGCGGAAGTCCAGCCGAATTTGTTCTCCCGCTCCGCATCAT
GCTTGTAATCGTTTGGAAATCATCCTCATATGCCTCGATCGCTTCATAGGTCAAGCCCAAACCCGGCAGG
ATGGGTGGCC Clone Rv25 (SEQ ID NO. 288)
:::::::::::::Rv25SP6.seq::::::::::::
CTTTACACTTTATGCTTCCGGCTCGTATGTTGTGTGGGATTGTGAGCGGATAACAATTTCACACAGGAAA
CAGCTATGACCATGATTACGCCAAGCTATTTAGGTGACACTATAGAATACTCAAGCTTAGTGGTTGCGCA
CGTAAATTCGTCAGGTGACCGATCCCCTGCTGTCTCACTCGCCTCACAGCGACCACCACGGCTGGCGCTC
AAGGCGGGCACGTGCGGAGCAGATGAGGAATGTGCGACGTCTTGATGCAGCCTGTCAGAACACCGAGACC
CTCGACGAACTTACGATCGAAACCGCTTAGGCCAACCGGTGACGGGGGTGTCTTTCCGCGGCTAGGGCGC
CTTATCGTCCGAAGGCCGTGGGTGGTGATCGCCTTCTGGGTCGCGCTTGCGGGTCTGCTTGCGCCGACGG
TGCCGTCCCTGGACCGATCTCCCAGCGGCATCCAGTGGCGATTCTGCCATCGG :::::::::::::Rv25T7.seq................. (SEQ ID NO. 289)
CAGGCATGCAAGCTTGCGATGTATCAACACGCCGTTGCGCAGCGTGAGCCGATAGTTGACATCCGGCTCG
GTGAAGGTGAAATCGATGGCCAGGTCGAGGTCCCATGCGCGTGGGCCATTGATGCTGATCGCCAGGACGT
CAAAGATTTGGTCCGGCGTCAGCTGGGCGAAAAACGTGGGCGCCGGGACTTGCCCGGAGCTGCCCGGGTT
CCCGTCGCGCAGCTCGGCGGCCCCGGTCAGAAAGAAATTGCGCCAGGTCGCACACTCCGCGCCGTAGGCC
AGCTGCTCCACGGTGTCGGCATATAGCCCGCGGGCCGCAGCGTGCTCGCTGTCGGCGAACACCGCATGGT
CGAGAAGCGTTGCCGCCCAACGGAAATCACTGCGTCAAAGCTTCGCCGGGCCACTCCAGCACTCCGTC Clone Rv260 (SEQ ID NO. 290)
:::::::::::::Rv260SP6.seq::::::::::::
ATACTCAAGCTTGACCGACGCTGATCGCACCGCACGCGGGAACCTCAAGGGCACTACTGGCACAAGGGCC
CACACGTCAACCTGTTAACTCCTGCGCCGACCCCGGCCGAAGTCCTTGGCGTTAACACCGAACGGGCCAA TABLE 3-continued End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character << - >> denotes an uncertain base residue.

CCCGGGAATTTGGGTTCCATCAAAACAAATAGCAGGTGCCTGGGCGGAGTGTTC

::::::::::::Rv260T7.seq:::::::::::: (SEQ ID NO. 291)
GTCGTCGTGTGCTGGGGCGTCCGTATCAGCACGCCCACGAAATGGGGCACAAGAAGGATTCCTGGAACGG
TGGCTGTCCAAGATCACCCTCGCCCAAAACTGCTACGGGCACTTCTACATCGAGCACAACCGTGGCCATC
ACGTCCGCGGTGTCCACACCGGGAGG Clone Rv261 (SEQ ID NO. 292)
::::::::::::Rv261SP6w.seq::::::::::::
ATATGCCTTGCTGAGCTTTTCGGATCGCAGCGAGTCGTACCCGCGCCGGTCACCTTCGTGGATATCGCCG
GCCTGGTCAAGGGGGCGTCCGAGGGAGCCGGGCTGGGTAACAAGTTCCTGGCTCATATCCGCGAATGCGA
CGCCATTTGTCAGGTGGTGCGGGTGTTCGTCGACAACGACGTGACTCATGTCACCGGACGGGTCGATCCC
CAGTCCGACATTGAGGTCGTCGAGACCGAGCTGATCCTGGCAGATCTGCAAGCCCTGGAGCGGGCCACGG
GGCGGCTNGAA ::::::::::::Rv261T7.seq:::::::::::: (SEQ ID NO. 293)
GACACCCTGGTCACGGGTGAGCAGGACTCGATTTCTTCGCTATTGGTCGGCGCTGTTGAGGCACAGCACG
CCGCTGAGGCCGTCGCGTCCTCGCTGTGCTCGGTCTGGTGGAGCGCGCTGCCCGCGGCCGAACATCGTAA
ATCAAGCGTATTCGTCAACAGATATCATCAATGTCGGCGCTGGACTATTCAAATCATCGATATACTGGTG
ACCTGGTCCTTCGCCATCGATCAATGGCGATAGTCACGCAGATCGTCACGGACATCGTCTGCGTCCCAGC
TGGCCCGTGCCAACAGATGCTGCAACCCATCGGGGTGGTATCNCCGCGGTGCTCGGCGATGGTCCAACAA
TTCTTGCGGTCCAAGCCCGAAACCATCCGGCCATGAGTTCACCGGCATGGCGCAACGGCTGGTGCCGGGC
AAAACGCGGCGCGATCGAATTC Clone Rv262 (SEQ ID NO. 294)
::::::::::::Rv262SP6.seq::::::::::::
TGTAGAAGGTGGGTCCCGTCCAACTTCGCGGCGGCGGCGCGATATGCCTTGCTGGTCTTGCTCATTTGAT
ATCCAATCTATGGGTCGTGGTTACTCAACGGGCCGAAGCTGGCCCTCCCACGGGTAGGGTCCTATTCGAC
GGTGATGTCC ::::::::::::Rv262T7.seq:::::::::::: (SEQ ID NO. 295)
CCCGAATCCGGTGGCCGGCAGGGGGCCTGGCGACGTGGACACCTTCTAACTTGTCTTTACCGGTCACTGT
TGCACCCCAACACCTTTAACGACGTGGACGGACGTTACATCGGATTCGACGGTGTCATCCACAGCGTTGC
CATTGGGCACACCCACTACGCCAATTTCTCCGACTGGGACACCTACCGCAGCCTCGCCCCACTGCAGGGA
CTGTTGTTCCCGCAACGGGCCATCGACATGATCCAGTCGTTGGTGACCGACGCGGAGCAGACTGGTGCGT
ATCCGCGTTGGGCGCTGGCGAAATTCCGCCACCGGCATGAT Clone Rv263 (SEQ ID NO. 296)
::::::::::::Rv263SP6.seq::::::::::::
TTGAGATGCTGGTCGGGATGCCGATGGTTGGAACATGGTCCCCTGGCGTCGAATACGCGCGAGCGCATGA
GCTCACCGGTTCGGAACAACGTATCGAAGAACTCGCACTGCTGGCAGATGGTATCTCCGATGTGGTTGTA
ATTTGTATCCCAACTCTAACTGTGCTATCGGATCTGCGTGAATA ::::::::::::Rv263T7.seq:::::::::::: (SEQ ID NO. 297)
CGTAATCACGATCCCGCTGAGACACTTGACCTTACGGCCGAAGTGACTTCGCTGCTGCTATGCCGACACC
CGATTTCCATACGCTGCTGTACACGACGGCCGGGCCGGTGGCCTCCATCACGCTCAACCGCCCGGAACAG
CTCAACACCATCGTCCCGCCCATGCCCGACGAGATCGAGGCCGCTATCGGGTTGGTCGAACGCGACCAGG
ACATCAAGGTCATCNTNCTGCGCGGTGGCGGGCGCGCCTTCTCCGGCGG Clone Rv264 (SEQ ID NO. 298)
::::::::::::Rv264SP6.seq::::::::::::
CAAGCCTAAGCTGGTTCCGGCCACTCCATGAGCCGTAGTGCAATGGTTCGTGCACGGCGAGGCCGAACTT
GCCATAAACATCCCTGACGAAAGTCTCCGGCAAGCCGATTGCTTCTTCGGGCCGCTTCTTGTGGATTGTC
CGATAACCCGGTCCCTCATGCTGGAAGTTGTGCGCACTCTTTCCTTCCGCGATGTGGGCTAACGACTCGT
CATTGAGCAAGAAGTACGTGCACAGGCATCGTCCGCCGGGCTTCAGCACGCGGGAGATCTCGTCCAGATA
GTGCTCCACGTCCGGNGGGAAACATGTGGGTGAACACCGAGGTNAGAAACACCNCATCCAACGACGCATC
CGGGATATGGAAAGCGAAA ::::::::::::Rv264T7.seq:::::::::::: (SEQ ID NO. 299)
TATGGTCTTCGTCGACCAGTACGTCGTAGGCGCCATGAGCCAGCGACTGAAGCCGCGCCATGCCTGCACG
GCCCGCTCATCCAGCGAGGCGGCCATCTCCCGCAGATAGCCTGCCGCCTCGGCGCGCACGCTGTCCGGAT
CGCGTCCGAGCTCGTCGGCCAGCGCACGCAGCCGCTCGTCATACCATCGGGCATCCAGCAGTTGGGTAAC
CTCAACGGGGTCGGTCGCTAGCGGCGTCATTGATTCAGCAACAATACCGATGCGCTGCAGCAACTTTCGC
AGTCCGATGCGGCCCACCTCCCGTGCAGTCACTGGCTAGCCCCCGTCATGCCGGTTGTGTCGATGGCACG
GCAGCGGGCTCGTAAACCTGCGGTCTCAGCTCGCTGG Clone Rv265 (SEQ ID NO. 300)
::::::::::::Rv265SP6.seq::::::::::::
GCTTAGCGGTCTTGCTCGAACCGACATTGCGTGCCACTCATGAGCGGGTGGCGGTCGCGGTGCTTACACA
TCT TABLE 3-continued End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character << - >> denotes an uncertain base residue.

:::::::::::::Rv265T7.seq::::::::::::: (SEQ ID NO. 301)
GTATCTGGCGCCTCTCGAATATCCTTGAACGTCCCGCGGTGCCACCCAGATAGATCGCAGCGCCCTGCAA
TGGAGTTCCCTTTATGGCCTCTCTAGCCTCCCGCTTGATCGGCTCGACCCGAGAGATGCCCTCGGGCGTT
GCGGGATCTCCCTCCA Clone Rv266 (SEQ ID NO. 302)
:::::::::::::Rv266SP6.seq:::::::::::::
CTTCACGCCGATCCGCGACCGCGAACGCGACGGTGACGGTGGGCGACAAGGTTCGGTTGGTCGCCGCGGC
GCTGGGCGATATCAGCTCACCCGGTTTCGAGGTGTTCGGCGACCGGACGGTGCTGCAGACATTCTTGAGC
GTCCTCGACCGGCCCGATTCGGCCTTCAACATCGTGACGCCGTATTTCGGCGGTACCGCTCGGCGCCGAG
TCGAAGGCGGCCTGAGCTAAAGCCGGGCATTGCGCGAGTGGTAAACAAGTTCGGTGACTTCGGTTGACCG
ACTCGACGGGCTCGATCTGGGCGCGCTGGACCGGTATCTGCGTTCGCTGGGGATCGGGCCNACCGCNANT
TGCGTTGCGANCTGATTCCGGTGGAGCTCCAATCTGACTTCCGG :::::::::::::Rv266T7.seq::::::::::::: (SEQ ID NO. 303)
GCAGCTACCGACCCTAGCGACGAGTGTGTTCGCAGCGTCGAATGTGAACGTTCGGCGTGATTCGGCGCGC
GGGTTCCCGCTCTCAGCGCACGTTCGGCGCCGAGGNGGCTAGTCCCTGGTTAAGCAATGTCTCGGTCGCC
GCCAGCAGCGCGCATGTCGCCAACCCGTCNACCGCGTTGCGCATGTCCGGTACCGACGGAAACGACGGCG
CGATCCGGATGTTCTTGTCGTCCGGATCCTTTCGATACGGGAACGACCCCCCGCCTCGGTCACCGCGATA
CCAACGTCCTTAGCCAANGCTACNGTCCGGCGCGCGGTCCCGGGCAACACGTCGAAGCTGATGAANTAAC
CACCCTTGGGCTCGGTCCAAGANGCGATCTTGGACTCCTTAACCGCTGATNCAA Clone Rv267 (SEQ ID NO. 304)
:::::::::::::Rv267IS1081N60.seq:::::::::::::
TCCCCATCGGCGCCGGACCGTTTGAAAGTCCAAGCACGGGTGGGATGGAATCGACGACAGTTGAGCGCCG
TCGGTGGCCGTGGTCAGCAGCTGTTCGCGAACGCACCAGGTCACATCCCTTCGACATCTCACCGACGTGG
CACGGGCGACATCAACAGGAAGATTGACGAATCCCTCGCAGGCGCGGCACGTCCGCAGGCCAACGCCAAC
TACGGGGCCACCAGCGATCCTCCGCTCACGCACCAGCCCAAGCCAGGCTCANCCACCCAAGTCGGCCCGC
GCTCTCCCTCGCCCCCTGGTCTCCGGGGCCTTGTTAAACAACTACCGGAAGTCCACCAATCCTCGCTGCA
TCTCGACACCGTCCGCCTCACTCCCTTCCTCCCGCCCCTCTCCACACNACACACCTCTTGCATTAAGGTC
ACGGAGCGGTCACTTTTCGTCGGACGAAATTCGCAATCCGGCCGCTCGCCGCCAGAGAT :::::::::::::Rv267SP6.seq::::::::::::: (SEQ ID NO. 305)
CGGAAAGTGGATACTCCCAGCAGGTAGCAGGTCGCCACCACGCTGGTCAGTGCGCGTTCAGCTCGCTTGC
GGCGCTGCAGCAGCCAGTCCGGGAAATAGCTGCCCTGGCGCAGCTTGGGGATCGCGACGTCGATGGTTGC
GGCACGGGTGTCGCAAATCACGGTGGCGGTAGCCGTTGCGCTGATTGGACCGCTCATCGCTGCGTTCGCG
GTAGCCCGCCCCGCACAGGGCGTCGGCTTCAGCCCCCATCAAGGCGGCGA :::::::::::::Rv267T7.seq::::::::::::: (SEQ ID NO. 306)
GGCCGAGTCCAGCACTTCGCACTATGTGCAGACCAAANACCCGGTGGTCGCCGCGCTGCGGCAGCGGCTG
GCAACGGCGCCGGTGATCACCGAGTGGTGCGNAGTTGCCGACCGGCAGTTCGCCGCGGGCTTACTACGAG
AAGGGCCTGCGCGACGTCATCAGGTATCACGTGTCGATGACGTCGAGCGTTAACTTCCCCGACCAGACGG
CGACCTCGCCGATGGACCCCGCGTTGTACCTGGTGTGGGCGCAAGCTAACGCCGCCGCANGCTATCGGTA
CTCGGTCGAAGCGCAGCCGGGGTCGCAAGCGCTAGCGGGCAAGGTCGCGACGATCTCGGTCACCTGGACC
AACTACGGCGCTGCTGCCGCCACCGAATAGTGNGTGCCCGGCTACCGGCTGGTGGATTCCACGGGACATG
TGGTTCGGACCTGCCGGCAGCGGTGGAACTGAAGANGCTGGTCT Clone Rv268 (SEQ ID NO. 307)
:::::::::::::Rv268SP6.seq:::::::::::::
AGCTTCAAGGACATCGTCATCGCGACCAAAACCGCGAGCTAGGTCGGCATCCGGGAAGCATCGCGACACC
GTGGCGCCGAGCGCCGCTGCCGGCAGGCCGATTAGGCGGGCAGATTAGCCCGCCGCGGCTCCCGGCTCCG
ATTACGGCGCCCCGAATGGCGTCACCGGCTGGTAACCACGCTTGCGCGCCTGGGCGGCGGCCTGCCGGAT
CAGGTGGTATATGCCGACAAAGCCTGCGTGATCGGTCATCACCAACGGTGACAGCAGCCGGTTGTGCACC
ATCGCNAACGCCACCCCGGTCTCCGGGTCTGTCAN :::::::::::::Rv268T7.seq::::::::::::: (SEQ ID NO. 308)
GCTCGCGGTCCAGCAGCAGACGTGTCTGACCCCGACGCCCGGCCGCCGGTACCGAAACCGGATCGGCCCG
CCGATGGCCGCGGCCACGGCGTCTGCCTTACCCGGCCCGGATACCAGCAGCCACACCTCGCGGGAACGCT
GAATCGCCGGCAGGGTCAAGGTGATTCGGCGTGGCGGCGGTTTCGCGAATCGTCCACCGCCACCACCATG
CGGGTGCTCTCGAAGACGCGGGGCTGTGCGGGAACAGCGAGTTAATGTGGCCCTCGGGCCCCATGCCCAG
CAGGTGGACGTCGAAATTCGGCCCGGGTCACCTGGTGCGGCACTGGCGGCC Clone Rv269 (SEQ ID NO. 309)
:::::::::::::Rv269SP6.seq:::::::::::::
AGCTTGTCGATCGTCCGGCAGCGTCCGGCGAGTCAAGTCGAAGCCAGTCCGGTCTCCTCTCCGACTACGG
CCAAGAACTGGGCGACGGTGTCAGTGCATACCAGCGGANACTGGTGGCGCCCTAGGCGAGCGACCGCCTC
ACAAACGGCGGTGACCGCGTTCTGGTCGTGCACCATCGAGCCGTGCCCATCCCGGCCGCGTGCCGTCAGC
CGCATCCACTGGATGCCCTTCTCGGCGGTTTCAATCAGGTACAGGCGACGTTCGCCANCATCGTGCCGGG
GCANGG :::::::::::::Rv269T7.seq::::::::::::: (SEQ ID NO. 310)

TABLE 3-continued

End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character << - >> denotes an uncertain base residue.

TTGGTGATCATCGNCCCAACGACCCCGAGGCGATGTTCTTGCACACCGAGGAGTGTCGCAAGCTGGGGCT
GGCCTTCGCCGCCGATCCGTCTCAGCAGCTGGCGAAGCTGTCGGGGTGAGGAAATTCGCAGGCTCGTCAA
CGGTGCTGCTTACTTGTTCACCAACGACTACTAATGGGATCTGCTGCTGTCCAAGACCGGCTGGTCAGAN
GCCGATGTGATGGCGCAGATCGACCTGCGGGTGACCACATTGGGTCCTAAGGGTGTCGATTTGGTAGAAC
CTGACGCACCACCATCCACGTCGGCGTTGGTCCCCGAAACAGCCAGACCGA

Clone Rv26 (SEQ ID NO. 311)
::::::::::::Rv26SP6.seq::::::::::::
GGCTCGTATGTTGTGTGGAATTGTGAGCGGATAACAATTTCACACAGGAAACAGCTATGACCATGATTAC
GCCAAGCTATTTAGGTGACACTATAGAATACTCAAGCTTGATTTTGATCATCATGATGATCATCACCCGA
AGTGTGGTAGCCGCAGTGGTTATCGTGGGTACCGTCGTGCTTTCCATGGGCGCCTCTTTCGGGCTTTCCG
TATTGGTCTGGCAGGACATTCTGGGTATCGAGTTGTACTGGATGGTGTTGGCGATGTCGGTGATCCTGCT
CCTGGCGGTGGGATCCGACTACAATCTGCTGCTGATTTCCCGGTTGAAAGAGGAAATTGGGGCCGGATTG
AACACCGGAATTATCCGTGCCATGGCTGGTACCGGGGGAGTGGTGACGGCTGCCGGCATGGTGTTCGCCG
TTACCATGTCGTTGTTTGTGTTCAGCGATTTGCGAATT ::::::::::::Rv26T7.seq:::::::::::: (SEQ ID NO. 312)
CAGGCATGCAACCTTGGCGTGCCGTTCCAACCCGAATTGGCTTTCGGCGCCATCGGTGAGGACGGCGTGC
GGGTGCTCAACGACGACGTCGTCCGCGGGACACACCTCGATGCTGCCGCCATGGACGCGGTCGAACGCAA
GCAGCTGATCGAGCTACAACGCCGCGCGGAACGCTTCCGCCGCGGGCGTGACCGCATCCCGTTGACCGGG
CGGATCGCGGTGATCGTCGATGACGGCATCGCCACCGGAGCGACGGCCAAGGCGGCGTGCCAGGTCNCCC
GGGCGCACG Clone Rv270 (SEQ ID NO. 313)
::::::::::::Rv270SP6.seq::::::::::::
GGCATCTTGGCCGCCATGTTAGCCACACTGCCACCGGCTATAGAAGCGATGCGCACCGTCCTGCCAGCAC
ATTGCGGCGCTCCTCCCTGGAAAGCAAGATAACCAAGCTCATGCCGTGGTTGTGGGTGGCGTGGTTTGGT
TTGGGTAACTTTGG ::::::::::::Rv270T7.seq:::::::::::: (SEQ ID NO. 314)
TCGGCTAATAATCGTCGACGCCGGCCTCCTCTGCAATCGCCTTGGCGGTCGCCGGGTTGTCACCGGTGAT
CATCACGGTGCGGATGCTCATTCGGCGCATTTCGTCGAATCGTTCCCGTATGCCCACCTTGACGATGTCC
TTCAGATGGACGACGCCGATGGCCCGCGCGCTGCTGTTATCGGTCCATTCCGCAACGACTAGGGGTGTCC
CCCGCCGGAGCTGATGCCGTCGACAATGGCACCCACCTCCTCGGTGGGGTGGGCACCGTGATCGCGAACC
CACTTCATCACCGCAGCCGCGGCACCTTGCGGATTCGACGGATG Clone Rv271 (SEQ ID NO. 315)
:::::::::::::Rv271SP6.seq::::::::::::
CTCAAGCTTGGAGGCGTGGCGATCGCGGTCCAAGCCGCGCTCTCCGAGCACAACGAGCGAAGACNGCTCG
GCGACGGAGCCTTTATCGACNTCCGTTCGGCCTGGCTGACGGCGGCNAAATAATGCTGGACTCGTTGTTG
TCGACGGTGCCGTGGCGAGCCGAGCGCCGTCAGATGTACGACCGGGTGGTCTATGTGCCGCGGTTGGTGA
GTTTCCACGACCTGACCATCGAAGATCCGCCGCATCCGCTGCTGGCGCGGATGCGCCGGTGGCTCAACTA
ATTCTACGGCGGCGAACTGGGTNATCCCTTCNCCACCGTCGG ::::::::::::Rv271T7.seq:::::::::::: (SEQ ID NO. 316)
CCTAGGTCAACCGTACCGTCATCGGATCGGGGTCGACCGCACAGATGGACTGGAGCTTCGGCGAGGTCAT
CGCCTATGCCTCGCGGGGGGTGACGCTGACCCCGGGTGACGTGTTCGGCTCGGGCACGGTGCCCACCTGC
ACGCTCGTCGAAGCACCTCAGGCCACCGGAAATCATTCCCGGGCTGGCTGCACGACTGCGACGTGGTCAC
CCTCCAGGTCGAAGGGCTGGGCGAGACGATGCAGACCGTCCGGACGAGCGGCACTCCTTTTCCGTTGGCT
CTTCGGCCGAATCCGGACGCGAACCCGACCGGCGCGGGGTCAACCCGGCACCGACGCGGTGCCGTTTAC
CCGCGGGCTGCACAAATCCCGACGGGTATGGGCTTTGACCTGCCGACGGGGGA Clone Rv272 (SEQ ID NO. 317)
::::::::::::Rv272SP6.seq::::::::::::
AGCTTGGCGTGACACCAACACAGGGCACTTAAGATGGCAATGCGCCGCCTACCTGCACGTTTTCGCGATG
TCAGAGGATGCCGAGGGGAGAACAATGCGAGCACGGCCGCTGACGTTGCTCACCGCTTTGGCGGCGGTGA
CATTGGTGGTGGTTGCGGGCTGCGAGGCCCGAGTCTAGGCCGAAGCATATAGCGCGGCCGACCGCATTTC
GTCTCGACCGCAAGCGCGACCTCAGCCGCAGCCGGTGGAGCTACTGCTGCGCGCCATCACGCCGCCTAGG
GCTCCGGCGGCGTCGCCGAACGTCGGGTTTGGCGAACTGCCTACCCGGGTCCGGCAGGCAACCGAT ::::::::::::Rv272T7.seq:::::::::::: (SEQ ID NO. 318)
TCATGCCGTTGGACCGACCATCGGAGTTAGTTGCCGAACCGCGGGACCACCGCAAGCACCCGGTCCTGGT
CGCGCACCGCGTCGGCCAACCGCTTGAGCACCACCACGCCGCAGCCCTCGCCGCGCACGAATCCATCCGC
GTTGGCGTCGAAGCTGTTGCATCGGCCGGTCGGTGACAGCGCCGACCACTTGGACAGCGCGATGGCGGTG
AACGGTGACAAGGTGAGCTGCACCCCGCCCGCCAATGCCACGTCGGTTTCACGCAGGCGAAGCTCTGACA
CGCCAAGTGAATTGCCACCAGCGACGACGAACAAGCGGTATCTACGGCGATGG Clone Rv273 (SEQ ID NO. 319)
::::::::::::Rv273SP6.seq::::::::::::
GGGTCGACTTTCTGCAAGGCGAGGCTACACCGTCGTCGTCGTGGTATGCGATAGCCATCCCGTCGGGCTA
CTCGCCATCACCGATCAGCTTCGCCCCGAAGCCGCCGTGGTGATTTCCGCTGCGACCAAACTGAACGGGG TABLE 3-continued End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character << - >> denotes an uncertain base residue.

CCAAACCGGTATTGCTTACCGGCGACAACCGGGCCACCGCCGATCGGCTCGGTGTTCAGGTTGGCAT

::::::::::::Rv273T7.seq:::::::::::: (SEQ ID NO. 320)
AATCCGAAATCCTGACCGATACTTGAACCTGGTCTCGTTCGGCAATAACTCGTCGGCGTGCAGGACGCGG
CGCAAACGTACTTCGGCATCAACGCGTCCGACCTGAATTGGCAGCAAGCGGCGCTGCTGGCCGGCATGGT
GCAATCTAACAGCACGCTCTTCCCGTACACCAACCCCGACGGCGCGCTGGCCCGGGCGGAACGTGGTCCT
CGACACCATGATCGAAAAACCTTCCCGGGGAGGCGGATGC Clone Rv274 (SEQ ID NO. 321)
::::::::::::Rv274SP6.seq::::::::::::
TTCCGAATTTCGGGTCCNGGTCATATGACCCTCATGGAAGAAGAAGCGGCCGCCCCGCGCCCGTGCGACG
GCGAATGAAAACCCTCACCCAGGCCGCATTGAACGCCGACAAGACGGTGGAGCAGGTCGAAGACGTCCTG
GACGGTCTGGGTAAGACCATGGCCGAGCTGAACAGCTCGCTGTCACAGCTGAACAGCACCGTGGAGCGCT
TGGAGGACGGTCTGGACCATCTCGAAGGTACCCTGCACAGCCTGGACGATCTCGCGAAACGGCTCATCGT
GTTGGTCGAGCCGGTGGAAGCCATCGTCGATCGGATCGACTACATCGTGAGCCTCGGCGAAACGGTGATG
TCACCGCTGTCGGTC ::::::::::::Rv274T7.seq:::::::::::: (SEQ ID NO. 322)
NCTCGATCTTGGGGTACGTTCGATGAGGCTGCTGACCAACAACCCGGCCAAGCGGGTGGGACTGGATGGA
TACGGATTGCACATCATCGAGCGCGTGCCGCTGCCGGTGCGGGCCAACGCGGAAGAACATCCGTTACCTG
ATGACCAAGCGTGACAAATTGGGGCACGACTTGGCTGGGTTGGACGATTTTCACGAATCCGTGCATCTGC
CCGGAGAATTCGGCGGTGCCTTGTGAAGGTGGCGCCGGGGTGCCGGATCTGCCGTCGCTGGATCGTCTGG
TGTGCGGCTGGCGATTGTCGCCAGCAGCTGGCACGGAAAGATCTGCGACGCGCTGTTGGACGGCGCCCGC
AAGTGGCCGCCGGGTGTGGCCTCGATGACCGACTGTGGTTCGGGTGCTCCGCGCGATCGATAT Clone Rv275 (SEQ ID NO. 323)
::::::::::::Rv275SP6.seq::::::::::::
TCATCCCGACCAAAACGCGAGCTAGGTCGGCATCCGGGAAGCATCGCGACACCGTGGCGCCGAGCGCGCT
GCCGGCAGGCCGATTAGGCGGGCATATTATCCCGCCGCGGCTCCCGGCTCCGAGTACGGCGCCCCGAATG
GCGTCACCGGCTGGTAACCGCTCTTGCGCGCCTGGGCGGCGGCCTGCCGGATCAGGTGGTAGATGCCNAC
AAAGCCTGCGTGATCGGTCATCACCAACGGTGACAGCAGCCGGTTGTGCACCAAGCGCGAACGCCACCCC
GGTCTCCGGGTCTGTCCAACCGATCGACCGCCCAAGCCCACATGAACAAACCCCGGCATCACGTTGCCGA
TCGGCATACCGTGA ::::::::::::Rv275T7.seq:::::::::::: (SEQ ID NO. 324)
TTGGCGGGTTGGCCCAGCAGCCCGCCGGTGACGGCGACGATGCTGGGCTGGTTGCGGCCCTGCGCCACCG
CGGCTTGCATGCTGGTTGGCTGTCTTGGGACGATCCCGAAATAGTCCACGCGGATCTGGTGATTTTGCGG
GCTACCCGCGATTACCCCGCGCGGCTCGACGAGTTTTTGGCCTGGACTACCCGCGTGGCCAATCTGCTGA
ACTCGCGGCCGGTGGTGGCCTGGAATGTCGAGCGCCGTTACCTACGTGACCTGATGGATCGGGGGGTGCC
GACCGTGCCCGGCGATGTGTATGTGCCGGGANAGCCGGTCCGGTTGCCACGCAAAGGCCATGTCTTCGTC
GGTCCGACCATCGGTACCGGGACACGGCGCTGTATTGCCCGGTTCGCTGCCGAGTTCGTCGCGCAACTGC
ACGCNGGCGGGCCAGCGGTGCTCGTTCANCCCGGAGGTTCCGGTGACGATGATCGTGTTGGTCTCCCT Clone Rv276 (SEQ ID NO. 325)
::::::::::::Rv276SP6.seq::::::::::::
GTAGGAGAGAACAAAGACCGTCGATAGGACACGTGTTACGCCGGTAGCTGTCATTGGTATGGGGTGCCGC
TGCCGGGGGGCATCTACTCACCCGATCGGTTGTGGGAGGCGTTGCTGCGGGGCGACAATCTGGTCACCGA
GATCCCCGCCGACCGCTGGGACATCTACGAGTACTACGACCCCGAACCCGGCGTGCCCGGACGCACCGAC
TGCAAATGGGGCGCGTACCTCGATAACGTCGGCGACTTTGATCCCGAGTTCTTCGGGATCGGGGAGAAAG
AAACGATAGCGATCGATCCGCAGCACCGCTTGTTGCTGGAAACCTCCTGGGAAGCCATGGAACACGGCGG
GCTAACACCGAACCATATGCCTCCCGACANGGGTTTTCGTGGGGTT ::::::::::::Rv276T7.seq:::::::::::: (SEQ ID NO. 326)
CGAACTGAGCCCATAGAAAGGCAGCGACTAATTCGCTGGGCAAATAGGAAGACCCTTTGTCCTGCCACGT
ATATTTGTCGACCTCGTTGCGAAGGAAGCGGCTGCGATTGGTGCCCTTTTCCCTGGAGAATCTCTGCCCG
GAGCAGGAAGTCTTATGAGTTGACAAGCAGGGGCGCCGCCTTCGCCGGAAATCACATTCTTGGTCTCGTG
AAATGAGAGCGCTCCCAGGTCGCCGATGCTGCCGAGCGCCCGCCCACGATACGACGCCATCGCGCCTTGG
GCCGCGTCTTCGACCACCGCCAGGTTGTGGTGCGTGGCGATCTTCATGATCGCGTCCATCTCGCAGGCCA
CCCGGCATAGTGAACGGGGACCATGGCCTCGGTTCGCGGGTGAA Clone Rv277 (SEQ ID NO. 327)
::::::::::::Rv277SP6.seq::::::::::::
CTTAGACGCCACCTCCGGGCCGAGCTCCACGGGGTGGATAAGTACGGCCGGATGTGGCCGCAATGGGAAG
TTGTTGCCCGCTTGACTGTCCGGGTTAACGCCGGATTCCACCACATCCCCTTGCGAAAGGCCGTTGGGTT ::::::::::::Rv277T7.seq:::::::::::: (SEQ ID NO. 328)
GATCGCGATCGTCGATGTGGCCATCCGGCTTGGCGTCGACCCGCGTAAGGCAGACCAGATGGTTCGCGGC
ACGGTCAACCTGCCACACGCACTGGTAAGACTGCCCGCGTCGCGGTATTCGCGGTTGGTGAAAAGGCCGA
TGCTGCCGTTGCCGCGGGGGCTGATGCTGTCGGATCGACGATCTGATCGAGAGGATCAGGGCGGCTGGCT
GGAATTCGATGCCGCGATCGCGATACCGGATT TABLE 3-continued End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character << - >> denotes an uncertain base residue.

Clone Rv278 (SEQ ID NO. 329)
::::::::::::Rv278SP6.seq::::::::::::
AGCTTACGCCGCTTTCGCTTCNGATTTGGGACGCCGCATCGAAAGCGCAGTTGGAAGCGCGGCGCCCGGC
TGGTCGAGCTGCTCAAGCAGCCGCAATCCCAGCCCATGCCCGTTGAGGAGCAAGTGGTTTCGATCTTCCT
GGGCACCGGCGGTCACCTGGACTCGGTGCCCGTCAAGGATGTCGGCGGTTCGAAACCGAATTACTGGACC
ACATGCGGGC ::::::::::::Rv278T7.seq:::::::::::: (SEQ ID NO. 330)
CGACGGGACCTCGTCGCATCTTCCATAGCCCGCCACACCTTCAGTTGCTCACCGGAATCCAACCGGTATA
AGGTCGGCGAAGCGCTCGGCATTGGTCATCGGGATATGCCGCTCGGGACGGTCAGATGCCCTCGGGTCCN
GCCAGCACTCCTCAGGCTTCGTCGGGGTGGTCGCGACCGCATGGGCCACATCGCATTCACCAGGTCTGCG
CGAATCACCAGCACGTANACGGTTCCTTTCCTAAGCAACACCGAAATTTCAGGACCCGAATGCTCCGGGA
AAACATGTCACGGTAAGTCCGGTATTCCGGGTACCGGTTGAGCATTGA Clone Rv279 (SEQ ID NO. 331)
::::::::::::Rv279SP6.seq::::::::::::
CGGCATCGGTTTGGGCTGTCACCAGCAGTTGGTAGTTCTTCACTACTGTTGTTCGAGCGTCGAGCCGCCG
CGCGTGTCGAGGTCGCCGGACGCGTACCCGCCAGGCCGGTCAGGGTGCCCTTCCAGTCCACGCNGCTGTG
GTCGGCTAACCGCTTATCTTCAATCGAGACNATCGCCAGCTTCATCGTGTTGGCGATCTTGTCCGAGGGC
ACCTCGAACCGGCGCTGCGANTACAGCCACGCGATCGTGTTGCCCTTCGCGTCGACCATCGTCGATACCG
CAGGCACTTGCCCCTCGAGCAGCTGGGCCGATCCGTTGGCAACGACCTCAGAGGCACGATTGGACATCAG
CCCTAGCCCGCCTGCG ::::::::::::Rv279T7.seq:::::::::::: (SEQ ID NO. 332)
CCGTCGANGCCGCCGACTTGGCTTGACCGACACCAACATGGCCTGAGGGTGTTCAACAAGACCGTGGCCG
ACGGGCTGAACATCACCATGAGCGGCATGAGCCACGCCACCGAGTTCATCATGTTGATCGCCGAAAACCA
TTGGCGGGTAGCGGAAGAACGGTCGAGGTGCTCTACACCGAGTATTCGAAGTCGAAAGGCCAACCGCTGC
TCAACGGCGTCAACATCATTTTCGACGGGTTTCTGCGAGGGAGGATGCCACGATGAACTGGATCCAGGTG
CTGTTGATCGCGTCGATCATCGGGTTGCTGTTCTACCTGTTGCGGTCGCGCCGAAGCGCGCGGTCCGTGC
CTGGGTCAAGGTGGGCTATGTCTTGTTCGTGCTCCCGGCATCTATGCCGTGCTGAGA Clone Rv27 (SEQ ID NO. 333)
::::::::::::Rv27SP6.seq::::::::::::
TTACACGNCCTGCTTCCGGCTCGTATGTTGTGTGGAATTGTGAGCGGATAACAATTTCACACAGGAAACA
GCTATGACCATGATTACGCCAAGCTATTTAGGTGACACTATAGAATACTCAAGCTTTTTGAGCGTCGCGC
GGGGCAGCTTCGCCGGCAATTCTACTAGCGAGAAGTCTGGCCCGATNCGGATCTGACCGAAGTCGCTGCG
GTGCAGCCCACCCTCATTGGCGATGGCGCCGACNATGGCGCCTGGACCGATCTTGTGCCGCTTGCCGACG
GNGACGCGGTANGTGGTCAAGTCCGGTCTACNCTTGGGCCTTTGCGGACGGTCCCGACGCTGGTCGCGGT
TGCGCCGCGGAAAGCGGCGGGTCGGGTGCCATCAGGAATGCCTCACCGCCGCGGCACTGNACGGCCAGTG
CCGCGGCGATGTCNGCCATCGGGACATCATGCTCGCGTTCATACTCCTCGACC ::::::::::::Rv27T7.seq:::::::::::: (SEQ ID NO. 334)
CAGGCATGCAAGCTTTGTCACACCAAGTGTTTCGACCAGGCGCTCCATCCGGCGAGTGGATACTCCCAGC
AGGTAGCAGGTCGCCACCACGCTGGTCAGTGCGCGTTCAGCTCGCTTGCGGCGCTGCAGCAGCCAGTCCG
GGAAATAGCTGCCCTGGCGCAGCTTGGGGATCGCGACGTCGATGGTTGCGGCACGGGTGTCGAAATCACG
GTGGCGGTAGCCGTTGCGCTGATTGGACCGCTCATCGCTGCGTTCGCGGTAGCCCGCCCCGCACAGGGCG
TCGGCTTCAGCCCCCATCAAGGCGG Clone Rv280 (SEQ ID NO. 335)
::::::::::::Rv280SP6.seq::::::::::::
AGCTTAGCCAGTTTTTCTACTCTTGGGCCCACACCCACAGTGCTTCGACGGTACGGTCACCCATGATGGC
CATCCAGTTGGCATCGGTGAGCTGATAAATGCCAGCTGGTTTCGCCAACCCGGTAGCGATCTTGGCGCGC
TGCTTGTTGTCACTGATACCTATCGAGCAAGACAGCCCGGTTTGCGACAAGATGACTTTTCGGATCTCTT
CGGCGACTTCGATGGGGTCGTCGGGAGTCCCGGGCGCCACCGCGAGGTAAGCCTCGTCCCAGCCCCATAC
CTCGACCGGGTATCCCAGGTCGCGCAATAACGCCACCACCTCCTCGGACGCCGCGTTGTAGGCGGCTGGG
TTCGACGGCAAGAAGTGGCCTCAGGGCATCGTCGGCGCGGTCCCAACGGCNTGCCGGCGCGCACACCGTA
GGCGCGGGGCTC ::::::::::::Rv280T7.seq:::::::::::: (SEQ ID NO. 336)
CCGGCGGAACTCAGACGTGCTGGTGGTGCGGCATGGCACCGCGGGCAGCAAAGCGCACTTCTCCGGGGAC
GACAGCAAGCGACCGCTAGACAAGAGGGGTCGTGCGCAGGCAGAAGCGTTGGTACCACAGCTGCTGGCGT
TCGGCGCCACCGATGTTTATGCCGCCGACCGGGTGCGCTGCCACCAGACGATGGAGCCACTCGCCGCGGA
ACTGAACGTGACCATACACAACGAGCCCACCCTGACCGAAGAGTCCTACGCCAACAACCCCAAACGCGGC
CGACACCGAGTGCTGCAGATCGTCGAGCAAGTAGGCACACCCGTGATCTGCACGCAGGGCAAGGTCATTC
CCGATCTGATCACGTGGTGGTGCGAGCGCGACCGTGTGCCCCCGACAGTCCCGCAATCGCAAAGGCAGCA
CGTTGGTGT Clone Rv281 (SEQ ID NO. 337)
::::::::::::Rv281SP6.seq::::::::::::
GTATGGTCAGCTGTCCATCCGGCGCTGTCGGCCGAGCTGCCAGATCTCGTCAGCCGTAACCGGGTTGCGG
GATCCACGCGTGCGGGTTGTCTAC TABLE 3-continued End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character << - >> denotes an uncertain base residue.

::::::::::::Rv281T7.seq:::::::::::: (SEQ ID NO. 338)
CCGACTTTCCGCGGGTACCCGCTCAACTTTGTGTCNACCTCAACGCCATTGCCGGCACCTACTACGTGCA
CTCCAACTACTTCATCCTGACGCCGGAACAAATTGACGCAGCGGTTCCGCTGACCAATACGGTCGGTCCC
ACGATGACCCAGTACTACATCATTCGCACGGAGAACCTGCCGCTGCTAGAGCCACTGCGATCGGTGCCGA
TCGTGGGGAACCCACTGGCGAACCTGGTTCAACCAAACTTGAAGGTGATTGTTAACCTGGGCTACGCGAC
CCGGCCTATGGTTATTCGACCTCGCCGCCCAATGTTGCGACTCCGTTCGGTTGTTCCAGAANGTCAGCCC
G Clone Rv282 (SEQ ID NO. 339)
::::::::::::Rv282SP6.seq::::::::::::
GCACCGATGTCGGCGAGCACTTCGTCAACTTCCAGGGGTGCCCGCACCAAGTATTTCGACGAGTATTTCC
GTCGGGCCGCCGCCGCCGGTGCGCGGCAGGTGGTCATCCTGGCGGCGGGGCTGGGACTCGCGCGCGTACC
GGCTGCCTCGGC ::::::::::::Rv282T7.seq:::::::::::: (SEQ ID NO. 340)
TGCACCCAACTTACTGAGCATGCTAACGCTGGTCGTGCGGGTCTTGTTCCCGCGTGTCGGCAGGGCACAC
GCTCGGGGCGTAGCTGGGAGAGGCCCCGGTCAAGCCCGGAGAGCAGTGCTCAGTCCGCCAGCTTGACCGA
CTTTCGATGAGAACGCGCTTCTCGCCGTATTGAACTGGCGTGCTGACGGTCGCTGAGCAGCGCTCGCCGA
GTGCGGCCGCTGATTCTTTCATCGAGCCAGGACGCGCATTCGTGTTCGGCCGC Clone Rv283 (SEQ ID NO. 341)
::::::::::::Rv283SP6.seq::::::::::::
AGCTTACGGCCGGTCGACGCGACGAGTGGTTCATGACACCACAAACCGTCAACGCCTACTACAACCCGGG
GATGAACGAAATCGTCTTCCCGCAGCGATTTTACAGCCACCATTTTTCGATCCGCAGGCCGACGAGGCCG
CCAACTACGGCGGGATCGGGGCGCGTGATCGGGCACGATGATCGGGCACGGTTTCGACGATAGGGCGCCA
AATACGANGGCGACGCAATCTGGTCNATTGGTGGATCGA ::::::::::::Rv283T7.seq:::::::::::: (SEQ ID NO. 342)
ATGTCGTCACGTCACCACAATCGCGAGGACCCAATCATGCCGCCCAGGGCGGCCAACCCAATGGTGGCCG
CGAAGCGGCAGCTCGATCGCAGCGCGGAGGTGCCGGCCGCCAGTTGATTCACGAACAGGGTGAGGTCATA
GGCGGGCAGGATAGTGACGAACGCAAGACCTATATCTGCCGTCGGAGTAAGAATCGAGTAGCCGGTCGAC
CAACGGAAGCGAAAGTGTCCGCGATGTTGATGAGCGTCGCCGGTTGTGGCGGCGGTGGC Clone Rv284 (SEQ ID NO. 343)
::::::::::::Rv284SP6.seq::::::::::::
AGCTTCACCAGCGTGCCGATGCTGTTCGCNACACCTCCCTACTATGCGCAATTCGCCGACACGGGTGGCA
TCAACACGGGCGATAAGGTGGACATCGCTGGGGTGAACGTCGGGCTGGTGCGCTCGCTGGCAATCCGCGG
CAACCGCGTGTTGATCGGATTCTCGTTGCCCGGCAAGACAATCGGGATGCAAAGCCGGGCAGCAATTCGC
ACCGACACCATTCTTGGCCGTAAGAACCTGGAAATCGAACCCCGCGGTTCGGAGCCGTTGAAACCCAACG
GTTTCCTGCCGTTGGCGCAGAACACTACGCCATACCAAATCTATGACGCGTTCGTC ::::::::::::Rv284T7.seq:::::::::::: (SEQ ID NO. 344)
CTGCCGCGGTGGCGGTCAGCGCCTGGCAAGTCACCGCACCGCCGTCCGGTTCATCGGCAGGCTCCCCCGA
AAAGGGCCCTGGCAACAGAAGGTGATCAATGAGCTCCCGCAGACCTTCGCCGATCTGGGACCGACATACG
TGAAGTTCGGCCAGATCATCGCGTCCAGCCCGGGAGCATTCGGTGAGTCGCTGTCGCGGGGAATTCCGCG
GCCTGCTCGACCGGGTGCCGCCCGCAAAAACCGACGAGGTGCACAAGCTCTTCGTCGAGGAACTCGGCGA
CGAGCCGGCCCGGCTGTTCGCCTCCTTCGAGGAAGAACCGTTCGCGTCTGCGTCCATCGCCCAAGTGCAC
TACGCGACCTGCGCAGCGGCGAAGAAGTGTGGTCAAGATCCACGGCCGGGCATCCGCCGCCGCGTTT Clone Rv285 (SEQ ID NO. 345)
::::::::::::Rv285SP6.seq::::::::::::
GATCGTGCCGGCCCCCCGGCGGCAGTAGCAGATCAGCTCGTCGAAATCGCGGCAACCAGTCCAGTCGATT
TCCATACGGGCGCCGTCAATCAACTCTGCGAACATCGCGATCGGCACCGGAAACCGGCGAGCCGCGTCAG
CCAGCGCAACCAGCACCGGGATCGGATGAATCATCAATATTATCAAGTGATTTCCTGATGGCATCGAGCT
CGGTGATCTTGGTCTCGGGGGCCAGCTCGCCGTCGGCGACGTCGTCGATCCGGCGGCCGAGCGCATAGAC
CGCAAATAGTGCCGCTCGCTTTTCGCGCGGCAAGAGTCGGATGCCGTAATATANGTTTCTGGCGGCCGTG
CGCGTGATCNACTCGGTGATTCGATACGCCTGTTCATCTCGGTCATGCCGTCCTC ::::::::::::Rv285T7.seq:::::::::::: (SEQ ID NO. 346)
GGTGGCGCAATGACCGAAACCACCCCAGCCCCGCAAACCCCGGCGGCCCCGGCCGGGCCCGCACAATCGT
TCGTGTTGGAGCGGCCCATCCAGACCGTTGGGCGCCGTAAGGAGGCCGTGGTACGAGTGCGGCTGGTGCC
CGGCACCGGCAAGTTCGACCTCAACGGCCGCAGCTTGGAGGACTACTTCCCAAACAAGGTGCACCAGCAG
TTGATCAAGGCACCCCTGGTCACCGTGGATCGGGTGGAAAGTTTCGACATCTTTGCCCACCTGGGCGGCG
GCGGCCCGTCGGGTCATGGCCGGCGCGCTGCGCCTGGGTATCGCCCGGGCATTGATTCTNGTATCGCCGG
ATGACCGGCCCGCGCTGAATAANGCCGGCTTCTTGACCGTGATCCACGCGCCACCGAACGCAAA Clone Rv286 (SEQ ID NO. 347)
::::::::::::Rv286SP6.seq::::::::::::
CACAATAGATTACTCAAGCTTCGAACCAGCGGCCTTATCACGTATCCCCGCTGAGACCTTGACCCTTAGG
GCCGAAGTGACTTCGCTGCTGCTATGCCGACACCCGATTTCCAGACGCTGCTGTTACACGACGGCCGGGC TABLE 3-continued End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character << - >> denotes an uncertain base residue.

CGGTGGCCACCATCACGCTCAACCGCCCGGAACAGCTCAACACCATCGTCCCGCCCATGCCCGACGAGAT
CGAGGCCGCTATCGGGTTGGCCGAGCGCGACCAGGACATCAAGGTCATCGTGCTGCGCGGTGCCGGCCGC
GCCTTCTCCGGCGGTTACAACTTCGGCGGCGGGTTCCAACATTGGGGGCAT

::::::::::::Rv286T7.seq::::::::::: (SEQ ID NO. 348)
TCAGGACGCTTATGGTTGGCAGATGGTCGCCCTGGCGTCGAATACGCGCGAGCGCATGAGCTCACCGGTT
CGGAACAACGTATCGAAGAACGTCGCACTGCTGGCAGATGGTATCTCCGATGTGGTTGTAATTTGTATCC
CAACTCTAACTGTGCTATCGGATCAGCGTGAATATCGAGATATTGCGAATGCGATGACAGGCCGCCATTC
GGTTTATTCGCTTACGCTTCCCGGGTTCGATTCGTCTGATGCACTGCCGCAAAACGCGGATATGATTGTT
GAAACCGTATCTAACGCAATTATTGATGTGGTAGGCGGCAGCTGCCGTTTTGTGCTGTCGGGCTATTCAT
CGGGTGGGGGTGTTTGGCTATGCCCTCTGCTCCCAT Clone Rv287 (SEQ ID NO. 349)
::::::::::::Rv287SP6.seq::::::::::::
CGCAGCTGTCGCCGATCTGGTCCGGATACCTAGCTCCAGGTTCTGAGTGGAGATGAGTCGGCCATCGAAG
TGTTGTCAATGTACTCCAGGATGTCAGGTGCCAGGCCGCTGGCGAGGATCTTGGGCACCGCCGCCATGAC
TTGGTCGAAGTCGGCGAACGGGGCGAGCACGCTGGCGTCGTGGTC ::::::::::::Rv287T7.seq::::::::::: (SEQ ID NO. 350)
GTAGTTCGTTCATCCAAACACAGTGCGGTACCGGCTCAAGCGGATCACCGACTTCACCGGGCGCGATCCC
ACCCAGCCACGCGATGCCTATGTCCTTCGGGTGGCGGCCACCGTGGGTCAACTCAACTATCCGACGCCGC
ACTGAAGCATCGACAGCAATGCCGTGTCATAGATTCCCTCGCCGGTCAGAGGGGGTCCAGCAGGGGCCCC
GGAAAAGATACCAGGGGCGCCGTCGGACCGA Clone Rv288 (SEQ ID NO. 351)
::::::::::::Rv288SP6.seq::::::::::::
TCCGCTCGCTTCTCCGAGAGGTTGAGTGCCAACGCTCTGCCGATGCCCGAAGCCGGCCCCGGTGATGACG
GCGACCTTGCCTTCGAATGAGCTCATTTGACTACTCCCCGTGGTTGTCCCTGCGATTGGTGGAGGTGGCC
GCGCAGCCTTGCCCCGAGGTCGGCGATCGCGTCTCGGGCTTCGGGGAGCAGACTGACCTGCAGATGGAAG
TCGTGCCACATGCCCGCGAACCGGCGATGCTCGATGCTTGTTTTCGAAGCGGCGCAGGCGGTTTCGATCT
TGTCCGCGTCAACACNGATCGGATCGTCGCCCGCGGTCTGCATGACGAATGGGCG ::::::::::::Rv288T7.seq::::::::::: (SEQ ID NO. 352)
ATGGGAGGCCACCGATTACCATCTTGCACACACCGATTCCGGGCTATTGATGTCCACGTTCGGTCCGCGA
ACCGCGCTGTGGCTGCTGCTGGCCAAAGGCGGAGGCGATACCGAAGTCAGTGCCCAAGCTTGGGTTCCAC
GCTCGCGCAGCCACGCCGTCACCTTTCCACGAGACCTCACCTGCCGATCCGAAATGGAATCGGCCGTGAC
GGAATTGGCGCAGCGAACACTCAACGAGGTGGTGGCTTCGTCGCGAACCGTCACCCGAGTCGCGGTCACC
GTGCGCACGGCGACGTTCTACACCCGCACCAAGATCCGAAAGCTGCAAGCTCCCAGCACCGATCCCGACG
TCATCACCGCTGCCGCCCGGCACGTTCTTGAACCTATTCGAGCTGGAATCGGCCGTCCGGTTGCTGGGAA
TTGCNGTTAAGAACTGGGCCT Clone Rv289 (SEQ ID NO. 353)
::::::::::::Rv289SP6.seq::::::::::::
GCTTTGCGCGCTTCTCCGAGAGGTTGGAGTGCCAACGCTCTGCCGATGCCCGAGCCGGCCCCGGTGATGA
CGGCGACCTTGCCTTCGAATGAGCTCATTTGACTACTCCCCGTGGTTGTCCCTGCGATTGGTGGAGGTGG
CCGCGCAGCCTTGCCCCGAGGTCGGCGATCGCGTCGCGGGCTTCGGGGAGCAAACTGACCTGCAGATGGA
AGTCGTGCCACATGCCCGCGAACCGGCGATGCTCGATGCTTGTTTTCGAAGCGGCGCAGGCGGTTCGATC
TTGTCCGCGTCAACGCAGATCGGATCGTCGCCCGCGGGTCTGCATGAAGAAT ::::::::::::Rv289T7.seq::::::::::: (SEQ ID NO. 354)
CTCACGCAGCCACGCCGTCACCTTTCCACGAAGACCTCACCTGCCGATCCGAAATGGAATCGGCCGTGAC
GGAAATTGGCGCAGCGAAACACTCAACGAGGTGGTGGCTTCGTCGCGAACCGTCACCCGAGTCGCGGTCA
CCGTGCGCACGGCGACGTTCTACACCCGCACCAACATCCGAAAGCTGCAAGCTCCCAGCACCGATCCCGA
CGTCATCACCGCTGCCGCCCGGCACGTTCTTGACCTATTCGAGCTGGATCGGCCCGTCCGGTTGCTGGGA
GTGCGGTTAGAAACTGGCCTAGAAACCGGCGGGCACACCGCACCTGGGCGGGGN Clone Rv28 (SEQ ID NO. 355)
::::::::::::Rv28SP6.seq:::::::::::
TGCTTCCGGCTCGTATGTTGTGTGGAATTGTGAGCGGATAACAATTTCACACAGGAAACAGCTATGACCA
TGATTACGCCAAGCTATTTAGGTGACACTATAGAATACTCAAGCTTGATGCCGCCGAAACCGAGCGTGAG
CACGCCGCCAGCCACCACNCGCGGGTCGGGCGCCGGGCCCGGGTCGCCANGCTGCTCCGCTCGGTGATGG
CACGCCACCGCGACACCACCCGGCTGCGCTACGTCGAGCCATACCGGGCGGAGCTACATCGGCTCGGCCG
CCCAGTGTTCGGGCCCTCTTTCGAAGTCGAAGTCGATACCGATTGCGCATCCGCNGCCGCA ::::::::::::Rv28T7.seq:::::::::: (SEQ ID NO. 356)
CAGGCATGCAAGCTTCACGTCCGTACGGCTCGGGTACGCTTCGGTCGCAGTGTGCGAGTGATAGATGACG
ACCGGGACCTCGTCTGCATCTTCCATAGCCCGCCACACCTTCAGTTGCTCACCGGAATCCAACCGGTAGA
AGGTCGGCGAGCGCTCGGCATTGGTCATCGGGATATGCCGCTCGGGACGGTCAGAACCCTCGGGTCCGGC
CAGCACTCCGCAGGCTTCGTCGGGGTGGTCGCGACGCGCATGGGCCACC Clone Rv290 (SEQ ID NO. 357)

TABLE 3-continued

End sequences of the polynucleotide inserts cloned in the named recombinant BAC vectors contained in the I-1945 *M. tuberculosis* H37Rv genomic DNA library. RvXXXSP6 corresponds to the SP6 endsequence of the clone RvXXX; RvXXXT7 corresponds to the T7 endsequence of the clone RvXXX. RvXXXIS 1081 corresponds to a region located close to a copy of the IS1081 repetitive sequence (Insertion element) The character << - >> denotes an uncertain base residue.

::::::::::::Rv290SP6.seq:::::::::::
GCTTGTCTATCGTCCCGGCCAGGTCCGGCCAGTCAAGGTCGAAGGCCAGTCCGGTCTCCTCTCCGACTAC
GGCCAAGAACTGGGCGACGGTGTCAGTGCAGACCAGCGGAAACTGGTGGCGCCCTAGGCGAGCGACCGCC
TCACAAACGGCGGTGACCGCGTTCTGGTCGTGCACCATCGAGCCGTGCCCAGCCCGGCCGCGTGCCGTCA
GCCGCATCCACTGGATGCCCTTCTCGGCGGTTTCAATCAGGTACAGGCGACGTTCGCCACCATCGTGCCG
GGGCACGGTTAGCGAGAAACCGCCGACTTCACGATTGCCTCGGTGATGCCGTCGAAACAGATCGGGCCT ::::::::::::Rv290T7.seq::::::::::: (SEQ ID NO. 358)
GCGCGCCATGTTGAGGTTGTCCGACGGTGACGACGGTGAACCACAACTGTTTGACCTGTCCGCACACACC
GTGTGGATCGGCGAGCGGACCCGACAAATCGATGGCGCGCACATCGCGTTTGCCCAGGTGATTGCTAATC
CGGTCGGGGTCAAGTTGGGCCCCAACATGACCCCGGAACTGGCCGTGGAGTACGTCGAGCGGCTCGACCC
GCACAATAAGCCGGGCCGGCTGACTTGGTGAGCAGGATGGGCAACCACAAGGTCCGCGATCTGTTGCCAC
CGATCGTGGAGAACGTCCATGCCACCGGGCATCAGGTCATCTGGC Clone Rv291 (SEQ ID NO. 359)
::::::::::::Rv291SP6.seq:::::::::::
TTGCCTTCCATGCCGAGCAAGGTCGACTCAGCGATGACGAATTGTTCTTCTTCGCGGGTGTTGCTGCTGG
TTGCGGGCTATGAGAGCACTGCTCATATGATTAGCACATTGTTTCTGACGCTGGCCGACTATCCAGATCA
GCTGACACTCCTTGCGCAGCAACCAGACCTGATCCCGCCGGCGATCGAGGA ::::::::::::Rv291T7.seq::::::::::: (SEQ ID NO. 360)
CGACGCTGGGCCCAACTGCGACCACCAGGTCCTGGTATGGCAGGACATGGCCGGGTTCAGCGGCGCCAAT
ACCG Clone Rv292 (SEQ ID NO. 361)
::::::::::::Rv292SP6.seq:::::::::::
TAACGACTCGGGTCCAGCGACCGCGCCAACACNAACGGCCGGACNACGTGGGCCAGGGTCGCGGCCTCCC
CTACAAACAGGATCCGTTGCCTGCGAACGACAGGCTCCGGTGCGGCGTTGGGCGCCGTGCTCGTCCCAGC
GTCCGGTCCCGGGTCGCCGGCGACGCTTGTTTCCTCCATACTCGCCCCCTAATCTCGAGGCAGCCCGTAC
CCGCAGGCAACCTCCCAAAAATGCAATCCCCCAAAATGCAATGCGTCNAGCTATTTCTCACACCGACCGC
TAGTTGCGGATCANAAATCCGTTGGGCGCGGA ::::::::::::Rv292T7.seq::::::::::: (SEQ ID NO. 362)
CNTGGCGGTGGGTGCGGTGTCGAACACGACCACACTTCTTTGCGGTTCGGTGATCTCGACACCGGCCGCG
AGCCGACCACCATGCGCGCGTAGATCGGCGATCAGCGCGTCGGCTATCGCCTGGGTGCCGCCCACCGGAA
TCGGCCAGCCGACCGAATGGGCCAGCGTTGCCATCATCAGTCCGGCGCCGGCCGACACCAGTGACGGCAA
CGGTGAAATCNCGTGGGCGGCAACGCCGGTGAACAACGCGCGGGCATCCTCGCCCGCCAGCGACCGCCAG
GCAGGGGTGCCCTGGGCCAGCATCCGCAGCCCGAGACNCAGGACCGANCCCAGTG Clone Rv293 (SEQ ID NO. 363)
:::::::::::::Rv293SP6.seq::::::::::::
GCTTTTCNGATCGCAGCGAGTCGTACCCGCGCCGGTCACCTTCGTGGATATCGCCGGCCTGGTCAAGGGG
GCGTCCGAGGGAGCCGGGCTGGGTAACAAGTTCCTGGCTCATATCCGCGAATGCNACGCCATTTGTCAGG
TGGTGCGGGTGTTCGTCAACAACNACTTGACTCATGTCACCGGACGGGTCGATCCCCANTCCGACATTGA
GGTCGTCGANACCGAGCTGATCCTGGCANATCTGCAAACCCTGGAGCGGGCCACGGGCCGGCTGGAGAAG
GAANCGCGCACCAACAAGGCGCGCAAGCCGGTCTACGACGCGGCACTGCGTGCCCAGCAGGTGCTCGACG
CCGGCAANACGCTGTTCGCCGCGGGGGTGGATGCCG :::::::::::::Rv293T7.seq:::::::::::: (SEQ ID NO. 364)
GTCGTACGCCATTNGTCGGTGTGCGCATACCAGTACGACGCGCCGGGCACCTGACGCGGCGGCCGCGACC
AGTCGGTGGCCATCGCCATCGTCTGCCACCCGGTCAACGGACGCACCTTCTCCTGGCCGACGTAGTGCGC
CCACCCGCCGCCGTTGCGTCCCATCNATCCGGTCAACATGAGCAGCGCCAACACCGAGCGGTACATGACA
TCGCTGTGGAACCAGTGACAGATTCCGCCGCCCATGATGATCATCGACCGTCCTCCGGATTCGGTCGCGT
TGCGGGCGAAATTCCTTGGCAAACCGGATTGCCTGCGCGGCCGGCACACCGGTGATCGACTCCTGCCAGG
CCGGGGTGTTCTGCTGGGTTCGGTCGTGGTACCGGT Clone Rv294 (SEQ ID NO. 365)
::::::::::::Rv294SP6.seq::::::::::::
GCGAGGCGGTATCGCTTCCCGTCGTACCGGCGACCGCCAGCCGAGAAGCTCGTTTTCCCAGTGTTGCTGG
GGATTCTCACGCTGCTGCTGANTGCGTGCCANACCGCTTCCGCTTCGGGTTACAACGAGCCGCGGGGCTA
CGATCGTGCGACGCTGAANTTGGTGTTCTCCATGGACTTGGGGATGTGCCTGAACCGGTTCACCTACNAC
TCCAAGCTGGCGCCGTCTCGTCCGCAGGTCGTTGCTTGCGATAGCCGGGAGGCCCGGATCCGCAATGACG
GATTCCATGCCAACGCTCCGAGTTGCATGCGGATCGAATACNAATTGATCACCCA ::::::::::::Rv294T7.seq::::::::::: (SEQ ID NO. 366)
TGGGTCTTGCCGGCGAGCCCAGCGAAGTCGCTAGCGTGGCCGTGTTTCTTGGCTTCGGATCTATCCTCGT
TACATGACCGGCACCGTGTTGGACGTGACTGGCGGCCGGTTCATATGACACCGAGATCATTGCCACGGTA
CGGCAATTCGTCAAGAAGGAAATCTTTCCCNATGCACCGGCCCTCGAACGTGGCAACAGCTACCCGCAAG
AAATCGTCGATCGGCTGGGTGTTATTGGCTTGCTCGGTCGCCGGCTGCAAGGGTATCGACACCACCGAGT
TCATTCTCGGGCGTGCCGGCGCATTCGAGCTGGCGGTGCGCGCTGCCCAGCACCGTCATAAGTACTTGAN
GATGGTCAAACGTCGGACGAACCGCCACCACGTCGCTGCCGAACGG TABLE 3-continued End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character << - >> denotes an uncertain base residue.

Clone Rv295 (SEQ ID NO. 367)
::::::::::::Rv295SP6.seq::::::::::::
TAGATGCCCAAGCTTGCCNTTANAGACCTCGTCGACCAAGCACGGACGCGACCGTCGAAGGTGGCGAATC
CGGGCTTGGCGTCNACCCGCGTAAGGCAGACCAGATGGTTCGCGGCACGGTCAACCTGCCACACGGCACT
GGTAAGACTGCCCGCGTCGCGGTATTCGCGGTTGGTGAAAAGGCCGATGCTGCCGTTGCCGCGGGGGCGG
ATGTTGTCGGGAGTGACGATCTGATCGAGAGGATTCAGGGCGGCTGGCTGGA ::::::::::::Rv295T7.seq:::::::::::: (SEQ ID NO. 368)
TCTCCACGGCGTGGATCAAGGTACCGGCCGGGATGTTGCGCAATGGCAGGTTGTTGCCCGGCTTGATGTC
TGCGTTAGCGCCGGATTCCACCACATCCCCTTGCGAAAAGTCCGTTGGGTGCAATGATGTAGCGCTTCTC
CCCATCGAGATAGTGGAGCAACGCAATCCGTGCGGTACGGTTCGGGTCGTACTCGATGTGCGCGACCTTG
GCGTTGACACCATCTTTGTCATTGCGGCGAAAGTCGATCATCCGGTAAGCGCGCTTATGACCGCCGCCTT
TGTGCCGGGTNGGTAATCCGGCC Clone Rv296 (SEQ ID NO. 369)
::::::::::::Rv296SP6.seq::::::::::::
GCCCGGTTCGATCGGGCATGTCCGCAGTCGTCGTTACCGGAGGCGGTCGTGGCCGCGCTAATCGGCGTCG
GCGCCGACAAGATGTGGGATATCCGCAATCGGGGCGTCATCCCTGCGGGCGCGCTCCCCCGCGTCCGAGC
CTTCGTCGACGCAATCGAGGCAAGTCACGACGCGGATGAGGGGCAGCAGTGAATTACAGCGAGGTCGAGC
TGTTGAGTCGCGCTCATCAACTGTTCGCCGGAAACAGTCGGCGACCGGGGTTGGATGCGGGCACCACACC
CTACGGGGGATCTGCTGTCTCGGGCTGCCGACCTGAATGTNGGTGCGGGCANCGCCGGTATCNACTCCCG
TGGAACACAGCCGGGGC ::::::::::::Rv296T7.seq:::::::::::: (SEQ ID NO. 370)
CTCGGCGTGGATATCGGTGTAGCCGGCGCCGGTGAANGTCGGCTCCTTACGTCCACTCGACAACAGCTCA
TAGCGATCCAACCAGTANGCAACCGCCTTCAGCAGTACAACCGCGCCGGCGAACACTGCGAGTTGAACGC
GAGCTGCCTGGGTCAGCATGCCTCTGCCGGTTGTCAGCCGAAGGCCGCCGAACAGGTAATGCGTCAACAG
GCTCGCTAGAAACGCCAGAACCACGGCCACGAACAGCCAGTTCAGCACCGACCGGTAGAACGGCAGATCG
AAGACGAAAAAACCCAATGTCATAGCCGAATTCGGGGTCCACGATGCCAAAGGTGCCCCCGTGTACAACA
ACTGAACCTTCACCCA Clone Rv29 (SEQ ID NO. 371)
::::::::::::Rv29SP6.seq::::::::::::
TCCGGCTCGTATGTTGTGTGGAATTGTGAGCGGATAACAATTTCACACAGGAAACAGCTATGACCATGAT
TACGCCAAGCTATTTAGGTGACACTATAGAATACTCAAGCTTCACGTCCGTACGGCTCGGGTACGCTTCG
GTCGCAGTGTGCGAGTGATAGATGACGACCGGGACCTCGTCGGCATCTTCCATAGCCCGCCACACCTTCA
GTTGCTCACCGGAATCCAACCGGTAGAAGGTCGGCGAGCGCTCGGCATTGGTCATCGGGATATGCCGCTC
GGGACGGTCAGAGCCCTCGGGTCCGGCCAGCACTCCGCAGGCTTCGTCGGGGTGGTCGCGACGCGCATGG
GCCACCATCGCATTCACCAGGTCTGCGCGAATCACCAGCACGTAGACGGTTCCTTTCCTAAGCAACACCG
AAGTTTCAGGACCGAATGCTCCGGGAAACATGTCA ::::::::::::Rv29T7.seq:::::::::::: (SEQ ID NO. 372)
CAGGCATGCAAGCTTGATGCCGCCGAAACCGAGCGTGAGCACGCCGCCAGCCACCACGCCCGGGTCGGGC
GCCGGGCCCGGGCCGCCAGGCTGCTCCGCTCGGTGATGGCACGCCACCGCGACACCACCCGGCTGCGCTA
CGTCGAGCCATACCGGGCGGAGCTCCATCCGCTCGGCCGCCAGTGTCCGGGCCCTC Clone Rv2 (SEQ ID NO. 373)
::::::::::::Rv2SP6.seq::::::::::::
CCTGCATCCGGCTCGTATGTTGTGTGGAATTGTGANCGGATAACAATTTCACACAGGAAACAGCTATGAC
CATGATTACGCCAAGCTATTTAGGTGACACTATAGAATACTCAAGCTTCCAATCCCCCTGCCCTGATACG
CGTCGGCAACCGTGAACGCGATCTCGGCGACCGTCGGATCGGTTTCATCCCGCACAAAACGCGCGTCGGC
TACGGGGTCGCTTCCGTCGGTCACCACCCAGACGAAGTGGTCGACGTAGTCGACTTCCGACAGGTAGTGC
ATCAACGCCGGACTGGGAACACNAGCCGACATGAACCGTCGATACAGCGTCTCNCCGGAGAACTGGATGT
GTCCGTGCACGGTCCGCTCGCGGTCACCGGGCAGCACGGGGCGTAACATCAGTTGAGTCCCGTCGGCAAG
CCGTACCGGAATCGGGGAGACGA ::::::::::::Rv2T7.seq:::::::::::: (SEQ ID NO. 374)
CAAGATGATCGCCGGTGCCACCCCGATCCGTGCCTCGGTCAGCGCGAACGTGCTTTCCGGTCCGGCGACC
ACCATGTCGCACGCACCGACCAGGCCGAACCCGCCGGCCCGCACATGCCCGTTGATGGCGCCGACCACCG
GCAGCGGCGACTCGACGATGGCGCGCAACAGCGCCGTCATTTCCCGCGCCCGCGCCACCGCCATCCGGTA
CGGATCACCACCACCACCGCCGGCCTCGCTGAGGTCCGCGCCGGCGCAGAACGTTCCGCCGGTATGCCCC
AGCACGACCAGCCGCACCGCCGGATCTGCTTCGGCCGCACTCAGCCCTTGATGTAGTTGGCTGACCAGCG
TGCTCGACAGCGCGTTGCGGTTGTGCGGAGAGTTCAGTGTCAGCCTGGCGAAGGGGCCGCCGCAGGCGGC
CGGGCCAGCGTAGTCGACGGGGCTG Clone Rv301 (SEQ ID NO. 375)
::::::::::::Rv301SP6.seq::::::::::::
CTCAAGCTTCGATCGACAGTACTCCCGCCTTGGGTCTGGTCTTCGAGCTGGTCGGTCATGGTCGGACCTG
CTGGTAGTGGGGATCTAACGCAACATGGTCGGGATTCATCATGGTGTACCCGTGATACCCATTCGCAGCT
GCCGGTGAAACCCCGCGATGCCGGGATTTCCAGCCGCACTAGGATGTCTAGCCGGCCAGCCGCTGCCGCC TABLE 3-continued End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character << - >> denotes an uncertain base residue.

GGACTTCGGGATGTTCGGTATACCACCGATCGGCAATCTTGCNTATCCGCCGATGCTCGAACGCTAGCCA
CCCCAAACCAACCACTGTGACNACAATC

::::::::::::Rv301T7.seq:::::::::::: (SEQ ID NO. 376)
TGAATTTCCCGATCCCACAATCTCGGTTCAGATACAGGTCGCCATACCCCTTACTTCGGCAACGCTGGGC
GGATTGGCCCTGCCGCTGCAGCAGACCATCGACGCCATCGAATTGCCGGCAATCTCGTTCAGCCAATCCA
TACCCATCGACATTCCGCCGATCGACATCCCGGCCTCCACTATCAACGGAATTTCGATGTCGGAGGTCGT
GCCGATCGATGTGTCCGTCGACATTCCGG Clone Rv302 (SEQ ID NO. 377)
::::::::::::Rv302SP6.seq::::::::::::
TACTCAAGCTTGAACGCTGCGAGCGAGCCCATGTAGAGCGTTTGGTACCAAACCGATCGGTGGGCCAACT
TGCCATGGGCTCACAGCGGCTATCGCGAGCGTGTAGCCGATCATCGGCCAGGCGACGGTGGCCTGAGCGG
CAGGGGTTGCCTTATCCATCCTCTTGCGGCATGGTTGCCGCAGGGAGTGCCGGTAAGTCTGGTCGGCAAC
CTGGCCCGCTGCGGGTTGGGTTCGGATTCCCTCGGCTAGTAAGGTGCTCGCCTGGTGTTACAACGAATCG
CTAGACAGCTCTTATCGGGAGTGGCCGTCGCGATCGTTGCGCTGCCGCTGGCGATCGCGTTCGGCNTTAC
CGCCACCGGAACGTCCCAAGGTGCGCTCATCGGGCTCTACGGCGCCATCTTCGCCGGATTCTTCCCNGCC
GTGTTCGGTGG ::::::::::::Rv302T7.seq:::::::::::: (SEQ ID NO. 378)
GCGGTGTCTGAACTTCGCCCGTTCCCTCCAGCGCATTGAGCTTCAGCCCGACCGGCAGGTAGGGAGTCGG
CATGCGGTCCTTCGCCCCGACCCCGCTGGCTAAATAGCCACCCCCGAGCGCGGTCACGGTCTTTGCACCG
GGACGACGGCATACCGGCAGCGCGAACATCGCCGCGGGCTGCAGCGTGAACGTCGAATACGAGTCGAACA
GTGTCGGCGCGTAAAAACCCGAGCCGGCGGTCGCTTCGGTAATCAACGGCTCCTGCGCAACCAGCTGCAA
NTCNCCGGTGCCACCGGCGTTGACAATCTTGATNTCGGCGACCTCGCGCACCAN Clone Rv303 (SEQ ID NO. 379)
::::::::::::Rv3033P6.seq::::::::::::
TACTCAGCTTCGGCTCAGGTGGTGCTGCTGGTAAAGTTCNCTGAACGGTGCAGGTTTCGACAATGTGGTG
CCGGTTCGGCGGGTACTGCCATCGAGACACTGGCGCAGGCTATCGCACCCGTTATCGGCTACAAACAAAT
CGCGGTATGCGTTCTTGAGCATGAGTCGGCGACCGTCGTCATGGTCGACACCCACGACGGAAAGACGCAG
ATCGCCGTCAAGCNTGTGTGCCGCGGATTATCAGGACTGACCTCCTGGCTGACCGGCNTGTTTGGTCNCG
ATGCCTGGCGCCCGGCCGGCGT ::::::::::::Rv303T7.seq:::::::::::: (SEQ ID NO. 380)
CATCACCTGGTTCATGAAACTGGAAGCAGCGCAGCGCTTCCTTTTCGGCCGCAACATGAGCCAGCCTCTC
GTCGGCGGTCGGGTGCAGGTGCTCGGGCAGCTCGGCCGCGACAGCCGCCTGACCCTGAAACCAGCTTCCA
TATCCCGCGACGAACGACGCCAGTCCGCTACGTAACCCCTCCGCGACTGTCCATGGACAACANCGCGTTC
TCCACCGACCGGGCCCGGGTGTGGGGTGTT Clone Rv304 (SEQ ID NO. 381)
::::::::::::Rv304SP6.seq::::::::::::
CTCAAGCTTCCCGGCGGCCAGTACCGAAAGCGCGAACAGCTCGCGGCAGCCCACAACNTGCTGCGTCGGA
TTGCCGGCGGCGANATCAATTCCAGGCAGCTCCCGGACAATGCGGCTCTGCTGGCCCGCAACGAAGGACT
CGAGGTCACCCCGGTGCCCGGGGTCGTGGTGCACCTGCCGATCGCACAGGTTGGCCCACAACCGGCCGCT
TGATGCCCGGTCGGCAAGCCCGGCAGTTGCCAAACCCAGCGTGATCAGGCTCGGCTCGCGAGTTCGGCGA
AGAAGTGGCTCGCCTGATCACCTACCATCGGCCAGGATCTGCGTGTCATCACNACGCTCGCCAAGGAGGT
TGTTGTGGTGCT ::::::::::::Rv304T7.seq:::::::::::: (SEQ ID NO. 382)
GCCACGTTTCGCGCCGCCCGGCATACGGCGGCGTACCGATCTCCGCGTCATACACCCGCGGGTAATCGCC
GACGGTGCCGGTTCGCGAGCCGAAGGTGACGACGCTGATTGAATCGAGTTCCAGGTCCAGCGGGTGGCGC
AGCAACGGCGCGAGCTCAACGACGTCAATCACGTTGTCGCTTTCTACGGTCACCGACCCGGTGACCGTAG
TCGCCCGGTGCGCTCGGCCGAGAAGTTGCACCGCCACCACCGCGACACCGTCTTGCACGCGGACGCCACC
CCCGGATCGGTTGTTGGCCAAGGTAATTGGGTCATTCCATTTGACGGGACGCCGACCCCGCAGCCCCAGT
ACCGCCCACGACCACGCCGGCTGACCCCACCACTGTACGAACACCAAGGCGACGCCGACCA Clone Rv306 (SEQ ID NO. 383)
::::::::::::Rv306SP6.seq::::::::::::
CTCAAGCTTGATGCCGCCTAAACCGAAGCGTGAGCACGCCGCCACCCACCACGCGCGGGTCGGGCGCCGG
GCCCGGGCCGCCAGGCTGCTCCGCTCGGTGATGGCACGCCACCGCGACACCACCCGGCTGCGCTACGTCA
AGCCATACCGGGCGGAGCTACATCGGCTCGGCCGCCCAGTGTTCGGGCCCTCTTTCGAGGTCNAGGTCNA
TACCGATTTGCGCATCCGCAGCCGCACCCTGGACGACAGAACCGTGCCCTACGAGTGCTTGTCGGGCGGG
GCCAAAGAACANCTTGGCATCCTGGCGCGATTGGCCGGCGCGGTCCTGGTC ::::::::::::Rv306T7.seq:::::::::::: (SEQ ID NO. 384)
CTCGGGTACGCTTCGGTCGCAGTGTGCGAGTGATAGATGACGACCGGGACCTCGTCGGCATCTTCCATAG
CCCGCCACACCTTCAGTTGCTCACCGGAATCCAACCGGTANAANGTCGGCGAGCGCTCGGCATTGGTCAT
CGGGATATGCCGCTCGGGACGGTCAGAGCCCTCGGGTCCGGCCAGCACTCCGCAGGCTTCGTCGGGGTGG
TCGCGACNCGCATGGGCCACCATCGCATTCACCAGGTCTGCGCG TABLE 3-continued End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character << - >> denotes an uncertain base residue.

Clone Rv307 (SEQ ID NO. 385)
::::::::::::Rv307SP6.seq::::::::::::
CTCAAGCTTCAATTCCTCCACGACGCGTTCCCAAATGAATTTCCCGATCCCACAATCTCGGTTCAGATAC
AGGTCGCCATACCCCTTACTTCGGCAACGCTGGGCGGATTGGCCCTGCCGCTGCAGCAAACCATCGACGC
CATCGAATTGCCGGCAATCTCGTTCAGCCAATCCATACCCATCGACATTCCGCCGATCGACATCCCGGCC
TCCACTATCAACGGAATTTCGATGTCGGAGGTCGTGCCGATCGATNTNTCCGTCNACATTCCGGNGGTCA
CCATCACCGGCACCAGNATCGACCCGATTCCGCTGAACTTCGACGTTCTCAGCAGCGCCGGAACCA ::::::::::::Rv307T7.seq::::::::::: (SEQ ID NO. 386)
TTAACCCCCGTGGCCTCTACGCCGCCTNCGGGTCGAACATGCATCCCGAGCANATGCTCGAGCGCGCACC
CCACTCGCCGATGGCCGGAACCGGCTGGTTACCCGGGTGGCGGCTGACGTTCGGCGGCGAGGACATCGGC
TGGGAAGGGGCGCTTGCCACCGTCGTCGAAGACCCAGATTCGAAGGTGTTCGTCGTGCTCTACGACATGA
CCCCGGCGGACGAGAAGAACCTTGACCGGTGGGAAGGCTCCGAGTTCGGCATCCACCANAAGATCCGATG
CCGCGTT Clone Rv308 (SEQ ID NO. 387)
::::::::::::Rv308SP6.seq::::::::::::
CTCAAGCTTGATTTTGATCATCATGGATGATCATCACCCGAAGTGTGGTAGCCGCAGTGGTTATCGTGGG
TACCGTCGTGCTTTCCATGGGCGCCTCTTTCGGGCTTTCCGTATTGGTCTGGCAGGACATTCTGGGTATC
GAGTTGTACTGGATGGTGTTGGCGATGTCGGTGATCCTGCTCCTGGCGGTGGGATCCGACTACAATCTGC
TGCTGATTTCCCGGTTGAAAAANGAAATTGGGGCCGGATTGAACACCGGAATTATCCGTGCCATGGCTGG
TACCGGGGGAGTGGTGACGGCTGCCGGCATGGTGTTCGCCGTTACCATGTCGTTGTTTGTGTTCAGCGAT
TTGCGAATTATTGGTCAGAT ::::::::::::Rv308T7.seq::::::::::: (SEQ ID NO. 388)
CGNCCAACCCGAATTGGTTTTCGGCGCCNTCGGTGAGGACGGCGTGCGGGTGCTCAACGACGACGTCGTC
CGCGGGACACACCTCGATGCTGCCGCCATGGACGCGGTCGAACGCAAGCAGCTGATCGAGCTACAACGCC
GCGCGGAACGCTTCCGCCNCNGGCGTTACCGCATCCCGTTGACCGGGCGGATCGCGGTGATCGTCGATGA
CGGCATCGCCACCGGAGCGACGGCCAAGGCGGCGTGCCAGGTCGCCCGGGCGCACGGTGCGGACAAGGTG
GTGCTGGCGGTCCCGATCGGCCCANACGACATCGTGGCGAGATTCGCCGG Clone Rv309 (SEQ ID NO. 389)
::::::::::::Rv309SP6.seq::::::::::::
CGTGACTGCCACCGGGGCCACTCCGCAGAATCTGTACCCGACCAAGATCTACACCATCGAATACGACGGC
GTCGCCGACTTTCCGCGGTACCCGCTCAACTTTGTGTCNACCCTCAACGCCATTGCCGGCACCTACTACG
TGCACTCCAACTACTTCATCCTGACGCCGGAACAAATTGACNCAGCGGTTCCNCTGACCAATACGGTCGG
TCCCACGATGACCCANTACTACNTCATTCGCACGGANAACCTGCCGCTGCTAGAGCCACTGCGATCGGTG
CCGATCGTGGGGAACCCACTGGCGAACCTGGTTCAACCAAACTTGAAGGTGATTGTTAACCTGGGG ::::::::::::Rv309T7.seq::::::::::: (SEQ ID NO. 390)
TCGCTCAAGCGCNTGAGGCCGAANCGGCTGGTTACGACTCCCTGTTTGTGATGGACCACTTCTACCAACT
GCCCATGTTGGGGACGCCCGACCAGCCGATGCTGGAGGCCTACACGGCCCTTGGTGCGCTGGCCACGGCG
ACCGAGCGGCTGCAACTGGGCGCGTTGGTCACCGGCAATACCTACCGCAGCCCGACCCTGCTGGCAAAGA
TCATCACCACGCTCGACGTGGTTAGCGCCGGTCGAGCGATCCTCGGCATTGGAGCCGGTTGGTTTGAGCT
GGAACACCGCCAGCTCGGCTTCGAGTTCGGCACTTTCAGTGACCGGTTCAACCGGCTCGAAAAGGCGCTA
CANAT Clone Rv30 (SEQ ID NO. 391)
::::::::::::Rv30SP6.seq::::::::::::
ATACTCAAGCTTCCGCTGGGGCCTGTTCAACCATGGCGATCCCGTTGGTCCCGGACATCCCGAACGAGGA
CACCGCGACCCNCTTCGGTGTGTGATCATTACCGTTGGGCCACTGCGTAACCGCTTGCGGCACAAAGAGC
CCGGTCTCGACGTCGGAAAGCTCATCGGGCACCCGATTGAAATGCAGCAGCGGCGGCACCACCCCGTGCC
GCAGTGACAGAATTGCCTTGATCAGCCCGACGGTCCCCGCCGATGCCGTGCTGTGCCCCATGTTGCTCTT
GGCCGATCCAAGCGCGCAGGGGGTGCCCGCGCCATACACCCGCGCCAGGCTGCGGTACTCAATCGGGTCG
CCGATTGGCGTACCGGTGCCGTGCGCCTCCACCACACCGACCGTTTCGGGCTG ::::::::::::Rv30T7PEG.seq:::::::::::: (SEQ ID NO. 392)
CAACAGCGTTCCAGCGGCATACCACCGCACATGCCGTGCACCCGGCGCCGGGCGGAGTCGCCGCATAACA
CANGTACACCTTGGGAATCGGTGTGCGCCAGGGATTCNACCGCGGGGTGGGGCCGGCGATCGCGCGCCAG
GTCGAGTTGGCGCCGACCGTGATNTCACCGCCGACGTAGTTGGCGTTGTGGTCCGCCATCCGCGCGGCGG
GCACGGCGCGGGCCGCCACCACGATGTCACGGAAGCCGGGGGCGAACGCTCGACGACCTGGTTACCGTCT
CNGTCGCNTCNANCGTGGACCCGACNGCACGTGGGCATATGTCCANAACGGACGNGGCCGGTTTCNTCGA
TGCNGCCGGGGTCCGCGACNTGCGGACNCNCNGNCACACCATCCGCCAGTCCGCGTGGCGTCCCGCCGCG
ACTCTGCCTCGGCCGCGCCA Clone Rv310 (SEQ ID NO. 393)
::::::::::::Rv310SP6.seq::::::::::::
CTCAAGCTTTGNCGACGATCGGGCGATGTCGATGANAGGAAACCCCAGCGCACAACCGACNATTTTGGCG
TAGCCGGCGGACNTCTGCTCGATTCCGATCACGTCGGCGCTCGCATCGAGCATGGCGCCGGCGACGGCTA
GCAGCGATCCGCCGTCGTCGAGGAACACGACACGAGCCGTACGCCCGGCCGTAAGCCGCGCCCAGGATTC
GGCGAAAAACCGTTCTACGTGGCGGGTGTACTGGGTGTCCAATGATTCGTGGGGTGCGTAGGCGTCGCTG TABLE 3-continued End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character << - >> denotes an uncertain base residue.

CAATCGTCGACATAAATGCCGTCGGCCCGCATCGCGTCAACAACTCCCGGGTGAGTGGAATANCACTTGC
CGA

:::::::::::::Rv310T7.seq::::::::::::: (SEQ ID NO. 394)
TCCAACGCGGTGACAGATTTGTCTATCCTGGACCTGACGGTGAGGTCGAAGTTTTCCAGGAATTCGGCAA
AATCGGTAAGAGCCTGAAGAATTCGGTATCGCCGGACGAAATCTGCGACGCATACGGGGCAGATACGCTT
CGGGTTTACGAGATGTCGATGGGGCCGCTGGAGGCTTCACGTCCATGGGCCACAAAGGATGTTGTCGGCG
CGTACCGTTTTCTGCAGCGGGTGTGGCGCTTGGTCGTCGACGAGCACACCGGCGAAACTCGGGTGGCTGA
CGGCGTGGAACTCGACATCGATACGCTACGGGCGTTGCACCGCACCATCGTCGGCGTGTC Clone Rv311 (SEQ ID NO. 395)
:::::::::::::Rv311SP6.seq:::::::::::::
CTCGTCCTTGACTACGCCCAGTATCGAAANCCTCCTGTGCCGGTNCGCTAAACACCCGGCGGACACTCAN
ACGGTGCTGGTGGTGCGGCATGGCACCGCGGGCAGCAAAGCGCACTTCTCCGGGGACGACAGCAAGCGAC
CGCTAGACAAGAGGGGTCGTGCGCAGGCAGAAGCGTTGGTACCACAGCTGCTGGCGTTCGGCGCCACCGA
TGTTTATGCCGCCGACCGGGTGCGCTGCCACCANACNATGGAGCCACTCGCCGCGGAACTGAACGTGACC
ATACACAACGAGCCCNCCCTGACCGAAGAGTCCTACGCCAACAACCCCAAACGCGGCCGACACCGAGTGC
TGCAGATCTTCG :::::::::::::Rv311T7.seq::::::::::::: (SEQ ID NO. 396)
GTATCGCCTCCNCCTTTGGCCACCAGCAGCCACAGCGCGGTTCGCGGACCGAACGTGGACATCAATAGCC
CGGAATCGGTGTGTGCAAGTTGGTAAACGGTGTTGATCCCAAGCTTTGCCAGCCTTTTCGTAGTCTTGGG
CCCCACACCCCACAGTGCTTCGACGGTACGGTCACCCATGATGGCCATCCAGTTGGCATCGGTGAGCTGA
TAGATGCCAGCTGGTTTCGCCAACCCGGTAGCGATCTTGGCGCGCTGCTTGTTGTCACTGATACCTATCG
AGCAAGACAGCCCGGTTTGCGACAAGATGACTTTTCGGATCTCTTCNGCGAACTTCCAATGGGGGTCTCC
GGGANT Clone 312 (SEQ ID NO. 397)
:::::::::::::Rv312SP6.seq:::::::::::::
CTCAAGCTTTTGGTCTAGCCGGCCGAGCACGATACGGGTGTCCTTGGCCACCGGCGGCGGCTGTCCGGGA
AATGGCGGGTCCCCGGTGGTTTTGCTGANGANTGCTGAACCGTAGTCGAAGTGGGCGGCGTCAGACTCCA
CCCAGCCAGCAGGCAGCGCGAAGCTGAATCCTCCAACCGGGTTGTCGATCCGGACAGGTTGGGGTGCGTT
TGGGGCAATGACAGGTGGCGGCGGTGCGTTCGGGTCGGCCGGCGGAGGTGCTGCGTTGGGATCNCCCGGC
TGGGCATTCGGCNTNTTGGCGGCGGCCGGTGGTGGGGGGGCAACANGTGTCCCGGTGCGGGTGGCGCTGC :::::::::::::Rv312T7.seq::::::::::::: (SEQ ID NO. 398)
ATCTGTACCCGACCAAGATCTACACCATCGAATACGACGGCGTCGCCGACTTTCCGCGGTACCCGCTCAA
CTTTGTGTCGACCCTCAACGCCATTGCCGGCACCTACTACGTGCACTCCAACTACTTCATCCTGACGCCG
GAACAAATTGACGCAGCGGTTCCGCTGACCAATACGGTCGGTCCCACGATGACCCAGTACTACATCATTC
GCACGGAGAACCTGCCGCTGCTAGAGCCACTGCGATCGGTGCCGATCGTGGGGAACCCACTGGCGAACCT
GGTTCAACCAAACTTGAAGGTGATTGTTAACCTGGGCTACGGCGACCCGGCCTATGGTTATTCGACCTCG
CCGCC Clone Rv313 (SEQ ID NO. 399)
:::::::::::::Rv313SP6.seq:::::::::::::
CTCAAGCTTGCAATGCGGGTCGGGATGCCCATGGTTGGAANATGGTCGCCCTGGCGTCNAATACGCGCGA
GCGCATGAGCTCACCGGTTCGGAACAACGTATCGAAAAACGTCGCACTGCTGGCAGATGGTATCTCCGAT
GTGGTTGTAATTTGTATCCCAACTCTAACTGTGCTATCGGATCAGCGTGAATATCGANATATTGCGAATG
CGATGACAGGCCGCCATTCGGTTTATTCGCTTACGCTTCCCGGGTTCGATTCGTCTGATGCACTGCCGCA
AAACGCGGATATGATTGTTGAAACCGTATCTAACGCAATTATTGATGTGGTAGGCGGCAGCTGCCGTTTT
GTGCTGTCGG :::::::::::::Rv313T7.seq::::::::::::: (SEQ ID NO. 400)
CAAATACACGCCGGACGCACAGGCGGACATCGCCATCCCGAGCACACCCAAAACGGGATACAGGATGGAG
GCCAACGCCACGGCCGCGCCCAGGATCACCAACCACACCGGCTTGGTCAGCTTGTCGGCGGCGGTATAGG
CATCGGGCCGCTGCAACGCAGCATGCACAAACGCGTACACCGCTGTCACCAAGACGGCGACCAGCAATAC
CAGCATGACGGTACCCACGAGGTGGCTCACGCATTCAGACTATGCGGTTTGCATCCAACACG Clone Rv314 (SEQ ID NO. 401)
:::::::::::::Rv314SP6.seq:::::::::::::
CTCGTCCTTCGGCCTCGCTGCAGGAGTGGGAGCCGCAGGGCTGGAAATCCGAAAAACGAGCCGGTGATCG
CACTGTCGCCGATCGGCGCCGCACCTGGTTGGTGTTACGGATGAATCCGCAGCGAAATGTGGCTGCGGTG
GCGTGTCGTGACTCGTTGGCGTCGACGCTGGTGGCAGCCACCGAGCGGTTGGTCCAGGATCTGGATGGGC
AAAGTTGTGCGGCCCGGCCGGTGACGGCCGATGAGCTGACCGAGGTCGACAGCGCCGTGTTGGCTGACTT
GGAACCGACATGGAGTCGCCCCGGTT :::::::::::::Rv314T7.seq::::::::::::: (SEQ ID NO. 402)
GTCTAGNCCGCCGAACACGATACGGGTGTCATTGGCCACCGGCGGCGGCTGTCCGGGAAATGGCGGGTCC
CCGGTGGTTTTGCTGAAGANTGCTGAACCGTAGTCGAAGTGGGCGGCGTCAGACTCCACCCAGCCAGCAG
GCAGCGCGAAGCTGAATCCTCCAACCGGGTTGTCGATCCGGACAGGTTGGGGTGCGTTTGGGGCAATGAC
AGGTGGCGGCGGTGCGTTCGGGTCGGCCGGCGGAAGTGCTGCGTTGGGATCGCCCGGCTGGGCATTCGGC TABLE 3-continued End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character << - >> denotes an uncertain base residue.

GTGTTGGCGGCGGCCGGTGG

Clone Rv315 (SEQ ID NO. 403)
:::::::::::::Rv315SP6.seq:::::::::::::
ACTCAAGCTTGAGATTGGCGTCAACGGGTGTCGGCACCGGCGTCCTGCAGTTGGTAGGCCTGCAGTTTGT
GCATCAGGCCGATGCCGCGGCCCTCGTGGCCACGCATGTACANCACCACGCCGCGCCCCTCACGGGCGAC
CATCGCCAGCGCGGCGTCCAGCTGAGGCCCGCAATCGCAGCGGCGTGACCCAAACACATCGCCGGTCAAG
CA
CTCCGAATGCACCCGGACCAGCACGTCG
TCACCGTCGGCGTTGGGCCCGGCGATCTCGCCGCGGACCAGCGCGACATGTTCCACGTCCTCGTAAATGC
TGGTGTANCCGATGGCGCGAAACTCCCCATGACAANTCGGAATCCCGCGCCTCGGCGACCCCGCTCAATG
TTGCTTCTCNTGCTTG :::::::::::::Rv315T7.seq::::::::::::: (SEQ ID NO. 404)
TCGACNAGCATTCTTGACNGTTGTTTTGGCTCGGCATGGTTAGCCAAGGTTCTGCGGTCCCACCAGATCA
TCTTGGTCCGGTAGCGCTCGTCCGGGTATGCTGCCGCCGGGATTCTCGCTGCTATTACTCCCCCCGAAGA
ACGCCACCGGTCCAGCGCGTGGGCCGCCGCGGTCCCCATCACAAACTGAACCCCCAACAGGGGACATGCT
TAGCGGTAGGGCGCGCGCCAAGGCGGCAGCAATCGCATCACTGCGCTGCGCGTCACTATTAACCCACCCG
GACTTCACTTCACGACCCCGAATGGCGCCCGGTCATTGATCATCTTGCGCACCGCGGATAATCCGGGAT
TG Clone Rv316 (SEQ ID NO. 405)
:::::::::::::Rv316SP6.seq:::::::::::::
ACCGGGGCCACTCCGCACAATCTGTACCCGACCAANATCTACACCATCGAATACGACGGCGTCGCCGACT
TTCCGCGGTACCCGCTCAACTTTGTGTCNACCCTCAACGCCATTGCCGGCACCTACTACGTGCACTCCAA
CTACTTCATCCTGACGCCGGAACAAATTGACGCNGCGGTTCCGCTGACCAATACGGTCGGTCCCACNATG
ACCCANTACTACATCATTCGCACGGANAACCTGCCGCTGCTAAAGCCACTGCGATCGGTGCCGATCGTGG
GGAACCCACTGGCGAACCTGGTTCAACCAAACTTGAAGGTNATTGTTNACCTGGGCTACGGCGANCCGGC
CTNTGGTTATTCCACCTCNCCGCCCAATGTTTGCNACTCCCGTTCGGGGTTGTTCCCNNAAGGTCAACCC :::::::::::::Rv316T7.seq:::::::::::: (SEQ ID NO. 406)
CGCTCAAGCGCNTGAGGCCGAANCGGCTGGTTACGACTCCCTGTTTGTGATGCACCACTTCTACCAACTG
CCCATGTTGGGGACGCCCGACCAGCCGATGCTGGAGGCCTACACGGCCCTTGGTGCGCTGGCCACGGCGA
CCGAGCGGCTGCAACTGGGCGCGTTGGTGACCGGCAATACCTACCGCAGCCCGACCCTGCTGGCAAAGAT
CATCACCACGCTCGACGTGGTTAGCGCCGGTCGAGCGATCCTCGGCATTGGAGCCGGTTGGTTTGANCTG
GAACACCGCCAGCTCGGCTTCGAGTTCGGCACTTTCAGTGACCGGTTC Clone Rv317 (SEQ ID NO. 407)
:::::::::::::Rv317SP6.seq::::::::::::
CTCAAGCTTGCGTTCGATGAAGTAGTCGTCGGTCAGCGCCGCCTCTTCGAGCTCCTTGGCGATGCCCAGC
AAGGAGTCATCGCCGCCGAGCTTGGCCAGGATCTTGTCGGCCTGTTCCTTGACGATGCGGGCCCGCGGAT
CGTAGTTCTTGTAGACACGATGACCGAAACCCATCAATTTGACCCCGGCCTCGCGGTTCTTGACCTTGCG
TACAAACTCGCTGACGTCGTCGCCGCTGTCGCGAATGCCCTCGAGCATCTCCAGGACAGCCTGATTGGCG
CCGCCATGAAGCGGACCCCATAGTGCGTTGATGCC :::::::::::::Rv317T7.seq:::::::::::: (SEQ ID NO. 408)
GGTCAGGCCGAGCAGGCGCGAGGAACGACGAACCCAACAAGCCATGGTGGTTGGCGCCGTCGAGAGGTCG
GCGGTCGCCACAACGGGAAGATCGCCTTGAGCGTCGCTCGACCGCCGCCTCGAGTTGGGTCATAACGAAG
TAGCTGATGCCGATCATGTCGACGTTTCCGTCGCATCAGCGTGCAGCGGCGACCCACTCNACGAGGTCTC
GGTGCCGCCGCGGCCAGGGCACCAGCAGTGACGAGTCCAGGCGCCGTCGGGCCAAGCAGTCGCGGTGCCA
NCCGTGGTGGGTCGGGCGATGGTTGGGTGTGCTCATTTCGGGAACGCCA Clone Rv318 (SEQ ID NO. 409)
:::::::::::::Rv318SP6.seq::::::::::::
CTCGAAGCTTTAACAGCATCAACCCCGCCCCGCACCAGCACCGACACNATGTCGATGCCATCGAGGTGAA
TGTCGAACTGGCGCAAACCATCGGCGACCGCGACCACCGGCAACATGGGTACCGGCGATTTCCGGTGCCA
ATGCCGACCCGACGGGCCGCTCTCACCGCAGGTGACCTCGATCACCGAGACCANCCGGCCGTTNTNNTCA
CGCACCCCTACCGTGTCACGCCCAAAACGGCGCTGGTGGTCGATTGCCGGAGTGCACCCCNCACCCAGTG
TCGTGCCCGGATCC :::::::::::::Rv318T7.seq:::::::::::: (SEQ ID NO. 410)
TGATGCCGCACCCGATCGACGGTCGTTGGTCGGGGTTGACTGGCCGCCCGGCGAAGCAGGGCGTCGACCG
CGGCCCGGACGTCGGCGGCCGTCACCGGTCGGCCATTGCCCGGGCGGGAGTCGTCGAGCTGACCACGGTA
GACAAGTCGGCGCTGGCCGTCGAAGACNAACGTGTCGGGTGTGCAGGCCGCGGAGAAGGCGCGGGCGACN
TCTTGGGTTTCGTCGTANAGATACGGGAACGTCCAGCCGTGGCGGCGGGCCTCGGCGACCATCTGATCGG
GCCCGTCC Clone Rv319 (SEQ ID NO. 411)
:::::::::::::Rv319SP6.seq:::::::::::::
TTTCGGGCGAGGCGGTATANCTTCCCNTCGTACCGGCGACCGCCAGCCGANAAGCTCGTTTTCCCAGTGT
TGCTGGGGATTCTCACGCTGCTGCTGANTGCGTGCCAAACCGCTTCCGCTTCGGGTTACAACGAGCCGCG TABLE 3-continued End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character << - >> denotes an uncertain base residue.

GGGCTACNATCGTGCGACGCTGAAGTTGGTGTTCTCCATGGACTTGGGGATGTGCCTGAACCGGTTCACC
TACNACTCCAAGCTGGCGCCGTCTCGTCCGCAGGTCGTTGCTTGCGATAGCCGGGAGGCCCGGATCCGCA
ATGACGGATTCCNTGCCANCGCTCCGAGTTGCNTGCGGATCGACTACNAATTGATCACCCANAACCATCG
GGCGTNTTACTGCCTGAAGTACCTGGTGCGGGTCGGATACTGCTATCCGGCGGTGACAACCCCGGCAAGC

:::::::::::::Rv319T7.seq::::::::::: (SEQ ID NO. 412)
GTTTTGGCTCGGCATGGTTAGCCAAGGTTCTGCGGTCCCACCAGATCATCTTGGTCCGGTAGCGCTCGTC
CGGGTATGCTGCCGCCGGGATTCTCGCTGCTATTACTCCCCCGAAGAACGCCACCGGTCCAGCGCGTGG
GCCGCCGCGGTCCCCATCACAAACTGAACCCCCAACAGGGACATGCTTAGCGGTAGGGCGCGCGCCAAGG
CGGCAGCAATCGCATCACTGCGCTGCGCGTCACTATTAACCCACCCGGACTTCACTTCCACGACCCCGAA
TGGCGCCCGGTCATTGATCATCTTGCGCACCGCGGATAATCCGGGATTGCCAGCCCATTCNACTACCGCA
TGCGAGTCATCGGCTGACCGCAGCGGTC Clone Rv31 (SEQ ID NO. 413)
::::::::::::Rv31SP6.seq:::::::::::
TCGCCTAGGCGGGCTTCCCCTTCCGTCCGAGCNGTCAGAAGCTCCTATGACAATGCACTACCCGAGACNA
TCAACGGCCTATGCAATACCNAGCTGATCAAACCCGGCAAGCCCTGGCGGTCCATCGAGGATGTCGAGTT
GGCCACCGCGCGCTGGGTCGACTGGTTCAACCATCGCCGCCTCTACCGGTACTGCGGCGACATCCCGCCG
GTCTAACTCGACGCCGCCTCACTACGCTCAACGCCAGAGACCANCCGCCGGCTGACGTCTCAGATCAGAG
AGTCTCCGGACTCACCGGGGCGGTTCATCCCCACTGTCGATAGCGTCTGTGGATAACTTTGTCTGCA ::::::::::::Rv31T7.seq::::::::::: (SEQ ID NO. 414)
GCGCGTNGAACTGATAGGTGCGGCCCGGCTCGAGCANGCCGGCCATTTGTTCGATGCGGTTACCGAAGAT
CTCTTCGGTGACCTGCCCGCCGCCGGCCAGCTCGGCCCAGTGCCCGGCGTTGGCCGCCGCGGCGACAATC
TTGGCGTCCACGGTGGTCTGGGTCA Clone Rv321 (SEQ ID NO. 415)
::::::::::::Rv321SP6.seq::::::::::::
CTCAAGCTTCAATACAGAGTTATAAACTGTGATAATCAACCCTCATCAATGATGACNAACTAACCCCCGA
TATCAGGTCACATGACGAAGGGAAAGAGAAGGAAATCAACTGTGACAAACTGCCCTCAAATTTGGCTTCC
TTAAAAATTACAGTTCAAAAAGTATGAGAAAATCCATGCAGGCTGAAGGAAACAGCAATAACTGTGACAA
ATTACCCTCAGTAGGTCAGAACAAATGTGACGAACCACCCTCAAATCTGTGACAGATAACCCTCAGACTA
TCCTGTCGTCATGGAAGTGATATCGCGGAAGGAAAAT Clone Rv322 (SEQ ID NO. 416)
::::::::::::Rv322SP6.seq::::::::::::
CTCAAGCTTCGATCGACATTACTCCCGCCTTGGGTCTGGTCTCCGAGCTGGTCGGTCATGGTCGGACCTG
CTGGTAGTGGGGATCTAACGCAACATGGTCGGGATTCATCATGGTGTACCCGTGATACCCATTCGCAGCT
GCCGGTGAAACCCCGCGATGCCGGGATTTCCAGCCGCACTAGGATGTCTAGCCGGCCAGCCGCTGCCGCC
GGCAAAGGTCATGCCCTCGGCGTGATGTCCGGTGCCGAAAGCCGCAAGAGCTCCGACGCCGCC ::::::::::::Rv322T7.seq::::::::::: (SEQ ID NO. 417)
CATTCCCAATTGAATTTCCCNATCCCACAATCTCGGTTCAGATACAGGTCGCCATACCCCTTACTTCGGC
AACGCTGGGCGGATTGGCCCTGCCGCTGCAGCANACCATCGACGCCATCGAATTGCCGGCAATCTCGTTC
AGCCAATCCATACCCATCGACATTCCGCCGATCGACATCCCGGCCTCCACTATCAACGGAATTTCGATGT
CGGAGGTCGTGCCGATCGATGTGTCCGTCGACATTCCGGCGGTCACCATCACCGGCACCAGGATCGACCC
GATTCCGCTGAACTTCGACGTTCTCAGCAGCGCCGGACCCATCAACATCTCGATCATCGACATTCCGGCG
CTGCCGGGCTTTGGCAACTCGACCGAGCTGCCGTCGTCGGGCTTCTTCAACACCGGCGGCGGTGGCGGCT Clone Rv327 (SEQ ID NO. 418)
::::::::::::Rv327SP6.seq::::::::::::
CTCAAGCTTTCGGCGGAGACGGACANNTTGCGAACATTGATGACAAAATAGAAATCATTGATGGTTTGAG
TCACCAGGCCGATCAAGCCTTCGCCGAGCCAAATTCCAATCAAGAGGCCCAAGCCCGTACCAATCAGCCC
GGCAACGAGGGATTCCGTCATTATCAGCCAAAATAACTGCTCTCGGGTTACACCCAAACAGCGCAATATG
GCGAAAAAACGGTCGCCGTTGCACGACATTAAATGTCACGGTATTG ::::::::::::Rv327T7.seq::::::::::: (SEQ ID NO. 419)
AGCTTAACTGCTCCCTAATACCTGGGGCTGTGCCTGCGGTGTATGCACGGCATACGGACATCCNTCCCCT
GAGACCCNCGGTCTAATCAGCCACGTGTCCACCATCAGGGGTCAACCCCGGCCAAGGGCGACGGCACCCC
AAGTTCGCCGACCGTTAACCTATTGCTGTGAGCTTCATTTGCTGCGAGCAAAACAGTTGGTCGGCCGTTA
GGAACTGAATTGACACTCAACCGATTTGGTGCCNCCGTAGGTGTCCTGGCTGCGGGTGCGCTGGTGTTGT
CCGCGTGTGGTAACGACCACAATGTGACCGGGGGAGGTGCAACCACTGGCCACGCGTCCGCGAATGTCTA
TTGCGGGGG Clone Rv328 (SEQ ID NO. 420)
::::::::::::Rv328SP6.seq::::::::::::
CTCAAGCTTGGGGTGGCGCTGTCGGTCGGTGTGCTTGGCGGCGTCGGTATCAACACCGCCCACGAAATGG
GGCACAAGAAGGATTCGCTGGAGCGGTGGCTGTCCAAAATCACCCTCGCCCAGACCTGCTACGGGCACTT
CTACATCGAGCACAACCGTGGCCATCACGTCCGGGTGTCCACACCGGAGGACCCGGCGTCGGCGCGGTTC
GGCGAAACGTTGTGGGAGTTCCTGCCCCGCAGTGTTATCGGCGGCTTGCGCTCGGCCGTTCATTTGGAGG
CCCAACGGCTGCGTCGGCTCGGCGTCAGCCCCCT TABLE 3-continued End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character << - >> denotes an uncertain base residue.

::::::::::::Rv328T7.seq:::::::::::: (SEQ ID NO. 421)
GCACCAAGGCCCCACACGTCACCCTGTGACCTCCTGCGCCGACCCCGCCCGAGGTCCTGGCCGTTACCAC
CTGAACGGGCGAGCCGGGAGTCTGGTACGCATCGAACAAAGAGCAAGGTGCATGGGCGGAGTTGTTCCGC
CACTTCGTCGATGACGGGGTCNATCCATTCGAGGTCCGTCGCCGCGTCGGTCGAGTGGCGGTCACACTCC
AGGTACTCGACCTCACAGACGAGAGGACTCGATCCCATCTAGGTGTGGACGAAACAGATCTTCTGTCCGA Clone Rv329 (SEQ ID NO. 422)
::::::::::::Rv329SP6.seq::::::::::::
TCGCCTCCGCATATGGGTCGACGCCAAGCGGGTCCGGATTTCTGGGCTTCATCGCTCGCGCCGTCGCGAC
AAACAGCGCGGTCGAACCGACACTCGTTGTGATGTCCCAGCTATCACCTTCGGTACGCACCCAATCGACC
CTACNCGGCTATCTCAGCCGCGATCTCCAGGCTCCGCCGAGCCAGGTGCATCCCGGTCCGGATCCCACTA
ACCCGGCACCATTGGCGTCN ::::::::::::Rv329T7.seq:::::::::::: (SEQ ID NO. 423)
GTCCTCGAGTGCCGCCGTCGNCACNCCCAGCGCCCGCGCGGCCACTTGGATGCGACCCGTTTCAAGTCCC
TTCATCATCTGCGAAAAGCCTTGACCCATGGCTCCGCCCAGGATCGCCGAGACCGGCACCCGGAGGTTGT
CGAACGACAGCTCGCAGGATTCGACGCCCTTGTAACCCAACTTCGGCAAGTCCCGCGACACCGTGAGTCC
CGGCCCGGGTTCGACGAGCACGATCGACATGCCTTGGTGCCGCGGTGTGGCGTTCGGGTCGG Clone Rv32 (SEQ ID NO. 424)
::::::::::::Rv32SP6.seq::::::::::::
GGCATACCAATGTGGACTTCTGCTCACCCACGATATCCGTGGTCTGATCCGCTGCTGCGGCGGGCTGCNA
CCTGCNTCTCNGCGGCACCCGTNACTACATGGCNCGCGCCGCACGCATACGTCGCGGCGGGACCCACTCC
NACTGGTCGACGGTGCTGGCCGCGTGTCCGCANGTCCCNAACCCGGCCGCACCGACGAAACCGGCCGCCG
TCCGTTCTGGACCAACGCTCATGTGCCGTCGGGGTCCATGCTCGACGCCATCGAGACCGTAACCAGCGTC
CTCGAGCGGTTCGCCTCCGGCTTCCGTGACATCTTCGTGGCTGCTCGCGCCGTGCCGCCGCGCGGATGGT
CGACCACAACGCCAACCACCTCGGCGGTGACATCACCGTCCGCGCCACTCGACCTGGCGCGCGATCGCGG
CCC ::::::::::::Rv32T7.seq:::::::::::: (SEQ ID NO. 425)
GTGAGCAGACCTACGCCNCCTGGTTGCGCCAACTCGGTACCGATCATGGCGCGCNGCCTGTCGTCACCGA
TACCCAGCGAACAAGACAGCCCGGTCCGCGACAAGATGACTTTCCCGATCTCTTCGGCGACTTCCATGGG
GTCGTCCGGAGTCCCGGGCGCCACCGCGAGGTAACCCTCGTCTCAGTCCCATACGCGACCGGGTATCCAC
GTCGCGCAACAACGCCACCACCTCCCCAGACGCCNCGTTGTACGCGGCTGGGTTCCACNGCAATAAGTGG
CCTCANGGCATCGTCCGGCGGCGGTCCNCAACGCA Clone Rv330 (SEQ ID NO. 426)
::::::::::::Rv330SP6.seq::::::::::::
CTCAAGCTTGAGGTTAACTTTGAACGGATCGAGCTGGACGTTCGAGACGGTGATCGGGCCGAACCTGAAT
TGTCCGGTAATGCCCAACGCAAAAAGCAGGGTGGTGGCCGGGGCGGTGAAACCGGCGTCGGCGGCACCGT
CGAAATCTATGTGGATTGCCGGAATGGGGATGTCCGGCACGGCGAAACCGTAGTTCGCTTGTCCCGTGAG
GCCCAGGTGGATGGGGGGAAAGATCCTGGTGTCCGGGATAATAATGGGGCCGATGCCGCCGGTTGAAGTC
CACTGGATCGGGAATTCCGGAATCTTGATCCGACGTTCAGGCCGAACAGGCCCCTC ::::::::::::Rv330T7.seq:::::::::::: (SEQ ID NO. 427)
CGGCGACGTCGCGATACGCCGAGCAGTTGGGAATCGCTCTGCAGCAAACCAATATTCTGCGCGACGTTCG
AGAGGACTTTTTGAATGGACGGATCTACCTGCCGCGCGACGAGCTGGACCGATTAGGCGTACGCCTCCGC
CTGGACGACACCGGGGCACTCGATGACCCCGACGGACGGCTCGCGGCNCTGCTGCGGTTCAGTGCCGACC
GCGCCGCAGACTGGTNTTCGCTGGGACTGCGGCTGATTCCACACCTCGACCGCCGCAGCGCTGCCTGCTG
TGCGGCCATGTCTGGCATCTACCGCCGTCAGCTCGCCTTGATCAGAGCATCGCCGGCGGTCGTCTA Clone Rv331 (SEQ ID NO. 428)
::::::::::::Rv331SP6.seq::::::::::::
CTATAAAATACTCAAGCTTGATGCCGCCGAAACCGAGCGTGAGCACGCCGCCAGCCACCACGCGCGGGTC
GGGCGCCGGGCCCGGGCCGCCAGGCTGCTCCGCTCGGTGATGGCACGCCACCGCGACACCACCCGGNTGC
GCTACGTCNAGCCATACCGGGCGGAGCTACATCGGCTCGGCCGCCCAGTGTTCGGGCCCTCTTTCGAGGT
CNAGGTCNATACCGATTTGCGCATCCGCAGCCGCACCCTGAACNACANAACCGTGCCCTACTATTGCTTG
TCNGGCGGGGCCAAAAAACAGCTTGGCATCCTGGCCCNATTGGCCGGCGCGG ::::::::::::Rv331T7.seq:::::::::::: (SEQ ID NO. 429)
CTTCGGTCGCAGTGTGCGAGTGATAGATGACGACCGGGACCTCGTCGGCATCTTCCATAGCCCGCCACAC
CTTCAGTTGCTCACCGGAATCCAACCGGTAGAAGGTCGGCGAGCGCTCGGCATTGGTCATCGGGATATGC
CGCTCGGGACGGTCAGAGCCCTCGGGTCCGGCCAGCACTCCGCAGGCTTCGTCGGGGTGGTCGCGACGCG
CATGGGCCACCATCGCATTCACCAGGTCTGCGCGAATCNCCANCACGTANACNGTTCCTTTCCTAA Clone Rv333 (SEQ ID NO. 430)
::::::::::::Rv333SP6.seq::::::::::::
CTGGCACCAAGGCCCCACACGTCACCCTGTGACCTCCTGCGCCGACCCCGCCCGAGGTCCTGGCCGTTAC
CACCGAACGGGCGAGCCGGGAGTCTGGTNCGCATCGAACAAANAGCAAGGTGCATGGGCGGAGTTGTTCC
GCCACTTCGTCGATGACGGGGTCNATCCATTCGAGGTCCGTCGCCGCGTCGGTCNAGTGGCGGTCACACT TABLE 3-continued End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character << - >> denotes an uncertain base residue.

CCAGGTACTCGACCTCACAGACNAAAGGACTCNATCCCATCTAGGTGTGGACNAAACAGATCTTCTGTCC
GACNACTACACCACCACCCAGGCCATCGCCGCCGCCCGCGATGCCAACTTCGACGCCGTACTGGCCCCGG
CGGGGGGCGCTCCCCGGTTGTCAACACTTGCCGTGTTCNTTCACGCNCTGCCCCACATCCAACCCCAACG

Clone Rv334 (SEQ ID NO. 431)
:::::::::::::Rv334T7.seq:::::::::::::
GTTCTTGGGCCCATGCGGAGGTATCGCCGTTTCCACCACGCGGTCGGGGTGGCGTTGCATTAGCTCACCG
ATGGTGCGCTTGTGCAGGCCGCCGGGATACCCCGAGTGCCGGTAAACCATCTTGTGCTGC Clone Rv335 (SEQ ID NO. 432)
:::::::::::::Rv335SP6.seq:::::::::::::
CAATACTCAAGCTTGGCGTGCCGTTCCAACCCGAATTGGCTTTCGGCGCCATCGGTGAGGACGGCGTGCG
GGTGCTCAACNACNACGTCGTCCGCGGGACACACCTCGATGCTGCCGCCATGGACGCGGTCGAACGCAAG
CAGCTGATCGAGCTACAACGCCGCGCGGAACGCTTCCGCCGCGGGCGTGACCGCATCCCGTTGACCGGGC
GGATC :::::::::::::Rv335T7.seq::::::::::::: (SEQ ID NO. 433)
CNTCATGATGATCATCACCCGAAGTGTGGTAGCCGCAGTGGTTATCGTGGGTACCGTCGTGCTTTCCATG
GGCGCCTCTTTCGGGCTTTCCGTATTGGTCTGGCAGGACATTCTGGGTATCGAGTTGTACTGGATGGTGT
TGGCGATGTCGGTGATCCTGCTCCTGGCGGTGGGATCCGACTACAATCTGCTGCTGATTTCCCGGTTGAA
AGAGGAAATTGGGGCCGGATTGAACACCGGAATTATCCGTGCCATGGCTGGTACCGGGGGAGTGGTGACG
GCTGCCGGCATGGTGTTCGCCGTTACCATGTCGTTGTTTGTGTTCAGCGATTTGCGAATTATTGGTCAGA
TCGGTACCAC Clone Rv336 (SEQ ID NO. 434)
:::::::::::::Rv336SP6.seq:::::::::::::
ATACTCAAGCTTTTACGGTGATCGCNCATCACCTGGTTCATGAACTGGAAGCAGCGCAGCGCTTCCTTTT
CGGCCGCAACATGAGCCAGCCTCTCGTCGGCGGTCGGGTGCAGGTGCTCGGGCAGCTCGGCCGCNACAGC
CGCCTGACCCTGAAACCAGCTTCCATATCCCGCGANNAACGACGCCAGTCCGCTACGTNACCCCTCCGCG
ACTGTCCATGGACAACAGCGCGTTCTCCACCGACCGGGCCCGGGTGTGGGGTNTT :::::::::::::Rv336T7.seq::::::::::::: (SEQ ID NO. 435)
GCTGGTAGAGTCGCTGACCGGTGCAGGTTTCGACAATGTGGTGCCGGTTCGGCGGCTACGTGCCATCGAG
ACACTGGCGCAGGCTATCGCACCCGTTATCGGCTACGAGCAAATCGCGGTATGCGTTCTTGAGCATGAGT
CGGCGACCGTCGTCATGGTCGACACCCACGACGGAAAGACGCAGATCGCCGTCAAGCATGTGTGCCGCGG
ATTATCAGGACTGACCTCCTGGCTGACCGGCATGTTTGGTCGCGATGCCTGGCG Clone Rv337 (SEQ ID NO. 436)
:::::::::::::Rv337SP6.seq:::::::::::::
GCTTTCCGCCGATACCCGCCATGTCNCGCACATCCAGGACTTCTGGGGGGATCCGCTGACAGCGGCGGGA
TCCCAAAGTGCGGATGATCGGGCCGCCTACGTCGTGGTGTACCTCGTCGGTAACAACGAAACCGAAGCGT
ATGACTCGGTCCACGCGGTGCGGCACATGGTGGACACCACACCGCCACCGCACGGGGTGAAGGCCTATGT
CACCGGTCCGGCANCACTCAATGCCGACCAGGCCGAGGCCGGANACAAAANTATCGCTAAGGTCACCGCG
ATCACNAGCATGGTGATCGCAGCAATGTTGCTAGTGATCTATCGCTCCGTAATTA :::::::::::::Rv337T7.seq::::::::::::: (SEQ ID NO. 437)
CTTCCAACCCGAATTGGCTTTCGGCGCCATCGGTGAGGACGGCGTGCGGGTGCTCAACGACGACGTCGTC
CGCGGGACACACCTCGATGCTGCCGCCATGGACGCGGTCGAACGCAAGCAGCTGATCGAGCTACAACGCC
GCGCGGAACGCTTCCGCCGCGGGCGTGACCGCATCCCGTTGACCGGGCGGATCGCGGTGATCGTCGATGA
CGGCATCGCCACCGGAGCGACGGCCAAGGCGGCGTGCCANGTCGCCCGGGCGCACGGTGCGGACAAGGTG
GTGCTGGCGGTCCCGATCGGCCCA Clone Rv338 (SEQ ID NO. 438)
:::::::::::::Rv338SP6.seq:::::::::::::
TACTCAAGCTTCGCGAGATCCGGATGGCACTCACGCTGGACAAGACCTTCACAAAATCTGAAATCCTGAC
CCGATACTTGAACCTGGTCTCGTTCGGCAATAACTCGTTCGGCGTGCAGGACGCGGCGCAAACGTNCTTC
GGCATCAACGCGTCCGANCTGAATTGGCAGCAAGCGGCGCTGCTGGCCGGCATGGTGCAATCNACCAGCA
CGCTCAACCCGTA :::::::::::::Rv338T7.seq::::::::::::: (SEQ ID NO. 439)
CCCACGACTTTCTCCTCGATCAGTTGGATTTGTACGAAGAGGCAACGAAAGCAGTGATCCTCGGGATGGT
CGACGCCTACATCGACCCGCCGTTCACGCCGCACAGCCTGCTAGATGCGCTGGGCGAGCAGGTCCCACAG
TTCGCCGCTAAGGCACGGCGTCTGTTCCCGTCCGGATCGCCATTCGGCCTCGGCGTCCTGCTCCCATTCG
ATCAATAGGGCTGGCAGCTCCGTCGGCAGGGGCCTACGCCTCACCCCGTCACG Clone Rv339 (SEQ ID NO. 440)
:::::::::::::Rv339SP6.seq:::::::::::::
CTCAAGCTTATGCGCGCCGGCCGAGGTCTGCTCACGGCAACCCCTGAAGTTTAGGGGACNACCTACTCAG
CGCAAAATTTCGCTAATGTGAGTCCGCCCCACCAGGGGNANATCAACCCATGTCGATCATGATCTACCCG
GATACCGGATTGGCGGTAGCGCCCACGATCGTCNAAATNTCCGCCTGAATCATCGGATAGCTGATCCGGC
GTCAACGCGTTTTGANTTCACCGCGCAACAGCCGCCAGGCCGGCCCGCANCGANCCGATCTCNTCGGGCC TABLE 3-continued End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character << - >> denotes an uncertain base residue.

GCATGGGCCCCAATCTTNTCG

::::::::::::Rv339T7.seq:::::::::::: (SEQ ID NO. 441)
GTGTGTGGTGGAACCCATCTGAGCAGTGTGCCAAACCGGGGCAGACAGCTCCCAATTGACGTGAGCCCGC
TCACTTGCTGGGTAAGCGTC Clone Rv33 (SEQ ID NO. 442)
::::::::::::Rv335P6.seq::::::::::::
CTTTACACTTCCTGCATCCGGCTCGTATGTTGTGTGGAATTGTGAGCGGATAACAATTTCACACAGGAAA
CAGCTATGACCATGATTACGCCAAGCTATTTAGGTGACACTATAGAATACTCAAGCTTGGGCGTGACGGC
CACCGGGGCCACTCCGCACCATCTGTACCCGACCAAGATCTAC ::::::::::::Rv33T7.seq:::::::::::: (SEQ ID NO. 443)
CAGGCATGCCAGCTTTAGCTGCCCGAATGCGTCACCCCGATGCGCCCAGATCGGGGCTTCGCAGATAAAG
CACGAACAGGCGGGCAAAACGTCNATCTCGGAGCCGGAAGGGCAATCAGCCGACCGTCGACGAACGACAC
CGGCGAGACCACTTAGGCAGTGACGGCCGGCCCGAACATTACGCGCTCGTTGATTAGGCGTTCGGTCTCG
TCCGCGGTCATGCCGAGCAGCTTGCGGCAGATCTGAACGCTGTCCTGTCCGGGCAGCGGCGCCGGGCGTT
GGGGTGCCTGCCCGAATGTGACGAAACGGAGCCGGACCCGTCTCGGCGGGCCGCGGACGGCGATCCGC Clone Rv340 (SEQ ID NO. 444)
::::::::::::Rv340SP6.seq::::::::::::
CNCAAGCTTGCGGATGTTACCCCTGACAGCCTGAACTATGTCNAAACACACGGCACCGGAACGGTGTTGG
GGGACCCCATCGANTTCGAGTCGCTGGCGGCCACTTATGGCCTGGGTAAAGGCCAGGGCNANAGCCCGTG
CGCATTGGGGTCGGTCAAAACCAACATCGGCCACCTGGAGGCGGCCGCCGGTGTGGCTGGATNCATCAAG
GCGGTGCTGGCGGTGCAACGTGGGCACATTCCCCGCAACTTGCACTTCACCCGGTGGAACCCGGCCATCN
ACGCGTCGGCNACGCGGCTGTTCGTGCCNACCNAAAACCCCCCGTGGCCGGCGGC ::::::::::::Rv340T7.seq:::::::::::: (SEQ ID NO. 445)
GGAACCGGTAACCAGATCAGCTCGTCGACCTCACTGCCGGGGGTGAATTCCCCACCGGTGCTGCGCGCTG
CCCAGTAGTGCACCTTCTTGACGCCTCGAAAAGGGGAGTCGGTCGGGTAGGTCACCGTCAGGAGCCGCCT
ACCCAGGTTGGCGCNATAGCCGGTCTCCTCGAGTATCTCCCGCACCGCCCCCACCGGTGCGGTCTCACCC
ANATCCACTTTGCCCTTGGGCAGCGACCAGTCGTCGTANCNGGGGCGGTGAATGACAACGATCTCGACCG
GCCCTTCCN Clone Rv341 (SEQ ID NO. 446)
::::::::::::Rv341SP6.seq::::::::::::
TACTCAAGCTTCAGAACAGGCCTGTTGTGGGCNCACCCGGCTCGCCGAGTTCTGCACGCACCGCCTCAAG
TGCGGCCCGCACCGCCGGCATCTCCCGGTCACGCAGGGCCGCGGCCCGCGCCGCAGCGACGGCGTGTTCG
CGCAGTTCGCCGTCAATGATGCTGACCTGATCGGCCACCCGGGCGTTCTCGGCGTCGTCGCGTTCACTAA
TCGCGGTGCTCAGCAGCGTCTCGACAGCCACCACCCGAGTGGCGACCAGCTGC ::::::::::::Rv341T7.seq:::::::::::: (SEQ ID NO. 447)
TAATGTCTTGCCAACGTCACCACAATCGCGATGAATTCAATCATGCCGCCCAGGGCGGCCAACCCAATGG
TGGCCGCGAGCGGCAGCTCGATCGCAGCGCGGAGGTTGCCGGCCGCCAGTTGATTCACGAACAGGGTGAG
GTCATAGGCGGGCAGGATAGTGACGAAGGCAAGACCTATATCTGCCGTCGGAAGAAGAATCGAGTAGCCG
GTCGACACAACGGAAGCGAAAGTGTCCGCGATGTTGATGAGCGTCGCCGGTTGTGGCGGCGGTGGCGGC Clone Rv343 (SEQ ID NO. 448)
::::::::::::Rv343SP6.seq::::::::::::
TACTCAAGCTTTCGTCAGTTCATCGCGCCAGCAGACCAACAAGAGCATCGGGACATACGGAGTCAACTAC
CCGGCCAACGGTGATTTCTTGGCCGCCGCTGACGGCGCGAACGACGCCAGCGACCACATTCAGCANATGG
CCAGCGCGTGCCGGGCCACGAGGTTGGTGCTCGGCGGCTACTCCCAGGGTGCGGCCGTGATCGACATCGT
CACCGCCGCACCACTGCCCGGCCTCGGGTTCACGCAGCCGTTGCCGCCCGCAGCGGANNATCACATCGCC
GCGATCGCCCTGTTC ::::::::::::Rv343T7.seq:::::::::::: (SEQ ID NO. 449)
CCACCCGTGTAATTTGGGATGGGCNAAAAGGCNAAGCACCGCGTGGCCACGAACGCCGGGAGGGACAATC
TCGGGCGGCTAGGGCTTCTCGCGGGAAGGCCCGAACGTACGGCGTTTCAACACGTCGCGTCGCCCTCCGA
CCGCGAACATTCGGGGATGGCAGCAACCTGGTAGCACCCTGGCCGGGCGATGATCTGCAGCGTCGCCGCG
GGTAGTCGCCGCCCGGGCGGCTACAGTCTGAAACGCGATGACCATCGATGTGTGGATGCAGCATCCGACG Clone Rv344 (SEQ ID NO. 450)
::::::::::::Rv344SP6.seq::::::::::::
TCAAGCTTTAGCTGCCCGAATCCGTCANCCCGATGCNCCCAGATCGGGGCTTCGCANATAAAGCACNAAC
AGGCGGGCAAAACGTCNATCTCGGAGCCGGAAGGGCAATCANCCGACCGTCNACAAACGACACCGGCGAN
ACCACTTAGGCAGTGACGGCCGGCCCCGAACATTACNCGCTCGTTGATTAGGCGTTCGGTCTCGTCCGCGG
TCATGCCGAGCAGCTTGCGGCANATCTGAACGCTGTCCTGTCCGGGCAGCGGCGCCGGGCGTTGGGGTGC
CTGCGGAATGTGACNAAACGGAGCCGGACCCNTCTCGGCG ::::::::::::Rv344T7.seq:::::::::::: (SEQ ID NO. 451)
CCGGGGCCACTCCGCACAATCNGTACCNNACCAANATCTACACCATCGAATACGACGGCGTCGCCGANTT TABLE 3-continued

| End sequences of the polynucleotide inserts cloned in the named recombinant BAC vectors contained in the I-1945 *M. tuberculosis* H37Rv genomic DNA library. RvXXXSP6 corresponds to the SP6 endsequence of the clone RvXXX; RvXXXT7 corresponds to the T7 endsequence of the clone RvXXX. RvXXXIS 1081 corresponds to a region located close to a copy of the IS1081 repetitive sequence (Insertion element) The character << - >> denotes an uncertain base residue. |
|---|

TCCGCGGTACCCGCTCAACTTTGTGTCGACCCTCAACGCCATTGCCGGCACCTACTACGTGCACTCCAAC
TACTTCATCCTGACGCCGGAACAAATNGACGCNTCGGTTCCGCTGACCAATACGGTCGGTCCC

Clone Rv346 (SEQ ID NO. 452)
::::::::::::Rv346SP6.seq::::::::::::
NCTGGCCTTTGGTCCACACTAAACAATACTCAAGCTTCCGGCCGCAGAGCCGCCAACTCACGATATCGT
TAACCGATATCCCGAGCCGATAGCTGGCGGGCTCGGGTGGTGGCCAGCGGCGCTGCGACNAAAGGTGTGA
CCGTCATGAAACAGACACCACCGGCGGCCGTCGGCCGTCGTCACCTGCTCGANATCTCAGCATCCGCAGC
CGGTGTGATCGCGCTTTCGGCGTGTNGTGGGTCNCCGCCCGAGCCCGGCAAAGGCCGGCCCGACACAACC
CCGGAAC ::::::::::::Rv346T7.seq:::::::::::: (SEQ ID NO. 453)
CATCTGCCCACCACACGGACCGCGGTGCGGACGCGGCTGACGCGCCTGGTGGTCAGCATCGTGGCCGGTC
TGCTGTTGTATGCCAGCTTCCCGCCGCGCAACTGCTGGTGGGCGGCGGTGGTTGCGCTCGCATTGCTGGC
CTGGGTGCTGACCCACCGCGCGACGACACCGGTGGGTGGGCTGGGCTACGGCCTGCTATTCGGCCTGGTG
TTCTACGTCTCGTTGTTGCCGTGGATCGGCGAGCTGGTGGGCCCCGGGCCCTGGTTGGCACT Clone Rv347 (SEQ ID NO. 454)
::::::::::::Rv347SP6.seq::::::::::::
GACAATACTCAAGCTTGACTGGCCACCCACCGGCATGACCACCGACAGGCCCGACTGGTCGTACCACTCG
AACGCCGGGGTGTTGATGTCCCAGCCGCTGAANTCGTCCTGCGCGCGCAGGCCGTCNAACAGGTACAGGG
CGGGCGAATTGGCACCACCACTTTGGAATTGGACCTTGATGTCACGGCCCATCGACGGCGACGGCACCTG
CAGGTACTCCACCGGCAAGCCCGGCCGGGAAAATGCCCCCGCGGTCNCCGTGCCACCGACGGCGCCGANC
AAACCCGACACTAGGGCCGCGCCNACGGCCCCGACCACNANTCNACGCGACATACCCGTGACGGCGCCAC
NAACCCTGTCAACA ::::::::::::Rv347T7.seq:::::::::::: (SEQ ID NO. 455)
CCTCCAACTCGGCGGGGAAGCGACNCCAGCCTACCGAGCTTGGAGTCCANGACGCCAGCGGCGGCGTCGG
TCTGCGTCGTGGTGCCGCCGGGGTGGCGTTGGCTGGCAACGATCTCCACCCAGCCGGTCGGGTTACCCAC
GATCTCGGCATANACGCGGGCCGAGGCCGGTGCGATACCGTATTGCGTCAATTGGGACGCGGTTGTGCAT
TCGGCTAGCTCGGTTGCCACACCCGTCAGGGGTTCGACGTTGGCGGGTTCGGCGGGCCCCANCACCGCTG
TCACCATGCCCGCCAAGCCGACCTGCGGCGCCACCAACTGCAGCACCANCATGTCGCCGTCGCGCGCCGC
GATCACATGG Clone Rv348 (SEQ ID NO. 456)
::::::::::::Rv348SP6.seq::::::::::::
CTCAAGCTTTTTGAGCGTCGCGCGGGGCANCTTCGCCGGCAATTCTACTANCGAGAANTCTGGCCCGATA
CGGATCTGACCGAANTCGCTGCGGTGCANCCCACCCTCATTGGCGATGGCGCCGACNATGGCGCCTGGAC
CGATCTTGTGCCGCTTGCCGACGGCGACGCGGTAGGTGGTCAAGTCCGGTCTACGCTTGGGCCTTTGCGG
ACGGTCCCGACGCTGGTCGCGGTTGCGCCGCNAAAGCGGCGGGTCGGGTGCCATCAGGAATGCCTCNCCG
CCGCGGCACTGCACGGCCAGTGCCGCGGCGA ::::::::::::Rv348T7.seq:::::::::::: (SEQ ID NO. 457)
CNCCAGCTTGATTGGTCTGGTTGCATTGGCCAGCTGCGCGAGCCTGGCTCACTTCAACTACGACGACCGC
AAACAATTGCCGCCTTCGGATCCGAGTTCGGTTGGGTACGCGGCAATGGAGCACCATTTCTCGGTGAATC
AGACTATTCCTGAGTACTTGATCATCCACTCTGCACACGACCTGCGAACCCCGCGCGGCCTTGCCGACCT
GGAGCAGCTGGCGCAACGTGTGAGCCAGATCCCAGGCGTTGCCATGGTTCGCGGTGTGACCCGGCCAAAC
GGGGAAAC Clone Rv349 (SEQ ID NO. 458)
::::::::::::Rv349SP6.seq::::::::::::
CAATACTCAAGCTTGACTGGGCCCGCACCTTCGGCGCCACCCACACCGTCAACGCCCGCGAAGTCNACGT
CGTCCAGGCCATCGGCGGCCTCACGGATGGATTCGGCGCGGACGTGGTGATCGACGCCGTCGGCCGACCG
GAAACCTACCAGCAGGCCTTCTACGCCCGCGATCTCGCCGGAACCGTTGTGCTGGTGGGTGTTCCNACGC
CCGACATGCGCCTGGACATGCCGCTGGTCNACTTCTTCTCTCACGG ::::::::::::Rv349T7.seq:::::::::::: (SEQ ID NO. 459)
TCGACGGTTTGGCGGCCTTAAATGCACTGAGGTCGTCAATTGACCCCACAGCGGAAATGCCGACTATTCG
CAGGCCTCCTTCGCCTTGGCTGCCGGAGAGGGGCTCCGCGGGAACCGCATGCAGGTATATGACCTCGGTT
TCTCGGGTGCTACCGCGTGCCTTGTNTANGATNANCTCGGCGTTGGAATTGTCCAGCCGGCCCAATTCAT
CGAGCGCANATTCGTACACNTGGCCGGCGGCGACATACGCTTCACCGTGGATCTGCTCCACACGGACCGC
CCTGTCGGGATCCTGCTCACGGGTAANGGAACTTACGTGGCACTCGG Clone Rv34 (SEQ ID NO. 460)
::::::::::::R34SP6.seq::::::::::::
GACCACGCCAGGCTAATCACGTGACGCTACCGAATACCCTNCCTAGTGGTGCAGGCTCCCGCTGGAAAT
GGCCCTGTACCAACTCGCGCACCGGTGCCAG ::::::::::::Rv34T7.seq:::::::::::: (SEQ ID NO. 461)
CGGCACCCGACCCCTTTGAGCCGTCCGCCGTGGCCGCGGTGGAACTGGCCGACGAGGGACTGATCGTGCT
GGGCAAATTGGTCGATGGCACGCTGGCCGCCGATCTGAAGGTCN TABLE 3-continued End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character << - >> denotes an uncertain base residue.

Clone Rv350 (SEQ ID NO. 462)
::::::::::::Rv350SP6.seq:::::::::::
CTCAAGCTTGCCGTTACCCCGACTTCCGGAGGGACACCATGAGCACCGCCAGCCGAGCACGAGGCCAAAC
TCCGCCGACGCAGGCCGGTTGGACTTGTCGTGCTGGACAAGGGGTTTAGCCGCCGAAGCAGTGACGTACA
TCGGCGAAAAGCAGTTCGCCTGTCGACCGACGGNGCNNACCGTGAGGCTAGGGAAGCGAGGAGCACATGG
CCGCCGACCCGCAATGTACACGCTGCAAGCAAACCATCGAACCCGGATGGCTATNCNTCACCGCCCATCG
CCGCGGT ::::::::::::Rv350T7.seq::::::::::: (SEQ ID NO. 463)
CATGTCGCGCACATCCAGGACTTCTGGGGGGATCCGCTGACAGCGGCGGGATCCCAAAGTGCGGATGATC
GGGCCGCCTACGTCGTGGTGTACCTCGTCGGTAACAACGAAACCGAAGCGTATGACTCGGTCCACGCGGT
GCGGCACATGGTGGACACCACACCGCCACCGCACGGGGTGAAGGCCTATGTCACCGGTCCGGCAGCACTC
AATGCCGACCAGGCCGAGGCCGGAGACAAAAGTATCGCTAAGGTCACCGCGATCACGAGCATGGTGATCG
CAGCAATG Clone Rv351 (SEQ ID NO. 464)
::::::::::::Rv351SP6.seq:::::::::::
ATACTCAAGCTTCGGTACGGTGGCGGGCCGTGCTGCTGGCCGCGGTCGCGGCGTGCGCGGCCTGCGGTCT
CGTTTACNAGCTCGCGCTGCTGACACTGGCGGCNAGCCTGAACGGCGGCGGGATCGTGGCCACCTCCCTG
ATCGTCGCGGGCTACATAGCCGCGCTGGGAGCAGGCGCCTTGCTGATCAAGCCGCTACTTGCACACGCGG
CCATCGCGTTCATCGCCGTGGAGGCGGTGCTGGGCATCATCGGCG ::::::::::::Rv351T7.seq::::::::::: (SEQ ID NO. 465)
TGTCAAGTCCTTTCAGATCTCNTTTTTATGACATGACTGGAGATCTGTCTAGATTGCAGCTCCTGTGAGC
GTGGGTACCGGATTCAAGCCGGTCGGTCACGCCGCGGTGGTACCGGCTTTGCGGCAGTGCTCGGCCTCGA
GTTCGGCGATCGCGCGCGAAGTGCGTTCGCGCAGCAAGATCGCGGCCGTAATGCCGGCGATGACCGCGAT
GACCAGCGCGATCCAGGAGAACCGTTCCAACCAGTGCTGGGCGGCCATCCCGGCGAAGTAGACCAGTGCA
GTGGTGCC Clone Rv352 (SEQ ID NO. 466)
::::::::::::Rv352SP6.seq:::::::::::
CAATACTCAAGCTTCAAAACAGGCCTGTTGTGGGCGCACCCGGCTCGCCGAGTTCTGCACGCACCGCCTC
AANTGCGGCCCGCACCGCCGGCATCTCCCGGTCACGCAGGGCCGCGGCCCGCGCCGCANCGACGGNGTGT
TCGCGCAGTTCGCCGTCAATGATGCTGACCTGATCGGCCACCCGGGCGTTCTCGGCGTCGTCNCGTTCAC
TAATCGCGGTGCTC ::::::::::::Rv352T7.seq::::::::::: (SEQ ID NO. 467)
TACGCTGGCGCTGGAGGGAGCCANNTACAACATCCACGCCAATGCTCTTGCCCCGATCGCGGCGACCAGG
ATGACCCAGGACATCCTGCCGCCCGAAGTACTGGAAAAGCTCACACCCGAGTTCGTCGCACCGGTGGTGG
CCTACCTGTGCACCGAGGAGTGTGCCGACAACGCATCGGTGTACGTCGTCGGTGGTGGCAAGGTGCAGCG
AGTTGCGCTGTTTGGCAACGACGGCGCCAACTTCGACAAACCGCCGTCGGTACAAGATGTTGCGGCGCGG
TGGGCCGAGATCACCGATCTGTCCGGTGCGAAAATTGCTG Clone Rv353 (SEQ ID NO. 468)
::::::::::::Rv3535P6.seq:::::::::::
GCTTTTCCCGTCCGTCNNCGCTCAACCGCGTGAGGCCGAAGCGGNTGGTTACGACTCCCTGTTTGTGATG
GACCACTTCTACCAACTGCCCATGTTGGGGACNCCCGACCAGCCGATGCTGGAGGCCTACACGGCCCTTG
GTGCGCTGGCCACGGCGACCGANCGGCTGCNNNTGGGCGCGTTGGTGACCGGCAATACCTACCGCAGCCC
GACCCTGCTGGCAAANATCATCACCACGCTCGACGTGGTTAGCGCCGGTCGAGCGATCCTCGGCATTGGA
GCCGGTTGGTTTGANCTGGGACA ::::::::::::Rv353T7.seq::::::::::: (SEQ ID NO. 469)
CNGCTTTTTAATGGCCTTGACNTGGGCGNGCCGGCCACCGGGGCCACTCCGCACAATCTGTACCCGACCA
AGATCTACACCATCGAATACGACGGCGTCGCCGACTTTCCGCGGTACCCGCTCAACTTTGTGTCGACCCT
CAACGCCATTGCCGGCACCTACTACGTGCACTCCAACTACTTCATCCTGACGCCGGAACAAATTGACGCA
GCGGTTCCGCTGACCAATACGGTCGGTCCCACGATGACCCAGTACTACATCATTCGCACGGAGAACCTGC
CGCTGCTAGAGCCACTGCGATCGGTGCCGATCGTGGGGAACCCACTGGCGAACCTGGTTCAACCAAACTT
GAAGGTGATTGTTAACCTGGGCTACGGCGACCCGGCCTATG Clone Rv354 (SEQ ID NO. 470)
::::::::::::Rv354SP6.seq:::::::::::
CTCAAGCTTGCCGGGAGGGTGCATGGCCGACTCGGATTTACCCACCANGGGGCGCCAACGCGGTGTCCGC
GCCGTCNAGCTGAACGTTGCTGCCCGCCTGGAGAACCTGGCGCTGCTGCGCACCCTGGTCGGCGCCATCG
GCACCTTCGAGGACCTGGATTTCGACGCCGTGGCCGACCTGAGGTTGGCGGTGGACGAGGTGTGCACCCG
GTTGATTCGCTCGGCCTTGCCGGATGCCACCCTGCGCCTGGTGGTCGATCCGCGAAAANACGAANTTGTG
GTGGAGGCTTCTGCTGCCTGCGACACCCACNACGTGGTGGCACCGGGCAGCTTTAGCTGGCAT ::::::::::::Rv354T7.seq::::::::::: (SEQ ID NO. 471)
CCGACGCCGTCGTGGCCACCAACACCGCGACCAGCACCGTGACCCGGACCGGGGTGCCGCGCGAACCGGT
CTTGGCCAATTGCCGCGGCACCAAGCCGTCGCGCGCCATGGCGAACAGCACGCGGCATTGCCCGAGCATC TABLE 3-continued End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character << - >> denotes an uncertain base residue.

AACACCATCACCACCGTGGTAAGCCCGGCCAGCGCGCCGACGGAGATGATGCCGCTGGCCCAGTACACCC
CGTTGGCCTGGAACGCGGTGGCCAGATTTGCCGGCCCGCGGCCCGGTACGGTCCGCAGTTGGGTGTATGG
AACCATGCCCGACAGCACCACCG

Clone Rv355 (SEQ ID NO. 472)
::::::::::::Rv355SP6.seq::::::::::::
TTNACTGGCCTTTGGTCCACACTAGACAATACTCAAGCTTCCAGGACATCGTCATCGCGACCAAAACCGC
GAGCTAGGTCGGCATCCGGGAAGCATCGCGACACCGTGGCGCCGAGCGCCGCTGCCGGCAGGCCGATTAG
GCGGGCAAATTAGCCCGCCGCGGCTCCCGGCTCCGANTACGGCGCCCCGAATGGCGTCACCGGCTGGTAA
CCACGCTTGCGCGCCTGGGCGGCGGCCTGCCGGATCAGGTGGTAAATGCCGACA ::::::::::::Rv355T7.seq:::::::::::: (SEQ ID NO. 473)
NGACGTCTTCCATCCGCGCGTCGTTTTGGCGGGTTGGCCACAGCAGCCCGCCGGTGACGGCGACGATGCT
GGGCTGGTTGCGGCCCTGCGCCACCGCGGCTTGCATGCTGGTTGGCTGTCTTGGGACGATCCCGAAATAG
TCCACGCGGATCTGGTGATTTTGCGGGCTACCCGCGATTACCCCGCGCGGCTCGACGAGTTTTTGGCCTG
GACTACCCGCGTGGCCAATCTGCTGAACTCGCGGCCGGTGGTGGCCTGGAATGTCGAGCGCCGTTACCTA Clone Rv356 (SEQ ID NO. 474)
::::::::::::Rv356SP6.seq::::::::::::
CTTCCTCCTGAGTACCNCCCGTNTACTTTGGGATGGGTAAAAAGGCGAATCNCCGTTTGGTCACGAACGC
CGGGAGGGACAATCTCGGGCGGCTGGGGCCTCTCGCGGGAANGCCCGAATGTACGGTGTCTCGACACTTC
CCNTCCCCCTCCG ::::::::::::Rv356T7.seq:::::::::::: (SEQ ID NO. 475)
GAGCATCGGGACNTACGGAGTCAACTACCCGGCCAACGGTGATTTCTTGGCCGCCGCTGACGGCGCGAAC
GACGCCNGCGACCACATTCAGCAGATGGCCAGCGCGTGCCGGGCCACGAGGTTGGTGCTCGGCGGCTACT
CCCAGGGTGCGGCCNTGATCNACATCGTCACCGCCGCACCACTGCCCGGCCTCGGGTTCACGCAGCCGTT
GCCGCCCNCAGCGGACGATCACNTCGCCGCGATCGCC Clone Rv357 (SEQ ID NO. 476)
::::::::::::Rv357SP6.seq::::::::::::
TACTCATGANCATCCTTTAATCANNGCTTTGCGTTTTTTTATTAAATCTTGCAATTTACTGCAAAGCAAC
AACAAAATCGCAAAGTCATCAAAAAACCGCAAAGTTGTTTAAAATAAGAGCANCACTACAAAAGGAGATA
AGAAGAGCACATACCTCAGTCACTTATTATCACTAGCGCTCGCCGCAGCCGTGTAACCGAGCATAGCGAG
CGAACTGGCGAGGAAGCAAAGAAGAACTGTTCTGTCAGATAGCTCTTACGCNCA Clone Rv358 (SEQ ID NO. 477)
::::::::::::Rv358SP6.seq::::::::::::
CTCAAGCTTCAGGTCAATGTGCNCCAAGCCCTGACGCTGGCCGACCAGGCCACCGCCGCCGGANACNCTG
CCAAGGCCACCGAATACAACAACGCCGCCGAGGCGTTCGCANCCCAGCTGGTGACCGCCGAGCANANCGT
CAAAAACCTCAAGACGCTGCATGACCAGGCGCTTANCNCCGCANCTCAGGCCAAGAAGGCCGTCNAACGA
AATGCGATGGTGCTGCACCANAAGATCGCCGAGCGAACCAAGCTGCTCAGCCNG ::::::::::::Rv358T7.seq:::::::::::: (SEQ ID NO. 478)
CATGGTGGCACTGTAGCGACGTGCTGCAATCAAGGTCATGCCCGACTCTGGTCAGCTCGGANCCGCTGAC
ACCCCGCTAAGGCTGCTCAGCTCGGTGCATTACCTCACCGACGGCGAACTCCCCCAGCTTTACGACTATC
CGGATGACGGCACCTGGTTGCGGGCGAACTTCATCATCAGCTTGGACGGCGGCGCTACCGTCGATGGCAC
CAGCGGGGCGATGGCCGGGCCCGGCGACCGATTCGTCTTCAACCTGTTGCGTGAACTTGCCGACGTCATC
GTGGTCGGCGTGGGCACCGTGCGCATTGAGGGCTACTCCGGCGTCCGGATGGGTGTCGTCCAGCGCCAGC
AC Clone Rv359 (SEQ ID NO. 479)
::::::::::::Rv359SP6.seq::::::::::::
TACTCAAGCTTGCGGGTGATCGCCTTGGTCAACGGCACCGTGATCGGATCGGGGTCNACCGCACAAATGG
ACTGGAGCTTCGGCGAANTCATCGCCTATGCCTCGCGGCGGGTGACGCTGACCCCGGGTGACNTGTTCGG
CTCGGGCACGGTGCCCACCTGCACGCTCGTCTATCACCTCNGGCCACCGGAATCATTCCCGGGCTGG ::::::::::::Rv359T7.seq:::::::::::: (SEQ ID NO. 480)
GTTGGNGCCTCGTCGGCGAACAGTTCTCGCACGATTTCCGGATTAGCGGGACTGGTCACCAGTTGGGTAT
GCGGGAAGGCGCTGACGTTCGCCGCGATTAGCTGTTTGATGGACGCGGTGGTGATGTTCTGATCACGGAA
CTGGCTGTAATAGCCCAGGGTCGCCACGCTTTCATCCGGGCCCGGACCCGGCGCACCGAGCGTGTCGCGC
AGGTATGCGACGTGATTTTCGCTGAAGTCCCCGTACCCGGAGAACT Clone Rv35 (SEQ ID NO. 481)
::::::::::::Rv35SP6.seq::::::::::::
TGCTTCCGGCTCGTATGTTGTGTGGAATTGTGANCGGATAACAATTTCACACAGGAAACAGCTATGACCA
TGATTACGCCAAGCTATTTAGGTGACACTATAGAATACTCAAGCTCCAGGTCAATGTGCGCCAAGCCCTG
ACGCTGGCCGACCAGGCCACCGCCGCCGGAGACGCTGCCTTTGTCACCGAATACAACAACGCCGCCGAGG
CGTTCGCAGCCCAGCTGGTGACCGCCGAGCAGAGCGTCGAAGACCTCAAGACGCTGCATGACCAGGCGCT
TAGCGCCGCAGCTCAGGCCAAGAATGCCGTCGAACGAAATGCGATGGTGCTGCGGCATAAGATCGCCGAG
CGAACCAAGCTGCTCAGCCAGCTCGAGCAGGCGAAGATGCACGAGCA TABLE 3-continued End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character << - >> denotes an uncertain base residue.

::::::::::::Rv35T7.seq::::::::::: (SEQ ID NO. 482)
CAGGCATGCAAGCTTCGGAGGCAGACCCGTGCATGGTGGCACTGTAGCGACGTGCTGCAATCAAGGTCAT
GCCCGACTCTGGTCAGCTCGGAGCCGCTGACACCCCGCTAAGGCTGCTCAGCTCGGTGCATTACCTCACC
GACGGCGAACTCCCCCAGCTTTACGACTATCCGGATGACGGCACCTGGTTGCGGGCGAACTTCATCAGCA
GCTTGGACGGCGGCGCTACCGTCGATGGCACCAGCGGGGCGATGGCCGGGCCCGGCGACCGATTCGTCTT
CAACCTGTTGCGTGAACTTGCCGACGTCATCGTGGTCGGCGTGGGCACCGTGCGCATTGAAGGCTACTCC
GGCGTCCGGATGGGTGTCGTCCATCGCCA Clone Rv360 (SEQ D NO. 483)
::::::::::::Rv360SP6.seq::::::::::::
TACTCAAGCTTGGGGTGGCGCTGTCGGTCGGTGTGCTTGGCGGCGTCGGTATCAACACCGCCCACGAAAT
GGGGCACAAGAAGGATTCGCTGGAGCGGTGGCTGTCCAAAATCACCCTCGCCCANACCTGCTACGGGCAC
TTCTACATCGAGCACAACCGTGGCCATCACGTCCGGGTGTCCACACCGGAGGACCCGGCGTCGGCGCGGT
TCGGCNAAACGTTGTGGGANTTCCTGCCCCGCANTGTTATCGGCGGCTTGCGCT ::::::::::::Rv360T7.seq::::::::::: (SEQ ID NO. 484)
GGCCATCGCCACCGCNCCGCGGCGAACGCTCAAAGGCACCTACTGGCACCAAGGCCCCACACGTCACCCT
GTGACCTCCTGCGCCGACCCCGCCCGAGGTCCTGGCCGTTACCACCGAACGGGCGAGCCGGGAGTCTGGT
ACGCATCGAACAAAGAGCAAGGTGCATGGGCGGAGTTGTTCCGCCACTTCGTCGATGACGGGGTCGATCC
ATTCGAGGTCCGTCGCCGCGTCGGTCGAGTGGCGGTCACACTCCANGTACTCGACCTCACAGACGAGAGG
ACTCGATCCCATCTAGGTGTGGACGAAACAGATCTTCTGTCCGACGACTACACCACCACCCAGGCCATCG
C Clone Rv361 (SEQ ID NO. 485)
::::::::::::Rv361SP6.seq::::::::::::
GCTTGCGGGTGATCGCCTTGGTCAACGGCACCGTGATCGGATCGGGGTCNACCGCNCAGATGGACTGGAN
CTTCGGCGAANTCNTCGCCTATGCCTCGCGGGGGGTGACCCTGACCCCGGGTGACNTGTTCGGCTCGGGC
ACGGTGCCCACCTGCACGCTCGTCAAGCACCTCNGGCCACCGGAATCATTCCCGGGCTGGCTGCACNACG
GCGACNTGGTCNCCCTCCAGGTCGAAGGGCTGGGCNAAACAANGCAGACCGTCCGGACAANCGGCACTCC
TTTTCCGTTGGCTCTTCGGCCGAATCCGGACGCCNAACCCGACCGGCG ::::::::::::Rv361T7.seq::::::::::: (SEQ ID NO. 486)
GTTCTCGCACGATTTCCGGATTAGCGGGACTGGTCACCAGTTGGGTATGCGGGAAGGCGCTGACGTTCGC
CGCGATTAGCTGTTTGATGGACGCGGTGGTGATGTNCTGATCACGGAACTGGCTGTAATANCCCAGGGTC
GCCNCGCTTTCATCCGGGCCCGGACCCGGCGCACCGAGCGTGTCGCGCAGGTATGCGACGTGATTTTCGC
TGAAGTCCCCGTACCCGGAGAACTCGAACACGCTGAGGCGCTCGTCACCGTCGTNNCGGCGACCAAGCGC
GGCGAGCAACTGCGCAAAATCGTTAAGANAGGTCGAATCGTTGAAATTCGGCACCACCTGCACC Clone Rv363 (SEQ ID NO. 487)
::::::::::::Rv363SP6.seq::::::::::::
CACAAGACAATACTCAAGCTTCAGGTCAATGTGCNCCAAGCCCTGACGCTGGCCGACCAGGCCACCGCCG
CCGGANACGCTGCCAAGGCCACCGAATACAACAACGCCGCCGAGGCGTTCGCAGCCCAGCTGGTGACCGC
CGAGCANANCGTCNAAAACCTCAAGACGCTGCATGACCAGGCGCTTANCGCCNCAGCTCAGGCCAAGAAG
GCCGTCGAACGAAATGCGATGGTGCTGCAGCANAANATCGCCGANCGAACCAAGCTGCTCAGCCAGCTCG
AGCAG ::::::::::::Rv363T7.seq::::::::::: (SEQ ID NO. 488)
CCACCCGTGCATGGTGGCACTGTAGCGACGTGCTGCAATCAAGGTCATGCCCGACTCTGGTCAGCTCGGA
GCCGCTGACACCCCGCTAAGGCTGCTCAGCTCGGTGCATTACCTCACCGACGGCGAACTCCCCCAGCTTT
ACGACTATCCGGATGACGGCACCTGGTTGCGGGCGAACTTCATCAGCAGCTTGGACGGCGGCGCTACCGT
CGATGGCACCAGCGGGGCGATGGCCGGGCCCGGCGACCGATTCGTCTTCAACCTGTTGCGTGAACTTGCC Clone Rv364 (SEQ ID NO. 489)
::::::::::::Rv364SP6.seq::::::::::::
GCTTTCCGCCGATACCCNCCATGTCCCGCACATCCAGGACTTCTGGGGGGATCCGCTGACAGCGGCGGGA
TCCCAAAGTGCGGATGATCGGGCCGCCTACGTCGTGGTGTACCTCGNCGGTAACAACGAAACCGAANCGT
ATGACTCNGTCCACGCGGTG ::::::::::::Rv364T7.seq::::::::::: (SEQ ID NO. 490)
CAACCCGANTTGGCTTTCGGCGCCNTCGGTGAGGACGGCGTGCGGGTGCTCAACGACGACGTCGTCCGCG
GGACACACCTCGATGCTGCCGCCATGGACGCGGTCGAACGCAAGCAGCTGATCGATCTACNACGCCGNGN
GGAACGCTTCNGCCGCGGGCGTGACCGCNTCCCGTT Clone Rv365 (SEQ ID NO. 491)
::::::::::::Rv365SP6.seq::::::::::::
GGGATGGGCAAAAAGGCGAAGCACCGCGTGGCCACGAACGCCGGGAGGGACAATCTCGGGCGGCTAGGGC
TTCTCGCGGGAAGGCCCCGAACGTACGGCGTTTCAACACGTCCGTCGCCCTCCGACCGCGAACATTCGGG
GATGGCAGCAACCTGGTAGCACCCTGGCCGGGCGATGATCTGCCAGCGTCCCCGCGGGTAGTCGCCGCCC
GGGCGG TABLE 3-continued End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character << - >> denotes an uncertain base residue.

::::::::::::Rv365T7.seq:::::::::::: (SEQ ID NO. 492)
CAGCAGACCAACAAGAGCATCGGGACATACGGAGTCAACTACCCGGCCAACGGTGATTTCTTGGCCGCCG
CTGACGGCGCGAACGACGCCAGCGACCACATTCAGCAGATGGCCAGCGCGTGCCGGGCCACGAGGTTGGT
GCTCGGCGGCTACTCCCACGGTT Clone Rv366 (SEQ ID NO. 493)
::::::::::::Rv366SP6.seq::::::::::::
CTCAAGCTTGACTGGCCACCCACCGGCATGACCACCGACAGGCCCGACTGGTCGTACCACTCGAACGCCG
GGGTGTTTGA ::::::::::::Rv366T7.seq:::::::::::: (SEQ ID NO. 494)
TTGGTGCCCGGAATGGCGAGTCCCATTTANTCGCTGATTTGTTTGAACAGCGACGAAACCGGTGTTGAAA
ATGTCGCCTGGGTCGGGGATTCCCTCTCCAAGCAAGAGTAACTGGCCCCAAATAAAGTTACTCGTCGTCT
TGCAAAGACCGCTACCCGATGCCATTTATGTGTTTCCTTACGCTCNNNNTTCCGGTGCGCCATCATTATC
TGCACCTTTGCACTGCACATTGAGCTTAGCAGCGCTCG Clone Rv367 (SEQ ID NO. 495)
::::::::::::Rv367T7.seq::::::::::::
GAATTNGCTTTCGGCGCCATCGGCCCAGGACCGCGTGCGGGTGCTCAACGACGACGTCGTCCGCGGGACA
CACCTCGATGCTGCCGCCATGGACGCGGTCGAACGCAAGCAGCTGATCGAGCTACAACGCCGCGCGGAAC
GCTTCCGCCGCGGGCGTGACCGCATCCCGTTGACCGGGCGGATCGCNGTGATCGTCGATGACGGCATCGC
CACCGGAGCGACGGCCAAGGCGGCGTGCCAGGTCGCCCGGGCGCACGGTGCGGACAAGGTGGTGCTGGCG
GTCCCGATCGGCCCAGACGACATCGTGGCGAGATTCGCCGGGTACGCCGATGAAGTGGTGT Clone Rv368 (SEQ ID NO. 496)
::::::::::::Rv368SP6.seq::::::::::::
TAAAGCTTTCGTCAGTTCATNGNGCCCCCGGACCAACAAAAGCATCGGGACATACGGAGTCAACTACCCG
GCCAACGGTGATTTCTTGGCCGCCGCTGACGGCGCNAACGACGCCAGCGACCACATTCAGCAGATGGCCA
GCGCGTGCCGGGCCACGAGGTTGGTGCTCGGCGGCTACTCCCAGGGTGCGGCCGTGATCNACATCGTCAC
CGCCGCACCACTGCCCGGCCTCGGGTTCACGCAGCCGTTGCCGCCCGCAGCGGACGATCACNTCGCCGCG
ATCGCCCTGTTCGGGAATCCCTCGGGCCGCGCTGGCGGGCTGATGAGCGCCCTGACCCCTCAATTCGGGT
CCAANACCATCNACCTCTGCAACAACGGCGACCCGATTTGTTCGGACGGCAACCGGTGGCGANCGCACCT ::::::::::::Rv368T7.seq:::::::::::: (SEQ ID NO. 497)
CCGGGAGGGACCATCNCGGGCGGCTNCGGCTTCTCTCCGGAAGGTTCTANNGTNNNGCGTTTCNACNCTT
CCCGTCGCCCTGCGACCGCCGAACATTCGGGGTATGGNNGCANCCTGTNAGCATCCNGGCCGGGC Clone Rv369 (SEQ ID NO. 498)
::::::::::::Rv369SP.6seq::::::::::::
CTCAAGCTTCCGCATCAGATCGCTATAGAACCGGTGCGCGTCCCCACCGAGTGGCTGGTCGCCTTCCAGC
ACGATCGTTACCGCGTTATCGGAATCAAACTCNCCGAACACCTGACCAACGCGCTTGATCGCCTGAATCG
ATGCGGCGTCGCTGGGGCTCATCGATACCGAGTGTGCTTTTCCGACCACTTCCAGTTGCGGTACGGCGAG
ATTGACAAAGGCGGTGAAGCCCAGCCAGAGCAGGACGATCACCNCCGCAAACCGGCGGATTTGCCCG ::::::::::::Rv369T7.seq:::::::::::: (SEQ ID NO. 499)
GCTTGGCAGCCTGCGGCTGGGCGCCCTNGAGCTCTTCGATCTGGATCTCCGGACTCGAGATGCTCACTTG
CCCGGCCGTGGACGTACCCATTGCGGCCGGGACCCCAGCGCCCCAGGTGACCAGCGAGTTGGGCTGCACG
CTGACCGGCCCGTCGGGGTCGACGCCGGTAACGGTCAGCAGCTCCGANGTCCNNCTGATCCCGACCGCAG
CTGCCAATGCGCGGCTGGCAGCCGACGTGGATGTGCCGGGGCCTAGATCGCGGGGCAGCAGCGAGACCGC
GTCACCGACGGTCATCACCTTGCCGAGTTTNGGCCTGCCGCAN Clone Rv36 (SEQ ID NO. 500)
::::::::::::Rv36SP6.seq::::::::::::
GCTTCCGGCTCGTATGTTGTGTGGAATTGTGAGCGGATAACAATTNCACACAGGAAACAGCTATGACCAT
GATTACGCCAAGCTATCTAGGTGACACTATAGAATACTCAAGCTTGAGCCATCGGGCTATCAGCTGGTTG
ATGTCCCG ::::::::::::Rv36T7.seq:::::::::::: (SEQ ID NO. 501)
CAGGCATGCAAGCTTGTCGTCTATCACATCCGACCACCAACCGCCCGACGGCTCGGCAGAACGCCTCCGC
ATATGGGTCGACGACCAGCGGGTCGGACTTCTGGGCTGCCAGCGCTCGCGCCGTCGCGACAAACAGCGCG
GTCGAACCGACACTCCTTGTGATGTCCCACCTATCACCTTCGGTACGCACCCAATCGACCCTACGCGGCT
AGCTCAGCCCCGATCTTCCAGAGCTCCGCCCG Clone Rv370 (SEQ ID NO. 502)
::::::::::::Rv370SP6.seq::::::::::::
GCTTTTTGAGCGTCGCGCGGGGCGGCTTCCCCGGCAATTCTACTAGCGAGAAGTCTGGCCCGATACGGAT
CTGACCGAAGTCGCTGCGGTGCAGCCCACCCTCATTGGCGATGGCGCCGACNATGGCGCCTGGACCGATC
TTGTGCCGCTTGCCGACGGCGACGCGGTAGGTGGTCAATTCCGGTCTACGCTTGGGCCTTTGCGGACGGT
CCCGACGCTGGTCGCGGTTG ::::::::::::Rv370T7.seq:::::::::::: (SEQ ID NO. 503)

TABLE 3-continued

End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character << - >> denotes an uncertain base residue.

CGANCCTGTTCGACGGCTACCTGAATCACCCCGATNCCACCGCCGCGGCGTTCGACGCCGACAGCTGGTA
CCGCACCGGCGACGTCGCGGTGGTCGACGGCAGTGGGATGCACCGCATCGTGGGACGCGAGTCGGTCGAC
TTGATCAAGTCGGGTGGATACCGGGTCGGCGCCGGTGAAATTGAAACGGTGCTGCTCGGGCATCCGGACG
TGGCGGAGGCGGCAGTCGTCGGGGT

Clone Rv371 (SEQ ID NO. 504)
::::::::::::Rv371SP6.seq::::::::::::
NAAGCTTTGTCACACCAAGTGTTTTCNACCAGNCGCTCCATCCGGCGAAGTGGATACTCCCAGCAGGTAG
CAGGTCGCCACCACGCTGGTCAGTGCGCGTTCAGCTCGCTTGCGGCGCTGCAGCAGCCAGTCCGGGAAAT
AGCTGCCCTGGCG ::::::::::::Rv371T7.seq:::::::::::: (SEQ ID NO. 505)
CGCTGGNCGCCGGCGCTGGGCTGCGGTAACCAATTACCACAACACTTTTCGGTAGCCGAACAGCGGCGCG
TACCAGCGAAATGGCACAGCCACCGCAGTCGCCGACATCCCGCGAAGATGTGGCAGATTTTCGTGCGGTC
GAGCCGGCGAAGGCCTAGCGTCATTGTTGCCTGGCAAGGTTGCTGGGCCCGG Clone Rv373 (SEQ ID NO. 506)
::::::::::::Rv373SP6.seq::::::::::::
CTCAAGCTTCTTCTGCCCCTTGCCGTTNCGATNACATCCCGCAGCGACTCGGCTTCGGCGTCGATGTCGA
AGTTCTCGATCAGCTTCTGGATCGACTCCGCGCCCATGGCACCGGTGAAGTACTCGCCGTAGCGGTCGAC
NAGTTCGCGGTAGAGGTTTTCGTCNACNATCAGCTGCTTGGGCGCCANCTTGGTGAAAGTGCTCCAAATG
TCCTCCAACCGGTCCAGCTCACGCTGCGCGCGGTCACGGATCTGGCGCATCTCGCGCTCGCCGCCGTCGC
GAACTTGCGCCGCGCATCGGCCTTGGGGCCC ::::::::::::Rv373T7.seq:::::::::::: (SEQ ID NO. 507)
GTTCACACCTACCTACTATGCCNCAATTCNCCGACACGGGTGGCATCAACACGGGCGATAAGGTGGAAAT
CGCTGGGGTGAACGTCGGGCTGGTGCGCTCGCTGGCAATCCGCGGCAACCGCGTGTTGATCGGATTCTCG
TTGCCCGGCAAGACAATCGGGATGCAAAGCCGGGCAGCAATTCNCNCCNACACCATTCTTGGCCGTAAGA
ACCTGGAGATCGAACCCCGCGGTTCGGAGCCGTTGAAACCCAACGGTTTCCTGCCGTTGGCGCANACCAC
TACGCCATACCAAATC Clone Rv374 (SEQ ID NO. 508)
::::::::::::Rv374SP6.seq::::::::::::
CTCAAGCTTTACGCCGACGCCGGCCTACACAACACCAAGGAAACGATTGCCTACTGCCGAATCGGGGAAC
GGTCCTCGCACACCTGGTTCGTGTTGCGGGAATTACTCGGACACCAAAACGTCAAGAACTACGACGGCAG
TTGGACAGAATACGGCTCCCTGGTGGGCGCCCCGATCGAGTTGGGAAGCTGATATGTGCTCTGGACCC ::::::::::::Rv374T7.seq:::::::::::: (SEQ ID NO. 509)
TCCCNCATGGGATAACGGGTTTAGATTTCNACAACGGCACCGTGTTTCTCAACAAGCCGGTCATCAGCTG
GGCCGGCGACAACGGTATCTACTTCACCCGCTTTCGCCCGTACAAGAAAAACCACTAGGCCACCATCGAG
TCCAAGAACAACCACCTGGTCCGCAAGTACGCGTTCTACTACCGCTATGACACCGCCGAGGAACGCGCCG
TGCTCAACCGGATGTGGAAGCTGGTCAACGACCGCCTCAACTACCTCACCCCGACCATCAAACCGATC Clone Rv375 (SEQ ID NO. 510)
::::::::::::Rv375SP6.seq::::::::::::
CTCAAGCTTGGGTGTTGCCGATCACCGGAAGCCNCATGATCAGCCACGTTTCGCGCCGCCCGGCATACGG
CGGCGTACCGATCTCCGCGTCATACACCCGCGGGTAATCGCCGACGGTGCCGGTTCGCGAGCCGAAGGTG
ACAACGCTGATTGAATCNAGTTCCANGTCCAGCGGGT ::::::::::::Rv375T7.seq:::::::::::: (SEQ ID NO. 511)
TNAACAGCTCGCGGCAGCCCACGACCTGCTGCGTCGGATTGCCGGCGGCGAGATCAATTCCAGGCAGCTC
CCGGACAATGCGGCTCTGCTGGCCCGCAACGAANGACTCGAGGTCACCCCGGTGCCCGGGGTCGTGGTGC
ACCTGCCGATCGCACAGGTTGGCCCACAACCGGCCGCTTGATGNNNNGTCGGCAAGCCCGGCAGTNGCCA
AACCCAGCGTGATCANGCTCGGCTCGCGAGTTCGGCGAANAAGTGGCTCGCCTGATCACCTACCATCGGC
CANGATCTGCGTGTCA Clone Rv376 (SEQ ID NO. 512)
::::::::::::Rv376SP6.seq::::::::::::
GCCANCCGGCTTGGCGTCGACTCCCGTTCNGCACATCATACGGTCCCCGGTACTGTCCAACTGCGCCGGT
GCGCTAGCCAAACGTCACGACTCTCAGTGATCCCAGTTCGTGATCCGGCCGGTGGCGCCCGCTGCGGCGGG
GGCTNATNTACTTCGGACTNATTATCTCATCCAAAGGACACCGGGCCGGTGGCTGGAATCCCATGGTGCG
ATCGGCCACACAN ::::::::::::Rv376T7.seq:::::::::::: (SEQ ID NO. 513)
CCGACCTGGTATCTTCCGATAGCGCGCGTTGATATCCGGTCTGATCTCCTGCCCTTAACGCCGGATCTCA
GCAGGTCCCCATGCAAAGATCCGAGGTGTCCCNGATCTAGGGGTCCTCGTCCTCCAGATGATGGAGCAAG
TCGGCCC Clone Rv377 (SEQ ID NO. 514)
::::::::::::Rv377SP6.seq::::::::::::
CTCAAGCTTCGGCTCAGGCGGCGCTGCCGGTAACGTCGCTGACCGGTGCAGGTTTCGACAATGTGGTGCC TABLE 3-continued End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character << - >> denotes an uncertain base residue.

GGTTCGGCGGCTACGTGCCATCAAGACACTGGCGCAGGCTATCGCACCCGTTATCGGCTACAAACAAATC
GCGGTATGC

::::::::::::Rv377T7.seq:::::::::::: (SEQ ID NO. 515)
CATCACCTGNTTCATGAACTGGAAGCACCGCAGCGCTTCCTTTTCGGCCGCAACATGAGCCAGCCTCTCG
TCGGCGGTCGGGTGCAGGTGCTCGGGCAGCTCGGCCGCGACAGCCGCCTGACCCTGAAACCAGCTTCCAT
ATCCCGCGACGAACGACGCCAGTCCGCTACGTAACCCCTCCGCGACTGTCCATGGACAACAGCGCGTTCT
CCACCGACCGGGCCCGGGTGTGGGGTGT Clone Rv378 (SEQ ID NO. 516)
::::::::::::Rv378SP6.seq::::::::::::
AGCTTAGCTTCCCGCCCCGGCAATAGGGCTCCAGCTCATCCGGTGTGACCAGATAGGGGCCCAGGGTGAT
ACCGCTGTCTTTGCCCTTGGCCTGTCCGATGCGCAGCTGGCCCTCCAGCATCTGCAGGTCCCGTGCGGAC
CAGTCGTTGAAAATGGTATAGCCGATGATCGACCG ::::::::::::Rv378T7.seq:::::::::::: (SEQ ID NO. 517)
CCNGAACAGAAGCGGNGGTTCCTACCGCGGTGTGCGGCCGGCGCGATATCGGCCTTTTTACTAACCGAAC
CCGATGTGGGCTCCGATCCGGCGCGCATGGCATCGACGGCGACGCCGATCGATGACCGCCAGGCTTACCA
CCTT Clone Rv379 (SEQ ID NO. 518)
::::::::::::Rv379SP6.seq::::::::::::
CTCAAGCTTGCGCGACTCGACAAGCATTCTTGACAGTTGTTTTGGCTCGGCATGGTTAGCCAAGGTTCTG
CGGTCCCACCAGATCATCTTGGTCCGGTAGCGCTCGTCCGGGTATGCTGCCGCCGGGATTCTCGCTGCTA
TTACTCCCCCCGAAGAACGCCACCGGTCCAGCGC ::::::::::::Rv379T7.seq:::::::::::: (SEQ ID NO. 519)
GCNAGGCGGTATAGCTTCCCGTCGTACCGGCGACCGCCAGCCGAGAAGCTCGTTTTCCCAGTGTTGCTGG
GGATTCTCACGCTGCTGCTGAGTGCGTGCCAGACCGCTTCCGCTTCGGGTTACAACGAGCCGCGGGGCTA
CGATCGTGCGACGCTGAAGTTGGTGTTCTCCATGGACTTGGGGATGT Clone Rv37 (SEQ ID NO. 520)
::::::::::::Rv37SP6.seq::::::::::::
GTGTGGAACCGTGAGCGGATAACAATTTCACACAGGAAACAGCTNTGACCTTGATTACGCCAAGCTATTT
AGGTGAGGCTATATTAATACTCAAGATTGCGGTCGAGCACATCGGCCCAAGAACCGCCGAAGGCACGGCG
GAACGCCTGCGGCACATGGGGCGACGACCAGCGGGTCGGACTTCTGGGCTGTCCAGCCGGATCGCGCCGT
CGCGA ::::::::::::Rv37T7.seq:::::::::::: (SEQ ID NO. 521)
CACTGTCAGTACATATGCGCCGCTCCTCCTCATCGCTGCGCTCGGCATCGTCGCCGGCGGTCATGGCGTC
ACCCTACCCAAGCCGAACGCGAAACGAGAACGTGTTCCATTATTAGGGTGTGAGCACCAATACCAGATTG
CTCACCAGGAACTCACGCAGCACCGGGACGGATGTCAGCCACCACGCCCATCTGGGGTGGTAGCGGGGAA
ATACGGCTAACGCGGCTCCGGTGCCGGCAGCCCAGCGCAGACCCTCGGCGGCGGACACGGCAAACAACGA
CGACCCATAGTTGTTCTTTGCCGGATGGCCGTGTTTGCGGACATATCGGGCGGCGGCGCGGGCGCCGCCG
AGGTAGTGGCTGAGGCCCATCTCGTGCCCGCCGAATGGCCCCAGCCAAACCGTGTA Clone Rv381 (SEQ ID NO. 522)
::::::::::::Rv381SP6.seq::::::::::::
CTCAAGCTTTTACGGTGATCGCGCATCACCTGGTTCATGAACTGGAAGCAGCGCAGCGCTTCCTTTTCGG
CCGCAACATGAGCCANCCTCTCGTCGGCGGTCGGGTGCAGGTGCTCGGGCAGCTCGGCCGCGACAGCCGC
CTGACCCTGAAACCAGCTTCCATATCCCGCGACNAACGAC ::::::::::::Rv381T7.seq:::::::::::: (SEQ ID NO. 523)
CTCAGAAGCCGCTAGCTGGTAGAGTCGCTGACCGGTGCACGTGGCGNCAATGTGCGCTGCCGGTTCGCG Clone Rv382 (SEQ ID NO. 524)
::::::::::::Rv382SP6.seq::::::::::::
CTCAAGCTTGCGCTCATCAAGCGCGAACAGCAGGGCGGTCGGCTGGTCGCCATGACGGGTGACGGGACCA
ATGACGCACCCGCGCTCGCGCAAGCCGATGTCGGGGTGGCNATNAATACCGGCACCCAGGCGGCCCGGGA
AGCCGGCAACATGGTCNATCTCCACTCC ::::::::::::Rv382T7.seq:::::::::::: (SEQ ID NO. 525)
ACTTCTATTTCGACTGGTGTGCTGTGGCGCGATCCGACTGCCGGCGTGGTCAAGGCCGGCCAGTTGTGGG
ATNCCACAGGCAC Clone Rv383 (SEQ ID NO. 526)
::::::::::::Rv383SP6.seq::::::::::::
GCTTGTCGTATTCCGTGGCACTGTCAGACATATGCGCCGCTCCTCCTCATCGCTGCGCTCGGCATCGTCG
CCGGCGGTCATGGCGTCACCCTACCCAAGCCGAACGCGAAACGAGAACGTGTTCCATTATTAGGGTGTGA
GCACCAATACCAGATTGCTCACCAGGAACTCAC TABLE 3-continued End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character << - >> denotes an uncertain base residue.

::::::::::::Rv383T7.seq::::::::::: (SEQ ID NO. 527)
CGATATTCGTCGGCCGCGTTGTCTCGACTGGGTCGCGT Clone Rv384 (SEQ ID NO. 528)
::::::::::::Rv384SP6.seq::::::::::::
GACCTCGGCCACCAAGCCGGACGCGACCGTCGAGGTGGCGATCCGGCTTGGCGTCGACCCGCGTAAGGCA
GACCACATGGTCCGCGGCACGGCCANCCTGCCACACGGCACTGGTAAGACTGCCCGCGTCGCGGCN ::::::::::::Rv384T7.seq::::::::::: (SEQ ID NO. 529)
CCGGAAGTCTAGGGGACGACCTACTCAGCGCAAAATGTCGCTAATGTGAGTCCGCCCCACCAGGGCAGAT
CAACCCATGTCGATGATGACCTACCCGGATACCGGATTGGCGGT Clone Rv385 (SEQ ID NO. 530)
::::::::::::Rv385SP6.seq::::::::::::
AGCTTCAGTTCCTCCACGACGCGTTCCCAAATGAATTTCCCGATCCCACAATCTCGGTTCAGATACAGGT
CGCCATACCCCTTACTTCGGNAACGCTGGGCGGATTGGCCCTGCCGCTG ::::::::::::Rv385T7.seq::::::::::: (SEQ ID NO. 531)
CCGCCTACGGGTCGAACATGCATCCCGAGACCGATGCTCGAGCGCGCACCCCACTCGCCGATGGCCGGAA
CCGGCTGGTTACCCGGGTGGCGGCTGACC Clone Rv386 (SEQ ID NO. 532)
::::::::::::Rv386SP6.seq::::::::::::
GCGGCTGGTTACGACTCCCTGTTTGTGATGGACCACTTCTACCAACTGCCCATGTTGGGGACGCCCGACC
AGCCGATGCTGGAGGCCTACACGGCCCTTGGTGCGCTGGCCACGGCGACCGAGCGGCTGCAACTGGGCGC
NTTGGTNACCGGCAATACCTACCGCAGCCCGACCCTGCTGGCAAAGATCATCACCACGCTCGACGTGGTT
AGCGCCGGTCGAGCGATCCTCGGCATTGGAGCCGGTTGGTTTGAGCTGGAACACCGCCAGCTCGGCTTCG
AGTTCGGCACTTTCAGTGACCGGTTCAN ::::::::::::Rv386T7.seq::::::::::: (SEQ ID NO. 533)
GCCTTTCCGCACAATCTGTACCCCAGGACCNTCTAAAAAATCGAATACGACGGCGTCGCCGACTTTCCGC
GGTACCCGCTCAACTTTGTGTCGACCCTCAACGCCATTGCCGGCACCTACTACGTGCACTCCAACTACTT
CATCCTGACGCCGGAACAAATTGACGCAGCGGTTCCGCTGACCANTNNTGTCGGTCCCACGATGACCCAG
TACTACATCATTCGCACGGAGAACCTGCCGCTGCTAGAGCCACTGCGATCGGTGCCGATCGTGGGGAACC
CACTGGCGAACCTGGTTCAACCAAACTTGAAGGTGATTGTTAACCTGG Clone Rv387 (SEQ ID NO. 534)
::::::::::::Rv387T7.seq:::::::::::
GCAGACCAACAAGATGCATCGGGATCATACGCCGTCAACTACCCGGCCAACGGTGATTTCTTGGCCGCCG
CCCAC Clone Rv388 (SEQ ID NO. 535)
::::::::::::Rv388SP6.seq::::::::::::
CTCAAGCTTGCCAAAGAGACCTCGTCCACCAAGCNGGACGCGACCGTCNAGGTGGCGATCCGGCTTGGCG
TCCACCCGCGTAAGGCANACCANATGGTTCGCGGCACGGTCAACCTGCCACACGGCACTGGTAANACTGC
CCGCGTCGCGGTATTCGCGGTTGGTGAAAAGGCCGATGCTGCCGTTGCCGCGGGGGCGGATGTTGTCGGG
AGTGACAATCTGATCGANAGGATTCAGGGCGGCTGGCTGCAATTCGATGCCGCGATCGCGACACCGGATC
AGATGGCCAAAGTCGGTCNCATCGCTCGGGTGCTGGGTC ::::::::::::Rv388T7.seq::::::::::: (SEQ ID NO. 536)
CCACGGCGTGGATCAAGGTACCGGCCGGGATGTTGCGCAATGGCAGGTTGTTGCCCGGCTTGATGTCGGC
GTTAGCGCCGGATTCCACCACATCCCCTTGCGAAAGTCCGTTGGGTGCAATGATGTAGCGCTTCTCCCCA
TCGAGATAGTGGAGCAACGCAATCCGTGCGGTACGGTTCGGGTCNTACTCGATGTGCGCGACCTTGGCGT
TGACACCATCTTTGTCATTGCGGCGAAAGTCGATCATCCGGTAAGCGCGCTTATGACCGCCGCCTTTGTG
CCGGGTGGTAATCCGGCCATGCGCGTTGCGTC Clone Rv389 (SEQ ID NO. 537)
::::::::::::Rv389SP6.seq::::::::::::
GGCGGCTGCGTCGGCGAGATGATCGCCCGGTGCCACCCCGATCCGTGCCTCGGTCAGCGCCAACGTGCTT
TCCGGTCCGGCGACCACCATGTCGCATGCGCCGAC ::::::::::::Rv389T7.seq::::::::::: (SEQ ID NO. 538)
GCAATCGCCTTGGCGGTCGCCGGGTTGTCACCGGTGATCATCNCGGNGCGGATGCTCATNCGGCGCATTT
CGTCNAATCGTTCCCGTATGCCCACCTTGACGATGTCCTTCATATGGACCACGCCGATGGCCCNCGCGCT
NCTG Clone Rv38 (SEQ ID NO. 539)
::::::::::Rv38SP6.seq:::::::::::
CCGGCTCGTATGTTGTGTGGAATTGTGAGCGGATAACAATTTCACACAGGAAACAGCTATGACCATGATT
ACGCCAAGCTATTTAGGTGACACTATAGAATACTCAAGCTTCCACATCGGTATGCCAAAGCATTGCGCCG
CTATCGATTTCGCGCTGGCATCGCCAAGGTGGACTTCTTGCTCAGCGACGAGATCCCGTGGTCGGATCCG TABLE 3-continued End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character << - >> denotes an uncertain base residue.

CGGCTGCGGCGGGCTGCGACCCTGCATCTCGGCGGCACCCGTGACCAGATGGCGCGCGCCGAGGCAGACG
TCGCGGCGGGACGCCACGCCGACTGGCCGATGGTGCTGGCCGCGTGTCCGCACGTCGCCGACCCCGGCCG
CATCGACGAAACCGGCCGCCGTCCGTTCTGGACCTATGCCCACGTGCCGTCGGGGTCCACGCTCGACGCG
ACCGAGACCGT

::::::::::::::Rv38T7.seq:::::::::::::: (SEQ ID NO. 540)
CGCGTCCACCGCAGCGTGAGATTGGTGGCGCCATTCGTCGTGGTGTAGCTGCTGTTGGCGGCGTCGCCGT
ATTGTGCGGGCCAGCCTTGTGCGGGGGCCGCTTCTACCCACGAGTCGGCACTTCCGCAACCGCCCAGCTC
GACCGCGATTACGGCGGCCGCAACGGCCGCCGGAAGGCGTCTCGCAAGCGCCTTATCCTTTCGCAGGTTC
CCAGATCCTTCCGCTACGTGGGTCGCTCATCGGCGGGCCCGGCCGAATGAGTACAGGTGAGGGTAACCGC
TACAAATGAAGTTGGTCAGTGCTGGCCAACTGTGTAATGGTTGCCCGGCTCGGGTCACCACGTACATTCT
GGCAAGGCGGGCGAGATTCGGTTCCTCGCGTCCTTGGCCGGTGGCGGTTCCCGGTTGTCCGTGGGCGTGT
CGTGTACGTGGTGTAAGTGTCGTGAACTCCTCAGTTTGGGCT Clone Rv390 (SEQ ID NO. 541)
::::::::::::::Rv390SP6.seq::::::::::::::
CTCAAGCTTGCGCTGGATCTGGCGGCTGAGCCTGTTCTTGGGCAACATGCCGAGGGATCGCCTTTTCCAC
CACGCGGTCGGGGTGGCGTTGCATTAGCTCACCGATGGTGCGCTTGTGCAGGCCGCCGGGATACCCCGAG
TGCCGGTAAACCATCTTGTGCTGCAGTTTGTCGCCGCTGATGGCGACCTTGTCGGCGTTGATCACNATGA
CNAAGTCACCGCCATCGACATTGGGGGCGAACGTCGGCTTGTGCTTGCCGCGCAGCAGGTTGGCCGCCGC
GACGGCAAGGCGGCCAANCACCACGTC ::::::::::::::Rv390T7.seq:::::::::::::: (SEQ ID NO. 542)
TTTGGGATGGGCAAAAAGGCGAAGCNCCGCGTGGCCACGAACGCCGGGAGGGACAATCTCGGGCGGCTAG
GGCTTCTCGCGGGAAGGCCCGAACGTACGGCGTTTCAACACGTCGCGTCGCCCTCCGACCGCGAACATTC
GGGGATGGCAGCAACCTGGTAGCACCCTGGCCGGGCGATGATCTGCAGCGTCGCCGCGGGTAGTCGCCGC
CCGGGCGGCTACAGTCTGAAACGCGATGACCATCGATGTGTGGATGCAGCATCCGACGCAACGGTTCCTA
CACGGCGATATGTTCGCCTCGCTGCGCCGGTGGACCGGTGGGTCTATCCCGGA Clone Rv391 (SEQ ID NO. 543)
::::::::::::::Rv391SP6.seq::::::::::::::
CTCAAGCTTCGTCATAAGACCATGGTGCGCTTTCTTTCACCCGTCCANAGTCGGGGGCATCCGCACCGGC
TCGCATCGCATCATCCTCCCACGACGGGCCGCTCATCAGCTTGGGCCATTTCAATGTACTTGATACCCCG
CGCTGCGGGTAGGCCACTGCNACAATTCAAACACGGTGTCACACGGTGAATANTGTCNANATGGGCTCTG
ATCAACCGTCNCAAACCCGGTTTC ::::::::::::::Rv391T7.seq:::::::::::::: (SEQ ID NO. 544)
GAATTCTGCGTGCACCGCTATGGGTTGCAGCAGCGGCTGGCGCCGCACACCCCACTGGCCCGGGTGTTTT
CGCCCCGAACCCGGATCATGGTGAGCGAAAAGGAGATTCGCCTGTTCGATGCTGGGATTCGCCACCGCGA
GGCCATCGACCGATTACTCGCCACCGGGGTGCGAGAGGTGCCGCAGTCCCGCTCCGTCGACGTCTCCGAC
GATCCATCCGGCTTCCGCCGTCGGGTGGCGGTAGCCGTCGATGAAATCGCTGCCGGCCGCTACCACAAGG
TGATTCTGTCCCGTTGTGTCGAAGTGCCTTTCGCGATCGACTTTCCGTTGACCTACCGGCTGGGGCGTCT
GCACAACACCCCGGTGAGGTCGTTTTTGTTGCAGTTGGGCGGAATCCGTGCTCTGGGTTACAGCCCCGAA
CTCGTCNCGGCGGTGCGCGC Clone Rv392 (SEQ ID NO. 545)
::::::::::::::Rv392SP6.seq::::::::::::::
GCAGTTGGGAATCGCTCTGCAGCAAACCANTATTCTGCGCGACGTTCGAGAGGACTNTTTGAATGGACGG
ATCTACCTGCCGCGCGACGAGCTGGACCGATTAGGCGTACNCCTCCGCCTGGACGACTCCGGGGCACTCG
ATGACCCCGACGGACGGCTCGCGGCACTGCTGCGGTTCANTGCCNACCGCGCCGCANACTGGTATTCGCT
GGGACTGCGGCTGATTCCACACCTCGACCGCCGCAGCGCTGCCTGCTGTGCGGCCATGTCTGGCATCTAC
CGCCGTCNGCTCGCCTTGATCAGACCATCGCCGGCGGTCGTCTACCATCGGCGAATCTCTCTGTTCGGGA
CTGAANAANGCCCAAGTGGCGGCGGCAGCACTGGNCTCTTCGGTAACCTGCNGACCGCCCATTGGACCGC
TACCG ::::::::::::::Rv392T7.seq:::::::::::::: (SEQ ID NO. 546)
TTGATCTGGACGTCTGAGACGGTGATCGGNCCGAACCTGAATTGTCCGGTAATGCCCAGCGCAGAAAGCA
NGGTGGTGGCCGGGGCGGTGAANCCGGCGTCGGCGGCACCGTCGAAGTCGATGTGGATTGCCGGAATGGG
GATGTCCGGCACGGCGAAGCCGTAGTTCGCTTGTCCCGTGAGGCCCANGTGGATGGGGGAAGGATCGTG
GTGTCCGGGATGATAATGGGGCCGATGCCGCCGGTTGAAGTCCAGTGGATCGGGAATTCGGGAATCGTGA
TGCCGACGTTCAGGCCGAACAGGCCCTCCAAGTTGCCTCGCCACNAGATGCCGTTGCTGAAGTTGCCCGA
CATGAGGGCGCCGGTGTCCACATTGCCCGAATTGGCGACGCCGGTGTTGGC Clone Rv393 (SEQ ID NO. 547)
::::::::::::::Rv393SP6.seq::::::::::::::
CACGTAGGCGCCGTCCATAAATNACTCCGCCGCGCTTCGCACATCCTCGTANCGATCCTTGGCGAGCAGG
TCAACCGGGCGCTGCCCGTCNAGGAGCCGGTTTTTGGCGTGCAGCCACTGGCCGACACCTCGGGGGGTAA
GCGAATCCGAGAGCAGGAGGACNAGGTCACGAANCTGCGCCAGCCGGTCGTACCGCTCAGGGCGGATGTC
GCCGGTCCGCCACCCGCGTACCGCCCGATCGGACACCTGTATGACCGCGGCGACNTCGACCTGGGTGACG
CCGAAGGGTTTCAGGGCATCNACNATCTCGCTGGCCTCGACCGCCCGGTCCAGGGTGACCGCCATCGTGG
TTCCTCCGCAACTTCCGGTTCTACTACCGTAAACGCTACCG TABLE 3-continued End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character << - >> denotes an uncertain base residue.

:::::::::::::Rv393T7.seq::::::::::::: (SEQ ID NO. 548)
CGGGGAACGGTCCTCGCACACCTGGTTCGTGTTGCGGGAATTACTCGGACANCAAAACGTCAAGAACTAC
GACGGCAGTNGGACAGAANACGGCTCCCTGGTGGGCGCCCCGATCGAGTTGGGAAGCTGATATGTGCTCT
GGACCCAAGCAAGGACTGACATTGCCGGCCAGCGTCGACCTGGAAAAAGAAACGGTGATCACCGGCCGCG
TAGTGGACGGTGACGGCCAGGCCGTGGGCGGCGCGTTTCGTGCGGCTGCTGGGACNCCTCCGACGAGTTC
ACCGCCGGGAGGTCGTCGCGTCGGCCACCGGGCGAATTTCCGGTTCTTCGCCGCGCCCCGGGATCCTGGG
ACCGCNGGCGCGCGCTGTT Clone Rv396 (SEQ ID NO. 549)
:::::::::::::Rv396SP6.seq:::::::::::::
CTCAAGCTTTGTCCGACAAGCGTTCCCGGGCGGTCAGCAAGCGAACGTCGGTTGGCCCACTGCGGGTCGA
TATTGCCGCCAGGGA :::::::::::::Rv396T7.seq::::::::::::: (SEQ ID NO. 550)
CGTCAGCACGGCGACGTCGCGNTACGCCGAGCAGTTACACAATCGCTCTGCAGCAAACCAATATTCTGCG
CGACGTTCGAGAGGACTTCTTGATTGGACTG Clone Rv39 (SEQ ID NO. 551)
:::::::::::::Rv39SP6.seq:::::::::::::
CTGCATCCGGCTCGTATGTTGTGTGGAATTGTGAGCGGATAACAATTTCACACAGGAAACAGCTATGACC
ATGATTACGCCAAGCTATTTAGGTGACACTATAGAATACTCAAGCTTCGCGCAGCGGCGGGTTGACCCGG
TTCACGCCGTCATAGCTGGCCAATCTGGCATCGTCGATCANCATGTGGTGGGGGGTGACCTCGGCGGTGA
TCGAAATACCCTGGTCCTTATCCCATTTCAGGATTTCGACGGTGCCCGCGGCCGACGCGTGACAGATGTG
CACCCGGGCGCCGGCGTCACGGGCCAGCAAGGCGTCGCGGGCGACGATCGATTCCTCGGCGGCCCGCGGC
CATCCCGCCAGGCCCAGCCGCGCCGCCATGGGTCCCTCGTGCGCGACGGCGCCGACCGTCAGCCGGGGCT
CCTCGGCGTGCTGGGCGATCAGCACGCCCAAACCGGTG :::::::::::::Rv39T7.seq::::::::::::: (SEQ ID NO. 552)
CCGACGCGCACTACGTGCTGGTGTCCACCCGCGACCCGCACCGGCACGAGCTACGCAGCTACCGCATCGT
CGATGGCGCTGTCACCGAGGAACCTGTCAATGTCGTCGAGCAGTACTGAACCGTTCCGAGAAAGGCCAGC
ATGAACGTCACCGTATCCATTCCGACCATCCTGCGGCCCCACACCGGCGGCCAGAAGAGTGTCTCGGCCA
GCGGCGATACCTTGGGTGCCGTCATCAGCGACCTGGAGGCCAGCTATTCGGGCATTTCCGAGCGCCTGAT
GGACCCGTCTTCCCCAGGTAAGTTGCACCGCTTCGTGAACATCTACGTCAACGACGAAGACGTGCGGTTC
TCCGGCGGCTTGGCCACCGCGATCGCTGACGGTGACTCGGTCACCATCCTCCCCGCCGTGGCCGGTGGGT
GAGCGGACACATGACACGATACGACTCACTGTTGCATGGCTTG Clone Rv3 (SEQ ID NO. 553)
:::::::::::::Rv3SP6.seq:::::::::::::
TGCTTCCGGCTCGTATGTTGTGTGGAATTGTGAGCGGATAACAATTTCACACAGGAAACAGCTATGACCA
TGATTACGCCAAGCTATTTAGGTGACACTATAGAATACTCAAGCTTGCCGGGAGGGTGCATGGCCGACTC
GGATTTACCCACCAAGGGGCGCCAACGCGGTGTCCGCGCCGTCGAGCTGAACGTTGCTGCCCGCCTGGAG
AACCTGGCGCTGCTGCGCACCCTGGTCGGCGCCATCGGCACCTTCGAGGACCTGGATTTCGACGCCGTGG
CCGACCTGAGGTTGGCGGTGGACGANGTGTGCACCCGGTTGATTCGCTCGGCCTTGCCGGATGCCACCCT
GCGCCTGGTGGTCGATCCGCGAAAAGACGAAGTTGTGGTGGAGGCTTCTGCTGCCTGCGACACCCACGAC
GTGGTGGGACGGGCAGCTTTAGCTGGCATTCCT :::::::::::::Rv3T7.seq::::::::::::: (SEQ ID NO. 554)
GGAAACACCGNCGCCGTCGTGGCCACCAACACCGCGACCAGCACCGTGACCCGGACCGGGGTGCCGCGCG
AACCGGTCTTGGCCAATTGCCGCGGCACCAAGCCGTCGCGCGCCATGGCGAACAGCACGCGGCATTGCCC
GAGCATCAACACCATCACCACCGTGGTAAGCCCGGCCAGCGCGCCGACGGAGATGATGCCGCTGGCCCAG
TACACCCCGTTGGCCTGGAACGCGGTGGCCAGATTTGCCGGCCCGCGGCCCGGTACGGTCCGCAGTTGGG
TGTATGGAACCATGCCCGACAGCACCACCGATACCGCGACGTAGAGAAGGGTCACGACCCCCAGCGACGC
GAGAATCCCTCGAGGGACGTCTCGTTGAGGACGCTTGGTCTCCTCGGCCATGGTGGCCACGATGTCAAAC
CCGATAAACGCGAAGAACACGATCGATGCCCGGCCAGCACGCCGTA Clone Rv40 (SEQ ID NO. 555)
:::::::::::::Rv40SP6.seq:::::::::::::
CCTGCTTCCGGCTCGTATGTTGTGTGGAATTGTGAGCGGATAACAATTTCACACAGGAAACAGCTATGAC
CATGATTACGCCAAGCTATTTAGGTGACACTATAGAATACTCAAGCTTGTCCTCGGGCGTGGCCTCGGCC
AAGAAATCGTCGACGCCGGCCTCCTGTGCAATCGCCTTGGCGGTCGCCGGGTTGTCACCGGTGATCATCA
CGGTGCGGATGCTCATTCGGCGCATTTCGTCGAAGCGTTCCCGTATGCCCACCTTGACGATGTCCTTCAG
ATGGACGACGCCGATGGCCCGCGCGCTGCTGTTATCGGTCCATTCCGCAACGACTAGGGGTGTCCCCCCG
CCGGAGCTGATGCCGTCGACAATGGCACCCACCTCCTCAGTGGGGTGGCCACCGTGATCGCAAAACCACT
TCATCACCGCAGCCGCGGCACCTTGCGGATCCGAACGGATGCGCTC :::::::::::::Rv40T7.seq::::::::::::: (SEQ ID NO. 556)
TTCGTTCGATGGCGCCGCCCCGGCTACGGTTTGACCTGTGGGTGTCGAATTGGGGTCAAATTCCGAGGTC
GGCGCGCTAAGAGTGGTCATCCTGCACCGCCCGGGGGCCGAACTGCGCCGGCTCACACCGCGCAACACCG
ACCAGCTGCTGTTCGACGGCCTGCCCTGGGTATCCCGCGCGCATGACGAGCACGACGAATTCGCCGAGCT
GCTGGCTTCCCGCGGTGCGGAAGTGCTGTTGCTGTCGGACCTGTTGACTGAGGCACTACATCACAGCGGG TABLE 3-continued End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character << - >> denotes an uncertain base residue.

GCCGCCCGCATGCAGGGGATCGCCGCTGCCGTCGACGCACCGCGGCTGGGACTGCCGCTGGCGCAAGAAC
TTTCGGCCTACCTGCGTATCTCGACCCAAGCANGTTGGCGCATGTGCTGACGCCGGCATGACTTCAACGA
ACTCCCNTCCGACACGCCGAACGAAGTGTCGTTGGTGTTGCGTATGC

Clone Rv412 (SEQ ID NO. 557)
:::::::::::::Rv412SP6.seq:::::::::::::
GCGGCGAGTGTGGTGGGTGCCGAACACGAATCCAACGACGCACTGGCGGAGAGATACCACTTGCTGTACT
GGAAGCACGTGCTGATGATCTCCCGTGGAATGTGCCTCGCCGCCGTCTATCGAAAACAGTGAGCATGCTG
CG :::::::::::::Rv412T7.seq::::::::::::: (SEQ ID NO. 558)
CAACCGCGCTCGGCGCGTCTGGGCCTTCCGCCGGCTCCGCCGACAATTCTATCTCTGGATCAGCGGGGCT
CTCCGGGCCGGCCTCCGCGAACTCAACAGGCCGCGCCTTCCGGCCGAAACATTCCCTAGCCATATATGAT
CGCACCTCGATACACGATCTGGCGGCAACACCGCAAAGCGTCCGACGGGCCCAACCTCCGCAATTCAGGT
ATCCGGG Clone Rv413 (SEQ ID NO. 559)
:::::::::::::Rv413SP6.seq:::::::::::::
GAAGGTCGGCGAAGGTGTGGCTGGNTGCCGATCACGAATCCAATGATGCAGTGGTCGGAAGATATTAGCC
ACTTGCTGTTCTGGAGACAGGTGCTGATGATCTCCCGTGGAATGTCCCTCGACTCCGTCTATCGAAATCT
GTGAACA :::::::::::::Rv413T7.seq::::::::::::: (SEQ ID NO. 560)
TCCTGCGCTCTGGGCCATTCTCGGGTCTGCCGACAATTCTATCTCTGGATCTGTGGGGCTCTCTTGGCCG
GCCTCNGCGATCTCTTCANGGCGCGCCTTCCGGCCGAAACATTCCCTATCCATATATGATCGCACCTCTA
TACACCGTTTGGCGGCAACACCGCAAAGTGTCTGTCG Clone Rv414 (SEQ ID NO. 561)
:::::::::::::Rv414SP6.seq:::::::::::::
AGCTTTACGCTGGCGTATCAGCGTTGGGGCCGCTGCCATTTCGGTCGCCCAACGCGTTGCCAGCTCCCTG
CGCTGTCAGGGCTTGCGCGCCAAACTGGCCACCGCAACAAACTTGGCTGAGCTTGATC :::::::::::::Rv414T7.seq::::::::::::: (SEQ ID NO. 562)
CTCTATCTGGCGTCACATTCGCAATCTTTAGATTGCAGATATCGATAAAATCACCCGCGCGACAAGACCG
CCATGTCATCCTTTCGATGTTATTTCGCCGGCCTGGGGAAAGCGCAACGACGTTGCCTACACGTTCCGCC
GT Clone Rv415 (SEQ ID NO. 563)
:::::::::::::Rv415SP6.seq:::::::::::::
AGCTTTNCCTTGCATCTGCACCCCGATCCACGTCAGCCACGTCGGCGTTCTCCACCAAGAAGTTGCGGGC
ATTCTCCTTGCCCTGGCCGAGCTGCTCGCCCTCGTAGGTGAACCAGGCACCCGACTTGCGGATGAGGCCC
TGATCCACACCCATGTCGATCAGCGAGCCCTCCCTGCTGATTCCCTTGCCGTAGAGGATGTCGAACTCGG
CCTGCTTGAAGGGGGGCGAACAGTTGTGCACGACAACCCCTTCGGCGACGAGGGTGTGCAGTTCCTCGAC
CTCGAGGTCGAACGTTCGTGCCCGCCGCGTTGGCAGCACTTCTCGGATCACGGAATAGCGGANTTCTTCC
GCCAGCATGTCGTGCAGGAATTTGTCATCCAGGGCATCCGCGAGCGCCTGCACGCG :::::::::::::Rv415T7.seq::::::::::::: (SEQ ID NO. 564)
ACTGTCNAGGGAATGCTTCGCAGCATCTACCTGCAGTCGCTTGTGCATAAGCGGACGGCCCNACCTGTTC
GTGTTCCGGGACACCAGACGCGGGAGCACCGGCAGTACGGCGAAAGGTTTGAGCGGAAGGAGTTGCGCAA
ATCGGGGCGCCCCAACACCCGTCCGCAAGACGCGGTCAACGACCTGTTTCAGGCGATCAGGGTCACCGAC
TCACCTGCACTGAGAACAAGCGATCTGCTGATCTGCCAGAAGATGGACATGAATGTCCACGGCAAGCCTG
ATGGCCTGCCGCTCTTCCGGGAATGTTTGGC Clone Rv416 (SEQ ID NO. 565)
:::::::::::::Rv416SP6.seq:::::::::::::
TGAATTATGATCCCGACACAACTGCATCANTTTAGCCGCGTCGNGATGCTATCCGCCGACGGTTTGGANC
NGGTCCGTGTCGTTCGTGTTGATCTCACCCGAAGTTGTGTCCGCCGCCGCCGGGGATCTAGCGAACGTGG
GATCGACAATCAGCGCCGCCAACAAGGCGGCAGCGGCTGCGACCACGCAGGTGCTGGCCGCGGGCGCCGA
TNAGGTGTCAGCGCGCATCGCGGCGCTGTTTGGTATGTACGGCCTGNAATATCCGGCGATCAGTGCGCAA
GTTGCCGCGTATCACCANCAGTCCGTGCAG :::::::::::::Rv416T7.seq::::::::::::: (SEQ ID NO. 566)
AACGGGGACCNCAAGAAACCATTCAANAACGAGGGGTCGTCACCAACGTCGAAACCGACGGTTGCCAGCC
GGCCCACGATATTGCGTGCTCGAGGGTCCGCTGTACCCTCACCGAACGTGAGTCCCACACCGCGGAGGCG
GGCGACTCTGGCGTCGTTAGCAGCCGAGCTCAAGGTGTCCCGCACCACTGTCTCGAATGCTTTTAACCGA
CCGGATCAGCTCTCCGCCGATCTACGTGAACGAGTGCTTGCCACGGCCAAGCGACTGGGCTATGCCGGAC
CGGATCCGGTGGCGCGATCGTTGCGGACCCGCAAAGCCGGTGCGGT Clone Rv417 (SEQ ID NO. 567)
:::::::::::::Rv417SP6.seq:::::::::::::
AGCTTTGGAGCCNCNCCGANCCNCCGGTACGCCCCGCCACCGCCGTACCCGGCACCCGACCCCTTTGAGC TABLE 3-continued End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character << - >> denotes an uncertain base residue.

CGTTCGCCGTGGCCGCGGTGGANCTGGCCGACGAGGGACTGATCGTGCTGGGCAAAGTGGTCGATGGCAC
GCTGGCCGCCGATCTGAAGGTCGGCATGGAGATGGAGCTGACGACCATGCCGCTGTTCGCCGACNACGAC
GGTGTGCAGCGCATCGTCTACGCGTGGCGGATCCCATCGCGCGCCGGCGACNATGCANAGCGCANCGATG
CTGAGGAGCGGCGCCGATGAGGATGAGCGCGCCGGAACCCGTTTACNTCCTGGGTGCCGGTATGCACCCG
TGGGGGAAATGGGGTAATGACTTC

::::::::::::Rv417T7.seq:::::::::::: (SEQ ID NO. 568)
TTCTCNCATCGTTCGTACTNNGATGGGACGCTGCTGCCCGAGGCGATCCTGGCCAACCGGCTCTCGCCGG
CGCTGACCTTCGGCGGGGCGAACCTGAACTTCTTTCCGATGGGCGCTTGGGCCAAACGTACCGGGGCTAT
CTTCATTCGGCGTCAGACGAAAGATATTCCCGTCTACCGCTTCGTATTACGTGCTTACGCCGCGCAGCTG
GTGCAAAACCATGTCAACCTCACCTGGTCGATCGAAGGGGGTCGGACCAGAACGGGCAAGCTACGGCCAC
CGGTGTTCGGGATCCTGCGTTACATCACCGATGCGGTCGACGAAATCGACGGTCCCGAAGTGTATTTGGT
GCCGACCTCGATCGTGTACGAACAGCTGCACGAAGTGGAAGCCATGACCACCGAAGCCTATGGCGCCGTG
AA Clone Rv418 (SEQ ID NO. 569)
::::::::::::Rv418SP6.seq::::::::::::
TTCTTCCGGGTACCGCTGATCGGCGGCACCATCACGCACCCGGTGCAGGGCGAGGCGGCCGCCGGTGTGG
TGTTGCTACGGCCGGCCAGCCCGGGTACCGGTGTGATCGCCGGTGGTGCGGCCCGCGCGGTGCTGGAATG
TGCGGGGGTGCACGACATCTTGGCCAAGTCGCTGGGCAGTGACAACGCGATCAATGTGGTGCACGCCACC
GTGGCCGCGCTCAAGCTGCTGCACCGTCCGGAGGAGGTGGCGGCGCGCCGCGGTTTGCCAATAGAAGACG
TCCCCCCGGCCGGGATGCTG ::::::::::::Rv418T7.seq:::::::::::: (SEQ ID NO. 570)
GTCGAAAGTGACCATCTCTACCTTGAGTGCCATACCGCCCGACCCTATGCCTCGGATAGCTCGGCGGAAA
GAAACGCTTGCAGTGCCGCCGAATAGGCGGCTACGTCGTGAGCGCCCATCAACTCTCGCGCGGAGTGCAT
CGCCAGCTGGGCGGCGCCGACGTCGACCGTGGGGATTCCGGTGCGCGCCGCGGCCAACGGCCCGATCGTC
GACCCGCACGGCAGATCGGCGCGATGTTCGTAACGCTGCATAGGCACTCCCGCGCTGGCAGGCCAGTTGC
GAAACGCCCCCGCCGGGTGCCTTCCGTCGGTTGGCTTTACCGCAAATTTGGGGTTGCCCCT Clone Rv419 (SEQ ID NO. 571)
::::::::::::Rv419SP6.seq::::::::::::
AAAGCCACGGAAACGATTGCCTACTGCCGAATCGGGGAACGGTCCTCGCACACCTGGTTCGTGTTGCGGG
AATTACTCGGACACCAAAACGTCAAGAACTACGACGGCAGTTGGACAGAATACGGCTCCCTGGTGGGCGC
CCCGATCGAGTTGGGAAACTGATATGTGCTCTGGACCCAAGCAAGGACTGACATTGCCGGCCAGCGTCTA
CCTGGAAAAA ::::::::::::Rv419T7.seq:::::::::::: (SEQ ID NO. 572)
TTTCGCCACCGCNAGGTCGTGCGCGTTCCAGAAAAGCGTGGTTTCGCCGGGCGCGAGGATTCGACGGTCC
AACTGACCAGCCGGTCCCGCCACCCGTTAGGCAGGATCGCGGTGTCTATATGTTCGCCCTCGGCATAAAC
GCCATTGCTGCGGTGAAAATCGGACATCTCGCCGATTGCCACGTCTACATGATCCGCTTTGTCCCGCGCC
GGGTCGTTGACAAACGCGATGTCNGCCTCCTGGGAAGCGGTGGC Clone Rv41 (SEQ ID NO. 573)
::::::::::::Rv41SP6.seq::::::::::::
TCGCCAAGTGGATTCGTGCTCACCNACGAGATCCGTGGTCGGATCCGCNGCTGCGGCGGGCTGCGACCCT
GCATCTCGGCGGCACCCGTGACCAAATGGCGCGCGCCGAAGCAGACGTCTCGGCGGGACGCCACGCCGAC
TGGCCGATGGTGCTGGCCGCGTGTCCGCNCGTCNCCGACCCCGGCCGCATCNACCAAACCGGCCGCCGTC
CGTTCTGGACCTATCCCACGTGCCNTCGGGGTCCACGCTCGACGCGACCGANAACGTAACCAGCGTCCTC
GANCGGTTCGCCCCCGGCTTCCGTGACATCGTGGTGGCGGCCGCGCCGT ::::::::::::Rv41T7.seq:::::::::::: (SEQ ID NO. 574)
GTACCGTCACCATGATCGCCCCCATCGGCATCGGTGAGCTGATAGATCCCAGCCGGTTTCGCCAACCCCG
GAGCGATCTTGGCGCGCTGCTNGTNGTCNCTGANACNTAGCCACCAACAGAGCCCGGTGTGCGACAAGAN
GACTGATCGGATCTCTCCGGACACNTCGAGGGGGTCNTCAGGAGNCCGGGCGCCACCCCGAGGTAAGCCT
CCGCCCAGCCTCACACCGCGACCGGGTATCNCAAGTCGCGCAATAANCCCACCACCTCCTCGGACCCCAC
GTTGTATGCGGCTGGGT Clone Rv42 (SEQ ID NO. 575)
::::::::::::Rv42SP6.seq::::::::::::
ATACTCAAGCTTAGACCTCACTGATGTGGCGGGACGCGGGAGATAACCGCGGTTCGAGCCGTTCAACAGT
GGTGGTTCCCACACCAGTTGTTTGCCTTTGCGAAGTAAAGCGATTCGATTTGCTCGAAAAGAGGGCTGGC
TGCTCGTGAGGGACATCCATGGCCGATACCTCAGCGATCTCAACGGTCAAGCGACTGCATGTTTGGCGCA
AGGTATCGCTAAGCATAGGTTCGTGACGGATTTGACAGCAAGAGCTTTCCAAAGATTGCTGTCCACATAN
TGATTCGCATCTCTACACCTCTTCGCCGGTGCTGTCAAGAGCCATTCGAATCAGTTATCTCGCTCGTGCT
TGGAANAAATTTTCCCAGCCTGCGTTGGACAAACCGCGTCGCCAAAGCGGT ::::::::::::Rv42T7.seq:::::::::::: (SEQ ID NO. 576)
AGCTTCCCGAGAAACAGTGCATTCCCTAAGCAGCCCGTTGTCACGCCGATGAGTGAAGAGTGCACGCAAT
CGCCGGAATCCGGCAAAGCCCTGCACAAGCGAAATCAACCCGGAGGCTGACAAGGCAACGTCGGTGATCC
GTACCGCCTGGTTGGACAAACGGCAGAAGGCGGCCTCGTCCGGTCCATCTACGCCGAGCACACTGGTGAT TABLE 3-continued End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character << - >> denotes an uncertain base residue.

AGCGCGCATCGGCATCGGTGCGGCCACGGTGGAGACGACGTCCGCGGGCGTCTGGGTCAGTAACCCGCCG
ACCAGTTCTCGGGCAAGCTGGTCGACCATCGGGCGCCACGTCTCCAACGCGCCACGCGCCATACCTGGTG
CCAGTTGCTTGCGCATCCGGGTGTGCGCCGGCGGATCGGACGTCGCAGAAACGCAGCCACCCCGTGAGAA
GTGACCCACGGCGCTGGACACGTGTCTGGTTAC

Clone Rv43 (SEQ ID NO. 577)
::::::::::::Rv43SP6.seq::::::::::::
CGGCCGGGATGTGCGCAATGGCAGGTTGTCGCCCGGCTTGATGTCGGCGTTAGCGCCGGATTCCACCACA
TCCCCTTGCGAAAGTCCGTTGGGTGCAATGATGTANCGCTTCTCCCCATCGAGATAGTGGAGCAACGCAA
TCCGTGCGGTACGGTTCGGGTCGTACTCGATGTGCGCGACCTTGGCGTTGACACCATCTTTGTCATGGCG
GCGAAAGTCGATCATCCGGTAAGCGCGCTTATGACCGCCGCCTTTGTGCCNGGTGGTAATCCGGCCATGC
GCGTTGCGTCCACCGCGACCGTGCAGCGGGCGCACCAGCGACNTCTCCGGGGTTGACCGGGTGATCTCGG
CGAAATCAGATACGCTGGCGCCGCGACGACCAGGCGTCGTGGGCTTGTACTTGCGAATTGCCATGGTCTA
ATCAGGTCTTTCTCTCACCTCTCGTCGCCGGGCTAGGGCGCATTGCCTGCTCCT ::::::::::::Rv43T7.seq:::::::::::: (SEQ ID NO. 578)
TAGCGGTGTAACCAACTCCCGGGTCACCACCCGCAAACCTCTTGCGGCAACAGCACCGTCGACGCGTCAA
CCGGGCTGCCCGGAATCCTGTGGATGGGCATCGAGTGCATGGTCACGACGTCCCCGACGCGGCCGGTGGC
AACGACAAGTGGCCCGGATGCACCACAAATGACGGCCGCACACCGGTGGGGACGGCCAGCACGAGAGCCG
TGTCGCCGAAGTCGACGCTAATGCCGTAGGCATTGGCCGTCACAACAGGCGACGCCCCGCGTACCACCGA
GTCCACGGNGGTTGGGCGGTCTCCTCGGCCAACCAGGCGTGAACCCGGCGGATCCGAATGCAGCAAGACC
CGTGGGC Clone Rv44 (SEQ ID NO. 579)
::::::::::::Rv44-2ndSP6.seq::::::::::::
CCATTGGTCGGTGTGCGCATACCANTACNACGCGCCGGGCACCTGACGCGGCGGCCGCAACCATTCGGTG
GCCATCGCCATCGTCTGCCACCCGGTCAACGGACGCACCTTCTCCTGGCCGACCTAGTGCGCCCACCCGC
CGCCGTTGCGTCCCATCGATCCGGTCAACATGAGCAGCGCCAACACCGAGCGGTACATGACATCTGCTGT
GGAACCAGTGACANATTCCGCCGCCCATGATGATCNTCGACCGTCCTCCGGATTCGGTC ::::::::::::Rv44-2ndT7.seq:::::::::::: (SEQ ID NO. 580)
GCCGGCCTGGTCAAAGGGGCGTCCGAAGGANCCGGGCTGGGTAACAAGTTCCTGGCTCATATCCGCGAAT
GCGACGCCATTTGTCAGGTGGTGCGGGTGTTCGTCGACGACNACGTGACTCATGTCACCGGACGGGTCGA
TCCCCAGTCCGACATTGAGGTCGTCGAGACCGAGCTGATCCTGGCAGATCTGCAAACCCTGGAGCGGGCC
ACGGGCCGGCTGGAGAANGAAGCNCGCACCAACAAGGCGCGCAAGCCGGTCTACGACCCGGC Clone Rv45 (SEQ ID NO. 581)
::::::::::::Rv45SP6.seq::::::::::::
GATCCACTGACCACGATGACATATCGAAATGCTCGACGATTCCGATGGCGATCAAGGCCACGATGCCCTG
GCCGTTGGGCGGTATCTGGTGGATGGTGTACCCGCGGTAGGTTCCCGTGATCGTGTCGACCCAGTCCACG
CGATGGGCGGCGAGGTCGTCGGCACGCATCACCCCGCCGTNTGCCGCCGAGTGCGCCTCGAGTTTGGCGG
CCAGCTCTCCCCGGTAGAACTCTCACCGTTGGTCGCCGCGATCTTCTCTANCGTCGCCGCGTGGTCAGGA
AAGGTAAACAGCTCACCGGGTTTCGGCGCTCGTCCGCCGGGGATGAACGCATCTGCGAATCCGGGCTGGG
ATGCGAACAACGGACCTGTGCCG ::::::::::::Rv45T7.seq:::::::::::: (SEQ ID NO. 582)
TCTACTGCCGAATCGGGGAACGGTCCTCGCCCACCNGGTTCGTGTTGCCGGAATTACTCAGGACACCGAA
ACGTCGAGAACTACGAGCGGAGTTGGACANAATACCGCTCCCNGGTGGGCGCCCCCATCGANTTGGGAAG
CNGAAATGTGCTCTGGACCCCACCCAAGAATGACATTGCCGGCCGCCCTCCAACTGGAAATAGAAACNGT
GATCACCCGCCGCGTTCTTGGAAGGAATGGCATGCCCTGGGCCGGGCGTTCCTTCCGCTGCCGGACTCCT
CCCACCAATTCACCGCCGAAGGCGTCCCGTCTGC Clone Rv46 (SEQ ID NO. 583)
::::::::::::Rv46SP6.seq::::::::::::
ATACTCAAGCTTCTGTCACCGAAATCCCGCATGGGATAACGGGTTTAGATTTCGACAACGGGACCGTGTT
TCTCAACAAGCCGGTCATCAGCTGGGCCGGCGACAACGGTATCTACTTCACCCGCTTTCGCCCGT ::::::::::::Rv46T7.seq:::::::::::: (SEQ ID NO. 584)
CTGGCTCAAGCGCTCGGCGCGCAGGTGAACTCGGACCGGCTCGACGTCGCCGAACGCGAGGCGGTGCTGG
CCCACGCCGACGCCGTCGTCGCACATATCGGCACCGTGCACAAGTCTACAACAACGCCGGCATCGCGTAC
AACGGCAACGTCGACAAGTCGGAGTTCAAGGACATCGAGCGCATCATCGACGTCGACTTCTGGGGCGTCC
TCCACGGGCCC Clone Rv47 (SEQ ID NO. 585)
::::::::::::Rv47SP6.seq::::::::::::
CCGCCCTCCGCATTATGGGTCAAGAACCATCGGGTCGGACTTCTGGGCTTCCAACGCTCGCGCCGTCCCN ::::::::::::Rv47T7.seq:::::::::::: (SEQ ID NO. 586)
CCGTGGCACTGTCAGACATATGCGCCGCTCCTCCTCATCGCTGCGCTCGGCATCGTCGCCGGCGGTCATG
GCGTCACCCTACCCAAGCCGAACGCGAAACGAGAACGTGTTCCATTATTAGGGTGTGAGCACCAATACCA
GATTGCTCACCAGGAACTCACGCAGCACCGGGACGGATGTCGGCCACCACGCCCATCTGGGGTGGTAGCG TABLE 3-continued End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character << - >> denotes an uncertain base residue.

GGGAAATACCGCTAACGCGGCTCCGGTGCCG

Clone Rv48 (SEQ ID NO. 587)
::::::::::::Rv48SP6.seq::::::::::::
TACTCAAGCTTGTCCAAATATCGAAGCGTCGGGTCGCGAGGCTCGGTCGGCAGCTCCAGCAAAACCCGCT
CCACCCCTAGATGCCGGTATCCCTCAAGGTCTTTATCCGCCGCTTCACCCCACTGGCACACGGTCACCGG
CACGTCGCCCCCGGCCATGGCGCGCAACCGCTGAAGCGGACCCGACAGCCGCTGCGGTGATGGACTGATC
GCGATCCACCCGGCATTGAGCCGGGCTATCCGCGGGAAGTTCGCCGGTCCCCCGCCCACATACAGCGGAG
GATAGGGCTTTGTCACCGGCTTCGGCCAGCAGTAGATCGGATCGAAGTCCACATATGTCCCATGGAATTC
CGCCTGCTCCTGCGTTCAGATCTCGATTATCGCGCGCAACCGCTCATCGATCACACGTCCGCGCACCGCA
GGGTCCACACCATGGTTGGCGACTTCTTCGCGCAACCAGCCACACCCACGCCGAAACGAAACCGTCCCTG
CG ::::::::::::Rv48T7.seq:::::::::::: (SEQ ID NO. 588)
CAGGCATGCAAGCTTGGCCAACTCCTCATCGGACTTGAAGGTGCCGTCCTCGTTGGCGGCCCTGCTCCAC
GGCACGTTGATGGCACCAGGAATGTGTCCGGGCCGCTGGCTTTGTTCCTGCGGCAGGTGCGCGGGGGCCA
GGATCTTGCCGGAGAACTCGTCGGGAGAGCGCACGTCGATGAGGTTCTTGACGTTGATGGCCGCCAGGAC
CTCGTCGCGGAATGCCCGAATCGTGTTATCCGGCGGGGANGCGGTGTAGGAAGTCACCGGCCGGCTGACC
GGGTCGCTGGACAGCGGGCGTCCGTCGAGCTCC Clone Rv49 (SEQ ID NO. 589)
::::::::::::Rv49SP6.seq::::::::::::
ATACTCAAGCTTCAAAACAGGCCTGTTGTGGGCGCACCCGGCTCGCCGAGTTCTGCACGCACCGCCTCAA
GTGCGGCCCGCACCGCCGGCATCTCCCGGTCACGCAGGGCCGCGGCCCGCGCCGCAGCGACGGCGTGTTC
GCGCAGTTCGCCGTCAATGATGCTGACCTGATCGGCCACCCGGGCGGTCTCGGCGTCGTCCCGTTCACTA
ATCGCGGTGCTCAGCAGCGTCTCGACAGCCACCACCCGAGTGGAGACCAGATGCNCCACCACGGACCGCA
GCGATGCCAGTCACCTCACCCGTCC ::::::::::::Rv49T7.seq:::::::::::: (SEQ ID NO. 590)
CAGGCATGCAAGCTTTGCAGTTGCTGAGTAATGTCGGCCAACGTCACCACAATCGCGATGAATTCAATCA
TGCCGCCCAGGGCGGCCAACCCAATGGTGGCCGCGAGCGGCAGCTCGATCGCAGCGCGGAGGTTGCCGGC
CGCCAGTTGATTCACGAACAGGGTGAGGTCATAGGCGGGCAGGATAGTGACGAAGGCAAGACCTAGATCT
GCCGTCGGAAGAAGAATCGAGTATCCGGTCGACACAACGGAAGCGAAAGTGTCCGCGATGTTGATGAGCG
TCGCCGGTTGTGGCGGCGGTGGCGGCGGTAGCACCGTCCGCACATACCGCGGGAACGCGGGCATCCGAAT
TTGGGGCAGGGTGTTCAAGGCGGCTGGCAACTCACCATGAATCT Clone Rv4 (SEQ ID NO. 591)
::::::::::::Rv4SP6.seq::::::::::::
CCGGCTCGTATGTTGTGTGGAATTGTGACCGGATAACAATTTCACACAGGAAACAGCTATGACCATGATT
ACGCCAAGCTATTTAGGTGACACTATAGAATACTCAAGCTTGGCCGCAGGGCCGAGTCGATTGGTCGCGG
TCGCCTCGACAGTTAGCTTATGCAATGCTAACTTCGGGGCAAAGTTCAGGCGGATCGGCCGATGGCGGGC
GTAGGTGAAGGAGACAGCGGAGGCGTGGAGCGTGATGACATTGGCATGGTGGCCGCTTCCCCCGTCGCGT
CTCGGGTAAATGGCAAGGTAGACGCTGACGTCGTCGGTCGATTTGCCACCTGCTGCCGTGCCCTGGGCAT
CGCGGTTTACCAGCGTAAACGTCCGCCGGACCTGGCTGCCGCCCGGTCTGGTTTCGCCGCGCTGACCCGC
GTCGCCCATGACAGTGCGACCCTGNACCGGGCTGGCC ::::::::::::Rv4T7.seq:::::::::::: (SEQ ID NO. 592)
GTGTGCTGTCAATTCAGAGCTGAGCCTGATGCACTCAACTTACTGAGCATGCTAACGCTGGTCGTGCGGG
TCTTGTTCCCGCGTGTCGGCAGGGCACACGCTCGGGGCGTAGCTGGGAGAGGCCCCGGTCAAGCCCGGAG
AGCAGTGCTCAGTCCGCCAGCTTGACCGACTTTCGATGAGAACGCGCTTCTCGCCGTATTGAACTGGCGT
GCTGACGGTCGCTGAGCAGCGCTCGCCGAGTGCGGCCGCTGATTCTTTCATCGAGCCAGGAGGCGCATTC
GTGTTCGGCCGCCTGCGGGTCGGCCCCATCGTCGACGCGATCCGTCACCCACTCCTCGATCAGGTCTGCC
TCATCGAACGGGCCAACGGTGCTGTCGGAGTAAGTGTGCGTGGGCACGCGAGCCGGGTGCTGTGGTACAC
CCACCGTTGCATGAACAA Clone Rv50 (SEQ ID NO. 593)
::::::::::::Rv50SP6.seq::::::::::::
ATACTCAAGCTTCACCAGGCGCCGGCGGGCCGCGGCGCCAAGCCAGGCAGCCGCGCTCGGCGCGTCGGGG
CCTTCCGCCGGCTCGGCCGACAGTTCGATCTCTGGATCGGCGGGGCTCTCCGGGCCGGCCTCGGCGACCT
CAGCGGGCCGCGCCTTCCGGCCGAACCATTCCCTAGCCATAGATAACCGCACCTCAATGCACGGTTTGGC
GGCAACCCGG ::::::::::::Rv50T7.seq::::::::::: (SEQ ID NO. 594)
AGCTTCCGTCACGACCCGCCCTCGCCGGTGCCGGCGCCATCGGTCATCGGATCTCATGACGACGTCACGT
AGGCCCGCTAGCCGCGAGCGGGCGCGGTCAACTGGCGAGGCGGCGGCGACGTGACTGAGCTGGCCGAGCT
GGACCGGTTCACCGCGGAACTACCGTTCTCGCTCGACGACTTTCAGCAGCGGGCTTGCAGCGCGCTGGAA
CGCGGCCACGGTGTTGCTGGTGTGCGCGCCGACCGGCGCTGGCAAGACGGTGGTCG Clone Rv51 (SEQ ID NO. 595)
::::::::::::Rv51SP6.seq::::::::::::
ATACTCAAGCTTGCCGGGACCGCGGAACAGAACCGGCGGTTCCTACCGCGGTGTGCGGCCGGCGCGATAT TABLE 3-continued End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character << - >> denotes an uncertain base residue.

CGGCCTCCCGACTAACCGAACCCGATGTGGGCTCC

:::::::::::::Rv51T7.seq::::::::::::: (SEQ ID NO. 596)
ACGTTGGCTCTGCCGGAACGTATTTCCAGCGGCACGCATTCGGCGTGGGTGCCGGGCGCCGAGTTGCGTC
GCTGGGATCACGCAGCAGTCGCCGGCGGCTGCCGTCGGCCTATGAATTGCACCGAGCCGCAAAATCCNCA
C Clone Rv52 (SEQ ID NO. 597)
:::::::::::::Rv52SP6.seq:::::::::::::
ATACTCAAGCTTGTCGTATTCCGTGGCACTGTCAGACATATGCGCCGCTCCTCCTCATCGCTGCGCTCGG
CATCGTCGCCGGCGGTCATGGCGTCACCCTACCCAAGCCGAACGCGAAACGAGAACGTGTTCCATTATTA
GGGTGTGAGCACCAATACCAGATTGCTCACCAGGAACTCACGCAGCACCGGGACGGATGTCAGCCACCAC
CCCCATCTGGGGTGGTAGCGGGGA :::::::::::::Rv52T7.seq::::::::::::: (SEQ ID NO. 598)
CGTTGGTAGCCCGATATGCATAGTGTATCTTACTGAACATGATTTCCATTATGGAGCCCGGGGTGCCGGC
AGCGCGAACGGTGCGCCGTCAGACGCGGGCGGCACTGACCAGGGTGTTGCGGGCGAACATCGGCCCGGCT
TCGGATTCCGGTCCGGGTACCGGGCGACCCACCGCTTCGAGGTA Clone Rv53 (SEQ ID NO. 599)
:::::::::::::Rv53SP6.seq:::::::::::::
ATACTCAAGCTTGGCCAACTCCTCATCGGACTTGAAGGTGCCGTCCTCGTTGGCGGCCCTGCTCCACGGC
ACGTTGATGGCACCAGGAATGTGTCCGGGCCGCTGGCTTTGTTCCTGCGGCAGGTGCGCGGGGGCCATGA
TCTTGCCGGAAAACTCGTCGGGAGAGCGCACGTCGATGAGGTTCTTGACGTTGATGGCCGCCAGGACCTC
GTCGCGGAATGCCCGAATCGTGTTATCCGGCGGGGAGGCGGTGTATGAGGTCACCGGCCGGCTGACCGGG
TCGCTGGACAGCGGGCGTCCGTCCAGCTCCCACTTCTTGCGGGCGCCGTCCAACNACTTGACTTCTCCTG
G :::::::::::::Rv53T7.seq::::::::::::: (SEQ ID NO. 600)
ATATCTTAAGCGTCGGGTCCCGAGGCTCGGTCGGCAGCTCCAGCAAAACCCGCTCCACCCCTAGATGCCG
GTATCCCTCAAGGTCTTTAGCCGCCGCTTCACCCCACTGGCACACGGTCACCGGCACGTCGCCCCCGGCC
ATGGCGCGCAACCGCTGAAGCGGACCCGACAGCCGCTGCGGTGATGGACTGATCGCGATCCACCCGGCAT
TGAGCCGGGCTATCCGCGGGAAGTTCGCCGGTCCCCCGCCCACATACAGCGGAGGATAGGGCTTTGTCAC
CGGCTTCGGCCAGCAGTAGATCGGATCGAAGTCCACATATGTCCCATGGAATTCCGCCTGCTCCTGCGTC
CAGATCTCGATTATCGCGCGCAACCGCTCATCGATCACACGTCCGCGCACCGCAGGGTCCACACCATGGT
TGGCGACTTCTTCGCGCA Clone Rv54 (SEQ ID NO. 601)
:::::::::::::Rv54SP6.seq:::::::::::::
ATACTCAAGCTTGTCGCGGTAAACCCGCAGCAGGGCGGTGGGTGCGGTGTCAAAAACAACCACACTTCTT
TGCGGTTCGGTGATCTCGACACCGGCCGCGAGCCGACCACCATGCGCGCGTAAATCGGCGATCAGCGCGT
CGGCTATCGCCTGGGTGCCGCCCACCGGAATCGGCCAGCCGACCGAATGGGCCAGCGTTGCCAGCATCAG
TCCGGCGCCGGCCGACACCAGTGACGGCAACGGTGAAATCGCGTGGGCGGCAACGCCGGTGAACAACGCG
CGGGCATCCTCGCCCGCCAGCGACCGCCAGGCAGGGGTGCCCTGGGCCAGCATCCGCAGCCCGAGACGCA
GGACCGAGCCCAGTGCAGTAGGCAAAGACCGCTTGTCGGAGACATGAACTCCACGACCGT :::::::::::::Rv54T7.seq::::::::::::: (SEQ ID NO. 602)
AGCTTATTGAACCGCGGGTCGCAGGCAAAGTGGACCTCATAACGACTCGGGTCCAGCGACCGCGCCAACA
CGAACGGCCGGACGACGTGGGCCAGGGTCGCGGCCTCCCCTACAAACAGGATCCGTTGCCTGCGAGCGAC
AGGCTCCGGTGCGGCGTTGGGCGCCGTGCTCGTCCCAGCGTCCGGTCCCGGGTCGCCGGCGACGCTTGTT
TCCTCCATACTCGCCCCCTAATCTCGAGGCAGCCCGTACCCGCAGGCAACCTCCCAAAAATGCAATCCCC
CAAAATGCAATGCGTCGAGCTATTTCTCACACCGACCGCTAGTTGCGGATCAGAAATCCGTTGGGCGCGG
AAGTCCAGCCGAATTTGTTCTCCCGCTCCGCATCATGCTTGTAATCGTTTGGAAATTCATCCTCATATGC
CTCGATCGCTTCATAGGGTCCAGGCCAAACCGGGCA Clone Rv55 (SEQ ID NO. 603)
:::::::::::::Rv55SP6.seq:::::::::::::
CTTCCGGCTCGTATGTTGTGTGGAATTGTGAGCGGATAACAATTTCACACAGGAAACAGCTATGACCATG
ATTACGCCAAGCTATTTAGGTGACACTATAGAATACTCAAGCTTGGCCACCTCGCGGTGTGTGGTGGAAC
CCATCTGAGCAGTGTGCCAAACCGGGGCAGACAGCTCCCAATTGACGTGAGCCCGCTCACTTGCTGGGTA
AGCGTCG :::::::::::::Rv55T7.seq::::::::::::: (SEQ ID NO. 604)
TAGCGCCCCCTCCCGGGCGGAGCTCCACGGCGTGGATCAAGGTACCGGCCGGGATGTTGCGCAATGGCAG
GTTGTTGCCCGGCTTGATGTCGGCGTTAGCGCCGGATTCCACCACATCCCCTTGCGAAAGTCCGTTGGGT
GCAATGATGTAGCGCTTCTCCCCATCGAGATAGTGGAGCAACGCAATCCGTGCGGTACGGTTCGGGTCGT
ACTCGATGTGCGCGACCTTGGCGTTGACACCATCTTTGTCATTGCGGCGAAAGTCGATCATCCGGTAAGC
GCGCTTATGACCGCCGCCTTTGTGCCGGGTGGTAATCCGGCCATGCGCGTTGCGTCCACCGCGACCGTGC
AGCGGGCGCACCAGCGACTTCTCCGGGGTTGACCGGGTGATCTCGGCGAAATCAGATACGCTGGCGCCGC
GACGACCAAGCGTCGTGGGCTTGTTCTTGCGAATTGCATGTCTAATCAGGTCTTTCTC TABLE 3-continued End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character << - >> denotes an uncertain base residue.

Clone Rv56 (SEQ ID NO. 605)
:::::::::::::Rv56SP6.seq::::::::::::
TGAAACTATATAATACTCAAGCTTGCCAAAGAAGACCTCGTCGACCAAGCAGGACGCGACCGTCGAGGTG
GCGATCCGGCTTGGCGTCGACCCGCGTAAGGCAAACCAGATGGTTCGCGGCACGGTCAACCTGCCACACG
GCACTGGTAAGACTGCCCGCGTCGCGGTATTCGCGGTTGGTGAAAAGGCCGATGCTGCCGTTGCCGCGGG
GGCGGATGTTGTCGGGAGTGACGATCTGATCGAAAGGATTCAGGGCGGCTGGCTGGAATTCGATGCCGCG
ATCGCGACACCGGATCAGATGGCCAAAGTCGGTCGCATCGCTCGGGTGCTGGGTCCGCGCGGCCTGATGC
CCAACCCGAAAACCGGCACCGTCACCGCCGACGTCGCCAAGGCCGTCGCGGACATCAAGGGCGGCAAGAT
CAACTTCCGGGTTGACAAGCAGGCCAACCTGCACTTCTC ::::::::::::Rv56T7.seq:::::::::::: (SEQ ID NO. 606)
GCTGAGCTCCACGGCGTGGATCAAGGTACCGGCCGGGATGTTGCGCAATGGCAGGTTGTTGCCCGGCTTG
ATGTCGGCGTTAGCGCCGGATTCCACCACATCCCCTTGCGAAAGTCCGTTGGGTGCAATGATGTAGCGCT
TCTCCCCATCGAGATAGTGGAGCAACGCAATCCGTGCGGTACGGTTCGGGTCGTACTCGATGTGCGCGAC
CTTGGCGTTGACACCATCTTTGTCATTGCGGCGAAAGTCGATCATCCGGTAAGCGCGCTTATGACCGCCG
CCTTTGTGCCGGGTGGTAATCCGGCCATGCGCGTTGCGTCCACCGCGACCGTGCAGCGGGCGCACCAGCG
ACTTCTCCGGGGTTGACCGGGTGATCTCGGCGAAATCAGATACGCTGGCGCCGCGACGACCAGGCGTCGT
GGGCTTGTACTTGCGAATTGCCATGTCTAATCAGGTCTTTCTCT Clone Rv57 (SEQ ID NO. 607)
:::::::::::::Rv57SP6.seq::::::::::::
ATACTCAAGCTTGTTGGTGACCTCGCCGGCGAACAGTTCTCGCACGATTTCCGGATTAGCGGGACTGGTC
ACCAGTTGGGTATGCGGGAAGGCGCTGACGTTCGCCGCGATTAGCTGTTTGATGGACGCGGCGGTGATGT
CCTGATCACGGAACTGGCTGTAATAGCCCAGGGTCGCCACGCTTCCATCCGGGCCCGGACCCGGC :::::::::::::Rv57T7.seq:::::::::::: (SEQ ID NO. 608)
GATGATCGCCGGTGCCACCCCGATCCGTGCCTCGGTCAGCGCGAACGTGCTTTCCGGTCCGGCGACCACC
ATGTCGCACGCACCGACCAGGCCGAACCCGCCGGCCCGCACATGCCCGTTGATGGCGCCGACCACCGGCA
GCGGCGACTCGACGATGGCGCGCAACAGCGCCGTCATTTCCCGCGCCCGCGCCACCGCCATCCGGTACGG
ATCACCACCACCTCCGCCGGCCTCGCTGAGGTCC Clone Rv58 (SEQ ID NO. 609)
:::::::::::::Rv58SP6.seq::::::::::::
ATACTCAAGCTTGCCGCAATCGAAACCAACCTGTTTGTGCCGCAAGAAATTACGCCGTGGCCCGGCGCCG
ATCAAGAAACGCCCCGGCGCGCGGCGGTGTCGTCGTATGGCATGACGGGCACCAATGTGCACGCCATTGT
CGAGCAGGCACCGGTGCCAGCCCCCGAATCCGGTGCACCAGGCGACACCCCGGCCACACCCGGTATCGAC
GGCGCGCTGCTGTTCGCGCTGTCGGCCAGCTCGCAGGACGCGCTGCGGCAAACCGCCGCGCGGCTGGCCG
ATTGGGTCT :::::::::::::Rv58T7.seq:::::::::::: (SEQ ID NO. 610)
TTGGCGGGTTGGCCACANCANCCCGCCGGTGACGGCGACGATGCTGGGCTGGTTGCGGCCCTGCGCCACC
GCGGCTTGCATGCTGGTTGGCTGTCTTGGGACGATCCCGAAATAGTCCACGCGGATCTGGTGATTTTGCG
GGCTACCCGCGATTACCCCGCGCGGCTCGACGAGTTTTTGGCCTGGACTACCCGCGTGGCCAATCTGCTG
AACTCGCGGCCGGTGGTGGCCTGGAATGTCCANCGCCGTTCACCTACGTGACCTTGATGGGATCCGGGGG
NT Clone Rv59 (SEQ ID NO. 611)
:::::::::::::Rv59SP6.seq::::::::::::
NCGTGGACACCGGTGTCGANCGCCACCAGCCGCATGTCTGCANGTCNATTCCGTCCTCGGCAACATCTTG
AATGCCGAGCAGCGCCTGGGCGTGATCGGCAACCGGGGATGACCGCTCGCCGATCCGCTCGACAATCCCG
GCGGCACGTGACATGCCGGCGGACGGCTCGACGAGCTGGAACTTCAGCGACGACGATCCGGAATTGATCA
CCAGCACGGTGCTACTCATGGACCCCTGCGCCTGAATCCCGTGATGGCCACGGTGTTGACTATTCGTCGA
CAGTGCACCCGAGATAGTCTTCACGGCTGCGT :::::::::::::Rv59T7.seq:::::::::::: (SEQ ID NO. 612)
CATGTATTGCCGTGCTCACGGCGCCACGCTCGATGGTTTCTCGAAGTCTCCGGGCTGGTGTACAGCTTCT
CGTTGATCTCGTTCGCCACGCCGTCCTCTTCCCGCCGACGACCCGATCTCGATCTCCANAATGATCTTGG
CGGCCGCCGCCGCCTTGAGCAGCTCCTGGGCGATGGCCAGGTTCTCATCGATGGGCACTGCCGACCGTCC
CACATGTGCGACGGAACAAAGATGTCACCTTGCTCACGCGTGCGCNAGATCNCANAAGGGCCGGACATAC
TGTCNACTTGTCCTTGGGCAGTGGTCCGTGTCAGCCCACGTGACGGGTACTTGGCGCGATAACGTGGTG Clone Rv5 (SEQ ID NO. 613)
:::::::::::::Rv5SP6.seq::::::::::::
GCCACCACGACCCGGCCGTAACTCTGCTCACGGAAATGCGGCCAGGCCGCGCGTAGCACGTGGTATCCGC
CATAAAGGTGCACCTTAAGCACGGCGTCCCAATTCTCGAACGACATCTTGTGGAAGGTGCCGTCGCGCAA
GATCCCGGCGTTGCTCACCACACCGTGCACGGCGCCGAATTCGTCAAGCGCGGTCTTGATGATGTTCGCT
GCGCCGTCCTCGGTGGCGACGCTGTCCTTAGTTGGCGACCGCCCGGCCCCCCTTGTCGCGAATCTGGCGA
CGACCTCATCGGCCATCGCCGAACGGCGCCCGTGCCCGTCGCGGGCGCCACCGAGGTCGTTGACCACGA :::::::::::::Rv5T7.seq:::::::::::: (SEQ ID NO. 614)
CAGGCATGCAACCTTTGTCCACACGGCGTCTACTCCGTGCAAGGTCCGACCGCTTCCACGTCCCGCCGTG TABLE 3-continued End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character << - >> denotes an uncertain base residue.

ACGGTGCTCCATCTCCCTCAGCAACGCGTGAAGTGGTCCGATCCCGCGGCTTCAGG

Clone Rv60 (SEQ ID NO. 615)
:::::::::::::Rv60SP6.seq::::::::::::
GTTGAGACGCAACCAGCGCACAACGACGATTTGGCGTAGCGGCGGACGTCTGCTCGATTCGATCACGTCG
CGCTCGCATCGAGCATGGCCCGCGACGCTACACGATCGCCGTCGTCGATGACACGACCGAGCCGTACGCC
GGCCGTAAGCCGCGCCAGGATTCGGCGAAAAACGTCTACGTGGCGGGTGTACTGGGTGTCGAATGATTCG
TGGGGTGCGTATGCGTCCTGCAATCGTCGACATAGATCCGTCGCCGCATCGCGTCGACAACTCCGGGTGA
GTGGAATACACTTGCCGATCACGCGACGTGCGCGGATCGATGCCGACCGAAATACGACCACATGGCTCTT
GTTGCNCAGTGTTGGCGGCATCAAATACCCTCAGTGCCGTCCGAC :::::::::::::Rv60T7.seq:::::::::::: (SEQ ID NO. 616)
TTNCCGCCTTNACGCCTACTCCNAGACGATGCTCGACGCGTGTGAGCACACGGCGCTGCTGTAGACGGCA
CGGCGCAGCTGGATCGCGCTTGGTGCACCCAAGCCTCTACGCGCGTCGCTGCGTCGTCATCGGGTACCGA
ACATATTCCGGTCGTTGCGCAGAGTGTGCATGTGCGGCTCTTGTGAACGAACATAGCAAAGCGTATATGT
CTGTGGCGGCTCTGCAGATATCGCGATAATACGTATATACATAAGGTGGCGCGCGATCTATCGGTATATC
CGTTATGGCGGACGTGCGTGAGCGTGAGTCGCGGCGCATCGCGCACTTCGCGATCGCGTGACTGGTCCTC
GCGACTGCGCGCATGCGTAGC Clone Rv61 (SEQ ID NO. 617)
:::::::::::::Rv61SP6.seq::::::::::::
GGTGATGACGCACTTGCTTCGAATGAGTCATTGACTACTCCCGTGGTTGTCCTGCGATGGTGGAGTGCCG
CGCAGCCTTGCCCGANGTCGCGATCGCGTCGCGGGCTTCGGGGAGCAGACTGACCTGCAGATGGAAGTCG
TGCCACATGCCCGCGAACGGCGAGCTCGATGCTTGTTTTCGAAGNGCGCANGCGGTTTCGATCTTGTCCG
CGTCAACGCAGATCGGATCTCGCCGCGGTCTGCATGACGATGGGCGCAGGCCCGCTCATGTCCCGTAGAC
GGGGAGATACGGGCAGCCGCGGATCGAGACCTACGTAGCGCGGCGCCCATCGTGCCATCGACGAAGAATG
ACGGATCGCGCAGCGCCGTCGCGTCGCTTCGATGTCACGCGAGATCGCCACGGCAGATCAGCGATGCGCG
GGC :::::::::::::Rv61T7.seq:::::::::::: (SEQ ID NO. 618)
CGGTACGCCGGCAACAAACGCCTTGTGACGAGCGCGTCCGAGCGGTCATCGGCCTCCACCGTCATGCACA
GCTCCTTCTCCAGGTCTACGCCGACGTCGCGGTCCACATTGGTGAGCTTGGCGAATGCCTCGGCAACCTC
GTCGAAATGCGCCTCCGCGTCCGCATCGAAGGTCGCCATGTCAAAGATCAACTCGACGTAGTAGCTAGTT
ACCGCATCAGGTCAGTGTTTGCTGGCCTCGGAGTCCGGCCGAACAATGGCCATTTCCCGCGACTCTAGAA
TCCAGTCATCGTCTCGGTGACGACGCCTTGCCGATCACATAGCTCGACCGGATCGGAGAGAATCTGGTTC
TCGT Clone Rv62 (SEQ ID NO. 619)
:::::::::::::Rv62SP6.seq::::::::::::
ATACTCAAGCTTAAGCGCAGCAGTACCGGCGGTGCCTGGGCATCCCAGCAAAACGGGGAGCTCAACGAAC
GATTCCTGAACGAAGGGTCGTCCACCAACCTCCAAACCGAACGGTTGCCAGCCCCGGC :::::::::::::Rv62T7.seq:::::::::::: (SEQ ID NO. 620)
GCAAGTCCGCTCAATGTGGTTGTGATCACANGACTACGTCGCCTCAATCAGCTCAAACGTCACCCCGTGG
CGTGCTGCGCAGCATGAAGGTCGGCGCCCGCACGATGTGGGCGAAGCAACAGGTAATAACTGGTCGGCAT
GGGTCAACCCTCATTGGGCCGTTGCGGATCGGGTGCACGCCCGGAGTGCCGGTCGAACTCAACACCGCCT
TCACCGATCTTTTCGTCGAAAATGGCGGTCGTGTCGGGGTATACGTCCGCGATCCCACGAGGCGGAATCC
GCTGAGCCGCACTGA Clone Rv63 (SEQ ID NO. 621)
:::::::::::::Rv63SP6.seq::::::::::::
ATACTCAAGCTTCGCGCCCTCAAGCGGCTGAAGGTGGTTCCGGCGTNCCAACNGTCGGGCAACTCGCCGA
TGGGCATGGTGCTCGACNCCGTCCCGGTGATCCCGCCGGAGCTGCGCCCGATGGTGCAGCTCGACGGCGG
CCGGTTCGCCNCGTCCGACTTGAACGACCTGTACCGCAGGGTGATCAACCGCNACNNCNNGNTGAAAAGG
CTGATCGATCTGGGTGCGCCGGAAATCATCGTCAACAACNAGAANCGGATGCTGCNGGAATCCGTGGACG
CGCTGTTCGACAATGGCCGCCGCGGCCGGCCCGTCACCGGGCCGGGCAACCGTCCGCTCAAGTCGCTTTC
CGATCTGCTCA :::::::::::::Rv63T7.seq:::::::::::: (SEQ ID NO. 622)
TGCGCATGGCAGTTGTTGCCGGCTTGAGTCGCGTTAGCGCGGATTCCACCACATCCCTTGCGAAGTCGTG
GGTGCAATGATGTAGCGCTTCTCCCATCGAGATAGTGGAGCAACGCAATCCGTGCGTACGTTGGGTCGTA
CTCGAGTGCGCANCTTGGCGTTGACACCATCTTTGTCATTGCGGCGAAGTCGATCATCCGGTAAGCGCGC
TTATCGACGCCGCCTCTGTGCCGGGTGGTAATCCGGCCATGCGCTTGCGTCCACCGCGACGTGCAGCGGG
CGCACACCGACTTCTCCGGGTGACGGGTGATCTCGGCGAATCAGAACCTGGCGCGCGACACAGCGTCGTG
GCTGTACTTGC Clone Rv64 (SEQ ID NO. 623)
:::::::::::::Rv64SP6.seq::::::::::::
TGGGTGATCAGATACTGGCTAGTTGGTCGGGTGGGGTGATCGAAGATCGCGGTGGCCGGCAGCGTTACTG
CGGTGACGCTGTTAAGCGGTTACGTACTCCACGGCACTCAANGAATTANATCCCGAATCGGCAAACCCTG
GCCAGCGTCGAGTCCGCAGCGCCGTCGCGCCCCCCACCGCTGCGGCATGCTCACATACCACCTCGATCGC TABLE 3-continued End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character << - >> denotes an uncertain base residue.

TGCGGGAGTTGCTCGTCGGCCGACCGACCGGCCAGCCGGGCGGCAAACCGGAGGACCCAAGATTCAGCAC
CACCATCGCTAGCCCGATCTGGCCGCGCGTGG

::::::::::::Rv64T7.seq:::::::::::: (SEQ ID NO. 624)
TCGTAGCGGTTGCGACCANTCCGCGGACAGCTCCGCCACGCGACGGGTCGGGATCACCGCGGTCAAACCA
CCGAGCGGCGAGGATCTCTGGCCGTCGACGTGACCGCGCACGGCCGCGGTGATGGCCAGTCCCGACCGCC
GTTCCACTTGGCGTACGCGCTGGATGTGTTGTGCCGCAACGGAATCCCACCTCAATTATGACCTCGTTGT
GGGCGAGCGCGGTATCGTACGCCCGACCAGGAATCGTCGATGCTATCTCACGTCACCGAAGGCCTCTCCC
AGCACACCGCATCCAGAACGTGCACACNGTCGACATGTCTCGGCGGATCCGCCTGCAGAACGAACGCCAN
GTGCGCTGTGCGACACGGGTCGCGATCACCGCTCGCACGCGGAGATCGGCACACGCGCAGCGCATCGATC
ATAATCTCTCGATGCGGTCTCCACCACCGAACAG Clone Rv65 (SEQ ID NO. 625)
::::::::::::Rv65SP6.seq::::::::::::
ATACTCAAGCTTCGCTGAGGTGGTGGGGCACGATCACGTCACCGCACCGCTGTCGGTGGCGCTGGATGCC
GGCCGGATCAACCACGCGTACCTGTTCTCTGGGCCGCGTGGCTGCGGAAAGACGTCGTCAGCGCGTATCC
TGGCNCGGTCGTTGAACTGTGCGCAGGGCCCTACCGCCAACCCGTGCGGGGTCTGCGAATCCTGCGTTTC
GTTGGCGCCCAACGCCCCCGGCAGCATCGACGTGGTAGAGCTGGATGCCGCCAGCCACGGCGGCGTGGAC
GACACCCGCGAGCTGCGGGACCGCGCGTTCTATGCGCCGGTCCACTCACGGTACCGGGTATTTATCGTCG
ACGAGGCGCACATGGT ::::::::::::Rv65T7.seq:::::::::::: (SEQ ID NO. 626)
GCACTCACGCTGGTACAAGACCTTCACAAAATCTGAAATCCTGACCCGATACTTGAACCTGGTCTCGTTC
GGCAATAACTCGTTCGGCGTGCAGGACGCGGCGCAAACGTACTTCGGCATCAACGCGTCCGACCTGAATT
GGCAGCAAGCGGCGCTGCTGGCCGGCATGGTGCAATCGACCAGCACGCTCAACCCGTACACCAACCCCGA
CGGCGCGCTGGCCCGGCGGAACGTGGTCCTCGACACCATGATCGAGAACCTTCCCGGGGAGGCGGAGGCG
TTGCGTGCCGCCAAGGCCGATCCGCTGGGGGTACTGCCGCAGCCCAATGAGTTGCCGCGCGGCTGCATCG
CGGCCGGCGACCG Clone Rv66 (SEQ ID NO. 627)
::::::::::::Rv66SP6.seq::::::::::::
ATACTCAAGCTTGTATAAAAAGATCGGTGAGCGCATCGATTCGCTCCGCCGGGTTTGCCGCTGCGGCGGC
GGAGCTGCCGTGACCGTCTATTTGGGTGATCAGATACTGGGCTAGTTCGGTCGGGGTGGGGTGATCGAAG
ATCGCGGTGGCCGGCAGCGTTACTGCGGTGACGGCTGTTAAGCGGTTACGTACCTCCACGGCACTCAAGG
AATTAAATCCCGAATCGGCAAACGCCTGGCCAGCGTCGAATCCGGCAGCGCCGTCGCGCCCCAGCACCGC
TGCGGCATGCTCACATACCACCTCCATCGCTGCGGCGAATTGCTCGTCGGCCGACCGACCGGCCAGCCGG
GCGGCAAACCCGGAAGA ::::::::::::Rv66T7.seq:::::::::::: (SEQ ID NO. 628)
CCTCATCATATGCCGATAGAGCTCTACATATTCAGGAGATCACCATGGCTCGTGCGGTCGGGATCGACTC
GGGACCACCAACTCCGTCGTCTCGGTTCTGGAANGTGGCGACCNGGTCGTCGTCGCCAACTCCGGAGGGC
TCCAGGACCACCCGTCAATTGTCGCGTTCGCCCGCAACGGTGAGGTGCTGGTCNGCCAGCCCGCCAAGAA
CAGGCAGTGACCAACGTCGATCGCACCGTGCGCTCGGTCAAGCGCCCATGGGCAGCGACTGGTCCATAGA
GATTGACGCAAGAAATACACGCCCGGAGATCTCGCCGCATTCTGATGAACTGAACGCGACCCGAGGCTAC
TCGGTGANGACATNACGACGCGTTATCACACCCCGCCTNCTTCAATGACCCCACGTCNGGCACCAAGGAC
CCGGCAATCGCGGCTCACTTGNGCGATNGTCNACAACCAACGCGNCGCCTGGCTACGGGCTCAACAAGGC
ANAAGACACAATCCGCTCTCGATTGGTG Clone Rv67 (SEQ ID NO. 629)
::::::::::::Rv67SP6.seq::::::::::::
ATACTCAAGCTTATCGAGGCGGCGCATACCGAAGCGTGGGAAATCCAGACCGAATACCGCGACGTGCTGG
ACACTTTGGCCGGCGAGCTGCTGGAAAAGGAGACCCTGCACCGACCCGAGCTGGAAAGCATCTTCGCTGA
CGTCGAAAAGCGGCCGCGGCTCACCATGTTCGACAACTTCGGTGGCCGGATCCCGTCGGACAAACCGCCC
ATCAAGACACCCGGCGAGCTCGCGATCGAACGCGGCGAACCTTGGCCCCAGCCGGTCCCCGAGCCGGCGT
TCAAGGCGGCGATTGCGCATGCTACCCAAGCCGCTGAGGCCGCCCGGTCCGACCCGGCCAAACCGGGCAC
GGCGCCAACGGTTCGCCCGCCGGCACCACCGGTCCGGTGACCGCAGTACGGTCCCCCCAGCCTGACTACC
GTGCCCCGGCGGGCT ::::::::::::Rv67T7.seq:::::::::::: (SEQ ID NO. 630)
TGGCCGGGCTGGTAGCCCGCGTATGGCAAGGTTCCGCTCAATGTGGTTGTGATGCAGCAGGACTACGTTC
GCCTCAATCAGCTCAAACGTCACCCCCGTGGCGTGCTGCGCAGCATGAAGGTCGGCGCCCGCACGATGTG
GGCGAAGGCAACAGGTAAGAACCTGGTCGGCATGGGTCGAGCCCTCATTGGGCCGTTGCGGATCGGGTTG
CAGCGCGCCGGAGTGCCGGTCGAACTCAACACCGCCTTCACCGATCTTTTCGTCGAAAATGGCGTCGTGT
CCGGGGTATACGTCCGCGATTCCCACGAGGCGGAATCCGCTGAGCCGCAGCTGATCCGGGCTCGCCGCGG
CGTGATCCTGGCCTGTGGTGGTTTCGAGCATAACGAGCAGATGCGAAT Clone Rv68 (SEQ ID NO. 631)
::::::::::::Rv68SP6.seq::::::::::::
GTCCAGTCAAGCATCGGTCCTCTCCGACTACGCCAAGANTGGCGACGTGTCAGTGCANACAGCGGANATG
GTGGCGCCTATGCGTCGACGCTCACAAACNGCGGTGANCGCGTTCTGGTCGTGCACCATCGAGCCGTGCC
AGCCCGGCCGCGTGCCGTCAGCCGCATCCACTGGATGCCTTCTCGGNGTTTCAATCANGTACANGCGACG TABLE 3-continued End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character << - >> denotes an uncertain base residue.

TTCGCCACCATCGTGCCGGGGCACGGTTAGCGAGAAACCGCCGACTTCACCGATTGCCTCGGTGATGCCG
TCGAACAGATCGGGCCTATTGTCGACAGCCAGTGTGATNCGTATTTGCCGCCGTGCTCCTCGTCGCAACG
ATGCGAACACAGATCCGTGGNGGACGATAGCGGCTGACAANGTGGGGGCAACACAATCACATGCCACATT
TCTTCATTTCACGCCCAGAACCCAGACTTCGTCTCGATGNGCCG

::::::::::::Rv68T7.seq:::::::::::: (SEQ ID NO. 632)
CACGCGGTCTGGCCCGATCCGAAGATCCCTTTGCCGGCGTGGCGGCTCTGCTCGGCGGTGTTGTACACTT
CTCGAACACCTCGGCACCGACACCACCACCGTNGCTTGAACACCGCCAACATCGGCAGCAGATCTTGATG
GTCCTGGTGAATCCCACGGTGACTTTGGAGTGGAAGGCGCCATACTGATCGCCGCGCCAGCACATGAGCT
AGCGGCAGGAAAACCAGCAGCCGCTCACCTTGCGCAGCAGCGTCNGGTGATATGCCTGGCGCCCTTAATC
TCGTGAACCAGTTGGATTGGGTCAACTGGCAGCCTTGGGTCTCCGGTGGTGCCGANGTGTANATAAGCTC
CCGGGTCCGTCAACGTANTGCGCAGGCGGCGGTTACTCGGCGGGTCAACGAGCCCCGCTCGTGAGCNATC
AGCCTTTGGACCGAACGGGATTCATACTCCGCAGGCGGCCCTCCGAAATCGGCACATGTCCTTTGATCGT
TCGCAACAN Clone Rv69 (SEQ ID NO. 633)
::::::::::::Rv69T7D3.seq::::::::::::
GGCCATGTCACATCGGTGGTACAGGTAAACCGCGCCGTGTGCGCGGTCTCGGAGATCAGAACGTGGTCGC
AGTTGAACCGCGGGCTTTCAGCCAGTCGCGATAATCGGCGGAAGTCGGCGCCTGCCGCCCCAACTAGCGC
GACTCGCCACCTAGCACACCGATGGCGAAGGCCATGTNTCCGGCCACGCCGCCGCGGTGCATCACCAAGT
CATCGACTAGGAAGCTAAGCGACANCTTGTGCAGGTGTTCGGGCAGTAGCTGCTCGGAAAATCGGCTGGA
AACCGCATCAAATGGTCGGTCCAATCGAACCGGTTACCCGATCGTCACAAAAATCTCCGTCCT Clone Rv6 (SEQ ID NO. 634)
::::::::::::Rv6SP6.seq::::::::::::
GGGTCTACAACCACCGGGTCTGACTTCTGGGCTTCCACCGCTCGCGCCGTCGCGACAAACAGCGCGGTCG
AACCGACACTCGTTGTGATGTCCCAGCTATCACCTCCGGTAGGCACCCAATCGACCCTACCCGGCTATCT
CACCCCCGATCTCCAGGCTCCGCCGATCCATGCGCATCCCGGTCCGGATCCC ::::::::::::Rv6T7.seq:::::::::::: (SEQ ID NO. 635)
CAGGCATGCAAGCTTGTCGTATTCCGTGGCACTGTCAGACATATGCGCCGCTCCTCCTCATCGCTGCGCT
CGGCATCGTCGCCGGCGGTCATGGCGTCACCCTACCCAAGCCGAACGCGAAACGAGAACGTGTTCCATTA
TTAGGGTGTGAGCACCAATACCAGATTGCTCACCAGGAACTCACGCAGCACCGGGACGGATGTCAGCCAC
CACGCCCATCTGGGGTGGTAGCGGGGAAATACGGCTAACGCGGCTCCGGTGCCGGCAGCCCAGCGCAGAC
CCTCGGCGGCGGACACGGCTAACAACGACGACCCATAGTTGTTCTTTGCCGGATGGCCGTGTTTGCTGAC
ATATCGGGCGCGGCGCCGGCGCCGCC Clone Rv70 (SEQ ID NO. 636)
::::::::::::Rv70SP6D2.seq::::::::::::
NCTACGCTGCTGAATGTTGTGCGCCGGAGGANCTCAAGACCCACGCGGTTGTACGCGGACNTGCGACATG
TTCAACCGCCGGA ::::::::::::Rv70T7D3.seq:::::::::::: (SEQ ID NO. 637)
CTAACCAACAAGCCATGGTGGTTGGCGCCGTCGAGAGGTCGGCGGTCGCCACAACGGGAAGATCGCCTTG
AGCGTCGCTCGACCGCCGCCTCGAGTTGGGTCATAACGAAGTACTGATGCCGATCATGTCGACGTGTCCG
TCGCATCAGCGTGCAGCGGCGACCCCTCGACGAGCCTCGGTGCCGCCGCGGCCAGGGCACCAGCTGTTTT
AGCGCATTGTGCTCCGCCGGTAATAAAGGANGTCGGTCGCCTCCGCTGCTGTGGTTGCGGAATAACATCT
TCCCTTCCTGCAACAGGATGAGAATGGTTTTAATTGCTC Clone Rv71 (SEQ ID NO. 638)
::::::::::::Rv71SP6.seq::::::::::::
CTAAGCTTTCGGGTCCGCCGCCACTAGTACCGCGTTGCCGGCCCCGCCGACCTAGAATGTTCCGCCCATT
GCCGTTTCCTCCCGCCGCCGGGTT ::::::::::::Rv71T7.seq:::::::::::: (SEQ ID NO. 639)
TCTGGTGCCGGGTGTGCCGACGGGTCCGTCCGCCTCTGCTTCAGTGATTCTGTGATGCGACCGGCAACGT
CCTCGTTGTTCGGTGTCTATGTGGTCCGTCTCTCCTTGTTCCGCATACGATT Clone Rv72 (SEQ ID NO. 640)
::::::::::::Rv72SP6D2.seq::::::::::::
GCGATCGNTNACCACAAGGGCGCAACCGTTCGCGCGTCGACTGAACGTGCTGCCGCCTGGAGAACTGGCG
CTGCTGCCACCTGGTCGGCGCATCGGCACTTCGAGGACTGGATTTCGACGCGTGGCCCGACCTGANGTNG
GCGGTGGACNNGTGTGCACCCGGTTGATTCCTCGGCCTTGCCGGGATGCCACCTGCGCCTGGTGGTCGAT ::::::::::::Rv72T7D3.seq:::::::::::: (SEQ ID NO. 641)
CGTGACCGGACGGGGTGCCGCGCGAACCGGTCTTGGCCAATTGCCGGGGACTGGGGCTGGAGTATAAAGC
GGGCCTGTTGCCGGAAGATAAAGTCAAAGCGGTGACCGAGCTGAATCAACATGCGCCGCTGGCGATGGTC
GGTGACGGTATTAACGACCGCCAGCGATGAAAGCTGCCGCCATCGGGATTGCAATGGGTAGCGGCACAGA
CTGGCGCTGGAAACCGCCGACGCACATTAACCATAACCACCTGCGCGGCTGGTGCAAATGATTGAACTGG
CACGNCCACTCACGCCAATATCCGCCAGAACATCACTATTGCGCTGGG TABLE 3-continued End sequences of the polynucleotide inserts cloned in the named recombinant BAC vectors contained in the I-1945 *M. tuberculosis* H37Rv genomic DNA library. RvXXXSP6 corresponds to the SP6 endsequence of the clone RvXXX; RvXXXT7 corresponds to the T7 endsequence of the clone RvXXX. RvXXXIS 1081 corresponds to a region located close to a copy of the IS1081 repetitive sequence (Insertion element) The character << - >> denotes an uncertain base residue.

Clone Rv73 (SEQ ID NO. 642)
::::::::::::Rv73SP6.seq::::::::::::
ATACTCAAGCTTCTTACCCANAGCATGAACCCCGCCGTCCAATGCCGCCACCGTGGTGCTGTCGGCCGGC
CGGGTGCGGGCACAATCGCCGAGTTCGGCGAACAGATCCTCGAAGGTCTTCACGGCCAGCGATTGTTGCA
CGTGTCAGCCAGCCAAGTCACGGTGGTTTGACGCCACACGTTCGCCACCGCCGCGCCGCGCATTAGGGCA
TCCTAATATAGGTTAGGCTACCCTANTTATTCCTGTGGTCNAAGGAGGCAGCCGAACGTGACCTTCCCGA
TGTGGTTCGCAGTTCCGCCGGAAGTGCCGTCAGCATGGCTGTCCACCGGCATGGGCCCCGGTCCGCTGCT
GGCCGCGGCCAGGGCGTGGCACGCGCTGGCCGCGCAATACACCGAAATTGCAACGGAACTCGCAAGCGTG
CTCGCTGCGGTGCAGGCAACTCGTGGCAGGGGCCCAGCGCCGACGGTTCGTCNTCCCCATCAACCGTTCC
GTATTGGCTAACCACCTGCACGGTGGCACCGCACAACGCCGCCACAAACGCGCCCCGGTATAC ::::::::::::Rv73T7.seq:::::::::::: (SEQ ID NO. 643)
GGCCGAACTTAATCGGTTGTTGGCGGCTGCCGAGTTGGGTCACTCGGGGGGTGTGCACTGGCACATGGTG
GGCCGGATTCAACGCAACAAAGCCGGGTCGCTGGCTCGCTGGGCGCACACCGCTCACTCGGTGGACAGCT
CGCGGTTGGTGACCGCGCTGGATCGGGCGGTTGTTGCGGCGCTGGCCGAACACCGTCGTGGCGAGCGGCT
GCGGGTTTACGTCCAGGTCAGCCTCGACGGTGACGGATCCCGGGGCGGCGTCGACAGCACGACGCCCGGC
GCCGTAGACCGGATTTGCGCGCAGGTGCAGGAGTCAGAGGGCCTCGAACTGGTCGGGTTGATGGGCATTC
CGCCGCTGGATTGGGACCCGACGAAGCCTTTGACCGGCTGCAATCGGAGCACAACCGGGTGCGTGCGATG
TTCCCGCACGCGATCGGTCTGTCGCGGGCATGTCCAACAACTTGAAATCCCGTCAACATGGTCGAC Clone Rv74 (SEQ ID NO. 644)
::::::::::::Rv74SP6.seq::::::::::::
GCTTCCCCTGATACTCGACCAGCCCCACTCGGGCCAATACGTGAATGTCCTAGCATTTTTCACCCGTTCA
CGGGCTAGTCGAGTAGTAGACGATTGATTAGCCTGAACGTACCTCCGACGGCCAGCTGACGAACGGGTTT
GACGGA ::::::::::::Rv74T7D3.seq:::::::::::: (SEQ ID NO. 645)
TCAGCTGTCTGTAGAAGGGCTGGCGATACTGTGCACTGTCTGATATCGCNNCGTNGTGGGACTATNCAGN
CCATNANGATGCGGTTCNGNNNNTGCAGAGNATCCTGGNACACATNCGGTTCACGTTAATCANCATCGCG
ANTTNCTNCGTNTTCGATTANTTCTGCTAACGNNTCTNNNAGTGCCTGCGGGTCGACTCTAGAG Clone Rv75 (SEQ ID NO. 646)
::::::::::::Rv75SP6D2.seq::::::::::::
NCTCTGCCGGGCNAGAGCGCAGAGTCGGACGGCTTCGTCGATCGTGAAGCGACCNTGCGATGANCAGATA
TCGNTNACACTGCTCANAAACTTCGGATCATCGNTGATACACAGGCCAACGGGTAGCGGTTGTCCAACCG
CTTCGTCAACGANATGGGATCGTGACGANCCTACGCTCGCAGGATATGTCGCNGACCNGNTCTAGANAN ::::::::::::Rv75T7D3.seq:::::::::::: (SEQ ID NO. 647)
CACTTCATGCTCGTGCGTTGGCNTCGATTTGCNCGAGNGGTTAGCTCCTCGAGTGNGTGACGTATCACTC
CGGCNGACTANCCGTATCNGCGTCCCGCACCGGTCAACTGGTCTAGCCACACCGGGGAGAATNCNCGACC
GGNGCTATCGACCNATCACGGCTTGTCGNNAAGATAGNCAGCC Clone Rv76 (SEQ ID NO. 648)
::::::::::::Rv76SP6.seq::::::::::::
ATACTCAAGCTTGCCAACCGCCACCCTGCATCCGGGGGGCGAGCACTGCTCCGCCGACCAGTACGAACCA
ACCTGCGGTGCCCAGGCCATTGACAATGTGCTGGTCGGCGCCCGCGAGTTCTAGCACAGCAACGCCGCGG
CCACCACAGGGGCG ::::::::::::Rv76T7.seq:::::::::::: (SEQ ID NO. 649)
CGGTCGGTGTGCTTGGCGGCGTCGGTATCAACACCGCCCACGAAATGGGGCACAAGAAGGATTCGCTGGA
GCGGTGGCTGTCCAAGATCACCCTCGCCCAGACCTGCTACGGGCACTTCTACATCGAGCACAACCGTGGC
CATCACGTCCGGGTGTCCACACCGGAAGACCCGGCGTCGGCGCGGTTCGGCAAAACTTTGTGGGATTTCC
CGCCCCCCC Clone Rv77 (SEQ ID NO. 650)
::::::::::::Rv77SP6.seq::::::::::::
AATACTCAAGCTTCGCGGAGGTGGTGGGGCAGGAGCACGTCACCGCGCCGCTGTCGGTGGCGCTGGATGC
CGGCCGGATCAACCACGCGTACCTGTTCTCTGGGCCGCGTGGCTGCGGAAAGACGTCGTCAGCGCGTATC
CTGGCGCGGTCGTTGAACTGTGCGCAGGGCCCTACCGCCAACCCGTGCGGGGTCTGCGAATCCTGCGTTT
CGTTGGCGCCCAACGCCCCCGGCAGCATCGACGTGGTAGAGCTGGATGCCGCCAGCCACGGCGGCGTGGA
GCAACCCCGCGAGCTGCGGGACCGCCC ::::::::::::Rv77T7.seq:::::::::::: (SEQ ID NO. 651)
GATGGCACTCACGCTGGACAAGACCTTCACAAAATCTGAAATCCTGACCCGATACTTGAACCTGGTCTCG
TTCGGCAATAACTCGTTCGGCGTGCAGGACGCGGCGCAAACGTACTTCGGCATCAACGCGTCCGACCTGA
AATTGGCAGCAAACCGGCGCTGCTGGGCCGGGCATGGTGCAATCCGAACAAGCACGCTCAACCCGTACAC
CAACCCCGAAGGGCCGCTGGCCCGGCGGAACCTTGTCCTCCA Clone Rv78 (SEQ ID NO. 652)
::::::::::::Rv78SP6.seq::::::::::::
AACAGCTATGACCATGATTACGCCAAGCTATTTAGGTGACACTATAGAATACTCAAGCTTCTGGGCGTCG TABLE 3-continued End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character << - >> denotes an uncertain base residue.

TGGTGCCCGGCCTGCCGGTGCAGGAACTGGATTTACTGCCATCTCTCGCGACCCTGAGGTGGTCCAGGC
TTACAACACCGACCCACTCGTGCACCACGGACGGGTTCCGGCCGGGATTGGCCGCGCGCTGCTGCANGTG
GGCGAGACCATGCCGCGGCGANCACCGGCATTGACCGCGCCGCTGCTAGTGCTGCACGGCACCGATGACC
GGCTGATCCCCATCGAAGGCAGCCGTCGCCTGGTCNAATGTNTNGGATCNGCCGACGTGCANCTGAANGA
NTATCCCCGGCTGTNCCACNAGGTGTTCAACGAACCGGANCGCAACCAAGTG

::::::::::::Rv78T7.seq::::::::::: (SEQ ID NO. 653)
CAAGGCATACGCCAAGACCCAAGGGATCGCAGTCACCTCCGTCAACGGCCTGGTCGCCGGCCACGGGTCC
GTGCAGGAGACGTGGCTGGCCATGCAAAGCGCCGCCGCCTTATCAGGAACGCCCCGGCTTGTCGGCTTTT
CCTGCATCGACACATTTCCGGAGGTGTTGTGGTTGGCGCANCGCGCGAGACAGGCCTGGGATGGCGTGCG
CATCGTCATCGGGAATGCGATGGCAACACTGAACTACGAGCGCATCCTGCGCCAGCATGACTGTTTCGAC
TACGTCGTCGTTGGCGACGGGGANGTAGCGTTCACCAAGCTGGCCTTGGCCCTGGCGAATGACCTGCGGT
TGACGACTCCCGGGACTAACCCGCCGTANTGAGCAAGGACAGATTCTGCGCACACCCTCCTCGCTGGTCG
ACCTTGACA Clone Rv79 (SEQ ID NO. 654)
::::::::::::Rv79SP6.seq:::::::::::
AACAGCTATGACCATGATTACGCCAAGCTATTTAGGTGACACTATAGAATACTCAAGCTTGCCGGTGATC
TGGGTGGCCAACTCGGCGGGCACCATCTCCATCACGACNGCAAACGCTCCGGCTTCGGCGACAGCGATCG
CGTCTGCGATNGTTTGTTCGGCGGCGTCTCCGCGGCCCTGCACCCGGAAGCCGCCCAAGGTGTTGACNCT
TTGCGGGGTGAAGCCGATGTGTGCCATCACCGGGATNCCCGCCGCGGTCAGACANGCGATTTGCTCGGCC
ACCCGCTCACCGCCCTCGANCTTGACNGCATGTGCGCCGCCGTCCTTGAAGAAACCGGTGGCGGNGGCAA
CCC ::::::::::::Rv79T7.seq::::::::::: (SEQ ID NO. 655)
CGTTGAGATCCAGCTGCGCACTGTGCAGCGCCTCGGTGGTCTGCTCGGCCTGCCGGGATAACTCGTTGAG
CTTGGCCAGCGCGTCGTCGGCCGGATCAGCCAGCACATTCGCGGCCAGGACGCCGGAGGAGACGGTGAAG
CTCGCAAAGAAACCTATGGCGGACCGCATGATTACACGCGCGATCAACCACCTCTGGTCGAGCCTCAAAA
TTTGCTTCCTTAAACGGGCCATCGACGGATGACGTCGAGCTGGTTTAGGTCTCAAACAGGTTACGAAACG
ATCTCGGAATTGTCCAAAAGGGGAAGTTAAGAAAATGGATAGATTTCTACCATTTCGCTGTGGACGATCG
TACTTCTGCTATAGGGCTCCAGGGGCATCGACACGCAACGACCTTACGCGACACCGGATCCGCGCTGGCG
GCGGAACGGCACCANGCGCAACCGAAGGGCCAATCCGACATCGG Clone Rv7 (SEQ ID NO. 656)
::::::::::::Rv7SP6.seq:::::::::::
ATACTCAAGCTTATCTAGGCGCCAGCTTGATTGGTCTGGTTGCATTGGCCAGCTGCGCGAGCCTGGCTCA
CTTCAACTACAACAACCGCAAACAATTGCCGCCTTCGGATCCGAGTTCGGTTGGGTACGCGGCAATGGAN
CACCATTTCTCGGTGAATCAGACTATTCCTGAGTACTTGATCATCCACTCTGCACACGACCTGCGAACCC
CGCGCGGCCTTGCCGACCTGGAGCAGCTGGCGCAACGTGTGAGCCANATCCCAGGCGTTGCCATGGTTCG
CGGTGTGACCCGGCCAAACGGGGAAACCCTTGAACAGGCCCGGGCGACATACCAAGCCGGCCAAGTTGGC
AACCGGCTGGGCGGCGCGTCGCGAATGATCGATGAGCGCACCGGCGACCTGAATCGGCTGGCATCGGGTG
CCAACCTGTTGGCCGACAATCTCGGTGACTTCGCGGTCAAGTCAGCCGGGCCGTTGCGGGTGTCCGCAGC
CTTGTCCAGCCCCTCGCTTACTCCA ::::::::::::Rv7T7.seq::::::::::: (SEQ ID NO. 657)
CAGGCATGCAAGCTTTTTGAGCGTCGCGCGGGGCAGCTTCGCCGGCAATTCTACTAGCGAGAAGTCTGGC
CCGATACGGATCTGACCGAAGTCGCTGCGGTGCAGCCCACCCTCATTGGCGATGGCGCCGACGATGGCGC
CTGGACCGATCTTGTGCCGCTTGCCGACGGCGACGCGGTAGGTGGTCAAGTCCGGTCTACGCTTGGGCCT
TTGCGGACGGTCCCGACGCTGGTCGCGGTTGCGCCGCGAAAGCGGCGGGTCGGGTGCCATCAGGAATGCC
TCACCGCCGCGGCACTGCACGGCCAGTGCCCGCGGCGATTCAGCCATCGGGACATCATGCTCGCTTCATA
CTCCTCGACCAGTCGGCGGAACAGCTCGATTCCCGGAACGCCCACGCATGGTG Clone Rv80 (SEQ ID NO. 658)
::::::::::::Rv80SP6.seq:::::::::::
AACAGCTATGACCATGATTACGCCAAGCTATTTAGGTGACACTATAGAATACTCAAGCTTGTAGAAAAAG
ATCGGTGAGCGCATCGATTCGCTCCGCCGGGTTTGCCGCTGCGGCGGCGGAGCTGCCGTGACCGTCTATT
TGGGTGATCAGATACTGGGCTAGTTCGGTCGGGGTGGGGTGATCGAAGATCGCGGTGGCCGGCAGCGTTA
CTGCGGTGACAGCTGTTAAGCGGTTACGTATCTCCACGGCACTCAAGGAATTAAATCCCGAATCGGCAAA
CGCCTGGCCAGCGTCNAGTCCGGCAGCGCCGTCNCGCCCCAGCACCGCTGCGGCATGCTCACATACCACC
TCGATCGCTGCGGCGANTTGCTCGTCNGCCGACCGACCGGCCANCCGGGCGGCAAACCCNGAAGACCCAA
GAATTCATCACCACCATCGCTAGC ::::::::::::Rv80T7.seq::::::::::: (SEQ ID NO. 659)
CCTTCTTGACACCCACCTCGCCATCGACCTTGAGCACTCCGTCGTAGTTGGTGAACATGTGACCGGCGAT
CGGGCGGGTGAACGCGTACTGGGTGTCGGTGTCGACGTTCATCTTCACCACGCCGTAGCGCAGCGCCTCC
TCGATCTCCGACTTAAGCGAACCCGAGCCGCCGTGGAACACGAAATCNAACGGCTTGGCGTCNGCCGGCA
GTCCGAGCTTGGCCGCCGCCACCTGTTGCCCTTGCGCAAGGATGTCNGGGCGAANCTTGACGTTGCCGGG
CTTGTANACGCCATGCACGTTGCCGAACGTCNCGGCCAGCANGTATTTGCCGTGCTCACCGGCGCCCANC
GCCTCGATGGTTTTCTCGAAGTCCTCCGGGCTGGTGTACAGCTTCTCGTTGATCTCGTTCGCCACGCCGT
CCTCTTCGCCGCCGACG TABLE 3-continued End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character << - >> denotes an uncertain base residue.

Clone Rv81 (SEQ ID NO. 660)
::::::::::::Rv81SP6.seq::::::::::::
AACAGCTATGACCATGATTACGCCAAGCTATTTAGGTGACACTATAGAATACTCAAGCTTGGAAAGGAGA
TCCCCGGGAACCTGGTGGCAACCCCGCCATTGGGGTTGTTGGGATTGCCGATCAGCGTGAANGAAAGCTC
GTCTGGAGACAGCGGGTCGGCCGAAGCCGCAAGATTGGCCATCACTAGTGACGANATCGTGGCGCTCTGC
GAGTANCCNAAGACAGTGACGTTGTTNCCGGCGGCAATTTGCTGCCGAATCGCACTTTCGAGAATGACNG
CACCCTGCGCCACCGANGAATCNAAAGTGAGGTTCTTGATCACGACCACCGGGTNGAGCCCTTGGGGCGT
GAAGANCGCCTGCGCNATAACACCCGGGACGCTGCCACTCATGTNCAGCGCGTTCGCGANCTCNACATAT
CT ::::::::::::Rv81T7.seq:::::::::::: (SEQ ID NO. 661)
TCCTGGTGATCGANGGCCGCGGTTCCGGCCGAAAATCCGGTTCGGGTTCGGGTCGCGGTTCCAACTTGAN
CGCGGTCCGCAGCTGATTCACCGTGGCAACGCCGGCCAACTGCGCATAATGCGCATCCGAACCCTCACCC
GCCCGCCCCGCGATCACCCCAACCTGATCCAACGACAACCGCCCCTCCCGCATACCCCGGGCGCAGCGCG
GAAACTCCGGCAACCGCCGCGCCACCGTGGCGATCGTGTGGGCGTTGCCTGACGAACANCCCATCTTCCA
GGCCACCAACCCCGCCACCGACCGCGCCCCCGTCACACCCCACAACCCGTCGCGATCCAGCTCAGCCACG
ATCTCCACAATGCGCCCATCAATCGCATTGCGCTGAACGGGCAACTCCGCCAACTCCTCCAA Clone Rv82 (SEQ ID NO. 662)
::::::::::::Rv82SP6.seq::::::::::::
AACAGCTATGACCATGATTACGCCAAGCTATTTAGGTGACACTATAGAATACTCAAGATCTGGTACCCAT
CCGTGATACATTGAGGCTGTTCCCTGGGGTCGTTACCTTCCACGAGCAAAACACGTAGCCCCTTCAGAG
CCAGATCCTGAGCAAGATGAACAGAAACTGAGGTTTTGTAAACGCCACCTTTATGGGCAGCAACCCCGAT
CACCGGTGGAAATACGTCTTCAGCACGTCGCAATCGCGTACCAAACACATCACGCATATGATTAATTTGT
TCAATTGTATAACCAACACGTTGCTCAACCCGTCCTCGAATTTCCATATCCGGGTGCGGTAGTCGCCCTG
CTTTCTCGGCATCTCTGATAGCCTGAGAAGAAACCCCAACTAAATCCGCTGCTTCACCTATTCTCCAGCG
CCGGGTTATTTTCCTCGCTTCCGGGCTGTCATCATTAAACTGTGCAA Clone Rv83 (SEQ ID NO. 663)
AACAGCTATGACCATGATTACGCCAAGCTATTTAGGTGACACTATAGAATACTCAAGCTTANCGCCACCT
CCCGGGCGGAACTCCACGGCGTGGATNAAGGTACCGGCCGGGATGTTGCGCAATGGCAGGTTGTTGCCCG
GCTTGANGTCCGCGTTAGCGCCGGATTCCACCACATCCCCTTGCGAAANTCCGTTGGGTNCNATGATGTN
NCGCTTCTCCCCNTCNANATAATGGANCAACGCNATCCGTGCGGTACGGTTCGGGTCNTACTCCATGTNC
GCGACCTTGGCGTTGANACCATCTTTGTCATTGCGGCGAAAGTCNATCATCCGGTNAGCNCGCNTATGAN
CGCCGCCTTTGTGCCGGGTGGTAATCCGGCCATGCGCNTTGCGTCCACCGCGAACGTGCAACGGGGGCNC
CAACGANTTCTCCNGGGTTGAACCGGTNATCT ::::::::::::Rv83T7.seq:::::::::::: (SEQ ID NO. 664)
TGTGTGTGGTGGTAACCCATCTGAGCAGTGTGCCAAACCGGGGCAGCCAGCTCCCAATTGACGTGAGCCC
GCTCACTTGCTGGGTAAGCGTCG Clone Rv84 (SEQ ID NO. 665)
AACAGCTATGACCATGATTACGCCAAGCTATTTAGGTGACACTATANAATACTCAAGCTTGCGGGTNATN
GCCTTGGTCAACGGCACCGTGATCGGATCNGGGTCTACCGCACACATNGACTGGAGCTTCGGCGAANTCA
TCGCCTATGCCTCGCGGGGGGTGACGCTGANCCCNGGTGACNTGTTCNGCTCNGGCACGGTGCCCACCTG
CACGCTCNTCNAACACCTCANGCCACCGGAATCATTCCCNGGCTGGCTGCACGANAGCGANNTTGTCNCC
CTCCAAGTCTAAAGGCTGGGCGANANAAGCANAACGTCCCGACNAACGGCACTCCTTTTCCNTTTGCTCT
TC ::::::::::::Rv84T7.seq:::::::::::: (SEQ ID NO. 666)
GAAATCATTGATGGTTTGAGTCACCAGGCCGATCAAGCCTTCGCCGAGCCAAATTCCAATCAAGAGGCCC
AAGCCCGTACCAATCAGCCCGGCAACGAGGGATTCCGTCATTATCAGCCAAAATAACTGCTCTCGGGTTA
CACCCAAACAGCGCAATATGGCGAAAAACGGTCGCCGTTGCACGACATTAAATGTCACGGTATTGTAGAT
TAAAAAGATACCCACCAACAANGCAATCAAACTGAGAGCGGTTAAATTGACCGTAAAAGCGTCCGTCATC
TGTTTGACNGTGTCCCGTTGGGTATCCGACGTTTCCATACGCACACCGGCCGGCAGTCTTTGTTGGATGC
GTNTTGCAATGGCCTCATCTTTGATGATCAAATCGATGTNGCTCAGTCTTCCGGGCATATGGAACAACTC
TTGGGCCGTGGAAATATCAGCAATGATA Clone Rv85 (SEQ ID NO. 667)
::::::::::::Rv85SP6.seq::::::::::::::
CTTTCGCCCAGGCCGGCGCGGATGTCCTCATCGCTTCACGAACATCATCCGAGCTTGACGCTGTCGCCGA
ACAGATCCGCGCTGCCGGCCGCCGCGCCCACACCGTTGCCGCCGATCTGGCCCATCCCGAGGTGACCGCG
CAGCTGGCTGGTCAGGCCGTCGGAGCTTTCGGGAAGCTCGACATCGTCGTCAACAACGTTGGCGGCACCA
TGCCCAACACGCTGCTAAGCACCTCGACCAANGACCTCGCGGACGCCTTCGCCTTCAACGTGGGCACCGC
CCACGCGCTGACCGTCGCGGCGGTGCCGTTGATGCTGGAACACTCCGGCGGCGGCAGCGTGATCAACATC
AGCTCCACCATGGCCGGCTGGCGGCGCGGGGTTTC ::::::::::::Rv85T7.seq:::::::::::: (SEQ ID NO. 668)
TGTGGGCTCCGATCCGGCGCGCATGGCATCGACGGCGACGCCGATCGATGACGGCCAGGCTTACGAGCTT
GAGGGTGTGAAGTTGTGGACCACCAACGGTGTGGTAGCGGACCTGCTAGTGGTTATGGCGCGGGTACCGC
GCAGTGAAGGGCNCCGAGGGGGAATCANCGCCTTTGTCGTCGAGGCTGATTCGCCCGGGATCACCGTGGA TABLE 3-continued End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character << - >> denotes an uncertain base residue.

GCAGATCGCGCTGACCACACTCAACGCCGGACGGCTGTCCCTACCGGCGATCCAACCGGAGT

Clone Rv86 (SEQ ID NO. 669)
::::::::::::Rv86SP6.seq::::::::::::
GAGCTGGCCGAGCTGGACCGGTTCACCGCGGAACTACCGTTCTCGCTCGACGACTTTCAGCAGCGGGCTT
GCAGCGCGCTGGAACGCGGCCACGGTGTGCTGGTGTGCGCGCCGACCGGCGCTGGCAAGACAGTGGTCGG
CGAGTTCGCCGTGCACCTGGCGCTGGCGGCCGGCAGTAAATGTTTCTACACCACGCCGCTGAAAGCCCTG
AGCAACCAAAAGCACACCGATCTCACAGCACGCTACGGCCGTGACCAGATCTGGCTGCTGACCGGTGACC
TGTCNGTCAACGGCAACCGCCGGTGGTGGTGATGACCACCGAAATGCTGCGCAACATGCTCTAC ::::::::::::Rv86T7.seq:::::::::::: (SEQ ID NO. 670)
GATCTCTGGATCGGCGGGGCTCTCCGGGCCGGCCTCGGCGACCTCAGCGGGCCGCGCCTTCCGGCCGAAC
CATTCCCTAGCCATAGATGACCGCACCTCGATGCACGGTTTGGCGGCAACGCGGCAAGGCGTCNGTCGGG
CCCAGCCGCGGCAATGCGGGTACCCGGGAGCGCGGGTCNGTANACCANCGCTGGACTGCGTCGCGCGGTG
CGTCNACNTCAAAGTCCCCGGCGTCCCATATCGCGTATGACGCGGGCGCGCCCGGCACCANGGGTGCCGA
TCCGGCCGTCTCGAACACCACCGGCCCGCCAGCCGCCGCGGCTCCGGCAGCNAACCCGCCCGCGCCGATA
CCCGCTGCCCGCGTGCGTGATTGACCGCCGCGCGCACGCTGGCCANGGATCAAAGCCCGTG Clone Rv87 (SEQ ID NO. 671)
::::::::::::Rv87SP6.seq::::::::::::
GGACGCGTAGCCCGCCAGGCCGGTCAGGGTGCCCTTCCAGTCCACGCCGCTGTGGTCGGCGAACCGCTTA
TCTTGAATCGAGACGATCGCCAGCTTCATCGTGTTGGCGATCTTGTCCGAGGGCACCTCGAACCGGCGCT
GCGAGTNCAGCCACGCGATCGTGTTGCCCTTCGCGTCGACCATCGTCGATACCGCAGGCACTTGCCCCTC
GAGCAGCTGGGCCGAGCCGTTGGCAACGACCTCAGANGCACGATTGGACATCAGCCCTAGCCCGCCTGCG
AACGGGAACGTCAGCGCAGTGGCGACGACACTGGCCAACAGACAGCACCCAGCCAGCTTCAGAACGGTGA
TCGCGGCCGGGAAGCGCTCGGGCATGCGTNCTACAGTAGCGACCTCCTGTCACTCCACGTGCCGCTCGGT
CCAATAGAATCTTTCCGCGGGCGGGTGAATCTCTGCNGGATCGGGGCNGGCGC ::::::::::::Rv87T7.seq:::::::::::: (SEQ ID NO. 672)
GCTCGTTGCCGGCGGCGATCTCGTCGAGCTCGTCTTCCATCGCCGCGGTGAAGTCGTAGTCGACGAGCCG
ACCGAAATGCTGCTCGAGCAGACCGGTTACCGCGAACGCCACCCATGACGGCACCAGTGCACTGCCCTTC
TTGTGCACGTNGCCGCGATCCTGGATGGTCTTGATGATCGACGANTAGGTCGACGGGCGGCCGATGCCCA
GCTCCTCGAGCGCTTTGACCAGCGACGCCTCNGTGTNNCGGGCCGGCGGGTTGGTGGCATGGCCGTCTGG
GGTCAACTCGACNATGTCCAACCGTTGACCCGGGGTCAGATGGGGCAGTCGCCGCTCGGCATCGTCAGCC
TCGCCGC Clone Rv88 (SEQ ID NO. 673)
::::::::::::Rv88SP6.seq::::::::::::
GTCTTTCGATGGCTGCTTCTTCGGCGCTGACGCTGGCGATCTATCACCCCCAGCAGTTCGTCTACGCGGG
AGCGATGTCGGGCCTGTTGGACCCCTCCCAGGCGATGGGTCCCACCCTGATCGGCCTGGCGATGGGTGAC
GCTGGCGGCTACAAGGCCTCCGACATGTGGGGCCCGAAGGAGGACCCGGCGTGGCAGCGCAACGACCCGC
TGTTGAACGTCNGGAANCTGATCGCCAACNACACCCNCGTCTGGGTGTACTGCGGCAACNGCAAGCCGTC
GGATCTGGGTGGCAACAACCTGCCGGCCAAGTTCCTCGAGGGCTTCGTGCGGACCATCAACATCAAGTTC
CAAGACGCCTACAACGCCNGTGGCGGCCACAACCGCGTGTTCGACTTCCCGG ::::::::::::Rv88T7.seq:::::::::::: (SEQ ID NO. 674)
GCCAGGTCGAGGTCCCATGCGCGTGGGCCATTGATGCTGATCGCCAGGACGTCAAANATTTGGTCCGGCG
TCAGCTGGGCGAAAAACGTGGGCCCCAGGACTTGCCCGGAGCTGCCCGGGTTCCCGTCGCGCAGCTCGGC
GGCCCCGGTCAGAAANAAATTGCGCCAGGTCGCACACTCCGCGCCGTANGCCAGCTGCTCCAGGGTGTCG
GCATAGAGCCCGCGGGCCGCAGCGTGCTCGCTGTCGGCGAACACCGCATGGTCGAGAAGCGTTGCCGCCC
AACGGAAATCACCTGCGTCNAANGCTTCGCGGGCCAACTCCAGCACTCGGTCGATG Clone Rv89 (SEQ ID NO. 675)
::::::::::::Rv89SP6.seq::::::::::::
NAAACGTTCCGGCTTNGGTGCCGGGCGCTTATTTGCGTCTCTGGGATCACNCTCAGTCGCCGGCGGCTGC
CGTTGGGCTATNANTTGCACCGANCCGGAAAATCCGCACNANAACTGCNAGTAGCGGCCTGCAGAANTGC
ATCCTCGGCGAANCNGACTACCGGTGGACANCNACAAGCGCCGCCGAACAACGCACTGGCCCGAGGGATN
GGCGTCTATCGGCCCCGCCCGTCGAACTNGGAACAGACNGTGCGGTTCTACCGTGATCTGGTGGGAATGC
TCNACCANACCTTCCCNANNGCTACGGAACNACGGCGCGATATTCNGCCNTCCCANCTCGAGCCTGACNC
TNGATATCGTCGANNCTCACCATCNCGATCNGCTGTGCCGGTNTTGCTCGGACTN ::::::::::::Rv89T7.seq:::::::::::: (SEQ ID NO. 676)
CGAACGACGAACNCCNCAAGCCATGGTGGTTGGCGCCGTCAAAAGGTCCGCGGTCGCCACTACTGGAAAA
TCGCCTTGAGCGTCNCTCGACCNCCGCCTCGAGTTGGGTCNTAACGAAATACCTGATGCCGATCANGTCN
ACGTCTCCGTCGCNNCAACGTGCAGCGGCGACCCACTCTACNANGTCTCGGTNCCGCCNCGGCCAGNGCA
CCACCAGTGACNAATCCNTGCGCCNTCGGGCCNAGCANTCCCGGTGCNACCGNGGTGGGTCCGGCGATGG
TNGGGTGTNCTCNNTACNGGAACGCCAGCGCNATCANCATCGGCANACTCNCGTCGATGTGCCGCGGCGC
AACCATCCCCCACAATGATCNGGTGCGTCTGATCAGGCN Clone Rv8 (SEQ ID NO. 677)
::::::::::::Rv8SP6D.seq::::::::::::

TABLE 3-continued

End sequences of the polynucleotide inserts cloned in the named recombinant BAC vectors contained in the I-1945 *M. tuberculosis* H37Rv genomic DNA library. RvXXXSP6 corresponds to the SP6 endsequence of the clone RvXXX; RvXXXT7 corresponds to the T7 endsequence of the clone RvXXX. RvXXXIS 1081 corresponds to a region located close to a copy of the IS1081 repetitive sequence (Insertion element) The character << - >> denotes an uncertain base residue.

TTAGGCGTGACGGCCACCGGGGCCACTCCGCACAATCTGTACCCGACCAAGATCTACACCATCGAATACG
ACGGCGTCGCCGACTTTCCGCGGTACCCGCTCAACTTTGTGTCGACCCTCAACGCCATTGCCGGC

::::::::::::Rv8T7D4.seq:::::::::::: (SEQ ID NO. 678)
CGTCACCCCGATGCGCCCAGATCGGGGCTTCGCAGATAAAGCACGAACTGGCGGGCAAAACGTCGATCTC
GGAGCCGGAAGGGCAATCAGCCGACCGTCGACGAACGACACCGGCGAGACCACTTAGGCAGTGACGGCCT Clone Rv90 (SEQ ID NO. 679)
::::::::::::Rv90SP6.seq::::::::::::
CTTTTCNCGATGTCTCATGATNCCNANGGAGAACNNTGCNANCNCNGCCGCTGACNTNGCNCACCGCTNT
GGCNGNGGTGACATTGGTGGTGGTTGCGGGCTGCNACGCCCGACTCGANGCCGANCCATNTNTTGCGGCC
GACCGCNTNTCGTCTCNACCGCANNCCCNATCTCNGCCGCNCCCGGTGGANCTACNGCTNCTTCGCCATC
TCTCGCCNATGGCTCCNGCGNNTCGCNCAACGTNTGGTTTGGTNANCTGCCTACCTGGTCNT ::::::::::::Rv90T7.seq:::::::::::: (SEQ ID NO. 680)
GCTGCGCCAGTCGTTCGGTGCGGTCATGCCGTTGGACCNACCATCGGAGTTAGTTGCCGAACCGCGGACC
ACCGCAAGCACCCGGTCCTGGTCGCGCACCGCGTCGGCCAACCGCTTGAGCACCACCACGCCGCAGCCCT
CGCCGCGCACGAATCCATCCGCGTTGGCGTCNAANCTGTNGCATCGGTCGGTCGGTGACAGCGCCGACCA
CTTGGACAGCGCGATGGCGGTGAACGGTNANTAGGTGACCTGCCNCCNCGCCCGCCAATGCCCACCTCCG
CTTCACNCATGCGAATGGTCTGACACGCCNAGTGAATTGCCACCAGCGACAACAAAAATCGGTATCTNCN
GCGACGGCGGACACGCNATCCCNACTGATACTCGATCCGCCCCACCGCTTGNANCTCCGGGTTCCNGTGC
TCATGTACCNTCATGTCGGTCTGCGCNCGATATTGACGATCGTGTTTCCCACGANNANAGANCCTCATCA
CGCCGGTTCGAGTGCCG Clone Rv91 (SEQ ID NO. 681)
::::::::::::Rv91SP6.seq::::::::::::
CTGTGTGCGGNCGGCGCGATATCGGCCTTTTTACTAACCGAACCCGATGTGGGCTCCGATCCGGCGCGCA
TGGCATCTACNGCGACGCCGATCGATGACGGCCAGGCTTACGAGCTTGAGGGTGTGAANTTGTGGACCNC
CAACGGTGTGGTAGCGGACCTGCTANTGGTTATGGCGCGGGTACCGCGCAGTGAANGGCACCGAGGGGGA
ATCANCGCCTTTGTCGTCTANGCTGATTCTCCCGGGATCACCNYGGAGCGCNCCCNCNANTTCATGGGACT
GCGTGGCATCCAANACGGCGTGACCGGCTTCATCCNTCNGGGTGCCCAAAGACAACTTGATCNGCNNGGA
AGCGACGTCTGAANATCGCGCTGATCNCACTCAACGCCGGACGCTGTCCTACCGGCGATCGCACCGGANT
TGCCAANCCGCGCTNANNATNCGCGNGAATGNCCGTCCACNANTGCATGG ::::::::::::Rv91T7.seq:::::::::::: (SEQ ID NO. 682)
TGGGGTGCCGGGCGCCGAGTTGCGTCCCTGGGATCACGCAGAGTCGCCGGCGGCTGCCGTTGGGCTATGA
ATTGCACCGAGCCGGAAAATCCGCANCAAAACTGCGAGTAGCGGCCTGCAGAAGTGCANCCTCGGCGAAA
CGGAGTACGGTGGACAACGAAAAGCGCCGCCGAACNACGCACTGGCCCGAGGGATTGGCGTCAATCGGCC
CCGCCCGTCGAACTTGGAAGANACANTGCGGTTCTACCGTGATCTGGTGGGAATGCTCCAACNNACCTTC
NCCGAAAGCTACGGAAGCNACGGCGCGATNTTCGGCCTTCCCAGCTCGACCTGACGCTGGAAATCG Clone Rv92 (SEQ ID NO. 683)
::::::::::::Rv92SP6.seq::::::::::::
NGGCNGGGAAGTTAATGCCCTACTGGTTCNATGCTCNCACNTCNCCNGTGACNNCCTGCNCCGACCCGCC
GAGGTCCTGNCCGTNACCACCGANCNGGCGATCCGGGACTCTNGTACGCATCCAACANNGANCAACGTGC
ACGGGCGGAGTNGTNCCGCCACTTCGNCNATGACGGGGTCGATCCNTTCGACGTCCGTCGCCGCGTCGGT
CGAGTGGCGGTCACNCTCCNNGTACTCGACCNCACNGACGAGAGGACTCGANCCCATCTACGTGTGGACG
AAACANATCTTCTGTCCNACGACTACACCACCACCCAGGCCATCGCCGNCGCCCGCGANGCCCCTTCGAC
GCCNTACTGGTCCNGNGGNGGCGCTCTCCGGTTGTCTNNCNCNTGNCGTGTTCCTTCACNCACTGCCCNA
CATCGANCCCGAGCNATNCNANGTCCGTCAATC ::::::::::::Rv92T7.seq:::::::::::: (SEQ ID NO. 684)
GGACACTGTTCGCGTGCCCCTCGTCAAAGCCGGAGTGGTCGTGCTGCGCCGGACCCGACCCGACCTTCAG
CGGGGGTTCACAGCTCCGTGGGTGCCGTTACTTCCGATCGCCGCAGTGTGCGCGTGCCTGTGGCTGATGC
TGAACCTCACCGCGTTGACTTGGATCCGGTTCGGGATCTGGCTGGTGGCCGGAACCGCGATTTATGTCNG
CTACGGGCGCCGGCACTCGGCGCATGGCCTTCGGCAAGCNCNANANAACGCGACCCGGAGGTGTTGAACT
AGCTTCGCCGCGTATTTACAAATTGCNTTATATGTCTACACATAAGACGCAAACTGCTCTATTGTCAANT
CCCANCGTGGTGTGGCNCATGAAGATGTTTGG Clone Rv94 (SEQ ID NO. 685)
::::::::::::Rv94SP6.seq::::::::::::
TCCTTCTCGGTATCGGTTTGGGCTGTCACCANCAGTTGGTAGTTCTTCACGTNCTGTTGTTCGAGCGTCN
AGCCGTCGCGCGTGTCNANGTCNCCGGACGCGTATCCCGCCAGGCCGGTCANGGTGCCCTTCCANTCCAC
GCCGCTGTGGTCGGCGAACGCTNATCTTCAATCGAGACCATCGCCAGCTTCATCNTGTTGGCGATCTTGT
CNNACGGCACCTCNAACCGGCGCTNCTAGTACNCCACNCNATCNTGTTNCCTTCNCGTCNACATCCTCGA
TNCCNCNTGCACTTTCCCTCGANCNCCTGGGCCGAGCCGTTGGCANTNACCTCNGAGCCCCATTGGACAT
CANCCCANCCCGCCTGCGAACGGGAACGTCAGCNCNCTGGCGACAACCTGGCCAACAN ::::::::::::Rv94T7.seq:::::::::::: (SEQ ID NO. 686)
CACNCCGTGATCGCNAGCCCCNGTAGAAATNGTTGAGCCAGTTGGTGCGGCGCTCGTTGCCGGCGGTNAT
CTCGTCGAGCTCNTCTTCCATCGCCGCGGTGAAGTCGTACTCGACNAGCCGACCNAAATGCTGCTCNAGC TABLE 3-continued End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character << - >> denotes an uncertain base residue.

AGACCGGTTACCNNNAACNCCNCCTCNTGACNGCACCAGTGCNCTGCCCTTCTTGTGCACGTACCCGCNA
TCCTGGATGGTCTTGATGATCNACTANTNTGTCGACGGGCGGCCGATGCCCATCTCCTCNAGCGCTTTGA
CCAGCGACNCCTCGGTGTATCGGGCCGGCGGGTTNGTGGCATGGCCGTCTGGGGTCANCTCNACNATNTT
CANCCGTTGACCCGGGGTCACA

Clone Rv95 (SEQ ID NO. 687)
:::::::::::::Rv95SP6.seq:::::::::::::
TGGCCTTCTTGNCANGGGCNNACATNNGCTATNGCGAGCGTGTAACCGATCATCNTCCNGGCGACTGTGG
CCTGANCGGCAAGGGTNGCCTNATTCNTCCTCCTGNGGCATGGTTNCCACACGGAATGNCGGTAAGTCTG
GTCGGCAACCTGGCCCGCTGCGGGTTGGGTTCGGATTCGCTCGGCTANTAAGGTGCTCGCCTGGTGTNAC
NACTAATCNCNATATACNCTTANCGGGAGTNGNCGTCCCGATCCTNGCCCTGCCGCNGGCGATCNCGTTC
GCANCACCGCCACCGGAACTCNCAANGTGCGCTCATCGGGCTCTACGCGCCATCTTCCCCGGATTCTTCG
CGGCNGNGTNCCGNGGGACCCCGGACTGTGACNGGCCCAACGGCTCATCATCG :::::::::::::Rv95T7.seq::::::::::::: (SEQ ID NO. 688)
CCGGATAGCGGTGTCTGAACTTCGCCCGTTCCCTCCANCGCATTGAGCTTCAGCCCGACCGGCAGGTNNG
GAGTCGGCATGCGGTCCTTCGCCCCGACCCCGCTGGCTAAATANCCACCCCCGAGCGCGGTCACGGTCTT
TGCACCGGGACGACGCATACCGGCAGCGCGAACATCNCCGCGGGCTGCAGCNTGAACGTCCAATACCANT
CNAACAGTGTCCGCGCGTNAAAACCCGANCCGGCGGTCGCTTCNGTAATCAACGGCTCCTGCGCAACCAG
CTGCAAGTCGCCGGTGCCACCGGCGTTGACGATCTTGATGTCTGCGANCTCGCGCACCAGCTCGACGGCC
CGGGCA Clone Rv96 (SEQ ID NO. 689)
:::::::::::::Rv96SP6.seq:::::::::::::
CCTCCCGACCACATACAGGCAAAGTAATGGCATTACCGCGAGCCATTACTCCTACGCGCGCAATTAACGA
ATCCACCATCGGGGCAGCTGGTGTCGATAACGAAGTATCTTCAACCGGTTGAGTATTGAGCGTATGTTTT
GGAATAACAGGCGCACGCTTCATTATCTAATCTCCCAGCGTGGTTTAATCAGACGATCGAAAATTTCATT
GCAGACAGGTTCCCAAATAGAAAGAGCATTTCTCCAGGCACCAGTTGAAGAGCGTTGATCAATGGCCTGT
TCAAAAACAGTTCTCATCCGGATCTGACCTTTACCAACTTCATCCGTTTCACGTACAACATTTTTTAGAA
CCATGCTTCCCCAGGCATCCCGAATTTGCTCCTCCATCCACGGGGACTGAGAGCCATTACTATTGCTGTA
TTTGGTAAGCAAAATACGT Clone Rv9 (SEQ ID NO. 690)
:::::::::::::Rv9SP6.seq:::::::::::::
CTTCACNTCCGTACGGCTCGGGTACGCTTCGGTCNCATTGTGCGAGTGATAGATGACGACCGGGACCTCG
TCGGCATCTTCCATAGCCCGCCACACCTTCAGTTGCTCACCGGAATCCAACCGGTANAAGGTCGGCGANC
GCTCNGCATTGGTCATCGGGATATGCCGCTCGGGACGGTCANAGCCCTCGGGTCCGGCCAGCACTCCGCA
GGCTTCGTCGGGGTGGTCGCGACGCGCATGGGCCACCATCGCATTCACCAGGTCTGCGCGAATCACCAGC
ACGTANACGGTTCCTTTCCTAAGCAACACCGAANTTTCAGGACCCGAATGCTCCGGGAAACATGTCACGG
TAGGTCGGTATTCCGGCTACCGGCTGANCATTGAGCACGCCGGCCAGCACCGCACGAACCAGGCAATCAG
CCGCCGCCGCACCCGACCGCGG :::::::::::::Rv9T7.seq::::::::::::: (SEQ ID NO. 691)
CAGGCATGCAAGCTTGATGCCGCCGAAACCGAGCGTGAGCACGCCGCCAGCCACCACGCGCGGGTCGGGC
GCCGGGCCCGGGCCGCCAGGCTGCTCCGCTCGGTGATGGCACGCCACCGCGACACCACCCGGCTGCGCTA
CGTCGAGCCATACCGGGCGGAGCTACATCGGCTCGGCCGCCCAGTGTTCGGGCCCTCTTTCGAGGTCGAG
GTCGATACCGATTTGCGCATCCGCAGCCGCACCCTGGACGACAGAACCGTGCCCTACGAATTGCTTGTCG
GGCGGGGCCAAAGAACAGCTTGGCATCCTGGCGCGATTGGCCGGCGCGGCGCTGGTCGCCAAGGAAGACC
CGTTCCGGTGCTGAT

TABLE 4

End sequences of the polynucleotide inserts cloned in the named recombinant BAC vectors contained in the I-2099 *M. bovis* strain Pasteur genomic DNA library.

RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character << - >> denotes an uncertain base residue.

Clone X0001
:::::::::::::::X0001SP6.seq::::::::::::: (SEQ ID NO. 692)
AAG-
TCGGGTTTCCACACGCGCGGTTTGACCCTAGTCATATGTAATCATGTGTACCATGTGCGGGCGCTTTTCGACGGC
CGCGAACCACCGGA-ATTTCCTGTGATTTCACTGCATGCGTACCATCTGGCACAATTGAGCA-TTGTCT-TCGCGG
TGGTCGG-CGGGTTGCGTGCCGCCTGCTGCGA-ATGCACCA-TAAGCCCGAACCCACCGGCTTGGTGACCACCGC TABLE 4-continued End sequences of the polynucleotide inserts cloned in the named recombinant BAC vectors contained in the I-2099 *M. bovis* strain Pasteur genomic DNA library.

ACGCTGCGTGTGGGGGGTAACCACTCCGCGACCCCAAGGATGGTCATTTCCAATGAACCGGCTGGACTTCGTCC
A-A

:::::::::::::::X0001T7.seq::::::::::::: (SEQ ID NO. 693)
GTCGCGGTTCGATCGACCCGATCTTCACCTCGTAACCTCGATGCTTAGCAGGATCCAGCTTGACCGCGTTTGGCT
CTACCCACTCTTTGAGTGGCGCCGTCGCCTGTGCCCCATCGGTGTTCATGACGAACGCTTCGAAAGACTTCCTCT
TGTGAGCCGGAATGTCTGCGTAAAGAAGTTCCATGTCCGGGAAGTAGACCCGGTCGCCCTCCACGTGGTACTCC
TTCGAGGTCCGCTTCTCGCCGGATCCGATAAACACCGGCCCCAGGCACCGCAGCGTGAGTTCGAACGGCTTCAG
GTAGGTGTTCATGCGGCGGACTCCGGGAGTGCGAGAAATAGCGGTCGCGCGTAGCTGTAGACCGGATGGTTTCC
GCCCAGGCTGACGTCGAAGATGCCTCCTTGGAAGGGGCGCGA Clone X0002
:::::::::::::::X0002SP6.seq::::::::::::: (SEQ ID NO. 694)
AACTCAAGTTTTTACGGTGATCGCGCATCACCTGGTTCATGAACTGGAAGCAGCGCAGCGCTTCCTTTTCGGCCG
CAACATGAGCCAGCCTCTCGTCGGCGGTCGGGTGCAGGTGCTCGGGCAGCTCGGCCGCGACAGCCGCCTGACC
CTGAAACCAGCTTCCATATCCCGCGAC-
AACGACGCCAGTCCGCTACGTAACCCCTCCGCGACTGTCCATGGACAACAGCGCGTTCTCCACCGACCGGGCCC
GGGTGT :::::::::::::::X0002T7.seq::::::::::::: (SEQ ID NO. 695)
GTGCAGGTTTCGACAATGTGGTGCCGGTTCGGCGGCTACGTGCCATCGAGACACTGGCGCA-GCTATCGCACCC
GTTATCGGCTGCGAGCAAATCGCGGTATGCGTTCTTGAGCATGAGTCGGCGACCGTCGTCATGGTCGACACCCA
CGACGGAAAGACGCAGATCGCCGTCAAGCATGTGTGCCGCGGATTATCAGGACTGACCTCCTGGCTGACCGGCA
TGTTTGGTCGCGATGCCTGGCGCCCGGCCGGCGTGGTCGTGGTCGGCTCGGATAGCGAGGTCAGCGAATTCTCG
TGGCAGCTCGAAAGGGTCCTGCCGGTGCCGGT Clone X0003
:::::::::::::::X0003SP6.seq::::::::::::: (SEQ ID NO. 696)
TTCGAGTCATGCGCCCGCCTCGACCACGAA-ATGCACGTCG-GGTTCGATCGACCCGATCTTCACCTCGTAACCTC
GATGCTTAGCAGGATCCAGCTTGACCGCGTTTGGCTCTACCCACTCTTTGAGTGGCGCCGTCGCCTGTGCCCCAT
CGGTGTTCATGACGAACGCTTCGAAAGACTTCCTCTTGTGAGCCGGAATGTCTGCGTAAAGAAGTTCCATGTCC
GGGAAGTAGACCCGGTCGCCCTCCACGTGGTACTCCTTCGAGGTCCGCTTCTC :::::::::::::::X0003T7.seq::::::::::::: (SEQ ID NO. 697)
GTCATGTGTACCATTTGCGGGCGCTTTTCGACGGCCGCGAAACACCGGAGATTTCCTGTGATTTCACTGCATGCG
TACCGTCTGGCACAATTGAGCAGTTGTCTGTCGCGGTGGTCGGCCGGGTTGCGTGCCGCCTGCTGCGAGATGCA
CCAATAAGCCCGAACCCACCGGCTTGGTGACCACCGCACGCTGCGTGTGGGGGGTAACCACGCCGCGACCCCA
AGGATGGTCATTTCCAATGAACCGGCTGGACTTC-TCAACAA Clone X0004
:::::::::::::::X0004T7.seq::::::::::::: (SEQ ID NO. 698)
AACAGCGCGGTTGAACTGATAGGTGCGGCCCGGCTCGAGCAGGCCGGGCCATTTGTTCGATGCGGTTACCGAAA
GATCTCTTCGGTGACCTGCCCGCCGCCGGCCAGCTCGGCCCAGTGCCCGGCGTTGGCCGCCGCGGCGACGATCT
TGGCGTCCACGGTGGTCGGGG Clone X0006
:::::::::::::::X0006T7.seq::::::::::::::: (SEQ ID NO. 699)
GCATCTGGGCTGGCGGTGGTTCGCCGCTCCGAAGCCGTCGAACACCATCGCCAGCGCGGCTTCCACATCAACGA
CCATTTCGGCCAGCTTGCGGCGCATCAGCGGCTTGTCGATGAGCGCCCCACCGAATGCCCGCCGCTGCCCGGCG
TA-CACAGCGATTCGACCAGCGCGCGGCGCGCGTTGCCGAGGGCGAACGAAGCGGTGCCCAACCGCAATCTGTT
GGTCAGCTCCATCATGCGGGTGAGTCCCTTGCCG Clone X0007
:::::::::::::::X0007SP6.seq::::::::::::: (SEQ ID NO. 700)
ATCGGTTTCCAGCAACAGCCGATCGACGGCTTCGCCCA-GGCCGCTCCCGGGCGACCCGACCATTGCTGTCGCC
GCGTAACGCCATCACGGATGACGCGCAGTTCGTCGCTGTCTAGCTCCACCATCGCCTGCACACCGGCGGCCAG-
ACCCATTGGCCGTCGCACTCGTA-
AGCAGGTAATCCTCGTCGACGGACTCGGTAACCACCGCCGCCAGCTCCGCTGCCAGGTCGGCGGGGTTGACACC
GGCGGGCATCGGGATGGACGACGACGCGGTGCTGACGGCGCCTGTC :::::::::::::::X0007T7.seq::::::::::::: (SEQ ID NO. 701)
AGCGGTTTCCCA-GCGGGATGTGCTGTGAGCGCCGCACCACCAGCGCCGACGCTAAGGATGGAACGCACGGCAT
CTTCTGACGCGTAACCGCGTTGTGATCGCGAGCTGAGGAGACGGTATGGGGAGGGTTCTCGGAGGCCATCTGG
GATGTTGATGTCTGTCGATCTTGAGCCGGTGCAACTCGTCGGCCCGGACGGTACGCCGACGGCCGAACGCCGCT
ACCACCGTGACCTTCCTGAGGAAACGCTGCGTTGGCTCTACGAGATGATGGTGGTCACCCGCGAGCTGGATACC
GAATTCGTCAATCTGCACG Clone X0008
:::::::::::::::X0008SP6.seq::::::::::::: (SEQ ID NO. 702)
CAAGCTTCCACAGGTAGGGATCGAGGAACAGCGCGTTGAACTGATAGGTGCGGCCCGGCTCGAGCAGGCCGGC
CATTTGTTCGATGCGGTTACCGAAAATCTCTTCGGTGACCTGCCCGCCGCCGGCCAGCTCGGCCCAGTGCCCGG
CGTTGGCCGCCGCGGCAACGATCTTGGCGTCCACGGTGGTCGGGGTCATGCCCGCGAGCAGGATCGGCGAGCG
GCCGGTCAGCCGGGTGAACTTCGTCGAAAGCTTGACCCTGCCGTCGGGGAGGCGAACCACGGTCGGTGCGTAN
CTCCACCAAGCCCGGGCAACCTCGGGGGTGGCGCC TABLE 4-continued End sequences of the polynucleotide inserts cloned in the named recombinant BAC vectors contained in the I-2099 *M. bovis* strain Pasteur genomic DNA library.

```
:::::::::::::::X0008T7.seq:::::::::::::                           (SEQ ID NO. 703)
TGGACCTCATGACAACGCGGCGGCGATTACCCCCGCTACCGCCAGCAGCATGACGGCGGTAGCGAACACCGCC
GGATGCAGCGCAGGTGCGTCGATGTGCTCACGGAATCGCCCCGGCACCGCGATCTCGAGGATCACCAGTGCCAC
CCCCTGCAGCGCGACACCGACGATTCCGTACACCGCCACGCCGATCAGGCCCTGGGCCAGCTGGCGTATATGGC
GGCGATGGTGACGATGGCCAGCGCCACATACATTGTGGCGGCCAGAACCACGGCGTTGGGGCGGCGGTCGATG
AACACTAGGCGACGCAGATCGCCCGGGGTCAACAGGTTGACCATCAGAAAGCCTGCGA

Clone X0009
:::::::::::::::X0009SP6.seq:::::::::::::                          (SEQ ID NO. 704)
TTTGGTGCGGCCGGCAATCAACTTC-
GCTC-CAGCGGTTTCCCAGGCGGGATGTGCTGTGAGCGCCGCACCACCAGCGCCGACGCTAAGGATGGAACGCA
CGGCATCTTCTGACGCGTAACCGCGTTGTGATCGCGAGCTGAGGAGACGGTATGGGGGAGGGTTCTCGGAGGC
CATCTGGGATGTTGATGTCTGTCGATCTTGAGCCGGTGCAACTCGTCGGCCCGGACGGTACGCCGACGGCCGAA
CGCCGCTACCACCGTGACCTTCCTGAGGAAACGCTGCGTTGGCTCTACGATATGATGGTGGTCACCCG

:::::::::::::::X0009T7.seq:::::::::::::                           (SEQ ID NO. 705)
CGCCCAGGGCCGCTCCCGGGCGACCCGACCATTGCTGTCGCCGCGTAACGCCATCACGGATGACGCGCAGTTCG
TCGCTGTCTAGCTCCACCATCGCCTGCACACCGGCGGCCAGGACCCATTGGCCGTCGCACTCGTAGAGCAGGTA
ATCCTCGTCGACGGACTCGGTAACCACCGCCGCCAGCTCCGCTGCCAGGTCGGCGGGGTTGACACCGGCGGGC
ATCGGGATGGACGACGACGCGGTGCTGACGGCGCCTGTCGCGACGCTGAGCTCGGACACAGCTAGTAAATGTA
GCCTAACCTACTTAATGGGTCGCAGCCCCCCGGGGTCGTCGCATGTCCAACGTTGCTCGACTGGAAGAAAATGC
TCGTCGGGGAGCAAATGGCACC

Clone X0010
:::::::::::::::X0010SP6.seq:::::::::::::                          (SEQ ID NO. 706)
AATACTCAATCTTGATCGGTTTCCAGCAACAGCCGATCGACGGCTTCGCCCAGGGCCGCTCCCGGGCGACCCGA
CCATTGCTGTCGCCGCGTAACGCCATCACGGATGACGCGCAGTTCGTCGCTGTCTAGCTCCACCATCGCCTGCA
CACCGGCGGCCAGGACCCATTGGCCGTCGCACTCGTAGAGCAGGTAATCCTCGTCGACGGACTCGGTAACCACC
GCCGCCAGCTCCGCTGCCAGGTCGGCGGGGTTGACACCGGCGGGCATCGGGATGGACGACGACGCGGTGCTGA
CGGCGCCTGTCGCGACTCTGAGCTCGG

:::::::::::::::X0010T7.seq:::::::::::::                           (SEQ ID NO. 707)
GGATGTGCTGTGAGCGCCGCACCACCAGCGCCGACGCTAAGGATGGAACGCACGGCATCTTCTGACGCGTAACC
GCGTTGTGATCGCGAGCTGAGGAGACGGTATGGGGGAGGGTTCTCGGAGGCCATCTGGGATGTTGATGTCTGTC
GATCTTGAGCCGGTGCAACTCGTCGGCCCGGACGGTACGCCGACGGCCGAACGCCGCTACCACCGTGACCTTCC
TGAGGAAACGCTGCGTTGGCTCTACGAGATGATGGTGGTCACCCGCGAGCTGGATACCGAATTCGTCAATCTGC
AGCGCCAGGGGGAAGCTGGCGTTGTACACGCCCTGTCGCGGGCAGGAAGCCGCGCAGGTGGGTGCGGCGGCTT
GCCTACGCAAAACCGACTGGTTGTTCCCC

Clone X0012
:::::::::::::::X0012SP6.seq:::::::::::::                          (SEQ ID NO. 708)
ATCACGACAACAGCGACGGTGTGTCGGATCAGCGGCCCCCGTTGCCGGGCAATGTTGAGGCGTTTCTGCGTCTG
GTTGAGGCCGGCTGGGAC-
CCGAGGTGGCTCGTCGGCCACATGGGCAGCACACCACCGTGGTGATGCATCTAGACGTGCAGGACCGTGCCGCT
GGCCTGCA

:::::::::::::::X0012T7.seq:::::::::::::                           (SEQ ID NO. 709)
GCGGCTACGTGCCATCGAGACACTGGCGCAGGCTATCGCACCCGTTATCGGCTGCGAGCAAATCGCGGTATGCG
TTCTTGAGCATGAGTCGGCGACCGTCGTCATGGTCGACACCCACGACGGAAAGACGCAGATCGCCGTCAAGCAT
GTGTGCCGCGGATTATCAGGACTGACCTCCTGGCTGACCGGCATGTTTGGTCGCGATGCCTG:

Clone X00013
:::::::::::::::X0013T7.seq:::::::::::::                           (SEQ ID NO. 710)
TACAAGCGGCACCTCGCCGGTGAACTGACCGTTCGCACGCTGCGCACCGCCGCCGGGCGCGTGCTCGGCGCGC
CGGCGGCCCCCGAGGCCTGAGQGGGGAACCAACCATGCAGGTGAACATGACGGTAAACGGCGAGCCCGTCACC
GCCGAGGTCGAACCCCGGATGCTGCTGGTCCATTTTCTCCGTGATCAGCTGCGGCTCACCGGAACTCACTGGGG
CTGTGATACCAGCAACTGCGGGACATGCGTGGTGGAGGTCGACGGCGTGCCGGTGAAATCCTGCACGATGCTCG
CCGTGATGGCCTCCGGGC

Clone X0014
:::::::::::::::X0014T7.seq:::::::::::::                           (SEQ ID NO. 711)
AGCGGCTGGTTACGACTCCCTGTTTGTGATGGACCACTTCTACCAACTGCCCATGTTGGGGACGCCCG-
CC-TCCGATGCTGGAAGCCTACACTGCCCTTGGTGCGCTGGCC-CGCGACCGAGCGGCTGCAACTGGGCGC-
TTGGTGACCGCAATACCTACCGCACCCC-ACCCTGCTGGCAAA-
ATCATCACCACGCTCGACTTGGTTAGCGCCGGTCGA-CGATCCTCGGCATTGGAACCGGTTGGTT-

Clone X0015
:::::::::::::::X0015SP6.seq:::::::::::::                          (SEQ ID NO. 712)
ACGCGCGCCGATCATATCTGCTATGGATGTACAATTCAGCTCTTGCTGTTATACCAGTATATGGTGTACTATTTG
ATCTATGCTGACGTGTGAGATGCGGGAATCGGCCCTGGCTCGACTCGGCCGGGCTCTGGCTGATCCGACGCGGT
GCCGGATTCTGGTGGCGTTGCTGGATGGCGTTTGCTATCCCGGCCAGCTAGCTGCGCACCTCGGCTTGACCCGA
TCGAATGTGTCCAACCATCTGTCGTGTTTGCGGGGCTGCGGGCTGGTA-
TCCCAACCTATGAGGGCCGGCAGGTTCGGTAT

:::::::::::::::X0015T7.seq:::::::::::::                           (SEQ ID NO. 713)
```

TABLE 4-continued

End sequences of the polynucleotide inserts cloned in the named recombinant BAC vectors contained in the I-2099 *M. bovis* strain Pasteur genomic DNA library.

CCGCGCTGCTGCTGACGTCGGTCGAACGTGCGACACGTCTGCGAATACCGGCCGAACGCTGGGTTTATCCACAG
GCTGGCACCGACGCCCACGACACACCGGCCGTCGCCGACCGCCACCGACTGCATCGGTCGACGGCCATTCGGAT
CGCCGGTGCCCGGGCGCTGGAACTGGCTGGGCTGGGGCTCGATGACATCGAATACGTCGACCTGTATTCGTGCT
TTCCCTCCGCTGTCCAAGTCGCCGCAATCGAACTCGGCCTGGACACCGACGATCCTGCCCGCCCGCTGACCGTC
ACCGGGGGCCTGACCTTCGCCGGCGGGCCGTGGAGCAATTACGTCACGCACTCCAT

Clone X0016
:::::::::::::::X0016SP6.seq::::::::::::: (SEQ ID NO. 714)
CAGGCGTGCAATGACCTGCACTGCGCCGGA-A-TCCCTAACCCACTAAACCGGGGCCGCTCACAAGCCGTGCAGC
TCGGTCAGCGTCAGGTGCGCGACCAGGAA-
TAAATGAGCAGACCCGTGCCGTCAACGATGGTGGCGATCATCGGCCCCGAAACGATGGCCGGGTC-
ATGCGCAACTTCTTCAGCAGCGGCGGAAGGACGGCA-CCACCAGCGAC-ACCACACCACGAT :::::::::::::::X0016T7.seq::::::::::::: (SEQ ID NO. 715)
GCGAA-CACTTCGTCAACTTCCAGGGCTGCCCGCACCAAGTATTTCGACGAGTATTTCCGTCGGGCCGCCGCCGC
CGGCGCGCGGCAGGTGGTCATCCTGGCGGCGGGGCTGGACTCGCGCGCGTACCGGCTGCCTTGGCCCGACGGG
ACCACGGTTTTTGAGCTGGACCGCCCGCAGGTCCTTGATTTCAAGCGCGAGGTGCTCGCCAGCCACGGTGCCCA
ACCGCGCGCCCTGCGCCGCGAGATCGCCGTCGACCTGCGTGACGATTGGCCACAAGCCTTGCGGGACAGTGGTT
TCGATGCGGCTGCACCGTCGGCATGGATTGCCGAAGGGCT Clone X0017
:::::::::::::::X0017SP6.seq::::::::::::: (SEQ ID NO. 716)
TTGGGC-TTGCCCCAATA-GGCCCCAATCAAAAGCCGAGCAGGTGGAACCTA-CGCATTCGCCTC-TCGT-TGTGC
ACCCGAGCCATCGCACGCGCGGGAATTCCCGGAT-TC-CCGTATTCTCCGGCGGCCGGGCTAACCCATCCCA-GCC
GAACGGTTGGCTC-TGCCGTGGGTCCCGTGTTGGCCGATCGGGGCGTCACCGGGGGTGCTCGGGTGCGG-
TGACCATGGC-AACTGCCCC-ATGGGCCGACCCTGGTGCAGATAAACCTG :::::::::::::::X0017T7.seq::::::::::::: (SEQ ID NO. 717)
TGGTGGAGGTCCCCACCAA-ACCCGGCCGTAACTCTGCTCACGGAAATGCGG-CAGGCCGCGCGTAGCACGTGGT
ATCCGCCATAAAGGTGCACCTTAAGCACGGCGTCCCAATTCTCGAACGACATCTTGTGGAAGGTGCCGTCGCGC
AAGATCCCGGCGTTGCTCACCACACCGTGCACGGCGCCGAATTCGTCAAGCGCGGTCTTGATGATGTTCGCTGC
GCCGTCCTCGGTGGCGACGCTGTCGGTA-TTGGCGACCGCCCGGCCCCCCTTGTCGCGAAATCTCGGCGACGAC
CTCATCGGCCATCGCCGAACCGGGCGCCCG Clone X0018
:::::::::::::::X0018SP6.seq::::::::::::: (SEQ ID NO. 718)
GCCGGCCAAACTGGCCGGCGGGGTTGCTGTC-TCAAGGTGGGTTCCGCCACCAA-ACC-
CACTCAAGGATCGCAAGGAAAGC-
TCAAGGATGCGGTCGCGGCCGCCAAGGCCGCGGTCAAGGAGGGCATCGTCCCTGGTGGGGA-CCTCCCTCATC
CACCAGGCCCGCAAGGCGCTGACCGAACTGC-TGCGTC-C-GACCGGTGACAA-GTCCTCGGTGTCCACGTGT-CTC
CGAAGCCCTTGCCGCTCCGTTGTTCTGGATC-CC-CCAAC-CTGGCTTGGACGGCTC-
GTGGTGGTCAACAAGGTCAGCGAGCTACCCGCCGGGCATGGGCTGAACGTGA Clone X0018
:::::::::::::::X0018T7.seq::::::::::::: (SEQ ID NO. 719)
CGAACCT-
AATTGTCCTGTAATGCCCAGCTCACCAAGCATGGCTGGTGGCCGGGGCGGTGAAGCCGGCGTCTGCGGCACCG
TCCAACTC-ATGTGGAT-GCCGGAATGGGGATGTCCGG-ACGGCGAATCCGTA-
TTCGCTTGTCCCGTGAGGCCCAGGTGGATGGGGGGAAGGATC-TGGTGTCCGGGATGAT-
ATGGGGCCGATGCCGCCGGTTGAAGTCCACTGGATCGGGAATTCGGGAATCGTGAT-
CCGACGTTCAGGCCGAAC Clone X0019
:::::::::::::::X0019SP6.seq::::::::::::: (SEQ ID NO. 720)
CTAACGGAATGAAAGCCCTGGTGGCCGT-TCGGCGGTGGCCGTCGTCGCACTGCTCGGTGTATCTTCCGCCCAAG
CTGATCCCGAGGCGGATCCCGGCGCAGGTGAGGCCAACTATGGTGGCCCCCCAAGTTCCCCACGTCTTGTCGAT
CACACCGAATGGGCGCA-
TGGGGAATTCTGCCCAGCCTCCGGGTCTACCCGTCCCAAGTTGGGCGTACA-CTCCCGCCGCCTCGGGATGGCC
GCTGCCGACCCGGCCTGGGCC-AGGTTCTCGCGCTGTCACCGGAAGCCGACACTGCCGGC :::::::::::::::X0019T7.seq::::::::::::: (SEQ ID NO. 721)
CCGCGGGACAC-CCTC-ATGCTGCCGCCATGGACGCGGTCGAACGCAAGCAGCTGATCGAGCTACAACGCCGCG
CGGAACGCTTCCGCCGCGGGCGTGACCGCATCCCGTTGACCGGGCGGATCGCGGTGATCGTCGATGACGGCATC
GCCACCGGAGCGACGGCCAAGGCGGCGTGCCAGGTCGCCCCGGGCGCACGGTGCGGACAAGGTGGTGCTGGCG
GTCCCGATCGGCCCA-ACGACATCGTGGCGAAGATTCGCCGGGTACGCCGATGATGTGGTGTGTTTGGCGACGC
CGGCGTTGT Clone X0020
:::::::::::::::X0020T7.seq::::::::::::: (SEQ ID NO. 722)
CTCTGGGACCGGCCACGGTGCC-CCGGCGTTCCCGGACGTGCTGCGCCAGGTGTCCGGCGGCCGCGTGCATGGT
GTTCCCGGATCGGCCGCTGGCCAGAGCCCACCGGTGAATCTGGCGCCTGGCCGACCACCGTGCGCCGTAGGCTT
GCGATCGTGCAGCGCTGGCGTGGCCAGGACGAGATCCCGACGGATTGGGGCAGATGCGTGCTCACCATCGGGG
TATTTGACGGCGTGCACCGCGGGCACGCCGAACTGATCGCGCACGCGGTCAAAGGCGGC Clone X0021

TABLE 4-continued

End sequences of the polynucleotide inserts cloned in the named recombinant BAC vectors contained in the I-2099 *M. bovis* strain Pasteur genomic DNA library.

:::::::::::::::X0021SP6.seq::::::::::::: (SEQ ID NO. 723)
AATACTCAAGCTTTCGTCAGTTCATTGCGCCAGCAGACCAACAA-AGCATCGGGACATACGGA-TCAACTACCCG
GCCAACGGTGATTTCTTGGCCGCCGCTGACGGCGCGAACGACGCCAGCGACCAC-TTCAGCAAATGGCCA-CGCG
TGCCGGGCCACGAGGTTGGTGCTCGGCGGCTACTCCCAGGGTGCGGCCGTGATC-ACATC-TCACCGCCGCACCA
CTGCCCGGCCTCGGGTTCACGCAGCCGTTGCCGCCCGCAGCGGAC-
ATCACATCGCCGCGATCGCCCTGTTCGGGAATCCCTC-GGCCGCGCTGGCGGGCTGATTAAC :::::::::::::::X0021T7.seq::::::::::::: (SEQ ID NO. 724)
TGCCGCGGATTTGGCTGGCTGCCCAATATTCAGAATCGGGCCTTTCTTTTTGCGCGACAATAAGGTCACAGTAAA
CCCTCGTTTTGTGAGATGCGGGGCGGGCCGGGCGAA-TCGACCTCGAGTGAATGGATCTCGAGTGAATGGACAG
GGCATCGCCTACGAGTCGCATCCCCATCCAACAGACCGGTGCTCTTGCATCGGACCCTGAAGGTCCCGCACGGA
GGGTGTGGTTGCCGGCGCGGGGTCACGGTGCGGTAGCGACGTAGTGTTTGAACGAATTTCTTGATGCTCCAACC
TGTTTGGTGTTCAATCCAGTTCT Clone X0175
......X0175SP6..... (SEQ ID NO. 725)
AA-CTTGCGCGCTCGGCCGGGTC-AGCATCCAGCTGCTCGGCAAGGAGGCCAGCTAC-C-TCGCTGCGTATGCCCA
GCGGTGAGATCCGCCGGGTC-ACGTCCGCTGCCGCGCGACCGTCGGCGAAGTGGGCAATGCCGAGCAGGCAAAC
ATCAACTGGGGCAAGGCCGGTCGGATGCGGTGGAAGGGCAAGCGCCCGTCGGTCCGGGGCGTGGTGAT-AACC
CGGTC-ACCACCCGCACGGCGGTGGTGAGGGTAAAACCTCCGGCGGCCGTCACCCGGTTAGCCCGTGGGGCAA ......X0175T7..... (SEQ ID NO. 726)
A-TCGAAAGTGACCATCTCTACCTTGAGTGCCATACCGCCCGACCCTATGCCTCGGATAGCTCGGCGGAAAGAAA
CGCTTGCAGTGCCGCCGAATAGGCGGCTACGTCGTGAGCGCCCATCAACTCTCGCGCGGAGTGCATCGCCAGCT
GGGCGGCGCCGACGTCGACCGTGGGGATTCCGGTGCGCGCCGCGGCCAACGGCCCGATCGTCGACCCGCACGG
CAGATCGGCGCGATGTTCGTAACGCTGCATAGGCACTCCCGCGCGCTGGCAGGCCAGTGCGAACGCCGCCGCG
GTGCGTCCG

REFERENCES

Altschul, S. F., W. Gish, W. Miller, E. W. Myers, and D. J. Lipman. 1990. Basic local alignment search tool. J. Mol. Biol. 215:403–10.

Balasubramanian, V., M. S. Pavelka, Jr., S. S. Bardarov, J. Martin, T. R. Weisbrod, R. A. McAdam, B. R. Bloom, and W. R. Jacobs, Jr. 1996. Allelic exchange in *Mycobacterium tuberculosis* with long linear recombination substrates. J. Bacteriol. 178:273–279.

Barany F., 1991, Proc. Natl. Acad. Sci. USA, 88:189–193.

Bensimon, A., A. Simon, A. Chiffaudel, V. Croquette, F. Heslot, and D. Bensimon. 1994. Alignment and sensitive detection of DNA by a moving interface. Science. 265:2096–2098.

Bergh, S., and S. T. Cole. 1994. MycDB: an integrated mycobacterial database. Mol. Microbiol. 12:517–534.

Bimboim, H. C. and J. Doly. 1979. A rapid alkaline extraction procedure for screening recombinant plasmid DNA. Nucleic Acids Res. 7:1513–1523.

Burg J. L. et al., 1996, Mol. and Cell. Probes, 10:257–271.

Cai, L., J. F. Taylor, R. A. Wing, D. S. Gallagher, S. S. Woo, and S. K. Davis. 1995. Construction and characterization of a bovine bacterial artificial chromosome library. Genomics. 29:413–425.

Canard, B., and S. T. Cole. 1989. Genome organization of the anaerobic pathogen Clostridium perfringens. Proc. Natl. Acad. Sci. USA 86:6676–6680.

Chu B. C. F. et al., 1986, Nucleic Acids Res., 14:5591–5603.

Chuang S. et al., 1993. Global regulation of gene expression in *Escherichia coli*. J. Bact., 175(7): 2026–2036.

Chuang, S., D. L. Daniels, and F. R. Blattner. 1993. Global regulation of gene expression in *Escherichia coli*. J. Bacteriol. 175:2026–2036.

Cole, S. T., R. Brosch, K. Eiglmeier, T. Gamier, S. V. Gordon, C. Churcher, D. Harris, K. Badcock, D. Basham, D. Brown, T. Chillingworth, R. Connor, R. Davies, K. Devlin, T. Feltwell, S. Holroyd, S. Gentles, K. Jagels, J. McLean, S. Moule, L. Murphy, K. Oliver, J. Osborne, J. Parkhill, M. Quail, M-A. Rajandream, J. Rogers, S. Rutter, K. Seeger, J. Skelton, R. Squares, S. Squares, J. Sulston, K. Taylor, S. Whitehead and B. G. Barrell. 1997. Genome Sequence of *Mycobacterium tuberculosis* H37Rv. Microbial Comparative Genomics, 2:174.

Collins, D. M., and D. M. Stephens. 1991. Identification of an insertion sequence, IS1081, in *Mycobacterium bovis*. FEMS Microbiol. Lett. 67:11–15.

Cousins D. et al., 1998, 36(1): 168–170.

De Wit D. et al., 1990, J. Clin. Microbiol., 28: 2437–2441.

Dear, S., and R. A. Staden. 1991. Sequence assembly and editing program for the efficient management of large projects. Nucleic Acids Res. 19:3907–3911.

Duck P. et al., 1990, Biotechniques, 9:142–147.

Guateli J. C. et al., 1990, Proc. Natl. Acad. Sci. USA, 87:1874–1878.

Kievitis T. et al., 1991, J. Virol. Methods, 35:273–286.

Kim, U. J., B. W. Birren, T. Slepak, V. Mancino, C. Boysen, H. L. Kang, M. I. Simon, and H. Shizuya. 1996. Construction and characterization of a human bacterial artificial chromosome library. Genomics. 34:213–218.

Kwoh D. Y. et al., 1989, Proc. Natl. Acad. Sci. USA, 86:1173–1177.

Landegren U. et al., 1988, Science, 241:1077–1080.

Liu, Y. G., and R. F. Whittier. 1995. Thermal asymmetric interlaced PCR: automatable amplification and sequencing of insert end fragments from P1 and YAC clones for chromosome walking. Genomics. 25:674–681.

Lizardi P. M. et al., 1988, Bio/technology, 6:1197–1202.

Matthews J. A. et al., 1988, Anal. Biochem., 169:1–25.

Michalet, X., R. Ekong, F. Fougerousse, S. Rousseaux, C. Schurra, N. Hormigold, M. Vanslegtenhorst, J. Wolfe, S. Povey, J. S. Beckmann, and A. Bensimon. 1997. Dynamic molecular combing—stretching the whole human genome for high-resolution studies. Science. 277:1518–1523.

Misumi, D. J., D. L. Nagle, S. H. McGrail, B. J. Dussault, Jr., J. S. Smutko, H. Chen, O. Charlat, G. M. Duyk, C.

Ebeling, L. Baldini, G. A. Carlson, and K. J. Moore. 1997. The physical and genetic map surrounding the Lyst gene on mouse chromosome. Genomics. 40:147–150.

Pavelka, M. S., Jr., and W. R. Jacobs, Jr. 1996. Biosynthesis of diaminopimelate, the precursor of lysine and a component of peptidoglycan, is an essential function of *Mycobacterium smegmatis*. J. Bacteriol. 178:6496–6507.

Philipp, W. J., S. Nair, G. Guglielmi, M. Lagranderie, B. Gicquel, and S. T. Cole. 1996a. Physical mapping of *Mycobacterium bovis* BCG pasteur reveals differences from the genome map of *Mycobacterium tuberculosis* H37Rv and from *M. bovis*. Microbiology. 142:3135–3145.

Philipp, W. J., S. Poulet, K. Eiglmeier, L. Pascopella, V. Balasubramanian, B. Heym, S. Bergh, B. R. Bloom, W. R. Jacobs, Jr., and S. T. Cole. 1996b. An integrated map of the genome of the tubercle bacillus, *Mycobacterium tuberculosis* H37Rv, and comparison with *Mycobacterium leprae*. Proc. Natl. Acad. Sci. USA. 93:3132–3137.

Poulet S. et al., 1995, Arch. Microbiol., 163: 87–95.

Ross BC, 1992, J. Clin. Microbiol., 30: 942–946.

Sambrook, J., E. F. Fritsch, and T. Maniatis. 1989. Molecular cloning: a laboratory manual, 2nd ed. Cold Spring Harbor Laboratory, N.Y.: Cold Spring Harbor. N.Y.

Sanchez-Pescador R., 1988, J. Clin. Microbiol., 26(10) :1934–1938.

Segev D., 1992, in <<Non-radioactive Labeling and Detection of Biomolecules>>. Kessler C. Springer Verlag, Berlin, N.Y., 197–205.

Sheng, Y., V. Mancino, and B. Birren. 1995. Transformation of *Escherichia coli* with large DNA molecules by electroporation. Nucleic Acids Res. 23:1990–1996.

Shinnick T. M. et al., 1987, J. Bact., 169(3): 108–1088.

Shizuya, H., B. Birren, U. J. Kim, V. Mancino, T. Slepak, Y. Tachiiri, and M. Simon. 1992. Cloning and stable maintenance of 300-kilobase-pair fragments of human DNA in *Escherichia coli* using an F-factor-based vector. Proc. Natl. Acad. Sci. USA. 89:8794–8797.

Spargo C. A. et al., 1996, Mol. and Cell. Probes, 10:247–256

Stone B. B. et al., 1996, Mol. and Cell. Probes, 10:359–370.

Trieselman B. A. et al., 1992. Transcriptionnally active regions in the genome of the archaebacterium *Haloferax volcanii*. J. Bact., 174:30–34.

Trieselmann, B. A., and R. L. Charlebois. 1992. Transcriptionally active regions in the genome of the archaebacterium *Haloferax volcanii*. J. Bacteriol. 174:30–34.

Urdea M. S. et al., 1991, Nucleic Acids Symp. Ser., 24:197–200.

Urdea M. S., 1988, Nucleic Acids Research, 11: 4937–4957.

Van Soolingen D., 1993, J. Clin. Microbiol., 31: 1987–1995.

Willets, N., and R. Skurray. 1987. Structure and function of the F-factor and mechanism of conjugation. In *Escherichia coli* and *Salmonella Typhimurium*: Cellular and Molecular Biology (F. C. Neidhardt, Ed) Vol.2 pp 1110–1133, Am. Soc. Microbiol., Washington, D.C.

Woo, S. S., J. Jiang, B. S. Gill, A. H. Paterson, and R. A. Wing. 1994. Construction and characterization of a bacterial artificial chromosome library of Sorghum bicolor. Nucleic Acids Res 22:4922–4931.

Zimmer, R., and A. M. V. Gibbins. 1997. Construction and characterization of a large-fragment chicken bacterial artificial chromosome library. Genomics. 42:217–226.

What is claimed is:

1. A method for isolating a polynucleotide of interest that is present in a genome of a first mycobacterium strain or that is expressed by said first mycobacterium strain and that is absent or altered in a genome of a second mycobacterium strain that is different from the first mycobacterium strain or that is not expressed in the second mycobacterium strain, said method comprising:

a) contacting under hybridizing conditions the genomic DNA of the first mycobacterium strain with the DNA of at least one clone that belongs to a bacterial artificial chromosome (BAC) genomic DNA library of the second mycobacterium strain; and b) isolating the polynucleotide of interest that fails to form a hybrid with the DNA of the second mycobacterium strain.

2. The method according to claim 1, wherein the BAC-based DNA library has been constructed from genomic DNA of *Mycobacterium tuberculosis.*

3. The method according to claim 2, wherein the BAC-based DNA library has been constructed from genomic DNA of *Mycobacterium tuberculosis* strain H37Rv.

4. The method according to claim 3, wherein the BAC-based DNA library has been deposited in the Collection Nationale de Cultures de Microorganismes (CNCM) on Nov. 19, 1997 under the accession number I-1995.

5. The method according to claim 1, wherein the BAC-based DNA library has been constructed from genomic DNA of *Mycobacterium bovis.*

6. The method according to claim 5, wherein the BAC-based DNA library has been constructed from genomic DNA of *Mycobacterium bovis* BCG strain Pasteur.

7. A method of isolating a polynucleotide of interest that is present in a genome of a first mycobacterium strain or that is expressed by the first mycobacterium strain and that is absent or altered in a genome of a second mycobacterium strain or that is not expressed by the second mycobacterium strain, said method comprising:

a) providing at least one polynucleotide contained in a clone of a bacterial artificial chromosome (BAC) DNA library of the first mycobacterium strain;

b) providing at least one genomic or cDNA polynucleotide from a second mycobacterium strain that is different from the first mycobacterium strain or at least one polynucleotide contained in a clone of a BAC DNA library prepared from the genome of the second mycobacterium strain;

c) contacting under hybridizing conditions the polynucleotide of step a) with the polynucleotide of step b); and d) isolating the polynucleotide of step a) that has not formed a hybrid complex with the polynucleotide of step b).

8. The method of claim 7, wherein the polynucleotide contained in a clone of a BAC DNA library of the first or second mycobacterium strain is prepared by the following procedure:

1) digesting at least one recombinant BAC clone by an appropriate restriction endonuclease to yield a polynucleotide insert of interest; and 2) isolating the polynucleotide insert of interest.

9. A purified polynucleotide of interest that has been isolated according to the method of claim 7.

10. The pruified polynucleotide of claim 9 which contains at least one Open Reading Frame (ORF).

11. The purified polynucleotide of claim 10, wherein the ORF encodes all or part of a polypeptide involved in the pathogenicity of a mycobacterium strain.

12. The purified polynucleotide of claim 10, wherein the ORF encodes all or part of a Polymorphism Glycine Rich Sequence (PGRS).

13. A pair of the purified polynucleotides as claimed in claim 9.

14. A *Mycobacterium tuberculosis* strain H37Rv genomic DNA library that has been deposited in the Collection Nationale de Cultures de Microorganismes under accession number I-1945, wherein said genomic DNA library comprises recombinant bacterial artificial chromosome vectors.

15. A recombinant bacterial artificial chromosome (BAC) vector, which belongs to the genomic DNA library of claim 14.

16. The recombinant BAC vector of claim 15, which is selected from the group consisting of:

Rv101; Rv102; Rv103; Rv104; Rv105; Rv106; Rv107; Rv108; Rv109; Rv10; Rv110; Rv111; Rv112; Rv113; Rv114; Rv115; Rv116; Rv117; Rv118; Rv119; Rv11; Rv120; Rv121; Rv122; Rv123; Rv124; Rv126; Rv127; Rv128; Rv129; Rv130; Rv132; Rv134; Rv135; Rv136; Rv137; Rv138; Rv139; Rv13; Rv140; Rv141; Rv142; Rv143; Rv144; Rv145; Rv146; Rv147; Rv148; Rv149; Rv14; Rv150; Rv151; Rv152; Rv153; Rv154; Rv155; Rv156; Rv157; Rv159; Rv15; Rv160; Rv161; Rv162; Rv163; Rv164; Rv165; Rv166; Rv167; Rv169; Rv16; Rv170; Rv171; Rv172; Rv173; Rv174; Rv175; Rv176; Rv177; Rv178; Rv179; Rv17; Rv180; Rv181; Rv182; Rv183; Rv184; Rv185; Rv186; Rv187; Rv188; Rv18; Rv190; Rv191; Rv192; Rv193; Rv194; Rv195; Rv196; Rv19; Rv1; Rv201; Rv204; Rv205; Rv207; Rv209; Rv20; Rv214; Rv215; Rv217; Rv218; Rv219; Rv21; Rv220; Rv221; Rv222; Rv223; Rv224; Rv225; Rv226; Rv227; Rv228; Rv229; Rv22; Rv230; Rv231; Rv232; Rv233; Rv234; Rv235; Rv237; Rv240; Rv241; Rv243; Rv244; Rv245; Rv246; Rv247; Rv249; Rv24; Rv251; Rv252; Rv253; Rv254; Rv255; Rv257; Rv258; Rv259; Rv25; Rv260; Rv261; Rv262; Rv263; Rv264; Rv265; Rv266; Rv267; Rv268; Rv269; Rv26; Rv270; Rv271; Rv272; Rv273; Rv274; Rv275; Rv276; Rv277; Rv278; Rv279; Rv27; Rv280; Rv281; Rv282; Rv283; Rv284; Rv285; Rv286; Rv287; Rv288; Rv289; Rv28; Rv290; Rv291; Rv292; Rv293; Rv294; Rv295; Rv296; Rv29; Rv2; Rv301; Rv302; Rv303; Rv304; Rv306; Rv307; Rv308; Rv309; Rv30; Rv310; Rv311; Rv312; Rv313; Rv314; Rv315; Rv316; Rv317; Rv318; Rv319; Rv31; Rv32; Rv322; Rv327; Rv328; Rv329; Rv32; Rv330; Rv331; Rv333; Rv334; Rv335; Rv336; Rv337; Rv338; Rv339; Rv33; Rv340; Rv341; Rv343; Rv344; Rv346; Rv347; Rv348; Rv349; Rv34; Rv350; Rv351; Rv352; Rv353; Rv354; Rv355; Rv356; Rv357; Rv358; Rv359; Rv35; Rv360; Rv361; Rv363; Rv364; Rv365; Rv366; Rv367; Rv368; Rv369; Rv36; Rv370; Rv371; Rv373; Rv374; Rv375; Rv376; Rv377; Rv378; Rv379; Rv37; Rv381; Rv382; Rv383; Rv384; Rv385; Rv386; Rv387; Rv388; Rv389; Rv38; Rv390; Rv391; Rv392; Rv393; Rv396; Rv39; Rv3; Rv40; Rv412; Rv413; Rv414; Rv415; Rv416; Rv417; Rv418; Rv419; Rv41; Rv42; Rv43; Rv44; Rv45; Rv46; Rv47; Rv48; Rv49; Rv4; Rv50; Rv51; Rv52; Rv53; Rv54; Rv55; Rv56; Rv57; Rv58; Rv59; Rv5; Rv60; Rv61; Rv62; Rv63; Rv64; Rv65; Rv66; Rv67; Rv68; Rv69; Rv6; Rv70; Rv71; Rv72; Rv73; Rv74; Rv75; Rv76; Rv77; Rv78; Rv79; Rv7; Rv80; Rv81; Rv82; Rv83; Rv84; Rv85; Rv86; Rv87; Rv88; Rv89; Rv8; Rv90; Rv91; Rv92; Rv94; Rv95; Rv96; and Rv9.

17. The recombinant BAC vector of claim 15, which is selected from the group consisting of:

Rv234; Rv51; Rv166; Rv35; Rv415; Rv404; Rv209; Rv272; Rv30; Rv228; Rv233; Rb38; Rv280; Rv177; Rv48; Rv374; Rv151; Rv238; Rv156; Rv92; Rv3; Rv403; Rv322; Rv243; Rv330; Rv285; Rv233; Rv219; Rv416; Rv67; Rv222; Rv149; Rv279; Rv87; Rv273; Rv266; Rv25; Rv136; Rv414; Rv13; Rv289; Rv60; Rv104; Rv5; Rv165; Rv215; Rv329; Rv240; Rv19; Rv74; Rv411; Rv67; Rv56; Rv80; Rv164; Rv59; Rv313; Rv265; Rv308; Rv220; Rv258; Rv339; Rv121; Rv419; Rv418; Rv45; Rv217; Rv134; Rv17; Rv103; Rv21; Rv22; Rv2; Rv270; Rv267; Rv174; Rv257; Rv44; Rv71; Rv7; Rv27; Rv191; Rv230; Rv128; Rv407; Rv106; Rv39; Rv255; Rv74; Rv355; Rv268; Rv58; Rv173; Rv264; Rv417; Rv401; Rv144; Rv302; Rv81; Rv163; Rv281; Rv221; Rv420; Rv175; Rv86; Rv412; Rv73; Rv269; Rv214; Rv287; Rv42; and Rv143.

18. A *Mycobacterium bovis* BCG strain Pasteur genomic DNA library, wherein said genomic DNA library comprises recombinant bacterial artificial chromosome vectors.

19. A recombinant bacterial artificial chromosome (BAC) vector, which belongs to the genomic DNA library of claim 18.

20. A method for detecting a mycobacterial nucleic acid in a biological sample comprising the step of:

a) contacting the recombinant BAC vector according to claims 15 or 19, or a purified polynucleotide of interest isolated according to the method of claim 1 or 7 with the mycobacterial nucleic acid in the biological sample; and b) detecting a hybrid nucleic acid molecule formed between said recombinant BAC vector or said purified polynucleotide and the mycobacterial nucleic acid in the biological sample.

21. The method of claim 10, further comprising before step a), making the mycobacterial nucleic acid in the biological sample available to a hybridization reaction.

22. A method for detecting mycobacterial nucleic acid in a biological sample comprising the steps of:

a) contacting a first polynucleotide according to claim 10 that has been immobilized onto a substrate with the mycobacterial nucleic acid in the biological sample; and b) contacting a hybrid nucleic acid molecule formed between said first polynucleotide and the mycobacterial nucleic acid in the biological sample with a second, labeled polynucleotide according to claim 9, wherein said second polynucleotide and said first polynucleotide have non-overlapping sequences.

23. The method of claim 22, further comprising before step a), making the mycobacterial nucleic acid in the biological sample available to a hybridization reaction.

24. The method of claims 22 or 23, further comprising before step b), removing the mycobacterial nucleic acid that is not hybridized with the immobilized first polynucleotide.

25. A method for detecting mycobacterial nucleic acid in a biological sample comprising the steps of:

a) violating a pair polynucleotide inserts of interest from a pair of purified polynucleotides according to claim 20;

b) contacting the mycobacterial nucleic acid in the biological sample with a pair of purified polynucleotides inserts;

c) amplifying said mycobacterial nucleic acid; and d) detecting the amplified mycobacterial nucleic acid.

26. The method of claim 25, further comprising between steps a and b), making the mycobacterial nucleic acid in the biological sample available to a hybridization reaction.

27. A kit for detecting a mycobacterium in a biological sample comprising:

a) a recombinant BAC vector according to claims 15 or 19, or a purified polynucleotide of interest isolated according to the method of claim 1 or 7; and b) reagents necessary to perform a nucleic acid hybridization reaction.

28. A kit for detecting a mycobacterium in a biological sample comprising:

a) a recombinant BAC vector according to claims 15 or 19, or a first polynucleotide according to claim 9 that is immobilized onto a substrate;

b) reagents necessary to perform a nucleic acid hybridization reaction; and c) a second polynucleotide according to claim 9, wherein said second polynucleotide is radioactively or non-radioactively labeled, and wherein said second polynucleotide and said first polynucleotide have non-overlapping sequences.

29. A kit for detecting a mycobacterium in a biological sample comprising:

a) a pair of purified polynucleotides according to claim 13; and b) reagents necessary to perform a nucleic acid amplification reaction.

30. A method for detecting a genomic DNA, a cDNA or a mRNA of a mycobacterium in a biological sample, comprising the steps of:

a) contacting the biological sample with a plurality of BAC vectors according to claims 15 or 19, or purified polynucleotides of interest isolated according to the method of claim 1 or 8 that are immobilized on a substrate; and b) detecting hybrid complexes formed.

31. A kit for detecting a genomic DNA, a cDNA or a mRNA of a mycobacterium in a biological sample, comprising a substrate on which a plurality of BAC vectors according to claims 15 or 19, or purified polynucleotides of interest isolated according to the method of claim 1 or 7 have been immobilized.

32. A method for detecting a polynucleotide of mycobacterial origin in a biological sample, said method comprising:

a) aligning at least one polynucleotide contained in a recombinant BAC vector according to claims 15, 23, 24, or 19 on the surface of a substrate;

b) contacting the polynucleotide in the biological sample with the substrate on which the polynucleotide of step a) has been aligned; and c) detecting a hybrid nucleic acid molecule formed between the polynucleotide in the biological sample and the aligned polynucleotide of step a).

33. A kit for detecting a polynucleotide of mycobacterial origin in a biological sample, comprising:

a) a substrate on which at least one polynucleotide contained in a recombinant BAC vector according to claims 15, or 19 has been aligned.

34. The method of claim 8, further comprising amplifying the polynucleotide insert.

35. The method of claim 8, further comprising digesting the polynucleotide insert with at least one restriction endonuclease.

36. The method of claim 34, further comprising digesting the amplified polynucleotide insert with at least one restriction endonuclease.

37. The polynucleotide of claim 23, wherein the mycobacterium strain is *Mycobacterium tuberculosis.*

38. The method of claim 25, wherein the amplified mycobacterial DNA is detected by gel electrophoresis or with a labeled polynucleotide insert of interest isolated from a polynucleotide according to claim 9.

39. The kit of claim 37, further comprising a polynucleotide according to claim 10.

40. The kit of claim 31, further comprising reagents necessary to perform a hybridization reaction.

41. A method for physically mapping a polynucleotide of mycobacterial origin in a biological sample, said method comprising:

a) aligning at least one polynucleotide contained in a recombinant BAC vector according to claims 15 or 19 on the surface of a substrate;

b) contacting the polynucleotide in the biological sample with the substrate on which the polynucleotide of step a) has been aligned under hybridizing conditions; and c) detecting the location of the hybridized polynucleotide from the biological sample.

42. The kit of claim 33, further comprising reagents necessary for labeling DNA and reagents necessary for performing a hybridization reaction.

43. A recombinant BAC vector according to claim 14, which is selected from the group consisting of:

X0001; X0002; X0003; X0004; X0006; X0007; X0008; X0009; X0010; X0012; X0013; X0014; X0015: X0016; X0017; X0018; X0019; X0020; X0021; and X0175.

* * * * *

UNITED STATES PATENT AND TRADEMARK OFFICE

CERTIFICATE OF CORRECTION

PATENT NO. : 6,183,957 B1
DATED : February 6, 2001
INVENTOR(S) : Cole et al.

It is certified that error appears in the above-identified patent and that said Letters Patent is hereby corrected as shown below:

<u>Column 633, claim 4,</u>
Line 57, "I-1995" should read -- I-1945 --.

<u>Column 634, claim 10,</u>
Line 58, "pruified" should read -- purified --.

<u>Column 636, claim 20,</u>
Line 19, "step" should read -- steps --.

<u>Column 636, claim 21,</u>
Line 29, "claim 10" should read -- claim 20 --.

<u>Column 636, claim 22,</u>
Line 34, "claim 10" should read -- claim 9 --.

<u>Column 636, claim 25,</u>
Line 52, "violating a pair polynucleotide" should read -- isolating a pair of polynucleotide --.
Lines 53-54, "claim 20" should read -- claim 13 --.

<u>Column 636, claim 26,</u>
Line 61, "steps a and b)" should read -- steps a) and b) --.

<u>Column 637, claim 30,</u>
Line 28, "claim 1 or 8" should read -- claim 1 or 7 --.

<u>Column 637, claim 32,</u>
Lines 41-42, "claims 15, 23, 24, or 19" should read -- claims 15 or 19 --.

<u>Column 638, claim 33,</u>
Line 5, after "claims 15", delete the comma.

<u>Column 638, claim 37,</u>
Line 15, "claim 23" should read -- claim 11 --.

UNITED STATES PATENT AND TRADEMARK OFFICE

CERTIFICATE OF CORRECTION

PATENT NO. : 6,183,957 B1
DATED : February 6, 2001
INVENTOR(S) : Cole et al.

It is certified that error appears in the above-identified patent and that said Letters Patent is hereby corrected as shown below:

Column 638, claim 39,
Line 21, "claim 37" should read -- claim 29 --.
Line 22, "claim 10" should read -- claim 9 --.

Column 638, claim 43,
Line 41, "claim 14" should read -- claim 19 --.

Signed and Sealed this

Eighth Day of January, 2002

*Attest:*

JAMES E. ROGAN

*Attesting Officer*

*Director of the United States Patent and Trademark Office*